US010358646B2

(12) United States Patent
Collard et al.

(10) Patent No.: US 10,358,646 B2
(45) Date of Patent: Jul. 23, 2019

(54) TREATMENT OF TUMOR SUPPRESSOR GENE RELATED DISEASES BY INHIBITION OF NATURAL ANTISENSE TRANSCRIPT TO THE GENE

(71) Applicant: CuRNA, Inc., Miami, FL (US)

(72) Inventors: Joseph Collard, Delray Beach, FL (US); Olga Khorkova Sherman, Tequesta, FL (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 14/533,371

(22) Filed: Nov. 5, 2014

(65) Prior Publication Data

US 2015/0159162 A1 Jun. 11, 2015

Related U.S. Application Data

(63) Continuation of application No. 13/133,039, filed as application No. PCT/US2009/066654 on Dec. 3, 2009, now abandoned.

(60) Provisional application No. 61/166,381, filed on Apr. 3, 2009, provisional application No. 61/157,249, filed on Mar. 4, 2009, provisional application No. 61/154,594, filed on Feb. 23, 2009, provisional application No. 61/119,973, filed on Dec. 4, 2008.

(51) Int. Cl.

| | |
|---|---|
| ***C12N 15/11*** | (2006.01) |
| ***C12N 15/113*** | (2010.01) |
| ***A61K 31/712*** | (2006.01) |
| ***C12Q 1/6886*** | (2018.01) |

(52) U.S. Cl.

CPC ........ *C12N 15/1137* (2013.01); *A61K 31/712* (2013.01); *C12N 15/1135* (2013.01); *C12Q 1/6886* (2013.01); *C12N 2310/11* (2013.01); *C12N 2310/14* (2013.01); *C12N 2310/315* (2013.01); *C12Q 2600/158* (2013.01)

(58) Field of Classification Search

None

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,754,065 | A | 6/1988 | Levenson et al. |
| 4,800,159 | A | 1/1989 | Mullis et al. |
| 5,034,506 | A | 7/1991 | Summerton et al. |
| 5,138,045 | A | 8/1992 | Cook et al. |
| 5,218,105 | A | 6/1993 | Cook et al. |
| 5,288,512 | A | 2/1994 | Seiden |
| 5,288,514 | A | 2/1994 | Ellman |
| 5,319,080 | A | 6/1994 | Leumann |
| 5,393,878 | A | 2/1995 | Leumann |
| 5,432,272 | A | 7/1995 | Benner et al. |
| 5,457,189 | A | 10/1995 | Crooke et al. |
| 5,459,255 | A | 10/1995 | Cook et al. |
| 5,474,796 | A | 12/1995 | Brennan |
| 5,491,084 | A | 2/1996 | Chalfie et al. |
| 5,506,337 | A | 4/1996 | Summerton et al. |
| 5,519,134 | A | 5/1996 | Acevedo et al. |
| 5,525,735 | A | 6/1996 | Gallop et al. |
| 5,539,083 | A | 7/1996 | Cook et al. |
| 5,549,974 | A | 8/1996 | Holmes |
| 5,569,588 | A | 10/1996 | Ashby et al. |
| 5,576,302 | A | 11/1996 | Cook et al. |
| 5,593,853 | A | 1/1997 | Chen et al. |
| 5,605,662 | A | 2/1997 | Heller et al. |
| 5,661,134 | A | 8/1997 | Cook et al. |
| 5,708,161 | A | 1/1998 | Reese |
| 5,739,119 | A | 4/1998 | Galli et al. |
| 5,739,311 | A | 4/1998 | Lackey et al. |
| 5,756,710 | A | 5/1998 | Stein et al. |
| 5,849,902 | A | 12/1998 | Arrow et al. |
| 5,891,725 | A | 4/1999 | Soreq et al. |
| 5,902,880 | A | 5/1999 | Thompson |
| 5,908,779 | A | 6/1999 | Carmichael et al. |
| 5,965,721 | A | 10/1999 | Cook et al. |
| 5,985,663 | A | 11/1999 | Bennett et al. |
| 6,005,095 | A | 12/1999 | Capaccioli et al. |
| 6,013,639 | A | 1/2000 | Peyman et al. |
| 6,013,786 | A | 1/2000 | Chen et al. |
| 6,034,233 | A | 3/2000 | Ecker et al. |
| 6,100,090 | A | 8/2000 | Monia et al. |
| 6,140,492 | A | 10/2000 | Morelli et al. |
| 6,147,200 | A | 11/2000 | Manoharan et al. |
| 6,165,712 | A | 12/2000 | Foulkes et al. |
| 6,165,990 | A | 12/2000 | Singh et al. |
| 6,175,409 | B1 | 1/2001 | Nielsen et al. |
| 6,221,587 | B1 | 4/2001 | Ecker et al. |
| 6,239,265 | B1 | 5/2001 | Cook |
| 6,242,589 | B1 | 6/2001 | Cook et al. |
| 6,268,490 | B1 | 7/2001 | Imanishi et al. |
| 6,303,374 | B1 | 10/2001 | Zhang et al. |
| 6,307,040 | B1 | 10/2001 | Cook et al. |
| 6,316,198 | B1 | 11/2001 | Skouv et al. |

(Continued)

FOREIGN PATENT DOCUMENTS

| | | |
|---|---|---|
| CA | 2686933 | 4/2008 |
| EP | 335451 A3 | 3/1988 |

(Continued)

OTHER PUBLICATIONS

WO 2002/085309, Oct. 2012 by Nyce et al: because of the size of the reference pp. 98-598 in the middle containing sequences are deleted.*

(Continued)

*Primary Examiner* — Ekaterina Poliakova-Georgantas
(74) *Attorney, Agent, or Firm* — CuRNA, Inc.; Monte R. Browder

(57) ABSTRACT

The present invention relates to antisense oligonucleotides that modulate the expression of and/or function of Tumor Suppressor genes, in particular, by targeting natural antisense polynucleotides of Tumor Suppressor genes. The invention also relates to the identification of these antisense oligonucleotides and their use in treating diseases and disorders associated with the expression of Tumor Suppressor genes.

10 Claims, 88 Drawing Sheets

Specification includes a Sequence Listing.

(56) References Cited

U.S. PATENT DOCUMENTS 6,335,434 B1 1/2002 Guzaev et al.
6,376,541 B1 4/2002 Nixon et al.
6,403,566 B1 6/2002 Wang
6,444,464 B1 9/2002 Wyatt
6,451,991 B1 9/2002 Martin et al.
6,525,191 B1 2/2003 Ramassamy
6,528,262 B1 3/2003 Glad et al.
6,528,631 B1 3/2003 Cook et al.
6,617,122 B1 9/2003 Hayden et al.
6,617,442 B1 9/2003 Crooke et al.
6,630,315 B1 10/2003 Miwa et al.
6,639,059 B1 10/2003 Kochkine et al.
6,656,730 B1 12/2003 Manonaran
6,667,337 B2 12/2003 Wilson
6,670,461 B1 12/2003 Wengel et al.
6,710,174 B2 3/2004 Bennett et al.
6,734,291 B2 5/2004 Kochkine et al.
6,762,169 B1 7/2004 Manoharan
6,794,499 B2 9/2004 Wengel et al.
6,833,361 B2 12/2004 Hong et al.
6,861,514 B2 3/2005 Cook et al.
6,867,294 B1 3/2005 Sanghvi et al.
6,936,467 B2 8/2005 Kmiec et al.
6,936,593 B1 8/2005 Agrawal et al.
6,977,295 B2 12/2005 Belotserkovskii et al.
6,986,988 B2 1/2006 Gilad et al.
7,034,133 B2 4/2006 Wengel et al.
7,034,145 B2 4/2006 Shen et al.
7,053,195 B1 5/2006 Goff
7,053,199 B2 5/2006 Imanishi et al.
7,053,207 B2 5/2006 Wengel
7,060,809 B2 6/2006 Wengel et al.
7,084,125 B2 8/2006 Wengel
7,087,589 B2 8/2006 Jacobson et al.
7,125,982 B1 10/2006 Frayne
7,144,995 B2 12/2006 Wise et al.
7,144,999 B2 12/2006 Ward et al.
7,148,204 B2 12/2006 Bennett et al.
7,153,954 B2 12/2006 Koch et al.
7,169,916 B2 1/2007 Krotz et al.
7,199,107 B2 4/2007 Dobie et al.
7,202,357 B2 4/2007 Crooke et al.
7,217,572 B2 5/2007 Ward et al.
7,220,549 B2 5/2007 Buzby
7,226,785 B2 6/2007 Kmiec et al.
7,229,974 B2 6/2007 Peyman et al.
7,229,976 B2 6/2007 Dobie et al.
7,235,534 B2 6/2007 Tanguay et al.
7,235,653 B2 6/2007 Bennett et al.
7,238,858 B2 7/2007 Marraccini et al.
7,276,599 B2 10/2007 Moore et al.
7,285,288 B1 10/2007 Tormo et al.
7,297,786 B2 11/2007 McCray et al.
7,314,923 B2 1/2008 Kaneko et al.
7,320,965 B2 1/2008 Sah et al.
7,321,828 B2 1/2008 Cowsert et al.
7,335,764 B2 2/2008 Crooke et al.
7,335,765 B2 2/2008 Kaneko et al.
7,339,051 B2 3/2008 Crooke et al.
7,371,833 B1 5/2008 Weiss
7,399,845 B2 7/2008 Seth et al.
7,402,434 B2 7/2008 Newman et al.
7,402,574 B2 7/2008 Iversen et al.
7,420,050 B2 9/2008 Park et al.
7,423,142 B2 9/2008 Vornlocher
7,425,545 B2 9/2008 Crooke et al.
7,427,675 B2 9/2008 Capaldi et al.
7,456,154 B2 11/2008 Soreq et al.
7,462,642 B2 12/2008 Wang et al.
7,468,431 B2 12/2008 Bhanot et al.
7,510,830 B2 3/2009 Baguley et al.
7,541,344 B2 6/2009 Bhat et al.
7,547,684 B2 6/2009 Seth et al.
7,569,575 B2 8/2009 Sorensen et al.
7,569,686 B1 8/2009 Bhat et al.
7,572,582 B2 8/2009 Wengel et al.
7,582,745 B2 9/2009 Sah et al.
7,585,893 B2 9/2009 Baguley et al.
7,589,190 B2 9/2009 Westergaard et al.
7,598,227 B2 10/2009 Crooke et al.
7,605,251 B2 10/2009 Tan et al.
7,622,453 B2 11/2009 Frieden et al.
7,662,948 B2 2/2010 Kurreck et al.
7,666,854 B2 2/2010 Seth et al.
7,674,895 B2 3/2010 Reich et al.
7,687,617 B2 3/2010 Thrue et al.
7,709,456 B2 3/2010 Corey et al.
7,691,995 B2 4/2010 Zamore et al.
7,695,902 B2 4/2010 Crooke
7,696,345 B2 4/2010 Allerson et al.
7,709,630 B2 5/2010 Gaarde et al.
7,713,738 B2 5/2010 Hansen et al.
7,718,629 B2 5/2010 Bamcrot et al.
7,723,508 B2 5/2010 Crooke et al.
7,732,422 B2 6/2010 Gleave et al.
7,732,590 B2 6/2010 Bhanot et al.
7,737,264 B2 6/2010 Thrue et al.
7,737,265 B2 6/2010 Akinc et al.
7,741,305 B2 6/2010 Crooke et al.
7,741,309 B2 6/2010 Hansen et al.
7,741,457 B2 6/2010 Seth et al.
7,745,609 B2 6/2010 Bennett et al.
7,749,978 B2 7/2010 Sah et al.
2003/0139359 A1 7/2003 Dobie
2003/0186920 A1 10/2003 Strois
2003/0191075 A1 10/2003 Cook et al.
2003/0228618 A1 12/2003 Levanon et al.
2003/0233670 A1 12/2003 Edgerton et al.
2004/0006031 A1 1/2004 Dean et al.
2004/0033480 A1 2/2004 Wong
2004/0101858 A1 5/2004 Ward et al.
2004/0137423 A1 7/2004 Hayden et al.
2004/0138155 A1 7/2004 Baird et al.
2004/0161777 A1* 8/2004 Baker .................... C07H 21/00 435/6.11
2004/0175803 A1 9/2004 Meritet et al.
2004/0180336 A1 9/2004 Gilad et al.
2004/0254137 A1 12/2004 Ackermann et al.
2005/0009771 A1 1/2005 Levanon et al.
2005/0026160 A1 2/2005 Allerson et al.
2005/0113326 A1 5/2005 Siwkowski et al.
2005/0143357 A1 6/2005 Pousette et al.
2005/0153286 A1 7/2005 Clements
2005/0215504 A1 9/2005 Bennett et al.
2005/0222029 A1 10/2005 Bartel et al.
2005/0246794 A1* 11/2005 Khvorova ............ A61K 31/713 800/286
2006/0009410 A1 1/2006 Crooke et al.
2006/0142196 A1 6/2006 Klein et al.
2006/0178333 A1 8/2006 Soreq et al.
2007/0082848 A1 4/2007 Alitalo et al.
2007/0197459 A1 8/2007 Milner
2007/0213274 A1 9/2007 Salonen
2007/0213292 A1 9/2007 Stoffel et al.
2007/0231816 A1 10/2007 Chaussabel et al.
2007/0248590 A1 10/2007 Milne et al.
2007/0275921 A1* 11/2007 Swayze .............. A61K 31/7052 514/44 A
2008/0146788 A1 6/2008 Bhat et al.
2008/0221051 A1 9/2008 Becker et al.
2008/0293142 A1 11/2008 Liu et al.
2009/0191263 A1 7/2009 Reich et al.
2009/0192106 A1 7/2009 Dobie et al.
2009/0208479 A1 8/2009 Jaye et al.
2009/0258925 A1 10/2009 Wahlestedt
2009/0318536 A1 12/2009 Freier et al.
2009/0326041 A1 12/2009 Bhanot et al.
2010/0105760 A1 4/2010 Collard et al.

FOREIGN PATENT DOCUMENTS

EP 335451 A2 10/1989
WO WO-1984/03564 9/1984

(56) References Cited

FOREIGN PATENT DOCUMENTS

| | | | | | |
|---|---|---|---|---|---|
| WO | WO-1991/19735 | | | 12/1991 | |
| WO | WO-1992/00091 | | | 1/1992 | |
| WO | WO-1992/08796 | | | 5/1992 | |
| WO | WO-1993/20242 | | | 10/1993 | |
| WO | WO-1994-026887 | A1 | | 11/1994 | |
| WO | WO-1994/28143 | | | 12/1994 | |
| WO | WO-1995-015373 | A2 | | 6/1995 | |
| WO | WO-1995/22618 | | | 8/1995 | |
| WO | WO-1995/25116 | | | 10/1995 | |
| WO | WO-1995/35505 | | | 12/1995 | |
| WO | WO-1996-027663 | A2 | | 9/1996 | |
| WO | WO-1997-039120 | A1 | | 10/1997 | |
| WO | WO 9835978 | A1 | * | 8/1998 | ........... C07H 15/203 |
| WO | WO-1999-014226 | A1 | | 3/1999 | |
| WO | WO-1999-039352 | A1 | | 8/1999 | |
| WO | WO-2000-057837 | A1 | | 10/2000 | |
| WO | WO-2000-061770 | A2 | | 10/2000 | |
| WO | WO-2001-000669 | A2 | | 1/2001 | |
| WO | WO-2001-21631 | A2 | | 3/2001 | |
| WO | WO-2001-025488 | A2 | | 4/2001 | |
| WO | WO 0122972 | A2 | * | 4/2001 | ......... A61K 31/7088 |
| WO | WO-2001-051630 | A1 | | 7/2001 | |
| WO | WO-2002-062840 | A1 | | 8/2002 | |
| WO | WO-2002-068688 | A1 | | 9/2002 | |
| WO | WO-2004-016255 | A1 | | 2/2004 | |
| WO | WO-2004-024079 | A2 | | 3/2004 | |
| WO | WO-2004-030750 | A1 | | 4/2004 | |
| WO | WO-2004-041838 | A1 | | 5/2004 | |
| WO | WO-2004-104161 | A2 | | 12/2004 | |
| WO | WO 2005018534 | A2 | * | 3/2005 | ......... C12N 15/1137 |
| WO | WO-2005-045034 | A2 | | 5/2005 | |
| WO | WO-2005-070136 | A2 | | 8/2005 | |
| WO | WO-2005-079862 | A1 | | 9/2005 | |
| WO | WO-2007-028065 | A2 | | 3/2007 | |
| WO | WO-2007-071182 | A1 | | 6/2007 | |
| WO | WO-2007-087113 | A2 | | 8/2007 | |
| WO | WO-2007-138023 | A1 | | 12/2007 | |
| WO | WO-2008-057556 | A2 | | 5/2008 | |
| WO | WO-2008-066672 | A2 | | 6/2008 | |
| WO | WO-2008-087561 | A2 | | 7/2008 | |
| WO | WO-2010-002984 | A1 | | 1/2010 | |
| WO | WO-2010-040571 | A2 | | 4/2010 | |
| WO | WO-2010-054364 | A1 | | 5/2010 | |
| WO | WO-2010-058227 | A2 | | 5/2010 | |

OTHER PUBLICATIONS

Telerman et al, WO 03/025177, Mar. 2003, search result attached, 31 pages.*

Ausubel, Current Protocols in Molecular Biology vol. 1, 1994, 6.0.1-6.4.10.

Barak, et al., "A β-Arrestin/Green Fluorescent Protein Biosensor for Detecting G Protein-Coupled Receptor Activation," J. Biol. Chem. 272:27497-27500 (1997).

Barber, et al., "Delivery of membrane-impermeant fluorescent probes into living neural cell populations by lipotransfer," Neuroscience Letters 207:17-20 (1996).

Baum, "Solid-phase synthesis of benzodiazepines," C&EN News, Jan. 18, p. 33-34 (1993).

Bernstein, E., et al., "Role for a Bidentate Ribonuclease in the Initiation Step of RNA Interference," Nature 409:363-366 (2001).

Boutla, A., et al., "Short 5'-phosphorylated double-stranded RNAs induce RNA interference in *Drosophilia*," Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6. Fluorescence Ratio Imaging Microscopy," Methods in Cell Biology vol. 30, Taylor and Wang (eds) p. 157-192 (1989).

Bright, el al., "Delivery of Macromolecules Into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics," FEBS Lett., 480:2-16 (2000).

Chabala, J.C., "Solid-phase combinatorial chemistry and novel tagging methods for identifying leads," Curr Opin Biotechnol. 6:632-639 (1995).

Cech, J., "Ribozymes and Their Medical Implications," American. Med Assoc. 260:3030-3035 (1988).

Chen, et al., "Expression of ssDNA in Mammalian Cells," BioTechniques 34:167-171 (2003).

Chen, et al., "Analogous Organic Synthesis of Small-Compound Libraries: Validation of Combinatorial Chemistry in Small-Molecule Synthesis," J. Amer. Chem. Soc. 116:2661-2662 (1994).

Cheng, J. et al., "Transcriptional maps of 10 human chromosomes at 5-nucleolidc resolution," Science 308:5725:1149-1154 (2005).

Cho, et al., "An Unnatural Biopolymer," Science 261:1303-1305 (1993).

Christiensen, N.K. et al., "A Novel Class of Oligonucleotide Analogues Containing 2'-O,3'-C-Linked [3.2.0] Bicycloarabinonucleoside Monomers: Synthesis, Thermal Affinity Studies, and Molecular Modeling," J. Am. Chem. Soc. 120:5458-5463 (1998).

Cubitt, et al. , "Understanding, improving and using green fluorescent proteins," Trends in Biochemical Science 20:448-455 (1995).

Curiel, D. T. et al., "Adenovirus Enhancement of Transferrin-Polylysine-Mediated Gene Delivery," PNAS 88:8850-8854 (1991).

Dai et al., "SIRT1 Intends With p73 and Suppresses p73-Dependent Transcriptional Activity," J Cell Physiol 210(1):161-165 (2007).

Davidson, et al., "A model system for in vivo gene transfer into the central nervous system using an adenoviral vector," Nat. Genet 3:219-223 (1993).

Davis, et al., "Direct Gene Transfer into Skeletal Muscle in Vivo: Factors Affecting Efficiency of Transfer and Stability of Expression," Hum Gene Ther 4:151-159 (1993).

De Mesmaeker, et al., "Antisense Oligonucleotides," Acc. Chem. Res. 28:366-374 (1995).

Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).

Dixon, et al., "Anthrax," New England J. Med. 341:815-826 (1999).

Dolle, "Discovery of Enzyme inhibitors through combinatorial chemistry," Mol Divers. 2:223-236 (1997).

Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).

Eguchi et al., "Antisense RNA," Annu. Rev. Biochem 60:631-652 (1991).

Eichler, et al., "Generation and utilization of synthetic combinatorial libraries," Mol Med Today 1:174-180 (1995).

Eichler, et al., "Peptide Peptidomimetic and organic synthetic combinatorial libraries," Med Res Rev 15:481-496 (1995).

Espeseth, et al., "A genome wide analysis of ubiquitin ligases in APP processing identifies a novel regulator of BACE1 mRNA levels," Mol. Cell Neurosci. 33: 227-235 (2006).

Faghihi, M. & Wahlestedt, C., "RNA interference is not involved in natural antisense mediated regulation of gene expression in mammals," Genome Biol (2005), p. 1-9.

(56) References Cited

OTHER PUBLICATIONS

Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008), p. 1-4.
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobs-DeWitt, et al., "Diversomers: An approach to nonpeptide, nonoligomeric chemical diversity," Proc. Nat. Acad. Sci. USA 90:6909-6913 (1993).
Houghton AN, Gold JS, Blachere NE, Immunity against cancer: lessons learned front melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomies in human disease: Cancer, heart and infectious diseases," Electrophoresis 20:2100-2110 (1999).
Jurecic & Belmont, "Long-distance DD-PCR and cDNA, microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification or enzyme inhibitors from phage-displayed combinatorial peptide libraries," Comb Chem High Throughput Screen 4:535-543 (2001).
Kenan, et al., "Exploring, molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-Throughput Protein Expression of cDNA Products as a Tool in Functional Genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, Properties, and Activity as Inhibitors of Replication of Human Immunodeficiency Virus in Cell Culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).

(56) References Cited

OTHER PUBLICATIONS

McNeil In Methods in Cell Biology vol. 29, Taylor and Wang (eds.) p. 153-173 (1989).
Morelli et al., "The antisense bcl-2-IgH transcript is an optimal target for synthetic oligonucteotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-153 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., In Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000.
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states of β-amyloid 1-42 mediate different effects on oxidative stress, neurodegeneration, and BASE-1 expression," Free Radio Biol Med 41:202-212 (2006).
Thakker, D.R, et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemisiry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien In Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression Science," 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46 (1994).
Walsh, et al., The role of cell-derived oligomers of Aβ in Alzheimer's disease and avenues for therapeutic intervention, Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-Oxide Synthase Antiscrise (NOS3AS) Gene Encodes an Autophagy-Related Protein (APG9-like2) Highly Expressed in Trophoblast" (2005), p. 18283-18290.
Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1β-inducible Genes in Rat Hepatocytes," HOAJ Biology; 1-10 (2012).

(56) References Cited

OTHER PUBLICATIONS

EP Application No. 06850393.7 Examination Report dated Oct. 18, 2011.
International Search Report and Written Opinion for PCT Application No. PCT/US2010/033078 dated Jun. 29, 2011.
PCT/US2010/026119 Search Report and Written Opinion dated Feb. 7, 2011.
PCT/US2010/024079 Search Report and Written Opinion dated Jan. 31, 2011.
PCT/US2010/027394 Search Report and Written Opinion dated Nov. 5, 2010.
PCT/US96/10287 (WO97/000271) The Regents of the University of California Jan. 3, 1997.
Collir R., et al., "Antisense Oligonucleotide (AON)-based Therapy for Leber Congenital Amaurosis Caused by a Frequent Mutation in CEP290," Molecular Therapy-Nucleic Acids, vol. 1, No. 14, pp. 1-7, (2012).
Flibotte, S., et al., "Experimental Analysis of Oligonucleotide Microarray Design Criteria to Detect Deletions by Comparative Genomic Hybridization," BMC Genomics, vol. 9, No. 497, pp. 1-12, (2008).
Han, J. et al., "Selection of Antisense Oligonucleotides on the Basis of Genomic Frequency of the Target Sequence," Antisense Res Dev., vol. 4, No. 1, pp. 53-65, (1994), Abstract.

* cited by examiner

FIG.4

(SEQ ID NO: 1)

>gi|187828868|ref|NM_005427.2| Homo sapiens tumor protein p73 (TP73), transcript variant 1, mRNA AGGGGACGCAGCGAAACCGGGGCCCGCGCCAGGCCAGCCGGGACGGACGCCGATGCCCGGGGCTGCGACGGCTGCAG
AGCGAGCTGCCCTCGGAGGCCGGCGTGGGGAAGATGGCCCAGTCCACCGCCACCTCCCCTGATGGGGGCACCACGTT
TGAGCACCTCTGGAGCTCTCTGGAACCAGACAGCACCTACTTCGACCTTCCCCAGTCAAGCCGGGGGAATAATGAGG
TGGTGGGCGGAACGGATTCCAGCATGGACGTCTTCCACCTGGAGGGCATGACTACATCTGTCATGGCCCAGTTCAAT
CTGCTGAGCAGCACCATGGACCAGATGAGCAGCCGCGCGGCCTCGGCCAGCCCCTACACCCCAGAGCACGCCGCCAG
CGTGCCCACCCACTCGCCCTACGCACAACCCAGCTCCACCTTCGACACCATGTCGCCGGCGCCTGTCATCCCCTCCA
ACACCGACTACCCCGGACCCCACCACTTTGAGGTCACTTTCCAGCAGTCCAGCACGGCCAAGTCAGCCACCTGGACG
TACTCCCCGCTCTTGAAGAAACTCTACTGCCAGATCGCCAAGACATGCCCCATCCAGATCAAGGTGTCCACCCCGCC
ACCCCCAGGCACCGCCATCCGGGCCATGCCTGTTTACAAGAAAGCGGAGCACGTGACCGACGTCGTGAAACGCTGCC
CCAACCACGAGCTCGGGAGGGACTTCAACGAAGGACAGTCTGCTCCAGCCAGCCACCTCATCCGCGTGGAAGGCAAT
AATCTCTCGCAGTATGTGGATGACCCTGTCACCGGCAGGCAGAGCGTCGTGGTGCCCTATGAGCCACCACAGGTGGG
GACGGAATTCACCACCATCCTGTACAACTTCATGTGTAACAGCAGCTGTGTAGGGGGCATGAACCGGCGGCCCATCC
TCATCATCATCACCCTGGAGATGCGGGATGGGCAGGTGCTGGGCCGCCGGTCCTTTGAGGGCCGCATCTGCGCCTGT
CCTGGCCGCGACCGAAAAGCTGATGAGGACCACTACCGGGAGCAGCAGGCCCTGAACGAGAGCTCCGCCAAGAACGG
GGCCGCCAGCAAGCGTGCCTTCAAGCAGAGCCCCCCTGCCGTCCCCGCCCTTGGTGCCGGTGTGAAGAAGCGGCGGC
ATGGAGACGAGGACACGTACTACCTTCAGGTGCGAGGCCGGGAGAACTTTGAGATCCTGATGAAGCTGAAAGAGAGC
CTGGAGCTGATGGAGTTGGTGCCGCAGCCACTGGTGGACTCCTATCGGCAGCAGCAGCAGCTCCTACAGAGGCCGAG
TCACCTACAGCCCCCGTCCTACGGGCCGGTCCTCTCGCCCATGAACAAGGTGCACGGGGGCATGAACAAGCTGCCCT
CCGTCAACCAGCTGGTGGGCCAGCCTCCCCCGCACAGTTCGGCAGCTACACCCAACCTGGGGCCCGTGGGCCCCGGG
ATGCTCAACAACCATGGCCACGCAGTGCCAGCCAACGGCGAGATGAGCAGCAGCCACAGCGCCCAGTCCATGGTCTC
GGGGTCCCACTGCACTCCGCCACCCCCCTACCACGCCGACCCCAGCCTCGTCAGTTTTTTAACAGGATTGGGGTGTC
CAAACTGCATCGAGTATTTCACCTCCCAAGGGTTACAGAGCATTTACCACCTGCAGAACCTGACCATTGAGGACCTG
GGGGCCCTGAAGATCCCCGAGCAGTACCGCATGACCATCTGGCGGGGCCTGCAGGACCTGAAGCAGGGCCACGACTA
CAGCACCGCGCAGCAGCTGCTCCGCTCTAGCAACGCGGCCACCATCTCCATCGGCGGCTCAGGGGAACTGCAGCGCC
AGCGGGTCATGGAGGCCGTGCACTTCCGCGTGCGCCACACCATCACCATCCCCAACCGCGGCGGCCCAGGCGGCGGC
CCTGACGAGTGGGCGGACTTCGGCTTCGACCTGCCCGACTGCAAGGCCCGCAAGCAGCCCATCAAGGAGGAGTTCAC
GGAGGCCGAGATCCACTGAGGGCCTCGCCTGGCTGCAGCCTGCGCCACCGCCCAGAGACCCAAGCTGCCTCCCCTCT
CCTTCCTGTGTGTCCAAAACTGCCTCAGGAGGCAGGACCTTCGGGCTGTGCCCGGGGAAAGGCAAGGTCCGGCCCAT
CCCCAGGCACCTCACAGGCCCCAGGAAAGGCCCAGCCACCGAAGCCGCCTGTGGACAGCCTGAGTCACCTGCAGAAC
CTTCTGGAGCTGCCCTAGTGCTGGGCTTGTGGGGCGGGGGCTGGCCCACTCTCAGCCCTGCCACTGCCCCGGCGTGC
TCCATGGCAGGCGTGGGTGGGGACCGCAGCGTCGGCTCCGACTTCCAGGCTTCATCCTAGAGACTGTCATCTCCCAA
CCAGGCGAGGTCCTTCCAAAGGAAAGGATCCTCTTTGCTGATGGACTGCCAAAAAGTATTTTGCGACATCTTTTGGT
TCTGGATAGTAGTGAGCAGCCAAGTGACTGTGTCTGAAACACCAGTGTATTTTCAGGGAATGTCCCTAACTGCGTCT
TGCCCGCGCCGGGGGCTGGGGACTCTCTCTGCTGGACTTGGGACTGGCCTCTGCCCCCAGCACGCTGTATTCTGCAG
GACCGCCTCCTTCCTGCCCCTAACAACAACCACAGTGTTGCTGAAATTGGAGAAAACTGGGGAGGGCGCAACCCCCC
CCAGGCGCGGGGAAGCATGTGGTACCGCCTCAGCCAGTGCCCCTCAGCCTGGCCACAGTCGCCTCTCCTCGGGGACC
CCTCAGCAGAAAGGACAGCCTGTCCTTAGAGGACTGGAAATTGTCAATATTTGATAAAATGATACCCTTTTC

FIG. 4 (Continued)

(SEQ ID NO: 2)

>hg18_knownGene_uc001akp.2 range=chr1:3558989-3640327 5'pad=0 3'pad=0 strand=+
repeatMasking=none
AGGGGACGCAGCGAAACCGGGGCCCGCGCCAGGCCAGCCGGGACGGACGCCGATGCCCGGGGCTGCGACGGCTGCAGgtagg
aggcccagggccgggggcggttcggctccgcgggcgggggctggagcgcagcgctgggcaggcacctgggctcgcagctcc
gaagctgggaggtgaggggagagcgatcggggacgagctgggacaaggcgacacaggggctccctcggagttggatcggccc
ctgggacttggcgctcgcgagaggctggagcggccagagtctagcctgcgaggagacgcgggtcctgccctcagcgccggcc
gccttggcgccaaagacagcccgcaggggttccgggagggccctcctcctgctgtcccctctccaccccgggctccgagg
gccgttgggagggtaaccccgggaagaggccggggtgcggggcgcgggtgcaggtggaaatcgccagcaagctcctcccgc
ccgcgcgctccctccgacctgcagggctgtgccaatcccgaggcctcagcttccctgaggagccagggccaggccccctct
ggacagggagaaggatctgggcgggggccttgacccatggagttggttactaagcggtttcgatggtttcccgagggacagc
tccctgtggctctgagtttgtctgtcgagggctcctggcctgtctccggagcggtcccaggtagagaaagcccgtgaagaaa
tggcccgggccggcctggagggagacacctcacgcccccttagctcctgggccgcctcctcctgcagcccctgcctttcccg
gggcttggacttggggagcgatgattacctttgctcagcttgtatttggcctggacgctaggagataagcccatgtagtat
gcacacgtctgctacataaacaggggacagatagacgatcttcaaccagcaagggtgcagggaaaagcaatgcaccccaaac
ttctgaccagaggtcatttgcttccaagatgctgccatctgtttattcactgtctggacatttggaaatggctcaggctca
ttaacacaatgctttggtttttgttgtttgtttttgttgctgtcattgctgtttatttgttcagccttagctctgggga
ggagtaaacaaagcgcgtggcctctggcacttactgagcgctgagccacccctctttggatttattcggggaaagattaaaa
agcatttcattaagaacaggacacggtgtttgaaatgttgccatatatgaatgtatgcattacgtatgtagtttttaaaata
agataaaaagttggctgggcacggtagctcacgcctgtcatccctcacagcctttgggaggccaaggtgggtggatcacctg
aggtcaggagttcgagaccagcctggccatcatggtgaaaccagtctctacttgaaatacaaaaattagctgggcatggtg
gcaggcacctgtactcccagctactcgggaggctgaggcacaagaattgcttgaacctgggatggagaggttgcagcgagct
gatatcatgccactgcactccagcctgggcaacagagcaagactctgtctcaaaaaataagatgaaataagataaaagttgg
tgtcagaggctgcagtgtggcagctgcctattgtcaatcagaggtagcctggggtgaacggaaggcggacctgagcggggct
tgtctatgcgcggcggccaccagagaatggctcgggatgtgagccctgccttgcagtccttctcgtgaaagctacagcgaac
agtagctgtctccaaatcccgaaggccagtcgcatggagaagctggtctggcacagtggttaatggggtagtatggaagtca
gaatgctggggttcaaatctcctcttccccatttactccagcaagtcacttaaccacttggagcctcaggttacccatctgc
agagtcgggtaatagtagttcctgcctcagaggcttggagaacagtcagtgaggtgccgtccgaaggcttgggagagtgcc
tggcacccactcagtgtcctcacacatgatggcttcgggtcccaggtgctgttccagagctgggagagccaggagccctggg
gagagacccggctccttagtatctggtaggtatctccagggcaggagggatggcagtgaggcaggcatctgcccaaggcgtg
ggtggaagctgatggcatctgtcagaagtatgcactggggcaaggatgcctggtttagtatttatttatagggcatgcccca
cccaggtccaagaatggattgataacactgagcacgtgtgaaaggcacggctaaagtggagagaagagaagaggctgagggc
cgagagaggagccgcacacccactccagaacccggacgaggccctgcccttgcccagcggcggtattaaccctgagattccg
agcacaccaaagtgacatcgcgtacacggtgaaccctgtgtttgcaaaaagtcagaaaaagtcttcaaaacatcctttaagg
ccaggcgccgtggcccacgcctgtaatctcagccctttgggaggccgaggtgggtggatcacttgagatcaggagttcaaga
ccagcctgggcaaaatggtgaaatcttgtccccaccaaaaatacaaaaattagccgggggtggtgtctggtgcctgtagtct
cagctactcaggaggctgaggcaggagaatcgcttgaacttgggaggcagaggttgcagtgagccgagatcaccccactgca
ctccagcccgggcaacagagcgagactctgtctcaaaaaaacacgcaaaaaatactttggtgtgtgtgtttcatgtaacgagc
tgccattttgcggcttgcctttgttttccagtgtggggagggctaaggcaacctttaagatatctgtatgttatttcctcg
tgatttgctttaaaagcaaaaaagaaaaaagctgagatgagttactaaatgacaataacgcctactttctttgaattcc
cgtgttatttgtatctgaatgtggtgaaagtttctaaatgtaatgtttatcaccagtaagtaggctgagtgatcacttac
tcctaccagtatttaatacttccatgttctgcccagattcctttaacaaatacacaaaacacacttgtagctggcaacatcc
actcgtgtataatgaaaacacacaatggctttcttagaagtttgccttcttaagtgggttacacaggatgcctcgaaaatcc
ttctctgtgggtcgtgcagaaggtatttattctaaaattccctctactcagccgggcgcagtggctcacgcctgtaatcc
cagcatttgggaggctgaggcgggtggatcacgaggtcaggagatcaagaccatcctggctaacacggtgaaaccccgtct
ctactaaaaatacaaaaaattagtcgggcgtggtgcgggcacctgtagtcccagctacccaggaggctgaggcaggagaatg
gcgtgaacccggaaggcggagcttgcagtgagctgagatcacgcactacactccagcctgggcgacagagcgagactacgtc
tcaaaaaaaaaaaaaaaaaatccctctgctcattggcatttgagtgtaagacagcttataccaaagtgggctcagacagaca
tatgcacatgtttacagactttctgcctgcccctggcagtccactctgtgctcagtatttctttgcaggctaaacactcgc
tcatccaaagtgctttctttcctggacaagttgcacatcacagacccaaagaagaaaaagataatccagcccaactccttgt
tttttaatgtttcctgtaataactcacatttagcccatggtggctgtgagctggtacttggctaaaagtttacattttttt
ccctgtaatccccacaatagcccgttgaagtagatactataattatgcccatttacagatgaggaaactgaggcttcaactg
gctattctacttgcacagggtcacacagctgcaaagtacgggagtggggactccagctatgaccacgaagctgggactgggg
ctgccaaaccatcctttgcctgggtctgccgttggctcagacacggcccccagacacctaggaccgtggaacattcaggccg

FIG. 4 (Continued)

gaagggcccttccagaacatctaagccaggggtagagagtccagggtgctgtgagcctggatggggaaaaatggcaccttgt
attaacctcaaagcaaatttcagcatttccctctagttttgaatgtaggcagcaaactacagtcatagcagtacctgtgacct
caccagtgggaaccactgatatttttcatggtgtccggtaatagctgcagcatcttaaaaagtggtttgtgcttgtcgctccg
ttgcaattatggcggtgattagatctgctctcaggcttacgacttaatgtatgaacaaagaagcgcacatatgatcacctcc
cagttttgctttttaaatattagggtcactttgtaagtttttctcaggctgctgttacaaatgaccacaaattaagtggctgg
aaacaatagagagtgttgtctcacggttgtggaggcaggaatctgaagccaggtgtgggcagggtcgggttccctcggaggc
tctgagagggggctcgcctcctgtctccctcctaggatctggggctgccggccatcctgtggttcccaggcatgcagatgc
accacccagtctctgccaccatcttgccatggccttctcctctgtgtccctgtgtgtctctccttttttgtccccttagatgg
acacctgtccttggatttcgggcccacctggaaaatccagaatgatcctatcttgagacccttacctaagtggcatctgcaa
agaccctgattccaaataacatcccattctgaggctcgttcccagaggctgcatccaacccactagagtggctatgtttcag
taactcgtgatcctgtgtattttgcttcacgtacttaaaacattctccggacaaggcgtctgagattccccaggctgccag
aggggccatggcgcaaacggggaagaaacctggtctaagccacgcccctctttcaggacgaggatcttggaacccggacac
tgaaggtcggggttgggcacagccggggatgggcagcccccctctcccccagcacctcccgcctggcgcctccttccacagcc
cctgcatcctggaaaacagactgttccacacactccagcagctcctctacctggggactgcttgggccgcatagcccccagt
tagggacagaaaccagaggtattgaacaagaagccccacccgggagaggcgagacccgggcccccagccctggacctggccgtg
ggtgctacagaaggtcgggggacatcggtctgcgcggaagggtctggagaggcacctctcagggagttggacagagaggaga
cgccgtcccagtggtggcctccagtgaggcctggagagaccaggtggcaggaagggccctgctggggccagagcaagggcac
ggaaggcaggtctcatggagcagggaccgtggaggggacatggggacacattagggatggacagtggccggaagattccgt
gggccttggagattaaatcgggttccccaaagagcaagctgtggagaggggaagggaaagttgcctccctcttccctacggg
gttcttgtcaataaacgattgacaaaagacagactcacaagagacaacagttttaaggctgtgcccccgcccggaagtgcca
taaaaacaggagactcagcagtaaccagatgggagcggtgcagatgtccgtcctctgtgacagaaaggaaagggggcctggg
cttctggggagcggtagagacaaatgaggagagggtgagggaggaaacgtctgggcataaaggctgcctcgtggtgcagcta
tcagtctcatggtgagaaaatgcgtcttggcgcgcggctctcttcctggcacacagaccattactaatgaaaatgtccttta
tagatgtcaatttttcttagaaaagagagttttttctactttattttagggagctgaagagctttttttctgttggctggttct
cagttgcttttagctcaaagtaatcaacatgtcaacatggcatatttggggtgacgtattctggtctcctacagtcatatt
ttggggtgacgtattctggtctcctacagtcatatttggggtgacgtattctagtctcctacagtcatatttaggggtggc
gtattctggtctcctacagtcatatttgggggtggcgtattctggtctcctacagtcatatttggggtggcgtattctggt
ctcctacagtcatatttggggtgacgtattctggtctcctatagtcatatttaggggtggcgtattctggtctcctacagt
catactttggggtgatgtgtcctgagccccattgtttcctagtctgaaacttccccaagaagctccacggtacagaaactgg
gtgggtgtgttgtcccataatgctttgaagaggcatttctatggaaacaaaagaaaaaaaaaaaaaagctaatcattggagct
gactaaaaaccagtttctgagcctgggggccgtggcggggcaggtttgtagatgttgggctccgagcatcttctgcggtttg
gtctctggcgatgtctgggcggcccacgcagcaacaggcgtgagggtccctcgcacctgggcttcgtggtaatctcgctgat
gagtatttcaagtcgtccagcctcagtttgcaggatttctgggcaaagggcagtttttgttcttcgtgattccaataagaacg
gtgggagaaaattgaaagtgttagtttgggagttgcagccagatactggaggaaactagaaacatcaggaacccgtccagtt
tgtagacatcaatagataacaaaacccccaaagacgttaaacaggacaagaatctaatatggggcgcacaatatggcttttcta
ctgaaatatatgtttcttttctacatcaccccctctttctactaaaaataatctcagtaagattattattattattatttttt
gagacagagttccactccgtcgctcaggctagagtgtagtggcatcatctcgactcactgcaaactctgcctcccgggttc
aagtgattctcctgcctcagcctcctggagttacaggcatgcaccaccactaatttttgtattattattactttttttagt
agagacagggttttgccatgttggccaggctggtcttgaactcctgacctcacaggatccacccacttcggcctcccaaagt
gctaggattacagacgtgagccactgtgcccagcctagtcagattaacttgtttgtaaagtaagtctagcctcattaaaatt
ggcctgattatttgcacaagtgcagcaagaatagtaagtggccagctaggctttctttaggtcagctttgctggaactttta
ataaatctcaggttaggctttcaaaagcctcttgaggctaagaagtcaagccaaggacttgatatcagacttcacctgcaat
acctatagatttgggtggattcctctttcctcaaggttccccaacgtattcttgagaattactgccaaaaaatcacagtctttc
ctcaacccgtgaggctgcagaagcccttaatccaggtacaagggcaatttttgtttcctccaacgggtttcattggctcca
taaagtcaaccttagttccttaaagctactcacatctgattttatgcacatcactctcaaatatgatattccggtcaaacac
ttggtgagctaaccaacatttccagttgtttcctacttacaaggcagcagattcatcttgaacttaagcaaataactctatgg
ccgtaaaaataaaaatgctaatagtttctaaattctggagagatcaggtagggagaaaagtcatcatttcaattttgcttat
aaaagtgtaatgtaccagaatgctgtaagttataaatagtttcttcatttacattctggaaattcttgccatccagtggtgt
gatcttaatgtatcagaaacctgtactggtcaagtcttccccatgaaatcttctcgaagacacaacatttttagaattatag
ttgcttgcaaaagctttcgggaaagcatcagagccaaacagttaactgtgtatgacagaaaggcttaaaatggccttggcta
aagatgtgatgacatcattacaatgtaaccgatgaggaagtttggttattcctgtggtgtatactttcacataataactaga
attacaactaatatagaatgtatcagatttctaagaatttcatataatttctggaactcttatatgaatatatatccatgca
aatataactcacccagagaaggttaatcatcacttcatatttttacagtgcttccatgcaaatttagttgatcaaataagccc
aatttatttaatatctttttactttatctaaaacaatttcccttaacattggcaaaataatctatgtttttataaggaga
gaaaataaatcctttttgagatattccaggggccaatctaggaaatcccaaacgttaattcagggtcaaaaagacttaattta

FIG. 4 (Continued)

gagtgtgtgatttggaaagttgtcaaaatgtcaaaaggttgaaagcacttgattaaatagaatcccagatcattatgaaat
aatacttaattctcatttaatcaaagtaacaatgaatattcaaagagaaatgcagaaagttagatagtttaaaatactctt
agatctggccaggcatggtgggtcatgcctgtaattccagcactttgagaggctgacatgagcggatcactagagcccagga
gttcgagaccagcctgggcaacatggcaaaaccccgtctctaccaaaaatacaaaaattagccaggcatggtggcacatgcc
tgtaatctcagctactcgggaagctgagataggaggatcccttgaacccagggagattcatgccacagtgagctgagatcgc
accactgtactccagcctgagcaacaaactgtatatacacacacatgtatttgtgtatatatatatatatataatatgtat
tacatatatacatacactatatataatatgtattatatatacatacactatatataatatatgtattatatatatacacg
ctatatatataatatatgtattatatatatacacacaatatatatttttatttcatttttatttttatttttttttaatt
agctgggtgtggtggtgcccacctgtctcccagctactcgggaggctgaggtggcaggatcccttgaagcccaggagttgag
gctgcgatgaactatgatggtgccactgcactctagcctgggtgacagagtgagaccctgtctcaaaaaaaaaaaagaactag
ttcacacccatgtttcctcctgctgccccaaattgccactctcctggagcagcccctgaaggtggagaccaggcacctgctg
gagcaggaactcttccttcacggcttctgttggggcccaggatcctgcagctgtggcatccacagggagtaaggccagcc
acggaggtcctttcatgtcaccaagctgcaggggaggaaaagtgacatcagacagatcaacaggagaaaacccatttaatg
atatgtccacgaatgggagtccccacacggagatgaaactggggaagggggccagatggcggaggcgtctgcgtcatcctcag
ctgcaggaagatacaggactgtggggctgctgcaggctgaaccagctatagcagggagttgactggtgaatgaaggtggtt
tcgtcacgcggacatgcgtctctcaggcgatcagagttacctggagccgctctcctcccggcatagagaccttacgaatgg
aaatgtctttcatttctctcccagacaggcagctgggcagagccactcctgtgtctgcagttactcgaaataatggatatac
ccaaggcatgtttggggtggcacattctgcccctcaagccatgttttggggtggggtggcgtgtcctgagccccaacccag
gtgtcagggctatggaggggacattgcaagggggcctagaggggcctctatgggccttggagatggaatcagctccccacca
ggccccaggacagacctggctggggagcgcagggaggggtccccagtgtgaggacagcatggggctgcctcttccagcagct
ccgagcgctctcagagaaaaacgaatttctcttttataagagaaacttgtctctggtcccatgtgttgccctttgggcactg
gcatgagtaatctgagggcggcgctttcctcactgcagtggcatcatacagatgagggctttgctgatcattatctggaaac
agtgatcactgtcccattcacagatggggaggctgaagcctgggagatcaattcatgccaccaagatcagctgcaggccggg
ccacccatgcctgagggggagaaggggcctctcttcttcacgaggctggtggctgcggcacctacaaagacaggttaacaaga
ggaccctctgcctatcacgagcctggtggctgccgtaccagtaatgaaagacaagttaacaagagggccgtgcaggcttatt
tacgagaagttccatgtgacacaggagccttgagaatggaacacccatcgaaccggggaactctgcatatttcctcctggg
tttgtggggtgtggacagcacggagcgtgatgaaaggatacaggcggctgggcgtggtggctcacgcctgtaatcccagcac
tttgggaggctgagtcgggcggatcactaggtcaggagatcgagactatactggctcacacggtgaaaccccatctctacta
aaaaatacaaaaaattagccaggcgtggtggcgggcgcctgtagtcccagctactcgggaggctgaggcaggagaatggcgt
gaaccaggaaggtggagcttgcagtgagccaagatcgtgcaacaatgcgagactccatctcaaaaaaaaaaaaaaaagaaaga
aagaaaggatacagacatcctgaaccggggggctggggccaggtctgaaggctctgatcttcctttcttctgggtctagggca
catgagggtctgtgacctaattcagaggaaggccagagaactcttttatggcctgcctcagggtgacagggagcaggagaga
gcatacctgctttccctggcttctcagatgccaccgtgccaggttttggggtagtggtatgtcttgagcccaatcagtaccc
tgggggtcgtggccggcccccctccctccatgccacaggctctctggagaggccactgctgtatccccactgtgagctcgat
ctgagctgcctatgggaccacacctgagaacccccaagggtggcactggcagacttgaggtgcccaagtgaggctggtgcag
cccctctgccctgccagtctgggcacgggcccctgggcatcgcgactcctaccttcctaccagcccagatgcagggcctgag
ccggcagggcttccacccagcccagggtgtgtccccctaccagaggcgctgcattggataggaaggacccacctgtttccct
gcccagtaccagctggcaggccccccgtggctcagggtgcctgtgaggaggggtggggctctaattgctcacctgctgctc
tgaggtgtcaggcagggttgggggtggcacctggggaaggctgggctgagggggcaggctgcccctcctgcaggagaggtgc
agtatttcactgggtcctttggaaagggcagggaagctcctgctcgcccgtactgcaccatttcctgtgatcttagcaatga
cttcctggctccatttctccaccagtccgaatacatgagccagacccgcagctttctcttccacagcctcctggcctccgg
gtccacctgggtggtgcccacccgccagactggggcctggtggttgtaggggacggggagcagccttgcttcagtgtgggtc
attcctgactgtgagatggttgggggcaggggttgtagagtctgtgggaggcctcggctgggcctcagagaggggtatctc
ttctgcagaaaacccagccacccttaccagatgcggtcaggctacaaagggaagatgtgctccctctttagaggcaggtgat
tcctgtgaatccgatgaccgagataaggtgcacgattcagtgggcaaggcaactcaccatcctctctttatggtcctcgcaa
tttgcaccatgcacaatgcagggtgaagtcagcccccaaattacagaggaaagactctgcggtctttgtcagttaaacagga
gatgcaaactccaagctagttaatgagctgtgatcggccacgctcacgattcagtgcaggtctctccttcctgctatcacag
tctttgccggctgcatcatgactaccaaccagtcccctcataattacaagagtctcctgtcatgtttcttcggagcgagg
catgctccaacttgcttctgggttcttaatttttgatcagggacggctccttgactaatttatttggcagtaatgagggagga
cagatcgagttgtgaaagtccccccaagcttttagaaggaagctgcaaattaaaaaatgaggtattggtaaacaggatgct
aattggattaatatgaaaatgatgaattctgataaaaatagcaaaatacaccgttgtaagattgaggccagtataactccaa
gaattcattgtctaatgttcagctggtcagtctggtctttgaaagtattagaataacagaaagagtctactcttgacgatga
agtatacggttagtaatttatgcaaaacagaactttaaaaccggaaggacttgatatgagtggggtgcatggaaatcattcg
tatttgaagtttcataactctgaccctaggtcctttggtttgtctctctttcctttttttttttttttagacaatttct
ctctctgtcacccaggctggagtgcagtggcatgatcttggctcactgaaacctccacctcccaggttcaagcgattctcct

FIG. 4 (Continued)

gcctcagcctcctgagtggctgggattacaggcatgaaccaccgtgcccggcctttttttttttttttttttaagagaca
gaatcaccaggcaaggtggctcacacctgtaatcccagcactttgggaggccaaggcaggtggatcaccaggtcaggagttt
gagaccaacctggccaacatacagtgaaaccccatctctactaaaaatacaaaaattagctgggtatagtaattccagctac
ttgggaggctgaggcaggagaatcgcttttgaagccaggaggcggagtttgtggtgagctgagatcgcaccattgtactcca
gcctgggcaacaagagcaaaactctgtctcaaaaaaaaaaaaaaaaaaaaaaaaaaaaagagagagagagagagagaatctcac
tctgcagcctaggctggtgtgcagtggtgcagtcacagctgaccacagcctccaactgctgggctcaggccatcctcttgcc
tgtgtcctgagtagctgtgaccatagacacacaccaccacatccagttaatttagtttgttgtttcttgcttttagagaca
gggtcttgctatgtatcccacactaatgaatgtaaaatcttaaaatggtgcctggtgcagagtaagctgtgtgttggtgggg
tgtaattatgggtcatattgacagtttcacttctgcggcatgccctcaggaactcactgatgcacacagagggacctgctgg
caaatactgaagagctgtggggagaaaggaaggggtctgacagtgaaggtgggtgcgtgggcgggggctttcaatggtccc
tctgctggctccctccccaccacctcctgcccacctccctggccttggctgcaggctagggtgccctttgacctcaaagagg
cctgtcctgtgtgtctcactgagcaggaacaaaccgtcccagaagcccttcagctcggaagtgagtaagcattggcggtggg
gatggtgctctgagcagacgcgactcagtgccatgcgggcgtctctcccagggcggctttcagactgaccccaaacagagg
gctcagaaaagatgtttttcaatgagggacatttatggttggcaaaaaaagtggctccccaaaggtcttcacgtcccaatc
cccagaacccgtgtctatgttatttcccatggcaaaggggaccgtgattcagctatttgagatggggaggccatctggcag
gatccaggtgggtccagtgtcatcaggggccccacaagaggggtgagagagggagctgatgatggaggcagaggttggagg
gatgcatttcagagatggaggaaagtgtcacatgccaaggaatatgcctgcggaagcaggagaggacggggaggtagggatt
gtcccagggcctccagaaccaagagaagacaggggagtagggattctcccagggcccccaaagacaggaagagggggaaat
gtattctcccggggtctccagaagcagccagccctgcccgcagtttggctttagctccctggtacccatctcggactctgac
ctacagaactgtaagagagtaaatttatctcattctgtgctgctcattgtgtggtcattggttacggcagccacagaaaaca
gacagtgcgcacatccgcatggtcccctctccagctcttgcctgataggcataaacgagggcagctgggcgcggtggctcac
gcttgcaatcccagcactttgggaggccgaggcgggtggatcatgaggtcagaagattgaaactatcctggcccacatggtg
aaaccccgtttctactaaaaatacaaaaaattagccaggcgtggtggcacgtgcctgtagtcccagctattcaggaggctga
ggcatgagaatcgcttgaacctgggaggcaaaggttgcagtgagccaagatggagccactgcactccagcctgggcgacaga
gagagattctgtctcaaaaaaaaaaaaaaagaaagaaaaaaaagtaaaaaagaaaaaaaaggaaataaacaagggcttgccctg
tagttcacatctggaccacccagcttaaaatagggcaggggagttcaggaatagctttgcaacccctgtgttacggtgcaca
ggtgtgcaaaaattctccttgaactccccttcagtgtccccccagggctcatggccactgtcactctgtgctagttgctct
tcagaccagggaacagacttggccatggctatggccagggtccagctgctattgctcctcctgtcacccacccaccttttgt
ctccaacaaggatgttgagaggagccaggcaccagcctccctgggttcaggtctttcctctcccctcactttcctatgaact
aggggtgggggaggaggagtgcctgccaggaggtcactgcagccaaggaacccaaattggtgtgcttgagaatgacccatgg
atacactttccaaagagtcacccggctgcgatgaggggccatctcccctcctggagccaacagccatgagtagctgtcacac
acatccgtgcagcacctagacacacatccgtgctgtccactccgtgctgctgcaattgtgggggaggaaggtggcacagtgg
cagcgacacacacttccctctccaaaattggggcggggctcctcaaaatcctctgaccagcattaaagattcagaatttgat
attatggctgcatataatgttgaattatctgaacttgctgcacgtgtgtgtgtgtgtgtgtgtgtgtgtgtgtgtattgttg
gtaggaccaaaacggttaattatcagcaatttcatggtttgacctaatattttaaaagagaggttcttacctgctggaagca
tgtactggtgtattacggatgagacggtctcataggtggaatttgctgtgaaatgccccaggaaacaaaaagccagaggtca
gagtgatgagagctggggacgggtggatgggttcctgggccgttccctgtagtgctgagtgtgcttggaagtgtccacaatg
aggagtagaaacgagtacaaagctgggtggagacagccctgtcctggctgccctgagctcggccctgtcagtcgccttgagg
agggttgggggagcagggatgcagggtggcgcgtgcatgccaggtggcaggcggcaggtgctggctccaggcccgtctcca
gccccagggctccaggccatgctccgccccccagctgccctgcagctccaggccggccacgctgccgcctagtttcgcaactc
caatgtcatcacctaggtgacagggacgctgctgccaccgcccgcctgcgggagccaggagccagccgagggccacttccac
ctggccccaccgaccctccggggcccaggcttagccaaggtaggcttgggcttggctcgccctcctctcggcctgagtcggg
gggagtctccttgccaccgtgggtgcagtggctccgggggcccaccctggggtgcagagagcccctctacggcctcccagga
ggcggcttggaaatgcagtactgttcaggccagggtggggaggccttgcccacagttctcctgatgggacaagccacagctc
tggggagccatctgccccaagtggcacatcagggctcctcgtgtgaccctaggatcgggggcagaagtggctctggtaccgc
cacctccaccccttggacccaccaggagctctttccacttcctgccaaggaggcgcagagtgactgccccagcctggcacgt
ccggggggcttcccggctgggggccgccatcctcagcctcacacagctgatccagaacctcccagttctccccagcccccctca
ctctttgtggccccggagcctctccggcaacagcaagccatgccccggcctccccggcactcacgcagctactcccaagc
ctgaccatgacgtggacggcaggaaggggctgggcatgtcctgttccttctgcctgggtcctgcttccagggctggactccc
aggctggggaatcctcagggacccatcaaactgggggacaggggaggggcttgtggggatttgctgtgaggagggcagagtg
tgtacgtggcagtgcctgcggacacatgtgtgcgcatatgtgaataggtgtgtccatgtgcatgtatgtgcaagtgtgttgc
tagaggtgagagggtgggtagggaaactgagtgaccagctcctccctgaagccttggggggaatgtccgagggggccagggcct
ctggatcctgttcccttggctctttgcaaagtctccagcctggcctcctggatgggcatgtggctcgggggggcgagaccatg
ggctcttcctggcttgctgtgtcgctctgggtgcgttttacaccactctgaggatctctctgctcatccctaaggcagggat
gatgatggggccaggggaccacatgggcacaggtaaggcagggatgatgatggggccgggggaccacatgggcacaggcttc

FIG. 4 (Continued)

tggaatgtgggtgtcgtctccctggggtcccgcagtctgaactcaagactcaagagccccatgtccaggtggggatgtacag
gagcccttagaagtggggaagaaggccaggcgtggtggctcacatctgtaatcccagcactctgggaggctgaggcgggtg
gatcaacagaggtcaggagttcgagagcaacctggccaacatggtgaaccctgtctctactaaaaatacaaaaattagctgg
gcgtggtggcgcacacagctgtaatcccagctactggggaggctgagtcagaagaatcatttgaacctggaaggcggaggtt
gcagtgagctgagatcgtaccactgcactccagcctgggtgacagagcgagactctatctcaaaaaaaataaaataaaataa
aaaagataggaaaagaaaaagaaaaagtgaggagaaatgaggaggaagtcgagcaatttaaccccaaatggtgcttctccag
cagtcactctgttcctgtcctgacctgacctgctgggccccgcccgctcaaaccaaatcatggattctgtcatcgcttcttc
acggagcacctactgtgtgccaggcgggtgctggggctgcagcgcagagagcagtcagggcttggtggtctggcccgcaaag
agtcagcatgtgaatgtctctccatgcgatgggtgctgggagggaggagccctggcaggtctggggaagaccagcgtctctt
aaatggggggtgcgcggggccctgaggagtgaggcttcctgacagccgtccctcgtgggtgccatgctggtcagagtggggtct
ggctgcacagcctccctcagggctgggctggaagcacaggtcggctggcacctgtccaggtttcagggttccagggctccag
ctggaactgcctcagggatggcaggggtgggcctgtccctggagaggcgtggggtgtgggagctgggagcgtgacgggaagc
agcccccctcagacctggagtagcatggagcctaggatccattgtgaccttggtggtcctgtaccctgtccagctccagttgc
tgttcctgcctctccctgacctactggctgcccaggctgccccttggccgagctccaccatggccagtgcccctccattcgc
ttgtgagtcccacaagatcacagccctgcccagggcctaggcagctcttgggctgacccagccatcgtcgggagccccttc
gtgacgggggcaaaggctggatcgttgtctgccctgcaggagccggggcctccagaggacgggctgcctggcgggaaggtgg
agctcaccggagcccagcctaagccagctgtggtgcttctgagatgtgcggccctgggcaggctgctcgccctctcggggcc
tctgggaacacctggggacttcccgctgggttcctctgaggattgaatgagcttgaaaatatggaggatttggcacagggaa
tgctgggcagcaatatcagaaaggcaaccctgagagccagcggacagccactctgaggaacagcagtggctgcctctggaag
gagtgaggggtgggtggaccccgtgatcgctgcacgggggaggtcacggggctgagcggccaccactgtgcaggggaggtc
acagggctgagcggctgactccagaacaggaagggaacacgccaggagggaggattgctcactgagtcagggcgggactcag
agggacgcatgacaagttcagggagttgacagctgtctggaagggcacgtctgctcagaccgcagggtagggagtggtcagc
agggagacatgtccactggtgcagcgggcgtgtcccagacccttagagaaaagcccagagccaggggtgaggggtatgtgt
agggtggggacatctcagagtggagcatccccaccaagggtgtccagaggagggtggccaggtggggacagcagcttgagaa
gggtcattctctcttggttggaggagtggaagtgcttctctggggaaagaaagaagattctggaggacagcacaggcacttc
caacatgggcgctggccgcacaaaggctagtgacacccggtgtgatcccttggggtagaaagggggtgtgagaggaggatcg
gagggggcagaggacagggatgtgtctgtgcagaacgaggctgtggcagctccagcgaaggcggctgcggccccatcagtca
cctgccctgctgagggcagcgctgtactcatcacctgtgaacacaggtatcgactcagacacccactctggccataagctcc
gctctgtcccagccctggacccctcacccccctatccttggcagtcggtcctctgggtcttcttcctgtgcccacgtgctgg
tctgaacctcccttagtgacagatctgctcctaccacccccgccagggtcgcccttcctctaacaggtgggctcctggcagg
aaacatcaccaagctcagcgcccagttccctgacagggcccacttccctcctgccgccaacctcgtcccccaagggcca
tgtccctgcccacccctccacccctttcttagaggaagctcagcccatcaggccgctcatgcttctgacccccacctccaaa
ccctcctgacccgcttaccccaggagcaccgcccactccaaggcgcaagcaagctggggctggggtgcagacttctcttcc
accacccaccctcctcatacccagcctctgagggcctcacagacatacatgatttgcctccagtgggccagggttatctgtt
taccgcgttgcatgccccgggcatggagctggcaccggctgccgctgcaactgggcactacccgtttcgaggacgcctcat
tccctgagagactgaggataggctggtgctctgcaaaagggtgcggagaccactgtaaaagtggggtgagacacgcgtgctg
accatgaaatggagaggcactcgaaggagccagggacccggcagccagcagacccccacctttccgcccccgtgtgtgcagtt
ctgtcgctcagcctggtgcctttgggacccgggcctcattggttcttcctccactgccaccacctgatactaaataacgtc
ggtcaatggcaactcgatacggtttatggggcatccacggtgtgcccagatagaggagtgctttcgctttgatatgcgtag
agttacttcattccacctagcgcttctaggaggcactacaattatctccatttacagacaaggaaacagaggctcagaatg
ggcaagacatctatctgaggtcacacagctagagcgcggcagaggtgggctgcgtgggcagagcaggagagggaactggagt
gtgtgcccggcagtgctgggcttcagggcacgaagcggtggggcaggaatcatgtgtcttggtatgacccaaacacatatat
gacagcaagaaggcctgggcaggcagcagaggacaaggcgggcctcttggatgtctggatgtggattgggcctcaatgtacc
ggtgaagatagatggacaggcaggggatttccagagaggggcttcccaggcagggtgcggggtgtggctgtgcggtgggaac
acggactggggaggggattgcagccgggcccgtgcctcccttgctcagctccaggtcaggccagggtagagccaggctgctg
ggttcgacctccaccctgaccagctgtgtgcccatggagggctggtcttccctctctgtgcatgtctcctggttggtaacag
gtgtgtggcctcactgggccgtcgtggggtggctggaatccccgggaattagccatgctttggtgtttctacatttcacttg
gctgagtgtgaactgacccaggaagctggttgggggcacccccacccacggggggtcgggcatttggtttggtcatggcct
caaagcttctggggtgaggctcagggattcccccagactgtcctgggcatctgcctcccctccctccgcttcccgtgggc
cacggcccaggagagagagggcagcttgctcaggcacctccagctgtccgcatatttcacacggtgcacgctacccccaccgt
gggaggctgtgtttgtctttcatcccatgctgggcttcccccaaactaggggagtggggcagcaggcgtgccatctgtgggcg
gtgaggggggctctcagccgcatcctcctcaccaggccctgcggacaggccttcgtccctgcccctgacctgctgacgaagc
cgtcctggcaaccctgtctgaaggacctggccccatcgtacccacagagggaggccacatggtccttagcctctgtcgggag
gggcaggcaatgctggcagagggccttgcccctgagagggaggccctcctggccctcactcgggggacccctgtccttggc
cccagcctgccaagcgagagcggccccctcttcttgcggtggctggaggggagagtgaggcccccttggcacagagggcccccag

FIG. 4 (Continued)

gaggctgggctctgatgacgccctgcaggaattccgctgggctgctgcctgggagagccgctgtctcacacagggccagcct
gcctggcttcattctggtgcgctgaccgcccgaccctctgcccaggcggggctcttctgggttctgggtcctgggacctg
cctgagtccctgggaaaaggcacaaggggattgagacggtctcctcccacaatggcccaggtgtctcctcccacaatggcc
caggtgtctcctcccacaatggcccaggtgtctcctcccacaatggcccaggtgtctcctcccacaatggcccaggtgtctc
ctcccacaatggcccaggtgtctcctcccacaatggcccaggtgtctcctcccacaatggcccaggtgtctcctcccacaat
ggcccaggtgtctcctcccacaatggcccaggtgtctcctcccacaatggcccaggtgtctcctcccacaatggcccaggtg
tctcctcccacaatggcccaggtgtctcctcccacaatggcccaggtgtctcctcccacaatggccccaggtttctttgcca
cttcagattggaatcgttgatctgctgaaataacaggtaaaatcattggtggtttgggaacccacccggaatcagaagtgcatt
gagatgtttgctttaggggtggcccggggcgggtggagctcctgggggctttccctcctccctgaatggaggaggacaccc
tgcaccctcctgtgatccccccttaagagccagtgtccgggatggctgggccagacggggcagagggcctgtgtctcctgc
ccaggctgagtgcggacggctcggtctcagagctccaccgagggggtgggtaggtaacagcagccctgcggccagggcccctg
caggtgggagtgggtgtccccatggggagtgcctcttccagagtgggctcagtcggggtggagtgtcctggcttatcaaagg
tggttgtggagccctgtctgccccaggcctgggcagaggtggaaggggttggggaactgacgaggccttacctgtgggccca
tggccaaggaaatgtctggtctcccacctcctgtcaggtggtgaggggagaggatggggcgtcagccggagacggggttcct
agaggaggctgggtcctggcctggcctggagagatagggatgagatgggagggcaggaaggggggtggtagacaaaggctgaa
cacagagagcacatagccaggcatgtggggactggggacaggggacaaggagggcacccatggggacaagagatagggagag
gacagagggacaggagacggggagggacagaggatggggacaaggaggggacaggaggacggggacagggaggggacacag
aaacaggagctaggacggggacagaggatgggagaaggagaggtcaaagggacagggaacagggaggggacccatggggata
gggcagggatctatggggacaagggacagggaggggacagagaaacaggagatggggaggggacagagggatgcagacaggg
aggggatagaagatgggggctaggggacaaagggaaaggggacagggaaggaacctatgggggacagggagacagggggac
agggagaggacagaggaacaggggacagggaggggatgcttggggacagggagggaatgcttgggacagggcaggggacag
ggggctgtggctttcgtgggaagctatggaagacgaggccagaggggttgggcagggtgagatgagagaggctgagagcccc
tcaccggctgcggactcctccccacagggcagaggggagcattcgggtgcggccaggccatcagaggacctgggcttggctg
gagtcccagctcctcagccctcagtagctttgggccagccactgggcctcctggcctccacttgctcatctctgaactgggg
cagggttggcgtgtgagcctgaggccctgcaaagtgcctggccagcctcagctcggagccatggcacagcacccctctccg
ccacggccccgacagctgggcgtgcgttctgctgtgggcagctgccctgagcaacgtagggtgctaagcagcatccctgtct
tgcacactagattccacagcaccctctgacccgtggaaaatgtccccacatgggaatatcctctgggggtggaactgcccc
tggtgagaaccccctaggctgagacctcagaaggccctgagtcaaaccgagaagtcatcagagagccttgttttcagctccag
ggagcttgggcaggctggttttctgggccacacagtcccctccccagcccacctgtgctccgtgggtccggggaagctgtg
ggggcctaattgctggtgtgagttcctttcctgttctgagtcacacgtgtgtggggggctctccctgtggtgcagctggtaca
gcggcccctggagttgaggatccaagcaggctgaggtctgggtttgccggagggccctcggtggctggtctttgtcctgctc
ccactgctgtgggcactgtaggacttggaacgctggtcacctttccagcctggcaaagggaggggacttgtctgaggcctca
tggaagttggggcagggtcgaggtgccctgcttcctgggtgtgccagcagcctacagcctggctacagcgtaaccaggaaca
cccagcacaactgtcctttgcaactctgtgccctgacttgatggtgccagggctgggggggtgccggccagcagctcccca
tgaccacccccaaatgctgtggccacacaaagccttccactgcaagacctgtggtaatacacactggacgcccctgttacaa
ctgagaactcatttatttcatttccttccttcccttttttttttttttttttagagttgtggtctagctctgttgcccag
actggagtgcagtggtgcaatcatggctcactgcagcctcgagcccctgggctcaagtgattctcccacctcagcaccctgc
gtggtttggactgcaggcacatgccatcacgccctcatgcccagctaatatctttttaagttttggagagctgaggtctcc
ctgtgttgcccaggctggtctcaagcccttgggctcaagtaatcctccctccttggcctcctaaagtgttgggattacagtt
atgaaccactgcacccagcccatccctcctagactaaatcttcttagaaaaacctacacttccaataatgtatttgcatttt
atgatgttgataaaacttcctaaagatgtcttatgaaattggtctcctttccccattgatacacatgatttttaaaactatt
ggcaacgtttcaaaagcaatttctgtttgtcccagaaccgtgatccccttgtgaacgaatttcaaattaaaggcaaatg
gttgggaaaattggatttaattgaaaggccattttattagaattgacttatttttctcgccactgggatccttgcctgaaag
gcggctgtgggcagagggcacatactccccctgcccagcgcagcgtccctgcaccccaacagagcttcctgttcctcatg
cccagtactcccagatgcctgcggagccagtcatcagctcaggtgtgtgaggccggttggggagccctgcctggcgcctg
tgcctgtgagcagtgttcctgtggggccctgggaccaatgctaccagcgttggcgtttcccaggaagttgggaatcaggca
tctcgtggcttccggttcaagttccccgtgtgctttaagtctgggcaggtctccgggtcctggctttggctaatgaggaac
ccgattcccatgggggaggccggtggctgcagcagggccccgagcagtggcaaggctggccctcatgacagtgtcctcctca
ggggccctgtcccaggctcttcatgactccctggaggcttgttaaagggcagattcctgggccctgccccagccccactg
tggggaggggtgtcctggaagatgcatctgcccagggcttccggctggtccacacgcctgcacctggaggcccactgcccac
atctcaggcaaacaggcctggggatgtttggggacccaactcctggcgtggaggaagccccttcccacccccacatgctcct
ggtggtggcctgtcctgtgagcctggagggccggacgggtgggatcggggacccacgaccacgctcgctggcctctgtcctg
tgcccaggcagggatgagaggccaagctggtgtcctgcagtgcacagtgggtgccggtcaggggatgtggaagctgggtctc
cggcaggcagaggcgcgctgacaagaagggtcgctgttcctcattcagggttcagtgggaagagagggtgtcgcttcagggg
gagttcacaggatgccgacttgaaaatacagccaacgcccatgtcccaggcataagatcacaaatcatgttttgccgaccag

FIG. 4 (Continued)

ttcctgtgagccctgagccctgcgggagggatgccccgtgcacacctgttcacggaacccctggacctccagtaggggtgc
ggcgggatgccgtcggctcccacgctgtctgtctccctgtccctctctctttccctctgtttctctgtctgtctctgtctgt
ctctgtctccctgtctctctccatctctctctgtctctctccctgtctctctgtctctgtctctctccatctctctgtctct
ctttgtccttgtctctccctgtctctgtctctctcactctctgtctctcttgtccttgtctctctgtttgtctctctttg
tccctgtctctctgtctctgtctctctctctctttgtccttgtatctctctgtctctctttgtccctgtctctctctgcctt
tgtctctctccgtctctctttgtccctgtctctctctgcctttgtctctctccgtctctctttgtccttgtctctctgtttt
gtctctctttgtccctgtctctctgtctctgtctctgtctctctttgtccttgtatctctctgtctctctttgtccctgtct
ctctctgcctttgtctctctccgtctctctgtctctcttcctgtctctctctatctctttccctgtctctttctgtctctct
ttgtctctctctttgtccctgtctctctgtctctcttcctgtctttctctcttctttgtccttgtctctctctctctgtctct
ctcttcctgtctctatccctgtctctatgtctctgtctctctttgtccttgtttctctctgtctctctgtctctgtctctct
ctgtctttgtcccaccttagccttgggagggacagctcacaggctgacagatgaggtcatgtgtcctgagcatgaggtttt
caggtctcacccacgctgtagcatgtcagagcttcgttccttttcatggccgcgtaatgttccattgcttgctggcaccaca
tctcctgtgccggcccctctgctgatgggcgtctgggctatgtgcaccgttcagctaccaggaatggtgctgctgtgaaggg
agctgggatttgtcatccacctgctgtggatggcaagtccatttccatctctggactcaggtggcccatctacaaaatgaa
ggggatgcgacccagaggcctctggcggcaaaaccttcccaggcttgtcctcttggatctaagggaatttctttcctccgag
tccagcccctccagtgctcctgcccttcaggaaacatgcctgggacccctcacttgtgcccacccagccttggcccacatac
ctgcaccaagaggctaccctactcatactgctcagcccaaagggacccacccgtggggtatgggcaaggggcgggttctgctct
ccccgggggccctgtgccagcctcagctggacctgcggttctgcttcctgtcacactctcccatttaaattaacggaatgg
tgcggtccccatgcacaccctcagctccactggggttttagcccagcccaggatcggaggcctgcaagggcacacccacctg
gccacgtgatggtgaagtggggtggggcagggcaaccaaattaacttctaattctaagagcccctggagcattcatcaccag
cacttacagccgtgtgacctcacacaagtcacttaacccctctgagccttggggctcctgaaaagtggatggagcggtcacg
cccacctgggagaggtggcttgggccagcaccctctaagctgcttgtcccaggccatcatggctcacggaccgcccctcagc
ctggcctgtgccacttctccagggcccggcacgtggcagccacaggcttctatcagctcccgcctgcctggggaaggacaaa
aacgacaggttccaggccatggcctgcaccccgctggccgtgggcaggtccaggcctgcctgcctgagcattgcagggcgg
tggccaagcctgtcccatagcacctcaccgaggacctgggaggctggcccaggggagaggtcacctcagccggggctggggg
ctgtgggcagggtgggctcgggtttccctgtcccctccccagctgtgctctgcctggacactgccacctcctcatgggtgt
ccagggccactgggagctgggcccaggggttctcaggggagcaatggtggagacaaagaccagcggacgggcgctggggtca
gagctctccaatccctgggtgtctccttctcaaggcgtgaccacccaggcagtggccggctgcaggacagggcagcttcaag
ttcccagccttgccaggcttccctgtggccctggggtgcaggaaggagcccagctcagaaggcgagggggcgtctgtgtcc
tgcagcagtgggcacagctaggctctagcgggggcttggctgcagcctccagcgcagccctcacacacgctgttcccaaga
tggggtgaccgggaccggagccacctccaggtcccgggcatcagggagaccccaaacctggctgcatcccccaggccaaacc
cagacacaggggatcgtaacagaccacaggcctcacacacttgttccggcccaagcatcccccaggccaaacctagacacag
tggatcataacagaccacaggcctcacacgcttgtcccggcccaagcatctcaaagagtctgctctcctgaaggccctcaag
gcagccccaggagcgggtgttgctgtcaccccctcttccaaggcgacggctctgagaagctcctgcctgcccagggcacccc
cacggatgggtctgatccaggcccgccacctccaaggcagagctgcccacctggccttcggtttccagccgcggggaacagg
gtggacgaaatgacagtggagagggcacagggagggcaaggcgggggcacctgctccagggatgccccaggcaggcccactt
gcctgccgcccccaccgaggctgtcacaggaggacagagcacgagttcccagggtgctcaggtgtcattccttccttcctgc
agAGCGAGCTGCCCTCGGAGGCCGGCGTGGGAAGATGGCCCAGTCCACCGCCACCTCCCCTGATGGGGGCACCACGTTTGA
GCACCTCTGGAGCTCTCTgtgagtgcgcttggctggccagagctgggggcccccctgggaggcactctgggctagcctcagc
caccttcgctgggctaactgggccagagcaggagggtggcccgggaggactctgggctagccccagccaccctcactgag
actttgggctaaacttggcaaccctcactgggattctgggctagcctcgaccaccccttgctgcactaactggaccagagcag
gagaggtggctccacactagtcttgggctagccttagccaccctcatcagcttggggacagggcgggtcggagggggcaggga
agagggactgctgccctaggccttccctggggatgcaggaccaaaattcagactcttttctctggccagctctggagagggc
ccatggccagcagaggcccagaataacagagcccatgactggctctgcctctctggcactcacagcagccctggaatggcag
gtggaggacagagatgggatgagagggaatgggaagggcaggagacgtaggcctcaccaggagtctcaggctagccttgagc
tctgggcctgggaggtattggggtgacacccaaactggggactgacgcttctatttcctctccctgccccagGGAACCAGA
CAGCACCTACTTCGACCTTCCCCAGTCAAGCCGGGGGAATAATGAGGTGGTGGCGGAACGGATTCCAGCATGGACGTCTTC
CACCTGGAGGGCATGACTACATCTGTCATGGtgagtggggggggctgccctctgcaagaggactggagtggggacaacaaatg
tggcctgtcctgtcttgggagcctggcagaaccaggagatagcctcttggttgtacagcttcccctgtgggtttctgaggac
acttcaaattgcaaaggagaaaatgtatcagctcatgtaactgtcaatccagagataggaatggattcaggcatggctggat
ccaggtgtaggaagggcttcaggcatggctagatccaggtgtaggaagggcttcaggcacagctagatccagatgtaggaag
ggctttggacatgggtgggtccaggtgtaggaagggcttctactggtggatccaggtatagaaagggctttgggcatggctg
tgtccaggtgcttcacagctgcctcgctcagtctcttggtctgctttcccctgcagtgactttgttttaggccgcatctcc
tctcatggtgaagagtaccaggctccaccagcatgccctatccctgtggagaggagatcctctttcccatagtccagcag
tcctgcctcccgttgatctgaatgtggtcatgggcccatctctgagccacatctgtgcctctgattggcctggcctccacca

FIG. 4 (Continued)

tcagtggaacagggtgacaatggaatggagtggggtgggcctccccacacagggaccccaaaggaagatggaggtgctgtt
tccaggagaagaggactggatagggggcaggcagggccagtgaggcctcggcaccccatcttggcaggctccccattcct
gggagtctcaagccctgccccattggctgctcctctgggggaaaggccaggctgtgggagctggtgggggccacgctcctg
cctacctctctggctgccatagccaggcctcgactgtgccgggaggtggatggcaggtgggcaccacacgtgaggagagag
caaagatcccgacctgggaggcccagcgaggccagccgtccccgctggactcgtcagctgctcggcccgcccacaggctgg
ctgccccgccccgcctccgccgcccagggattcgtaggtggggaatttgtttgcgctgcggaaaaccagcccgaactgtggg
gatacgcggaacagcgcgtctggggcagggtcgggcctccctcacttatgctcagcccgaaagggagggaggcgatgctggg
cctctgggggcctgagagcacccggcctggcctcctcctccctcaagtccccattccaggagctggagccccttccttgcc
cctgcgcacgactgactgtctgaggcatggggtgggcggcccagccaccctgagcactggagggagtgggggctgtggggc
tccagtcagaacgaacagagtgaagcggggtggggagtgtagaggtggagggggccgtgttgcctgttccgtctccattgcg
gatgctgggctggcccagagccatgtggggccagagaaggcacctccttgggcagccacagtcccgggggtcaattcctcc
gaggagcccctcagcctgtatctgagggttcgaccgcctgccctgccctcccacccctgctcaggagacgtcccagtgga
aacactcgacagtgtctgcgcgtgttctagtcccgtgttatgggtgaggaaaccgaggcagatgctgggaaagggtgggctg
gggatgggccgggtagtgcaagaaagtgagactgcaacctctccctctctcgctttggaacagttctgccggctgctctc
tggggacaagggtcctgaccccacccctccaggtccccttctggacatccgtgtcctccaatctggggagggggcaggaact
ggccgctggaccccagggagggagggaggaagacccataagattgtcccctgagatccagaagccacctcccaaccccaagt
tgctcagccactcccctgcagagggcagaaggcccctaagatggcacagacccaccctgtgtcgggaggaggacctggact
cagggaggcagaaggagcagttctacattcctgagtgggtggagcgtgcttgtcctccccagccccggagggttccctgagc
tccatatcggggtctggtccgagcccccgcctgctggaacgtgccactccccagccacagggtgacagtgggagcctcgaac
ctccgcaaacagcaaggtggctggatctgtctggcagcgacacgcctcctcccaaagccatgtatgaaattcctaggtgcac
agctcgactcacggagatgggggattccctggaatgaaggcaggcccaggcctgcgtggggagagccaagcctcattctgac
cccagggcccagcccctcacaacagtggctgctgggccaagagcatgctgtcccctaccccctgactcccatgggagcgcca
ggtacaaagacagagactccgaagggcgccaacgggtgggctcgggcagcctggcacagggcccagggcttagctgccttga
gaatggcccctggcccgctaactccaggggtcccagagtggggctggagctgaactgggggcattgtttaaagttcagcc
caggagctcagggaagctgctgtgctggggctggggacctggacccggttcagtgcggatgcgggcatgggggctctgagt
gcccccctggaaaactgccacctgcagctcagggcccagttctagcccaccacgaggctggtgaccttggacaagaaacac
cacacaggcccggcctcgggtcagacaggcggttctagtgccggatgtttccggggctaccgatagtcctgagttcgtggct
caggtgggggcctgcttgtggaagtggctgcacacgcacctgcccccacctgcccctggcggctccctctggccacctgtc
cctgggtgttggtggcatctggctgctcccatactcagggggcgggtctgggactcatccagcaaggggcctcagctcgggc
aggcacagtgcttgagcgcaggacactggtcctctgcagtggggcgtgccttccgcatctggggacgtgggtctccccgaa
ccacgagcaggcagattggttccgttggacacagggtgtctgagggatgccttagccacctgcttagcagccgtgggagac
aggcggagcaggtggtttcaagctcccacaattcctctgagcctccatgtccctgctggtgaagctggggtgacagggggtag
gagcccagagcagagagcccttgggaggtggcatagactctgggatgccaggtgctgggtgctggctctgcccaacccgt
gggcctcggacaaccctcctgccacactggcccctgcagaggaggctgagtttaggcagttcaggagagtggggtgtgggca
agagcagttgaaccctcagtgggctctagaggagtcccaggccacagacttattggggagactgtgagctctgtgtggccat
agcaggaaacagaccccgtggtcactgtggccatctgactgaggtggcccagaaagtccagcaggccgaggtgggtgtggct
gggggctccgaggccaggtttgctgagctcaggacctaccccttcccttctgagctgggcaactttaaagaattacatagc
cctctgggcctcagtttcctgtctataaatggcgctactgagaggctccaagtcacccacgatgtgaggatgtccagtggtg
ccgggcccatcgggagtatgtgacaaacgctaggtgtgagggtgagggcagggaggaggccctgtgtttaagaaagctgctc
ctcggacaccagaacagcagagccaggagggcctaggataggatctgggaccagggcctgctgccttgcctggcacagttc
ctgcctgagctgtcccgtgccttaggctctggctgtccctgaagaccctacatggctcacaggacctcactctaaaatagg
gccccgttctgcaagaggagagcagggggaagcctgtggcccgggcctccccatgggctgggagggtggccgaggagcca
cagctaaaactggcccagcccctgccctctcaggaccctggctggttccctgaatgaggaaggcttgacgggcttctggatg
ccacctgggtggggtctgccctggccacccccacaccgtctgggaagagctgcagaggataaagctccctcgtaggctcgca
ggctgcgaggaggcagtgtgggtgtgatggtggggcgggggtcctatcctcacccggacccacccgaggagtctctgcagtg
ctgggcctgggcttggaagcgaatccctgcccctctgagcgctagcgtcccctcggacaaaaccagcgcagggcaatgagac
ctgcggcccttgctggctctcaggatgctccacaaggagggaggacacaggagggagaaaggagagagaggcaagtgtct
cctccctcccctcccctccactctgctccgctcccgtcctctcccctcccctctctgtccctagagcctcctccagggctgg
ccctcccctgtgcccctttcctgcctctcctggcgcctttctctgacaacaggtgttgtgggcaggtgggccacagagcggg
gtctacagctggtggggcagaaggcaggctgatctaccctgggagcccccgggaacccagtggcaggacagacacccggggtc
agaacctcggacacttgggggcttgagaccctagaggtcaccccagataggcccttggtgacttcagggagaggtattctcc
ccaggcccaggagaaggaagggcgcaggtcccgtgcatgtgtggcccccaggaaagggcaggcggacagagggagaaggaca
cccctcccttccagggaggatctgtagctggaggaagggtggggtcatgcgtgggagcagggagggggctcagctcaccacg
gtcagctctgagactccagcccacccgttacccctcccagagagcccccactcagcctttcctttggtgggctttcgtgac
aaagcactttggggctgcacagaagtgaaccccacccagcacccaggtctcagagccttgcagcttctgcggcctcttccat

FIG. 4 (Continued)

gcggtgggatgaagccagctgcccagcagggaccctgtgccatgagtttggccttgaactgacacatcactggcaccaggaa
acgaagtccccctgtctgtttctggcacataacccctcccactaactggttcctgaagagtgccgtggcctgcggcagcgtcg
ttccccccctgtcctgcggcccagggtcctgcggaaagtcaggcggaatccccggtgagtcagaagcagaatgaaagcagaat
ggaggacccagcagggagggaacctggaggaggcgctaagggccacgccaaggggggtgtggccccagatcccctgtccctgt
cctctgcaaggctgggccttgggaacgtttgcagaaagctgggtgccgctctggggcagaggccagtggttttgggtgcttt
tgagttggaaacgtgtagctcagccgcactgggatccccgcagcctggcccagatgctaagggtggagagatgcggggtctc
aggcacggtgccctgggcatgggtggggctcgtgctgaaggcagcctggctgtcttccttcctcacgtccttccacttggcg
ctctcctttggctatttataaaaccatcaggccggccctgtgcatgggactcgcctgagtctccttttcaatgcatcattc
cctttggcaggagaggacaccgcctacagaggctgaggatgtgccctgtgggggtcgggagcggaacccaggcccccgcctcg
gccctgctctgagggtctgtccatcctggggagcccgccccccaacccaagaggggtcccaggctcagaagcagaaggcacc
ctcatccccagggcatccccgatcccagcaggagtctcctagtgctcgccctgggctctcctgcaaggaggctgctgctttc
cccagaacatccagtctgggcccagccgacccccctgcaggggcttcccagagacgcccttcctgaacctgatctaccaga
caaaactgtctttttctcagtcgtctcctcctgagtgctgctgcccttcctgttggggggctgagatcctctgccacaggaag
agacgggcgtccaggactcacctgctgcctccggccctagggccctgagctgggctctccaggccccagccccttggggca
caacacctggaatcgtcctttcgtcctcagcccggcctgctggtggggcagggcgggtccccagggctcctcaggcagctgc
agtccaaacctcccctgccctcacccagctctgcccgctctcccggggggtgggggtggggagcgatgaggcccctgccggct
ctcggtggggacgacagggaggaaggaagctggggagatggagacaagagaaagcaggcaggtggtttgggatttggcagga
aaaggttggaaggaaaggggaaagggtctccgcatggatttctcagctccccatggatttctcagccctcgtgagagccacg
gcgccctggggactggaagtgtgggtccgcaggcccccagtccccaggtttgtctgagcatagatgccctgcctgcttccagg
gggactcggggcccctctgccagggtcaactttgtacccaagacggctgaaatacaatggaaattcagacggcccaacaggga
gtggcagtcacctcaaaggcccccactagacgggtgcggggcaccactgcagagcccctccctggctgtgccaaggccgtcca
cgcctgcaggggggcccactgccgggctgttctttggcaacagtggcttgtcccctgtttcctggggggcttggccagtgccag
ggtgggctccaaacgcacggctctgggctcttggactcacccctgctttgggcaggcagtggaaggcaggccccacaagagc
tgctcactcccgtcacctgtctcctcggggggtctagggtcgaacctcctgtgagcccctcctctcccatgcagcccttggac
tggtcctggcggaccaccgagttccccgcgcagggggcaggtgcgcccccacctgggtgccaagggaggcgacaccatctctc
cccctggggtggcccagccttgcctaccatgatctccagggccggggctcagccctcatgcctgggaacagaggctgcttt
acggggtgagggcctggggcccccgagcctttccccaggcaggcagcatctcggaaggagccctggtgggtttaattatgga
gccggcgctgaccggcgtccccgccctccccacgcagcctccttggtgcggtccaacacatcaccgggcaagctgaggcctg
cccggacttggatgaatactcatgaggaataaggggtgggccgcgggtttttgttgttggattcagccagttgacagaact
aagggagatgggaaaagcgaaaatgccaacaaacggcccgcatgttccccagcatcctcggctcctgcctcactagctgcgg
agcctctcccgctcggtccacgctgccgggcggccacgaccgtgacccttccccctcgggccgccccagatccatgcctcgtcc
cacgggacaccagttccctggcgtgtgcagacccccccggcgcctaccatgctgtacgtcggtgaccccgcacggcacctcgc
cacggtaggtgtgacgcgccattcataggatctcttcggggactttgcgggggatttgctgcagtgtagggttcagaggggg
catccttctgcctgccttcctggcctggagtctgctgccagttggggtgagcagaggtaggaagggaggcgttgaggggcta
gaggcaggtcccaggcatggaggcaagcagattcgggctccaacagcctgtgcccacctgctgggcagggacccgcagccag
ggagaggaggccgggtccatgccgatggggctgctggtgtttctgcctcgtgctcgggggtctctgatgctccttggctttg
gggctggcggcttggtccaggctcagagtttccgagctgccctgccctgccccagctgccaggagctcagtgcaccctagaa
gtcatctttgctcctgggcttgggtgtgaagctgccccgccctcatcagggaatttgctcatttgacagcagtggcagacg
gtgcttcttgtcagccccacgggctcttctcggtgtgggtctgagctccagggccaggacctgtggcaaactgggcttgagg
cctcttgcgccacccgcccccctgcagtgggctgctggcttggaagaggggagggaagggtctgcagcttgtggttggcccct
gcagcctgagccctggggacctggcctcacttccagacttgccaggtccctgggggccaggcaggcaccagctgctaattga
gaaggtggaaggctcggcacagctgctccacgtggggccgttcctcctcccagggaagcagacagctgggaccatgggtacc
tgtgccacacgggaaactcagccatgggcagggggcagcgggcagataggcagagtccaagtgccccgaagctctgctggca
ctgggatgtagaggcccaaagatctggggacggaggccttggagccgtgggctccccaggcagtgtgaccagggtgtgtgt
gacagcgatgtgtgtgagcgtgcacatcaatgtgcatgtggcgggtgggtattggtgtgcgtgcatgtgtgtgtctaagcgt
ggatgtgcatgcaatacgcaggcgaggatatgtgcagatgtgtgtgtgtatgttatgggtgtgtgtacaggctggtgtgtgt
gtatgtacacgtgtttgcctgtgtgttgtggtgtgtgtacgtgtgagcagattggtactgcaggtgtgattgtgtgatttgg
gtgggtaggtgctcacgtgtgtccgtatgtgtgttgcgatggatacatggatgtctgtgcctgtagctgtgtgttcccaggc
aaggcttgagaagagaggcagtgtgtgtgtgtggcccagagggtgggtgagggtgtgggtgacccagccccacagcctgcc
cagatgctgggtccatgcactcgagtctggcggcaccatggcctctccacacgcctgcgtgatctttttatctgaaacccag
tgctgggactgtagcccagagcgtggaacggctacatcaggcatggggtgtccctctctcccttgtctggctgtcacccact
tgtgcattgatacatgtatccaccaacacgttgctattagaaacgcacagcaggcctggggctcctggggggctgccttgta
ccccagactctcccaggaggtgtgtgagctgggagggctatctcccggctgctggaccgcctggaacccgaggtggatcc
agaagcctcgggtggagaggccagtgtcgctgcctggccagccgagaagcctggggacctggggactctagtacaatcttt
tcccttgaatggagcagatgtcaccatgtgactcaccctctcggggactccaccaaggttgagtatgtggttgcgcagacg

FIG. 4 (Continued)

ccattcccgggaggggtggggaggtggagccctgctgccctggcctgcagaccctcactgcctgcaggagctgctggtgtcc
actcggctgctgctgcccggtgccctgggcgtcagcaatggccagctgtgccatcactgtttcttttacaccaaggattac
tgtggttcgttcgttcatttgtccattcattcatcccatcagcaagtgttaactgggcacgttttgtgtgttaggctgagtg
ccaggagcaggtggaggcagtgcccagagccagccatgtctccagcacctcttccctctcgggggaggtgggctaggctgg
gccatcctaatgggcggagtggtgactcagtttccctgtttctgtgccagagagagtattcatgacctcatcttactgcagg
aacgtatttgagagagaaagtggtatttggcccaaagggttttaaacccaaagtgagcgaatagagttgtattggagttgg
tggctttgtgaggccctggttattcctatcaaagcacagtagctgctccggagcccgctgggccagcctggccctgggaaga
ggcccctgggttgcaggacactgtctgagcccccagctgggcccgccaattgcccccagcctggcacagggttccaggtgtg
ggcttggggtctgtctctctggcatctgccagctgagtctttggtcagtgacgccgctctctgagcctcagtctcctctatg
atgaggacggtgttcaccgtagctgctcggctgcggggcccaatgggagccactggttacttgctgcagatggggacgcagg
ggggcctggcctggagagctgccgcctcagccctcctcccacaatcccacccatgcagccttagccctcctcctgcaatc
ccagccctgcagcctcagctcctcctcccacaatcccacccatgcagcctcagcccctcctcccgcaatcccagccctgcag
cctcagcccctcctcccgcaatcccagccatgcagcctcagctcctcctcccacaatcccacccatgcagcctcggcccctc
ctcccgcaatcccagccctgcagcctcagcccctcctcccgcaatcccagccatgcagcctcagcccctcctcccgcaatc
ccagccctgcagcctcagcccctcctcccgcaatcccagccatgcagcctcagcccctcctcccgcaatcccagccatgcag
cctcagcccctcctcccgcaatcccagccctgcattctcagcccctcctcccgcaatcccagccatgcagcctcagcccctc
ctcccgcaatcccagccctgcagcctcagcccctcctcccgcaatcccacccatgcagcctcagcccctcctcccgcaatc
ccagccctgcagcctcagcccctcctcccacaatcccacccatgcagcctcagcccctcctcccgcaatcccagccatgca
gcctcagcccctcctcccgcaatcccacccatgcagcctccgcccctcctcccgcaatcccagccatgcagcctcagcccc
tcctcccgcaatcccagccctgcagcctcagcccctcctcccgcaatcccagccatgcagcctcagcccctcctcccgcaat
cccagccatgcagcctcagcccctcctcccgcaatcccagccctgcagcctcagcccctcctcccgcaatcccagccatgca
gcctcagcccctcctcccgcaatcccagccatgcagcctcagcccctcctcccgcaatcccagccctgcagcctcagcccct
cctcccgcaatcccacccatgcagcctcagcccctcctcccgcaatcccacccatgcagcctcagcccctcctcctgcaatc
ccagccatgcagcctcagcccctcctcccgcaatcccagccatgcagcctcagcccctcctcctgcaatcccagccatgcag
cctcagacccttcctcccacaatcccacccatgcagcctcagcccctcctcctgcaatcccagccatgcagcctcagcccct
cctcctgcaatcccacccatgcatcttcagcccctcctcccgcaatcccagccctgcagcctcagcccctcctcctgcaatc
ccagccatgcagcctcagcccctcctcccgcaatcccagccatgctcttcacttgcttcccacactgtccttccacatgggg
gactggataatcctgtggtggctctggccaaacaaggccacgttctgagtctgcggctcccacggactggggttgatcaatg
cccaacccccgaggtggacacagagacattacccacttctgcctgtagcaaggaaggagccgatggctggatgagtggggccc
ctctagaagaggctgagcgctggagacgtcggagctgggtgctgtctaccaacacccaggagtctccctgacttcccaaatg
tccagttcatggccccttgcccccccacttcctcctggggccgctgttcttcagctttagggtctcaggaggttagccagggt
gatgggagacaccccctagctctcctgcgccctctctatggaggggctggagcctgtctcgccgcagggcctgggctgtgcac
ccttgggcctggcctgttcccacccctgcccctccgcatggtgggcatccatgcgttgcgggaacgtggccacccctgtgctg
aggagcagcacggacggatctggagctttggacaccccactcccgtgcgccccatggagccagtgtccactctgttcctgc
agaaagtgaaacctctgggcaggatgggcctccaggacagggccctggggcgggggaagccaatcagtgcagcaagctgca
gttactaggcacctactctgtacgtggggctacggaaccaagggacgcagctggcagacgttctgggagggccccggctgc
agtgctggggatagaccacaggggggcagggccaaggccaggagccgcctgcaggctgggacgatccagggaatggggcagc
ccgccggtcaggtggtacccacaccgtgggattctgggcaagatttgctgatgggctggatatgagggaagggggtgggggag
accccaagtttctgccctgagattggtagaactgcagcagagcaggggtgaaaacgccgcggtcggccgtggctgtgttgg
agatgcccggcagccattgcatagctgagaaggagccgcatgcagggaggaggacgacgagcgagcagttcccaaagcccca
tgagggaggggttccagtggtcctggggcctgaaaagtgtgaccacctggtggctcagtcctgtgtgcatcagaggaggtg
gtgggtggtggtcaggcttagggtggagtttgaaggtgaccttagaggaagagcaggggaggattccagaaagatgctgagg
ttccatttgcacccttgcaggaggctctgctgctccccaaggcaggaaaggccggcagggtctggatgtgaggtgggtaagg
agttggggccacactggcaggagcggccatgtggacactcagttgctggtgtgggcaggcaggctgtggagacgacctccag
ggagtcctgcacatgggcacttacagtcagggctctggggatctgcacggaggcagggagagacagcggctggagctgagc
actgggcactacgacatccgagacaccaagcagaggggagatgcagaggggcagcctgggaggccaggaggcacgagaggc
tggctgggagaacagaaagggactggggcttggcaacccagaggctgctgagttcccacggtttggagagggcagggccca
actgggaatggctcatgggattgctgagcatggccaagggagccctcagcatcctctccaggccttgtgtcatgaaagaccc
cgagcagcggtggggctcaagccatgtggggccaggggagggaccagttgtcctaactggagatccagggatcagaggagcc
accccactcacccgcctgctgtgcctagtgcacgcccgcctccggccccctgccaccctcggccagctgctatttctgtct
cctttgttctgtccccattggacctcccccagtcaccagcctaataggacctcaacttgctaaacccaaactaaacttat
cttcccctgagaggggatggtgccgtgtctcagccagcaggaaatccactctcgcctttgctcaggccagagccctggaggc
actctccatgcctgaggtcctgtgaatcctgcctgcaaatgtgcctggggcccctgcggggcccacctcgcacccgcggccc
acgtcgcacccgcggcccacctcgcacccactgctcagatacatctcacaattgctgcctttgctgacgcccgccctgtgtt
ctcaacacccggagccagagggagcgctttgcagcccggggcgtctctgctcagctccgaccacctctcccgctatcccctg

FIG. 4 (Continued)

ggctccgtctctccctgcacaggccctcggccctttcctctggctgcaggctctctgccctgctggtccccagcctggaaaca
cccccaggcccacccaatacctggggcagatctttcccttcctgcaggcccgccttcaccttttcccgagcccgtccttgcc
tggacgccagccctggccccgtgcctggctctgtgtttctgagaccactttgatcccaagccccctgcacgcttgctggct
ggtttgtttactgtcgtcagcatggagggccggggtcgtgtctcgtgccggctgccatcttcctgcacctgggagggtgcta
ggatgtcaagcctaggaaatgggtgtgaagaggagacctgccttgcaggagctgaccaaggccagtgcactgggcgggacc
atccgtcactcctgagcccactaactgggagggacaggcagagcggggctgggtgattcctgagcaagcatgctgctgtc
tctctggctctggggcctctgccctctgcctcgatggcccccacagccgtcctggaccgccttctccacctttgggctcct
gctccaatgtccgcttatcaccgagggccatcggaggtggcacgccccgtgactgcctcccccctccctgtaccctgcactgc
acgtgtcataattcaagttctcggctcagccacccattctcggctcagccactaatgtgtgctggaaggtgtccaggaagcc
ctgctaagcatctgtcagtgtctccagcacagcaggaggctgttacaggtggcgcctgattcacatctgcaggacaggtgga
tggatgggcagacagatgggcaggggcatgtgtgcaaggacacaggatgtcagggctgacacctgggttgggctctggggtg
ctggcagcagggttcggagagggagagaagcgtgtgtgagctgtgccttcccctcgtcttcccgggcactcggcattctg
ggtgggagggcctggaccagcccgtttccaggtggttaaataaagtctgtgcatcctgttggccacctgcctctcataggca
gcagcacagggcctgatggggatacagcctggataccccactggggcctcccgcagacactcagggtccaggctgcccctcg
ccacaacctggaagggaggggctggtgggccagccctctggaggaggcctctcaggggaggtgggctttgagcgggatccgg
gaggcaggggcagaagctgagggacgtggagaagggtctgggggaggaggcggcggcaccgtgagtggactccgggcggt
tagcaggtggaaggcagtgagggttgaggagagggtggggcgaggcccttgcaccaggccacagtgggcggctcaaatgtgg
gtccgtggaggcccgggggcaccaggctaccctggagtcatctgaagtcacctgggcgtgtggagggacatgcatctgcaa
ggcccccatgtggcgctaagcacagagtgggtgctgcagacgggctcagccgctgcgggcaggtgcaggcaggatagcagcg
gtggccctgggcctcgcagtcctgcagacacacgtctggggactgctcctggggggcgcgtttctccggtgtgaggtgtggaa
agttccacatggccctggcacgggattgggcaaggcctcgcctcagccccgggtgagagcagagggtgctgtgggtgagagc
acagggtgctgtgggtgagagcagagggtgctgtggatgagagcagagggtgctgtgtgcacattgtcgggagagggaggct
tccccccagccgcatgtcgaatcttgttggcatttccattcgtttaatcacgggctccgggagatgctgtgggaagtaccgg
caggacggaggtcttgccctggtgggatgggctctcttcctccgaagcccaggctgcttgtcagtcactcacccctgggtga
ggttggggcccaagttcagacatgcccacgagagatcagggagtttgaggagcggcatactctcaaaaaaccacaacagtct
ggtctcaatattctccagggaacgaggacacggacctccttgttctacaagagctggggtcacagctcagagccctgtcca
ggctggagggagaaggccaggaggccagagggaggccagctgagccctcaggagactccaggcaggccccgatgccagactc
cagccctcaaacatgctgccttctggaaacgtctgtcacgggcacaccatgcaccatgccatggctgccagtggtggatgaa
gaagagcatgtctctgccccgtctggagctcccggttcctgtcctagttgaacagaatgaatgagagtgcgggataaatgcc
gggcggggagcagggatgctcgggcgggggcaggagctggagaggtgacaggagcgagggaggcggaggtggagctggggag
gggccagcggggcgtcaggatttcagctgacatccctactacgcttttcacgtgcctccctctctgactcggatcctaagt
gattaggatcagaggaatctctgtttccaagagaagggggactgcatggccagaccgtgggctcgggccccagtctcctgat
ctccgccaagcccagggccccaggaagcggccccatccttgggagctgtcctggcctcagctcccaaggatggggtccctcg
ggaagctgttattgctgtctacggggcaggagctccgtctttcgagcctctgcacttgtggagacaaaggtttccgaatgag
catttgtgccccgccctccccaccaccctgccaggcccaatgcagggaccaggctgcatgtgccttccccgcctcacatct
cctccgctggaggagtcagccaaaaccgtggcctttggagatgtggccagagtcattgtgaatttgctggcaggtttctct
gttgtcatttccactaaaaaatacgttccgttctggacagtacccacatctgtcccctgtcatccgatggcacggtcgtgacc
tcccatgccttgctttgcattgtgtcttaaatatcctaggctctgataaaaggcactgtggatacccgggaaagcgagaggagt
ggactaggggggaacagggacacaaacttgaaaaagatttatttcccatctacttgtaaaaaaatcactcaaatgccccac
gcctgtaatcccagcactttgggaggctgaggtgggcagatcacctgaggtcaggagttcgagaccagcctggccaacatgg
tgaaaccccgtctctactaaaaatacaaaaattagcgtctgtaatcccagctactggggaggctgaggcaagataatcgct
tgaacccaggaggtggaagttgcagtgagccgagatcccaccactgcactccagcctgggcgacacagtgagacttcgtctc
aaaaaaaaaaaaagtcacttgagacggtttacacattttaaacagtcaacaggtgcaatgggaatcttttaacaaaaccaca
aaatccaacttaatctgaaatagaacagaacccatgcggcgggagggtgatgatggggcccagctcccctccagctcctggc
cggtgaggacaaagagtctttcaagggggctgtcccgcccctccacattctgaggaaggcagcctggaccctgggcactgtct
gggcttggggctgtggccgacatggcgggcagtggcacacgtggccacttcccccagttggatggcccgcgtggatttcag
ggtctgtttcatccaaccaagagtttctgagcgtcctgtcggtactggctatctggacacctcggggaacaggagagacccc
gacccctgtgagcacctgcccccgagagcacctgctcttcccccatccgtccctgtgcccagggcttagcgactgtcctctgc
gtagtgaatctggattccggtccctgttcctcggcggagcctgcccagccgtcgttcctcctggctgggttttttgtgccaag
gcgtggaggtcatgcctcgtgcatgggagcttcctggacattggttccaggagggctcccgggcgagagtcacttccgatga
agtctcaggttaccatacttctggaccctcttgatccccacaaccatcctacgaagtccacgttgactttctttttttggtttt
tttcgagacagagtcttgctctgtcacccaggctggagtgctgtggcgtgatctcagctcactgcaacctctgcctcccggg
ttcaagcaattctccttgcctcatcctcccaagtagctgggattacaggtgcccaccaccacgcccagctaatttttttttgt
agtttttagtagagacggggtttcaccatattggctaggccagtcttgaactcggacctcaggtgatccgcctgcctcgtcc
tcccaaattgctgggatgacaggcatgagccaccacgcctggccagtacatgttgatttcatccccactctgcagatgagaa

FIG. 4 (Continued)

aacgaagacctagggaggtggagcgatgggccaggttacacaggtggagctgagacttggccccaggactcctgacctcaga
gccctgcttggccccccaggtccctgggaggtctctcctgccccctctcctggatgggcagagaggcctggtttccaggatgg
tggcgtaggggcatcagtagacccagaagaacctgctgttctgggatgggcagccctggccaccacttcctgcccaccttgt
gggaaccccccagacctcagccatcaccgtccccagcttggccgacggtagatgctggtgcttggattggggtgtccagccag
tgggatggggcttcagggctgggctgagctctggcctcccccacactgctcctctctgctctcagacaggcaggccagggggg
caggcgggaccctccacagccctcctggagggggcccagctactgggtggcctctcagtctctgacccctcatttggagca
aggtcactggcctgctgccacccagggggcatgggtggatcaaaccagtgaggtctgggaactgtgttgatacctgtgactg
gcccaggcgagagagcagccccatttaccactgcctgctgcccacacccagccccagcccccagcccccagcccagagct
aatctccagcacaggtgcacccagggaggtccccaacccatccgcagggaggagagatgaggcctcctgggtgggtgcgtgg
gggctgcagtatttcccctggcagagcactcctgccccgcaacaaggccctggggcccagcagggcctggtgcgtccgcgg
cctggaggctggcgggaaggccacccgctggctctctggctcccgcgcactccttgggtcaggcccaggagccctgcacaca
catgtaggcacttgtggccgccgcgggccgggcgtgtcctaattagcccactatcttgggagctcttgttgaaagcaaaaca
aaccaaaaaagtcctggttgtgcccgggttcctccccgtggcttccgggggccctctggttgtgggagaccccgggctcctg
tgcaggcctgtgttaggttcagggttccctgtttcagcagcttgaccccgagcaggagccaggccccagggaaagctcctttg
ccgccaggcaggaagcgaaagggaagaccagagtccccgagccaggtggagggcttgtggaggatgcctggggaggccta
aggggaggtcagagacccagaaagcccccctacacttcccagatgctgcgttcccagctgcattcataactgcagctgcaaa
gcctctgccacccactggggtgtgacaggggcggtgaccacaggcagggccagcgtgcagggagagaggtcccctggaagc
aggaggagaggacagcgtcccctgggcagaggacaggcccagtaaccctggggaggagggggcttcagaggccccccacccg
tgtcactgagcctgaggatgagaggggaccagagggagaggccgacatcggggccctgcctgaggaaggccctgctaaggga
gcctgcctggggccctgggccacagaggacggcaccgagagggcttcaggcctgctgtccggacacttgtccactaattagg
attcccgcgtggggccgcctgccgcaagggcctggctcactcccgctgggctgtgctaggcgcagagatcctatcagctctt
ctccctcttgcctcaatgactaattccttggcaccttccctcagatcatacaagaatgtggacaagttaaaatatgaaacacgt
tgtcgtgggtctgcatcctgcttctcccaaacaagggaggcatgggcttttgccccactggctgtcctgttctcagggatg
gagcagggatgggagtcgggcaggggaccctggagcctgcccttgcctgtcatcctgacctgagaagcctcagctgggcag
cccttgagccccgggatgttcttgcccggggactcaaatgagtcaggaatggggaagtcgtgcatccctgaggccatcccc
gggcccaaaacagggaagaccttccaggaaggccaccgctggtcacctggaagagagagggcaccacggagagggagggt
gggcaggctggcacccggtacccggtgatgggagggggccggctcatgtcccacactcactcctgggcagctggactgggga
gccgtcctgcattcgcttgttcgtttgttctgccagctcgcttgttcagcgagcctttcaagcagccacgctgtaataggag
cacggactgagggtgtcggctccgagccgtgtgtgtaattctgctttttctagtagccgcattcaaaaaggtggaaaggagc
tggcggaagtcatttaattatttcctgtattcacccgtaactgtgatcgtttcagcctgtaatcagtaggaaatggtgagcg
aggtgtttccgttctttccgtggtcctgagcccttggaatcggggtgcgctcacacactgggctcaggtccatccacattt
cacacaccccccaccctgtgtggccagtggccaccgtatccagggtcctcgtgggttcacagtcgagtaggggagacagaagc
catgggggacatgcgagcctgcccttccggagaatggctagaaagatgctcaaaccgggtgacgaaagagaacacctgaggc
ctgggcgctgctcctgcccgtgtggccagggctgaccccctcggaacagtgacctctgagcccggacagggctggtgaagggt
cgtgtgcagaccacaagtgcaggcttccaggaagggcctgggcccgtggtcgtaagcaggtctcagacacctcagaggcctc
ttgggcctcggtgaggagtctgggagccggggactctggggcggggcctgggctgtgcgaccagagcctggcactgcccctt
gtcaccccccaccatcacccaacctccatgtgtgtagctgaggcaggggtccatccctctgtgccagaagcctactggcagct
cgccggtgcccagggtgacacccaaccagacaccaggaggagcaggagtagcctttctacatctttctctgagggggggcagt
ggctgcttccccagacccccctcacaatagcccaggagccaggagaggcgagggtcacccttccctgggatgttatatttgt
ttcgtttttttgagacaaagtcttgccctgtctcccaggctggagggcagtggcgtgatcttggctctctgccgtctcagatt
cctgggctcaagagatcctcccgcctctgccccccagaatgctgggattacgggcgtccccccgtgatgtttttaagctggc
accatggcttatccacgtggcagcgtgtgggagcttccttctgtcttatggccgaggaagaggccactgtacagacacactg
tttctttatccatttgccattcagtgaaccctgggctcctgggaaggacctgtggtgcaggaagttagggaggttgtgggga
gcgcgacagaccaggaaggaggctgcagtggtgccggagaggtgggcagggcccgtgctgcaggggggtccccgttccactgg
tgggtgggctcccccaggttgacagctcacagccagcttaatggtgccagatgatggcagcttcagccgaggcctcgtgccaa
gacccttgcagtggagccagggcacgggtcgcccctgacggctcaggcctgctggggctgttggctgtcctgggctggagca
cacagggagagggcctgcctggcctttggtggccctgggaacagtggtgatggctctggtgagcagcagtcccctgcctcct
gcccctccggcatcccgggctgagctgcctccacgttggactgcactcagtggaggactcagtagaggactcagagaggacg
caaactctggacttgcctggcgtccttctccattggatgctggaggggccgggggatgcggccctcgtcagggacctcagtg
gatgtgtgtcctaggacctgcagagccgagggcctctgggtcactaaacccaaccacctctgatggagaaggctgaggtgca
ggaaggggctgagcctgggagtcccggcgaggcccctgcaccctcctgtgcgggcagtgcacgtttgtttttggattgga
gggggcaggctggtgggagggaagagtgtgctcacagcacaccacagcttctctaaagagggacacagggcagaatgaccgc
cccccgcccccggcccgcctccgcctggctctgccccttcctgccctgcaatcccagttcacggtctggggtctcagcctg
caccttgctgactgctggtgacctttgtgccgtctgctggggccgctagatcactggggtcaatcgtttccccagccccata
gctcagtttcctcatctgtaaaatggggacaatcatggtgcccaccgcaggcctggggagaggggtaataggacaatcacg

FIG. 4 (Continued)

gtgcccgccgcaggcccggggagggggtaatagggacaatcacggtgcccgccgcaggcccggggagggggtaataggga
caatcacggtgcccgccgcaggcccggggagaggggtaatagggacaatcacggtgcccgccgcaggcccggggagaggggg
gtaaaggcatttgtttgcgttgagcctcggggtcacagggaaagcgctgtttatacatgtgcagtcttcctccagcacccg
cctctggatttggaaggagggtcttcctcagcagcccaccaagtgaggtctgccctgccctggatctgagacatcgaggcca
gaccagcacccccctccctcagctggggcctcccttaagctcctggcagaggctgatccatgctggggtcccggggcgccaca
gacggtggcgcaggggacacacccacaggggttcctgttccttggtgtgtggtcctggcgggggagctgcgggtaggggcct
aacgagagaaccccgggccaggggcagcaggggtgaggctttgccggcccctgagcgtggagcggcctttccagtcggggt
gaggccgttcaccgagagatgaggccgcccaactgggaaaattgggctcagccattgaacagcagttccaccttatcccacc
acctagagggccagacctagtgagagcccggatctggtctccagcacctcaggggcacccacgcacccaagcccaggtgtgc
gcaccctgcactcagggcccacttgtgcccagcccacctcccccactgcctggctccctggggctggatctccccactttga
gctgtgaggtccagacccgatgccgcccggagggtacagtgaagcccgtgtgggcatcagggcctgggagcctcccccacc
cgacgcctcccctccaggtgtgcagagagtctattccgcctcatcaacggctgggtggatccccagaaccctggcaccggg
aggctgatggagggagggcgaggtgaatatgtcagtttatcccaatgcaagtagtggcctgttgggatggggagagaccc
ggggaaatatttgggatgactggagccgctggcccttaaggctcctgtaacaggacacctcctagacgggacaggacgact
gactgtgtgtgtttcccctccctcctcccctttcccgcgccagGCCCAGTTCAATCTGCTGAGCAGCACCATGGACCAGAT
GAGCAGCCGCGCGGCCTCGGCCAGCCCCTACACCCCAGAGCACGCCGCCAGCGTGCCCACCCACTCGCCCTACGCACAACCC
AGCTCCACCTTCGACACCATGTCGCCGGCGCCTGTCATCCCCTCCAACACCGACTACCCCGGACCCCACCACTTTGAGGTCA
CTTTCCAGCAGTCCAGCACGGCCAAGTCAGCCACCTGGACGgtgagttcccctagtccctgagggctgcgggctgcgggctg
cgggctggagaggaggtggctgcgttccccgcacctcaagaggtctgagctcgccccactgtctgctcggggttcccacctg
gcccgggccaggaggagcatcgggcaggaggcgggtctcagggccgggcagtctgggtgtgcccaccctctagacgtgagt
ggccagagccagtcagcctccaaagggccacagaggggacggacttggccctgctggtgagatctctgccaagactggccag
cggcttccccatgctcaggtgggatctttggtttgaaatcctgtcctggacagaggcacgggctctgctgccaagagttgtc
tgtccgagacaggcccacagccctagggtctgcagaacctgcctcctccaggcagcgagacgcatctgcgggtgggtggatt
tgggctttgctggcactgtctctggagtgtcatttccaggaattggcatgcaccaaggagatggggtggaaccaccgtgcca
agggctcaggtcctcactgcggtgcccctggagacagactggcccacggtggggatcttgctaattctgataacatcacctg
tgcacaaggccagtctcctcgagccaggcaccatgctcagggctttgagttgagctaactcttgcacccaccaacaacgcac
agggctgactccatcactgctcccctttacagccaaggaggctgaggctcggggagggaagtggttcgcccagagttctgc
tcatagtaagtgggggcagccacctctgcatctgtattcctaaccactgagctgccctgcccagacagcttcaggggagggg
gtctgtcaggaggggcaaggtgaaggctgcatgaccccagccaggagtggagggcacgcaggggctgggcgggaaaagcagc
cccaagagccctccgggtctcccctcctgcaccgaggagggggcaagtgagccctgcctgggcacccaggccatggctgcag
gaggggctctatgggacacatgttggtccggcccactgggcagcgtcccctcccccacgaggcccggcctcccgggcacag
ctcagtgctggcccccctgaagtccatgcagggcggccgcattcccaccccctgtcgggagtgctgagcaagggcccctcag
gtttttccgctttaagaatcgggtcccactgccctgctggccatagctgcggtttcccacgctcctggagggccgagggc
agggcggagcctaaggtagactgtcaggctctgcaggtagccggacagtcctgccgggctggtctggggtctgggttccagg
ccccgcccgccccaacctgcggttgtttctgattctcactccagccacgggctccccagctgctggctccgggctaagaga
aggctcagcccggactcgctgggcttgatggagggggctctgtgggctgttgggctgaggggcagaggacctggcacctcc
tccggggcctcccacctccatctggcaggcaatgccgacccagtgctaacacccgttttctccatttggaaattactcct
ccacgcaccttactgcacgatggagataaggatgggaagaccgtgccagggctgtggccagcacggtgcttagctcgcagca
ggaggcccatgcgttgtcttaattgtggtggtggtgtgctggcctgggcctcccaaatgagtggttccgtggcagctgcacc
tgcctgtggggcaaggggaccaggcctatccttccacccacttggaggtctgaagccaggtcagaaagcccccaaggcatc
ctcacctgcacacctccagcagcaggagcctcaccactgcttctctcccacactcaggcttgttgcctaagtccactctctc
ccctctaaggacactgacctcctgccctggggtttatgatgctggtggtttctggagagtgtctccctggagtcctggcagg
cagcttgtgggagctctgcctcccttcctcccatggtctgaggatgctgatggggtcttcaccatgcttggaatgcactgca
tgtggtctgagctgatcctcatggaaggacaggagcaacccccctctctggctggcttcccccatctagggtatctgccaccc
ccaccccctgccaggtgtgtggcatcaggttcaagggacttcatggttttgtctcaactgccttgtcctgcaggacggggtg
gccttgccctgtgggatgggctggtctgctcagaccaggcatcccgggctggtcagctgcaccagcgggaggggaaagctgt
gcctggtgcccagcagaggagcagtgacacctcctcgctccctccctgctgggctctgtggatgctgggcgggggagggt
ggggggcgcgaactggggaggaaaatgctgtcgcctgcacccagggctcctcctccgaagccctgtggatccagggggtgg
gacaaacattgataatgagatttttggcacctcagctctctggggccagaaccccctccaccagggctctcttccttgccca
gggaggggcaggcaagtggtcggctcacagtgcagaacggggccgccgggcagcccgcttgctcccagctctggggtcccac
catgcgggtgctgcccagccctgctgcctgtgcttgcgtccggcctctgcaccgtgactcctggggctcccggcacgccagc
cggctggtaactgatagataattcatatttttctcaagtacaagtccacattggctgccgccctccttctccccgatcagg
aaaaacaccctcaccagcccccaagtgaccacagatcagacctcagatctccttgggcactgagaggtctggaggctgcggt
tcacaggtctgtgcatatgtgtgcatacacacgcatgtgcacacacacagacacagcaccctcccacatgcatgcacacacg
tggatacacaagtaccttatgcacacgcagacacatgtaaacacacaggcatgcgtgtacatgcacaggcctcccccatca

FIG. 4 (Continued)

ctgcccagggttctagtagctcccaccccatggaaacccaggaggaggaggaggcgagtcgtgggtaaccgagcagccagag
gaaggatttgtgtttagccacgagagtgtaaccagtgaccagtgacagggcaaggccggcatttggtgagagggaccctgca
tggtgagaggggtggagctggcgtctgctggggtcccaatcccagagctgcccgtgagcaccttctgcttcgcccctctgcc
ctggcatcctcacctgcaaagagaggtatggcctgccagccatggtggggacaaaggagctggctcttgggacttcttaggt
cagggcagggtacctggggagcgctccacacacgtgagctctgagtgcagtgctgatggtgacaccagtgcccttctcccag
ttcaacaccctctgtgggacagtgtgggctcagagtgtgggcagagctctctgcagggcatgcatgacctggcctctgagcc
ctgctggccactcctgtcctgggagccctgcaggttggcagtggtgtggacagctggttccaggaggccctcggggcagaga
atgaacaggagttcctctagctgtcagaacagcccgacgcgatgggcatcggatgctgtgacaccccggctcagccgttctg
ccccagctcagcctcatcagggaaggtggctgtccttggtgtttgggaagtttggggacggggctctgaggtcaggcaaga
aggcagtgtggggttggaagccctggcccagcacagcatctgtgggcacctcagggcatgctgagtgacaccacccacagcc
cacgaggcaggctgccatggcaggatggtgaggacacacacaggtgcgatggccagctgccccagcattcctccagacagaa
agatggcccggacacagcccctgagtgccctccagctgctctcagactcagcgtgtgtgtgtgcgcgagcgtgtgtatgtg
tgtgtgtgtgtgtgtgtgcgcgagcatgtgcacacatgtttgtcttagggggagagctggctccacgggtaggaaagcccccc
gtccaggagggacatatggaaggacggccagggaagcacaaaggctctgcacgggattcctggggagaatgaggctgagtca
acactaatgggtctggagcaaccttcccagcgcctcggaggcttgcaagcaggagaataatagcggaggtgtcccaacacga
tcatggtatcaattgcattatcctaaaagtttatggaatgcatgagtggaattaataccttttactggcaccagaagcaatt
atatgtgcgtaaagctgagggaagagttctaacaatgtttattgtggagatgaaacgtggattattaggggaaacaagagta
cttagggcgaaattgcagcaattgctgatatcatgtggcgcagggatctgcagcagggacggagcttccagcaggcctgctc
tggctgtggtcagcgcctcggggctcgtggcccgagccggggttggctcttctctcttcactttctggagcagccagaggaa
ctcactcttgggccctggaggtcacagaacttagccttggaggccccaagtgaggctggggaggccccagctctgagaccct
gggtcctgctgccccacccacactgcctggttcttggaggagacaggagggagaacccccttgggggacaggattcccttcc
ataggcatgagactgttgggggagaggcatgatccaatttacgtttaggaagaatcatctatttctaggacttctttcca
gtttggggacagccctgtggacccagcatgtctgattagtagcgttggcagcagcattgcccctatgtgcagggcctcccac
actccccatttacagatgaggaaactgaggctcccagagggcacaccagggtcacctgtcagcagagggcagagccggacc
tggccccagcagccagaccctaaccttgcccttgcagcccgtgtggtgccccacccggcccctacaggtccctggacagg
tccccacgagcagccctgcccctgccccaccctctgctcccagctctgtggggcaggtccctgtgaccctcagggccccc
aggggaaccagtgataaggaggtgctgacacctcagagggacctgcctgtccctaggggagaaagccttggaccgaatgggg
tgtgggggagcccaggctgtaccttggccccatgagccttccactgctgtctgccagtgaatcaaactgggactggggt
ggagagctgtccctgtctgctttcactgcttggtttgttgacaaaggaaaatccctcaagaacgctttatcactggagtgc
tccgaggctggcgagcctcatgggcgagaagccaggcagctgggcttggggaccggcctctcctggtgcctccctgcccct
ctgccttcacccctcccaggcctggcctcactgccactaactcccgttgacagggggaaagagaggcccacaggggagggcc
gtcccaggcttctcctggacccagtgctgacgccaagatgcggtcgtaggtgacctggaccttggccgtgtgggactcggg
gcaaggtggggggctcagctgggcagtgagttagctttgcttcccggtctggtgggtttctgccacccaggccagtggtca
cttctgggattttctgagattccaaaagttgaagccacggaccctggagacccggaccctggaggcccagcccctgcctctg
ggtagagaaggccctgagcgacctccagaccttctgtccctttccgaggagcctcaggaagaggggacagacaattccag
ggtgtcccggctggaaagaaaagcatcttctctgcactccaggcggacagcgtgaggctcagagattacgtggcggccgagg
ctggtgtccacagccaggggttacgatggggctgcagaggccgtgagcggaacagggcatttagggcagaaagacccttt
ggagaaggtaacagcactccaggcttcagtgaggcagaagtcagagcccatggggaaaccgcacaggggggattacctaaagc
ccagagccacccccaagggttgcaaacccaccctcccccagccatgccactggagcgaggcacccagctccttgcacctggc
gttggggagacaccactctctgcaggggtcagagattcggaggccaaaattctccttcccccaggcatttcaatgaagattt
acaaagtttagcaaaaacctagattctagccaactattaccttaaaagctgaagagggaccaccccaccatgtccacagctt
actcccctccctccgctgtctccggccacctccagctgctgccaattccagcccccaaggctgtcccaggaagctgtggcca
gagactccgggactgtcctgtgagcagagggcacccactgaccctggggcacccttccaatccccacagctgacaaagccgg
gcctcaaaaggctgggttaatcctggcttctcctcaaagccaccagtcagggtgggggtgaggatggtgggggcaaggatgg
tgggggcttcctcccccaggagttaaggggccctctctgcagtgagcagagcaggcctgttgccagcctgctgggcccctcgt
gggacagctccagggcctggcccacagtcccgctagctaggtccttgccagaggccggaggagaggccaggctactggcaac
gggccctccagctggcgctgtcaaaaagcaagttgcgggcagaggaccctgcgcttggtcccggcccagggcagaggctgag
tgtggtgctttgaacactctgtgtcttcagagcggaggggcagctgctggtgggcattccggggccctctgcaagccccagc
tttgtctctgcggacccagggcactgccctgccaccccctctgtccccaaggccccagatgggtacctgggtcctggaat
aagagcagatggagttcctcgccctgcctgggcagctcattccttcccgggcttgggcagagtgacagtgatagtagcagcc
acagggcacccgcacgcggtctcagtgaatcaggacagcggcgaccgggtggggactgggccctgagctcctcacacagcat
ctcggcagcaaagtggaggctggagctgtccaggctgggccacccaatcccagccagacacaaggcagtctgtgtgagtctc
agtctctattgtccatggagacccatccccagcaggaccagggcaggtgaggcccctggctgttgttccccttaccctaag
gggcttaagtccagccacggggtaagaagcccatgtcccacctgacacctctgtagtaccgtctttctggaacccggggtga
cgcctctgcagtgcccagtcttcctggaacccaggggtgacgcctctgcagtgccgtcttcctggaacccaggggtgcttaa

FIG. 4 (Continued)

ggcgggtctctgcctagaccccgaccccaggccccaggacccaagtcaagcccagcagtgacaaagggctgggagatggagc
ttgggggtcagacagctatggtctgggtgctggtccaccccagcttagcaggcaggtttgggtcactaaacggagtgacagt
gcctgacctcccagggccaaggtcaggtgagggccccgcgcagggcaggcaccagtgggcagtggatgtggccatgagggtg
gacccaggtgccccattccctggcaggtggacagcactcactgtctccccaggtctccacaccaacagaggcagacaccttg
ggcaaacgctgcctcgcagcctccccaacactaggccctcttatctcctctgcctgtggccctcgtctcctactggaccc
ctgggccttcactatgcactggagacaaagccaccaagtctatcctgggctcagcacatacctgcttccctccccctacccg
atcatagcccaggatggagatccctagaggcagccgtgcatggacgaggatcgagcaggctccagctcctgtggtctgggt
gcactcagtgtctcccagggagccgcgcttccaggccgttgagagtccccgtgtggctcctgctcacctgtttaggacatg
gctcaaggtcgtggtggggcagactgcccagctcctcagggttcccacttgcccctggcctgcctccccagtgagcagttt
cttgtccacagcctctggggctctagcaggcctccgtcagggctgaggatcgcttggcatctgcagaggatgtttctgcctc
tggttcatcctccatagagctcctggcctgggagccccggctggccagcatgggggtgccagcagacacatctgtctcctgc
agccccccagccaggagctctttcacagcagcctctttcttgggcagcgctgggcctggcactggctgtggcctcacagg
cattctgaagctcgcttgggcctctcatctgcctggcccatgggctgtggatgtcctggtgagtgagccgtcactgcctcga
ccatgggagccccagcttaacaccaaggtgttctgaaacaggggcgattgccacatgtgtcctttcccctcccccaggctag
tggcttccctggggcagggagggaccagccctgtgacatcctgccaggcctccctgacatctgtcagagcccagcctgtgct
cccagcagctctctgagggcgacagtgactgtgcaccagtgaaggccacagcctcccacgaaggggctgtcaccaaggggg
ccctgtggctgccacctgaggatacccttcctctctcagaaggagaaagggacccaggaggaccctaatccacaggctgttg
accctggctcaggcatgtgtttaggggtccatctgtgaacccacgaatttaatggaaagggttctgtggctcagccccag
gagctttctagggagaggaagggtccagggccttggcagagggtgggctcaaagaggcccgtaaccccagagaggagagag
atgcaccccctaaacacacagacgcacacacaagcaaggaactggataaaagtgagcaataaaaaaatcgtttaaaaata
aaagcccccactgcaggccccatcttccagaatctgttgcaacagattcacccacgctggttaacggtatttgcggtttgca
agatgctacacgtcccaggaaaatgacagacaagttattatcacctctccgctgtcctcctgcccaaacctgcccgtgccgg
gcacccagctgccgggagcgaggagcgggcacaaggaaattagcagccccccgctgcaccctcccctcacccaccccgca
ccagccctgccaggcccagggctcccagccaggccgggcccatgttgtactggggcgggggaggaggggaaggagaggaggg
tcggagaggagccggcagcgtggggagggatgggcacagtggcgtttgggcaaacccttcctgcaagcaggacggtgcacg
caccctgggcaggcaagtccaggcggctccgtgtcaacagccgaagataaatacgatttatcagctcggaatctgttgaaa
cacatccatctagcggttctagggaaggagaaggcaggagggggcggcggaggggaagtgtctccacgtgacctttcctat
agaataggctccaccggagtcctcctcctcctgccgttttccacagggccaagcccaggcctgaagcctagaggcctgctg
gggagacaggaggaaggagctgggggagcgctggagccgtcctgggctcagccaccctctagaaggacctggatctctcagg
gctcccttccctcctgtggccacctgtgtcacccaccccagatgctgccagggcaggggacatcacagacatcctccccga
ggccacccagctccggcccggctgggcacctggggtccagttagtgccagggtgaggtctgccaggcatgtatgccccaaag
gccatgtgagcactgcactggggacacctgtggggaggagagccaggcccaggaccttggtggccttactggccagagggga
ggagaagtgctcacatcgcctgaggacaggggcctccttgctctccaccctgaggcctgggcctccctccgccactggccca
ggtcgaagacctgtccgttctaggccgctccacactccagtccgagccccacttcccgggggtgggtggtccggccgccgcc
tgcaccgagtaccagggacagctccgggcgcgcccaagctcctcccgggggcgggggcgggggcatccacagtgctccc
cgcgcctgggccccaggacctcttgcagacgggagtccctcagacagtgcagagacgggagcacgcactgggccctgcacc
cacttcgtagcgccctggcctgggacgccccaccacgcagcttccagagcaaggatcgccacttcaccctgcccggagaccc
agagggagtggggcgggctcagcagggcgctgctgagaggccgctgcctaggtctgcgaaatgggagcactgctgaccctga
ggcccaggcggggcgggagctcaggctccgcagaggactatggccggggtgctggggcaggggcctaggggaggggctgcag
gggccaggcaggagctgtgaaaccctcacgctgttgagactccatggggctgtcagggagcgacggctgccggggcctctg
cccgcaggcttggttgcacccagagccttactccatctgtgtccaactggctgaggagcccaggcggcctccctcccctg
agtgtctggggctccttggtggatctaatgaccccatctcaggccatgggctgtggcactagggtggaagaagcctcgggg
gactcagccccggaaagggaactgtagggaagcggggcctgtgtggctccagccccccgcaaccaacacctcctcacctggt
gctgagaataacgagggcgcagtagccactaacacctgcaggccactgtgttcccaggggacacgcagtgagtcagagatgc
aggtggagaggcttgtgcagtggctagaggcatcccagctgacgagcacaaagccaaaactgccacccacagggccggacct
cagaggcccttctcctttgccgcccctgagactctgacctgagccacccggccggggtctgtttcaaggggggtctgccg
cgccctccctgctctgtggtttccctagggagcggctaggatggatggcatttgttgagtaccacctgtgtacctccatctg
ctacacgttactgaggagagacgagggggacagagccaggtgcctgaattccaggggggcctgtgtgctctgcacacaagagg
tgctccataaatgctcagcaatgggcagctcgccctgcaggctgccctggcctcggagaagcctggcgacacggctgccggc
cctgtgttcctctcccctgctcggggcactggcagacaagagcctgccaccacctggccctcctccttctgtccccaacca
gcacagatggagaccaggcgtggtgtgtagcttcaggcagggcctttgtccaagagaccagtgcctggacacaggccactgc
aagtttgggccaagagccctccctgtctgagtctcctgagggtccgagtcccagagggtctgtgctgcgagctgttcccatg
tgccctgggggcagggctacctgcttatccttccaagtgatgctgtggggagcaaaggggcatttgtaatggtggggacac
tgtacatcagtggtcacctccagggaagccagactgacccacaacaaggagactgctgtacttccgctgtgcccaagcct
gcagctccgacagtccagggcaggcgcccgcacaggggtgggctgctagctctgcaaggctgtttctgctttcttttttc

FIG. 4 (Continued)

tctttgtgtgtgtgtgtgtgtgtgtgtgtgtgtgtgtgtgtgtgtgtgtgacggattctcactttgtcacccaggctggagt
gcaatggtgcgatctcggctcactgcaacctccacctcccgagttcaagcgattctcctgcctcctgcctcagcttcctgag
tagctgggactacaggcgcccgccaccttgcctggctaatatttgtatttttggtagagacagggtttcaccatattggcca
ggctggtcgaactcctgacctcagctgcctgccttggcctcccaaagtgctgggattacaggcgtgagccaccgccctcagc
ccgtttcctgctttttctaaacagcgcccagcctccctgcagggctgtgcatgatggttccttcctgtgttttaaacaggac
tggggatgggcggcttcctgcctaaggccctgtgcccaaggtgggggtcgcaggcaggggcagtggagccactctggctcca
ggggctccaggtggacggaggacctaggagggggccagctctttggtatccaattcccatcctgaggaggccactgaaggacc
cctttccacttgtccctccagccccctcacacccatggcagggacagaccagcgttcctggctgggtctcattggggagcc
caagtagctcaccagagaggggacggctcccactgcacaggaacaagggcactcagggtgccggggacccaggccccaccca
ccatggctcgcagcctccgtcagctccatctcccctgtctctttccctttccttcctggctttcgtgtgcctgcacctgc
caaggacctatgtggctcctgagagccctcatgtcccttgatggccagagaggcagtactggtggccagtggggtcaggg
ggtcagggccccctaacttccttggcaaagggaagactccacctgcagcttccctggttctgccagtagctccctgtctctg
acctcagtttccccaactgttccacggtggagtgcgatgggacattctccagggcacttgcggctgcagtgacttgtgattc
tgagtcatcggggggctggtgagggcacagagggcatggggtggcagcagaagtcattctctgagcctgagactggggatca
ttcctgatggccctttggggagagagcatgaggactcccagcaggtgaccaggagccagacgcttgggaatcagccagctt
ggaagtgagtggacgccctgcagcggcctcagcggggtcactttagaactcatgagagccggcctgggtcctcagatggg
cagccgggccctgtgaggcaaagaagctggaggcctctgcaggggctggctcaggaagggtgtcatccagtcctcctgcagc
agggcccacgccagctccagacagacctattagctcctcgagtcccaagctggggatactggggctgtgagcccagagggc
ccccagagtggccaagaccaagccacacagctcggctgctcagacttggtggccccagcaggagagggtgtcagagtcacca
gggctgctgaggccatgagaggccttcacaccaacccagagagctctctatggaagcttgaatgcatagtgggcaaccagcc
catcacacattaaccacttgctctgtgcaaatgccagagaagcctagctctggtcttaaaaacagattcaatgctgcaaacc
cacctcttcaaaatgccgcagtcagggacatggcttccacaggcctggctcccagccccgttcccgccctcactctccagc
agcccctccttgctctcctggcctttcttgtccccatccataaacctaaagcctctctgcctgactgccaccggcactcaca
cccctgctgtcatggagcccaaatgacccgatggctgtggagtgggtgccagggcagctgtgcctggattcacgcctcaaag
gacagacacctggagggattcagcagaggggctgcttggggcagtcttcatctgggggtgtggaagggcacccatgggga
ggacgtggctcccaatgggggtggcctggacaggggtgcagttgggaccactggtctcacccgctccctctcccccactcc
agTACTCCCCGCTCTTGAAGAAACTCTACTGCCAGATCGCCAAGACATGCCCCATCCAGATCAAGGTGTCCACCCCGCCACC
CCCAGGCACCGCCATCCGGGCCATGCCTGTTTACAAGAAAGCGGAGCACGTGACCGACGTCGTGAAACGCTGCCCCAACCAC
GAGCTCGGGAGGGACTTCAACGAAGgtgagggcccccagctcctctgcccacggtggcactttgcccagcatcccggacagc
acagccgggggctgcctaactgggagagagtggggctgacagcatgggcttagccattcccctgcggagggctttcagtgcc
tcccaccagccccccatttttcccagttctgagtgggacctgggggggcccatgctcctgggcaggggcaagtggtctgggcaga
gtctgaggggcagcggccttctggggccccagagatcctatgagtcatagcccctctctccagtgtgcctggcagggcctac
gggctaccccaaggattagcaggagaatcaggggggcagagccactgggcaggcacccccagagcacaagggctgccagctgg
cctgagcctcacctggaagcccacaggactgggcctggtggtctcagttctgctgcgatgcacctggcacagctgggcgcct
ctctgcacctggcacaggggtgggcacctctctgcacctggcacagggctgggcacctctcttcacctggcatggggctggg
cacctttcttcacctggcatgggactgggcacctctctgcatgtgacacagaggtgggcacctggcatggggccgggcacct
ctctgcacctggcatggggctgggcacctctttgcacctggcacagggtgggcacctctgcacctagcacaggagtgggcac
ctctctgcacctggcatggggctggacacctctctgtgcctggcacagggctgggcacctctgcatctggcatggggctggg
catctctgcacctgacaccggggtgggcacctctctgcacctggcatgcagctgggcacctctctgcacctggcactgggct
gggcacctctgcacctaacaggggtgggcacctttgcaggtggcacagagctgggcacctctctgtgcctggcacggggcca
gcacctctctgcacctgacatggggctgggcactttctttgaacctggcacggggctgggtacctctctgcacctgacatggg
gctgggcaccctttgaacccggcacagggctgggcacctctctgcacctagcacaggggtgggcacctctatgcacctctct
gaagtgtcgacccctcccggcagGACAGTCTGCTCCAGCCAGCCACCTCATCCGCGTGGAAGGCAATAATCTCTCGCAGTAT
GTGGATGACCCTGTCACCGGCAGGCAGAGCGTCGTGGTGCCCTATGAGCCACCACAGgtaggccaggagccaggctgtgccc
agggccctgcagtcagctgtacgggtcgggggaggggtcccctgaggcagcccctgtccctcctcagttggctgatctgcct
gcctgtcctgtcggcatctgtccagggctccctgctctgtgataagtctgtgtcggcggctccttcctcacccacaccgcc
ccactgtgcacactgctgctctgtccccacatccgcctcgggcactctcggggcctcagtgtgcccagctccatagtgggga
gtgggtcttcagccttgccctctgttggtgcccaacactggttccggcctggggctcccagacacagggatttgggagatgg
ggaggtccccgcccatttagaccctggattggctggggcagaaccaaaccagcaacagcgcctgaagggtggcaaattcta
caaaggggggttgagggatggtggaaagactcctaggccaggccaggggcccaggagaggtggcctgcaggaggctgaggctg
gtcagcagggtggagagccgggaggcccgctgggcaccacgtgggtgggggtgcaggggactgggggcatataggctgg
aggggaggggacacggagaggctgggggctttgacttttggcccaaaggcagcataagtttctgggacacaattctggagct
gatgtggggcccaactggtgtgaaaggctggggtagggggaaacagagggtttgaagttactgcgggatggtggggcagggg
cagaacaggaggtgaggagtgggtaccaggcccccaggggaaggcaggcaatggcaggcctctgccttccctgtacctggtt
ctgagaccaggctccatgctgtacccagccccagcctcccccaccaggtccccatccctgtaccagaccccaggacaccc

FIG. 4 (Continued)

agactcctgtacccagtctccaggtcctccacaagcctctaccctgtacccaggccccttcgacgtccccatcccaccatc
ctctaagagcagccccttatgtcagcagaaccagggcccgggagggctccctgaaacccatgtcccaccctcacctgcctag
gcctgccaggaaggcagagctctatcgccccctggtggctgccgtgtgacagcagttctgagaaaggccaagatttcccaa
accoctaatagctttgtatttgtccccagggtgacatgaaactgcccacattgtggtctggggacactcattgatcaacg
gttttggttcatggctgggcgcagtggctcacgcctgtaatccaagcactttgggaggccaaggcgggtggatcacttgagg
ttaggagttcaagaccagcctggcccacagggcgaaaccctgtctgtactaaaaacacaaaagttagccgagcctcgtggcg
catgcctgtaattccagctacttgggaggctgaggcaagagaatcgcttgaacccgggaggcagaagttgcagtgagccaag
atcgcgccattgcactccagcctgggggacagagagagactccgtctcaaaaaaaaaaaaaaagagttttggttcatgtctca
gctgtactgcaaaatccctgggaaacaggagtgtgctgggggtgggttcgctggggacagctctggttcctctttctgccca
ggtgagcccgcagcatgcaacacacacgtagggccacaaaatctgtgcaggcacactcacacccagcatctgggcttgacct
ccagcctgtgtcaggggagaaggttggggcaaacagaccacaggactctgtgcttctctgagagcagagaccaggtctgagc
cctcccagaacccagaaccagcccagtgcttggggttcagtgatcttcatgaatgggtggctggatggggtgagtgggtgga
tgggtggatggatgggggtgggtggggtggatgaatggatggatgggtaggtaggtgggtggatggatggatggataaatgg
ggtgggtgggtgagtggatgaatggatggagtggtgaatgggtgaatggatgggtgggtggacggatggatgaatagggtgg
gcggatggatggggtgggtgggtgaatggatggatgggtgggtgggtgaatggatggttgggtagagggatgttgaatggat
gggtgggtagagggatgggtagatggggtgggtggatggatggatggatagactgatattgttgaatggatgagtgggtgga
tggatgttagatggatggatagataataaatgggggagtggatggatggatggggtgggggggtggatggatggatggata
ggatgatggatggatggatggggtgggtgtgggggggtggatatgtgggtgggtgagtggatggatggagtgggtgggtgggt
ggatggatggatggattgactgatattgaatggatgggtgggtgaatggatggttggatggatggacagataatggggggag
tggatggatggatggggtggatgggtggatggatggatgggatgggtggatggatggggtgggtgtgggggtggatgtgtgg
gtggatggatggagtgggtgggtgggtgggtggatggatggatttattgatattgaatgggtgggtgggtggatggatggat
ggatttattgatattgaatggatgggtgggtggatggatggttggatggatggatagataataaatgggggggagtggatgga
tggatgaatggggtgggtgggtggatggatggatggataggatggatggatgaggtgggtgtggggggtggatgtgtgggtg
ggtgggtggatggatggatggatggagtgggtggatgggtggatggatgaatggatgggttgatattgaatggatgggtggg
tggatagatgggtagataataaatgggggagtggatggatggatggatggatggggtgggtgttgggggtggacgtgtgggt
gggtggatgggtggatggatggattgatattgaatggatgggtgggtggatggatggggttggtggatgaatggatggatgg
atattgaatggatgggtaggtggatggatgggtagataataagtgggggagtggatggatggatggatggggtggatggatg
catggatagacgggtgggtggatggatggggtggatggatggatggattgattgatattgaatggatgggtgggtggatgga
tggttggatggggtgggtggatggatggggttcgtggatggatggggttggtggatggatgcatggatggatattgaatgga
tgggtaggtggatggatgggtagataataaatgggggagtggatggatggatggatagatgggtgggtggatggatggggtt
ggtggatggatggatggatggatggatgaatagataaatgggttcgatggatggatggatggacggatggatggatggatgg
ggtgggttggtggatggatgaatgagtggacagatatacaaatggcaacaactatagagcagggcatcccctgcctacgtg
gagccaggaccagacatggagctggggctgccaccttagtggattggggctgcgtgctgatgctagcccctctccctgctc
cccatgtgcagGTGGGACGGAATTCACCACCATCCTGTACAACTTCATGTGTAACAGCAGCTGTGTAGGGGGCATGAACC
GGCGGCCCATCCTCATCATCATCACCCTGGAGATGCGGGAgtgagtcccgggcacacggggtggaggtgggacagggctggg
caggcacggccgggggagaaggggagctgtcatggagacctgcaggccaaggctagcttggggaagagactttggggtgtgc
tgctggaggaaggaaccgccccctggcctgcagggcctgcctgggcacaagctgggcctccggagggaggtgggagtccccg
gcgaggtctcagggcagcctcacagctttgagcctctgactccctctagcgggaacactcgctgccggcactgggtgctctg
tggtgaccgagggctctcaaggccggtcctgcagggtccgaggtgggtggggaaggtgggcaggttgagggtgggcagggtt
gagctcacaattctggctgtgcccacccgacagTGGGCAGGTGCTGGGCCGCCGGTCCTTTGAGGGCCGCATCTGCGCCTGT
CCTGGCCGCGACCGAAAAGCTGATGAGGACCACTACCGGGAGCAGCAGGCCCTGAACGAGAGCTCCGCCAAGAACGGGGCCG
CCAGCAAGCGTGgtgagcggccggccaggggaactggacgcgtgtgggaggagaaggggacacattggcaggacacaatgtg
agcccgcgtcccagggacagggccagtccctgaacggccccccacgcccagactcctccctgacggagcctgagagcagccc
ccatataagtcgcttgtcctgggccaagggcacctcagaggcctgggtggcaccgcaggtttgcccgtccctgtgggttgct
caccacggacccacctggagaatcgattggccccaagggtggggcaggtctccctcctcccggaaggaggcctcaccctct
ggtcctgcctgctcaccccgcctgccctgcctggccttccagCCTTCAAGCAGAGCCCCCCTGCCGTCCCCGCCCTTGGTGC
CGGTGTGAAGAAGCGGCGGCATGGAGACGAGGACACGTACTACCTTCAGgtgagtgtgtgctcctgcacggcagccgggaga
cctgcctcacctctgtcgtctgctgagcccaggctgggccatggggagggactctggagaccatggtggagggggcgggagg
agcccagccctgtgtgagagggtccagagggcagaacctgcttgcaagagccagaccagcaggacccaactgcagggcattc
ctgagagtcccctcagtcccaaaaacccagcgtcatgccatttacaatgaagccatgtgtacatagcacaggtagggtggtg
cggagtgccaccagggtagaagttcagcaagaatccaggaccctaacgttggccaggacccgtggccacggccagcccccat
gagtgtgcctctcacatgtggcctccaacaggtgaattaaatcggcacaggcttggctgggagtcatcttccatgatgtgaa
ctttctgtttttgagctccagaatgagccccagttggggtcagtggctcatgcctgtaatcccggcatttgggaggctga
ggcgggtggatcacttgagcccaggagtttgagaccaaagtgggcaacatggtgagaacccatctctacaaaaattagctgg
gcgtggtggtggcgtgcagctgcagtcccagctactcagaagactgaggcaggaggatcacctgagggcaggaggatcgcct

FIG. 4 (Continued)

gagcccaggagtccaaggctgcagcgagctatgatgatgccactgcactctagcctaggcgacagagcaagacgctgtcgaa
agaaagagagagagagagacagagagacagagagagacagacttggtttctaaaaacccagtatctgttggtaggggaggaa
gagggaggcttgggggccacaaggagcaggcatggttcttggggacaggatacctgcccactgagtcaggggctctggttag
acctgcttcttgggaagaggaaagaagatcaggggatcctgagcctctggggtgctggggaacccccagaaaggacagatgc
tttgccaagcccaggtcctcctgaggctgcggccacccccctcccgtggggtctggggcacgtgggcagagatctgctcct
ctgtgctcagGTGCGAGGCCGGGAGAACTTTGAGATCCTGATGAAGCTGAAAGAGAGCCTGGAGCTGATGGAGTTGGTGCCG
CAGCCACTGGTGGACTCCTATCGGCAGCAGCAGCAGCTCCTACAGAGGCCgtgagtcagccctagcccaccatcagtgtggg
gaaggaggacatggcttaacccccaggagaaggccaggaggaccagaaccctccagaaggcatcatctgccagggacag
gcagcagggtccagagcagagcccaccccacatctcctcctccaggaagccttctagcacttggggctgccctgggaccctg
ggtcatggcccttgctatgcctctgccactgaggggccttgtaaatgtcctgctgagtggaaaggccaggaggggtggccaga
gtgaccatgacccaccaagaccagagtccgattccagtggcacaggtcatcccctgcctcccggccccgccatggccagtg
tccttctcaggcgcaggcccagtggccgtgcatggccatggttggggacagggaggctgggggaggatgaagccactctctg
acatcagaggctccacccattcgcagcatggggcatcacgggcatgggtggtcggtgggcacgaggctgccttgcttccca
cccatgcgagccgttgcttctgagcagGAGTCACCTACAGCCCCCGTCCTACGGGCCGGTCCTCTCGCCCATGAACAAGGTG
CACGGGGGCATGAACAAGCTGCCCTCCGTCAACCAGCTGGTGGGCCAGCCTCCCCCGCACAGTTCGGCAGCTACACCCAACC
TGGGCCCCGTGGgtgagtcccttgggcagtgcgggcccacgggcagggcggggaggcccactggggggcgcctagctcaggac
acaccacccagctcgggacccagggcaggtgtctctgtggctggctcctttccagcggttccaccctctgggcaggaggcgca
gccacggatagccctctctgcccactcctggctgtgggaggtggagggggcgtggttaagagcgtggaacccacatgcatg
cactgcctcttggcaggcgagggagcttggggaaggctcttaacattacacagcctgtttccccatcagcaaatggccacag
aagtaccaggctcactccttgtgaggaataaatggtgcaagacctcatcaggggccccagcacaagccggggctccattgg
atagagtttgggcccccttcccctggaaggtcctcatgtgggcaggaccaagcatgttcccagtgccgtgagcaagcacccc
caggtgtttcctgaggccctgggatgtggccagcactccagtgccagctgcgattgcccttacaacccagtgccccgtacgc
acggtcaccccgtccctactaggcggggcgaggagacagggccccaggtgttcagcccttgctcaagcctctagctggcag
gggtgatgcccagcgtcacatcgccaggccttgggatggctccctggtgtccagaggtgtctggagcctgggtggaggctgc
acctggatgcccagcctggctgccctgatggcccccacctgcctctcacccagGCCCCGGGATGCTCAACAACCATGGCCACG
CAGTGCCAGCCAACGGCGAGATGAGCAGCAGCCACAGCGCCCAGTCCATGGTCTCGGGGTCCCACTGCACTCCGCCACCCCC
CTACCACGCCGACCCCAGCCTCGTCAGgtgcgtgggctgccgagggcctgagcatgtgctgtcaccctgtctgttcacctct
gtccttctggccatgtcagctgccctgccccaccctgtgtgctcaccactcgcaaccctggatcagacaggcgggcgggggc
agtcaggccaggagcatctgcagatgctggggaaatggtccacttagaggaaaagcacaaaaagccggggtcctccactgac
ctgtccccagctgagcacgtcccctccctgagggatgccgtggccacctgtgggctggagccacccttcggagacagcggca
gtctccgccccagccaggccactctcagagatgggggctcgcgcagccctgtgctcggaagctaatgctgcttcctttctca
aattctctctgcagTTTTTAACAGGATTGGGGTGTCCAAACTGCATCGAGTATTTCACCTCCCAAGGGTTACAGAGCATTT
ACCACCTGCAGAACCTGACCATTGAGgtaacgcccgggtggaccccgctctgcagaggcagtagctggaggggccctgtcc
ggagggcaaagagcccttctcttccttgctcctcgtggctgggaaacttggaaacccttttcccacgggcaagcagatgcgatga
tttgactctcgagagcttaggcagatgcagccaggcacgtggctggtggcgcgggacacaggcccaggcctccggatgctga
actggtcatttgagcctttttggactcccagcagccagtgtgcctttgatttagggatgggctgtttccaaggcacaaag
aacagaagaatgtaaggccccgagggagtcagtccagttcagtgccatttacagagaggtcagcgccatttacacagacagg
aaaggggacctagggaaggcaagcacctggcccgaggccacacagctcttggcacccatggcagctgactgcaggcaccatg
attaaacagccacggcttgtctttgggttagagactagtggagtacaaagcctgctggtagcctaggacggtgtgaaccaca
gggcaccgtcagtcaaggaagagcaagccctctggtgggaacctgccccccagccagtgccgcggcccaggtccaaggcccg
tcccagaccatccccagcctggggctgcagacagagatgagggtcagtgcgagctagggccagctgctcagcctaactgtcc
ctcgtgcagagagtggccgcgtctgtgtccactaaccgccctccccgcaacctgtccccagtgacccacgctgagccagctc
caggtcacgttaacccttgcctcccctgagtgatgtgtgtgcttggtgtggtgcccagagggtgttgggagctcagggatga
gctgggggtccactccaggggggcagggacatggagaccaaggagggccctgccctgaggctgggaggcagttcctccccag
ggccaggtagatgctcaggggctccatgtctaacactcccaggtcagggcccaggccccgcacaggccaggagtgactctg
gtgggctctcccctccccgtctcctgcctactctggttggggtgtaggggccagggtgtggtgtggccagacctccagg
cccagggcgaccccccctgctctcctgctccactgcccctgcccctaatgcgccggcctctcgcaggacctgggggccct
gaagatccccgagcagtaccgcatgaccatctggcgggggcctgcaggacctgaagcagggccacgactacagcaccgcgcag
cagctgctccgctctagcaacgcggccaccatccccatcggcggctcaggggaactgcagcgccagcgggtcatggaggccg
tgcacttccgcgtgcgccacaccatcaccatccccaaccgcggcggcccaggcggcggccctgacgagtgggcggacttcgg
cttcgacctgcccgactgcaaggcccgcaagcagcccatcaaggaggagttcacggaggccgagatccactgagggcctcgc
ctggctgcagcctgcgccacgcccagagacccaagctgcctcccctctccttcctgtgtgtccaaaactgcctcaggaggc
aggaccttcgggctgtgcccggggaaaggcaaggtccggcccatccccaggcacctcacaggccccaggaaaggcccagcca
ccgaagccgcctgtggacagcctgagtcacctgcagaaccttctggagctgccctagtgctgggcttgtggggcgggggctg
gcccactctcagccctgccactgccccggcgtgctccatggcaggcgtgggtggggaccgcagcgtcggctccgacttccag

FIG. 4 (Continued)

gcttcatcctagagactgtcatctcccaaccaggcgaggtccttccaaaggaaaggatcctctttgctgatggactgccaaa
aagtattttgcgacatcttttggttctggatagtagtgagcagccaagtgactgtgtctgaaacaccagtgtattttcaggg
aatgtccctaactgcgtcttgcccgcgccggggctggggactctcctgctggacttgggactggcctctgcccccagcac
gctgtattctgcaggaccgcctccttcctgcccctaacaacaaccacagtgttgctgaaattggagaaaactggggagggcg
caacccccccaggcgcggggaagcatgtggtaccgcctcagccagtgcccctcagcctggccacagtcgcctctcctcggg
gacccctcagcagaaagggacagcctgtccttagaggactggaaattgtcaatatttgataaaatgatacccttttc (SEQ ID NO: 3)

>mm9_knownGene_uc008wbh.1 range=chr4:153432953-153514317 5'pad=0 3'pad=0 strand=-
repeatMasking=none
GGTCCCGCTTCGACCAAGACTCCGGCTACCAGCTTGCGGGCCCCGCGGAGGAGGAGACCCCGCTGGGGCTAGCTGGCGACG
CGCGCCAAGCGGCGGCGGGAAGGAGGCGGGAGGAGCGGGGCCCAGACCCCGACTCGGGCAGAGCCAGCTGGGAGGCGGGGC
GCGCGTGGGAGCCAGGGGCCCGGGTGGCCGGCCCTCCTCCCGCCACGGCTGAGTGCCCGCGCTGCCTTCCCGCCGGTCCGCC
AAGAAAGGCGCTAAGCCTGCGGCAGTCCCCTGGCCGCCGGCCTCCCTGCTCCGCACCCTTATAACCCGCCGTCCCGCATCCAG
GCGAGGAGGCAACGCTGCAGCCCAGCCCTCGCCGACGCCGACGCCCGGCCCGGAGCAGgtaggcagctctgggaccgagct
agggccaggtatttcgcacgaggctccgaggctggagttcgggtgtgcggctgcccgggtgctagccgagtgaacggcccca
gggactccgcgtcagtggcaggaggggcggcggagtgaggctaggagtagaagcagttggcacctcggcaacccatggac
ctgcctcctgcccacactgtccactacaggtggcaaggagtcgccataccggagattctggggctcgggtctggtaatagg
ggaagttgggaggtgcgtgggtatcctacctcacaaggaatgcaaatccccacctctgtaaggcagaaggcctttcaggtcc
cgctatggaagcagactaagagagaggaaagccaactagagcccaacctctatgctggtcccaaggtgtggggtcctggtgg
gttactgctgttctgtgatgagtttactgtggtgcctcaccagcctccctagtcttccaggtagagaacccgggcagcccac
actctctcctgctccactgggcagctgtcaccttctcactcttgagagatgagaacatctgtaggcacctatccacatacac
acccgtatgtgtgcgtgggcgggggcgggggggtggtggtgtcaggaaaaaagctctgacttctgagccccaagacacttgg
ttccctgtatgtgctgaggtctgttaattaattaagtgggcacttgggacctgggtcgtaacaatatttggggggaaggttgt
tgttgtttttcttcatttaaaagttaaattgtgtctgtgtgagtcgtgcacgggtcagaggacatctttaggagtcgattcc
catttccatttatcagtctcaaagatttactcaagtggccaggataggcagcaagcacctctacctgctgagctccactg
cctcggattggtttcgtggtcgttgtttgtgttgctgtttagctctagaaaaaaaactcaacagagacaaaatgtatcctg
aatccttggtgtgttgcaaacgctgtcccggccccccacccgccccccatcctttgatttattcaataaaatgtaaaacatt
actttgtgaacaaaagataagtatttaacatttctcatccatgactgtatagattgtgtatgcagtttgaaaatcaggta
atcggtttcaaaggtgttgcatacccactaactagtcttgagctactggcgggcctatgggagcctgcctatcaagcacagg
taactaacgacaggatgctgagcaatgttgtccttctagcgatggctctgtggaacaggcagggcttgcccattctgatggc
caccctgtgtgacaacattctggattagaagtcagatgctgagttcaaatactctctgtgccctgggaccttgagcaagtta
cttaaatcctcagaacctcagtttacccatcttcgaaatggagtcatagcactgctttctcaaagagcttatagaaacctg
gtcagtatgcctttgtaaacagaatggaaactgcctgaccctggctgaagaaggatatgagtgagatgcttgtgttcataga
ggtagagttatttgtataagaagaaactggctcgggacctgtgagatggctccttgtagaagggtgcttgctgccaagggt
gatcatctgagttccatccatggaatcccacaagctggattgtggatccacattgtcttctggccatcacatgtgcactgtgg
cccacgggtgcacacatacatacaaatagaaaagtaaccaggatgctatatccaaagtccttggacaagtgctgataccaag
tgatctttgagtcctagattttggctctgggactgggtggaccaagaaagaactcagagaagaaggccagttcctaggttt
tggagagatcatggcagtaaggcaggaatttgcctgcgacctgggtggaggctagcagcatctgtcaggagtatgtcctgtg
atgaagatgctcctgtttcatgtttatttatagagtatgcccaacccaggtcctggaatgggcttctagtgctgacacatgc
gaaggagaatagctaaagtggagatgaagaagggagacagggatgagggctaaagggagcttcatcaccctgctgatatcca
gggatgcaccaacccaaggctcctagcactccaaagttcttgtcatttttgtcattgcatttttaaaaagtcccatgtacat
ctcagtgagaaactatttctgtcaccaaattcaagggtgatttacctcccagaagcaagcacacacacacacacaaaaaaaa
ttgcacttggtgaatggtgttggggcagggggcggagagaaatcctcaaaacactcttctgtgttccttctaagaaggaact
ttgaggcagcctttagttttcgcagaggatactttaaatgttgctgacaacaactctacttatgagtaacagtgtggcaga
gactcctggaacccagatcattcaatcttgtttcggtttgaatgtgcagcaaagagtgtaacggatacatttagtacagcta
cagccaccttacaaacaggcaaggtcctctctatgggacccagcctgcagaacaacccgtggtccatctgcctttgtagact
ctgactctctctgtctctctctctgtctctctctctgtctctctctctctgtctctctctctctgtctctctctctgtctct

FIG. 4 (Continued)

ctctctgtctctgtctctctctctctctctctctctctctctctctctctctccactttatctttaaaccagtttgtt
ttccctgaacttgttgctccacaggggaggatcaaagagaagggattgcttggcaaaactattgcttatgaagtatctgcag
gaattagcacccagtgcacatactggctgtgtgctggtattaggcttaataatttaggattttacctttgcttgtaattctc
caacatccccttgatgtaggttctgtaattatgcccattttcagatgaggtcatggaggctttagcatgtgattcaaggggc
ctggagttgtgccatcacagtgtgggatttgagatctcagatctgacaaacagtccagggtatgggcttctgggtcgttctc
gccagtgtagctagtgctggatgtataaatataacctattaaacagagccacaggaccctagaacccttgcacagggcattc
tgttgagaggactgtttgaggctaggtgactagaattaggcgtgatgtgaactcatgtagggagaaaagacgcatcgtaatt
tcatcagtaccgaagtgaaatttctcatcttcagtcatgagtgtataaacaaacaagtttacagtccgtggtactttataca
gtccatggtactttatacagtccgtggtgctcttctcactcattgcagttactgatcttttcactggatgtcccagcttggc
agaaagctcaaatttttgttctcatcgccaacctgaaattctgagttatgacagctgctgcttgacttgaccttgtcctaac
ccagaggtatgattgtcatagattaatgtcacttgaacactgtggccacttcattagaaccatgggtgggaccaaacaccta
caatggcagcactggagaggctggggtaaaggcatcaagaatccaagcccccacccccagggtcagctctgttgtgctgtcc
ttattatgctgaaggtcaagagcacaaaccagtagtctaatttgccactatatattctgatggccagaggctacatgtcagt
gtgtgggcaagactagttcccctcagataggaatcccctctatgttcctccaagatctggcaattctggcagctccttgccc
tgcaggtctgcctctgtcctatagtctctgactctgtgcagcatggccttctctttgctttctctgagtctaccctctttga
ttgtagtcagatgtgtggctcgtctgaggttctggggagaattccttgtatttaatttatgtatttacaacactcctccct
gcataaggttctacagtgtcagggtcaggcaggttctgcttgccccagctgtctgtttaaacagaggctgctggggtgcttc
acaagacatcaacatggctttcgggataggagaggcatcctgaagaagtagaaagagaaggggaggtgttatcctaggacat
ctccactgaggctggagcgccggaccaaagaaacaaccctgtctgtgaaggaacaagagctctgaagacaggtctaggcaat
ggaggagacatgtggacatcagagggccagtggatgtaacacttgatggcccttgcagatggagtcaggttccccagagagt
ggcctatgagggaggaaagcagtcttcttccacctgcccagactctttgcttggtgcgtgactttgatggacattgcccaga
ttgatgggagaaaaaaaaaatttttagaaccatgggtaggaccaaacacctacaatggcaacactggagaggctggggtaa
aggcatcaagaatccaagcccccacccccagggtcagctctgttgtgctgtccaagcagggtgcagggcccactctcccaaa
tgttgcagccagtgaggggcagggatagctctcctgaacttatgaccttgtggacagctttccaactactggaagtgtggag
aggaggggcatcatctctacaccgtgccacctcatgacagacaagtggcagagtcagctattccacactcatgctctgagg
gtctgctcacccacactccacacccacgagggtcatgtccactgtgctgcctgggtgagggtgcagggcctgctctccctag
tgctgctggtgagtgatggggcaagctctccagagggcggcaaccagtgaagggaggggccagctctgcccagttcttggac
atctgctctgacaagggatatcccatgttctttaatggtaatgtgagccgtggacatcaacacccacctctgcatagccatg
aacccagctcaggctgccacctcactatggcccccaggtggctggccactcacaacaggctgctcctctccatcctccagtct
ccagatccagctctcttcataatccttaagctgttccacttctctctctcccatctgaccaccacatgctcgcacattgtgg
tggctcccactgcaggctggccatgttgctgggggccctggggtgacatcctttggtccaagctgcacggccgtgagcagg
ccctgcacctcacccaggcagcacagtggacatgaccctggtgggtgtggggtgtgggtgagctgcatggcatttggcaag
tggttgtccacagcctgcctgtgctgtgctccagaggcagatctgtggatgctgtggcaggtttctgtctgcctttttccct
cctcatgtgctgcactgcaggtggctatgtgtgtctatggcctgctcatacagggtagagggcagatctatggctatcttc
cctgcccaaacattgtggcatggtggaacacagatctctgtctatcttcctcttcccgtgccatgctacctagatttgattt
gatttgatttgatttgatttgatttgatttgatttgatttgatttgatgagtcctagacataaaacagctttggtca
ccaagccaggcatcgggccaggatgaacataggactatcatctgctctaccccctgactgatgtaagaatggcatcaccaata
aggtgtctctttgtccattgacaggggttaaagtttttaattggtaaattttactatgtagctctggctagcctggaact
ctttatgtagaccaggctggcctgaaactttcagagctctacctactattctctgcctcctgagtgctgggatcaaaggcgt
gcattgcttggaatctcgaggggatgagggtgtggggcttctgcaggagaaaggcaggtctcaggagcctgaggaggaatgg
aaggtcattagcagtctccttgctatgcagatatcttctgtcagggaatgctctctctctctctctctctctctctctcct
ctctgacatttctatgtagtactgatttcctgcacaagtagcggtttctcatttgctttaggcagttgggtggggttagg
ctttgtatgtgttgctagttctccatcgatttggcttctagtatcaggtaacgtcaaagtggcgggttctggtttcctaca
gccccggtctgaggtgacaccatgaatcccagcagttgtccacctaacactctccaaagcaggctcacagtgcagaccttgg
tgagtgtatttcttatcacagtccactaaagagggctttatacagaccaagggcaaaacagacatgaaccattggaagaggc
tgcaaagcagtatgaactgcgagggcagggcagggcaggcacgggtagggatggagaggtctgcgggctgggccttccagtt
cttgcacagttgaggtcccaggaatgtgtgagtagccactgtcaccccctttgaaacctgcccacagcagaagcaccggagc
ggggttatgatgtgcagcctcagcctgaaggactttcgggagaagggcaggatctacgctccaaagcagaagcctgagagg

FIG. 4 (Continued)

aaattagaaccatggatttgggcagtgacagccatgcacgggagctaactagctgattcaggatcctgcccatttgtagat
gtttagtagtccagaaaggcagaagatagtagatgctagggacaaacgtagtttctatgaaaatatgatttttctctatat
catttcttcttaaaaaacatttaggtggggctggtgagatggctcagtgggtaagagcacccgactgctcttctgaaggtc
aggagttcaaatcccagcaacccacatggtggctcacaaccatccataacgagatctgactccctcttctggagtgtctgagg
gcacctacagtgtacttacatataataaataaataaatctaaaaaaaaaaaaaaaaaaaaaaaaacatttaggtgtctatttg
ttcatgtgtgtaggtgtgccagggtgcatgtacaggtcagaggtcatgtccagtgtcatctttgcttcctgcccacctttatt
gttttgagacagggtctgtctcattgactctggactcagtgatttgggctggactaaccagccagggaactctggatttcctc
tgacttctgctccccagagccacgcttgcaggcatttgttgcctacagtctgttttgttttaaatttatatttattcatttc
attttatttgcatttcgcctgcatgtatgtctgtgcaccacaagcctggcatgcctgtggaggtcagaagagggcatctga
tcccttggaactggagttacagatatttgtgaaccagcatgtgggtgctgcggactaaacccaggtcctctgcaagagcagc
aagtgctcttaaccactgagacacccctccagcccctttgctgttgttgtttaatgtggattgtttattggtattgcttttt
tttaaatgtgggttctggcatctgaacacaggtcttcacactttcctgactgagttagttatcttgctagtaaacccatttc
taccaaaggtgatcacagtaaactgattttatttttcagaagcatgcctagtcttcctgaatgtgccctgcgtatttgcata
ggtctggtgaaattactaagtggctgtgctagtcaaataaggagcgtcagagcagatctcagaagcctgtgctggcagcgga
gccaggtcagggtcccagcatcaaaatccatctgcagagcttctcccgctagagatgcccaaagaacttttaaggctggtggt
ccctctgtcagttacagtccttgtctgtgagaccatagagcccttgtaagccagggaccaaacaaagcatttatctgtctg
tctgtctgtctgtctgtctgtctgtgtgtatgtgcacatgagcatgccacagtgcatgtgtgatggtcagaagacaatgtta
tctccttccaccatatgaattccatggatgacactcaaataatcactattggtagtaagcatgcatatacacagagccatct
tacaggccctgattcagtttctttccttatacaaataactcgacctctatggaaacaagcatctcactcatttcccttcag
ccagggtcaggcagttccaattcagtttacaaaggttaattgaccaggtttctataacctatatatagcttccttaagtttc
tagacatttgtacccagttcaaggggcctgcctttgaaatgtgtgctgggcagagtcctttctcaaatctccttgatcgaag
ctactggcagaggccgtgagaacatgggtagacagcggctaactgccagtggctggagaaatggcctgaatttgtgggactc
atcatccggtgggggtgtgtcttaaggcaactggacgtgaaaatctagatatttcctgtattagagaaaaaacaatctgtt
ttaagaaaagtttagaaggctcagtggttaagagcaccgactgctcttgcagaggacctgagttcaattcccagtacctaca
aggcagcccacaaacactgtgactccaattattctgacatccatgggcacatggtactcacactacacgctgacaacgcatt
tatacacataaaataaaatgaatcttttttttaaaagtaactagaactactatagagaagtaggatttcttggggtatcata
taattaaataaatactcacacaagtgtgacaggattgattttgtactttattataagggaaccatttttttttttaatcgtc
cagggttgcatctcagcctctggagtaaggattcatggagagttttgtggggccaatctgcaaaagttcagcagaaatcaga
agttaagaaaggtgatacagaacttagcattggaaagttctggaactagagctggaaagatgcctttgtgctgaagagcact
cgctgttcttccagagaaccagagttctgttcccagtggcccacaactgcctgtatgtaactccagctccaggagacctgac
accctcttccagtctctgcaggagcctgcacacacatgcaatacacatacataaaaaataataaaattaagctttaaaacat
tttttttatgaaaggaagttatcagccaggcatccccgcactcacaaaacagaggcagaggatctcttgtgagtttgaagct
gtagtggtagatacataaaaagttacaggtcagtcagggatacatagtgaaactctgtctcaaaaaatatctacaatgaatc
caattttagacaatttgtgctcagagatgtagggcattcctgtgatcccagtacctaggatgctaaagcaaaggagaagctg
agacggaagagaaagatttggagcttgaggccagcctgggtcacacagtccaaatatatataaatatccaatatataaaat
agtttatgccaacttgacacaggctagagtcatttgggaagagggaaccttaatttttaaaaaatgactctactgaattta
cttgtggtacattgtcttgattgatgattgaatgtgaaagggtctagctcactgggaggagggccactcatgggcaggtggt
tccatggtgtaagaaagcagaccaagaaaacaaaaccacaggaagcaagtcagtaagcagctttcttcatggcctctgacaa
tggtcaacatgaccactgacacagtcctttgtctctgttatggttctttctctccctcccctccctctccctcttaaagat
ttatttattttattaatatgagtacactgtcactgtcttcaggcacaccagaaaagggcgtcagatcccattacagatggtt
gtaagccaccgtgtggttgctggaaattgaacttaggaccctctggagggtcagacagtgttctcaactgctgagccatctc
tccagccccttatctctttccaactttctgtatcagttgagttttttttatccttcctcttccccccacagtctgtcttccta
cccttctttctcccttccatcccagcctcccttcctgtccttcctcccctctccagtctaccttcttgtcctttctctccc
agccccattctaagcccccctttttttcctttcctttcctttccttttcctttcctttcctttcctttcctttcctttcctttc
ctttcctttcctttccctttccctttccctttccctccccctccccctccccctctcctctcctctcttttttctttcccctc
ttccctccttctccctccctcttctcttttcctgaagctgtttttcaattaaccttcaaactaaacacattcctttcccttga
acctcagactttctttaccacaaaatgtccctgcatcttctcatgtagagtgggttctcttatagcttccacacacagacaa
aagaattttaactctcctgtaattccaactcccagaagaaaacgaaaggtgagtacggacggacggggcaagtgtgggaacgc

FIG. 4 (Continued)

ccacccgagtgccacagagcggttttgctagctgctcttgccaagggctggggtctggtcttgctatgcacacagtggctca
ccatcaccagtaacttctgtcccagggaatctgacattctcttctgatcctccttggacaccaggaacacacatggtacaca
tacatatatgtaggaaaacccaatcatacacataagataacaaaaaagtaaatctaaaagcattttcaaagatgtgggcagc
tatttttaaagcaggcatattatgattcctcattgtcatagaaatctttgcttcttatacttttatttttttgagattcattt
aattttatagtttctaacaactgtgccttaattatgaaaacaccaggagaaattttatgaaagcatcctgttttaaaatgtt
tattttaaaagtttaggttttattattattatttacgggtatgtgtgtatgtgtgtgcttgtggggtgtgcatgtgaatgca
ggtacttccaagccagagagggtgtcacagtcctttggagctggaggtacctctccatccccagagtttcctgttttaaac
aaggctagctattacccaacaaccgtacctcctgctaaatattttcagcacgtttgtatcaggaagagtcagaaaggcaaa
gcctgagagaggtatacttagttctgctcatttattgttgagatgacctgcagacactgctgtgtgcctgttagttcctggg
ttactgcaaggttagctgtcccagggttcgaacagacatggccaggaaacacaggaagagcagcagttgtatgtctgccttg
tgtttggatggcttggaagatatgtgtatgttagttaatccagtaaacgtaagctagcagcccaggcaggctaggtggtcat
gattcttctgccttgtcttctggagtgagccatgccttgatttggaactttaagaaacttttccactcttgcttcatctcac
agcaaacagctctgccaaattcagtctctggaggtgaggccaacttctgataatagagttgtgaaaaaaatcctttcaagta
ttttattatcaggttttagccagccaaatacttaagtgtttctgaaagtactagggtctctctctctctctctctctctctc
tctctctctctctctctctctctctctctctccttccctccctccctccctccctccctccctccctccctccctccctt
tctccttctctcttacttgtattggaaattcaacacccaaaccagcaagacttttatgacaaccatgaatataaaatagtca
tgttcaaacaggggcgggcagcctgcagcccctgtgaccccaagttcactttagacaggtgggtaaagactacatgggct
ctccagtctccacttgctattctatgatggatgtagggaagttcctgtgggaaggtaccctaccagcactgaccaggcatga
aggatgaaggaggacggagagccccctaatagacctgggcctcttgtttatataggatcttttgagagctggggccatggtga
gccattgaactctgcctgactcaggccagcattgtgctatacccacagctgagagagggagaagaatgtctaccaatcatag
agcagagtggtcaggactcaggacaaactaaagggaggatatcatctagtttgactcataacaaaactgctctatgcagatg
tcagcctaccagaacccagagccgctaacctgggaagccagtgggcagcagccttccaggctggggttcttgtcctgaccaa
gatgctattcttcctgcaaagacagaggggaagaagccagaaatgagcatgctcataccaatagagcccagggctcagtagt
aggaatgtgtctggtgtgtcctggaggctctgggttccatttcctgctgtctagaaagccagcaaggtttccgaatgagaact
gtgttccactgcattccttctaaatgagaactgcgttccactggattccttctactgagcagagtctgaaaaggtaaagaca
gtttctgttcttattcccaccaggtccaggaaggagtgtccctcagtcaaacctggtacctttgctggcctcctgctagggt
tccaaatcctacagctgctatgatcatcccagagaaggcaggcttcagccactgaggtcccttcccagtcactaaagtataa
gggaaaaaagattacatcagatagggtacagtaagttgtgcctatccatatgcacgggtgccgtacaggggaaggtggctct
tctgagtcccagagagaaaagtagctctgggtggcacagaggctaatgtagggatgtgaggggaagtgggcaaggaatatgc
agatatagcattgtgtgtgtgcatgtgtgtacatatgtgtgtgcatgtgtgtgtgtgtgagcaaggaatatgcagatata
acattgtgtgtgcacatgcatgtgtgcatgtgtgtacatatgtgtgtgcatgtgtgtgtatgtgagcaaggaatatgcagat
ataacatgtgtgtgtacacgtgcatgtgtgcatgtgtgtacatatgtgtgtgcatgtgtgtatgtgtgtgtgtgtgtatgtg
agcaaggaatatgcagatataacattgtgtgtgtgcacgtgcatgtgtgcctgtgtctacatatgtgtgtgcgtgtgtgtgc
atgtgagcaaggaatatgcagatataacattgtgtgtgtgcttgtggatgtggatgtgcatatttgtgtgtgtgtgtacatg
tgggcaaggaatatgcagacataactgtgtgtgtgcatgtgtgtgcatatgagtgtatgcatgtatgcatgtgtgtttacat
acatgtatgtacatgtgcgtgtgagtgcatgtgtgtgttgttcctcaggaggcatccactttttttttttttttttttttt
tgagcatgagcctctccctgaatctctccatcaggtctccatttcccatctctaccttcaaagcactgtgataacaagaaca
tactatcacgcctgtttttgttttaaaggcgccaatatctccttaaatttagtgcatttattatttttcacatgtgcggg
tactcacatgccacagcatgcccatggtggtcaaagtacagttttcagagttgggtctctcctgccatgtggggtctgggt
ttcaaactcaacattccaggcttggctaccaatgcctgctgagccaactcaatgactcctcacacccccacctttgaaacaca
cctttctggggatcacactcaggtcctcatgcctacaagtgtgtactgacccagccccagacgtgactttggtttgatggttg
cccagctgggaccccttccctgatgtatgtgtccttcagagctgtaccatctgctcctacacagggcagcttctccatgttc
agtgcatctgcagcctcagggtcacctggactcactcagggtgcccaacaggttgttctgcaatcatgtgtcccagtgtcct
gcagacatgtgtcatgcagttatatgttctgaatctcaatatagaccttagaactgtggctgaagaaaggggatgtggtgcc
agactcagtttgcccaaagagctagtgcaggatggagctggctggcactggcctagggcagactgaaaggtgcaaggggccc
ttgggtggtgacacctggtgtttagacgttatgtgggttcccaggaaaacccccctcttctgcaaaggaagcacttgtgtt
ttcccagtatgctatgggtacaaggatgactaacaatcatgacatttgcatggtgcttccttcaccgtagctgcacacaaag
gcccgtgctttgctctcttggcagaggtaggctttgtttcctcagtttacagatagggaggtggagggctgggaggtcatta

FIG. 4 (Continued)

tagtcacaagaggagtagagggctcagcacaaagtacgacaaagtcaccgtaataaaattcaggcctgggccatgatcctaa
ctactggggaggctgaagcaggaggatccaaagcttaaagtgaccttcaagccggtcctggttgacttagtgagaccctgtt
tcaaagggaaagtcaaaagagtctggggtgcattttggcaatacagtgtcctgggtttgacctcagagctgcggtgagagc
aacgagaagaacagattcgcaacaggaaagttcacaatggatccagcactagctttcaatttttaagaaagattttacatt
ttatgtctgttgtatggccatatgcttgtactctgtgggggggggagaaagagagagatagggagggagagagagagggag
agggagagagagaaagagagagagaaagagagagagagggagggagagagggagggacggagagagggagggagggagagag
ggagggagggtgggagagagaggaagaaggagagaggagagagagagagagagaggaagaatgagagagagaaagagagaga
gctctcttaactgctgagccatctctccagcccctcaacaatagttttattggacactaaggacttcagcgatgaagatcca
aagacctgactaactttctcccaagtttgtgtgtgtgtgtgtgtgtgtgtgtgtgtgtgcgcaaacatgtgtgcatgcatgc
tagagggagcctgcccaactgaaccattgttagaggacaagggttagaacaggaatgagtcaatcccatagtagggagggtc
tgcatccctgtgggatcctgtcccaagaacaggacacacaaggtctcatgctattcagggtcaggctgagaatttgctctt
caaggtttcgtggtatgtattccttgtatgtcatactgtgttgcgtaaggacatcttcctgcaggcatctattatacagcaa
gtgtacatgcttcttccccttggtccatttatcccttagacaagtcacttctgctttcctgtcacgtatacatatgtgat
tttagatacatatgcaaaaacccaggaacaaaatatgagagaaaacatgtgatgctcgctttgctgagactggcttaattc
acatactacaatcatgtccgattgcctccatttcatgaaaaggatgtaactttgtccttctttatggctggataaatgtat
gaccatgtatagttgtcatactttttcttgtctgctcctctgctcttgggactagtgctacactgagcgctccttgatatact
atgttctacaatgtgcgttgactttggggtaggtgtccgtgggtggtatggtcacatggtagatctatttctaaagaccctc
catactgacttccatagtggtgggaatggtttgccttgcctctgttggtctgggagggcgtccttctgtccacgtcccccacc
agcattggccacttctgttttcagccggtggctgagatggattctcagtatggtcttgatttgcatttctcagattgcacct
tttaaatgcatgtattagctccttgtacttcctcttttgagaattgtctgctcaattccgttttaagcaccaggttgcttgt
gtgtgtgtttagttttttaaatatttgctttaggtttacgtgtgtgtgtgtgagcctgagtgtccatctgtgcaacatgtgt
ttgcaggaacccaaacataccagaaggtgtcgaatccctggaactggagatacgggcaggtgtaagtcagctgacacaggt
tctgggaattgaactccgtcttatgcaacagcactaagtcttttgactgctgaaccacctctgtcaccctgtgtttagtttt
ttgagttctctgtatattctattatttatggcaaggaatgttttgcctgtatgtatgtcttatgtacaccatgtgtgtgc
ctggtgcccatgaaggccagaaccagaaaagagagtgttaggtcctggaacagttacagatggttgtgagccgccgtgtggg
tgctacaggttgaatctagctccgctggaagagcagccaatgttaacagctgaactgctgctctccagtcgctttttgtaaa
ctccagatgtcaatcctctgccagactgacagccagcaatgactcccctaccctccctgagctgttcttcacccaaatagtt
gttttcatctctgtacaaagcctttttgaatttctcaaagcctcatttatcaacggtcttctgccggaggaagaggctaggga
cagaaagcacggcctgcctactgctctctggagtgccatggtgccacgtgctgagctagagtgttctgagccccatcctggg
agttgtgagtcacctacctgcctccactgcaggctctcctacatccctcctgtgatctttcctgagacaccacaaaccacac
ctgagaccccgggggagaaccttacagggataccaggtacccaggaacatcatcacagcctccctaccaaccaactccagc
atagatgccttgggcatcttcttgtcaaccagggtcaggtcctggagtaggcagggcgtggaaggagacccatgagagcgg
gctttgtcagcctgctcagggctactgtatctacgaagggctgttccagtgtccctgcccagtggcagctgccagatccctt
ccatggggacagcagggactctaattgctcacctgctgctcagagtctctgccagccctggaggtgtgtctggggaagctgt
gctaattaggcacacggtccatccttgtagggcaataggcatagtgtcaacctttcggtgcgtccttcacagcaagtaaag
gagctccagtctcccattctgatctacatcccggaccttagggatgacgtcctagctgttgcctcattgatgtccaccttcc
agatggacactgccctgctcaagcacagacctggtgactctcagctcagctgacctatgggaagccttggtccttgtgggga
ctgaggagagcatcccaggttgggaagagagcatgtaggatctttagggtgtttccaccagcagcagaggggggcctcatag
tagagagggggtctaacttttgcagagaccacacagcggcccttgctaaatgctgtagcgccgcaaaggggagtcgagctcc
acagtgggtacgtcctggtatctgtgccgcccagatcatgaacagtaagcggcatatcttatcattcatttaccaagcctcc
attctctggggtccctgggactccttacccacacagtacagactagattcagctcctgctcgctatagaaggaggctctgctg
gtgatagtcatgtaagttagagacagcaggtccctgatctgcaagacttggattagacaatgtggccccctccttctcgcc
accactgtccctctgtctccccgtggtcaaccgccatcaacaagcctaattacaaggcctcctggcactttttcctttggag
taaggcatgctccggcttgcttctgggcccttaatttttgatcagggacacctcttcgactaattatttgtcagtaatgagg
gaggagagatgaggttgcgaaagcgtccctgagcttatagagagaagctgcaaattaaaatacgaggcatccgtaaacaggg
cgctaattggattaattcaaaagtgatagattgggataagaacagagaggaagaccacaggcagattgaggtcagaataatt
ccaggagcgttgcccgggcttcctgtgatagatgtgagcctcaaagtccgagagctacagaaagtaaaatatgctgctgtgt
gtgcaaaacacatctgagtcactcaggcacaccaaccacccaggatgcatggccgtttcttaagccctggcactatctgacc

FIG. 4 (Continued)

cttgagtcatttttggagagaccagaactttcatatgacaaccgcctttctttcctctgttgtaataaagccctctctattt
gttttaaggtttttaaattatatgtacgtgtgtatgtaagggtatgtgcacatgagtgggagtgcccatgaaagccagaatc
tccttgtagctgcagtcccaggcagctgcctggtatgggtgctgggagctaagctcccaagtacatgggcctatgtgcatgt
tcttgaccgctgagccatctctccaggccctcattctgatttctcttggtgctgtttagtgtttttgcattctttgaatctt
gagccacacttatgcgtgggctatctaatgtaattgaatttaaaaaaaaaaccattatgtcagaaggtgataaaaattatga
tgggaacatcccacttctgaacaggcagaggtgagctgaactttcaagataaggggaagcatctccctgtgtcccagtgag
cactgtctgtccgtggctgcttctcctggtatctcagcgaggcatcaggtttctgtagggcatttgaatcgcctcatagacc
aaatgtgccctgaccacttcccctggccacagtgatgctttatagtctggattaactctgggctactggcctcactcccagt
cttggctgacacctaggctgtgggagagctaatagcttattcatattatttagataagtagcatagtatttgagccgtgtac
gtttttaaaagcatcaagtctttattcttagggtgagccttatcatataatcacaactgtgcaccatttcagttctcatggt
tcttccatggatcacactgaacagtaagtcctggctgcagaagagaattatttttgcacctgtctccaagtctattggttca
acataaacacaggcaatactcgaaccatatgttatcattccaccgagggctcctagacacaccccagtcagcttcctgaa
tttctaaattcagaaagggaatgtggagctgggaagaaatagtatttcacttaagactttacttacccatccgtccattta
tccatcccatctatctacccatccaacacattctcccatccatctatccatccatccatctatccatctcttcatcccatat
gtccataaagcccatcatatctacccatccattgtttgtttaaccatctatccatccatccatctatccatctcttcatccc
atatgtccataaagcccatcatatctacccatccattgtttgttcatccatctatccatccacccatccatctatctatcca
tccatacatccatccattcatccacccatctatccttccatccatatgtccatccacccacccacccatccatcatccagtc
tatccatctacccgcctgtatatccactcacccgcccacccacccacccacccacaaaaccactataaaaacatccatctct
cattcattactgagtacctgctgcatactaggtcctgatctgggaccagacaattcaaactttatacactcactcagtcttc
accattctgtgacatcaacttgaagctgagggtttaattctgcagagcgcaggcctcttggaggtccccggggcacaccaca
gtataagacacttcgtgtggagcacagaagccagtgtgccaaggacaccctttgctcctgttgttcaggtgtgggtgggat
gggtctggcagtgagacaagaggggccatgttggatatgcgcctcaagggaccatcatctagcaagcagggtagcttccagt
gatgccctaggcacctgctctccgaggtcactccctttaacttctggaagacaggagaggacacagccaaatgtactgaagg
cagatttgcttaggatccaggccaggcgtccatggatctctgcaaagagtgaaagtagacactgcaggggagctcggatgga
tgctctgtcaaggcagacgaagtgggcactgttccagtcatgaactgtatgttatataaatcgacccctctgtttcctcatc
ggggaacagaggtagaaactcttctcacggtaccagtgtaatggttgtgctatggataggtgtagacgctgaaattcatgct
tagtgagcagcatcagctagggcatgaggtgtttgtcacattctctgtgtgactcctatgtgctctcagaactcactgagtt
gaggatgagagcgccgacggcccggatggaagagtcagatgagacaaagaacaggtgctctggcaatgtcaagcaggttggg
agggcagggagtcttaactgggcctccatctgccaacctccctggccttggctgtcagccagggcagcctctgacctctgaa
gggcgtgtcctctgtttttctgagcaggagttgggcccacaaaggcagcccttcagtctcggacgtgagtaaatattgacgc
tggggctttgggggccctgaccgttgccacttaagcatgatgtggatgtctctattggaagctcagagtggctgaggactga
gctagctgggcaaacctgctccctaaggcaaccacgttctaaccagcccccccactccctggagttcttcctcctgcttcag
ggctaggacgaccctgatcatcctgcacaattaatcaggcaggcaacccagtgccgccacaagcagtcattacgcaggtatt
tctaagatggaagaactggttgcttagaatagctaagaggaatggaagccagtccttccagcagcctctgtggaatgggga
gacccatggtctcatatgttcagttgaaccaatttagctgtcccccccctgccatcgccaccccagtcccgtgtgagaag
aggcacacgtggtttgaagccaccaagcaccacctcagctttgtattcatgagcactcgcgtgtgtgttcgttcacaagctc
tctctgctgtccatgggaatgcacagaggatatctttaaagtcagcacctagacaccatcttgggcccggtgtacagtgaca
gcagatcttcaaccttggcctcattcgagagagatgtgcagaaacacttgttgaattccccacaggattccctgcccggtgc
tgtcctgtcaccttaacagttaagctactgttgcccaccgcacagttgggcatatcttactttccaaacattttttttaat
ttgtattccctttatccagttagtcctctcgatcctttccctccctctttacccaagcctttccaccctcagcattcccct
ttttacttatgttctttatactgacggtctaccatctccctgcctctaaaagccagctgtatgaggccactgtccctgaaat
gactaggtgtgaacagggaagattccctcatgagcatcagggggaaatcctatgatataaaaatgtctgcagtgggcgttgg
agagaccaactagccattaagagtgcatactgttctctaaagggacctgagttggtacccacattgggcagctcaaaaacc
actctcagctccagttccgagggacccgacactccagcctccaagaggatttgcacccacatgcacatacagtcacaaatgt
tactttttaaccttaaaaatggctgcagtgggatgagaagctgggaagtttaggcctggagattcattcatagaaaggaagc
tggctctgcttcccagccaatctctgctggatgtttgtaaaccccaaatttgatgctgttaacctttgctctaccagccag
gctactccagatggctctaccggatgttgtaagcatctgatttgatgacctcatgaatttgagcaatagaaatgtctgctgg
aaatggtttaccttctagagacagggtcttactatacaaccttggccgtccctgaactcactccatacctcggaacgcaggc

FIG. 4 (Continued)

tggcctcaaactcacagagatctgccgcctctacctcccaagtgctggggttaacggtgtgcaccaccacactaccagcaag
ggctatatttttatgctcttgctgtggactgttctccttgttacagagactggggccagcctgtaccaagacatagggctt
tgaggagacaagggaacctccccacccccagagtctgcttctgcagagcctaactggcacatgagagtttaccaatataatg
tgtattacaacaggaatatagtagggtgccctcaaaacccgtacactagtggttaagaatatgggatagaaattctgaattc
agcattctggctgttcattatcctgggtccacagcaactggagtctggtgtggtatgaacaggcaaagtagatttctgacat
ttaagagaggagttcttatctgccgccagcctatggagacctgtgttgttgagatgacggtatacaggacgtattgtgaatt
gcagggggagggcaaaaaacagggagagagatgagcccaaggtgttaagggggtccattgtaccatccttggatttagcttatg
tgcttgagaccatcaacagggggagcagacattgtagggttgccctctgagattcacccccccagttcacttcccaggta
gtgggagcctgcccccatgttggtcgccaggagtaggatcaaacacaatacccgtaagcctggtagccagtccccagaccca
gggctccctgccaggctccacccactggcttggagctggccacacaggcctcccagcttccgtaacttcaatgtcatcacct
aggcaactggacgctgccgccactgccctgccactgcaagccaccacggggcctccagcacctctacccaagtctatggacc
cacccagggcccaggctcagccaaggtaggcaggggctctgcttgactctcagctctcaagtcagggttcgcttgctgtccc
ccttccccacagggcaacagcctcaaggttccatcaggataaggaaaccccctccccatcaactcacctggtagcccagaagt
aaggctccatgtaagcaggcctgccacacgggcaggctggtggccgagacagtctgaagagacaccatctgtggctctggtg
gcacaaggcaacatggtatggcactttggaaagtcacatgtactgagtagtctccagggtctctctgtgcccctgtactgtg
acaggtcaggatggagacaagggattctgagatctcccaaaagtggttctggtatctccacagccttcattcctttaagcca
cctgaatttctctttattccatgtccaagagacaccaaacagctacctggatcttccaaggccatggttagtgctataagat
gttgcccctacccagtgcctcttcctaactctccctccgctacttagtctcagagtctctttcatccttagcctgtgctggg
ctttcccgcccctcacatggctggtgctcaacatgtctacatgcaggcctaagtgttgagagatggggcctcggtaggccctg
ttcctgatgttgtccacttgtgctgctgtcctgtgaacagggctggatgtcctaggactggcaaactatacagcgtcatatc
aggatgagatagagaaaatcctgtatagaaattattgcaatgaggccagagtgagtgagtgagtgtgtgtgtgtgtgtgtgt
gtgtgtgtgcgcatacacgtgaacacctcggttgtgtggtgcattgtgagccagtgtgcacacgtgggtggagaagcagagt
atcaggagtgtatgggccatacactctttgtggtttaccacccgtgttctcagcaggacctagcggtggccctggagcccaa
atggctggagtattgcctgaaagagagatatctgccccccagtttaaagtcagatctcatttgtagcccaaactagaatt
cactgtgaaccccaggctggtcttggatcctgatcctcctgcctcagtctccccatggttgaaattacagacatgttttacc
atggctagttgtcttgggtttctctaatttgattggttacttccactgctggccctgttagcatacactgtatgcacaaga
ccatcatagcctgagacccatagcctgagaccctcatagcctgaaacacccatagcctgagatcctcatagcctgagacccc
catagcctgagacacccataacctgagatacccatagcctgagaccctatgcctcgagggtcttgtgcctacagtggatgct
gacaagaccagcaagaagacacagggccctgctatgtgtcacacaaagccagtgctatttccttgggtcccaaaatctgaac
tcctaagggcccaaagcccaaatgaggatatatttgctttttcttattgttttaattttatatgtatttattcattgtgtcct
atatgtatgaaggcatgtgagcatatcctgagactgaactcacgtctttgagcttggcagctgtacatttagttgctgagcc
atctcacctagcccctggggtgtgaatggtgagttttgacctctaactgctcactcctgggtctgcccaactttccctgacc
tgcaaggccttgagatcatcatactaaccggttaattctgcctccaatgtctattcactgagcaccaaacttgtgctgtgca
cttgctgagctacatggctaagcctgtccatcctcggcattacatctgaacacacatagggtttaccctgcagcagatgc
catgatacttggggggctaggggctgtccagaaacccgagggggcaaggctctgtagctgttcccattctgagatgactagt
aagagtctatcaggcagcacagagcctttcctcatggccccagggctgagcacaagggattctgatgtgtttgacatcgaat
tctaccaggttaaaggccacctggaaccttctccaaggtagccccttggaggggtaagtgggactggtagtgcctgcgagaa
gccactttccaaattcaaaaccaaatggaagctgggccatgaggccccacaggtggctaaattacagacatagaactgttgg
gcccttggtaaccttgtccagcaatctcctgaaagccttgtgtagaccattcatgcaaggaaggtgtgatagcctacttgag
ggacaagaggctacagactccacacacaggaagagatggagggccctgaattgtggcttgttgagggttctgatgttggtca
gtccagaggtctgagggtcaggatggacactctagactccgtttctgtctgtgtcctcacttgttctacctgtccctaccac
ggcactccggtcaagtcagcttgccaggcagggatgcctaaaagctgctcatgaggcaaaaagagtttcacagaaactcact
cctggagtccggcgtgctctctaaattttccattcccgcgttagtctagtggatggatccacatgctctctttactataagt
gcctttttaagattgaattctgacatagctaaagcctttcgccagtgttccaacagtcctagaacgtctttgagctagacagt
gacattcagaatagcctctggtattacactatcaataaaagccaagtcgttcccatatacaggaatttacaatggtttagga
agtagatcgggctgtggtttagagtattgcattatttatgagatggttaagtagaacagaactccctagttagaaccatga
cttgggtgtgaaagcccttgccctaggagagtaaagacctcacacctggcttctaagactatagctgagtcacacccataca
cacgtatttacaatggcttaaggggaaggtagactattcaatagactaaaataggagctatggcaagggcacgaagcccttg

FIG. 4 (Continued)

accctggcttttaagattaagcaaatcttagatagagccctttttgatcccagttgttaacaatgaattttatcccaggtgg
ttcctgttagaccttctgtgtttacattcctctgtttttatgtaagaatccagtaacctctttgtaccttgctagtgtgtcac
ccaacttccttattgtcttttgcataaaaagtctgatgctcaatttgacattacattcagattccacacgacctctcctgtg
tgtgtctgtctgtcaattcatcctacgctttgtccacccgcgactagagacccgttccacacaaacaaaggggcccagaggg
tctatggcagttggcgccttcgaacagggacaccagagcgggttagtctttatttctttttctttcgtgtcctggatcgggc
ttgtctctgtgacttgcagtctctgcaccccacagctctgtcagggagttgggctgagtgtggaagagctagggctgcgaca
actcctgtgaagaggatgcttgccctgctgagacctgttctggctacctgtacacacagtctagacagacacccaccctgac
tacagtctcctgtctctcctgacttcagcatgagctccactctgccctcgatgtcgatggacctggtcctctttcctctcca
tcccttgctggcccaaaccagtcttgccactcactcccccaccctgcctggtctcccttggaagctctcggccacattgccag
gaggggctgctccccttgaattgcccctctatcaggcctggtgtacctctgaccccgccctccaaattcaccggtcccctt
attttcagccacgataacttggaggcataggtaggagtccagactccctgggcttcctggtccttctccctagtacccagc
cttggacatcagcacaggatgatcatccattctgcctcctagtaaccaggttacccaggatcccctcttctatacaatagga
atcaatttggtttttgagacacccagtgctagggacagtgctcagcaggcttgagaacactttcaaagagtggtgagaccac
agttgccgtgatggggcagagaccagatcaacgtatgtatgacacacgtatgtctgtctctgtccacagacgtagtttctca
ccaggccttcccctgacaagaggaccggacttgttctcttccactctgagccctatactaaagggggctgtgactttgctgtg
gtttgtcccctgctctatgcaggattgtcacctgcccgatgcttcacgctcatcctattacatcattccacaggggtgggtg
tgacaatccgcagttatcacagaggacactctgtgagtgtcctctttacagaggaggacactgacactcatgtgggcatgtc
acctgccctggttcgcacagctggagaatggcagagggccatgtggccagcacaggaagagccccagcttaagtgcctagca
gggctgaatttcaggttagggaatggtggagctagaggccatatgtcccacatggccccacccatggggtgaagaaatggaag
cagaaggcaggcctgagcaggtcagcagagagtagggtcgtctttggttgtctgaacatgggcagggctttggaaatgaggg
tgtgggcttccccaggaaggtaagagtgtgtactcgaagtactatcatctccagggaggggagagtagagtgcaggggtcaa
tagctaggcactgtgtgccctgagtgagcaaataagatgcaagacacacttactctctgtatatcgaggggttcctgctgtc
ttgggtagatgcatggaggtcagcatgctacaatgttcacttcctttggtcttgtctgagtttccacgtggtgccaggtgac
ttagcatggatgggaagtttggtcaactactgtctctttcaagaagcacagggaatgttgggtggcctgagggatgcaggct
agtcttcctccagccctgttcccattccctggcggatggcctgagcccaggcgagagaaggttaatgcttcacatagcacac
cctgccccacatggggcagctaaatttgtcttccttcaccagtacttggctcccccagcttggggagaaggccacccgctgcc
atctggacatctagggccacacctggctagggaacagaatgtcctgctgaaggatgaggttgtcttgtgagagaaggggagg
gatccagccagtttccagatggggcaggaccaagatggttgccacactggccctgaagaaggaggtacttctgcctgcatcg
ggtgggacctcagcctctgtgtagcctcctttctggaggtagcttgagggaaacaggcttccggcaccaaggccccgatgt
ggccaggttcttgatactctgagttctgtgtctttgccactgcccagagatacccgtcatttcaggagagacactccctggcc
atgttcctgagcctggcacgccctctgcccacacaaggatctcatggtgctagagccttcatgtccgctggagggaattca
cacagtggctgacatgggtccagagggcccctcctgtcatcaccactaatatactagttacttctgatttcaattcccctgt
ccactggaacaaattattagaagggatgacagtggagacaaaccacagtattgatcacgtcatgtagacataccataacaga
gatttcccaggccgggtaagtttctctggggatttccttgctgacccgaaaaaggcccttgccatagccaggggacccagtg
tcatcatgctgaagatcctgcctctcctgtgtctgggctatatgtggacagacttgctttagtttccactagggaaggtggg
tattcaggctcctagaaggtgggggtacatccccatggatggggtacccctttccagagcaggttcgggataattatgggca
tctggtatatcacaggtggcagtgaggctggggctgagcaggggtgagaggagatggggaataacaaggaaggaggtcccca
tcctgtgtgattgaagtgttctatgtggccaagtgacatctgtgtctcctcctccagtcaggtggcagggatggggaaggaa
ggctcagactcagagctggtcaagacagaggtttttcttgaggagccagccacctctggcttttaagggagagggggggcttgg
agagccaaacatttgaagtcacatgtatcccaaagccgtggtgacagggcatgatggggaatgcttgggagaaggactcggc
tgagttgggagtatgtgggggccaggcaggaggttcgaaggttggtagctcttgctgggaagttgagactcgcggccacgtg
cagggtgaggtaatgggagagtcggagacttccttaggggccagaggatagaggacatccccggcaaacctgctctggtgca
agccctagctgaattacttgggcaagccccttgggtctcaaacacagtttactcatctctgaactagttgggggagcccatc
taggctgctgcgtgggcccagaagtcctgccaggagtctggttagcatccctgggctctctctctccgtggaggcccacggg
gcctccacccacccagttttgaggatggaattgttcccagcagatgtaaatatccatgggctcaagtccagtcagagctgcc
ggagctccgtggaggagccgcgcccgccgttggctcagtgaggagctgtgtcctccagtgaggaggcctgtcattggctcgg
tgttggctcagtggaggagccgtgccgttggctcagtgagcatgtgctatccgtgtgtgtggctttccgtttacagccttat
tctcctccgcatatcctggcacccacaggtctggctgctgtaccccctgactctcatgctgttgggactccttgggggggggg

FIG. 4 (Continued)

ggcgggtagcaggtgctgaggtctgagtttggcacagaccatctttgtcagcttgctgtggtcctgtttcatgatgcaggca
ctgccaggcctggaggagatccagctcagcaaaggaggaggctcatctgaggctttgacggagctggaggcaaggctagggc
agggccagagacagcccagatccctgccatgcccacagcctgtgacctggctgctgacagagcttctgacacggcgggccag
gcggggccagccctccttggttggtgcttctccctaaagtctccctctgccgattctgggccttctatgcctctcctcacac
cacgggatgcgtgttctctctaggaaaactcaagtcttcagtaaaaactacaatctcagagccagtgagatggctcagtggg
tgaaggtgcttgctaccagttctgaaaactcgagtttgatccctgggacttacagagtaggaggagaaaactgactcccgga
agctgtcctctgacctctgagttgagcatctgcactcacaggcatgcacacacgcacaacgtgattatttctatatctgtg
cttcccaacactgatttttttttgtactttccagaggacaagtagtttctcaaaactggcctctttgccatcatgacttgat
gttttaaatcactttccgtgcttatgtaatctgttcctgcggtgtctggggatcgctccctctggtggacacatctcttagct
agaggagtgtgtgggacctatagaaagggctcagtaaagagcttgccatgcatctatcaatctatcatctatctacctatct
atctacatctatatatctatctatcatctatgtttgtatgtatctatcatctatctatctataatctatcaatctatcgtct
atcagtctatcatctatgtatctatcatccatgtatctatctatgtatctatcatctatgtatatatgtatgtacctatcat
ctatctaccatctagcaataatctatcaatctatcatctatctatctaccatctatcagtctatctatccattcatttatct
tgcctctgccctgcctctgactgtcatatgtctgtctctctataatctatctatctatctatctatctatctatctatcta
tctatctatctatctatctatccatccatccatccaactatcctatccctgcccctgactctggctctgactcttcaattat
ctctctgtctctctgtgcccctccctcccttcctccctccctctttcccttctgtctctctgaagagagagactataagtt
tataatatagtaaggttgggttaccagctgcaggaatttgtagaaaatgggggagggtgacagggctgggtgatagtggt
ggcttccgtgaggctgtggtgctccatgagttcagagctagatgctagtaaggaccatttaaggacgtgggcaaggaggcat
gtcccagctgaaggactagaagtacagagccaaacactagcaggtggcccatgtgcctcccattaagactgttaggactcta
gcaaccagtgaggggcaagataggagggtgagcaggggcctgtgtccctggcaagcaggtcagaatttgatcttcagcatga
gaggtttggttggatgctccttccttgtgtgggtgcaggaggacctggtaggcaggaggtgtggaaagcagaggacttggca
aggggtcttggggcagagctgcaaactctgccaagctcctggaagtctgctgcctgcaggtagccccttcccacctcccgc
tctatttccaggcactgggcacctgccattttttcttccctctgcttgagctggccatgtggacacaaggggtgaagaggg
acccaaatcctcccttgctttctcagtaggctgtccaccttcagatatgccgtttctggaattgggaaggcaagccagcatg
ggtgtcaacaggtggggtaaggtgtggcaggtagagttaccagcagagtactcctggtacaatctgtactgtgataccaga
tcccatccaatccaaggctcttgctgacaacttccaaggctacatctatgatgggaatcttccaggaacatacacttggagt
cctcagcctaacaggggggtctcaaagtgctcattcctatcctgagaacatcagtgggtgtggcaaaggaatttgggagacca
tctcagacagtgtggtcacagcaggactgacattcattccaggtgctgcctgccacaaatgtctttcccttttttttttttc
aattaaaaaaaaaatgtgggccagtgaaatggctcagtgggtaagggtgattgctgccaagcctgatgacctgagttcaatcc
ctgaaccccatgtactggaaagaaagaatccactcctcacaatcaatcaatcaatcaatcaatcaatcgaccaatgtaatta
agtaaaaatttaaggaatgccctgaaattctcctaacatataactagcatttattctaaaagtattattgttgttgtttt
gactgaccttgatctgatgagcttgcctcagccttgtcacagcagggactgcacgtgtgcaccactgctgtcttccaaacaa
catttgaagcttgaagctcagcgacttccagcgtcttaaatccccaggagaaacctggccccatgagccttgctcgctg
ccgtagcacctcaggctggcaccccaacctgcctttgcctccctgttcggatttcctgttcagtacatgttgctcggacac
taggtggttcagcacggtcttcacagtccgtctacactgtgctgttttgaatcagcagttcgttcctggtcacagtcaaatg
tcacctaacatgtccgggtcatattgtatctggcagttcctcttctgatgtgttcccagtctctcaccctgtctggctaaag
tgaataatgtcactgcgaaggggcctggagtccattcactgtgtgacatgagccatgtcctttcccttctgagcttggcgt
agtccttgtaaaagggagaagaggaccaagtggtccctggggtaggacttctaagcatgtcctcttgggtctcagggtgtcc
accagcctggcccagctgaccagcccactctgactgcgaagagatacctccctgaccaatggctcctcaccagaaagtacca
ttcccccggagctggtgaaggcagctctgtccaccttccatgctggttggccaatggcttgtcaaaaccttcatgactgtga
taaatgggaggtgggaaaaattaatccttattactggagaagagcataaattatgttaattcctgtgcttattatagttgtg
tgaccttgggcaaggcatgtaaggcctctgagcctgtccttctgagtagggcaggactgcgatatgtacagggtacttgtcct
gtgtcatcctcccttgctgactgagccccacccccactctctacctgtgctcagctggtccccttttactggccctctcagc
ttgtgccacttctctgaggacccatggcctggcgcgtgccatctctagatgcgtgccacaaaccactatgagcagcctcctg
cctggggtcagacaaagcgacagatctgccctgccagccctgggcaagtctggacctgtctgcttggcagtgcagagctgg
gccaagctggtttgcgggcttagaaggctgccccagggaggctgctccttaatgggcagcgggcaggtgggctggggttccc
ctgccccaccctcccacaatttactgtgcctgagcgccccttacgctgcccgcctccagggtgaccgtgagtgggcggagcc
tccgcgtgggaggctgtgctgaggaaatcgtggggaaagcggttgtgggtactagctggggctagagtgaccctgctcccct

FIG. 4 (Continued)

ttatctcctttgaggagaccatccacaggtgacaactccagggcagtcctaggactttagccttagaccttggagggtgagg
accatagagggtcttgagtcccacggtaacctgcataactgtgcattacaggcatggttccagcaggggcgccctacacac
gctcttactaagaggaacggatgaagtttgagctgtctcgaagacctggcgacaagtcacagcctttcccctccaacataca
caaaccaagacctggcttgacctaaccctggccgtcattgtaggtttaggacacggtgacggcagtcatggcccattctctc
aaaaaactgacccaagaccacaaagactaaattcccttctccaacagcatctacccaatgtgagggcacatgcccttcttac
ccgtttttctggcagcagaatccgggaatggcgtctctaaaaccaagcttgcctcagtctcacctcctggaccagagaatgag
ctgcttgggagtggtgatggtagggaggaagagaaggggagctagacagggaaaagggaggcaagggggggggagaaagca
acgtgagtggaaggacttagcacagctctggggtctccttgcaccatcataggcagccccgccgtccacttggctcgcctgg
tactgaggaaggcaggattccccaattctcagtgtcctccctcttcttccagAATGAGCGGCAGCGTTGGGGAGATGGCCCA
GACCTCTTCTTCCTCCTCCTCCACCTTCGAGCACCTGTGGAGTTCTCTgtgagtatggagaactccgcctcactgggtttgg
ttggcttagctggcttggaataaataggttgggagaggggtctgctgaggtagcagctgccttgggccatgtcctgtgtgca
tgtgacccacagtcatggtctgtccctctggccagttctctagagggctgtgggcacagagatcatgtgtatgaagcatttc
taatagtcctgaagggcaagccgagggctggcagggattgtgggagctggaaaactccggaagtccaaggacatatggctta
tctcctgggatggacacacacacatggggtagcctgatatcctgaaccaggggagcacagcggattctggagcagatgctaa
catccagtgtccttcccctccacccccacagAGAGCCAGACAGCACCTACTTTGACCTCCCCCAGCCCAGCCAAGGGACTAG
CGAGGCATCAGGCAGCGAGGAGTCCAACATGGATGTCTTCCACCTGCAAGGCATGGgtgagcggggctgcgctaaagactgga
tgttggtgataaatgcgggttggctttctccggtggaacgaggaagcagggctttgggtagcccaccttgggtcggaagaa
aaatatgcaatgagctcatggtactgtcgattcctaggtaagaatggattcaagcatgattggacccagcggtaggaagagc
ttcgggcatggctggacccaggtggttccctgggaccacttcctctttcacttgcatctctctttctctggtttttcctggg
gtacctttgttctttggaagcctcggccctcagagattgtccaacattttgaggccccgtggagaggccacccctcttttc
ctttgcccagaaacactgcttcttcatgttggtctgagcatacttgtttgctatgtgcctctgagctgtccctatctttctg
attggcccatgtttctatagctatctctggactggtcaggatgaagggtactaaggcaggctccttatattaggagaggaag
atgtggccagtggagacagtggtttattcctcatcttgtgcgctctttcctgggaccaagaggggtaccaagcagccagcc
tttggaatttgcctcctattgggagctcctcttggcaagaagacacagtagctgtgggattctgttcctgcctcactctctg
gctaccactgccgtgccctggtggtgccaggaactggaggaaggtgactgaagcatgcaaagggcaagtgaaggcctctgtt
cccgaggaagtccctcgaggccttctgtcctcagcatcctcccctactggaccaccaaagtgctaggatcccaaaggcgaga
gggttgggaaagcgtcaggcggggacttgttggaggaaccctgcaagcacattaaggaagagcaaagcccaagccgagttgg
cacatgtcggctgcagaggcaccagacagctgagcatgtctccagtgtagccttcctccccactagcacctgatgagccatat
gctagaggcccagggactctagaagccaagcaaagtgtgaggctaacccctacttggagggagaagcctggccacttaggc
attagtgaacaagggttgaagagacaggaggcactatgcccttactctccccctctctctgtagaggtggaaggttggtcaga
gcccactgatctcccatggaactgggtgagactctctatagtggcagcccagggggtaagggtatcatcctggtgatgccc
acttctctgagctctgcctgtccagccctgatctctgccagctcaggagcctgtttcagaatagcagttcacctgtaagtgt
ccatttacaggcaagggaactgaggcagatgctgtggaaggagagcctggggcttggggaagagaatggtcctgcatcatg
gtgaggatagtccccatcctgcctgttactccgtagagacatgattctgacacccatcatctaggatatatgtgttctcca
gtatagagggataggaggtggctactaggctcagggagggagggccttacacaaagactctaaagatgcctgctttaggag
ttctggaagctgcctcccacagtctaagctacccagcttatgcctgagagggcagagtgctcagagaccccactgtgactga
aggaagaagcagggaacagccctggggccccggaggctagggatgtggtacccacccggccccaaagatgcccaacgtaaa
cgtgttggcgggtgctcctgggtgctcacctgctggggcatgctgctcccagcaggggtaacacgggcggggctcaacacct
ccacaaacaaggggccgctttctcaggtagcaacacgccttgcagtaaagccatggacgaaattcctgggcgcacagctcag
ctcctagaagtgggaattccctggaaacaggacttcctggcctcccttctgcagggctcagctgaccctcatgcacagttct
ttcaagagacagctactggtccaacagcttcctgtatgctcagaacttccagcagtcctgacagcaaaaatcaagactcaga
gatgagtgacagatagggccatgtggcagcaatgctccagagctcatctggactgcagggaactggggtggggtgaggtct
tgcaggtgctgcaggaagttgggggtgggtgggggatgcagagagcactagacattgcatgccatgaaatgaggtagatga
agtttgatctcataaattacatggtcgattacagcttattaggatggcagaggaaagggcatccaggcaccacagggagca
tctttgagtccagggatggaggcagctatggaaatgacagtttggggtacagatgtgtgagagtggtttggggacctacaga
atccatcatcgtttcagggtgcagcccggaggaagcaatggtctgggtatagactacagagtacagactggtctgtgaatgc
tgcagacagggtagcctgcccaggcccacattcagctccacaggtgctctgctatgtccagtgtctgaagtccaggagctga
gcctgctgactcaccctgggggggggctccaaagtctgatgggcatcagaggaggggttgtggagcactctcagaggga

FIG. 4 (Continued)

ggagttggtgagcactctcatagggaggagggtgtgcatgccatggattcacgtgttgtttgcagcggcttctaaagtgctg
ggaggtttaagagagtgcctgagtgtgtgtggtttagagttccaggggctatgggaggcacagagaggaaagggccctaag
agggctgggataccagggccagctcagcgctgtgatgaggtggaagctcccaaatgctatccccatccctgagaactctagc
cccatccctagctgggtccaggacaagaaacactacccaggcatgttctcaggtcaataggcagttcctggcatttgaggttc
taaggacttccagcaactccacctcctgtgttctcaggtaccccctccacccccacagagccctactcagtgatgactggtg
tccagttgttcctgtgtgctggacaatcccacccaaataccaggatagtccagcaaaggtgtcatggcttaagccagcatgg
cccttgagtagatgggatatgtattctcttcaatggttcctctgtgtctaagggacctcaaacgggagattgctttctgtc
acatggaatgtcctgagcaggtctaccagctgtggtgaaccctcagaactccatgatgctcttctcccccaacttaatggct
gtcagaaaccggtgcagtcagtgagttcaagttctcacatgctcccgagtctccacatccttgcttgtgaagttgaggtgat
ggaaagggctagaatggagaggaccctgggagatcggtgcagcctcctgggtaccagcttgtctgcctggccttgtgcagag
gggtgggccaggcctcgacatctaaccattcccgagtctcattggagtagagtgtgtttgtaagattaaagcaaatgggatgg
gcaggagcggatgaacccctagtgggtctgaggagaaccctaggcatggtgagggacgcccttgtggccttagcttcctgtg
gccatgtagatggcatagcagagcctagacagttgtgataggtaaagagggaactgaaggtctctggggctcgatgtcctgg
gtttgtagcccatcctggtcttcctagttgggaggtctcaggatccttagtctcctggatctgagtggccccatctctaa
gatggggaagtggacagatcagaagcccataagtgctgtttctcccacagggagtgacagttagctcaagggcgaaggccta
tgttttccacactgttggagactctgcacagtttgccatgcaggggcaccggactctagagctggctttgccccttggccat
tttggcttctgcatatggagctccttgctcctgcaaatggccttcagttctagctgtcctttagattccgggtgcttcaca
gaaactccactttaaaaatggcctggagactaggtgcggtggcacgtgcttaaatcacagcccctgggtggccagtggaggt
ggatctaaagtttgaagccagcctgacctacacagagaaaccctatctcaaagtgaaatgatcccccctgcccagctagaag
agaactcagagatgcctctcccgggtgctgtgtagggtgagctgaggggcccatgccaaaggctagggctagtcacagggtg
ctcagcaaggttgagaatcaatgggtgttgtcacatgtcggggggacaggtcccagatcaataaggccctaccacagggtctt
gggagattgagtggagggcaaagttcacattgtgagcaccgtgtgccaagaggcagtggagggcttgaccctgagggcagaa
atcccagttctcaccctccatgcccagtgtttgagcagacctttctctctgcttccctggttctccatggaccacaagaagg
tggacaccaagagccagaggccggtccagctcttcaaatacagaaaaaggacagagtgctgatggtcagcagaggaaagggg
agagaggcaggtgccctgggcgcggctgcaggatcactgccctttcccgcctcttcatgtcctcctccaggcctgcacctcc
cctcagatgcccctttcccgctgtttctggcgcctttctctagcaacagctgttaggaacagatgggccgcagagggttggg
gaggtgctgcagctggctgggcagaaggtgctctgctgatctccctgtggcctgcaggggactgagccagggagtagatgcc
ctgagaccccaaggacacccaaggaaaccttgctggctttgagaaagggatcgtctctctcctgcccaagagaagcatgtg
tatgggccctgtgtatgaatccttggggcaggtaggtcaggaaggatagaccttggcagggagaatttatatcaagggaagg
gcagggcaaacggagatggagactgagttttatgtgatcctcttggggaccccagctcccccaccacttccagtggtttct
gaccactcttccttggcaggctttggtagcaagagggtcgaaggtgtatagtactgaacttagctgagcccctcccccagtt
ccagagtctcactgagagcccattcctctccccaactccagggtccagaggaagagggacaaagccaccagcagggacagta
tgtggtgtgtttgctcctgaatcaacacaccatacttgggcactgtagtcttgagcatgtgttgtggagagaacgccagggg
agcctgcagaacttcacttccacctcagctgtgagagctacaggagcagtcagcaaggcagagcctccagtgtgttacccc
agagaagcaggtgctgaggaccctggcactacctaggggcaccggcagtggaggcagacaggcaaaccacctaggaggaagc
aggagccaggctggggctgtggcagagaggagagctcagtggtgggcgtccctttccctggccagaccgttcctcagggctc
acagactctcaggccaggtgcttcctctgggagtcaggtgtgagttctcacggacagtcccattctcctttccggccttaat
ccttccctttattttctccttggggtgtttgtgaagccaacacgacaattgattgatgaggacccagagtggctgagggaca
caattccttaaaccccaatctagaaacttgaaggccatctcttcagggctctcctggagcagcctggccacacctacggggtg
ggagtctgtaaactcagcccttagtccccatggagggaggctgcagttgacccctggtctatctattataaatagatccctg
agcagtgtttctccaaagattgctccccaaaattagactagaaactgactttattgttcatagctgacttatgagcagtgca
cacctgtgcagccccagccatgaacatgcctctcagaccagcgtagggatcagtatgaagtagtccatctttactgcttctg
tgaattccagagctttgaacaggggctacagccactgccacagccctctgaccaagcccagatactgcaagctctctggagg
gagaaggaagctggtttggaacttggcgagaaagggttaaacagaggactctgtcttcacaccatctctgcgtcttcttgaa
catccttagactctaaatgtgtgtgtgtgtgtgtgtgtgtgtgtgtgtgtgtgtgtgtgtggcggaggggctcaagctgtc
cctctaggaggcctagagattcagggccgatgacccctttcacaggacacgcatctgttgtggaccactatggtgacttcat
gcgtgaaccagacctgaaactcaaatgcccccagacaaggggcagtggtatccactgtatggtccccactaggcagatgctg
atatagagcccctggctctacaaactctaccatgcctgtggtgccttctcgggtggtccttcaaaaattctctttggtggag

FIG. 4 (Continued)

tggccctgtctctgcttcctggacttagctagagccaggacaaaaatgctgtctgtaaaactctgttatgggttctttggct
ccaaccgccactttgggcctttgacggtagttggccgtgttctcgactctcccctagcccaagcatactggtgtgtctttcc
tctactcagtccttggggtggtccctgtaggtccacgattccctggaaggaggcaggttctctcccctgggtcgccaaggct
ggcggcaccatctcttccctcagggtgacccaacccagactgcaaaggtctccaggaccagggctgactgctcatgctttag
agtgtaggctgtttgtaggtgactgccacagccctcgggagccttccctgagtggcagcttagaagggtccgagtgggagtg
tatgatctccaagccagccactgaccctgcatccccacctgctcccctgctcagcctgcttggtgcggtccaacacatctc
cgggcaagctgaggcctgccctgagttgatgaatagtcataaggaataaggggcgggccccggtttgttgttggatgcagc
cagttgacagaaatgagggagatgggcagggtgagaatgccaactctcagtccgcacgcctctgagcatcctccgctcctgc
cttcctagccacagagcctcaacccctcagtccaccccacgggcagccaccagtctacccctaccccacctagccacccag
acccatgcctcgtcccgcggcacaccagctcctcagcgtgtgcagaccccacgagcctaccatgctttacgtcggtgaccc
catgagacacctcgccacggtaggtgtaacgtgcctggtatagggtctgcttagaggcctgatgccatccacctaggggct
tggcagagtctgccatggttggggttcagagagacgttctcttgactgcctgatggcagagggtaggctggagagtggaca
ggttctgcttctgttcatccttggggcagctctcgaggatcagcagctccgggctgggcaggaagtgggatgtgggatggga
ggcttggctggcgtctggtcagggtggtagagctgctgcccaagcccctgggttggatacttctgagatgactgttgaggct
ggtggctctggccatgctcagggtccccaagatagtctgccctaggagcgctgcaaagaggtcatctttgtttgggctttgg
cgtgaagctgccccaccctgccaagagcatcctcacctgggagtttgttcacttgacagcgcagatggggcgtttctcatag
ccatgggctctcctccgtgtgggtgtgaactccaaggcagagacaggcagcgggctggacccaaggctccctgttgctcctc
tcaagcaggtacagccagcctggcagagagcagaaggacagaaggatggaaggagccacagcctgtgcttggcctgagccca
agggacttgggctcatttccagacttgccaggtccctggggtcaggcagacaccaggctgctaattgagcagcctttattga
ccagttaaaatggggagatatcacatgagatcacctgagtaagtgacccactgcatgatcgtcattggggccagcccttc
ttgatgaagcagaattaacatcagaatacaaagggcagcttagaagcagaattaacatcagaatacaaccagcagcaggaca
acccacaacacctgggtacagctgccccacaaggctatttccctttaggagagcagagagagtaaggaattgtacaggaat
cctgggatggcagaggtgtgtgtgtgggtgtaggggtgtgctggtaagggtgtgcatgtggcgtgggggtgtgcatgtggcg
tgtatgcatcctcttatgatcagggaaaagactgagtgtgggttgaatcacggttttgcacaggtgcccttcctgaggccag
taggaggcagagtcactatccaggaccacacagagacctgccccaagacagccgctgactctggtcctggtgccgctgccc
taggtctcagaaccagtggtggctaccatgtcatgatatttctcatttgtgtgtgctgtggagcagtgtgctgtggtgtgt
gtgtgtgtgtagtacaggtggtgtagtgtgtgtgcatgtggtatgtatgcatgtgatgtgtacatatgtgtgtgcatatggt
gtgtgtgtgcgcgcgcgcatgtggtatgtgcatggtgtggtgtgtggtgtgtattcacatatgtgtgtgtttgtacccacaa
accatgtgtggtgtgtgtgtgtttatgtgtatgcaaacgaaggctagaggtgaaccttgggtatcactcctcaggtgctgtc
cctgtactctgagtctctcacttgcacctggggtatgctgtgtgctgagtaggctagactggtctatctgtctgtctctgcc
tcccaacactagaattacaagcacacactgccatgtctggtctgttacatgggtcctttggatcaaatgcaggtcctattt
ttttgtggcatgcacactaccaacagagccacctccctgggccccgttgtttcttcttaaaacgcaggctctgtggctttc
tctcccttcattgcttcatcacagcaccatgcgcttcctctgcattctgaccagcgtagcagtgtagcttgggatttgctg
gggctccaaggctgggctgagccatcattctacctgcgtgggtgacttagtttcctcatttcttgtgagaggatcgtgtag
gagagcatagcctttgcccagagaatgttaaatccaatgtggatggagccttcgccgtgtgtcactcccccaccatctgc
ctttgttgtccttacaacttgcagcagtcccttgggagctcacaggcaagacctgtccttggagaccggactgatttcagg
atgccaccttatccctggatgggtttctcataagtgtatcccatcttggtttgggggctcagtatacaagttcaggctttat
ctctggtgaccactagctatggttttgggatgagacatgtgaggccatgggctgagacagtttcctttctctgtaagcagggt
agtagcaactaactctcatgcctgctcaggccgcagatatgagctatgaggtaccatggcctctggccatgactgtgccagc
cttttataagtcagtggaggtacagagaagctggcctagagaactgggcacatgttcttcctcctgtgagcctgcctcccac
cttcccttctctctctgaggactagagactttgaccgagtgatgacctacagctgagtgcagccctgtatgtaaggcgaggt
tggctcggtcctcctgcacacggtgagcccatttacagagctggaaagagctgaggccactggagctgggcctgatagatgg
gatgagatgagcggggagaggctgcaactgccactatctcctgatgccccaaactcttagcttcttcatcagcttccagttc
tcctgcatgtacacgtctctctctctctctctctctctctctctcacacacacacacacacacacacacagagagagagaga
gagagagagagagagcagctcccaggatatagtaaggcaagtgtgctctggtttcttcagtgtcttctgtgtgaagtggggct
cagctttctttctgcagaaccagcatcatggttgcaggactggtgaacctggttatcctccaatcccttaaccccagacca
acacacacacacacacacacacacacacacacacatgctcttataggcaccacacatacatatgaacacaaacacaccat
acatgcacacacaaacacacacatatgaacacacacatatgaacacaaacacaccacacatgcacacacaaacacacacata

FIG. 4 (Continued)

tgaacacaaacacaccacacatacacacacaaacacacacatatgaacacaaacacaccacacatgcacacaaacacacaca
tatgaacacaaacacaccacacacgcacacacaaacacatagcacagcacatatcaatatacagtggtgcatgaatacctca
tactcttgtgtaaggcagcatagacgtgcatgcacagcccagggctggagttcaccctgtctggagcaggcttccctgtgct
cctgcagaaagcatggcttctggaccggaggagcccgagggggcagccccaggtgagagaaggtagccgagtaacaggaaag
agctgtaggacagacgagtggagctggtgcagtgctggtaactgaccacacgggggcagggccgagactgggagaagggatt
tggtccaggtgggggccaccagcacctagggaagtcagagtagaggaaattctggagattctgcactggacttgctgactgg
ctagatgtcggggaaggagtgtgttagagtggcctcaaaggctttcgactgtgatggggaattgctgcaggggctgagaagt
gagattgggcatttctgtgcagtgtttgggggggggggggcttcagcagttgagcagatgaggtagagagggtggccgggac
aggacatctgtggaggtggtcagatgtgagaccaagaccaggctagaggacaaggccacaattaccttagaaggcctgtagt
gatgattagaaacactgtagggttcttctgtgtgggaggtagacaaagagcctgagcatgtgggtgggagtggccaggtgga
cttgcaggtgtgggaggcaggtgggcagggtggtgtgatggacagatgcatgggtgggagtggccaagcagacatgcagttg
tgggaggcaggtgggcagggtggtgtgatggacagatgcatgggtgggagtggccaagcagacatgcaggtgtgggaggtag
gtgggcagggtggtgtgatggacagatacatgggtgggagaggacaggtggacattcaggtgtgggaggcaggagggcaggg
tggtgtaaagtggacatgagtgttatttaagtcggggaagggggctgtgttaagaggagtgggagacaatttgggaaagag
agccacactgaggagcagcctggaagccagaagagggcttcatggtgacccgggacaaaggaccccattacaaggttagaaa
agggaccagaatcagctgcattgagggagctggtgacccgggggagggtagaactaagtaggatcaggtctgaggccaaggc
atacccaccagagtcggatccaagtaggtcatcctggacccatgtcccttctcagtcccctcgctgtgttggaacgcatctg
ctttccatgctccgtcccgctcccctgaaagccagctgatggggtgtcagcccatggagccaatctgagctcctaggaaaca
tcacctcagctggtgggaagtcttctccactggcccaaacccaaaccctggaactatcctcgatccccggcacaacacctca
tctatgccgtctgtgtgtccaagggcctcagagctggccacccagtgctcagacgtgcacggatccactgtcagatgtcctc
caccaccaagcaaggggactgtgcacggctagcctataaccctctctgctgaacccagaagttatgctctctcacctcttct
gctgtgttcatcacccatgcacttgctctggccagggtccttccctgccacccacacagaaccttgccgaatcccacaag
acctacagattaaaaaccatggcagctcttgcctttcccagagccccacccttccaggacaccggcttctgcctctttggtg
gtcagtatttttctcccttacgtcccggaggccctaagccttgaatgctggttagctggatggcttgttactgtactacgaggg
gagagctcagaagcctctaccaagagatgtcaggagcctaactgagccagtcgatgccctggatatgtgggcagcctttgtc
ctcacctttcacagcccatcccccagcttatattgggatgccttctccatgggggggggtcccaagacaacgtcacagcct
cgctatgggtcgctgcaggtgacagggcgacacacatgggcccacatcacgcttagtgaacatctcatgtgtcactatctaa
tttctcagcttagctgctcattctttgtttctccctgacctaagatttaggaagagcccgggaggtccccactgactgtccc
atgaatggggacagtcccagtggggactgtcccatgaatgggacagatgggcagaaaggcagtagggggcgggggaatgca
cgaacaccaatgctggatttgagactacaagaatgtgccagggagaggtgctggcagagctgtgtcccctcttctgttctct
cagacagacaactcgcctttgctgttggggtacactcggtgatttaaaaattcctgtgaatcactgcagcttgtaggcagtg
ccaaagagatgggggagctgcctagagaaccctggaaggctctgctctgtgatacccctggttcaggctatgttggtggagg
ggtggcctgggtgggtcttgcagacacatgcctggcagcccagtagagcttctgggggcacgtttcccgggtttgaggtgtg
gaaagttccacatggccctggcatgggacccgggcaaggccctgcctcggcgggcaaaaggagggtgcaatgcacatacctct
agggaggcagccgtcccccatgcacaagtcctgtcttgttgacatttccattcgtttaatcataggctcggggagactgtg
ggaaacaccatcaggatggaggtctccagctagcacagaggcgggagagatggctgtctccacagagccaggggctgtcag
tcactaacccaggcaagcggaacccaggctctgacctgcctgcaggggaagacccggtttcagacgctttcttcccttta
gaagaatccacagtgttggctggtgtttggaagcaggaggaccctaactccccatccctcagtgctgggctcagagcagaa
tgagtgacatttgtcaccagggggccctggggtgagccattcctgcagaacaccaagattcctggaaacagatgtggtcac
aaggtcatgtcactcatacctgtgctggatgggtgaatgcctcttgaccctacccagaattacttcctagtaagggagcgg
tgaaggccatggggcagcaaatcacgtgcccagaggctgggccttgaatcgaggaagtgatgttgggataaaggaatggagg
ctgcgcagtggaacctgagaagccacagcacactatgctctgtaagctagctcctgtctccagttcctacccagttgcttc
tgtgaggcagctagggtgggccacaactaacctgaatccataggacgggggtgtgcagaggccagggcaattctagaaag
aagggaggaaagaaaatggaggaagggagaaaggcaaagaagggagaaagggaggaagaagagggaagggagagagtgaga
gaaggagagggagggaagaaagagagggaggaagggaagggagaggagaggtgagggagggagagaggaagggaaggagaga
gggaagaagaaaagggagaggggtagagggagagaaggagggagggagagggaggagggagggaaggagaaagggaagaag
ggagagaaggagagagggaggaaggagagaagacagaaaggaagaagaggaagtgatggagaaaatgcaggaaaagatggag
aaagtgtgggggaagggaggaagtagaagcctaggcaaaatcctctcctactgaggtcactggatttgggtagggctgtgct

FIG. 4 (Continued)

ccatactctccagttgtccggtggtctatgagaccatgttcccagccgggcatggtggcgcacgcttgtaatcccagcactt
gggaggcagaggcaggtggatttctgagttcgaggtcaacctggtctacagagtgagttccaggacagccagggctacacct
cgaaaccctgtctcgaaaaacaaagcaaaaaaacaacaaacaaacaaacaagagcccatgttccctctgtacactttgggga
ccacggtgggaactctgaccttaaggctgagttcccctgctgtgtgctggggatcctggtatcattcctgagagcctggct
gaggattagaattggtgggaccaggaagactgtcagagctgctgtgggctcagcatgaggccagcacacaggaagttctcct
tctgaaagggcatgctcaatacagggtatggagatggtgggtgccccctgccggccaggcagatgagcctctggctggtggc
tgtgaatcagggactggtgggtcactgtggcgagatctggaggcctgtgtgtggcttctcagaagcacaacagtgacagagt
caagtgcctgtgcctctctgagagggcagcgccgggtcaggacccagcacacttgaggccctgtgtgctaccgtgacctgtt
ctcatttctttgtgtgtactgactccgagtccctcatcagcatcacaccgaatcacctcgatgtaaactgaggcagaggagt
cacggaaagggtttctgtgtgaagcagggttaggggagaccggagataacacagataaactggaagggaagcccagagcgct
ggggcggcttcaggaggtaggatggctccgcaggctgatctcctgccgaggagatgcaggtcagcctattctcctggaactc
cgcatttaaatgtgacaaccgacaggcaggctttctgtcactgttttatttgagaaataaacttctcgggggaattgggt
gtaatatgccctttgttgctaagcactggatgcagccagtccacctctgaggtccgtcttggtgttctgtgctatagcaaag
gctgccgtgggtactgaagtcagagaggagtcggtgtggaaggcacctgctcccaaccttaagaggtcgttcattttctgt
ctacatatataagaacagatcgatgagattgtttgtaggttagaaacagttaagatgtgagatgggagtcttcggggtaaaa
tcatagtatccaatgtgtgcatgtgagggcaggagcctgatagcaggacggtaagagcctccttgtctggttaggacaagag
agtggtggagaaaggagaggatagaggggaggccctgccctcaatcaggcatcaaagagcttgtctaactatggttgggta
tccacttcaatgccacgtgttggtacaaccagtacacgtccaagagtgagaccccggctgctgttccccatgtcccctgctt
tatgacgctgctcagctgcctctggagctcagccttggagacagccttgctccttgtggcagacaggctctgtcccttcc
tcactgggccttgtgttagtgggctggtgctgatgatggatcagttgcaaagtgtcagagctcctggattctggcgtcctgg
tggctgaagcagggttgttccttctgaaagaacagccataggttttcttgctcccagacctcgccccacaaccatgcgaca
agctatgtgtggatttcattctcactatgcagaagataaaaatggaggcccagggatgtggaataatacccccattcctctcc
tgctcctactacctacctacctgccaaggtatagtgctcaccctgggctcatctgtcaacctagctcagccaagagagagtg
ctagaggagtgaaccagcgtcatctacgtctcccgatgctcaagggagataagaaactcagctgccttgtagcaggagcttg
gggacctaagggacccgttgtgagtgttctatgctgatgaccctctgctagtagagcgaggtcaccagcctgctgtcacccc
aggcctgaagaggccaagggagacaaggtgtgaatactgaagtctgagcctaaggaaagagagtagaagcaccagtggctg
tttccagcagaggtgccgggtaagccccagcagcactatctgcaaggaccaggaagagaccccgggactaagggaataaga
gatcctggcctctctgtagaggtggggctcactgagacccccatctgtctgagcccaaaataggtcttaccctcaattgcc
ctggggttttctggatgatcccagaccctgtggtcacagtccagtgagcgacacagacctggcaatgggcgtgttctcaa
acctcatccccatcggaactattgtccccaattctgatgttggcctttcccatgaaggctggtccaccagtggcctggac
actgtaggaagggacacccttggctccatgacgccctcattcctcagggcctcttcaggtcacgcccagacactccacttg
caagtataggcacatgtgtgccgccgcaggccgggcatgccctaattagccccactatcttggagttctcattgaaagcaaaa
caaaccaaaaaagtttgggtttgcccaggttcttccctgaggccaagtgggtctcgtctgggcttccgggggcctctgggt
ctggggacccctgggcttctgtgtagacctgcttaggcctctctgacgaggcttctcatttcaacagcatgacgggaggca
aaagtgggggccaggttgagcctcactgcctggcaatgaggaaatggtttccttcccatgagcctcaggaggagggaaccc
tgtgtagaaggaacgtctcttacactctccagtcactggggtctttaccatctttgggagacacggtagacactaagaccag
tgagggagtggaagatgaccttggacctgtaagaaacgagcaggcacaggagatccagcattcactagacaagggaacagac
tctactgggcagcctagtgccctatagaagtctgcagaggcctgcctctctgagggcccgggcttgccacaccagccagg
ttttgcacccagtgctgagggcctgccttcccgaagcgcctggtccctcctgcataagctcccacagatgctatcgctgtt
ccttttggttcaatgactaagtccttggcacccacctccaatcattgaagaatgcagacaagttaaaatatgaacctcgctg
ccgtgggcctgcaccctgcttctgagacagggctccctgcccatcaaggatgatggggatcgggcacggagggctgctgct
gccttctgcagatgtcatgacttcttccaaagcccttgctgggaagagagtgaacttggttgcaggaaggaggtggcgctg
cagcttcatcctggatctgaaacaatgtaaccaggttctgggatccctggaagcaggaaccaggaggtagagccatagtgca
tctctgctcattcctagacagccgcaccagagagagtgaccttcctgactatcacatagatgtgtgaagctgtcttcagact
tatcacattgttgtacattcactcattcattcactcatttgttaactctttcattcatccatccatccattcattcattcat
tcacttactcattcattcactcattcattcctctgccactttgtcctgacagaaaacgccttgagcaaccattccaaatcgg
gatcatgtggtccagatcagcaccactcagggaacacagtgggtgggatccctgtgtctatagagccatctgtctgtgggatt
gcctgagtctgttaaatcctttgtatcttcaggatccctgtgtctgtggggaccgtctctgtaggttctgcatcttcaaat

FIG. 4 (Continued)

tctaatgagtaggaatccagaaacatttggaaaaaatgcatttatactgaacatgtacagacatgattcccttcatcccta
agcagtgtgttctaatggctacacggcatctgcagtgggttaggtttgtgagccagctcggggatgtgtgcaggctctgta
taaatactacgccactgtctataaagggctttatttaagggtgtctgtggggttcctgggcctgatctctcatgaacgctga
gggtcacgggtagaatgggaaccacgtatggaattctgaaggtcagtagctggtttcacatggtgaaaagagggtcagagct
gtggctcagtagaggagtgtttgcctggtgtgtgtgaattgtgggttcgatccccagttctggaaagcaaaccaagaaagaa
actggtgaatgtaatcaataacttactcctgccactgtaggtcatagcggtgtgcagagagtccattggggtactttcttc
ccacactcaaacccttgtagccattggtccaaccttcagttctgtgtggttcctcacagactcacggctcaattgaggcat
aggagctgccttccagaggagagcattatgactggtcaaggccaacagcatgcaggcgctctagctgctgtagccagggcta
gcccctctgagctcagcagagactgtggcaagaccaaggtagaggcttccactgggcggttgggctgttgtcagaggcccgt
gggagaatgggggtgcttgaatggggggctgtgctgggccaaccggagttctgacttgatgttgctcaaattcctacctcag
cagaagtgggaccatgaattcctacctggagtctgttggcagaccttggagtggggtggggtctcctcagcctagaaacccc
acagagtgggaggtttacggcctgcctctttctgaagggggcagctgtcgtatcccttgttccctttgaatggccttggtgc
tgggagaggtaaaggttgggtgctttcctgttttagacagggttattaaggtataattcacagagcatacaatcttctcact
taaaatgtacagtttggtaggggttgtaactcgcatggcagagtgcttcttgcctagagtgtatgaggccatgggttcaatt
cccaacactgcacacagtgggtaccctggtgcctgcctgtaatcccagcactcgagaggcatcggcaggaggatcaggaaag
agttcaaggtcagcttcctatataatgagctccaggctagcctggctgacatgagaccatgtctcagaaactaaaaataata
aagcaagaaagtaaataatgaaatgtactgctcagaagctttgtctgaacagttgtatgtaagcattgcttctagaacatt
ccaccccaccagagagaaatcccgagtccctccactctcgatgtaaagcctagcagccttgtttgtgcctcccctctgtct
ggcttctgcctctctgtctttgccggttctgagtgtttacctagttgaagtcacactgtgtgtctgctcaaaacaaggttct
gaatttcatccacactgttgctatgttatcacacccctgtggccagtggcaattctaacttgtttgtccacttccctggggt
agaggtagggagacagggcaggtgtcctgtgacacaacaatttgggaaggcataggaaggactatgggggaggattcatggg
ttggactatgtcctacaaacccagcccctctgtagagggatagtttatcctatggaaacttggtccccttgacaaggctt
ccacccaagtaaagtagggccttgcatattggtgggaaggcgagtccgagatgccccagtgtcccagagctggggccgccaa
ggaaatctctgctggattctcagaggctcagggtacagaggtcacagtagtggcaagagccagcactcggggttcgagagat
ggctcagtggctaagagcatttacttcctttacagaggacacaagttcggttcctagcactcacacggcagctcacaaccac
ccataactccagttctggggggtctgatgccctctccgtaattgatctggggatcacactctgtgtccgcagccaggcttga
ccacccatacttagtaagccaaatgccacactaggaagtgggacaaagagagccactcaagttggcttcggggtccaaagt
gagagtgaaacttaagctgaggaccaagaagttgctcatctaacactgggtcaaggtgtggggcagcccactggtgaccat
cactgcagtttagtttcagtgggggcaaggcattagaactctgtgaagtctctttctgagagacaatcttccctttggggc
ctttcccttctccaagtaggagattcttggagggaaactcccatttctttggggtccgttgttttaaactcccatactcaga
cacaagtttagattaccttcatttctaccaatcctcttacacctttctggcctgcttctgcacaggacacaagtgtgctgca
catacacgcatccaggcaaatactcatacatgtaaatttaaaaaaatcttaaaacaaaacaaaacaaacaaccagggctgga
gagatggcttagaggttaagagcactagatgctctcttccagaggtcctgagttcaattcccagcaaccacatggtggctca
caaccatctataatgtgatctggtgccctcttctggcctgtaggcatacatgcaggcagaacactgtatacataataaatta
ataaatctttttagaacaaacaagcaaataaaccaacaaactagactgttacttgccctttgcacgctcagctttttctact
gtctcctgagctgctctccctcctgctgggcggtccttagtaggacccttcctttctgtatcagcttccttgacttctgaccta
accccaaaaactcctgtcaagggttcacagtggaccactgaggccttgtcttctctggccacctcctgcaaccatcctccat
cctggactgaggcacaggaggggctgagcacaaggtccccagcagagagagacccgtggcatggggcagtgtccagtccagg
ccttgggtcttagcctcccttgttgtctgcaaacacttcttgttctgaggcttagaggaggcaggctggtggcaggagatat
atgtgcagaggttccaaggcctctctgaagagggcaatggggtaaaggggggcactttgctctgagatcacacttccgcgtg
atctagtctcccgtagattgctggtcaattggacctgctcattcctgcctcacacctttgggcccctcttctgtgatgtggg
gacaaggacagtgcccacctcaggcctgcgggaatccatctgagcttgagggaaggttcgtcagcacagacaggatcgatta
agcatctacacttagggacccattctgcacagccattgggtagtcttccccaaatcctgcttgccatctctggacgtggact
gggtagtcctcccattgataatttgttgaaacacccaaggaaggaaggtgagacttcccttaaagctcctagggaaggctgac
ttgtcctggggtcccaaggacagagaaagagggttcccagagctcaggttccttgaatatgtgatttagggaaggactggg
ctgcctgggctagcctgagaaccagcagggatgctgggaggagctaccaacctggaggcctggggaaggcttgtaatgga
gataaagtcagtttaaataaattcctctggaggctgtcacttagatctctggtggctgagcagccttggcggagtccatcac
ttagagggctgtatctaagaatcctgccttccagggcacccatgctctaaatcctgctgtaccccaccccacccttgcagc

FIG. 4 (Continued)

cagcatccaggctctcaggtctatgtgagcactccagcctctgggctgacctgggagcatggtggtacccacaggggtctcc
ggctgggaactttcccaacccaaacagctcccttccaggtaggtgtgcaaagccccaatccaccttgctggcagctgggtgga
tcccaagaagccctggcacccgggaggcggacggagaggggcaggcaggagaggtgaatgtgcgtttatcccaacacaagta
gtggcctgttggggtggggtggggcccccaggaaatatttgggatgacttggagccccgctggcccttaaggctcctgtaac
aagacacctccccgacgggacagaagcggtagctggggcttccaccttagcccttgtttctcccctcccacctccccettcc
ttgccagGCCCAGTTCAATTTGCTCAGCAGTGCCATGGACCAGATGGGCAGCCGTGCGGCCCCGGCGAGCCCCTACACCCCG
GAGCACGCCGCCAGCGCGCCCACCCACTCGCCCTACGCGCAGCCCAGCTCCACCTTCGACACCATGTCTCCGGCGCCTGTCA
TCCCTTCCAATACCGACTACCCCGGCCCCCACCACTTCGAGGTCACCTTCCAGCAGTCGAGCACTGCCAAGTCGGCCACCTG
GACAgtgagtagccgtgttgccagtggatgcgtgaagggagggcagcggggttgagtgccacggtcctggtactgaggactg
aatgagcacacaggctgtccacatggggttcccacctggccagagccaggaggagcatcgagcaggaggcgggccctggggc
tgggcagtgtgggtgtggccaccccttggacttgtggccagagtcagccagcctcccactgagtccggaaaggtcagagtgt
tgttgccagtgaggtccatggggcaggaagagtggccgggttttctatactcagtgccttgaaattggtctggtcctgaact
tctgctgaaagtgttgggagcccacaggggcccaccogtttgctagttgtgggtttgtgttttgccctcatatctctctgtg
cattggcttgggactggctctccaggtgctgggggctctggtcctttccctggtgcctccaggaacaacctggcatgtggct
gggattagcagatgttgacaaagtcccacctgtacacttgctgagagttgggcagacagctaagtactttgacttgcccaag
gtggagtctgtgcccatttcacagtcagggaagctgaggtatgaaaagggaaagcagtttgctcaagttatgcagaaagtga
gtagatgctggactggggacacatggccgtgagtgttcttacccactgagcacccaggctctctgtgggagatggggctgca
ggaagagcagactgggacttcagaacgctggtctgggcacacaggacattgggtaggaagggcagccctagagccatccagg
tctccatacccagctaagtctgagtagagggaaccctgagcctgggacagtaggaggtgcactgagggatgttaagtcatcc
acccactctctccagggagcagctggagatgcagccatccacgcagtgcaagctctatctcactctcctccagcggctcttt
aaaaactaactcccacagtgtggctctcacattctctttggagactgaagagctggacagagccagaccttgtaggtggcca
ccggtgatcagctgtgcctgactggctctggtttaggctttgacctcctagagtttcttttacctactgttctggtgggct
ccccagtcactagaccatcaccaattgaatgctcagcccagctgctggagctctgaggggcttcagtgggccgagagggtct
gggtacctgtggtgctccatcccgagtcactgtgggccagtgtgctccactctccgtgaccacaaattattggaaggcactg
aggtcaggaggtctgaatgagacaggaatggtagagtacacagctgttactcctgtcctgggacagtggaggaaaccatcta
acatggcctcctgaagttggtctttgtgtagaactacctgctaaaggcctcctcttctgcactgtctgtagtttggggggtt
gaaggggacctaggctcttcctccacccaagctgagtgacctagggtcaggtcaggaagcccaggagacacatgggtaccta
cctcagtcacagcgggctctctacgctgctcttctacttccaatgcattccctagctccatcttagagtgaggcggggtcct
gtctgtcataaagatctggtgatgctgtatgtgggattgcctcccttcctcttccttgccagagagtgttgatgaggtcgct
ctttgccgtgcctatgggctcaggtgcctctgatggtcagggctggtctttgacaggggtgacagtgcccactctactgaat
tcttcctcccatttgggtcctgtgcagtcccctctgaggcactggacatcaagcgtcccatgatggcctgtgttcctgctgc
tctgctctaactgtccccaggggttagtctgctcagactggccagacataccaaagatcagggaaggcttggcctcccaacc
caacttccacccaggaccagggcagcagagctgagctgtcaggcaggaggatgctactgccagccccctccggccctgtca
cacaggggcagaggtgggaccaacattgataatgagattttggcacctcggcgatctgggagcagacacccaagggtttt
ctcgatgctgagagaagggactggcagcagctgctctcagctctggggggtccaactgtgtgggtgctgcccagacttgccac
cgaggcccctgccacgccaccggctggtaactgatagataattcatatttttctcaagtactattccatattgactgctgcc
cccattcctctcagattggcaaaaacatgctcactggcctctaagtgaccacagctgttaatggggcctttggtcttgccat
tgctgaagccactgtgggactctctgaccccaaaggatctacttacttgtcctgaccaacttcccttagcctgaaaatctgc
tggtgcaataagaggtctgggaccttagagtgtgaccctgcatgtatgaacacatacgtgtatatatacatgcacaaggtcc
catatgcccggacacctaggtacacaggtgtgtgttatgcatacatgtatatacctatgagcacacatgggtgtaaatatat
atgtgctcaggggcctatatatatggatacacagatgcactcacatatacctgtaaacatgccggcatgtgtgtacatatgc
acacacatacacatgccaacagatgagcatgtgaacatgcatgctaatctccctggttgctgcctggggacagctggtctc
aggagtccctcagtggaggaggaagtgggacaaggtccctttacatatccaaacagcaagatgggttccctgctgctgtctag
cgccagctcagcccttcaccctggctttgccttgctgagagagacggctcttttcagtattggagacattgagagacagag
ttctgtggttaggcaagaggacccgtgtggatggatggtaaccctggcctggtatgatgtctgtagaacaccaagggcaggc
tgtgacaccgccagcctactacagaggcagctgcagaggagcccaagagtgagggcgcgctcatgaatggcttgactgcctg
agagcattacagatagacagacagacagacagcctggacatagtcttaagtgaccttcaggtgaagctgccttcaacctgtg
tgtgtgtgtgtgtgtgtgtgtgtgtgtgtatgtctgtctgtctgtctttatgtctgtctatgcttatctgtcctgagaga

FIG. 4 (Continued)

gagagcccctacctacccacccacccacccacccacccagcaggcagcagcccctggagggaagcacaagcctctgtgag
ggattcttagggaggacagggctgagtcaacactaatggatttggagcaaactttccagcccctcggaggtttgcaaagcac
aagaatagaggaggtgtcccgacatgattgtggtatcaattgcgttatcctaaaagtttatggaatgcataaatggaattaa
taccttttactggcacggggagcaattatgtatatttaaagcccagagaagagttctaacaatgtttattgtggagatgaaa
cgtgaattattaggggaaacaagagcacttatggagaaatcgcagcaattgctcatattgtgtctagctttgccggagagaa
tgggctgccagtaggctggctccggcttggtctgagcagggtacctgcaccggagatgtatgtctgctctctccatccacta
gtggtctaaaggactttggtccccaggaggcacagaatctagcctggagactctgaactcctgaatccaactgcagctcgac
actggcaggctggtccctgtgtctaagggtgctccctccccagctgagtggtcacatcacatacctcagggtcctagcaggg
gacaggagacagggcaccttggaggacaggactctatcctgtgatgctgagatgcagggcagggctcagtccagcagggaa
atgtaccatgaatcaacaataggaaatgaaggaggggtgttccataggtctgactggcctcctcatcttggaggttggtcac
ttctagaacgttctaatcagaaaccatttatgaatctacccagggaggatggtgggcagatagtgtgtctctcggccagcac
agtgctaaggaacaagccaggcccccctttgaggcaagcaggcgggcctctgggcatcagagcctccttgctcctgctca
cagagctcctaggatcccagaaccactcctagggaacttggagcagtgggcagggcagagagaaagagagttcctcaaactc
ttgggatatgctgttgggttcaccatttgtttctgccctttgctgatgggtgacctgcccttgacggcctccgagatcc
tcttctgtaaagtgggaaaggaggtatacatgcctactgcaggccgagggatggcacctggggtcccgagatgcccattcgg
gtcgggtctctatcccctctcctgtaaagttctccccagtgtggcatgagcagatgtgagacagtctgaggaagggtcagct
ctaggccttccagagtcacaccagttctcctgaggggaggacggggagtgaaccaggaacacactcccagtacacacagcc
agccctgaaaaatggacagttcttgtaatgtgtgaattagcactcaatcctccattgacagcacccccccccccaaaccaca
ggggatagaggccagtgtgggagtgtccatggtaggttaaagctggtcaggagttggctaacactgccaggtgagatccagg
tgagttgaatgttgcttacctgggccctccaggctggtggtaggctctagggaaccacctgaaatgtattagactccatcc
tgtgccctgaaggctcaggccctgtcacctcctcttaggaaaaggtcacagccacatccaggacctcttgctcttatatgag
ttagaatattctaggctttgagagctgtaagtcagggtcctgcaaccaccacttatcagtgcaagaagccaaggtgggctaa
gactggcgctctgagatcggataaccgggttctaggtccggctgtgcggtacacctgaaggtagagatgctctttggaaaaa
ttgttggtgtggtaggtaaggcagaaacaattcagtgacccaaatcccacgcctgtgtctgcctctcacctctgtctgtgat
aggtcagctctcatggtgctgaacctggggagggtgagatgggctgtgccgcgctctgcacctgggcctggttccagggagg
ctctcactagctttgctcagtacaagatcagagatttagacccagagtgtccctgtcctatagttccaataaagatgttta
aagttcaatgacaacttatatttaaggagctattgcctacagcactgaagactggctctttcaaacatgcacacgcatata
tgcacatacacacactcaggtacatgcacacacacattaacacacacactcatgcacacacatacacacactcatggcacac
acacactcatgcacacacatacacacatacacacacacactcaggtacatgcacacacacattcacacacacacactcatgc
acacacacacatacacacacacacacactcaggtatatacacacacattcacacacactcatgcacacacatacacacacac
atggcacacacacactcatgcacacacatacacacacacacacacacacacacacacacacacgcgcactcacgcacgca
cgcaccttgcctccctggctcctggctatcactagccctgagactgtatggaaagtcacaggtccttagagaaggagctgg
ctaagatgagtgcttagaagggtcacagctggagcggaatgtgtgactgccctgagatacccttgcaatctcaagctgatga
ggttgatcccgactgtggaagctacagctggggatggggtagggacttcaccactgacagccaacaggggatccatactgtg
cacagagcaggctggctaccagcctcgctgtgggttcctgtactggacggtcctgtgacctgcaccccagccctaatcacag
gtgggagaggctgatggctggtggccagaggagaggctactcaggactgccctgaaggagtggccaaggcacagctctcctgc
tggctgggtcaggaagaagggcagcaggggcccctttgaactcacagggaaggtgagcctatggttctttggatctggtcac
agactgttctcagactacactcttttcttcctgaagtccccagatgggtcctgggtcctggaaaaagattagatgtccaagt
tagggctggagtgacggaggtgacagggcctcctaggaatatctctgaaaccccctgacagtggccttctggagctggagcat
catacagcaaaggaggtcagccgcacccagccaaccagccacctggagcctccatccccccatgacttgatgtcagggggag
acacttcccagtaagaccagggcaggccaggttcccccacccccacccccgcccctgcctggcagcttcctcacccccccagga
acacaacccccagcccagagctgcctgtctttcctgcctttggtgttctacttggtcacctgactgtcctcttaaccagccta
tctggatcctgatctctggtctctgacctggtaagtctgatggaaatgaaagaccaaagatggaggtgtcgggtcttgagaa
gacaaaaccaaactggaactcacttctaagacttctatgacccctcatccccaaaggtggttctcaaccttcctttaacac
agttcctcatgctgtggtggcccccaacccataaaattacctttattgctatttgtaactataattttgcatggggtaaggt
gaggtggggaaggaagtaagagacaagatggagaaaggatgtgagtctcccagtcctctctggctctgctctctctgggcac
catctccaagtacctcctcactcctagctgtccaggagctgaccaagccctgtcctttgggatttgtacagacacttcatta
tgtagccatgattagtctcctgacattcgggacctgattgaccttcatcctctgtgctccgtcccaaaggctggggctgagg

FIG. 4 (Continued)

ggtcacacatactaactggatctttcatcaggggtgctcaggaaagcagcccccagccctcagccccagcccccagcccc
caggccccagccctcagccccagccccatcccccagccctcagccttcagcctccaggccccagtccccagccctcagcc
cccagccccagccccagccctcagccctcagcccccagtccccagccccagcccttagccccagccctcatccagtca
ttagcatgtaaaagagcaactgttgcttggcagtcctctagattttatgagcattttaccagaaacccgaggtctacagcca
atgcaatgcaacctctgattactgctctacccccagctcagctggcaactttagaaacaaaattctagttcctaaaatgtc
caggtgaagggtcagagtaggcaccttacagagaaagcagcacagacgggcccatgttattcctttggtctctatgtaaag
ccatcagctgcagagctatgtagagcagcctcccaaattcccaaccactacctttctccctctctgagatgagactaccaggc
cctcacacatcagctcctccgcctggggcagaaactactggaaggttctctgctcctgccaaggataaatgggctccaaacc
ccatgacctgggaccctctgacttcccagtcttagtgcaaaaaaaaaaaaaaaagaaagaaagaaagaaagaaagaaagaaag
aaagaaagaaggagggggagggctggagagatggctcagcagttaagagcattgactgctcttccgcaggtcccgagttc
aaatcccagcaaccacatggtggctcacaaccatctgtaatgagatctgagaccctcttctggggtgtctgaagacagctac
agtgtacttacatataataaataaataactctttaaaaaagagagagagaaagaaagagagagagagagagagagagaga
gagaaagaaagaaagaaagaaagaaagaaagaaagaaagaaagaaagaaaagcactctgtctcccaggccaccaaggt
gcccatatggctcttgcttgcctgtttgagatcttgctcaagggtcgggggtggggagcaggttactcagctcctgaggggt
gccccagctagctcctggccaacctctctgtaggggaacagactatggccttccactcacagagcaatcagtcagacttcac
atctgcctcccggagtgtcctttatcttctttcagaccgctgttctttaggaacaactacagcctctttcctgcacacttgg
caggggcaggcactggggcctccaatgatgtgtttatagaacatggagcctccttgccctcagcctgcatcctggcttgatg
gtgccagtccggtgacggttacccgagcatcattcccctccctaaggttctatcggggctccctaagctgtgcaagagctcac
ccctgctctcaggtgctccctgaatgaccgaataattgaacaatgtaaattgtgcgagtcaaggccaagatgtacccacaaa
ggggctgccccaggacctcttcttggatgataggatccataggttgctcctctcgcagtggcatttctccaagagaaacgaa
aacatggtggggagtcatattcaggggctgtggacctgggttcctccagatttgagagatcagactgagtctaccagacctg
tgccctgctctgtggatctgccctaggaagagtaaaagcctgtgatcccagagatgattctcaaaggggtctacggcctcag
agatcagaaactctcacacacacgtatacacacacacacacacacacacacacacacacacacacacacacacaaagtgg
gctacaaaaaaaagtatttttaaaaagcccccacccacagcctttcgttctgaatctgtcctaacagattcacccaagctggt
taacggtatttgcggtttgcaagatactacatgtcccgggaaaatgacagacaagttattatcaccttcccactgtcctcct
gcccaaacctgcctgtgccgggcacccagctgccgggagcgggtgcgaggaaattaacagccctgtgccgcgcccgcccccg
cccgccctctcacccaccaccctgcaccggtcctgccaggctaggggcttccagccaggcccggcccatcttggactgtggc
gggggggggggggtgggggtggcggggggggtggcgagggggggcgcgggggggggagggagggagagaaggaggaggagg
ggtcaggatagcagccgtggcaggagggacgtctgctccgctccgatgttgggcaaagtatttcctgcaagccccgcggaac
acacgcatccgcgcaggcaagtctggacggcgctgtgtcaacagccgaagataaataagatttttatcagctcggaatctgtt
gaaacacatccatctagcggttctagggaaggagaggcaggaggagggcagcagggaggaagcatccccacatgacattctg
gaaacagagtctgaccctgtgtaggaaggggagcgctggcaacttcctagtctcccggagactcgatatcctggagtgttgt
ttttaccacctgatcttcggaggtgtgggaaagctttggtatctctcgctgaaattccccacctctggctaaaatggactac
cacaaacttaacctgtggccggggtggggctggtaggtgtgtgcgcccaaagccccacgatcattggattcaagacggcatt
caagggtgcagaagtgaaggagccatgtatcttcatgggcttggatttttccttccaccctgaccgggtgggagacgtgtccc
accagagatgactctctcaactctgattctttctctgagaggagacagcctttccgcagctgctgagttggtaccagggaca
gctccaggcgctttaagctcctcccccagggtggggcattcagtggctcatccttaccagcccggctactctgcaactatcct
tagctttccctagacctcctagggtcccactccaggccatggaaaacagtgccaccttctggggaggagggtcaggcctcag
ctacctctgaccacaccttggtagtgttagtgcatggtttggggttgtaaccaattatcctaggtcctcagaggacagggat
ggaaaggacaattgccttcagggtcacagcagggctccagggatgggcactgtggtcaggcgaggtttgaagcctcattgct
caggagtgggtgggtgaggggagctctgatgcccctccctgtggctgagctgtgccctgagcctggctccatcctgataaga
acacggaggtgaagctgatgcaccctttctccctccaggcatgtttgggcttcccaggaatgtggccttaggcaccattaca
cctgacttgctcccagcccatctcggctcctgccttggtgggtctatgaccccccctaggtcattgttcatgagctagagc
actggagggaaaggttaactctgtaggagactccaggtccatgagccccagcagctgtgccaacccacaaattaccttacct
ggtaatgagcaaccatgctagaataaggggcctctgaccttgctggctctctaccacacagctggcatctggggggttgagtg
gtaagtcagtggtagacaaacctggcaggtggtccaatttaggggaatccagcctgaattcctgagccagaacagggagcca
agggccagccttcaaaggctaatctcctttttccgcccctggtgactttggtctcagtgtctccccaacccactgtgggcaa
ggcctgtttcatggggggtgttggccacctccacccctcagtctattttctttaggtagctaggcctcacaaacaatgggcac

FIG. 4 (Continued)

tcgggagatgtttggtaatgcttgggactgtcacctttaccaggaagttgcctgattggcctcaggttgagtctctctgagc
tcaggatgagctgggttcccttcaccgttaggcctttgcaattgtcctgagcctggggcttgctgggaaaccttcatttgtgg
ataagcaagagcccagggcacttcactgtcactgtatatgaatttacttaatgtcgggaggggcacctcgcactgtgaactt
catgccaccccgtgtccttcctagggagccacagtaattacagagctagtgtgctttttaccaagtgcaggctgtagacccc
caacacctgcaggctgctgctgctgctgaaggacaggtgtgtgtgtgtagctgtttattggcctttccccagggaaccagct
actcctgctactctgtccccagcctgcacagatggagaccaggctgcagtgtactaacttgaggagaggccgttgcaaaaaa
ccaaagcccagatttggatgtgcagaggtcaggtgtaccctgtccaagtctcagagtcccccatgtatcctggggatgaggc
tgtggctccttcctccagaatgttaggatgaggatcccacacaccagcagacagtggtcaccccccctcccgaaagtcacac
caacctgctggtgtggccattagctctccctcagctgctcccccctcttaggctctctcagcttttcaaaacagtccctgaag
cctctgtggggtccctatagtgagtatctcttgctttttaaacaggagggaagggactatgtcatggcgcctctccctgcc
ctccctcattgcatttgcctatggtatatgctatttctgcatactccattgtggagaaccataagctatatagggttaggg
tggtcagaatcccccactgtcccttgcaaaggaaagatttggtgtgtgagcaccacctgccccattcctgtttgttaacagc
ttaccatctctggcctcagcttcattaactgtcacaagggagcatggtgtatataattcatgtgtggtggagactttagagt
gaagtggagcttcataaaaatcccttgggagccaggcggtggtggcacacccctttaataccagcacttgggaggcagaggc
aggcagatttctgagtttgaggccagcctggtctacaaagtgagttccaggacagccagggctacatagagaaaccctgtct
cgaaaaccaaaaaccaaaccaaaccaaaacaaaacaaaacaaacaaacaaaaaaaaaaaacccttgggaagagctagagaga
tggctcagaggtcaagaggtcctgagttcaattcccggcaacccacatggtgtctcataaccatctataatgagatctggtgc
cctctcttctggcctgcaggagtacattcagacagaacactatatacataatagatagatagatagatagatagatagatag
atagatagatagatctttttaaaacaaaatcacttgggaaggaagacaagaggagtgagtcaccagggggtttcaggagccata
gtgagagtcagctagcaggtgaataaatgggtatcttgctttccagcctagatcaggccgctggctgcataggtaggattt
gcagcattgagcccgtttgacaagctcagaattgcatcctctgccttgcatagaatagtctcactctgattctgaaactgac
ttggtcttggcagggccagtacaatccttagaagagtgacctgggacacggagggggcgggggaggcatgatgacgtcccat
tgtccctgagagacatcctggcatgacctcaggtccagtcagtttccaggatggggaaagcgggtcttgcccccacaacag
cttggctgcctggacttggtgactttacttggtggcacagtgctggtgactggtcaacagcatgcaaggtcttgctggttca
gagagttctccattggaggataaaggcaaaggcagaaggggcaagccacccacctactgagtgattcttctatgcaaggtag
aaggatgcaattctgagctcgtcaaaccacctcaatgctgcaaatcctacccctgcagccagtggcctgatccaggctggga
aagcaaaactaggactgattcccactgacctctgacccacacccccaacactgtcttacccttgtcatccttatgcaacgg
tccaccgctcgcagcctttgagatgcaggtgagacacatagccaggcaggtgatgagcaggcaccaggcacgcccatctcta
caatctgaagcatgcctgaagcatctggaagcaggcctcatcggagcgcttgggaaaggggtcttgtggaagcatccggaac
tgagctgccatctcaacctggccccttctctcctccagTACTCCCCACTCTTGAAGAAGTTGTACTGTCAGATTGCTAAGA
CATGCCCCATCCAGATCAAAGTGTCCACACCACCACCCCCGGGCACGGCCATCCGGGCCATGCCTGTCTACAAGAAGGCAGA
GCATGTGACCGACATTGTTAAGCGCTGCCCCAACCACGAGCTTGGAAGGGACTTCAATGAAGgtgagccccccctcccctc
ccagctgtgggacactgaccagaggcatagctgagagatgtaggccagtgagcacagcggtaagctgctctcaactctcccc
tcacaggaacccacaccctagccctctttccatttcctcagctctgactacagtccaagaggctgatggtccagcaagggtg
tagtctgagggaccagctgaccttggagaatcttgtgaagcatccctgcagtgtccctggtgaagcctgtgacaccccccagg
gtcagattatcctggggacagcttctgtcccgctcaaggccacctaaatgagggttgcacagctctgagccttgcctgggact
ctcacggggacaagccctgtggcctcagttctgccacacgcctggtacaggggtatgggatggaagatgggccctctctaa
agctgtgtcccctcctggcagGACAGTCTGCCCCGGCTAGCCACCTCATCCGTGTAGAAGGCAACAACCTCGCCCAGTACGT
GGATGACCCTGTCACCGGAAGGCAGAGTGTGGTTGTGCCGTATGAACCCCCACAGgtaggcggggtccaggctgggatacaa
agccaaccttacagggtggggttccctgggcctctgctctgacctcagcctgcctctcaggcctttcctgacagttcattt
cactgtgggcagcgagcttgggcctgtgctcaagccaactttagctctctgtctctctgtctgtctctcgtctgtctgtctc
tgtctctgtctgtctctcgtctgtctgtctgtctgtctgtctgtctgtctctgtctctctctgtctctgtctctctctcgcc
tcagctatatagcgaggtatagttatatgacctccaacctttcaaccctgccctccctggagggtctaatcttcaatcttct
tgcttgtttctctcaagtacagtcttctagacatggaagaaagagttcccagacatctcaggctccatttgcagggacaaaa
gcaagccagcaagcatggggtggtgggtagagggtgggcaattccatgtgtgggggggtagtgatcatgaaaggcctcctag
accaggctggggaatcacagaggacgcctacaggagattggagccgtggaacacaggctcaggagagtagggaagacagag
atgatcggtcagccttaagagggcctgtgtgcagagcctcgggagagtggtgccagctggatggagggtacagtggaggtga
ccagacatgctgcacactgaggtgcagggtggatacggaggttcaggctggaggcgaagggctcagaccacaggtgagggct

FIG. 4 (Continued)

ctaagggagggaaccaggctggaggtggtggttgccaaaagtagacaagtgaaggaagactggaggaggcagctgtccactt
tgacaccagaagagtgtgtggtcaccttctagatctgatatgagccccagttggggccaaaggcaaggtgaagggacttcag
tactgatgtgggaggtatcagggcggagactcaggaggactggggttaggtctcatctctgacccatcctctaccaagccct
ggggtcctgtgaggcagctttgaatgtcagtgggacagggccccatatacacacagacacacacagacagacatacacatag
acacagattcacacacacagacatacacagagacacacagagacatacacacctacacacacacagacacacacacacagac
aaacacacacacacacagacacaaactgagaaacacatggacaaacacagagaccccacccacccacacccacacacacagaa
acaggcagagacacacagaacacagaaacacacacacacacatacacacagacacacacacacacacagacacacagacaca
cagacacacacacccccacaagcatcctcccctctcatcagaaaaagcctcaccagctcaggcatgagacacaacgtaggttt
ctcttgccctctagtggttggcaggtgtaagttctgtgaaggactggggtttatggcgtttgtaccctaaccttgaaactc
ctttctggggatggagtccctttcattcctctgcccagatgagtccacagtactcatcacacacttgacacaaaggctcaca
cacacccactcacatacagccctgacatttgacctctgcctgtgttaaggaagatgactgcagcaagcacaccacaaactct
gtacctcccctaagagctgaaaccaagactgagctctcagcccagagccagcacagggctgtgacggcacagatggatcggt
gggagggcgggcaatctcacgtgagtgtagatggctgaatggatgggtgagtgagtggatgggtgggtaggtaggtgggtga
tagtcaggcaccactgggggtgggcaggagagcaggtgagcaggagtgtaagtgggtgtatgggtaggcaagtgagcaggtg
tgtggatgtatgtgtcaatggatgagaggttgaccggcaagtgagtggggtaggtggatacgtgggtgtgtagacaggcgtg
tgagcagatggatggatgtgtagacaggcgtgtgagcggatggatggtttggtggatggtaggtggataagtggcgagatgg
atggataagtgcaaagatggggtggttgggtagatagatgggtagatgaccgtgaaccatactgcagcgtccctatgcctcc
tcagaaccagggccagaggtggcagctacaagtcctttttcttagaaggtgggccctgcatgctgactgatactaagcccttc
ccctgtctcccctgtggacagGTGGGAACAGAATTTACCACCATCCTGTACAACTTCATGTGTAACAGCAGCTGTGTGGGGG
GCATGAATCGGAGGCCCATCCTTGTCATCATCACCCTGGAGACCCGGGAgtgagtctgccgtggaaggatggtagaggtggg
gccgtgggggggcatgtcatggacacagggagggcttgctctcctcggtgggcattcagcttcaaggccagtcacgaggggt
ctgcgggagttgggcagggtcaagagtggtctcttgagctcacagccacgctgtgccgacccaacagTGGACAGGTCCTGGG
CCGCCGGTCTTTCGAGGGTCGCATCTGTGCCTGTCCTGGCCGTGACCGCAAAGCTGATGAAGACCATTACCGGGAGCAACAG
GCTCTGAATGAAAGTACCACCAAAAATGGAGCTGCCAGCAAACGTGgtgagtggggctctgggtcagggtatgggcggaggg
tggagttggatgcacctgagtgtggggagtacctgctccaaaggtgccaagcatagcttcatccaaagatggatctgggtct
gaatggctgaggctgggaagcctctccaggcgggacagggcgaatgtggcccaagacatctcacttgtctatgctctgaggc
taggagcatgtgggaccctggtccagctccttccagcctaggtttgccctgtgtgcacaccacacccatggcaggtgttcac
ctgggcatctcagtctttgctctctggctcatttatctttcccgacctgcctttctagCATTCAAGCAGACCCCCCTGCCAT
CCCTGCCCTGGGTACCAACGTGAAGAAGAGACGCCACGGGGACGAGGACATGTTCTACATGCACgtgagtgggctgggaggg
caggtctgtgtgttcccatcacccaagatcccaggctggggaagtacagatgtcaccagagatgggcaagggtggcatgctg
acacctgaggattgaaactgtggccctgaaggaggtggggttcaaaggaggctctgtttagagtcagaccctgaactcactg
agtgtgaacatgccagccaagtcagctgtgcatcaaggagacctaagggcaccctttataatggagacccccagggtggagt
ttcagtaggaacccatgatcctatagggttcagcctgtgtttaaatccatggtcctatagggttcagcctgtgtttaaatcc
atggtcctatagggtatagcctatgtttaaatccatggtcctatagggtacagcctgtgtttaaatccatggtcctataagg
tatagcctatgtttaaatccatggacctatggggtatagcctatgtttaaatccatggtcctatagggtatagcttgtgttt
aaatccatggacctatagggtatagcttgtgtttaaatccatggtcctatagggtatagcttgtgtttaaatccatggtcct
atagggtatagcctgtgtttaaatccatggtcctatagggtacagcctgtgtttaaatccatggtcctataaggtatagcct
atgtttaaatccatggacctatggggtatagcctatgtttaaatccatggtcctatagggtatagcttgtgtttaactccat
ggacctatagggtatagcttgtgtttaaatccatggtcctatagggtatagcctgtgtttaaatccatggttgtatagggta
tagcctgtgtttaaatcaatagtctatagggtatcagcctacatggctcgatgtgactgtggtaccaatcccagtggtaag
atcatggtgcactccgaaagagtgctatttccttgcctgtgagtcctcctttaagacttagagctgttataacttagagcct
cttagcagggaagaataaacatggtctctgaaccccgagggacccacttctaaacctgcccctgggaagaggaaagccagag
tatcctgagcgttggggtacggggaaactccaagagcagatcaacactttgccatagcctggagtcctcctgaggctacggc
catccccgtcccaccaggggtttggggccagtggaatctcccaggtacctgggccgagactctgtttttctgtgcccagGTG
CGAGGCCGGGAGAACTTTGAGATCTTGATGAAAGTCAAGGAGAGCCTAGAACTGATGGAGCTTGTGCCCCAGCCTTTGGTTG
ACTCCTATCGACAGCAGCAGCAGCAGCAGCTCCTACAGAGGCCgtgagtgaacccaccatctgtatggggaagtagggata
ttctgacccagcagggagagggccaggagcacaggaggtatggtaccctggactggactggactgtaagatcagcacagctc
agctggcacctttctcctccaggaagccttctgggacttagcctgccctgagatcctgggtccctgtgttcagcacaccctg

FIG. 4 (Continued)

cctcccacacaagggccttggaaatgtggatggggaagggactggaagggctgtatttgctgaagctggtgaggtgttagct
ttcttcctaactctctgagaggcagggtctacatctacctgcatcccagggtgtccacagaggtaccacgtggggaggagt
tgcttttacctcttgcgaatgcgcactgttgctttccaagcagGAGTCACCTGCAGCCTCCATCCTATGGGCCCGTGCTCTC
CCCAATGAACAAGGTACACGGTGGTGTCAACAAACTGCCCTCCGTCAACCAGCTGGTGGCCAGCCTCCCCCGCACAGCTCA
GCAGCTGGGCCCAACCTGGGGCCCATGGgtgagtccctggagcattggaggcctcatgtgggtcatagagacccaagggagg
gcctgggtggatttaccgagatcacaaacaggatggcgggggacctttgatggccacctcttcctgcagctccagcctgcag
gagggcaatggctatggaggcgttcattccaatcccaggagttctatgcctgggaggttgcaaaggtggtagagttaagaac
tcatgcctgccacaggatcttgaagaagatccctagcctcagtttccccatcagtaaaatggcaacaccaaatcccctcttc
tcaggggttacaggacatgagacctcattgagaggcagctgtagggaacccttacaatgctgtaccacactgccaggctaga
ccacagcctgggacatacccactatgtgtggggcttgctctcaggttccctgaccactcttttgcccagGCTCCGGGATGC
TCAACAGCCACGGCCACAGCATGCCGGCCAATGGTGAGATGAATGGAGGCCACAGCTCCCAGACCATGGTTTCGGGATCCCA
CTGCACCCCGCCACCCCCCTATCATGCAGACCCCAGCCTCGTCAGgtgtgtgggtcgcggctggatctgggtttgtggttca
ccctccacccctcacccatgcctcccactaactgtgcggttcctgctggagggagcagccttgcatgtggctctgtctgac
cctgttttaattgcttggctggcctgagggaagacaggcctatcagggctcgtcagcagatgctgagaaaggcactagatgg
ttaggcactgagggtgggggtggggtttggaggggtttgggggcatcctcttggagacaggggggatgaggaatgagatgag
cagctgtgggaggtcagaccaggagaggtgggtaatgattggactgtaaaaatataaaagtaacatacacacacacgtatat
atgtgtatgtgtatgtgtatgtgtatgtgtatgtgtatgtgtatgtgtatatacacacatacacatatacacacatgtacat
atatacatatatatgtgtacatatatatatacacacatatatgtacatatatatgtaacaaaaattaaaataaaataaataa
taaaataaagaaataaaaaagaaaacctgccctgagggagggaccagcagttttgcccactgtaacaggcagttccctccac
gtcagggccactcctgtgagacccgagtgcacagccagttgatgctactttctcaaactctctctgcagTTTTTGACAGGG
TTGGGGTGTCCAAACTGCATCGAGTGCTTCACTTCCCAAGGGTTGCAGAGCATCTACCACCTGCAGAACCTTACCATCGAGg
taaatgtcccaggtctttccaaagggacggaggacctgtctggaggcacagtgcactgactagggtgactagtggggaaact
cccagagactcccaccagcaatcagattctgttctgaagtcagcaggattcggtaatgtgaaggagactgggtagacaatca
catgtcccggtccccggcagttacctggagagctttctctcttgttagagcctcctggtggcccagccaggctaccttgat
ttcttaggcagggttgtttccaggacccaatgtgtgagaagtgtagaagctaagggggggaacagacctagaaagaatgaatg
ggtctccacatccagcctacacgtgagacacagaacattctgggttgaaagtgggatagaaatcttctggaaggccctgcat
cctgttacagcctagccacacagactgccttgatgtatccatgagacatgggtccagtgtgcaacagctcagcccctcctgc
cccagggcccagtgtgcaacagctcagcccctcctgccccagggcccagtgtgcatcagctcagcccctcctgccccagggc
ccagggtgcaacagctcagcccctcctgccccagggcccagggtgcaacagctcagcccctcctgccccagggcccagagtg
caacagctcagcccctcctgccatgcctcccaaaactgttttctagactctcacccaggctaagaggccatatttgtcacct
acccaggaactcaggctggacacaaatatttataagaggttgtggggctagagtctaacacctgcatttatgggaccactga
ccactacctttcccatccttgagtcatacattaacccttgtctcaccagagcttgaagctaaaggatgtgcctggagttagc
tgccaattaatggcttccaagggacacctgtggccaagagatgcatgggtggtctcctaggtctccattgctgttctcgctg
tgtccaggcctcaggctgatgagcaggccctcgtcactgtccctctgtcacctacacatgtcatctagctgtcctagacaa
ttatgtgactagacattctgtgcaggtgaccctgatgctgtccctaccctgtcacccacacagtcaaggtctgataagtcag
ctgccccctcagacagaggcttcctagcaggtaggacacccttgcaggtgtgagggacacacaactctgtagcttccctctt
gtaacccaaaggtgcccatcgctcttgcagGACCTTGGGGCTCTGAAGGTCCCTGACCAGTACCGTATGACCATCTGGAGGC
GCCTACAGGACCTGAAGCAGAGCCATGACTGCGGCCAGCAACTGCTACGCTCCAGCAGCAACGCGGCCACCATCTCCATCGG
CGGCTCTGGCGAGCTGCAGCGGCAGCGGGTCATGGAAGCCGTGCATTTCCGTGTGCGCCACACCATCACGATCCCCAACCGT
GGAGGCGCAGGTGCGGTGACAGGTCCCGACGAGTGGGCGGACTTTGGCTTTGACCTGCCTGACTGCAAGTCCCGTAAGCAGC
CCATCAAAGAGGAGTTCACAGAGACAGAGAGCCACTGAGGAACGTACCTTCTTCTCCTGTCCTTCCTCTGTGAGAAACTGCT
CTTGGAAGTGGGACCTGTTGGCTGTGCCCACAGAAACCAGCAAGGACCTTCTGCCGGATGCCATTCCTGAAGGGAAGTCGCT
CATGAACTAACTCCCTCTTGG

FIG. 4 (Continued)

SEQ ID NO: 4

>gi|187830767|ref|NM_000546.4| Homo sapiens tumor protein p53 (TP53), transcript variant 1, mRNA gattggggttttcccctcccatgtgctcaagactggcgctaaaagttttgagcttctcaaaagtctagagccaccgtccagg
gagcaggtagctgctgggctccggggacactttgcgttcgggctgggagcgtgctttccacgacggtgacacgcttccctgg
attggcagccagactgccttccgggtcactgccatggaggagccgcagtcagatcctagcgtcgagccccctctgagtcagg
aaacattttcagacctatggaaactacttcctgaaaacaacgttctgtcccccttgccgtcccaagcaatggatgatttgat
gctgtccccggacgatattgaacaatggttcactgaagacccaggtccagatgaagctcccagaatgccagaggctgctccc
cccgtggcccctgcaccagcagctcctacaccggcggcccctgcaccagccccctcctggcccctgtcatcttctgtccctt
cccagaaaacctaccagggcagctacggtttccgtctgggcttcttgcattctgggacagccaagtctgtgacttgcacgta
ctcccctgccctcaacaagatgttttgccaactggccaagacctgccctgtgcagctgtgggttgattccacacccccgccc
ggcacccgcgtccgcgccatggccatctacaagcagtcacagcacatgacggaggttgtgaggcgctgcccccaccatgagc
gctgctcagatagcgatggtctggcccctcctcagcatcttatccgagtggaaggaaatttgcgtgtggagtatttggatga
cagaaacacttttcgacatagtgtggtggtgccctatgagccgcctgaggttggctctgactgtaccaccatccactacaac
tacatgtgtaacagttcctgcatgggcggcatgaaccggaggcccatcctcaccatcatcacactggaagactccagtggta
atctactgggacggaacagctttgaggtgcgtgtttgtgcctgtcctgggagagaccggcgcacagaggaagagaatctccg
caagaaaggggagcctcaccacgagctgcccccagggagcactaagcgagcactgcccaacaacaccagctcctctccccag
ccaaagaagaaaccactggatggagaatatttcacccttcagatccgtgggcgtgagcgcttcgagatgttccgagagctga
atgaggccttggaactcaaggatgcccaggctgggaaggagccaggggggagcagggctcactccagccacctgaagtccaa
aaagggtcagtctacctcccgccataaaaaactcatgttcaagacagaagggcctgactcagactgacattctccacttctt
gttccccactgacagcctcccacccccatctctccctcccctgccattttgggttttgggtctttgaacccttgcttgcaat
aggtgtgcgtcagaagcacccaggacttccatttgctttgtcccggggctccactgaacaagttggcctgcactggtgtttt
gttgtggggaggaggatggggagtaggacataccagcttagattttaaggtttttactgtgagggatgtttgggagatgtaa
gaaatgttcttgcagttaagggttagtttacaatcagccacattctaggtaggggcccacttcaccgtactaaccagggaag
ctgtccctcactgttgaattttctctaacttcaaggcccatatctgtgaaatgctggcatttgcacctacctcacagagtgc
attgtgagggttaatgaaataatgtacatctggccttgaaaccaccttttattacatggggtctagaacttgacccccttga
gggtgcttgttccctctccctgttggtcggtgggttggtagtttctacagttgggcagctggttaggtagagggagttgtca
agtctctgctggcccagccaaaccctgtctgacaacctcttggtgaaccttagtacctaaaaggaaatctcaccccatccca
cacctggaggatttcatctcttgtatatgatgatctggatccaccaagacttgttttatgctcagggtcaattctttttt
cttttttttttttttttctctttctttgagactgggtctcgctttgttgcccaggctggagtggagtggcgtgatcttgg
cttactgcagcctttgcctccccggctcgagcagtcctgcctcagcctccggagtagctgggaccacaggttcatgccacca
tggccagccaactttttgcatgtttttgtagagatggggtctcacagtgttgcccaggctggtctcaaactcctgggctcaggc
gatccacctgtctcagcctcccagagtgctgggattacaattgtgagccaccacgtccagctggaagggtcaacatctttta
cattctgcaagcacatctgcattttcacccccacccttcccctccttctccctttttatatcccatttttatatcgatctctt
attttacaataaaactttgctgccacctgtgtgtctgaggggtg

SEQ ID NO: 5

>hg18_knownGene_uc002gij.2 range=chr17:7512445-7531588 5'pad=0 3'pad=0 strand=-
repeatMasking=none
GATTGGGGTTTTCCCCTCCCATGTGCTCAAGACTGGCGCTAAAAGTTTTGAGCTTCTCAAAAGTCTAGAGCCACCGTCCAGG
GAGCAGGTAGCTGCTGGGCTCCGGGGACACTTTGCGTTCGGGCTGGGAGCGTGCTTTCCACGACGGTGACACGCTTCCCTGG
ATTGGgtaagctcctgactgaacttgatgagtcctctctgagtcacgggctctcggctccgtgtatttcagctcgggaaaa
tcgctggggctgggggtggggcagtggggacttagcgagtttgggggtgagtgggatggaagcttggctagagggatcatca
taggagttgcattgttgggagacctgggtgtagatgatggggatgttaggaccatccgaactcaaagttgaacgcctaggca
gaggagtggagctttggggaaccttgagccggcctaaagcgtacttctttgcacatccacccggtgctgggcgtagggaatc
cctgaaataaaagatgcacaaagcattgaggtctgagacttttggatctcgaaacattgagaactcatagctgtatatttta
gagcccatggcatcctagtgaaaactggggctccattccgaaatgatcatttggggggtgatccggggagcccaagctgctaa

FIG. 4 (Continued)

ggtcccacaacttccggacctttgtccttcctggagcgatctttccaggcagccccggctccgctagatggagaaaatcca
attgaaggctgtcagtcgtggaagtgagaagtgctaaaccaggggttgcccgccaggccgaggaggaccgtcgcaatctga
gaggcccggcagccctgttattgtttggctccacatttacatttctgcctcttgcagcagcatttccggtttctttttgccg
gagcagctcactattcacccgatgagaggggaggagagagagagagaaaatgtcctttaggccggttcctcttacttggcagag
ggaggctgctattctccgcctgcatttcttttttctggattacttagttatggcctttgcaaaggcaggggtatttgttttga
tgcaaacctcaatccctcccttctttgaatggtgtgccccacccgcgggtcgcctgcaacctaggcggacgctaccatgg
cgtgagacagggagggaagaagtgtgcagaaggcaagcccggaggtatttcaagaatgagtatatctcatcttcccggag
gaaaaaaaaaaagaatgggtacgtctgagaatcaaatttgaaagagtgcaatgatgggtcgtttgataatttgtcggaaaa
acaatctacctgttatctagctttgggctaggccattccagttccagacgcaggctgaacgtcgtgaagcggaagggggcggg
cccgcaggcgtccgtgtggtcctccgtgcagccctcggcccgagccggttcttcctggtaggaggcggaactcgaattcat
ttctcccgctgccccatctcttagctcgcggttgtttcattccgcagtttcttcccatgcacctgccgcgtaccggccactt
tgtgccgtacttacgtcatctttttcctaaatcgaggtggcatttacacacagcgccagtgcacacagcaagtgcacaggaa
gatgagttttggcccctaaccgctccgtgatgcctaccaagtcacagacccttttcatcgtcccagaaacgtttcatcacgt
ctcttcccagtcgattcccgaccccacctttattttgatctccataaccattttgcctgttggagaacttcatatagaatgg
aatcaggctgggcgctgtggctcacgcctgcactttgggaggccgaggcgggcggattacttgaggataggagttccagacc
agcgtggccaacgtggtgaatccccgtctctactaaaaatacaaaaattagctgggcgtggtgggtgcctgtaatcccagc
tattcgggagggtgaggcaggagaatcgcttgaacccgggaggcagaggttgcagtgagccaagatcgtgccactacactcc
agcctgggcgacaagaacgaaactccgtctcaaaaaaaagggggggaatcatacattatgtgctcatttttgtcgggcttctg
tccttcaatgtactgtctgacattcgttcatgttgtatatatcagtatttgctcctttttcattagtatagtccatcgatt
gtatatccgtcctttgatggcctttgagttgtttcccatttgcggttatgaaataaagctgctataaacattcttgtaca
attctttttgtgatcatatgtttcgtgtttcttggagaaatacttaggaggggaattgcgagtttggaagtaaaaagtagc
tgtactttgaacttttcagaagctctgagttttccagagcggttgtaccatttacactcccaactagcaaggtatgggagt
tattatggttgtgccacagccttccggacattaggtattgtcagtctttctaatgtggtatatccttgtggttgtaatttac
agttctctattgactaaggatgttcagcatttttcatgtgcctattggccattcgtatttgttgtaaagtagctcttcg
agtcttttacctgttatttggtttttgtttgtttttattgttcagttgtgggactgctttatacattctggatacaagtc
ctttatcagatccatgtgtcgtgaatgtttctttctgatctgttgcttgcctatttgtttgctttacagagtttacagtatc
ttaagaggagtggatttatcttttttatgttcagtatttgcccttgtcctgtttaggacatcttttttttttttttaacccc
agggtcatgaagatattatcctacatttctttttaggaccttatggttgtaagttttacagtaaggtccttgagccattaa
ttaattcttaaaattaattgtttatggtgtgaggtgtaggagtcagtctctggtatctttcctgtatggaaatccagttatt
ctgtctccacttgttgaaataggcttcctttctctactgaatgctttaattttaattattttacagttggagtatagggct
accattttagtgctattttctttttttctttgttaattttgagacagggactcacactgttgcccaggctagagtacaatg
gcacaatcaaggcttactgcagcctcgaacccctgggctcaagcagtcctctagcagcctcacgagtagctgggattactcc
accacacccagctaactatttttatttttttgtattgacaggatctcactatgttgcccaggctggtctcaaactgctggcct
caagctttcatcccatctcggcctcccaaagtgctgggattacaggtgtgagccaccatgcctgacctcttagtgctatttt
ctatttatctcctctgttctctgctctctttaaacgttggaggaagaaacagtacccatcttacacaaactcttcagaaaac
agaggaacagactgggcgcggtggctcatacctgtaatctcagcactttggtacgctgaggcaggggatcatttgaggtcgg
gagttcgagaccagcctggccaacacggcgaaaccccatctctactaaaaatacaaaaagtagctaggcgtggtgacacata
cctgtaatgccagttactcaggaggctgaggcacaagaatcccttgaacctgggaagcggaggttgcagtgagccgagattg
cgccactgcactccagcctgggcaacagagtgagaccctgtctcagaaaaaaaaagaaagaaagaaaaaatagaggaatatt
tcccaacttgtttcgaagccagcataatcctggtaccaaaaccaaacaaggacattataagaaaagaaaatatagaccaat
attcctgttagcatagacatgcaacagctaaccaatttagcaaaccaaacctggtaatatagaaaaaggataaataggcc
agtcgcggtggctcacgcctgtaatcccagcactttgggaggctgaggcaggcagatcacttgaggtcaggagtttgagacc
agcctgaccaacatggtgaaaccccgtttctaataaaaatacaaaaatcaggctgggcacggtggctcacgcctgtaatccc
agcactttgggaggccgaggtgggcagatcacgaggtcaggagttcaagaccagcctgaccaatgtggtgaaacgccatctc
tactaaaaatacaaaaatcagccggtgtggtggcacctgcctgtaatcccagctactcaggaggctgaggcagaattgcttg
aacccgggaggcagaggttgcagtgagccaagatcgtgccactgcactccagcctgggcgacagagcaagacttcatctcaa
aaaaaaaaaaaaattagctgggcatggtggtgggcacctgaaatcccagctactcgggagtctgaggcaggagaatcgcttg
aacccaggaggcagaagttgcactgagctgggatcacaccattgcactccagcctgggcaacagagtgagactccatctcaa
aaaaagaaaaagaaaaaggataaatacattctaaccaaataatgtttatctcatgattgtagctgattcaacattcaaaaat
tggcctggtgcagtagctcaggcctgtaatcccaacatttaggaggctgaggcaggaagatctcttgagcccaggatttca
agaccagcctgggcaacatagtcagactggtctttactgggggaaaaaatcagtctgtgtaattcacccattaacaaag
ggaaacataaaaccctatgatcatttcaacagatgtagcaaaagcagttaatgatattcaacacatatgcatgattacaaa
ccaaccaacctcctagcaaactagggaaaggaaacttaacctagtttgataacagggcgtccacagtcggagttccactagc
agcatacataatggtagaaaactcagtgctgccgggcgcggtggctcacgcctgtaatgccagcactttgggaggcctaggc
gggcggatcacgaggtcaggagatcgagactgtcctgactagcatgctgaaaccccgtctctactaaaaatacaaaaacaaa

FIG. 4 (Continued)

aaattagccgggcatggtggcgggcgcctatagtcccagctactcgggaggctgaggcgagagaatggcgtgaacccgggag
gcggagcttgcagagcctagatcgtgccactgcactccagcctgggtgacagagtgagacttcgtctcaaaaaaaaaaaaaa
aaaaaaagaaagaaaactcaacgcttttcctctaagatcaggaactagaaaggatttgactctcacaacgttgatacc
atactggaggttttaaccaggcaagaaaaagaaataatgagggccgggtgcggtggctcaggcctgtaatcccagcactttg
ggaagccgagacgggtggatcacgaggtcaggagatcgagaccatcctggctaacacggtgaaaccctgtctctactaaata
tacaaaaaattagccgggcgtagtggcgggcgcctgtagtcccagctactcgggaggctgaggcaggagaatggcgtgaact
caggggcggagcttgcagtgagctgagatcgagccactgcactccagcctgggcgacagagcaagactgtgtctcaaaaaa
aaaaaaagaaaaagaaataatgattagtggccgatgtctcacgcctataatcccagcactttgggaggccgaggtgggcag
atcacctgaggtctggagttggagaccagcctgacaaagatggtgaaacctcgtctctattaaatattaaaaaaatagcca
ggcgttggccgggtacagtggctcatgcctgtaatcccagcactttgggaggccgaggtgggtggatcacctgaggtcagga
gttcaacaccagcctggccaacatggtgaaaccccatctctactaaaaatacaaaaattagccgggcgtagtggcgggcgcc
tgtaatcccagctacttgggaggcttaggcaggagaatcgcttgaacctgggaggcggaggttgtagtgagccgagattgca
ccattgcactccagcctgggtgacaaaagcaaaaactccgtctcaaaaaaaaaagaattagccagggtagtggtgaacgcc
tgtagtcccagctactcaggaggcagaggcaggagaatcacttgaacccaggaggcagaggttgcagtgagccgagattgtc
ccattgcactccagcctaggcgacaagagcaaaattccatgtcaaaaaaaaaaaaaaaaaaggaaagaaaaaaaataacgat
tagaaaggaagaaataaaacacattcacagccagtatgattctatacatacatgtcctaatggggccaggcgtggtggctca
tgcctgtaatcctagcactttaggaggctgaggcaggtggcttccctgggaccagcctggccaacatggtgaaaccccaac
tctaataaaaatacaaaaatcagccaggcgtggtgacgggcacctctaatcccagctactcaggaggctgaggcaggagaa
ttgcttggacctgggaggcagaggttgcagtgagccgagatcgcgctattgcactccagcctgggcaacaagagtgaaactc
cggcagggtgtggtggcttacgcctgtaatcccagcacttcgggaggctgaggcaggccgatcacctgaggtcaggagtttg
agaccaacctaacatggtgaaaccccgtctctactaaaaatacaagaattagctgggtgtagtggtgggcgcctgtaatccc
agctacttgggaggctgagacagaagaattgcttgaacccaggaggtggaggttgcagtgagctgagatcatgccattgcac
accacgccgggcaacagagcgagattccgtctcaaaaaaaaaaaaaaaagagtgaaactctatctcaaaaaaaaaaaaaagtc
ctaatggaaaatccataaaagctaccaaaactaataaataaatatagcagggttgcaggttacagggcaatatagttatcc
ctctatctgtaggggcttggttctgggactcctcacacaccaaacccacagatgtctaagtcccatatataagacggtatag
tatttggatttaacctacacatatcctcccatatagtttaaattatctctagattacttacattaccccatacaatgaaaa
tgctaatgtacatgcaagtatgtatgtaagtacttgtactatattgtttagggaatcactggacatataggccttcaagact
gataccagcagccactgttaagattctggtcaggcctgcccctgtttggggtctcagttgatctcattgccttcccacccag
ccaagggcacctgcatttctcttggctccctggccatttggaaggcctagttcagcctggcacatttgtatcctggcccact
gatgctggtacccctgggaaggtcctgctctgaaaacacggagatttagttgctactgaagatttgagagataaagacag
ggagacctgtctgtagacctgtgtccctccaagtgggattgagactttgggcccccatttcaggacagcacctcctggcct
gttgactgaatagatccctgaaggaggtgtacttgcattaatggagtgggggtgggagcagtaccacagatccgcactaaca
atcacacagttctctctagaataataatatagaacaagtgaaatagaacaattgcagaaagagctaacctttgttgagctct
tactgtgtgcccagcactttcctcaactctacatttcccataatacacagagtactaggtaggccaggcttggtggctcacg
cctgtaatcccagcactttaggaggccaagggggtggatcacctgaggtcgggagttcaagaccagcctgaccaacatggt
gaaaccccgtctctactagaagtacaaaattagccaggtgtggtggcacatgcttgtagtcctagctactcagcaggctgag
gcaggagaatcatttgaatccgggaggaggttgcagtaagcggagatagtgccactgtactccagcctgggcaataagagct
gagactccgtctcaaaataaaataaaataaaataaaataaaataaaataaaataaaaaaagaaaagagcctgccattaaagg
agctgtttggtaggggatgttttgtcagtgcaaacaacagaaaagtgggctgggcacagtggttcatgcctgtaatcccagc
actttgggaggccaaggcgggcggatcacctgaagttgggagttcaagaccagcctgaccaatatggagaaaccccgtctct
actaaaaatacaaaattagccgggcgcagtggcgcatgcctgtaatcccagctactcgggaggctgaggcaggagaatcgct
tgaacctgggaggcagaggttgcggtgagccgagatcgcaccattgcactccagcctggacgagagcaaaactctgtctcaa
aaaaaaaaaaaacagaaaagtgtaacaaacacttacagtaggcatgtttcttagcaaatctgatgacaaatttggcataaa
gaaagagagcatccctgaaaaaaaaaaaaagaaaaagaaagagagcatcctgcctgggcaacatagtgaaaccctgcctcta
caaaaaaactcaaaaattggccgggtgcagtggctcacacctgtaatcccagcactttgggagtcggaggcgggaggatcac
ctgaggtcaggagttcgaaaccagcctggccaacatggcaaaaccccatctctactaaaaatacaaaaaattaatcaggcgc
attggtgggcgcctgtaatcccagctactcaggaagttgaggcaagaggatcgcttgaatctgggaggtggaggttacagtg
agtcgagatcacaccactgcactctagcctgggtgacagggcgagactccgtctccaaaaaaaaaagaaaaagaaaaagac
taaaaaattagccaggcaggcctctgtggtcccagctacttgggaggctgaggcaggagaatcactgagcccaggagtccga
ggctgtagtgagccatgattgcaccactgtaccctagcttgggcaacaaagcaagaccctgcctcaaaagaaaaaagaaaga
aagaaagaacatggcgggccaggcacagtggctcacacctgtaatcccagcgctttgagaggccgaggcaggtggatcacaa
ggtcaggagttccacaccagcctggccaacatggtgaaaccctgtctctactaaaatacaaaaaatcagccaggcatggtg
gcaggggcctgtaatcccagctactcgggaggctgaggcaggagaattgcttgaaaccagaaggcagaggttgcagtgagcc
tagactgcaccactgcactccagcctgggcgaaaagagccaaactccatctcaaaaaacaaacaaaaaaacaaaacaaaaga
aaacatggcaaagcctttgaaagcttgtctgggagaaggtgcgatgatagttgcataacttcgtgcaagatgctggtccaca

FIG. 4 (Continued)

cagggggctgcccccttgctctttctcgctctcttaacctctcatataacaggcttgtgtgttattcacatttattgagcccaa
gcaggtgcaaggcattgtgatcctaatactttggtcagcaagacaacaagatagatcactgccctgcccttaggaagtgtata
tgctattagaggaaacagataaaataaacaaggaaaagtatcagacaatgtaagtgctatgagaatgcaaatgaggtgatgt
gaattaaaataggatgacttaaagtctgcacgggaaggagcctacccccatgttcctggctagccaaggaaccaccagttga
ttagcagagaagggcagccagtctagctagagcttttggggaagagggagtggttgttaagagatgagattaaagaagccga
gacgggccattcgtgaggggtttgtaatgcagggctgaggagtgtccgaagagaatgggcaggtgagcggtgagacagttgt
tcttccagaagctttgcagtgaaaggaatcaaagaaatggagccgtgtatcaggtggggaagggtgggggccaagggggtgt
cctttcccatacagagattgcaggctgagaatgactatatccttgttaacaggaggtgggagcagggcacggtagctcacac
ctgtaatcttggcactttaggaggctgaggcgggccgatcacctgaagtaaggagttcgagaccagcctggccaacatgcaa
agccctgtctctactaaaaatacaaaaattagctgggtgtggtggtactcgcctgtaatcccagctactcgggagactgagg
caggagaatggcttgaacccggaaggtagaggttgcagtgagctgagatcatgccactgtgctccagcctaggtgacagaga
gagactccatctcaaaaaaaaaaaaaaaaatacaggaagggagttgggaatagggtgcacatttaggaagtcttggggattta
gtggtgggaaggttggaagtccctctctgattgtctttcctcaaagaagtgcatggctggtgaggggtggggcaggagtgc
ttgggttgtggtgaaacattggaagagagaatgtgaagcagccattcttttcctgctcccacaggaagccgagctgtctcaga
cactggcatggtgttgggggagggggttccttctctgcaggcccaggtgacccagggttggaagtgtctcatgctggatccc
cactttttcctcttgcagCAGCCAGACTGCCTTCCGGGTCACTGCCATGGAGGAGCCGCAGTCAGATCCTAGCGTCGAGCCCC
CTCTGAGTCAGGAAACATTTTCAGACCTATGGAAACTgtgagtggatccattggaagggcaggcccaccacccccaccccaa
ccccagccccctagcagagacctgtgggaagcgaaaattccatgggactgactttctgctcttgtctttcagACTTCCTGAA
AACAACGTTCTGgtaaggacaagggttgggctggggacctggagggctggggacctggagggctgggggctgggggctga
ggacctggtcctctgactgctctttttcacccatctacagTCCCCCTTGCCGTCCCAAGCAATGGATGATTTGATGCTGTCCC
CGGACGATATTGAACAATGGTTCACTGAAGACCCAGGTCCAGATGAAGCTCCCAGAATGCCAGAGGCTGCTCCCCCCGTGGC
CCCTGCACCAGCAGCTCCTACACCGGCGGCCCCTGCACCAGCCCCCTCCTGGCCCCTGTCATCTTCTGTCCCTTCCCAGAAA
ACCTACCAGGGCAGCTACGGTTTCCGTCTGGGCTTCTTGCATTCTGGGACAGCCAAGTCTGTGACTTGCACGgtcagttgcc
ctgaggggctggcttccatgagacttcaatgcctggccgtatccccctgcatttcttttgtttggaactttgggattcctct
tcacccttggcttcctgtcagtgttttttatagtttacccacttaatgtgtgatctctgactcctgtcccaaagttgaat
attcccccttgaatttgggcttttatccatcccatcacaccctcagcatctctcctggggatgcagaacttttcttttttct
tcatccacgtgtattccttggcttttgaaaataagctcctgaccaggcttggtggctcacacctgcaatcccagcactctca
aagaggccaaggcaggcagatcacctgagcccaggagttcaagaccagcctgggtaacatgatgaaacctcgtctctacaaa
aaaatacaaaaaattagccaggcatggtggtgcacacctatagtcccagccacttaggaggctgaggtgggaagatcacttg
aggccaggagatggaggctgcagtgagctgtgatcacaccactgtgctccagcctgagtgacagagcaagaccctatctcaa
aaaaaaaaaaaaaaaagaaaagctcctgaggtgtagacgccaactctctctagctcgctagtgggttgcaggaggtgcttac
gcatgtttgtttctttgctgccgtcttccagttgctttatctgttcacttgtgccctgactttcaactctgtctccttcctc
ttcctacagTACTCCCCTGCCCTCAACAAGATGTTTTGCCAACTGGCCAAGACCTGCCCTGTGCAGCTGTGGGTTGATTCCA
CACCCCCGCCCGGCACCCGCGTCCGCGCCATGGCCATCTACAAGCAGTCACAGCACATGACGGAGGTTGTGAGGCGCTGCCC
CCACCATGAGCGCTGCTCAGATAGCGATGgtgagcagctggggctggagagacgacagggctggttgcccagggtccccagg
cctctgattcctcactgattgctcttagGTCTGGCCCCTCCTCAGCATCTTATCCGAGTGGAAGGAAATTTGCGTGTGGAGT
ATTTGGATGACAGAAACACTTTTCGACATAGTGTGGTGGTGCCCTATGAGCCGCCTGAGgtctggtttgcaactggggtctc
tgggaggaggggttaagggtggttgtcagtggccctccaggtgagcagtaggggggctttctcctgctgcttatttgacctc
cctataacccatgagatgtgcaaagtaaatgggtttaactattgcacagttgaaaaaactgaagcttacagaggctaaggg
cctcccctgcttggctgggcgcagtggctcatgcctgtaatcccagcactttgggaggccaaggcaggcggatcacgaggtt
gggagatcgagaccatcctggctaacggtgaaaccccgtctctactgaaaaatacaaaaaaaattagccgggcgtggtggct
gggcacctgtagtcccagctactcgggaggctgaggaaggagaatggcgtgaacctgggcggtggagcttgcagtgagctga
gatcacgccactgcactccagcctgggcgacagagcgagattccatctcaaaaaaaaaaaaaaaaaggcctcccctgcttgcc
acaggtctccccaaggcgcactggcctcatcttgggcctgtgttatctcctagGTTGGCTCTGACTGTACCACCATCCACTA
CAACTACATGTGTAACAGTTCCTGCATGGGCGGCATGAACCGGAGGCCCATCCTCACCATCATCACACTGGAAGACTCCAGg
tcaggagccacttgccaccctgcacactggcctgctgtgccccagcctctgcttgcctctgacccctgggcccacctcttac
cgatttcttccatactactacccatccacctctcatcacatccccggcggggaatctccttactgctcccactcagttttct
tttctctggctttgggacctcttaacctgtggcttctcctccacctacctggagctggagcttaggctccagaaaggacaag
ggtggttgggagtagatggagcctggttttttaaatgggacaggtaggacctgatttccttactgcctcttgcttctctttt
cctatcctgagtagTGGTAATCTACTGGGACGGAACAGCTTTGAGGTGCGTGTTTGTGCCTGTCCTGGGAGAGACCGGCGCA
CAGAGGAAGAGAATCTCCGCAAGAAAGGGGAGCCTCACCACGAGCTGCCCCCAGGGAGCACTAAGCGAGgtaagcaagcagg
acaagaagcggtggaggagaccaagggtgcagttatgcctcagattcacttttatcacctttccttgcctctttcctagCAC
TGCCCAACAACACCAGCTCCTCTCCCCAGCCAAAGAAGAAACCACTGGATGGAGAATATTTCACCCTTCAGgtactaagtct
tgggacctcttatcaagtggaaagtttccagtctaacactcaaaatgccgttttcttcttgactgttttacctgcaattggg
gcatttgccatcagggggcagtgatgcctcaaagacaatggctcctggttgtagctaactaacttcagaacaccaacttata

FIG. 4 (Continued)

ccataatatatatttaaaggaccagaccagctttcaaaaagaaaattgttaaagagagcatgaaaatggttctatgacttt
gcctgatacagatgctacttgacttacgatggtgttacttcctgataaactcgtcgtaagttgaaaatattgtaagttgaaa
atggatttaatacacctaatctaaggaacatcatagcttagcctagcctgcttttttttttttttttttggagacagagtc
tcactctgtcacccaggctggagtgcagtggcgggatctcggctcactgcaacctccgcctcctgggttcaagcgattctcc
tgcctcagcccactgagtagctgggattacaggcacctgccccgacgcccagctaatttttgttatttatttatttttttt
tttagtagagatgaggtttcaccatgttggccaggctagtctcgaactcctgaccttgtgatctgcctgccttggcctccca
aagtgctgggattacaggcgtgagccaccgcacccggcctgcctagcctacttttattttattttaatggagacagcatct
tgctctgttgcccaggctggattacagtgatgtgatcatagctcattatacctcctgggctcaagcaatcccccctaactct
gcctccccagtagctaggaccacaggcatacaccaccatacccagctaattttaaaattttgtagatagatagagtctc
actatgttgcccaggctggtctctagcctactttttgagacaaggtcttgctctgtcacccaggctggatagagtgcagta
gtgcagtcacagctcactgcagcctccacctcccaggctccatccatcctcccagctcagcctcccaagttgcttcaactac
aggcctgcaccaccatgcctggctaattttattttatttattttatttttattttatttttttgagactcagtctca
ctctgtcgcccaggctggagtgcagtggcatgatcctggctcactgcaacctctgcctcctgggttcaagtgattctcctgc
ctcagcctcccgaatagctaggactacaagcgcctgctaccacgcccagctaattttgtatttttagtagagacagggttt
caccatgttggccaggctggtctcgaacttctgaccatgtgatccgcccgcctcggcctcccaaagtgctgggattacaggt
gtgagccaccacgcccggctaatttttatttatttatttaaagacagagtctcactctgtcactcaggctagagtgcagtgg
caccatctcagctcactgcagccttgacctccctgggctccggtgatttcaccctcccaagtagctaggactacaggcacat
gccacgacacccagctaatttttatttttctgtgaagtcaaggtcttgctacgttgcccatgctggtatcaaaccctgggc
tcaatcaatccttccacctcagcctccccaagtattggggttacaggcatgagctaccacactcagccctagcctacttgaa
acgtgttcagagcatttaagttaccctacagttgggcaaagtcatctaacacaaagcccttttttatagtaataaaatgttgt
atatctcatgtgatttattgaatattgttactgaaagtgagaaacagcatggttgcatgaaaggaggcacagtcgagccagg
cacagcctgggcgcagagcgagactcaaaaaaagaaaaggccaggcgcactggctcacgcctgtaatcccagcatttcggga
ggctgaggcgggtggatcacctgaggtcaggagttcaagaccagcctagccaacatggtgaaaccccgtctctactaaaata
caaaaattaaccgggcgtgatggcaggtgcctgtaatcccagctacttgggaggctgaggcaggagaatcgcttgaaccagg
aggcggaggttgcagggagccaagatggcgccactgcactccagcctgggcgatagagtgagactccgtctcagaaaaaaa
gaaaagaaacgaggcacagtcgcatgcacatgtagtcccagttacttgagaggctaaggcaggaggatctcttgagcccaag
agtttgagtccagcctgaacaacatagcaagacatcatctctaaaatttaaaaagggccgggcacagtggctcacacctgt
aatcccagcactttgggaggtggaggtgggtagatcacctgacgtcaggagttggaaaccagcctggctaacatggtgaagc
cccatctctactaaaaacacaaaaattagccaggtgtggtagcacacgcctgtagtcccagctactcgggaggctgaggcac
aagaatcacttgaacccagaggcggagattgcaatcagccaagattgcaccattgcactccgcctgggcaacagagtgag
accccatctcaaaataaataaataaatatttttaaaagtcagctgtataggtacttgaagtgcagtttctactaaatgcatg
ttgcttttgtaccgtcataaagtcaaacaattgtaacttgaaccatcttttaactcaggtactgtgtatatacttacttctc
cccctcctctgttgctgcagATCCGTGGCGTGAGCGCTTCGAGATGTTCCGAGAGCTGAATGAGGCCTTGGAACTCAAGGA
TGCCCAGGCTGGGAAGGAGCCAGGGGGGAGCAGGGCTCACTCCAGgtgagtgacctcagccccttcctggccctactcccct
gccttcctaggttggaaagccataggattccattctcatcctgccttcatggtcaaaggcagctgacccccatctcattgggt
cccagccctgcacagacatttttttagtcttcctccggttgaatcctataacccacattcttgcctcagtgtatcccacagaac
atccaaacccagggacgagtgtggatacttctttgccattctccgcaactcccagcccagagctggagggtctcaaggaggg
gcctaataattgtgtaatactgaatacagccagagtttcaggtcatatactcagccctgccatgcaccggcaggtcctaggt
gacccccgtcaaactcagtttccttatatataaaatggggtaagggggccgggcgcagtggctcacgaatcccacactctgg
gaggccaaggcgagtggatcacctgaggtcgggagtttgagcccagcctgaccaacatggagaaaccccatctctactaaaa
atacaaaagtagccgggcgtggtgatgcatgcctgtaatcccagctacctactcgggaggctgaggcaggagaatcgcttga
acccgggaggcagaggttgcggtgagctgagatctcaccattacactccagcctgggcaacaagagtgaaactccgtctcaa
aaaagataaataaagtaaaatggggtaagggaagattacgagactaatacacactaatactctgaggtgctcagtaaacata
tttgcatggggtgtggccaccatcttgatttgaattcccgttgtcccagccttaggcccttcaaagcattggtcagggaaaa
ggggcacagaccctctcactcatgtgatgtcatctctcctccctgcttctgtctcctacagCCACCTGAAGTCCAAAAAGGG
TCAGTCTACCTCCCGCCATAAAAAACTCATGTTCAAGACAGAAGGGCCTGACTCAGACTGACATTCTCCACTTCTTGTTCCC
CACTGACAGCCTCCCACCCCCATCTCTCCCTCCCCTGCCATTTTGGGTTTTGGGTCTTTGAACCCTTGCTTGCAATAGGTGT
GCGTCAGAAGCACCCAGGACTTCCATTTGCTTTGTCCCGGGGCTCCACTGAACAAGTTGGCCTGCACTGGTGTTTTGTTGTG
GGGAGGAGGATGGGGAGTAGGACATACCAGCTTAGATTTTAAGGTTTTTACTGTGAGGGATGTTTGGGAGATGTAAGAAATG
TTCTTGCAGTTAAGGGTTAGTTTACAATCAGCCACATTCTAGGTAGGGGCCCACTTCACCGTACTAACCAGGGAAGCTGTCC
CTCACTGTTGAATTTTCTCTAACTTCAAGGCCCATATCTGTGAAATGCTGGCATTTGCACCTACCTCACAGAGTGCATTGTG
AGGGTTAATGAAATAATGTACATCTGGCCTTGAAACCACCTTTTATTACATGGGGTCTAGAACTTGACCCCCTTGAGGGTGC
TTGTTCCCTCTCCCTGTTGGTCGGTGGGTTGGTAGTTTCTACAGTTGGGCAGCTGGTTAGGTAGAGGGAGTTGTCAAGTCTC
TGCTGGCCCAGCCAAACCCTGTCTGACAACCTCTTGGTGAACCTTAGTACCTAAAAGGAAATCTCACCCCATCCCACACCCT
GGAGGATTTCATCTCTTGTATATGATGATCTGGATCCACCAAGACTTGTTTTATGCTCAGGGTCAATTTCTTTTTTCTTTTT

FIG. 4 (Continued)

TTTTTTTTTTTTTCTTTTTCTTTGAGACTGGGTCTCGCTTTGTTGCCCAGGCTGGAGTGGAGTGGCGTGATCTTGGCTTACT
GCAGCCTTTGCCTCCCCGGCTCGAGCAGTCCTGCCTCAGCCTCCGGAGTAGCTGGGACCACAGGTTCATGCCACCATGGCCA
GCCAACTTTTGCATGTTTTGTAGAGATGGGGTCTCACAGTGTTGCCCAGGCTGGTCTCAAACTCCTGGGCTCAGGCGATCCA
CCTGTCTCAGCCTCCCAGAGTGCTGGGATTACAATTGTGAGCCACCACGTCCAGCTGGAAGGGTCAACATCTTTTACATTCT
GCAAGCACATCTGCATTTTCACCCCACCCTTCCCCTCCTTCTCCCTTTTTATATCCCATTTTTATATCGATCTCTTATTTTA
CAATAAAACTTTGCTGCCACCTGTGTGTCTGAGGGGTG

SEQ ID NO: 6

>gi|110224474|ref|NM_000314| Homo sapiens phosphatase and tensin homolog (PTEN), mRNA.

cctcccctcgcccggcgcggtcccgtccgcctctcgctcgcctcccgcctcccctcggtcttccgaggcgcccgggctcccg
gcgcggcggcggaggggcgggcaggccggcgggcggtgatgtggcgggactctttatgcgctgcggcaggatacgcgctcg
gcgctgggacgcgactgcgctcagttctctcctctcggaagctgcagccatgatggaagtttgagagttgagccgctgtgag
gcgaggccgggctcaggcgagggagatgagagacggcggcggccgcggcccggagcccctctcagcgcctgtgagcagccgc
gggggcagcgccctcggggagccggccggcctgcggcggcggcagcggcggcgtttctcgcctcctcttcgtcttttctaac
cgtgcagcctcttcctcggcttctcctgaaagggaaggtggaagccgtgggctcgggcgggagccggctgaggcgcggcggc
ggcggcggcacctcccgctcctggagcggggggagaagcggcggcggcggcggccgcggcggctgcagctccagggagggg
gtctgagtcgcctgtcaccatttccagggctgggaacgccggagagttggtctctccccttctactgcctccaacacggcgg
cggcggcggcggcacatccagggacccgggccggttttaaacctcccgtccgccgccgccgcaccccccgtggcccgggctc
cggaggccgccggcggaggcagccgttcggaggattattcgtcttctccccattccgctgccgccgctgccaggcctctggc
tgctgaggagaagcaggcccagtcgctgcaaccatccagcagccgccgcagcagccattacccggctgcggtccagagccaa
gcggcggcagagcgaggggcatcagctaccgccaagtccagagccatttccatcctgcagaagaagccccgccaccagcagc
ttctgccatctctctcctcctttttcttcagccacaggctcccagacatgacagccatcatcaaagagatcgttagcagaaa
caaaaggagatatcaagaggatggattcgacttagacttgacctatatttatccaaacattattgctatgggatttcctgca
gaaagacttgaaggcgtatacaggaacaatattgatgatgtagtaaggtttttggattcaaagcataaaaaccattacaaga
tatacaatctttgtgctgaaagacattatgacaccgccaaatttaattgcagagtttgcacaatatcctttttgaagaccataa
cccaccacagctagaacttatcaaacccttttgtgaagatcttgaccaatggctaagtgaagatgacaatcatgttgcagca
attcactgtaaagctggaaagggacgaactggtgtaatgatatgtgcatatttattacatcggggcaaatttttaaaggcac
aagaggccctagatttctatggggaagtaaggaccagagacaaaaagggagtaactattcccagtcagaggcgctatgtgta
ttattatagctacctgttaaagaatcatctggattatagaccagtggcactgttgtttcacaagatgatgtttgaaactatt
ccaatgttcagtggcggaacttgcaatcctcagtttgtggtctgccagctaaaggtgaagatatattcctccaattcaggac
ccacacgacgggaagacaagttcatgtactttgagttccctcagccgttacctgtgtgtggtgatatcaaagtagagttctt
ccacaaacagaacaagatgctaaaaaaggacaaaatgtttcacttttgggtaaatacattcttcataccaggaccagaggaa
acctcagaaaaagtagaaaatggaagtctatgtgatcaagaaatcgatagcatttgcagtatagagcgtgcagataatgaca
aggaatatctagtacttactttaacaaaaaatgatcttgacaaagcaaataaagacaaagccaaccgatactttttctccaaa
tttaaggtgaagctgtacttcacaaaaacagtagaggagccgtcaaatccagaggctagcagttcaacttctgtaacacca
gatgttagtgacaatgaacctgatcattatagatattctgacaccactgactctgatccagagaatgaaccttttgatgaag
atcagcatacacaaattacaaaagtctgaatttttttttatcaagagggataaaacaccatgaaaataaacttgaataaact
gaaaatggaccttttttttttttaatggcaataggacattgtgtcagattaccagttataggaacaattctcttttcctgacc
aatcttgttttaccctatacatccacagggttttgacacttgttgtccagttgaaaaaaggttgtgtagctgtgtcatgtat
ataccttttttgtgtcaaaaggacatttaaaattcaattaggattaataaagatggcactttcccgttttattccagtttat
aaaaagtggagacagactgatgtgtatacgtaggaattttttccttttgtgttctgtcaccaactgaagtggctaaagagct
ttgtgatatactggttcacatcctaccccttttgcacttgtggcaacagataagtttgcagttggctaagagaggtttccgaa
gggttttgctacattctaatgcatgtattcgggttaggggaatggagggaatgctcagaaaggaaataattttatgctggac
tctggaccatataccatctccagctatttacacacacctttctttagcatgctacagttattaatctggacattcgaggaat
tggccgctgtcactgcttgttgtttgcgcattttttttaaagcatattggtgctagaaaaggcagctaaaggaagtgaatc
tgtattggggtacaggaatgaaccttctgcaacatcttaagatccacaaatgaagggatataaaaataatgtcataggtaag
aaacacagcaacaatgacttaaccatataaatgtggaggctatcaacaaagaatgggcttgaaacattataaaaattgacaa
tgatttattaaatatgttttctcaattgtaacgacttctccatctcctgtgtaatcaaggccagtgctaaaattcagatgct
gttagtacctacatcagtcaacaacttacacttattttactagttttcaatcataatacctgctgtggatgcttcatgtgct
gcctgcaagcttcttttttctcattaaatataaaatatttcgtaatgctgcacagaaattttcaatttgagattctacagta
agcgtttttttctttgaagatttatgatgcacttattcaatagctgtcagccgttccacccttttgaccttacacattcta

FIG. 4 (Continued)

ttacaatgaattttgcagttttgcacatttttaaatgtcattaactgttagggaattttacttgaatactgaatacatata
atgtttatattaaaaaggacatttgtgttaaaaaggaaattagagttgcagtaaactttcaatgctgcacacaaaaaaaaga
catttgatttttcagtagaaattgtcctacatgtgctttattgatttgctattgaaagaatagggtttttttttttttttt
ttttttttttttaaatgtgcagtgttgaatcatttcttcatagtgctcccccgagttgggactagggcttcaatttcacttc
ttaaaaaaaatcatcatatatttgatatgcccagactgcatacgatttaagcggagtacaactactattgtaaagctaatg
tgaagatattattaaaaaggtttttttttccagaaatttggtgtcttcaaattatacctttcaccttgacatttgaatatcca
gccatttgtttcttaatggtataaaattccatttttcaataacttattggtgctgaaattgttcactagctgtggtctgacc
tagttaatttacaaatacagattgaataggacctactagagcagcatttatagagtttgatggcaaatagattaggcagaac
ttcatctaaaatattcttagtaaataatgttgacacgttttccatacctttgtcagtttcattcaacaatttttaaattttta
acaaagctcttaggatttacacatttatatttaaacattgatatatagagtattgattgattgctcataagttaaattggta
aagttagagacaactattctaacacctcaccattgaaatttatatgccaccttgtctttcataaaagctgaaaattgttacc
taaaatgaaaatcaacttcatgttttgaagatagttataaatattgttctttgttacaatttcgggcaccgcatattaaaac
gtaactttattgttccaatatgtaacatggagggccaggtcataaataatgacattataatgggctttgcactgttattat
ttttcctttggaatgtgaaggtctgaatgagggttttgattttgaatgtttcaatgtttttgagaagccttgcttacatttt
atggtgtagtcattggaaatggaaaaatggcattatatatattatatatataaatatatattatacatactctccttacttt
atttcagttaccatccccatagaatttgacaagaattgctatgactgaaaggttttcgagtcctaattaaaactttatttat
ggcagtattcataattagcctgaaatgcattctgtaggtaatctctgagtttctggaatattttcttagacttttttggatgt
gcagcagcttacatgtctgaagttacttgaaggcatcactttttaagaaagcttacagttgggccctgtaccatcccaagtcc
tttgtagctcctcttgaacatgtttgccatactttttaaaagggtagttgaataaatagcatcaccattctttgctgtggcac
aggttataaacttaagtggagtttacccggcagcatcaaatgtttcagcttttaaaaaataaaagtagggtacaagtttaatgt
ttagttctagaaattttgtgcaatatgttcataacgatggctgtggttgccacaaagtgcctcgtttacctttaaatactgt
taatgtgtcatgcatgcagatggaaggggtggaactgtgcactaaagtgggggctttaactgtagtatttggcagagttgcc
ttctacctgccagttcaaaagttcaacctgttttcatatagaatatatatactaaaaaatttcagtctgttaaacagcctta
ctctgattcagcctcttcagatactcttgtgctgtgcagcagtggctctgtgtgtaaatgctatgcactgaggatacacaaa
aataccaatatgatgtgtacaggataatgcctcatcccaatcagatgtccatttgttattgtgtttgttaacaacccttttat
ctcttagtgttataaactccacttaaaactgattaaagtctcattcttgtcaaaaaaaaaaaaaaaaaaaaaaaaaa

SEQ ID NO: 7

>hg18_knownGene_uc001kfb.1 range=chr10:89613175-89718512 5'pad=0 3'pad=0
strand=+repeatMasking=none cctcccctcgcccggcgcggtcccgtccgcctctcgctcgcctcccgcctcccctcggtcttccgaggcgcccgggctcccg
gcgcggcggcggaggggcgggcaggccggcgggcggtgatgtggcgggactctttatgcgctgcggcaggatacgcgctcg
gcgctgggacgcgactgcgctcagttctctcctctcggaagctgcagccatgatggaagtttgagagttgagccgctgtgag
gcgaggccgggctcaggcgagggagatgagagacggcggcggccgcggcccggagcccctctcagcgcctgtgagcagccgc
gggggcagcgccctcggggagccggccggcctgcggcggcggcagcggcggcgtttctcgcctcctcttcgtcttttctaac
cgtgcagcctcttcctcggcttctcctgaaagggaaggtggaagccgtgggctcgggcgggagccggctgaggcgcggcggc
ggcggcggcacctcccgctcctggagcgggggggagaagcggcggcggcggcggccgcggcggctgcagctccagggagggg
gtctgagtcgcctgtcaccatttccagggctgggaacgccggagagttggtctctccccttctactgcctccaacacggcgg
cggcggcggctggcacatccagggacccgggccggttttaaacctcccgtgcgccgccgccgcaccccccgtggcccgggct
ccggaggccgccggcggaggcagccgttcggaggattattcgtcttctccccattccgctgccgccgctgccaggcctctgg
ctgctgaggagaagcaggcccagtcgctgcaaccatccagcagccgccgcagcagccattacccggctgcggtccagagcca
agcggcggcagagcgaggggcatcagctaccgccaagtccagagccatttccatcctgcagaagaagccccgccaccagcag
cttctgccatctctctcctcctttttcttcagccacaggctcccagacatgacagccatcatcaaagagatcgttagcagaa
acaaaaggagatatcaagaggatggattcgacttagacttgacctgtatccatttctgcggctgctcctctttacctttctg
tcactctcttagaacgtgggagtagacggatgcgaaaatgtccgtagtttgggtgactataacatttaaccctggtcaggtt
gctaggtcatatatttgtgtttcctttctgtgtattcaacctagggtgtgtttggctagacggaactcttgcctggttgca
agtgtcaagccaccgattgctttccttaggctacctatatggtctcttcctgagggctattgtccgttaatacagaatacagt
acactgttagtggattagcgagctcggtaatccggtctcctaaatgaacaaaaagtagacgctttttgaggttgagcatat
ttcgattaaatcttggcttaggccctagatcaagggtttagatcagaataaaatgaaaattagtgttgcacgtacgcatatt

FIG. 4 (Continued)

gcatcagaatcttgcagtgattgttttagtttcctgagttgcattgatagattcttttaaaatatgactgatttgcataact
ttagaagcagaatcattttcagtatatatggtgcacattgagggcaaaaagtagttttgttaatgtttaaacttaagttacc
tacaactttgaactgtatgtagaagttttgtagtttgaagtcaatagtgccataatataccttataaggcgttcttactaga
tctttgttatatttaccttttctctccctatggggtgatgtaggatagtgcttgaaatttgcacttcagtagcatttaatg
ttcagtgctcttgtcataaacatagaatggatattgagtagtttctgatcccagatggtaatgtgtaggttcaagggtattg
tgtgtagcaagtgaagattgcagaaataaaacttcagttcatgcttgaaatttaagtattgttgtgatgccagaattgctgc
tcaccgtttttaggtttcaggtcctctgacacctttggtatcgttaatttttactgatttgtgtagaatgtcagttgtattt
taccagctaatatctagaaatgctggcaagaggggtttactccagctttagattgtaggtatgttagctttttcatacagt
gtattaatttactgagtcagcttgctgaataagacagaagcccaagaattttaacagtgtgtagctttagttgtctaaaag
ttaggccttcgggcttcaaaagttagtggtcatcgaaaagcattaatctttgcagtttcaggtacaacacattggttttgat
tagggatggggatggggccctcttttgcagaatggggaaagtattgacaggaattgagagctattggtaggccagtgtata
aggtatgtgaaacagaattaagttattggtctgaagtgactgaagcatttaggtctatcaaggcctaaaatttggtaata
tgagtttggtaatgcgaattgtggcagtggacaatatttagttaaaattatgtaattgcataagtactagcacagtattttt
aataaaagttatttcttagcaaatgtcagttgcattttgtctaaaggtagagtgacactacagtgtctatatgtcctgctaa
aaattgtggggaatattttttttaagacagcgtttatatcgggagaggttttattccgttggattatgttagctgcatata
aatgtgcacagttaatttgcccaagtttttgttttgaaatgaatgtaaaacttactgaagaagtagcttcccaaaatttag
ttttctgttaagccaaaaatattatttttaaaagagtatttgcaaattttgaagttgacattaattgagaatgttactaaggc
taaactggacccgcttgcccagaagataattatggaaaaattcttttgtgacttccaaagcagtctactattagcatgaatt
actgacagtcatccaaatatataggaacaaaaaattaaatgtttatgtaacttgaaaaaaaagcctttgaagaaaataatt
gaatgctgtctgggagacagatttctttcagcacttaaagtacataacacactacttttacttttcccacttgattttaaat
tatcagggttattaagaccttaaaattatttaccaggtttttacatgtgagctgtgacatgactggcatttttctttgattt
cagcgtatgttggtctctacacatgaaatttgtgtgacttaaactttctctaaaactgtactttagttatgatatgcata
gaaagcagtatcaaatattgcgtcaaatgactaataacacttaattctagagttgtggctttattgagccaaaagttgata
tgaaaaaaagtcagtaaggaaagtcagtgaagtgcttgcttttttgataattgcactcccaataattttgatattccaacgt
acttggtttgcttgtttcacgttaatgtttctgtttattggagtgggaaggcattaaaattgtcattgaagactttgtct
ttgacatgttgtagtatttatttcagtaactaacctgtgaaaagttaaattcctttatgaaagtagtgattggagtatttt
atctgataaagaaagattaataatgaagccatttctccgaggaaaattgaggacaataattcagtttaaaatattatcgca
aaattaaattattctaaaaattgttagtagggttatatgcttaatattagtctgaaatatagtgctgaatttgagactata
gaaaaattaagtgtatttagggtatgtggaaacgttaggcttctgttgtatttttattgtttggtagatttgcctcttttca
aataaatgttcacagggaatactttaacttgtagagagtacagtgactattgaagttacctaaattacctcaaggtaagtg
attactgaaattaatcatgagggtttaaaaagtattctattcacaacatttatttacattgttttgtatctgctaagtta
tatttcctgaaaaacatgactggaccacctaattgctgtatgataacttacaaacttcatttttcatagtgcttattcaagt
gtaaagcacaactgaaaggagtaatgtacagtttatatgaggaaaaaggaatttattgctgccagtgtaaaagtttgcaca
gcagtatagtcatcaatgcagatttacattgcttataatatactaagtaaatactaaatgattaagataataaaatatggt
gaggtataaccaccttcattttaaacttagttttagaagatagtaaagaaagattcctttattaccttttagaattttatt
tttaataacatgggaaaggcaactggtgatatttaattttgtatggaacagtgcatctgctttctcatagccacataaaa
tacataaacttcttagtgttatgaaatggcttactttttggaagtgaagaagtcttcaattcttattttctaatgttatttt
gaaatttgcctccatttgctgtttgttcatttggtgatagcgcaacacttaaaaaaatatttaagccgcttctgaagtaat
cacttcagtgacttttaatggaggagtatttgttatgggaaattcacttcacaaagttttaacattaattcacttgaagtaa
acgtgctatttttaaatttcatctcaatctttaagtaagacgaaagcttaggaaatcacttttattattgatattgtgtg
tgacttcagagtttgtaaagagaattgtagaagtgttgcatgcatatgacaatttctgcttaattgaaatgtgaggcctct
gccatactacaaggatttagcttccagaaaatgtaatattaacatagcttaagaaatgtattttttttttctgtagaaacc
gttgggttaaacaaacagttcagaagttttattacatggaacccattagttcttaatcttgttaccttttcttcattttt
ctgttaaacttgattttcacagtcagcattgaagaattcatcttgtggcctgaattcattaagaaaagatgttaggatttgt
tctgaagatagtgacttaggaaatttgtgagactggggtcagtcagttctgttttacaattgctttctatttggtagctttg
aaattaatttagttgcttatcagagagaataatgttgaggttagactaaccttaaattggtaaggctttgcttgagcaaactg
ataactgtaagtcttttatagggtgcattactgccacatatacgttcttccataggtggttaaaagtatattggtctgtgtt
tggtgattctctttgtacatattgagtatatgcattcactaatgtaaaataatttgccaagaaaggtgaaattagtatattg

FIG. 4 (Continued)

tacttgactattcacctttcccttagtttttgaatttttttcattggttgcagaggaagtattagcaatttaattcttta
aaataatttgcactggaataaataagtatggcaaatataagaagagtaacataatttaagggtgaattaattttatttggg
aagtttagttctgtatagttaaggcagattcttcatttgcaacagttgacattgggacatgtgtgaacatcttcaaggtat
taggacatcttcaaggcattactttttggcagtgttgagaattttttttttttttttttttttttgagatggaatctcgct
ctatcgcccagtctggggtgcagtggcaggatctcggctcactggaacctctgcctcccaggttcaggcgattctcctgcct
gaacctcccaagcagctgggattataggtgcatgccaccacgcccagatagttttgtactttagtagagatggggtttta
ccaccttggccaggctggtctcaaactccagacctcaagtgatccgcctgcctcggcctcccaaaatgctgggattacaggc
gtgagccactgcgcctggccagtgttgagaatattgagagatggatattgtagctgtacctgccatcaaaagaatttcttg
acctccacatagtgtgaaaagaagactgtttacacattatatttaagtaattatacacataattattatcagtactcacc
acttcaaatatgaacagtgaatctaaccagtgtttgatttctctgtgtgtgtatgtgtatacaaagttagcaaaccttttat
cttaatatttattaaaaaacgaattttgtttctttaaagaaaagactaccttagagaatattgttctatagttttaaata
tggtcagatctattttaaattatgttaaaattttgagtattacgtttatctatactttaagcatatatacattgtttcatt
ttagatttagggaggcagtgtgggctctggagccagactgcttgttttgtaatcctggatcttccatttagtagctggatg
actttgagtaggttatttagatttctcaatctattttatctgtaaaatggggatgataatggaacctaccgcatacgttta
tcttgaatagtaagtgagataataataagtaatttcatttagcatagtacctgccacattgtaaatacttaaatggtagcta
ctgctctgaaaaactgtaatttcaggttatgtatgtagggaaattatttgtatttcatttatggtgtatgattgtaactga
atttcctcagtttgggccatgttaggatttgtttcaagttataagtgtttttaaaaataagggtattcctttaggaagtct
gggtatgacatgtctgtgatttgctggttcatcacaaatgggaaataaatctctgctaactcaaactgttgaccaaagtaa
aattaattatgccaatcaaaaactatttgctttaaaatataaaaggcaaaaacttcctattagcataatgaagtagaattt
taaactttgttataatcttaaatttctttagtgttgaagataggtcaacttaactatcatacatttttattcacataaagt
aaactctgcctcaaatgtaataaacttaatatgagttatgtaaactttggtcaatagaggtatatttttagcatttccttt
tgaaaatttcagcctttgagggagtcttgcaactgaatgtcaagttacatttattacaataaaatggacacttaatataat
ctgtaatgcattaacataatatgggaacttttaaagtattcagtctctgtattattgagtcctatttccacatttggccagg
atttctcaatatgatttaggcccaagacgtgggaagaagaagtaaagaactaaaggatttttttcttcatttttttaattga
atatggggaaagatggaataagcttatctgtccagtaaaggccattatgtgtacatagggattattatttttccccccttg
ggctgtactgatttcccagatgtaccacagcactcttagtagtgaagcacttgacttctagtgagtggatttttttgtgtgtg
tgttttatattgcagagtgaatacactctgtctgatactatgtgactttctgattatgtgatttttatgcatttatgtgtt
ttgtaaactagctgtatttttggtccatgtctaggttgtagaattgaattgtgcatttggcatctgagcacagctgagttt
tctaaatcaatctctctccttgcacctagttttttgctttagatcactacctaagacttactgttgatttaatattagagcac
ttaagcatagctttgacttttatttcctttgatctttgtagattttcaggctgaagtacaataaggttctctgttcctttact
agtaattgcaaagattgtatttctgtgaactttatttgtttaatactttgatcttttgaagaggatgtaattatttaaggta
ttatgaaatgcattgtgatttgaattagatactctttggagatggagttttgctgttgttgcccaggctggagtgcaatggt
gtgatctcggctcaccacagcctccgcctcctgggttcaagcaattctcttgccgcagcctcccaagtagctggaattacag
gcatgcgccaccacgcccggctaatttttatattttttttttcagtagagatggggggtttctccatgttggtcaggctggcc
tcgaactcttgacctcaggtaatctgcctgtctcagcctgctaaagtgctgagattacaggcatgagccactgcgcccggcc
tcagatactctttaattagatgcgtttaaaaatttaacccaccattgctggcatgaatagatgtattttagagtgattca
taaatatcgtatacatgtttaaagttacaaactttttgcttatttcaaaatgcaggattcttttccatttaaaattccctct
ctttgtgagacttctttttgagtattctggttactctaaactgattggagatgaaattagatagaattgaaaactgtacttt
taaaatgaaattttggggatgtcattaagcttgatttttaggtttttttttttagtgtgtattataaattatttacactga
ttgtcagcgataaaatggaatgcctgggatttttaaaatttatttattcatttttataaggtaaaaacagtgtttgcta
ggcttaatttgaccatgttgtaaaatttattgtatacctttgaaagaatcatttatgaaagatactgaattagctaatatata
ctctgtcttatgtagtttttgattaacaatacactttttaaatcattagctcatttgatttgcaaagaagaacaggtaacc
taagaggcagacagaacaggcattactttcattttccttccttttttatttatttatttatttatttattttttgca
gcttaggaattgtagctccagtggaatcagtatcttgttaatggctagtgaaagactgagtctgaagaaggatgcaggactt
ttttggcacttggtgcagtatttttcccattatgttacatgagtggttcttaaacttcagtgtgttagaacaacctgaaggg
cttattaagctatggattgcttactccaccctcagagtttctgattcagtaggtctggattgggacctgagaatttttattt
cttagaagttttcaagtgatgctgatgctggtgctctggggatcacactttgaggaccaccaatgaacattatctcccacca
agcaaacccttaacatgttatactcctttaggttattagaatttatacatgcattatttcatttgacctgtaaactctaagt

FIG. 4 (Continued)

aactttgcatggaaaatgttatcctgattttatagacgagatagtgagtttagaaaggcagtatggtggaatggagcataga
tttggagttggctagacctaaagtccagattaaatctctgctcaaggctgggcgtggtggctcatgcctgtaatcccagtgc
tttgggaggccagcgttggcagattgcttgagtctggaagttcgagaccagtctgggcaacataggcagaccctgtctctac
aaaaaaaaatacaaaaattagtcgggtgttatagtgcgcattggtagtcccagctactgaggaggctgaggtgggatcacct
gagactgggactttgaggctgcattgagctgtgattgggacactgtactcctgcctgggtgacagagtgagaccctctctca
aaataaataaataaatacatccccgctcagccacttatcagttacgtagatacactgcctaaccttagtgaaccctgcttc
gacaactccaaaatgggagtaaaaatcctaaacttgtacagtggtttttagttttgttaaaagtacaggtgaggtttttt
cagagtattggttgccatctgagagtgatcccctttcacctcctctaggactttagcattttctggagacattttggtggt
cacagctggggtggtagagtgtgctattggctaggggcttgaagccagtgatgccgcttaacatcctatatggcacaagacc
cctccccatcaacaaagaattatctagcccaaaatgctgtgtaaaatgtctggtatataataagtataatatttgatgaaaa
tcagtaccttgcccccaggtgtgatatttaagaaggtcaacttactaaatcagtgatggagttagtcctaacatctgggtg
ttctgactgctgctaggccagtattctttatatgataataagaactttgtccacagaagatatccctaataacaaaaaggt
ttatttgaagaggactcatgtgttctttggctgattgtgaaagtgttgctttgaacttctgttagaaaaggttgaagatgtt
ttccgtaagtgtttttaatactgtacgtagtattcagaaggatgtttaattttttttttaatttgctagtagtttttaaag
taatcctttttcctttaattatgtagttgttgaactgttgggagttacttttctcttactatttgttatttaatgtattct
ttgaccttatgctttttattctaaagctgcttttattatagtcagatatgatgaagttaaatgtacaatgtaaaattgcaa
atttccaacgagctatacaaacttaaatatttctaagtaaagaaaatagggctgactctaaggttctttgatccatgtgttg
cattctttctaggccctaaatttgctatgccagcctgttgaattaaagtgctttatttatctaaattagaaacttgtatta
aagtgaagttttagaaaaaagaaacaaaatcggaatggagttttaggttagcccagagatgggaagatgccaagaaggtag
ctttagtggattctgaatttttggttttgtttttgtttttagggcaggcaaatgtaattacaaaagggttctaggaatagat
tgctgtgatttttttttctgtttgcatgatttacagtttgctttgcctctcacttttgaatgcagaataaaatgtcaaggcc
ttatttttttttaaattcttaagaaatttaagatttgactgttaattcctttttgaaatatgggatatttttgagataccaatt
atttaagacaaataggactcattgttacaattcagttgaataaggcttatgatgtttatttcagtatatgaatgaaaactat
gtgcctattgtacttaagaaaatttctttattaaaaacatgactaaagagaatttaaaaatcagccactgtcctacttct
ctaaaacttaatgtttttcatattagcttccagtttgttcatatgcatatactttaaaacctagttcatggtgaacttaaga
gggtgttctttttaaaaacaatttccattgcactttgtcgttgccttaattaaatggtgaaatcatcagaaatatttattt
tcctatacttatacatttattaagcttgtttccattttttattttgtgatttttttaagtggatttaagataacctaaacat
tagagaggatttttcatggttttgattcatgaaatcataatgttatacaaacctaactgaagtgttagagccttgaagatttt
tcccccgaattacatatagtaactctacttgtatttaatactgaaagcatattttacttatttaagtgagacaaagtaaaat
ttagctgaatactttagatctatcatttcctttttcctgttgtaagaacattacattgtgttgaaattaaagtggatatagaa
ggtaattagaataaactgccacatcatttttatagtaaagtggtaataacactattgctttctgtttttttaatcagaagga
gtatgggcttataatgatgttactgttccctgaagcatattttgaatgatacggtttatatttgcacagttgcccaggtaat
cattgtgatattaattgatcaatttgctatttatttgcgtttttaaatcagtactagtatttgtgcttaaaaattttgcatat
gttttatcagatttaatttttaagtgtcagatactaaaacaaataaccttaactttattaaattataattttttatcatgag
gtggtattcatttattcatatagttagaacaaaaaatatttaaaatattgaggtagaaacaaattagtctctttttaattaa
aagccagattacttgttagagtaacatttttcccaaatgaggtaaaattgttgcgactgttaaacttaaggaaatttgatct
aggtgtggtatataccttcttgtggggtgctaatgaaaacagggatggcaaaaatattttgtttgtgagtgtatgcatttat
gctttttgacaacctaagaaacactcttacatctgagtatctttcatggactagctgtaggaaatctatataaaatagctta
gtatactgaaagtatgacatagttttacatatctagattgtggttgtgattatatataatactataaaatatgctaacgtgc
tgcttaataatactatttggatttttttttaatactgaaaaggtcacacagattgtgattattgtgtagtgtccaagaactaa
ggcctaccatctgttactcaaatgtatgaaaaagttaagataatttagtgatataagtggttttgacaccactgtttttgga
ataatctaattatgatttttataaagactaatatcaaattttaaacgtttgcaaaaatgaaacctaatagttatactgttat
ttatattttctattacaatacagatactggctgagaactcaagattgtgtaataaacgcctggccttcagtcatttggttt
ttttttccctcgattgtttggatagttaactggacatcatgtttttaacttgagaaattaagttatacaagatttgatatt
ttaaactagtttttcctaactggttgagatatataagaatttagtattacaggactcaatcagggaactgatttaataagaat
ttcttaaaaattgtttaaatatttttccaagttcctttcttcatcttctacaacttaattcttgtctgtatgcaaatgagct
tccccatttaaattttgctgttgcattttaggccactatagaagttgtttcttttcaatttttcactcacaagaatttggtctt
accaaattgtgtaaatctttaaaattgtgtatttggcttaatattatagaatctgattgatttaatctaccttgtttcattt

FIG. 4 (Continued)

agtatgttgacattttcctgagaaacttgttatgccaaatgattaacataataatatttaagtttagatatgattttgaat
ttacattttcaaatgcaacttgtgtctgtggccttttttcttttttctttttacgagaaacatcttgccaatttcagat
taatctgtgaggaaagtagattggtttactagactcagtttgtagactttggtgagaactgaattggaggctatgaaaaaaa
taccttttgggcctttctgaatagacatatatacataaattatatctcttacattaagtgaggcacatatgtaggtgagatt
tttacctgaatattaaagtttaaaagtcgttacctattctgttacttaatagtatttaaagggtgtgagaggtgttatgt
gtttctgtcccttgttttttattcctatccctcccatctaactgttggtactcttatcttcccaggtattaaacttgtatgtt
ttaaaagcttatttacttgttgaaatggttaacttaattagttttttccttgaagtttcagcctaaatattttctgtttttt
tatatgtcctttaaatatgaaaattctacagctaatcataattagtaattgtactttttcccctattacaataactggtttc
ataataaaatggtatcccttcaataacaagcatttatagtagtttattaaaactaagggtgttatctattcaaaccaagcaa
tgcagacttactgttgactctgttaatatatttaaaattgcatattactaaaatttaaaatatgatttgactagtatttt
ggtgtatgttattttagatattttgattatgcactacttaagaatgaattgtcaagtatgattataaagttgatataatagt
taaccttcagtgggaataggaatcatttaatattgttagatatttgtattattagaacaatctcctatgattcttactaata
tagtaatgaatgacagacaatatgttggctttcatatttaaaaattcacatgcatttctagtttatgtttttcttcgactaa
aattctgcagcacttaggcaaagctattttaccagttggaaaaaaagtaagtcatttccaaccaatttcctggcttgtag
tatagaataaagagacttgattttattacattaaagccaaatataaaatgatgcaatctagcacacacttgtttggaacttt
tctcttttaaatattcagattaagaggacgttgaaaggtaaatttttttttttttgagacggagtctagctctgtcaccc
aggctggagtgcactggcacgatttcggcttactgcaagctctgcctcccaggttcatgccattctcctgcctcagcctccc
gagtagctgggactacaggcgcctaccacggtggcgcccggctaatttttgtatttttagtagagacggggtttcaccgtg
ttagccaggatggtctcgatctcctgacctcgtgatctgcctgcctcggcctcccaaagtgctgggattacaggtaaattt
gattgttattagcaactataaaagttttgcagttggcttattggaaaaagaaaacctccttgccggagacggagacgcattt
gtattagaactttgtttttctgagtaccttacctatagtaggtttcaaatattggtgaattagttgatggttaggtctgcata
attactgcgtatggaaattctggaaccctatttttttcaaaatgcagctaatgttgagagaatatgcactaaatattactaga
tctttgtttttcaagatgctgatatcccttaacatcttctgcactttacctgtttgaatatctttttttgctgtaaaaattag
tggccttatgtctttctgcataaattatagagtagccaaaacctgttttaggttaatcacctctggcaaaataaatgataaa
gcatagcttttgtaagcagaatgatattacagaagttaacttataaatctaagtgtattaaagacacttaggaaatttatga
taatgctgggtcagcattacagttttaactttttacagtttttcatatgctttttttgtgattttgctgtagaaaattaaca
gttggcatttggcttagttcaagtataatgctgttgacaagtatatctgacacgtcattgaactaataatatttttgaaagc
tgataggtaagttatatctatttgtttcattcgtcattagtgatcggtcttagatgtttttagcgagagcaaaactgtaga
ggaatgtgtgtctgtgtgtgtatatgtgtgtgtgtgtgtgtgtatttaacagcaggagagttctgaaacaggaaaccagtc
ttatcatattcatccagagacctaggaagaaggtaattgtttggtatactcgttaaaaccagttggttgggcaacttaaatt
tttagaggatcacagatgtaggcttgagcagttgtagatagatgatttctttttttctttctttttttctttttttttga
gatagagtctctctctgtcatccaggctggagtgcggtggcgcgatcttggcttactgcaacctctgcctcccaggttcagg
cgtttctcctgtctcagcctcctgagtagctgggattacaggcgcatgctgccatgcccggctaatttttgtatttttagta
gagacggggtttcaccgtgttccccaggctggtctcgaactcctgagctcaggcaatctacccacctcggcctcccaaagtg
ctgggattacaggcgtgagccaccgtgtctggcgatagattatttcataattaacacctgctatgaagaaaattgattaaa
atagttgagaagtctagtacactctcagctaatatactaaattatactatggattttagagtattgttaacattatcagtga
cttgatatcttcctgaggttctaatttgcttaactttaaataattggggttcagatcaccttgattgttcccttaaagatta
aattttgtaaaactgtgtgtaatttcctgtatctggtttggatagctttaaaaatggttcttaagtttaatgagttcaact
gggaaaaaagttagttctattttagatgttgtgtcactggaaattatgtttccctgtttgttatatgcacattattacaaag
ttgtaatcaatgttttcatactgttctctggtctgtttttttcacaaatacactttttatttgtcgccaggtacttattttc
aaagctatagaggtaatatttcatcaggtgagggtaactaccatggtttgtttgctatactgtgttagggttatttcgttt
tttttttcttttataaactatagttgtgaatatgtttatgtagtttactttggcttattagaatatattgctagagtggga
ttacaggattaaagagtgtacagtatttttagtttttttttttttttttacaagttgcagatttgttgccaaatgaacgagttt
gtagtattgctaacaaggagaagaattactagcaagtcttgatgttactttgaagagtgtgatgattgcatttaggaagat
atctaaacttctgtttcaaagcaaaaagtatgtgcaaatttcttactcatgacaaattcatataatataaaaacatgaaagt
tgtgaggtcaggttgtttggagaagtagaaaacttcagtagagttatagataggcagtcttcctttctggtttggcactga
cagcagattaactagaaagtgttagaaggaacctaaatttatactaaagtcaatttaagttaattaatataccagaattcc
ttcttttacaatttatttataaaaacaccatattgagttgcccttgtaatgagacatttaaactaaatttaaataacagaatt

FIG. 4 (Continued)

catgcaccatctaataacaaccccttatttacaattatagagtcctttgcaattttatagatattttcatgtatcccatttg
gtccttgaaacaattaatgaagaagttacagcaagtggtattatcattatttacagaagaacaaaacaaaaatatatgtgg
cccagagattgagtgatttacctgaggttataggctttagattgcatagctggaagtagaaccttgttcttctatattaaat
gacaatattcattaagtacttagcacaggatttggtacctagtaaatatttaaatgttcctgtgttattcctgactattcct
tctttattcttaaaacgccatttttgagcactcttaatatttatagttcaaactttgtacctatgtacctttttctcttta
gaaaataagatttcaggctgcattaatttgatctgtacaggaatgattatatgttttacatattgggacaaattgctctttt
tttatatacttaagctctagggtacatgtgcacaacatacagatttgttacatatgtatacatgtgccatgttagtgtgct
gcacccattaactcatcacttacattaggtatatctcctaatgctatccctccccctccccatacccatgacaggcccctg
gtgtgtgatgttccccaccctgtgtccaagtgttctcattgttcagttcccacctatgagtgagaacacgcggtgtttggtt
ttctgtccttgcgatagtttgctcagaatgatggtttctagcttcatccatgtccctaccaaggacatgaagctcatccttt
tttatggctgcatagtattccatggtgtctatgtgtcacattttcttaatccagtctatcattgatggacatttgggttggt
tccaagtctttgctattgtgaatagtgctgcagtaaacatacatgtgcatgtgtctttatagcagcatgatttatactcctt
tgggtatataccagtaatgggattgctgggtcaaatggtatttctagttctagatcactgaggaattgccacactgacttg
aactagtttacagtcccaccaacagtgtaaaagtgttcctgtttctccacatcctctccagcacctgttgtttcctgacttt
ttaatgatcactattctaactggtgtgagatggtatctcattgtggttttgatttgcatttctctgatggccagtgatgatg
agcatttttcatgtgtctgttcgctgcataaatgtattctttgagtagtgtctgttcatatccttcgcccactttttgat
ggggttgtttgatttttttcttggaagtttgtttaagttctttgtagattctggatattagccctttgtcagatgggtagatt
gtaaaagtttctcccattctctaggttgcctgttcactctcatggtagtttcttttgctgtgcagaagctctttaggacaa
attgttcttaaataatgaacagttggcactttttcaactggaaaattcaaggaactgctctttctgctttctgctcaatatg
aatcttcaatttagaaatgagagtccatcattaacaattcaacatagcttattaataggaaaaaaaacctagtaacaaatg
taaaatctttgattaaatgagaaagtcatagaagttcatcagatttgtatttaaagcatgatttcattagaaaagttgataa
taaggatttaactgtgacataattggaaaatacttgtttaaacttaaaatttgaaaagaaatgtaaatgtgatgtaactta
tgaatcagtggttgagtttcttttttgctcacaagaaccctaactgtgtgttacttgaaagcactgatggaaatcagggaaa
aagctccagaagttcctacgaaataaaattaaatgataaagtcctggtatctgctaacttgccttccattcctgttatcttc
tctttcttagtctgacttcattaattctttcaccctggctactggtttagctcagtgttttatgagccaggcagcttcagact
ttgcttttgatgctctttgttcattacctctaaagctgtattatcactttcattttatcattaatgtttcatgtatatgtta
tagtttcatattgttactgcaacttttacttagctataatttaaaaaatatctgtgatctgtggaaataattattctatggc
agaaaagtagttattgcattttactttataagttgtttaaggataagcatacctatatattaagcactacaaagaaactttt
acaatggctttattttagcaaaccatcatagttaaaataagatttagtgtacatgtcaggaacacagtcttatgaaataag
gtttagggagctattttagttactatatcctacttgaaaattgtagttaaatttctagcatataccctattaatttagatg
caagtacagatttgagataaggtagatacattatttggatgtcaactcggaagttgttcaagaaaagatattttgttattta
gatgtaacttggaacatatttctagtgtttcaagtcatgattgtatgcctagaacaggcaataaaaatttacttagctggta
aaacagccacattatttcaaatatagtttagttatattatggattaaattgatttttgtggacagactttagaacttaattg
ctattaattacatttttttctttgggacggtatttgttctttggtgagaaaggattcttgtaacacctaaatcaagactgtcc
aaacatggcatatgcagtttaccagtcaaaacaaactaatcacttaagatctgtgtatttgtttatttgaattatacctc
aattaaaacaaatttagcatgtttacacaaaggtgggggaaactgtctaatatatctgagatctgttggagctggggtgac
catccaacttaggcaagatagctagtaccatgtatgcatttctttttacctttcttattgtatatacagtaatcactgatatt
atgagaaaaagaacttttttaataattcaggagatattttatcgctagtatatattgagtgcttattatgtgccttatatact
ttggactcatttaatcctcaacacaacaaccctatgtagttcatactagaattattcccatttaaagatggggaaagtgatg
tttagagaggctaagtgacttgcccatggccaaagtattagaactgggatttgaacacaggtagcctgattcctaaataaat
gaccactaacattaaaaagacataaacatagaggtgtttgttgcaatgttagtcataatacctaaaaattgtgaactagtta
aatgtccaatagtagtaaaatggttcattaaccatggtacacccatcaatataatgttatactgtcatttaaaattgtattc
ccaagtttcgtatcaggaaaatataataaattttttgaaaaatgtaatgggatatattgtatttataatacagtaatcactat
gtaaccaacatttttatttccatcaaaaattagttataaagaaatagaaatctaagaagtttaatagatattaccattgaac
actagatttgtattagtatcttttatatttatctctctccatttcctatattggccatgtttacttttaaatagtaaaagtc
ataagctcctatttttaaaataaatgttagtttattaacccaagaataatagctaactataaattcatatttgataaaataaa
aagatgacattcatcataagggatacatacctgtgctagcatatggcattttcaaaatcacatgagtaatttgtaatcatca
tagaaatattagaaaatacaaataagcaaacacatactgaaatttagtgttcccaaatctaaaacagagacactgtttttt

FIG. 4 (Continued)

tcttttgggattgtattttagatatgttcttaagttataataaagtaaatacttaaaaggcaaattgatacattaaggattt
caaagagtaaaactttttgttaagctttgatgttctttagaaagtttagattattccacaagtcactgtcgttgaaagaaaa
gtagttacagtggggtcttatgggataaggcattaccatttgttcagttgagagacagctatcactatgttttaagcattgt
tcatatattagctcatttaatcctcatagcaaccttatatgataggtacctttattagccccattctgcttaggaagcaaca
gaaagagtatgtattttgcctaaggttgcacaataagttaagctggggttccaattctagcaagttggttctagagtgtatg
ttattaaccattatgccgtagtgcctgcaagtagatctctagatgtcagaaatactcatcttcctctggttacctggttgtt
ataaatctttatgcttaatacttatgtcattatatgtaaatttcgtattaaacactcaacttattcagaagaatatcaggta
agtgtaggttaaggctgtttctatcagaaatcattatatgtatatatattcctcagttcttatgttgtttagtttttctaa
aatgtcaaattttataatatatggagaagtataaatgtatattagaaagattttgtttatttgtgtaatttgtggcataaga
aatatttgcctcaagatttggtgcttgtttaggtagttgctggcattacttttggaaatgtcagtaaattttcatactgtct
tggaatttttcaattttacatttcattagtaaatgtaattacaggttagtaaatcacttatttgaacctgtttccttga
aagttttatatttttatttggaaatagaaaaaccttaatttcctctcgttgggcagtatggtgtcaaaagcttgggctttgg
agcttcgtatatatatctgggttcaaattataacttactagttactaacttgggcaaattacccagtctttttgactctcaat
ttctttgtctatgaaatgtaatactatttaggattgttaggattaaatgagaatatatttggcatactgtctggtacatgat
acttaacaggtactagttgtctacatctttctaacttaggatggatgccgatgtcttgggtaacatctcaaactttatcagt
aaggaaggtgagaatctgaagaaaatgaaaccttaaaaagattgaattcctggactccatttaaaggagtaaatagctcacg
aacaagacttgctgctctgcaaagtcttccatgttgatcctggtctttgactccttatctgtctgattaaattgaattcgct
gccgtggcatccttaaagctggaccttactttgtcagtcctgccttctccatgttgctttgtgtgtaagcttcactggactg
tttgctttttgctgattatttatgtatttccatatgtctactttagcctttgcttggaatgttctaactgctcttgtttct
tcctctgtttactggtttctgacttaactcttaaggattatctaatatattacctacttggtgaaggtttatctgtgtcccc
acagaattaatccttccctctttaactcttaagctatcttatttttatctaatcgggtctttggcacaattataggtctgt
gtgtctgtcttcctaatagaataggaaagccttgaggacagtagtctttgcttacttagccttatattctcagtgcccctt
gtgcaaaacgttcaatatatgtttgaatgattatgtgaatgaaggagggggccagctgaatttactttaatgattatgtaac
acccatttatgtatagttatagacttgtctgaaatgagttaaatcctttgcaacgtttgctgctatgctttgaatgtctctt
acaaaactcatgttgaaatttaattgccattgtaatggtattaagagatggaacctttaagaggtgattagataatggtatc
tctatccttatgaatggattaatgctgtttgaatggtagtggatgagttatcttgggagtttggcctcctccgtctcacatg
cttccttaccttctgccatgtggtaactcaacacaaagatccttgccagatgctgatgccatgctcttggacttcccagtct
ccagaaccgtgagccaaatacatttctgttcattctaaactacctgttttgtggtattctagtaaagcaacataaaatttac
taagaaaactggtaccaagagtgtgattgttgccataacaaatacctgaaaatgttcaaatggcttgggttctggctagaga
aggatggaagagtttggatgaacaggctagaaaaagcctgtattgctgagaatagagcattaaggacaattctgatgaggat
tcagaagaagagagctgtagggaaaatctggaacttcttagagagttgtcatcagttggtagaactataagtggtaaaggtc
tttctgatgatatctcagaaatgaagaacaagatactggacactggagtaaaggccatccttgttaaatagttgcaaagaac
ttggcgaaattatgttcatatcctaagactttatggaatgcagaatttaagagtgatgaactaggatatgctgcagaagaaa
taactcagcagcagagcatttaggttactggatggctacttttaaccacttaaactaagctggggggaagggaatgacttgaa
gacagaatttataattaaaagagaggcagaatggaaatacttggaaaatttgcagcctggccatagtaaagaatgcaaaagg
tatgtttaggagagcaaaccaagggtgtggtccaggaaccatttgctgaagagattaatattcctagaggagacccaagggc
tatttatcaagacagtggaaaaagaccccagaggcatttggagatctttgaggctgcctgccccatcacaggcccagagct
ctaggagggcagaatggtttgtggctcaggtggtccttcacaagcttgctgcccagggctacctcagctccccatatttcaa
cccagtgggccttggctgtcctaggtctggttcagagggcccaggtgtggcttaggctactgctgagtactcaaatggtaa
accttggcagcgtctatatggtgctaattctgcaggctcacaggatgaaagagctgtgggagacatggctaccaccaccagg
atttcaaaggatgatggggatagtctgggagagacttgccacaggcttggagccctctgaagggtggaaatgtgggttggagt
cactacagagagtccctactagggcattgcataatggagccatggcagcaggcccaccaccaaagcttcagaactgtagagc
tacaagtatacagtgccagcctgggagaacttcaggcttgagaccctaacctgtgaaagctgcatgggctaagtacagcaaa
gccatggaggtggggcttcccagggtctattgggatgaaacgaatgtatttgtaggtgagaaggacatgagtttgaggcc
caggggcagaatgctatggtttggtctgtttccttcaaaactcatgttgaaacttcattgccatgtggcattattatgaggtg
gaacctttcagaagtggttacattataagggctttgccttcattaatggattaatgccattattgcaggtgtgggttagtta
tctctggagtttggccccctttttctctatcatgtgctcatgccctcttttgccatgtgatgcctctaccatgttatgatg
catccagaagactctcaccacatgcagccccttgatcttagacttctcagcttctagaactgtgagtgaaataaacttcttt

FIG. 4 (Continued)

tctttataaattaccccgtctgtggtattgtatagcagcagaaaatagacatcagcctgaagttccccaggctggcattaa
atactaattattaattagtatttatagtgcaaggataaattcaagtttagccctggttagaatgaccacatttcaagggagg
ggctttgtacttctgtgcatatctgtaaggataaaaatcttaatactattctcactgaaattaatggtttaggttaggtaag
gttgttagtgctaataattatttcttttaataaaatattcttagttgcgttgttcaaaaaacatagatgatttgaatttata
tttttggccaaaatatatttataattttgagtaggaattccagagtattggtagctataaccactttgggttccctgccat
tgcttctggtgcctcatttttttctgacgtcttccatttttcttacatttgtcttctaaggtggagttaagattactcagttaa
gattatttcactttaggcctctgctgtcttctgctttttttttttaaaatgaatggatataatatcccaatacattttgataa
ttgaacaacagctacatttttaagtgaggctactttcttctaatttttttaaatttatttttctcagtttttaaaaaaaaatgt
cagattggctaagagttggggcagctttcttatgtgagagtagtagatgacagcaaatatttgtgatgttaaaatgataatc
ctaatagtttttctttttagaatctttataataaaaacccttttgaggctgagggtgaatttgtatgttcctaaagtgacaaaaa
atgttcttgggcatagtaatttaaatcttagatgcttttattagtataatttttttggtagaaatttggcattaaaaaatgc
atacagagcttttttctacatacagggcaagacagcatttctgtcatggcaattagtaaatagataattataaaacatctaatt
ttaagcaatttgttacagaaacgatacaggtacattgtggcaaaaatagaagatacaaaacaagcaaatatgagaaaaata
tacatgccaccacctatatatgactttagtactttataatcttttgtctatatatgtctatatggatatatacgtattctt
tttatccaaatggtattacattgtacattctgttttgaaacctgcctttttttagtcatttacatctacttttccatctcagt
aactttttcatcttgtgtaatgcccggatcacattaaaatgtttccaattagctcaaaaatgtcctttatggctggtttggct
aaaacagtatccaggccagcattgcacctatgaaattggctgttaggaatcttgtatcttaaaaatcaagggcagcaaccc
atcctcccgcttccccccacctcccaccaccccccccaccttttttttttcttaaagatactggcttgttgaagagagaatggg
tcatgtcctacaaactgtctgaatttgtccagtttgctgtctcatagtgtcatttagcttgttttatcctatgtatttcctg
caaattaaaatttgtatctgaatccttggtggatttgagttgaagatcccttaaccatcatagatgatgctgtgtcctttata
ttgcatgtcagaagttacatgatctttacttgattcatgatgaggagatggccactgaaattggacagtgacagtctttttct
gcccattgttcaattatattcgtctctttacattagaaagtattttgggtagtagtattttggtgctgtaagaaagttcatt
ttctcatcaaccactcacctattggtttaacaccatttgttgatctttgagtatatcagtaatttcatcagggtttgcaaaa
taagacttttaaattctattgttttacattattaattgatgttttttgataaggtagaacttgtgaaatggactatttgttt
gtctttaaatacagtctctataggaaagacaaaataaatacttaaatctcactctttaccatttttcaaagtgaagaactat
tccgttaaccacctcaaaagatgataaataaaaagggtattttagttgtttcaacttttttttttttttttgagatggggtc
ttactctgttgcccaggctggtgtgctgtggtgcaatcatggtacaccgaagcctcagtctccctgggctcagatgattctc
ccacctcagcctgggactaaaggtgtacaccaccatggccagccaatttttttgtatttttttgtagagatggggttttgcca
tattgcccagcctagcctcaaactcctgggctgaaggaatccacccatctcagcctcccaaagtgctaggattacagacgtg
accaacaatatccggccttaacttttttcttttgagtgtctttatagactcaaggactttcatttaattcagggtgttagta
ccatttaaatgttttctttgatgctcagattatcacagctagtcattggaccctttataccacctcctatgtccatttgata
taggccattaatctctataagccttcctcctttctcttggaatgaaaggtatcctaggctcacctgtaccttccctactcca
gacctggcattaagtctttttccaaggagtttggtacctttagtttattatgatattagagatgaaaatctgtgttctagg
aatgtttattactgctagagtgatgttgcttttaggccatttcagagaaaagacctagaaaacagattttttacaaacatgaa
ttcatactgatattttttagttttttacatgatttcttgattttacaatattatctgctttcttaacttaaaattatgaacct
taaagtcattagcataactttctttgcttatttctacaacataaagaaaatagtcctggtgcggtggctcacactgtaatccc
agcactttgggagattgaggcaggtggattgcttgagctcaggagttcaagaccaacctgggcaacatgatgaaaccttgtc
tttacaaaaaattagctgggcatggtggcatgtgcttgtattcccagctactcaggaggctgaggtgggaggatcacctgag
cccaggaggtcaaggctctagtgagccatgatcatgccaccacactccagcctgggtgacaaagtgagaccctgtttcaggg
ggaaaaaaaagataaaatagtttgaggaggctggatgtagtggctcatgcatgtcatcctggcactttgggaggtcaaggtg
ggaggatggcttgagcccaggagtttgagaccagcctgtgccacatcatgagacctggtctctatttaaaaaaaaaaaaaa
agaaaatagtttgaggatatcaataatgatattactagaatcagtaaaactaccaaaagaagtttaaagtttcttcctagtg
ttttttttgttcttagaatacttcctaccaagaagtgcagtaaaagtgcagtgtccaaatagcccttgtaacaaaaccttttct
ctttctcctgggtgccaatttgacatttaatcagttttgtttctagcagtgttcaatttattagattataagtcttttttttt
ctttatattattctaagatcaaaaatatataaagatatacacaggagtcctgctgctacctgttcttgctatgcttttcccc
ttttcttccctttctctgtgaagcagccatttttattagtttcttgtttatcactcatgcatgcatatgtttattgaggatg
ttgacattcaagcaaatatatgggttaacattctttttgtcatccctatacgaaagatatacccagtatactctattgggtg
ggttttttttccttaaaatattcagtagatcctctccagttagcacatagttatcttatagatagaacatatacatataacctt

FIG. 4 (Continued)

ttcttaaactatgctattaaaataatagctttcagtaacttgataattattttggattgaaaatactactgaaatcaactc
aatcatgtgaaagctgcagaaagaaaaagacctagaaaaagggcattggattaggtcaactttgaattttatttggaagata
aatgagtccagaagtgagtgggcagagattattggagttggtcttgaaatgaggcgttaggcagattgactgggctggtgtg
aaaggtctgtcagaaaatcatgagattagattgaggtacctcaaaaaatgagagctggtatgatgagtgggtaagaatcata
aaagcgtagagtgttgatgatttttatagtttataaatggttcttgtgtgtagagttttgtttttatgctagctatagtctg
taacataattcactataatgggcatgctaaatatccatgacagttgacccttgaacaacacagagggtaggggcgcctaccc
ctgtgcagttgaaaattcacatgtaacttttgactccccaaaacttaatatttagcctatacttgactagaagtcttactga
tgacataatgttcgttaatacatatttatatatgtgtcagatagcatatttgtataataaagtaagctgcaggaaaaatat
taaaatcataaagaagagaaaatatacttactattcattaagtggaagtggatcctcataaaggtcttcatcctcactgcct
tcactttgagtaggccgaggagtaggagagagaggaaaggtcagacttgctgtctcatgggtggcagaggtagaagaaggtc
cacatacaagtggtccgacacagctcaaaccggtttgttcattggccaactgtagtttgattgaaagtaataataaatgaa
gtttctgcctcagttcagtattatcaagtcatagatagcaagggctggaagaaaccttagtagtaatctcttgagtctaat
tatcatgtagaataggaaattgcggtctagaaaggttaagtgacttgtccaaattacacaactagttagagacatagccagc
tcttaaatctgacttccagatttcactgtgtcttctttttctgtaacgtgttgccttttttagccatgaaaaattagaag
ttgaactcttgtcttttcaggcaggtgtcaattttggggttttgttttgattttggtttttgacataaagtactttagttc
tgtgatgtataaacogtgagtttctgtttttctcatatacctgaatactgtccatgtggaagttaccttttatctttaccag
tattaacacataaatggttatacataaatacattgaccaccttttattactccagctatagtggggaaaactttcttttcat
aactagctaatgtttaaaaagtattctttttagtttgattgctgcatatttcagatatttctttccttaactaaagtactca
gatatttatccaaacattattgctatgggatttcctgcagaaagacttgaaggcgtatacaggaacaatattgatgatgtag
taaggtaagaatgctttgattttctatttcaaatattgatgttatattcatgttgtgtttttcatttagaaaagatttctaa
gccacagaaaaagatactttgtgatgtaaactattattgtagtgctctataatcatttttggcttaccgtacctaatggac
ttcaggggatacagttcatttgataagaactgaccttatacattacataatcaggtacttatgtgatatcatttcctggac
tccataaaatgctggtcaccaggtttaatacctggattccattacagtgtgatttttgtcttatttcatagttggggattag
gcttaaaatcctagagtggatttatttcagttaaatttatttcacactaagatgtagatgactaatactgtatatttttatgta
gaccaaatttaaggtaccactgtgcatatgtataccaactacctgaagaagtatttggttggtacaagagatatagaaagg
aatcgctgggtgtaccaaggctaatcagttttataattttgcataatttctaactgcgattatcatttagtttagaacaat
ttatttctcaaggcccatgtaaatattatttttaaaatatacagtcttaagaattcatggcatattttatgaaaggaggaat
tcatgtctgatgtgcaaatagtcttaacatatttctaatttcagagcaaaaatatatatgtatgaataaattaactgtaaa
ttgtcagtaggaaccttaagaattcgtggcgtatttatgaaaggaattcatgtctgatgtgcaaatagtcttaacatattt
gctaatttcagagcaaaaatatatgtgtattaataaatcaactgtaaattgtcagtaagaaccttaatggctttaaaagtta
aaatttcaggtcaagcattgtggtgtgctcctgtagtcccagctacttgggaggctgaggtgggaggatcacttggcttgaa
ccccaggtagagggtagaggccagtctgggtaacacagcgagaacccatctcttaaaaaaaaagtttaagttgtggattat
ttcctttacactctttcattagtatctttcctggagactttcaatttaaatacttggtgcttatgacaattagatgttaaaa
tggatgggaaagtactttgtaacttataaagcattatgcagatgtagactcctttttataatagttgtgtaagtatataagac
aacctacattcttcatgagctagccataagttttagcaacttgctttgaaccacggtagatttacaatttctgtagtattg
agttgtgttcatttagaattttgtaatatttatattgaaaatcaaatttttgtacctacaaaaactacaaaaaatcccccta
gtttttatagtttctattaaaattatagctggtacatagggatgccagaaggactgtttaagaagctgaaaatagagaaatg
aatttatcttctcatagttaggcagggcacagtagaaggatgcttaacattgcaagctgatgggaacagcaggttgatatag
cttgtgataacacttctaaagaaaaagcaatgagccatagaaaaaagaaaaagatacatttgaattaaggaagatggtgaa
tctgggaagtgagcagtacagtcaccagacgtgtatccctctcctatggtacagaagtgtttattgggtctctttatggcctg
catgatatatccccacaagatgacctacttcacattattttaattctgtattcaactaagcactaattcaacccagccagatt
agtactcataccaaaaaagagtgaatactctgaatagagggcaggttttctgattatggtgagaatatctttgtggtaaatt
aatctggtgtgctagtttttacgttggtctcttctcagtgtcgttagtcactgaggctgattgatcatctttaggttactg
ataaagttcctgtacagctgatttttcagaccttagattgcaataacttcaccaagaaaatacttcattgggaagcatttgg
tccttccatttgattcataactcttacctttatgcctctgaaggaaaagatttatacattcagcttgtaattagtaatcaag
actgaggtttagtctatctagcttcacaatctatctagtttgttttgtctagccatatgatttcttcaaatatgccatttct
taaaaaaaaatgttttatgtatcccgattaatatttagccagtggttctttttagccgatggatcttgtcacctcttatgata
ctattaatagcatgtcaacatgaagaattatctgctgaatataatagctatgctgtccttgtttcctttttgtctcattcttt

FIG. 4 (Continued)

tttgattgggggataattggccaataaagctttgatagcctctattgcccaggcccctccctcttctttttatgagagaaagga
tgaacagtgaccagaaataaaggtattgttttttctatcaactaaaatggaataaataattcctaagtaatttgcctgtt
aggattaaagtctccaagagaatggctgtgcctagtacctaagtgattaatttccttgattggttcacattatattgaggat
attagtaatcagtagtgattcctttttggttcaaagatgatagtgtcacagtgaaaaatgttttaaaatttttgtatact
taatttttctgttaacgaaagtatttcagttggatttttgtttgccctctctattagaatgcccaaagaatatttaaaatt
ttcctttctcttatactgcatattttcctgtgatttttccccaaacggaaaatactctgcagagattagactttgttatt
gttgtactacatcattgctttgactaaaataaactcagattgcaaataccttcaagcttacattgctcagtattttttttt
tttttttttgagacggagtctcactcttgtcgcccaggctggagtgcagtggtgccatctcagctcactgcaacctctgc
ctcctgggttcaagcgattctcctgcctcagcctgcggagcagctgggattatagatgcccgcccccacgcccagctgattt
ttgtatttgtagtagagatggggtttaccttgttggccagtctggtctcaaactcctgacctcgggtgatccatctgtctc
ggcctctggaattacaggtgtgagccgccacgcctggctaaattgatcagtattatttaactttgagggatatgatttgtta
tggaatgcgaagttttatacttgaggtactcagagtcctttttgagacaaatatttaacttctcctttttgaggttaccgccta
cgattgggaattaatgtaaaaaataagccaaaagaaagtgagggaaaagtgaaccaagctgtaatttttttactcttttta
ttgttgttgttattgttgctgtttttactatcttgattgcaacagtttggcttatatatatagcatttggaattgacagta
agaaagccacatctcatagaagctaactattcccaaattgtttttttcttcttttcctcttactactgctgtttcctccct
tcttgctgctaagctcttgtcctgacatgctggtaatatgaaacagtgtttattcagataattgattattctgtaatatgt
atgttaatcttttttattacactttaagtaatagggtacatatgcacaacttacagattcgttacatatgtatacatgtgcc
gtgtttggtttgctgcacccattaactcgtcatttacattaggtatttctcctaatgctatccctctcccaaccccccacccc
aggacaggccccggtgtgtgatgttccccgccctgtgtccaagtgttctcgttgttcagttgccacctgtgagtgagaacat
gcggtgtttggttttctgtccttgcgatagtttgctcagaatgatggtttccagcttcatctatgtccctacaaaggacgtg
aagctcatcctttttttatggctgcatactactccgtggtgtatatgtgccacattttcttaatccagtcagtcattgatgga
catttgggttggttctaattctttgctattgtgaatagtgctgcagtaaacatacgtatgcatgtgtctttatagtagcatg
atttataatcctttggatatataccagtaatggaattgctgggtcaaatggtatttctagttctagatccctgaggaattg
ccacactgtcttccacaatggttgaactagtttacagtcccaccaacagtgtaaaaatgttcctgttcctccacatcctctc
cagcacctgttgtttcctgactttttaatgatcgccattctaactggtgtgagatggtatctcattgtggttttgatttgca
tttctctgatggccagtgatgatgagcatttttcatgtgtctgttggctgcataaatgtctataaatgtcttcttttggaa
agtgtctgttcatatcctttgcccactttttgatggggttgtttgatttttttcctgtaaatttgtttaagttctttgtaga
ttctggatattagccatttgtcagatgggtagattgcagaaattttctcccattctataggttgcctgtccactctgatggt
agtttcttttgctgtgcagaagctctttagtttaattagatcccatttgactatttggctttgttgccattgcttttggt
gttttagtcatgaagtccttgcccatgcctatgtcctgaatggtattgcctaggtttgcttctagggtttttatggttttag
gtctacatttaagtctttaacatttaagtctttaatccatcttgaattaatttttgtataaggtgtaaggaaatgatccaat
ttcagctttctacatatgactagccagttttcccagcaccatttattaactagggaacctttccccatttcctgtttttgt
caggtttgtcaaagatcagatggttgtagatgtgtcatgttatttctgagggctctgttctgttccattggtctatatctct
gttttggtaccagtaccatgctgttttggttactgtagccttgtagtatagtttgaagtcaggtagtgtgatgcctccagct
tttttcctttctgcttaggattgtcttggcagtgcgggctctttttttggctccatatgaactttaaagtagtttttccaatt
ctgtgaagaaatttactggtagcttgatggggatggcattgtttctataaattaccttgggcagtgtggccattttcacgat
attgattcttcctacccatgagcatggaatgtttcttccatttgtttgtgtcatctttatttcgttgagcagtggtttgtag
ttctttgaacaggtccttcacatcccttgtaagttggattcctaggtattttattctctttgtagcagttgtgagtgggagtt
cactcatgatttggctctctgtctgtctgttattggtgtataagaatgcttgtgatttttgcacattgattttgtatcctga
gactttgctgaagttgcttatcagctgaaggagattttgggctgagacagtggggctttctaaatatacaatcatgtcatct
gcaaacagggacaatttgacttcctcttttcctaattgaataccctttatttctttctcttgcctgattgccctggccagaa
cttccaacactgtgttgaataggagtggtgagagagggcgtccctgtcttgtgccagttttcaaagggaatgcttccagttt
ttgcccattcagtatgatactggctgtgggtttgtcataaatagctcttattattttgagatacgttccatcaatacctaat
ttattgagagtttttagcatgaagggctgttgaattttgtcaaaggccttttctgcatctattgagataatcatgtggtttt
ttgtctttggttctctttatgtgatggattatgtttattgatttgcgtatgttgaaccagccttgcatcacagggatgaagc
caacttgatcttggtggataagcttttgatgtgctgctggattcggtttgccaatatttattgaggattttgcattgat
gttcatcaggggtgttggtctaaaattctctttttttgttgtgtctctgccaggctttggtatcgggatggtgctggcctcc
taaaatgagttagggaggattccctctttttctatgaattggaatagtttcagaaggaatggtaccagctcgtctttttacc

FIG. 4 (Continued)

tctggtagaattcggctgtgaatctgtctggtcctggactttttcggttggtaggctattaattattgcctcaatttcaga
gcctgttactggtctattcagggattcaacttcttcctggtttagtcttgggagggtgtatatgtccaggaatttatccatt
tcttctagattttctagtttatttgcatagaggtgtttatagtattctctgatggtagtttgtatttctgtgggatcagtgg
tgatatcccctttatcatttttattgcatctatttgattcttctctcttttcttccttattagtcttgctagcagtctatc
aatttgtttttaaaaaaccagctcctggattcattgattttttttgaagggtttttgtgtcctatctccttcaatt
ctgctctgatcttagttatttcttgccttctgctagctttgaatttgtttgctcttgcatctctagttgtttaattgtga
tattagggtgttgattttagatctttcctgctttctcttgtgggcatttagtgctataaatttccctgtatacactgcttta
aatgtgtcccagagattctggtacgttgtgtctttgttctcattggtttcaaagaacatctttatttctgccttcatttgt
tatttacccagtagtcattcaggagcaggttgatcagtttccatgtagttgtgcagttttgagtgagtttcttaatcctgag
ttctaatttgatttactgtggtctgagagacagtttgttgtgattttttattcttttacatttgctgaggagtgagtgcttt
acttccaactatgtggtcaatttggaataagtgtgatgtggtgctgataagaatgtatattctgttgatttgggatggaga
gttctgtagatgtctattaggtctgcttggtgcagagctgagttcaaatcctggatatccttgttaaccttctgtctcgttg
atctgtctcatattgacagtggggtgttaaaatctcccgatattaactgtgtgggagtctaagtctctttgtaggtcactca
ggacttgctttatgaatctaggtgctcctgtattgggtgtatatatatttaggatagttagctcttccttgttgaattgatcc
ctttaccattatgtaatgcccttctttgtctctttgatctttgttggtttacagtttgttttattagagactaggattgca
acccctgctttttcttgctttccatttgcttggtagatcttcctccatccctttatttgagcctgtgtgtgtgtctgcatg
tgagatacatctcctgaatacagcacactgatgggtcttgactctttatccaatttgccagtctttgtctttaattggggc
atttaccccatttacatttaaggttaatattgttatgtgtgaatttgatcctgtcattgtgatgttagctggttattttgcc
cattagttgatgtagtttcttcctagcatcaatggtctttacaatttggcatgtttttgcagtggctgataccagttgttcc
tttccatgtttagtgcttccttcaggagctcttgtaaggcaggcctggtagtgacaaaatctctcagcatttgcttgtctgt
aaaggtttttatttctccttcccttatgaagcttagtttggctggatatgaaattctgggttgaaaattcttttctttaaga
atgtagactattggcccccactctcttctggcttgtagagtttcagcggagagatctgctgttagtctgatgggcttccctt
tgtgggtaacccgacctttctctctggctgcccttacatttttcctgcatttccaccttggtgaatctaacaattatgtg
tcttggggttgctcttctctaggagtatcttgtggtggtctctgtattccctgaatttgaatgttggcgtgccttgctatg
ttggggaagttctcctggataatatcctgaagagtgtttccagcttggttccattctccccgtcactgtcaagtacaccaa
tcaaacgtagatttggtcttttcacatagtcccatattctcttggaggctttgttcatttctttttactgtttttttctctaaa
cttctcttcttgcttcatttcattcatttgatctgcaattactgatacccttttcttccacttgatcgaatcggctgctgaag
cttgtgcatgcgtcatgtagttctcgagccatgatttcagctccatcaggtcatttatggtctttctgtacactgtttatttc
tagttagccatttgtctaatcttttttcaagatttttagcttccttgcgatgggtttgaacatcctcctttagctcggagaa
gtttgttactactgaccttctgaagcctacttctgtcaactcgtcaaagtcattcttcatccagctttgttccattgctggt
gaggagctgtgatcctttggaggagaagaggcactctgggtttttagaatttcagctttctgctctgtttttctccccatct
ttgtggtttatctacctttggtctttgattatggtgacctacagatggggtttttggtgtggatgtcctttttgttaatgtt
gatgctattcctttctgtttgttagtttttccttctaacagtcaggtccctcagctgtaggtctgttggagtttgctggaggt
ccactccagacactgtctggatatcaccagtggaggctgcagaacagcaaatattgcagaacagcaaatattgctgccggag
ccttcctctggaagcttcgtcttgggggcacccggctgtatgaggtgtcagtcggcccctactgggaggtgtctcccagtta
ggctacaagggggtcagggacccacttgaggaggcagtctgtccgttctcagagctcaaacactgtgctggtagaactactg
ctctcttcagagctgtcagagagggatgtttaagtctgaggaagtttctgctgcctttttgttcagctatgccctgcctccag
aggtggagtctacagaggcaggcaggcctccttgagctgtggtgggctccacccagttggagcttcccaaccactttaccta
ctcaagcctcagcaatgatggacgcccctcccccagccaggctgctgccttgaagttcaatttggaactgctacgctagcag
tgagcaaggctctgtgggcgtaggacctgctgagccaggcacgggatataatctcctgttgtgccatttgctaagaccgttg
gaaaagcgcagtatttgggtggcagtgtcccaattttcccggtatagtgtgtcacagcttcccttggcttggaaagggacat
ccccgaccccttgtgcttcctgggtgaggcaatgccccgcctgcttcagctcaccctccgtgggctgcacccactttcca
accagtcccagtgagaagaaccaggtacctcagttggaaatgcagaaatcacctgtcttccgcgtggatcatgctgggagct
gcagacaggagctgttcctatttgaccatcttggaatgccacctttttttttttttttttttttaaggcagtttcttgct
ctgtcacccaggctggggtgcagaggcatgatcacggctcactgcaacctctgccttctgggctcaagtgatcctcccacct
cagcctcccaagttgctgggaccacagccacgcatcaccaggcctggctaattttgtgtttttttgtagagatagggtttcg
ctgtgtttcccaggctggtctcaaactcctgcgctcaagcgatccgcctgcctcagcctcccaaagtgctgggattacaggc
atgagccactgcacccggccaatatgtatgttaatctcatccctcaagctgatactgaagtttttcaattatgttatttgg

FIG. 4 (Continued)

tgtaaatctaggcagtctttaacaaaattggtgcttcatgtgtttaagaggcataacttaagaattgtttgtttcttataaa
tcaggagaatggaggtttaatagaggtgaactgtctttctcactgcagaacctttaatatgccactatgcattgtaaatctc
ccaagagtgagattctagtatgatgcttttcttttcctttttctgttctttcctttccctctacctcctttttctttttcttt
gttggtggcatgagtcctatattataaggaaatgcttttagagtacagtcttctgatatatagtgattttgaaaaagattt
atttattgtcttgttcactgtgagcttttccccccatgtataagcagctgtgtaatagattcaagagcaccccctcgcccct
ttttttttgagacagagtctcgctcggtcactcaggctggagtacggtggtgctgtgatcatggttcacctcgacttctggg
ctccagcgatcctcccacctcatcctctcaagtagctgggaccacaggcgtgtgtcaccgtacatggctaatttttctattt
ttagtagaggcagagtttcgccatgttttccaggctggtctcgaactcctgaactcaagcagtccacctgtctcagcctccc
aaagtgctgggattacaggcgtgagcctccactcccagtctcaaatattcttttgaaatatttgaaatatgttgatctctca
gtctttcaaccttagttgtatgttgattttcaataaaaaggaagtatttgttgccctaacatcagtattggctattcagttt
aaaaaaggagttaaagagatgttatttataggcaggcttcaaaagaggaaagaatgatcagtttcattctctgtttctagca
tattctgactccttctctcatattacctcgtttttcccacatttttcttaataaagtgaaattcacataacagctaacca
ttttaaccacggaaagtgtacattccgtggcattattaccttcacagtgttacctctaccttatcaagtttcaaaacatt
ttatcaccccaaaagaaagccctgttcttattgggtgcctcttgcttttttttctttttttttttttttaaatcttgagacggg
gtcttggtttgtttcccaggttgtagtgcaatggggcgatctcatctcattgcaacctctgcctcccgagttcaagcaattc
tcctgcctcagcctcccgtagctgggactacaggcacgcgccacatgcctggctaatttttgtatttttagtagaaacgtgg
tttcaccatgttggccaggctagccttgaactcctgaccttaggtaatctgcctgccttggcctcccaaagtgctgggatta
taggcgtgagccaccgttctggccacctcctacttctttcattagtcttaattccttagtggatttgacagtgtttatatta
tctacaccaatgcatttttttgtatgttaataataggagatatttattgggcatttatttacatacttatttgcatgtgtaa
ctgttgtatagccagtttatgtatataatcttactaaatctctacagtaaatctatccccatttcatagatggtttaaaaga
agttaacttccccaagcattactttagtaagtagtgagactgaaggttgagttctggtctgtcagattccgaagttgtttc
cttaggaaccatattatcttgtgtacaactcttgggctaatcttgttaatattctttatttgacctcacactgttgattcat
accatgtttaaaattgaaatacattacctatatttaaaaattgagacctcacataaaaagctatatttctagctgcttttga
aatttcgaaggatcttcaacacttggctgacattcctgcgtgacaaaatcagctggagctgtgtaatgtccgacctgtct
ctgtcaatgaacagattattcattgtcatttctcatctgtttttgagattgtaactttgattctgtataactcatagaatta
gtagttagacctatatatgttagttattacattatttgtatatgtacagactgctttagacaatattgtagtgttatatgtt
aattttatcaattaaaatgtgctataggatcattgtagagatcttgtctctaattaacaggattcataaagagaaaacaaag
gagagaaacatccagattgaaaagacctacatagtgccaagcacaataaaagaaaccctatactaggcaaattattatgaaa
tttgttttaggacaccagaaataaagataatatctaaaaacttttagaatcgcctaggagggattaggaatatgaatagca
tctaacttgttggcagtagaattgaaggtagaaggtggtaaaacatcaccttgaaagttctgcattcagcctagaattctgt
atccagttaaaccatcaatcaagtgtgaaagtaggggggaaaaactcaaggactaaaaaaatgtgctcatgaagaacatttt
tttggacattacccagaagatgtggttcaacaaaacaagggaataaaccaagaaaggaaataaaagagcttcagtaaacaga
gaatcccactcagaagcaacaaagaagaaagtcccaggatgacagctgtgacacaagctgaaaagttaccagttttgcttgg
agcaggagattagaacttccgggaaaataatcaaattgatagatggatgttgaaatatttggagaaaaatgtaatggattct
tgcaaaactgagcaaattagaaaaaggaaacaattattagcattggtggtttgagttaacccaaaattgtgatgttgctatt
ttaggggaattaagataagtgaaacacgtatggaatactgctagttttgtaagtctcctttaccatggcaggacatctgtag
ttaataaatctgtaagaagcagtattaagaataatattttaaaatacctaattaaataggaggaaaaagaatccgagtagtt
gagggtgattgcatctggggagaagcaggaataaaggtttgaagataaataggggccagagatgagtaattttgttactgtga
taatatattttatatatatgtgtatgtgtgtgcgtgtgtatatatatatatgagatatatctcatatatatgagatatatat
gatatatatatgatatatatgatatatatatatataaaacatacagttcagtagcattaacatctagcattcagtacatttaca
ttgttgtgcaattgtcaccactgtccatctctagaactttttcattatcccacactgacataccacacccattaaataataa
ctcctcattgctcctcctgttagtaccaaccattgttctactttcatctctatgtatttgactattctaggtacctcgtata
agcggaatcacgtgatatcttttttgtaactggcttatttcactaactatcttcgaggttcatccatgttgtagcagttgtta
gcatttccttcctttttaaaaggccgaataatattccattgttatgtatataccatatttgtttatccatttattcatcaat
agacactttggctgttgtgaataatgctgctatgaatatgggtatgtaatacctgtttgagtatctgctttcatttctttt
ggatatgtacccaaaagtgagattgctggattgaatggtaattctatatttaaatttttgagaaaccaccatactgtttgat
atactggctgcccaatttacattaccaccagcaatacactagggttccgaatttgccacatcctcaccatcgtgttgtttt
gtttatgtttttttttaataatagccatcctaatgggtgtgaagtctcattgtggttttaatttgcatttcctaatgatca

FIG. 4 (Continued)

gcgatattgaacatttgcacatgcttatttggtcatttgtatatcagctttggagcaatgatgtctcttgaagcctttgcc
catttatgaattgagtagtttgggatttttaaattgtgtttagaagttctttgtatactctggctgggcacggtggctcgt
gcctttgggaggccgaggcaggtggatcacgaggttaggagttcaagaccagactggctggtatagtgaaaccccatctcta
ctaaaaatacaaaaattagctggtgtggtcgggcgtgatggtgcacacctgtagtcccagctgttggggaggctgaggcagg
agacttgcttgaacccggaaggtgggggggttgcagtgagctgagattgtgccactgcactcagcctgggtgacagagcgag
actctgtctcaaaaaaaaagaaaaagaagttctttgtattctctgaatattaatcccttattggatatgttatttgcaaata
tttctcccataaagaatgggttactttttcactctgttgattgtttcctttgctgtgcaggagctatttagcttgaaaaaa
tccaacttgtctgtttctttttgttgcctgtacctttggtgtcacattcaagaaataattgccaaattcataccatgaaact
ttcccccatgttttctcctgaaggtttttatagttttagctctcacatttaggtgtttgatccattttgagttcaaattttgt
atataatgttatgtaagagtccagcttcacactttggatgtgaatatctagttttcccagcattatttgttgaaaagagtg
tctttttccccattgaatagtcttggcactcttgttgaaaattatttgacaatagatgcaagggtttatttttgggctctct
cgactattctgttagactatatgtttgtttttttatgtcaggaccaccctaattttagtactgtagctttatagtaaaattt
gaaaccaggaagtatatgtcttgtgtatttatttacttatttttttgaaatagcatctggctctgttgcccaggctggagtgc
agtggcacaatcttagctcactgcaacctccacatctgaggttcaagcaatcctcccacctcagcctcctgagtagctggga
ttgtagacacataccaccatgctcagctagtttttgtatttcttgtagagacagggttttgccatattgcccaggtgggtct
cgaactcctgagcccaagcagtctgccctcctcagtgtcccaaagtgttgcgattacaggtatgagccaccgtgcatggccc
caacttcttacatttcaagatggttttggcccttcagggccctttgtgagttttaggatggatttttttttaacttttaag
tttaggggtgcatgtgcaggtttattacataggtaaatttgtgtcaaggtgttctgttgtatagattatttcatcaccagg
tattaagcctagtacccattagttatttttcctgagctcgcctcctcccacctggatttttttttttatttctaccagaaac
attgttgggatttttggtagggattgtattagtctgtagattgcattgaatagtactgacatcttaacaatattaagtctta
aagccatgaacaccagatgtctttccatttatttacgtattctttctttctttcagcaatgttttgtaattttcagtgtac
aagtatttacctccttggttaagttaattcctaagtatttattcattctgatgatcttataaatctgttttcttaatttc
cttccctaattgttcattcttagggtatagaaacacaactgattcttcgcacattaaatttgtgccctgcttcttcgcgggt
ttgtttattcctttttgtgtttgaaatccttgaggtttttctgcatataagattatatcatctgcaaatgagataatttac
ttgttcctttccaatttgagatgatttttattcatttttcttaatgctctctcatacattcaatactatgttgaatggaagtg
gtgaaagcaggcatcctgtcttgtttctgaccttataggaaaagctttcaattctttgccattgactatcatgttagctatg
ggattttttttttcccccccagatagagtctcgctgtgtcgcccaggctggagtgcagtggtgcgatctcggttcactgcacc
ctcctcctcccgccaggttcaagtgattctcctgcttcagcctcccaagtagctgggattacaggtgtccaccactatgccc
agctaatttttcgtatttttagtagaaacatggtttcaccatgttggccaagctggtctcgaactcttggcctcaagtgattc
acctgcctcggcctcccatagtgctgggattatagtcagccaccatgcctggccactgtgggatttttatatatggccttca
ttatgttgtggtaatttctttttattcttagtttattgagtgtttttatcataaaatcttgttgaatttttcaaatatttt
ttcctgtgctagttgagatgaccatgtgatttgttttcttctttctattaacatgatatattgtttttcatatatcgagccat
ttttgcatcccaggaataaatttacttggtcttcgtgtataatccatttaataagctgtggaattcagtttgttggttctg
tgttgaggactttatatcaatgttcctaagggctactggtctatagtttttcttttgtagtttctttgactttgctatcaggg
caatgctggcctcattgaatgtgttaggaagtgtttcctcatccatttttggcaaaactttgggaaaaaacgatgttcttta
aatgtttgatagaattcacagataaaaaaatcacatctagggcttttgtctggaatttttttattgttattattgattcagt
cttgttactagttataggtctattcagatttttcttttttgtgtgtgtgattcagtattagtacattttgtacttctcgttatt
tctccatttaatctatattatctaatttgttggcatacaattgttcatagtactgtcttctcttttttttaaacttctgtgc
agttgatactaatgtccctactttatttcagatttagtaatttgaatctttctttatcttaatacaggtaaagctgggtca
attgttaaaatttttttcaaagaaccagtttttggtttcattgatttttctctgttattttttctattatttatatcctctcta
agctttgttatttccttcatcctgctagctttgggtttattagtttgttctttttttctagttccttaagatttgaagttggat
tattgatttgagatcgttttcaattaaatgtgtacaactacaaatttccctcttaggactgcttttgctgttctgtaatttt
tggcatgttgtgtttttttgtttttaatttatttctaagtatttctaagttcccttgtgatttcttctgcgtttaacgtgt
atttttaatttccacagttggtgaatttttctactttttttcttcagttattgattttattgattttcagtggcatcctgttgt
gatagaagatactttatttggttccctgtttttttttttaaaacagagtgttgctctgtcacccaggctggagtgcagtggtg
cgatcttggctcactgcaacatccacctcctgggttcgagcaattctcctggtctcagcctccccagtaggtaggattacag
gcacatgccaccatgcccagctaatttttgtatttttagtagagacagggtttcgccatgttggccaggatgatctcgaact
cctgacttcaagtgatccacccgccttggcctcccgaagtgctaggattataggcgttagccaccttgcctggcccagatcc

FIG. 4 (Continued)

tctatttcttgcctatattctgactgggtgtttttgtccattattgagagtagggtatcgaagtgtccagctgttatttca
gaactgtctgtttaccttcaattctgtcaatttttgcttcatataactgggtggtctcttattaggcatgtaaatgttttt
gattattatatcttcttgctatattgacacttattgatgtgtaatatctttttgtctcaaccttgtttgatttagtttgt
ctaatattaatgtagctacctgcactctcatttggttattacttgtatagaatgtctttttacatcccttatttgtgtcttt
ggatctgaaatgagtctcttgtagacagcatatacaatctcttgtagattgtgtttttcttatacattctgtcaaactctgc
cttttgattgaagagttttatcatttacaattaaagtaattattgataaggatttaactgctgccatttgctgtttatttt
ctatatgccttacagctttttgtccctcatttcctgccttactggcacttgtgtttagttgatattttgtggtgaagtgtt
ttaatttccttgttatttcctttgtttatattctgctatttctgtgtgtgtgtgtgtgtggttgccattggggtcacat
ttaatgccctaaagttataacactgcaatttcaatttataccaatttactttcaatagcatacaaaaattcagctcataaga
ttcagtccctgctcccttccagttattgatgtcataaaattacatttttatgtattgtgtgtctaaaagcgtagactaataa
ttgtttttaatgcagtagtgtcttaatttgtggaaaacaaaaagtggagttgtaaaccaatgttacaataatgctagcttt
ggtaattgctcatgtatttatcatttctcagatctttatttcttaatacagcttcaagttactgtctagtctcctttattt
cagcctgaaagactcacttcagcgtttcttgcaggacaggtctggtgataatgaactctctcagattttgttaatctggaaa
tgtcttaatgtcttcatttttaaggacatttttgctggatatagtattctcagttgacaggtatttgtgtttatttgtttgt
ttcctttcaggatttaaatatatcatcccactgccttctgtccttcaagagttctgatgagaatctgctgatattgagga
tccctttgtatgttacaagttgcttctctcattccatgttcaggattctctttttcatagtttgattataatctatctcag
tttttcctacttggatctctgagtttttcctacttggagttaattgagcttcttgaatatttatattcatgtctcatcaaat
ttgggaagtttttgattaatatttcttcacataatctttttttgcccctttttctctcttttttattctgggattcccagagtgt
gtatgtgttggtccacttgatgatggtgttccacaggtgtcttaggctcttgtcttcaatttccttcagtttttttttttct
gttcctcagacacgtggtatttttcagctgttctgccttccaagtttactgattcttctgcctgcccaaattggcttttgaat
tcctctagtaaattttatttcagtttttgtactttcagctccagcatttattttttgattttttatgtttttctctttat
tgatatttcaatttttgtttttgacattatccatatcttcctttagcttttgagcacctttcaacatttgttttaaagtct
atgtctagtaagtgtctgccatctgatcttctcaggcacagtttctgttaatttatttttttccttttggcctatacttaat
gttttgcttggggtagttttttttttggtatgctttgtgattttgttgttgttgtcaaaaactggaatttgaatcttaaa
gagtggtaactttggaaattagatttttctcttttctctaagatgtgctatttgtttggtttttttatttgttgtagagta
tttctatgctgggtgtaatcttaagatcttctcggcctgtgtttttcccctgggcatgtgtagtgactttctaaattgccta
tgtatgcagttctttttgcagtagtatcctccttaaatgtttggctcctaaaaggcaaaataaataaataaataaataaaaat
taaaaattaaaaataaatcaaaggggtgaaatagctctggatccttaaatccctggagcaattttttcagccaatggcagtt
aaataatgatagtctgcctctgtgtcacattttgatcagaagcagcaattagcaatcagaacacagattcctgatatttgga
gggcaaggtctttgttgccaaccttgactcttacaaactgtgtgcagggtgctctgggaacatgtgcatggttgcctgcttt
gagagtgggtgatgggtagccgcgacggcacaaagagctgaaattgactcaaactaactgatttaccattcaagtctttcct
tagaaactgaaacctgaatagactccagagttccagaatcacagattctgcttacagtcgtctaggtgggagatgggttc
ctggtacttctgattctgccatctttctttgactaattttttttttttgttcttgagatggagtcttactctgttgcccgcc
caggctggagtacagtagcatgacctcggctcactgcaacctctgcctcccgggttcaggcaattctcctgcctcagcttcc
caagtagctggaattacaggcgtgcaccaccatgcctggctaatttttttgtatttttagtagagacagggtttcaccatgtt
ggccaggctagtctcgaactcctgacctcaggtgatcaacccgcctcagcctcccaaagtgctaggattacaggtgtgagcc
actgcacccagctcttagacaaatttttttattccaaacttttttttattttatcatttgaaaggtatatgtttattattttgt
caaaaataattttaaaacgtattcttgaagcttatttagatctgtttcataggaactgtgaagaaagtaaagaatttaaaaa
atgaagacagatttttctcaccctgcttatgggtgcttctcgtgctagccttttgcaagtgtcgggaagtgtaacctgcagga
ggcatcagggctttgggcctgcatggtctgagtgctgccctgtgagtttcagaaggcgcagcaacctgtatacctgaaagcc
atctctgctggggcaggtacctagtgtccccacctacctgggtcgtagtcaggccctgggcaagcctgctatgcttttcctt
ccctaatccctcaggggtgggatagagagcacagtggcctcccagggaggtagaagctgctccagactaacaatcagagctg
ccagttcttaatccccaagaccgccagacttcacaaagacatacccgaggtctgtgctgtcagtgccccactactacactccc
ttaagtagccccacattcttgtgcttgtttcttttttctgctctctttccttgcccaggtaagaggtctgcccataagggat
attttgcagcatgtgaagcttttaaaaagttaggcttattgaagtataatttacacacaaagtacaaaaaaaaaaaagactg
tgttctcaaatctgtgagtcattaatgggtttagatgtttatatattgaaattattggaagtaaggtatgtttatattagaa
agatttgtagtctagattatccaagtttgggagtattacctctctgcttttgtttatctactttttttagtctctactttcc
aagtatctataggcaaatttcccatttccctttggaaagtgctgttttcttgcttttttccgcctttccattgtgtcaga

FIG. 4 (Continued)

cttataaggcaatcagccaactgtgggcatgaaatccttgggaggaaagagaaggaagtgggaggggcagccatggtgaatg
tttccctaagttatagtcaagttctttgagagaacataacctcatcccttttttaaactgttgtaatactttcttttaaata
gattgtttattctcctgcaagtctcacagttgttcacagtggtaggtaagaaatcataaagttcaaatattaaagggagctc
acaaaagagcatggtttcaccagccctcactaaaaacaaaattatgggaaaatgctgtaaaagaaaccagaattcttggttg
caaatgatagaaagtgactctgatttacctaatcagaaaggaatttttaaaaagtattaggtaggtcatagtttgacaaca
agacttggaagataggtggaagctaagggaagcaagacatggccccaaggtttcaacaggagcaatctgcttaggactttgc
tgcttggacacttggtgtaatagctgctgccactatgcctcgaaactggtgactctgctcattaactcacctcctctggtga
tctctaggaataatctctgactctcctgtaccttgtcctcactaggattcggtatccacggcaaaaagatctattaatagtt
ggtatcaggcctgtacatgtgttaagagaaagatgaggaaagaagtatctgcttctaatctcttgaaattatctccaaattg
aaatggtattttggttgcctaacagcctgaagatgacaaatatccccctacaaatttctcctatttaccctcttcctaacta
tatctgtaatttaaagtttcacatattctttgaaaattgttttcattgtttacccactttttaagaaaagcaaatgggaac
atactaccactgtttggcccctttcaaaaatttatatctgaggaatcttccatattgttgtggacatctacctacctgatt
ctttattaactaccttttatttcatttatgatcatgctatcattaataggcccctatgatgaatatataagttgtttcca
gttttttcttgtcattgagaacagttcacatatgtatcttgttgtcttttccaagtatatctttaaggcaaattcttagca
gtggagttgctaggtccattgcgtctatggtttaaactagtgccttcaaaaatggtattttatatactcactgtttaagagt
gctttcttccttctatccccactaactttggcaaactgaatagtttcaaactttaacttttatagcttgttggcaaaaatg
gtatcttgttatttgatcgtgttttttaattgtgaggtttagcgactttttgatgtattggtcttatgtactttctggtgt
gtgtgtatgtatatactgaccctattttcaacttatttttcttttagtttgtttgtattttccttaatgattttcaggaaac
caatttattctttcttcagacagttgtctaatgttctgcttctcttgccatttgaattttgtgactacaaaattcagatga
aacaataatagcataaagaacttggtgggttatctttttgtttttgcattattgattgtttattaagaaatattcttaaaagt
caccttgcttaaattagcaagtaggaaatgctttcaataaagagaactgtcatgtacccactactccttacttactgaatca
tctttctttggatagagaagataaaagtgaaaagggaatttaagagttcctgccttttttccttgtctttagcattatatagc
tgtttaatgtgtgggagtctaatttctttttctttcttgagacaaagtctcactctgttgcccaggctggagtgcagtggc
acagtcttggcttactgcaacctctgcctcccaggttcaagcaattctcctgccttagcctcctgagtagctgggactacag
gcatgtgccaccatgcccggctaattttttgtatttttagtagatatggggacttcaccatgttggccaggctggtcttgaact
cctgacctctagtgatctgcctgctttggcctcccaaagtgctgggattacaggcatgagccactgcacctggcctaatttt
tttattgttctttttggtgtgaacattctcccctcctccaagcctttttgttttttactatttttcatgttcctttatatgtgct
gctgtttgtttcatctgtaattatctctcatcccctttttttggctattataaatatatatatgtacgttttgaatctgagct
ttgaaggtaaattcactgcagctgtgttggttgattttagataatttgtgtatttcctcctttgtctttttttaaactggagt
catttgtagttgtttatacagaatttttagtttttaaaaccacaagtctttcattataggttgagttatgaattcatagcctg
ttatttaaatgaagcttttgaaaatctgtttttactgatctgtatcatatctaactacgccagtatttccttccttgtctgacg
tgaactctaaaattatgtgaacactttctccctgtttcctggcatttccactcaaacttgttcctcattcttagttagaaat
atatccagaattgtagtttctttctaatctaatgacagaagcaaattaatcaagcatggcaagaatttattggaaaactgca
tgtagttgaaaatatgtttagtatatatttttgacagctgtgaagtctctaattttttactgtacctttttctctgttccaattt
tatgctctattctaaggatgtacccatttctactacctgactagggagcatgtgtattgtatcccagcagatttttttttttc
atagatagatatccttagatatctgttatccagtgtaggtagccactagccacatgtagctatcattatgtttaaatgtaa
ataaaataaaataaatttactgagttgttttgctagctacatttcttgtgctcagtagctacatgtggcttgtgattactg
tattaagacagcacagatacagaacattttcattattgcaaaagttctgttagacagtgctgttctatacagtgtcattctg
cctctcattctaaaaagttctaattcctgaagttgatgtactctttctgttgctgtccctctagcttaatcaaaataaatttg
agtctttttaaaggtaggttgcattttacatactgatatttctaaatcagaggctatttatattactttttttttatattactt
ttaaaaattagctttatttggagtataatttacatgcaataaaatctacccattttaaatgtacggttcattgacttttgaga
aatacacacacacacacacacacacacacacaccttcttgtaaacacacaccttcttgtaaacacaacaaccaagatttagaac
actcgctttatgaaaagtttccctcatgcccatttgtagtcagtccccaaacctggtttcaggcaatctctgatctgctttc
tatatgctttgcctatactaggattacatataaatacagtcatatagcatgtattcctttttgtgtctggctttcttttcttt
agtataatatttttgaaatttatccctgttgttactagtatcaataatttgtttctttttcattgctgactaatattacattg
tatggatatgacatttctttattagtgtggtgggcatttgagttgttttcagtttgggtctgttatgaacaaagctgctgta
agcattcatgtgcaagactttttgtggacatatatttttgtttctgtttattcaatacctttgagtagaattgttgggtcaca
tgatgtagatcagttgaacagagtagattccagaaaagttcacatacacatttcttgacaaaggtgctgagattattcatgg

FIG. 4 (Continued)

gaaaaggataatctttttaaacaaataatactggaacaatagagaaaacaaagtgaaccttgacttttatgtcttatcatata
caaaaattaatttgaagtggattgttgacctaaatgtaaaagtaaaatttaaaaatataaaacttctagatgaaaacatagg
agaaaatctctgtgacttttggtttaaagatttcttagacagtacatataaaattaactatataaggaaaaaatggacaaat
ttgactttatcaacattaaaaatttctgctcattgaaagactcaaaatgaaaaggcaagcagttttggagaaaatatttgca
atacatatatctgaaaaaggacttgaatgtataatatatacataaagatgctcttacaacttcataatgagaaaataacccc
ataaagagaagggcaggccgggtgcagtggctcatgcctataatgccagcacttttggaggctgaggtgggtgaattgcttg
agcccaggagtttgagaccagcctgggcaacatggtgaaacccagtctctacaaaataaaaaaatacaagaaattagctggg
catgatggcatgcacctgtagtcctagctgtttgggaggctgaggtgggaggatagcttgagcctgggaggcggaggctgca
gtgagctgtgatcgcaccgctgcacgcttgcctgagcaacacagtgagatcctgtctcaaaacaaacaaacaaaaaaaaaa
caaaaaatggaaacagaaattttacaaaagaagatatatagatggccagtaggcatatgaaaagatgtttaaaatcagtcat
cagggaaatgaaaattcaaacgtaatgagatagctcatatttactggaatggctcaaaaagggcttacaggaattggcaaag
acatagattaactggaactcttatgcatgttggttagagcacaaaatgatatgatttcttgggagaaatatttggcagtttt
taagattatttttgatagccttctgaatttcttagtgagttataggtcagttctgccactgtttctttctttttctttctttc
tttctttccttccttcccttccttcccttccttgcctgtcttgcctgccttccttgccttgcctgccttgccttcctttctt
cctttcttccctttctttctttctctttctttttttttttaaaggagtctcgttttgttgcccaggctggagtgcagtggca
cgatcttggctcactgcaacctccacctcccgggttcaagcaattctcctgcctcagcttccccaatagctgggattacag
gcgcgttccaccatacttggctaatttttttaatttggcagaggcagggtttcactgtgttggccaggctagtctcgaaca
cctgacctcaagtgatctgcccgccttggcctcccagagtactgggattacaggtgtgagccactgcgcctggcctggcact
gtttatttctttttccctccagttttatacctatttagagagattagatttccttgagtactaggaatcactatttttgagca
gaattattcaaaactgttattattttttctttaacttgaggcaatgtaggagaaagcagtactgtgcaggtgaaagttacaa
acaagaacatttaaacaagatagttactttccatgtattggatacgtaacagaattaattctaataaccatcctgaagatg
gtcaggaggcattagttaagaattgaaatgtttggagcttgcctgtgttgatgggattaaggcagggatgatttatgtgtaa
atttatgcgttagtaacagcagtaaccgctgtagttacactagggttctaagagcaaatgttgattaaacatgaatgtagca
ggagtgataaggtttggctctgtgtccccacccaaatctcatgtggagttgtgatcctcagtgttggaggagggcttggta
ggaggtgattggatcatgggagtggtttgtaatggtttagcactatcaccctagagctgtctcgcgaaagagttctcctga
gatctgcttgtatataagtgtgtagcacctcccctctttgctctctctctcctcctactcctgccgcggggacgtgcttgc
tttcccttggccttctgccatgattgtaagtttcctgaggcctctgattaaacctttcttcttctaaaagattacccagtct
caggtagttctttatagcagtgtgagaatggactaatacaaggggaaatatatatggttacccaaatagcgaattagccatgg
gaaaagtagcaaataaataattatttactttttcagatgctaatttttcttttcgtttatttaggattggtgggagctg
tccaatgtccttaggctgttttccaaatgagataccaaaagctagttctccatcgggtttctcaggctgctagaagcattca
ttattatggttgtcattacttcgagttctgttgccgctatgcccacagtagtatttgttacataacaggtgcttgataaata
tttgctaaatgaatttttggaaaatacaatctgccacacctttcttctacagtttacaatcttctgttgagatcatccgata
gattttttttcttagatattgtactttgaggcctcaaattgctgtcttttgtatttctatgtctgcagagactttccatc
tttcactcattgtattcattgtttttaacatctttgtacatatttatagtaactgttttaaagtcactgtctgttaattca
aacatctggttcatcttggagtctgattctattgcctgctcttttttctttgtaataggtcatgttttctgctttgcctgt
ctagtaaattttaatcgtatgttgaaatgtagggagtttggattgttacttcctttaagggtgctgagtttcattttgtcag
gcatttaaattgatagttgatttagtattgtcaggtttggttctctttgttaaagcaggcattttcagatttgtcttttgt
cctagggcatggtttttaacttcaaggttgccctttccaatgtctcagctaagtatctggggtgttccatgaggtctcttcc
actttgcctaggccagaactccagcttctcccagtattatatttcgttacctctggcgtcatctccgttatgctttcagatc
ctgcgcatagacagcccagccccagccaaggacctgagatgaaatccatacaaaattcttagtcccttgctccacaaactc
caacagccttagcagtctaatctcttcctgtttacctcagtgaaatctgtgttccacttgagttccatttccttctgtatca
gagaagagccaccatgctgaaagcaaggggcactatgtttctttgttcttaaggatggtagcctatctgcaacaactgtagt
gtgatataaaaatatataatttatgttgctgacagttacaaatactgcttgcagtactttgtaacataatttttcagattca
agttcatatactcttttttttccacatcaccacacacatatttcagacttcctcctcatccttcttcttgccagtagttgta
ttataattcctgccagtagttacattataatttggttatatcaatattgagtttttatgggattataactagataaatgcc
attcatagttaagtgatagagtatattgtgactttttcctgcatgttttattttttctggacttcacagttgtctctcttt
tttttaaaaaaattagtttttcaatgttcttagctttaattcataaactcacccctaattgtataaatctctcaacatgttta
agcacatttggcattatatcaatttcatctttccaggtgccttctaatctgtcccagtctggactaattgttcttcctggc

FIG. 4 (Continued)

ttgctgtatggctgtctactcaagatgtcccttcaccatcattctagggattccctttcctctcttgtgggttagattctt
cagttcctggagactgtcatctttctttcatggtttcccactcttgttttggcggagcacatctttagtaacttcctgacaaa
gtgtatggtttgagatttcgctgattttaaaatgcccttattatatagtcacacttgatttatagtctgtcttggtatagaa
ttctaggctgagaagagttttccctcaaaatcagaaggttttgcccaattgtttttagctgctagtattgctgttaaaaag
gataatgtcattttgattctagattctttatgaaacctgtttcttctctggcagcttttaggatcttctgtttctttggta
ttcagaaatttcatgagatatgtgtgcttctatttggtcttattttcatctgttttgccaggtactcatgcaactttccag
tttgaaaactcacatccttcacttttgagtatttttcttgagttatgtcttcggtttcttctcagtgttctctgtttctgga
actcctaaaatatatttaacatcctgaactcttagtttttgtttagtcttctgattttcatttgtctttttattctgtatat
tctgttaattcctcggcttcatggtcttctagcccttcttttgcctatcttatggggttgaggattaaacagtttatatacc
tgaggtgcttaggatatgtctgtcatatagtaagtgcttgtgttagctgtaattgttgtttactttcataactgtcttgagg
gaaaggtctttggtcttgattctttgacttcttggctgtacatgaccttggacgagttatgtaatctctttgagacctacct
cccctcctctgtatagtgttaataagctctagctctcagatgtttgtgagggtcgaatggagtatatatgtgaaaatgtttaa
taccctttgtacagaattaatagttagtacgtggatctttcaaatatcaaaagttttcagtttgatgggaaaatgatgtctga
attttcagggttatttttaagagtacttgattatgactgtcttgtaaatctctatgagctaggtatacttgcactaaatgct
aatgctttttaaagaagttatgtcttaatattcagtctcattatgttaggttgaagatagaagattatgaaaatattctctg
aaaagctctggtttacttcagattgtataaatctgtgtaatgtaataattatttaagaatgacatgattactactctaaac
ccatagaaggggtatttgttggattatttattttcacttaaatggtatttgagattaggaaaaagaaaatctgtctttggt
ttttcttgatagtattaatgtaatttcaaatgttagctcattttgttaatggtggctttttgtttgtttgtttgttttaa
ggtttttggattcaaagcataaaaaccattacaagatatacaatctgtaagtatgtttcttatttgtatgcttgcaaatat
cttctaaaacaactattaagtgaagttatctgcttgttagagtgaggtagagttaaagatacatttaacagaattgtatt
cctaaaccgattaagtcaagaagtccaagagcattgttagatcatttagaaagtgtagtgatgaggtaaaacattgttggca
cagattcatgttacttgatctgctttaaatgacttggcatctagcccatatttgagcccataaccgtgtggtaatttgaagt
gtaattcacagtagagcttctgttaaagcactaatagcatcttccatggaggtatacttcagagtgaatataatttgttta
tcctgtgtctctagagctattgactgaaaaagctgttagggcattctctaactgtacatcacctaagttatttaaaattgct
gaattaggtggcttgtcttgtctaggacagagttttaaggactgcccacctgattgatagagctagttgaccttatctttaa
ctttttgtttttcctttgactttgggagtagagatgtgaaaaggtaaaaaggaaggaaggaagagaaaacttaactctttt
gcccatgaagactgtttttccttctcaaaatattgactatttctgatttgtaaaaatcggcacataaaacgtgttatttt
tacttgactttatctttcccatgtgatatctataaattatagataggaaaaattatctgtaatttagtgatctttctagt
gtgataaaacgtcagaagtactgagagtggagtggacattgatattgttactctcagtaagttttcactgatttttctcaga
gtcatgaaggaacaaacgtttgttaagtccttatcacttattagataacacaaaacatgttgggggggtgtgtacagaggtg
agtaagatgtagctcccattctcaagtcgcttacattctaatgtaaaaggtagacaaagcattacagaagaagtaactctgc
tatagaaggttgcaatgaagagaacattggaaacactaatttacccttataaagaaggtttcataaaggaaggcaagtttga
gctggggtgaaaggaccagtaagggttgactttcaagccaaggagaggaggggaagtgatgttacaggccaaaggaatggc
attgtaagaagcttgttggcataaaagtgtttagaatatggcagcgaattcattatcatcagattgtggtgtctgtatgttg
ggggtgggagagaattgtggtggcaataggcaacaagataaaagaaagtaaaaggtgttatggaaacttaatgggtccagct
tacaaatgatctatgcatttaggggtctttctcttttcctgataaacctctcctacaaagagccttgttgcggataccatag
tgtttctttggaggaaaataaaaactacaaagctttgtatttttgcacaactggattcagaatataagtaataaaaaagga
caagaactttcaaaagctagaagccattaaactgagtcacttcagggttagactatcagaactggggatttagaaagtctca
gaatggaaatcgaaggacaccaaagacaaattcggcctttttcaaatttttattctagtttaacatattcaaagaaagggaa
ggaaattcttttcattcctgtgtgtagtgacttcctgctttaagaacttaggacttcagctgtactatcagtattgtaggcc
acttaacattattatggttaaagttggcattggagagagcctaggaacctaactgcctgtttgtttttatatttccaaccat
tggattcccaagttaatgaagtctgtttattagttgagggtagctcttaatgcatatattttaatgccccttccccacatgg
aatcataagctttcagaactggagagtacctgaaagagatcatttagtccaaccttctcattttacagatggggaatctgag
gcctagagaagttaagtgagttgaacaaggtcacacaggtacatatggtagccgaccatccactgtttatgccaatattccc
cttacgtttgcctttttgcttgttcgttttaacctctccaaatttttactgacttcagaagtttctagaactaagttatagc
atgtttgagttctaatgtcactttccgatcttctttaccttttttctacctctgtttgtatttctggttctggttaagtga
gtctggtaagcagcaggtgttctatttttatttctttttatttttaggatagtattacatgtgatatatatgtctttgcaaaca
tacataatttgaagatcttaaaatatttgcactaggcatacccacatttaatagtatgttaaatctttatagcaattatga

FIG. 4 (Continued)

tatacatgggtgaagaagagttcctaatatggcctttctgattaactgtatctgtttatatctgtgtttttcttcaggcattc
ataacattaagcaaattcaggtgtactgttacttaattgaattaatcagtttgttttgtacaagtatattttatttttgttc
cttgttgtataatctggtaggaatggggaaggggagatagtgaataaagagatgtatacttcttgcctttgaggaatttaag
ttttcactgtataccaatttttaaaggtatttactatatttcagtgcatattttatttgacatactttatcatttgtggt
aaacctttagctttactaattttcatctattaagtttctttttgtaagatggtgatagcttcatcaaagagagtaaagaaga
gacctgcctacctagctgattctatggcaaatctcacttctctggaagcttttcctgttaatcttattccttcagtttctgc
ctcttgtttcataaaactcattctttaaatgcttattcatttctcttgtctcatataaaccaatatgaggtactggtatct
tttgagtttagttataaggaagcataaatggttaaatttaaatggctaaaccccatttgccatttgtgtatctttaatttt
agtttgttgagagacttatcactaccaaaccacaaagaatttaaaagaaactgtcagtaggtataggtggaaggagggcatt
tatcagagatttaatttaagaagaaagtcttcatccttatcctaccaaccccccattccctgagcatatttatcattactag
tcccagcatatttgctccatatttcctatgcttacctgtgaagatttcataactttttccttgctttttactgtcactgt
tggttctgtgatttatgacagatactgctcttgtaggaatgctggctttgactgaaatttgttactgcttttgtatttaaaa
cttttttttattataagtagaactatggaacagtagtagaaaaagtttgactttgtaatcagagatactgagcttgagtt
ctggctctttcatttgtatactgttatttggggcaagttttttaatgctcttaagtcttagctttctcatatataaaatgga
gataataacagttatcacgtgattgtgaggatgaaacaaaaaaaagtggaaactctttgtaaggtgtgttcatctggttgac
acttagtagtcattacttccactttccgtccatatagtcctcttaacagtaatatttgagaggcatttttattaaagcagtc
ttaaggagtgttcgtcaaaccacatgttctgggatcctgagaaagtaggggaagtttagagaactgaagctgcacaaaacta
atgtttatttttctgttgtgttgtcctgagaccagcttcttagattgtgtttcctagtcctacatctctgattccttataaaa
tattccattatgaattcttcactattgacaatttctccccttttatcttaaaagtaccaaagaaagtgtaaaatgtgactgt
cttgtcagtcctctttttcctgttttcatgtcagtgggtatgaaattactagcaaggatgcatatatgtgcatatgtcatt
actaaatgcatttttctttctagaaaaactcaatatactaaattgtactaaaaggaaaagcttgttttgtttttgagtggtag
tatgaaagttgttttatttaggtctgaccagttagaaaccaatggattgtagtttatttataattagttaaaccttcatgt
gaatttggttttgaattacctttaaggtagagaagaaactatatagatgtttttcagggtttctaaatgtacaatacaggtt
cacaatcacttatttgaaactcttggggccaagtatgtttccatttttcagaaatttttagttttcaaaaggtagcacagataa
atatactttttacataaacaccccagtggggtgtgggtcagtacctgaaatgaaatgttttactcttcgctctaagtgtatta
aatattatgtacaatcttattacttcagatcaggatttgctgtagttgagtttgccataaaacttaagagaaaatttttagat
gttttgaacttttgggatattgaaattgcaggttaaggagctatggacctttatttgttttaaaatgctaagagtttatttt
aagtaatttttaaaaaatttgtttgcatagtagttggagttaccagggtactgctaaccacactgatatgtaagatctctt
tctgagcctttttattgtttgtaaacatggcctgttaatcattagaaagccagtacatactaacatatcactgctattaagac
aaatattagcatactctagtaatgacaagtcagcattttactattctgtattgattttacttattctttcattactctcata
ctgtaattaaaacttgcaatctgagagactgttgaaaaaggtgatcgttggctttttcaacagggagtaaggtctggtttaaa
aaaaaattagtaagcatttggccaagtagattaacaacattcagttttttctttactgtccttatgctttttactatttttaac
atatatctttttgaagaatagtttgagaattatgtatgcttaactatgagatacagatactattgaaactagtcagttgttt
ataggtacttgtaaaattaaaaatatattccaatagcatgcagatttttcatagaggaaatttgaaagcatggaagcacctg
aatttacagtactctgtattagtggcatcacaagtttttaagcaaatgtattagctctaattgcatacacttaatctttttaa
gctttggttttattattataatatggggtgataacagtatctacttaatagaattcttgttattacatgaaataattaatg
ttaaacacagcataatatgtgtcacattataaagattcaggcaatgtttgttagtattagtacttttttttcttcctaagtg
caaaagataactttatatcacttttaaactttttcttttagttgtgctgaaagacattatgacaccgccaaatttaattgcag
aggtaggtatgaatgtactgtactatgttgtataacttaaaccgatagactgtatcttactgtcataacaataatgagtca
tccagattatcgagtgagatacatatttaagaattatctttaaaaatttcaaaaatttaattttactgttgtgtttttagga
aaaagtattgcataaagctattaatattgtcaggaagactaaagtgcagcatagactaagaattaggaaaattcctagacta
aaaatagtataaggagagggtttacctactatttgaggcagttggtctaatagtaagcaatcacagggagaaagcagaacta
cttaactcttctgtgttgaggaatgacataaaggtaggaaaggatataacaaatgttgataagaggagtctgatggatgag
aggagggaactgctttaaatgagtttctacttcagacataagttaattctcagagcccacaaaaactttcactttttatttgt
gaaatacaactcagttctcatggcttaacactttaaaccatgagaaaactgaagagttgagaagcttggcagatgctgctgt
gatagtcaaaaagaaagtgggtgccatgagctactattgatgtatttgccattgatccctcctgaaaatctagaatggactt
tcagacaaatggcttgaaaattctaaatcactaatgattgagatttagtataggtttactaagaacgggtttttttttgtttt
tgtttttggtggatttaggctgttgcttactaagcaaagcaggctttagttgaggtttatcttgctttaaacagatatttaa

FIG. 4 (Continued)

cagattttcctggaggtttttgtgtaccactgggaaaatgaagttaggcagatgactaagtgaaagctgtcctgctgactccc
ttataatgatagtcattgtctaccagaagatctctcctgtcacaccaaaggataattgattatatcctgtaccatattatga
gtcacctgattggagatataagacatacttctcacatatttagatgacacaggttagtacattgaatatcagccagggtttt
taaggatcttaatagagtggaactaaggtagaaactattaagagcaattaatagtgatatatctatagtcctgtttctaaac
aagttttttaaaaacctcaactctgactatagtgaacagagaagtcttggactcttacaattcatgtgagaagacctgaaa
ctttgataacaattatatacatttttgtgagtaatttctttggtgtatgccttcacatatctctggtatgtgacctatgctgc
agtccattgagcatagattcccagaatgtattctcctgcagaaaatggaggaaaataatacttggcttccctaatgattaca
tgtgtatacaacactaacatttgcaagaccacctttaaataacacacttagcatttttatttttatgaaatgtaatatgtagt
tctttgcatagtttatcctattagtaatctattctgtctttggaatatgttttgtgatgatgaaataaatactataaatagt
attattcctttttgcattgagagtcctgacgaaatgtccatgtgacagttcattttgggtttagctctacctctaatatgtga
cctatgctaccagtccgtatagcgtaaattcccagaatatatcctcctgaataaaatggggaaaataatacctggcttcct
taatgattatatttaagacttatcaagagactatttttctatttaacaattagaaagttaagcaatacattatttttctctgg
aatccagtgtttctttaaatacctgttaagtttgtatgcaacatttctaaagttacctacttgttaattaaaaattcaaga
gtttttttcttattctgaggttatcttttttaccacagttgcacaatatcctttgaagaccataacccaccacagctaga
acttatcaaaccctttgtgaagatcttgaccaatggctaagtgaagatgacaatcatgttgcagcaattcactgtaaagct
ggaaagggacgaactggtgtaatgatatgtgcatatttattacatcggggcaaatttttaaaggcacaagaggccctagatt
tctatggggaagtaaggaccagagacaaaaggtaagttatttttgatgtttttcctttcctcttcctggatctgagaatt
tattggaaaacagattttgggtttctttttttccttcagttttattgaggtgtaattgacaagtaaaaattatatataaata
caatgtataatatgatgttttgatgtatgtgtatatacattgtgaaatgattactacagtcaaactacttaacatattcatc
acctcacataattattattctcccccccagggtgaaagcatttaagatctacaagctacaattttcaattatacaatgttatt
attaactatagtcactatgctgtccagtagagcttcagatcttgttcatcttgtgttcctccctccccacccctcagtcccctg
gaaaacaggtttttaaagatagttgctaatccttatttcttctaaatttttaaatcagttgctgcctcaatttctatatgaga
aatgactgattgatttcatttttctgttcacgctaccatttcatatcatactagcacatgttacccactaactgtattgca
gattggtctcacaaaattcttctaaaataacatttttaaaaagcatattaatcaaaaataagctttatatttctgaagctt
gtttgagcatagaatgcctttggataaaataccattacctagtaaagtgtgaacttttataatccataaaaattattctttt
ataagaatattcataaatgtagttagattaatagaagattctcgattctttgatcagaaaactaaggactatattgaaaaat
cagtgacaaatttaattcttatagtacatctgaaagaaaaaagaaaactcttgggagaacttttacagtgatttaattttgc
tgttgatatatttctttgggtggtaagtatggcaaaacatgttaaaatttaatgcaaagagattttgtacattttccatct
ctaagaaggacaaagcctaagcccctccagatagatagaaaaactcatttagagagttctccttcatgttaatctaatttct
tcttaattcagctgtaaaacagaaatagaatgatcgtattaatcatttaaagctgtgtaattgcatagattccttgttcctt
taccccctcttatatcttgtttcctatcctttgtgactttttttgcattatatataaggatgccgaaatacctgttactgtt
gatagtttacaaaattgaatcttacattagtgcataattttggtgaatgttgaagattatggtagattgccttacatttcctg
catattgtttgcaccttggaatgatagcactggcatgaattatagagctgaggatctaaagattttactttgatttatccc
attatcatctgcagggaaacaattgcttttactgattaaaaatgcaggctgggcacagcggctcacgcctgtaatcccagta
ctttgggaggccgaggcgggcggatcacaaggtcaagagatcgagaccatcctggccaaccaacatggtgaaacctcatctc
tactaaaaatacaaaaaattagctgggtgtggtggcgcgtgcctgtaatcccagctactcaggatgctgaggcaggagaatcg
cttgaacccgggaggtggaggttgcagtgagccgagactgtgccactgcactccagcctggtgatagagggagactccatct
caaaaaaaaaaaaaaaatgcagtagcaaaagcgatggtagaaatttaaaacagagttgatgagcagcatatatttggtagtg
gaaaaaaaggtaaaaaatttttttgtaataaaatagaaaaatttgtaatgtggaggcgcagaacactagatttaagccaggg
ggtcttaaattgtgttacattcctttaaagtctgatggaaggtataaatgttctcccctcaaaaaatgtgcatagtgtaca
taaaatttgcagtttttattacattgaaatatattctttagacagaatgtaaaagaaccttcatgaaaactatgtcactt
tttatgcaaaaaccagtggctactacatgagagcaatgaataaatcctaagtggtacaaattaaccaaaattaagcttagt
tctgttcaatactaaatttttaatgaaaagactgctatttaacttttaaaataacaagttgaaactatgctctttgacttga
ctttgcaacttttatatgatctttgatatccaatcagtgttgactttggtaaaaagtgctgaaaatgctattttacaaaaga
aagaagagtaaatggaatctgtagattctattgcctgatgaaagtagacgtgtcaagaaataagaatttctccaaggccctc
agataaactcatgtttcatcatttttctttgccttcaagttactgagatcatttttggcaagatcctgtatcattaatgctgtg
ttaggaaagaaaagattatgactccacattttacttttcaaggttgaagagttaaactgtttaaaaagagtgtatgttatcct
gtaaacagcagtatcaggctgtagaatttgtcttctgaaagcagggaacttatatatagcaaagaacttcatagtgctccca

FIG. 4 (Continued)

tttcttgacaaaacctctcgagaagctcttgattgaaagtcttggctttcatgaatctggcagctttcacaatagtggattt
ttcatgacaaatcatcttacacagggaattattcaagggttggcacttgaaacagtagaatactttcacaacaagagataag
atttctttcaggattgatgacagtcttgcaccctagcgcatactgatgaagagagcagtgggtgaccatgacatggagagct
tctgtctttaccagtgccccaatatcagatgtgttgtctggcagtaaggtgtactgtctgcctacagaatactgaggtttct
tcaggagaagtttttggtaaagaaactttaccattttgaaagtgttaatgttttctgaagcttccaaaaagattccaaaat
gggaatgtttccttgattgtgtcaccatgcttgcatttgatgaaaacttgtagccggctatactgagaaatcatatctgaag
aaaggtggtacttccaatctttttgtgacctactttattattgtttctttaatgtcagggtttttttggaatggagaaaag
tatttgatagaggtattgcaacagtcttattcttcttcatgctacaagtatatttgactctttctaagatacttgccttcac
tgttcaactgtgtgactttttgtttgtttagcattacaatcaatatcctagtaggatgatttaatcaatgatttttaattgg
aacaaatagtttttgtaatggtctaggcttttccaacttaactgtgctctcacatgtggtctcttttctccctctttcctc
cttcttatacactctcacccacacacatatgcatacatacctgtctgatgtatctgcttcttcagaatagttggctgtgct
ctgctgatgatgagaacttgccatttaagaaggacttgggatagtccatgtcatcatgttcagggataaaagtaaaacccaa
gggcatttaaacttattgtatttatttctgtttccagtccaaattaaatccaagagaaggctccataatcaaaaagtaa
ggacatatttaaatttgccaatgggaagatattctagtcattacagtctggtaatactatcaattctgtttctcttcagag
gtgaggggagactatttgatgaaatcgtaagtcctgtagggtgttgtgaaatagggccagaatgaaagatagcaagaatagt
gttatgaaaataaaatgcaaagtttataatatcatgtggtaaaatgtaatagtatttacttcatcagtagaactgctctagt
agctgtatattctccatccttgcataggttggaatatccccaagtgaaaagagattgatgggctaatagttaatagaaaat
ggagatctgtacatacagtgttaagaatgtagatattaaaattgttatatttagctgttacataatattaagactcagagtt
aagtaatttcactgaaattgattgctttttgtgtcttggagtcaaaataaataactgaaatctactatacttggctcatgct
taattaatatacttagaccatatttcggatgaattattcacagaatctaaaggagtatcctcgtgttcttacctttcttatc
cctgtgtttatttaaaaaggcaaaaaaaatggagcagatgctgttggttgaccatattttactgaacagtagcatttgtgtt
taggttgaaacagcattagaaaactagatacggattaaagtcagtggtaggttttttttttttttcttccaggaatgtttc
ttatagatgatcaaacaggcacaggaaggggaagtgttgtgatcaatattatccagttaatattagcattcagaggaaaatt
tgagtcctctgatacactgttaaatttctttctatactatcaagtccacaaatcctggaactgcaaaagaatttttgagactg
ttcaaaataattaatctctgtataggctcaggctttcctgcaaggttatgaaatgctgataaaattggtcttatttttgaaag
gctcctcagcttatacctttccttacaaatgcttccttacaaatgctaaagcatttaatgactcctgacttaaagggaattt
ggacagattgaggttgttggtcttggaaatataatactgcaggcttctgtaaaatacttgaaatgtaattgttttaaaactt
tcaaagataccacttgtttgcctgttggttagaatactggtgaaataattttaatcttttatgaataactaatttcatcat
aagaaaacttagctaagcatggtaaagctgttgttatacaactgtggaattcttcctgaggagtaactatcttataataaat
gtagttgattatctaaagtagtttattcttggaatatctcataataggtttattctcttcttgtcagtatttccttgtaga
ttgagcctgtggatttgcattttttgtaattgtgaatcaccattataggagatacatgcattttatctacttttcagtttgta
tggggttaactttattagaattatctttaatgttatttttgcttatatccttaattttaattatagacaaacattaagaagct
ggagaaaattatgttctagtgacatttatatagaagaagaatctttttcccccttttctttttttgaagggagatgaggcagt
catatttggtaaagaatttgtagactttgcagaggtctcttcaaaataatctggctcagagtcttgacatatcctcagcag
acatggtgcaaattagatggcagagtggtgggtacaagttgaccataaaataacgcattaggttagtaatgcccaaataata
ctttgggtttttcagtgttgcagagaagtcagacaactgatagttattataaagaaaaatgttctgagagtgaggtaaccgct
taagggaaggaagcctcctttctgtcttattcactaatttacaagaagataattgtgttacacttccttaggagtcattcatt
tgtatatttgacactttgctttatgaacatgtgaagattattcaaaagtaagctgttggtgatttttttcttccaagaaag
catgccacagggcaacttctagggttggttctcatctagtcctgtgctccacactatctgcatctgcacttaagtttcaata
ttagataactcacatgtttaaactatgaagaaagagttaaaacatcctgagaatgctagtaagtatgtatttttgaaaggac
ttccaaaatttgagtttaaagaggtaaactcctttttacatgacaaagttacttagaaacactactgctgtttccctctccct
tgccttctccctgtcccatgcatacccccagctgtgttccagaatgatggcacataaagtaaacattcatatttatttccct
ttttttgtttttttttttttttttttttttgcttgtttgttttgtttttttgtttgagacagtctcactcaatcacccagg
ctggagtgcagtggcaacatctcagctcactgcaacctctacctcctgagttcaagcgattctcctgcctcagcctcccgag
cagctgggattacaggcgcctgcccccacgcctggctaatttttgtatttttagtagagatggggtttcgccatgttggcca
gactggtcttgaactcttgacctcaagtgatccgcccacctcggcctcccaaagtgctgagattacaggcatgagtcactgt
gcctggcctcttattttttctttggttaaacttttagggaaaaagtttgagctgctttttaattttctttttgtttttaaata
aattattaaagtttctctatgttaggaactcttgtgtacatgagttcattgagcttattcttaataaagacaaatcttctag

FIG. 4 (Continued)

aaataatagttgtatctttaaatgatctcaaggaaaatgtttggtttctctggggaatgaattttcatgacctaatcttaaa
tcaggttatttttttctagcctgtttactaaatttctacatgttataacctaatgaaattttcttacttcctctttatttaaa
acaaactataattactgtctttttaaaaatcttccaatgtggcgttcttatttttcttaacatttgaattttcctgggccaa
accatgttactatgatacacattatttaaggctgttatataatacagtaaaattgtagaactttcatacctttgaaggatctt
agcaattatttaattcaaacccattctaacatagatgataaaacagatttgcagggttgggcacggtggctcatacctatat
tcccagcactttgggagactcaagcgggaagattgcttgagcccaggagttcaagaccagcttgggcaacatagtgagaggc
tgtctctacaaaaaaatatttaaaaaatagccgggcatggtgtcacgtgcctgtagttccagctgcttgggaggctgaggtg
ggaggattgccagagcctgggaggttgaggctgcagtgagccatgatcacaccacagcactctagcctagagcctccctgtg
tggcaggctctacacttcagataggcaacagatcgagaccttgtttcacaaaacgaacagatctgcaaagatcaacctgtcc
taagtcatataatctctttgtgtaataataaaaaccccatcttctaaccttaaacctggtatttttttctacgaaactatgt
tctgcagtccaaattatttttcttattatttgaatcctaaagtagaaatagaaacttagaaaaataaaaagcaactccctt
tatgacatatgaggactttttcagtttaaataagaaaaacccaactcaagtagcttaaataaaaggagacatttttgac
ttacataacctaaaagctctggcctggatctaggtgctcaacagatctcaagagtatctctcttattctctctccctccctt
accctcctcctctttctctcttctgtatatatgttattttcaaacaggctctcacaagtagtggcaagatatagttcctaa
tagcttcaggtttgcattctacctactttagcaactatgatgagaagagagctacaatttgagcaaaatttgtagggtgag
ttctgatttccctggattgaggcacatgcctattattcctgaaccaaatattctgtccagggaatggaattctctggggcat
gtatctaaagctgaagtgtagagcctgccacacagggataataatagttttccaaagaaaaatcaaggaggggaaagaatgt
tggaaagagaaaaaaatatcagttgtctgcttcacatttgttctcaataattagtttcatagaagtgaaatactgtgtaaca
ccctaaactttagagattcttcgtagacaggaaaaataagaactcaatgaagttgtgacttcattcaaatcacgtagtttat
atacatgctattagtaaaacccaggacagctgagtacaagttttaccctatattcacattgaggtccagatcctggttttg
aatgagataattacgtgcagtcggactgtttctgatcctaaaaatagagacaataatatctatcttgtaaagttatggtag
tgttaaagatatataaaatgttggcaagtaccttaatatacaataactactgctatatgttgtcattgtaataataatcata
tttcttcctttgttgaattgctttcctgtagtaatcttattgtgatcatcctgaaacatagatttccgagcttcaagcaaac
actattatgttgaaaaatctacattatttctaagtttagcagtgccagtggaaagtttattgaaatagaaaattactttttt
aactgaggagtgtagattgtgaattcgtgattcatcttcttaggagatgatcggaatattgataaatattgatgcatagaat
atgaacaaaacattacatatcttgtgctgtgatattaaagtagtattctgttctggtagtagtatggcagtatttaggtct
gaaagatgtacataatctgtactttgaagtctgtttttaagagattaatcacaagagatttacataaaacaactaaggtta
aaaataaatggtggattagagatacatcaggcaaatttcaatttcaaaagcagatgacagaatctcagtatcagggtagcat
ttaaagcaaaaagcattaaactggatcaaaaatgtcatttacatcaacacagggtacactccaggtaaagacttaacagtt
atgaacgaatgtgctaaacatcaaatgtattaagtaaaagctgaaagaaatgaagaataattggtagaaaagcaatgatag
gaatccttaatgtacttcaaaaggcacgaagtaagaaggtacagtcatgtaccacataatgatgtttgagtcaacacctgac
ctggtatacgacaatggtcctataaaattataatggagctaaaaagcttctatcacctagtgatgttgaagccgttgcaatg
caatgtatcacttcacatgtttgtggtaatgctggtgtaagcaaacttactgtactgtcagttgtataaaagcatagcacagt
tatgttcagcacataatactttataatgataaacgaatatgttactagtttacgtgtttacagtactattatttagcatgt
gcttctgcttattaaaaaatgttaactataaaataatctttaggcagatcctacaggaggtattccagataaaggcattatt
gtcataggagatggcagctccatggatgttattgcccttaagaccttccagtgggacaagatgtataggtggaagacagtg
atattgatgatcctgaccttgtagaggccaaggctaaagtatgtatttattagtttttaacaagagtttaaaaagtaaaaaa
aaaaaataaatttaaaaatagaaaaatcttaataaggatacaaagaaaaaatgtttttgtgtagctgtgtaatatgttttt
gtttaagttaaatgttacaaaagagtcagagttaaatttttttatatttataaagtgaaaaagttataaaatgctaaggtt
aatttactgaagaaagaaaaaatttttaaacagatttagagtagcatgtttataaaatctacagtagtttacagtaatatcc
taggccttcacattaactcaccactcacccactgactcacccagagcagcttccaatcctgtaagctccattcgtggtaagt
gccctatacaggtgtacaatttttatatccttataccatttttactgaacctttttctgtcttttagatacacaaataacat
tgtgttacagttgcctatgatattgaatacagtaacttactgtacaagtttgtagcataggagctgtatcatatagcctggg
tgtgtagtgaactataccatctaggcttgtgtaagtatatttttatgacacagtgatgaaatcatccagatacagtttctctt
aagcaacacataactgtatatatatatatataggtggctttaataataaaataatgaaatatatttcttttttttcctgtcatt
gacaaaacaattaccagtcttactaattagatcaactgcaaaacaaaatctcactcaaaaataaaaatatgtaagtcccatt
ccttgattacaattcattagaactggagatttttaaaaatgtttaaatttatatggaaatataaaatcatgtttttaaataat
ttttgattcaatgaggaaatgtaaatttagaactaaagattaataactagagatttataaaggcaaaaatgttaatgaatta

FIG. 4 (Continued)

ggaaacagtaaaccatttgaactaatctaaatactgattgcatgaaaatgccaataaaatcaatacatatttttaaaagcca
gtcaaggataaaagaaaagagggaaactaaaagtgagacattaagtatgagaaaggagataaaactaaagtgtggaggtgat
gttaaaaattatattcaggtctgtgctaatcatttttggaaatttcagtgagaagtgggcaattttcagtgaatatatcattg
taaatgctttgaggagagacaaaatctgaatagaccctgcaataatgaaaatgtctaggagccctcaagaaatacctggttt
aaattgcatttcaggtggctggttatcacaccttgaagtatcaagtaattatgttatctaaattggaccaggtgttagaaaa
atatgtgagacttcacaggtggctgcttatgtagcccttatacctaatctgataaaggtagcatatatttaaaaagagaga
aaaccagaaggtacaatttagggaaaattaaatacttctatttggccaaagtaagagtacattcaagggaattgtgagaggt
aagagtggaaacagaggttggagctgtatttttatgctgtgattgaattacagtgtgtgataaatattgctcttatttgggt
agattaccatttaacatttgaattaattggtaattggattaatcttaactttaaaaaactaatctgagagtggtataaag
gatagattacagaatggataaagggtgataaatcagttggctatggcaaaattgcaggaagaaactgaaataggccacagaa
aactgaaactgacattttgagtagtatttcagaatcaagatctggattttggcaactgaatagatgcgtaggaatcaaagat
gagtatactaaatgaacttaatctatgatttgtctgtcatttatttgtgtaccattagtgtgtatgcatgtatgtatgtgcc
aggtagttaataggctgactgtgtctcttagctccactctgctgcctgggcctttgccatagtgctggagttccctcacttc
tcttttctgtaaccctattatattactgctgtctctcagctgtgtttcattcctcaagcagaaagaagatgggaggatcata
tagtagttgactagaagctgtggagtttgagtgctgggattatatctagttccattacttatgaagattatatctagttcca
ttacttcacctcatctataaaatggtttaccaatagtacctaccttacatggtttttatgagtattaaattatgtatttctaa
agacatttagaacaatacaaagaatatagtgtgggctcaataagtgacgatggtgttagttattagaaggccatcgagtgct
ggagaaaataattgaatatcattgatggaaataaaggaagtttttccacgttaaaaagcttcggtttttggaaatgtgtgttt
tcagtatttctgagattaccaggtagaaattccagccagatgttggaattctgcactggcagttgggaataaagtcatgtta
aaggagataagttttggagttattgtgtaaaattggtaaagcactggaatagattggtttgacagaggggaaactcttttttg
agataggcctatatttagggacaagagaagagacaaccaataagggttgaaagaaaccttgagagagtaagtcctatgacag
aagcagggaagtttcagaatgattgcagaaagatcagccaggctctttcctgttctccatcgtggtgcaggatcaaggtgaaa
aggataaccccatgcaggaattttgcatctgcaggctccgcttcaacatctgtttaggagaaagtggagacagactgacctg
agtaactaaggtcttggaacagcttacaggtcagaaccaggtgtttcccaaagctagatatactgttagcgcctttggcaac
agaagaaatgaaaagactgttgtctgctgcacagttcgagggggccaaggcagacgaaatcctggagaatgatctaaaggtgc
aggagtgtgagttaagaaaaaataacttctcagatactggaaactttggtttttgggacccaggaacacattgatctgggtat
cagatatgacccaagcattgatgtctacagcctggacttctatgtggtgctggaaaagccaggtttcatcattgcaggtaag
aagtgcgggacaggcttcattggtgccaaatagaatcagcaaagaggaggccatgcgctggttccagcagaagtatgatggg
atcatccttcctggcaaataaattctcatttctacccaaaagggtaataaaaagttttcagtgaaatgtttaaaaaaaaaat
aaaaaaaagatcagccagcagccaggatgggattgtgaaacagcaggaaattagttgttgacaaagcattaatgaccatta
agaaatcagcctcggctgggcatggtggctcatccctgtaatcgtaacactttgggaggccaaggcagatttcttgagtcca
ggagttgagaccagcctaggcaacatggcaaaaccctcgttcctccttaataaataaataaatgaataaataaacaagcaag
caagcagggcttggtgttaggcgcctgtactcctagctactcgggaggctgaggggggttgaacctgggaggcaaaggttgca
gtgagccaagattgcactactgcactccagcctgggtgacagagtgagaccatggcacccccctccccttcaaaaagaaatc
agcctcataatcaatttctctggattaaggagtaagagcgtctcaagatttgctgtttatagagagggaggctaatagtttg
agagagatacagaatctagggagagtgtgggtttttggtctttcagttgtttgccagccttggataaagaatgaagattact
tgagcatattatttagagacaagtggagagaataaaggcacatgccagataggagataattaataaagcacttgtccaaaat
agaaacttgttgaacaggaagagacgtcaagtataaggagatttaagatgggagaaagggaatttgagtgtttgtattgga
tgacctcagggttcccagtaaagcaggagctgaattcatcgaaggtgatgtgttggtcaggatcaagagagaggttgggaga
acaaagtgctaaaatcgttgtggtcaagagtttaaaaagtgtataccagaagagttattgagtgatagggggtttgaaatagg
caaagctgtaggaaagggggctggaaggaatattaggaggaacactaaatatacttctgaggtctacctcctggtctgtgaa
cataaaggagctgaaagagtaatggctgaagttctttagtttagctaaagtttttagctaaagctagaattgttgaaagtt
gtatttgaggaaaaaaagttaaggatacagttgaccgttcgataatgtagcccactgttgaccagaagccctacccacaaca
taaacaggcaataacacatattttgtatgtgtattatatagtatattcttaacaataaagtaaactagagaaaagaacatgt
atcaagaaaatcataaggaagagaaaacacatttacagtactgtactgtatttattggtaccatacatttatgttgctgttt
acaagatgaagcatctgtctgaaatggccagcagctacagctgtacctatctactgtacatatcaagcaagtcactttattc
ttataatgtctatgacttctttctttgaaagcgcttcatcatcactgttggcacttcatatgggtctcatggtgttaaggt
ttacggcattgcactagacacaatgaaaactacacaagagggccgggcacggtggctcacgcctgtaatcccagcactttgg

FIG. 4 (Continued)

gaggccgaggcgggcggatcatgaggtcaggagattgagaccatcctggctaacacagtgaaaccctgtctctattaaaaat
aaaaaaattagccaggcatggtggcacgtgcctgtaatcccagctaatcgggaggctgaggcaggagaatcgcttttccca
gaaggcgtaggttgcagtgagccgagatcgtgccactgcactccagcctggatgatagagggagactctgtcgcaaaaaaaa
agaaaagaaaaagaaaagaaaagaaaaacacacaagagccgtgagagagatagcttttgattgcaatacacaatttactgga
gagatgagctgatcatacagagatgattagtgtcacacagtgttttaaacagattcttgcaaccctggagttcactgcagta
gcaacagaagttagctatgagattttaacagtagtatagtatgtactacagttaatattaggtagctatgatttaatgctgc
atctttgcatttgtttacatttatcttgactacaagtggtattatgtctggtcttaaggtttgtgtgcatatgttttgatga
attttaactttttataataggtttgtgtatattttatggcagtaaatgataaaacagactaatctacatatattttatgtag
tcatgacataaacctaacttttttcttaacttttttgatatttctagtctatgtgtttcatctgcaggtttttttcaaattgttg
aaatctctgaaaaatttattgaaaaaaaatccatatatgtaagtggacccacacatttcaaacctgtgttcaagggtcagc
tgtgtaaataatttttcctcaaaattaaagtggaaaaggagagttactactagtagaaagtagaactgtacccttgggcaggg
gtgtgtgtgtgtagttaaagatcaatttaacttaaaaggtcttggttagagaataaaaactggcccttattagctttaattt
acatgaaaaatgaaaaatttaggccaggcacagtggctcaggcctgtaatcccttaactttgggagaccaagggggagtgga
tcacttgaggtcaggagttcaagacagcctggccaacatgctgactcacccttccctactgaaaatacaaaagttagccagg
cgcagtggccatccctacagtgctagctactcgggaggctgaggcaggagaattgcttgaacccgggaggcaaggttgcggt
gagctgagatcgcaccactgcactccagactgggtgacagagcgagactccatctcaaaaaaaaaaaaaaaaaaaaagatt
tgaaaacagagtattttttaatctgcaagagctttacagccttttattcatatgtataagcttttaaagatgactaaaattt
tagtgtggactttccactcattggaaatcctatattgcaggtgttaattcaattttagtgagtgtgcatcatggctcagaga
gataggactagaatgaggaggtcacattggagactctgaaacagatacatgtgagcctcccaactttttaatatttgttaat
ctagaagtgttgaatttgggtgctgacaaggcagcaggtagataagaattgcaaagttaagaaaatagactgtaatattga
tggtaaactaattgattaaatttaaaatgtactttccatgttttttcttgaattgtcagtaattttgtttcaactggtat
tcatacatagattattcacccaatgttgacaactagtagatttatatatttttatgttgcctatccttttttgggtaagga
ttaacagaatgtataatcacctacattataggtacactactaatcacttgctacttgaaaaaacctaaagctttgaaatctt
tttattattgcacacaaacttatgccaaaaatggagataaagagaaaaatgtcatccactaaaccccaacaaataatgttga
caatgtggtctactcgtagactcgcattgacttaacttttttaaatcttattgcatatttgactagataataaatgcatat
ggttaaaaattcacatggttcaaaaagtacacctcccactcatcttccatgtgatatttccttttctgcttagcaattctg
tatttatcttgctaaacatgaatgacagtttgtttgctgaaattacattaaatgtgacgtaataaaatcattgtaagtttaca
tttttaactttaataactttaatgttttaatgaagagtatgaagagtagtagtactgctcttcaaagtactactactttta
ccttaccttttactgttttgttaagaaaattaggccgggcgcagtggctcacgcctgtaatcccagcactttgggaggccga
gacgggcggatcacgaggtcaggagatcgagaccatcctggctaacacggtgaaaccccgtctctactaaaaatacaaaaat
tagccgggcatggtggtgcgcgcctgtagtcccagctacacgggaggctgaggcaggagaatggcgtgaacccgggaggcag
agcttgcagtgagccgagatcgcaccactgcactccagcctgggcgacagagcgaaactccgtctcaaaaaaaaaaaaaaaa
aaaagaaaaaagaaaattatatagaaataaaattccagctattccaaaactgcaccttgaatacaggtacagaattgctaaa
accgtgtaccattttgtagttttagcatgcttttgtgtaactgcatctggtgtttgatcctcatgagagccctgttaaggaa
gggtacatattattgtcctcatttccttcgaaaacacatcagagtttgtatttgactgtcagcattcaaatacaagtctt
ttatttataaaattttggtctttatactgtggctaaaaatcttaaatcacttgtcatgatttgaaatggtttatacgattt
ttttgacatttatacacacatacacatattttaaattgtctataataaaatcatgctcatctttgaaaaaatattaggag
tactacagtggatacctacatacttgctattcagcatacctggttttttgtttgtttttgagacagtcttcctgtggtcc
aggttggagtgcagtggcacgatctcagctcattgcaacctccgtctcccaggctcaagtgattgtcctgcctcagcctccc
aagtagctgggactgcaggtacacatcaccacgcccagctaatttttgtatttttggtagagacggggtttcaccatgttg
gccaggctggtctccaactcctgacctcaagtgatcagcccacctcggcctcccagagtgctgggattacaggttgtgagcc
actgcacctggcctgttttttaaattcacataaatatgttttatatttttcattagggagaagaaggttgtgtctacaatttt
taagacattggggagatttagatgccagtagtaacttaaaagagaaataattgcaaattcttttttccttcttgagtatacttt
catttaaggtacagtgttctgtaagttacttttaccgttaaacttcttaatgttgcttattgtttgtcttacatttttaggt
tggattttttcttaagtcacatgtctaataaaaaaaacccttaaatacctcatttattcgtcttcgttagtgaatgcattgtt
gtacatattagatttttctctttagataactcagcttcccctattaagtgccacatgtattacaaaatttttatttatgtttt
atttgtttaatataaactcttgagaactagatacattttaatcatttgtaatacttacatttttctaaaacacttcattttccct
ggtttcttcaacaaagagatgcatgtagtacaaggatagctttacctgtgttagaagattgtttcacacatttacatcaact

FIG. 4 (Continued)

gcatagtcctgtttttgttgggccctaatgccagcatcactttttgctactgctgtttctgccttaaaggcaatatgcctct
gtctagtttgctgattctgatactctttcccctggaaagtaggtaatcaagtttgtgaggagctgtgtgtttaaggagtcca
taaatccttgtggggagccctaggtgtatagagcatagctgtagggcagaggcctttgacacttattctggatatgcagtgg
cctttgcctatggggttcatgggtcagagcgctgttgtgacctttgaataaatgggttgttatgataattgttttaaggggag
gagagttattctgatatcctttgtattgatattgctcttatttattattgagctggatttaagtattaatcatttaaggtca
aatttctaatgtatatatgttcttaaatggctacgacccagttaccatagcaatttagtgaaataactataatggaacattt
tttttcaatttggcttctcttttttttctgtccaccagggagtaactattcccagtcagaggcgctatgtgtattattatag
ctacctgttaaagaatcatctggattatagaccagtggcactgttgtttcacaagatgatgtttgaaactattccaatgttc
agtggcggaacttgcagtaagtgcttgaaattctcatccttccatgtattggaacagtttttcttaaccatatcctagaagttt
acataaaaatttagaaagaaatttaccacatttgaaatttatgcaggagactatatttctgaagcatttgaacaaattaatt
agctttgttgttcaactcattgggctaaagaagccaaaagcaatgggttttaatgtagtcgaagccaaattatatttatgaa
agaaatattctgtgttataaccaccaaatacagcccaattctgactagatgatggaagaacctgtcccatcagaggtccagc
atgaggtccagcagaggtccaccagaggagttcagcaatttgctgctcttagggcagggatcaattccttaatatcttagga
agactaggtattgacagtaatggtgacaaagcaatgaaaaggaaaggaagaagtgataagacgtggcagcaagctgaagtat
gatgagtaaagaataggaatcaagtatgtggagtgttagagaaacctggatttagatccagattctagtcctatctctgt
cattaatctattgcgtaaccctgagcatatcatctacctctctttgagtttgcttgtcaataaaatgaagagactttgaaat
ctgagacttcctggataagtactaaatacagattatgtcactgatgtctgcctctatttatttctcccttttaccctaatct
ctataagtctacctcagtcatcctgatcctattctacttctctgatgttgttgtcagataggtgtgatcatcctcatcagat
cttttctgtattcttagagacagataactttatcaaagaccacagatttattagtatagcatgttaaagtcttctaaagagt
ctcattgatgctctttccatctcagtacaatttttaaaactgctgaatgcaaggtactgagctgttggaagtgactgacaga
tgaatgtaacagattcatagagaaggaaaaaggaagaaaaactcatgctcttcctatagtattgatatcagtgtaagagcca
agagaaaggtataaagtatcatgcagatattaagggaaagaaaacattcactttagtaatctttcctcatttctagtttcc
tcttatgtactatgatttaatactgtagtaaagttttaataaaatatgagctatatgtaattaagtgggaggttgtggggct
aggcacgaggctcacacgtgtaaccccagcactttgggaggctgaggcaggcggatcgcttgatctcaggagttcgagacca
gcctggacaacaaggtgaaaccccatctctactaaaaacacaaaaattagctgggcatagtggcacacacctgtagtcccag
cttcttgggaggctgaggcaggagaatcgcttgaatccaggaggcagaggttgcagttagccgagatcatgccactgcactg
cagcctggacatcggagcaagactttgtcttagaaataaataaataaatataaaataaaataaatgggaagttgtgtatata
aattataaatgctacattcagaaaagcttttgaaggttgtcagacagtttcttaaaggaagttcaccagttctttattgaac
attgaagaaaacatacagtttagactggcattaaaactgaaagaagtggccagacgcagtggtagacgcagtggttcacgcc
tgtaatcccagcactttgggaggtcaaggtggatggatcacctgaggtcaggagtttgagatcaggctggccgacatggtga
aaccctgtctctactaaaaatacaaaaattagccaggcatggtgatgcgtgcctgtagtcccagctacttgggaggctgagg
caggagaattgcttgaagccgaaggtggaggttgcagtgagccgagattgcgtcattgcactccagccagggcggtaagagt
gaggctccgtcttaaaaaaaaataagtaaataaattaaaaactactgaaagaagtattacaggcaatgggaaatagcttga
gtggaagtgcagcagaaggaaaaagctggacaagaatgtagtgtcagagaataggtatggaacgtgtgagtgactgttagag
gatcttgaatggggataacagacttgatttcataaatactgagatgtcatgataatacttgaggactaaaccatgctttaag
gacagttgtatgcaaagttgtaatcgcaagaggaaaaaatagtggaaaagaaccagtaataaaacttgccttaatgcaggt
atgctaagacaatcaaatgggatttcattaatttttttatttgccatttatagccaaagattttgtaaaagttttgagcccag
tcaggtgaaatagtctcagaaagaaagaaaagtgaatctgagacttggagacattaatgttgatatttggtttaaacgtg
ttttaaatccggtaaaagtgagcttctcacatgacaatattcagtgggtacttgggagtatgggttcgaatctaggtaggag
atatatcgatatttgggcatcatcaggaaagggagagtagttaagcctttcatataaataatggtgtggcgtttgggcatg
ggaagtcttggaggaaaggaagaaaaggagagggtgaggactgagataagaatggcaacttgggtttaggaagaagaagagg
aatcaatgtagagaacagatagtgctgaaaaatacagcatcttctgtagggattggcagcttttcttgattttgtcttaa
tatttctaagagatggaaaaagctactatattctagacatttaacagggttaaaaatgttactaaaagatgatcaatgtggt
tttcattcaagactataacaatatgtatatatccaaggaaatttaattctgacttaaaaaattgttttgcttgtatagatt
tagggacacaagtgtaattttgttacatgcatagagtgtatagtttcaagtcagggcttttaggttgtccatcatctgaata
atatacattgtacccattaagtaatttctcatcttctactcacgtttcaagtctccactatttatcattccattctttaca
ttctgattttcatttactaggtgtattagtctgtttttgcattgctttaaagaaatacctgagactgagtattaaacaggtt
taacctgtttttctttatgaattcttctttaattggctcatggttctgcacgctgtacagaaagcatagcagcatctgcttct

FIG. 4 (Continued)

gggg aggcctcaggaagcctccaatcatggctgaaggcaaaaggggagcatggtgagaatgggagcaagaagagaaggagt
ggtgggggagaaggtgccacccactttttaaatgccagctcacttaccaccaagaggatggcccaagccattcatgtgggatct
gcccccatgattcaagcttcttccaccaggcccccacctctagcactggggattacaattcaacctgagatttgggagggaaa
gatatccaaactatatcactaggtctggatcttgttatctattttttggaacatagtcatatatatccaaggatatatattg
tagaagtccacagaaccatactaatattggacttctgcttagttaggtcttatctatctgaaacatgatattcatattgcag
agaagattattttctttagtgattgaggaaatctttactacttatacatttttaatataatactataatatttgaagatgca
cattttagatgtagtttaattgaaacctggaaatactattaatttgctttttaaagtcctaaaatcaggattatcagattct
gaattaatggagtttaaatcaaaaagattacaaggcagtttttcagttttattctggttaactttatcacagctttggaatc
ctactttgtttatttgcttcttgaagttagatttcccagtgaaatttcagtatcacataaagtcttatgaaatggctcattg
cactttgaactttgagtcaaggaagtgaaatttattgatagattgttggtgtaatatttatcctgtttgtggtagcttttttt
gaataataagtgtcttagaagaccatgttggagtagcctgcatgcttttatcaaacatattaattatgtgatggctgatact
gctttagatattacatagaaatagtagtaggtgtttactaaactggaaatttcatttaacttggtttagctttgccttgttc
tcagtcacattgataaaaatgtaagacttttgtttatctttagaataatgacacctttggtgctgagaatttttgtttt
atatatatatatatatatacgtaatataaatacaaaatatatttaaatatgtataatatttctcatacactttatgtaactt
tgtgttcctgtttctctattatcttggcatgttttcttcaaatggcacttcttaacctcctaaggttaataaatttctttgt
aatggacttttgttttctaattcctcagcgtatgacaaatgaattatactttgtcaaattatttaggtaactttcagtttt
gaagtcctgggatcataacattcatcagtctttaatttctgtcattaaggtcattagctataaatgaatttatgagtagatt
taaaaaataaaacatacaatccttcccttaacacactttcccaccatttggttcaactgctagtgtaaaagcatgatgaatt
ttgagaagttatatttttaccagttactttatttttaccagttatttaaaacagacatgagccaaagccagaatacttgtta
atgaaaatgaggtgttttggaggaaaggaaggttgtgctgcagtttttacttgaaatctgttacatttctttacagaaattt
caaatctcttgtttcctgttatgatggtggcattatatacctttaaaatgtgagctataggaaaatgaatgatggttaattt
tttaataaaatatttagacttgtgttttttgaaatttttataacattgttataggttttatcctctttctcttgtgaacatgt
agtgatttgtatttgtgatcttgcccgcatgctagagacttaagaatactatagcaaatatctgtcttctttacatttaaa
aatttttcgtgactactccctgttgatatctgtcttaaaagttactttgatgtagttcacaaatgtaccagataatttattt
catcgttttaatgcttaaagttttcatttgtattaggattttttagtatgattttaatgttaaagttttgaagttactctgc
cactagaagtctaatttttgggacttactattcatgaaatagaattgacttttatataagtaataggaccttattttgaagg
ttcaaactggagaaaatcttacattgtttatatttttatttcatttatttcagttgatttgcttgagatcaagattgcagat
acagaatccatatttcgtgtatattgctgatattaatcattaaaatcgtttttgacagtttgacagttaaaggcatttcctg
tgaaataatactggtatgtatttaaccatgcagatcctcagtttgtggtctgccagctaaaggtgaagatatattcctccaa
ttcaggacccacacgacgggaagacaagttcatgtactttgagttccctcagccgttacctgtgtgtggtgatatcaaagta
gagtttcttccacaaacagaacaagatgctaaaaaaggttctgtactttactttcattgggagaaatatccaaataaggacag
attaaagctatattttatttatgacatgtaaggaactataatttgttttctattagatctgcaggtgtttgcttactct
ggcattggtgagacattataagggtaaataatcctgtttgaaggaaaaggccttatggcattgtaacatgagaggaattttt
cttaacaaggatggttaactgagaagaaattagcatgggaccaatattttaaaaattttggtctataggtagaaatgagatc
tgttctgtggtcttatgtagtgacacaaaccacttttttctccatttttggcttatgtttctttttttctttcctttttttttttt
ttcctttttgttagagacagggtcttgttctattgcccaggctgagtagctaagactacaagcatgtgccaccacacccagc
taattttttttattttttattttttgtagggacagggtctcactatgttgcccaggctggtctcaaactcctgggctcaagcag
tcctcacgctttggcatcccaaagagttggaattacaggtgtgcgccatcatgcctggccttaacgtttcttaagacttgat
tattttctatttagcttctgtggatttactgattaatttttttaactaggagagaaatcagtatgaagaggaagtaataaaga
atgaaaacatggtatttaaatgtgcaggtttagaaagttaatgaagcttgaatttgattgatctgtatttagagaaggcaac
gtcttattactttaaaaccaactatccgccctgtgcggtggctcacgcctgtaattccagcactttgggaggctgaggtggg
cagatcagctgaggtcaggagttcgagaccagcctggccaacatggttaaacccatctctactaaaaatacaaaaaaatta
gccgggtgtggtggcaggcgcctgtttttcccagctactcaggaggcttgaggcaggataattgctgaacccgagaggcggag
gttgcagtaagccaagaatgcaccattgtactccagcctgggcaacaagagtgaaactccatctcaaaaaaaaagaaaaaaa
aaacaacaactatcttcatttaaaatattaaatgtgaatatttaaagtgagactaaggtgcaacatttttagatagtaatga
agaaaaggactaactttgtagtgttgctgccttgttaaacatactagatagcatattgccaatctttaaacattctcaatga
taggatttatttactttttctgatttttagctttttcttttgaaagaaaataagaggaagtttcatttactgcaaaatttttaa
atgctgctttgatgtatcagtagagatataatttttcctttatccagaatccaagtagctggaaaaaaaaatcaaaatatgct

FIG. 4 (Continued)

gaacttttttttttttttagccagaaacccatttcctatcgtctgtacaaataaaagttaaatatatctcaataacttagaaaa
attatttttgataatccaggaagtattagcaactgttttaaaattaagataactagtaagttttatttagctttcaaaaat
aggcatctacatcatcatctctgcatacctttaggaatttcctaattcttatttcccttcatctgtactttaacacatgcaa
aattgaaggttagattaaatatttatgatttatttgttctatccttgactacataaatttccatttttattgattttccctgcc
ttatttaagaatatgctatgattaaaacacaaaaaatttttagtataacccatatatatatagaattcacctttttgttattt
aaatatttattggcttattttcttctaagtaaaatacaattactggctaaaataattgaaataagcaaaaaaaaaatttttaaa
gaccttgtatacaagattactttgccaggtactgttaaaagatgcaatgacatttaagacgtaacatccttaaggatcttat
tttctggggggataaaaaactttaagataaattagaataaaagatttaaatggcattttaaggtaccaggtaccagataagat
gtcacaaggctgtatatcattaattgccaaatgatttatacaggccagatttctttgttggtcaatagaggtttaaagtgat
gaacttctgttgtgtttttttattaagaaggtattatcttattagtaagaagtgatttttttaagaacaagcatttttataa
catcaaaagaaatcagtagtactctttcctaccccctcatatttattctgaaagtattcaagcattatattgtcatgtaaga
aactggagcttctcatgtttgtattgctgtagaagtaaacatgtatttgccatgcgtcatcagggaagttgcactcaccgtc
caagaactttgttaaagtaaatcttggaataggtagctcatttgaatgtagaaaaaattaaatccatatctgaattttctgt
ttatatgtatgtacacgtaaactaaaaacgtatttaaagctagtattagatgagaaagaggttttttttacttaaaattttta
aggcaaaagtagtttatcttagatcttgtgagattgtatttttggtttaaaatttgagaatttgagtgaagaaaaatcatgt
gaatgaaaatgcaacagataactcagattgccttataatagtctttgtgtttacctttattcagaatatcaaatgatagttt
attttgttgactttttgcaaatgtttaacataggtgacagatttttcttttttaaaaaaataaaacatcattaattaaatatg
tcatttcatttctttttctttttcttttttttttttttaggacaaaatgtttcacttttgggtaaatacattcttcatacca
ggaccagaggaaacctcagaaaaagtagaaaatggaagtctatgtgatcaagaaatcgatagcatttgcagtatagagcgtg
cagataatgacaaggaatatctagtacttactttaacaaaaaatgatcttgacaaagcaaataaagacaaagccaaccgata
cttttctccaaatttttaaggtcagttaaattaaacatttttgtggggggttgttgacttgtatgtatgtgatgtgtgtttaatt
ctaggagtacagctgatgaagaacttgcttgacaagtttttaacttatgtattatttcgaagcagtgtttacgtagcagtaa
catgaaagtttctaataaaatacccaatgtacacagcgtcaaaaaagctgcatttttcctttttcctaattcttcgttgtttg
ctgaaatctggggcaaaggtgcgggagggggctaaatgactgggatatgaagtaggaatgggagaggaaagaaatagatggg
aactcagtcatttgggaatgattcatatggaatgtttttactgcttccactcctgtctgccttccaatttattctcaatccc
tcagagtgatcttaaaaatagacttgattgtgtcacttctgtttacactttataaggaccttgtgttttttttttttaccatg
acctacaaggcccagcataatttagcacagggctacctcctacatcagcactagtcacctttctctcctgtttcttgagatt
cagtcatactggtcttcttcagttccttcaaaatgctaagcttctgcctcttctagtctttccagttattttcccttctccct
gtaccttttcatctcagcctttttccccctgaccttcccatagctatcttcatatttccagcccttagcttcaatctcatattctc
tgaagtccttttgattgtcctcccgttattcttttttttaaaaatcctatttcctttatattgtatcttagaattatttggtttg
tttcattttttgcctatgtgtgatatatgtatttctacataggtatatatatcctacttatagacaagaatttcttcagattaaa
aaatctgatttgtaaacattcccaagtggttgtttaccatttttttcttcccccttcctatttcttattctacctgatttt
ccctgttcattcaccacactcgtttctttctcttttttactctctcttaatttttcattcaatttttataacatgtaataa
atctaactgtagcgtctgagtattaagaatattgctagtaatacttcacctgtaatcccagcactttgggaggctaaggcag
gcggatcacttgaggcccaggagtttaagaccagccggccaatatggcgaaaccctatctgcactacaaatacaaaaattag
ctgggcatggtgtcgcacacctgtaatcccagctacttgggaggctgaggcacaagaattgcttgagcctgtgagatggagg
ttgcagtgagccgagatcacaccagtgcacgtgcacttcagcctgggcaacagagcaagactctgtcttaaaaaaaaaaaaaa
aaaaaaaatatatacacacacacacacacacacacacacacacacacactattactaccaatatacatacatatatgtatg
tatgtatgtatgtatattggtagtaatagtaatacttgggcccctgcacgttttaagtgaaaatagatctaatattaaatgt
ctttagcccttaaattttttttaagtgttcagaagttcccttttaaaaaaatttttaatatataataattgtacatatttat
gggatacagagtgatatttttcatgtatgcagtgtgtgatgatcaaatcaggataattagcatatggatcacctcaaacattt
gtcatttctttgtgttaggaacattcaaaattctgtccttctagctatttgaaaatatacagtaaattattgttgactagtta
cagttctatagaacactataatttattcctcctgtgtgtaattttttttatcttttaaccaacatctccctatcctcccctccc
actcccttttcccggcctctaataaccacactcttatgagctcaacttttttttagcttccatatatgagtgagaacatacggta
tttatctttctgtacctgacttattttacttaacatcatgtcctccgggctagacattctctttagaatccacaggtttcct
ttctttcctcctaaatctgcatttgctcagccattaactttttaaaatgtcttttcccctttagttttattgttttctatttt
aatattgcaagatgttttatatttgtgattacaaataaaaactccattattagtaaacaaatacaatgtcatatagtagtaa
gtgctataaaaaatagacaggatagaaagtaatcttggtttgtatgtttttttgtttttcttagcaaagatgattagagaaggcc

FIG. 4 (Continued)

caaccaagcagataacatttaagcagaggcctaaatcatataagtgagttatacaaatatctgggaaaagagttaagagtac
agatgcaaaagcccttagacaagagaatgagcttggtatatctgaagagtggataagtcatttgactgaaacagagtggac
aagaaaaccagtccaagtgtaaagacactagtgtgtgttcagcataggaaggatgtaatctgaatttgtgtttaatattcc
ctgtgttcatgctttcaaaatacagatgagtgaggaaagtagggagaaggggtaataaaggaagctgagagatcagttaaga
ggtacttgaatagtttagtaaagatgagagaagatgtttgcttcttgttgccccctcactgcttagaatagtggcagtgaagg
gtaacaagaagctgtcagattaacttaaagagtttactgatgcagtggatgttggttgtaagagaagaattgataatgactc
ttggataataggggagggaggggctgtcaatataatataatgaagaagggatttgaagtcatttctgatttaaatctcacat
ccactacctacttttaatagatatgtagcctttaacaagttccctaacctttctgggccttagctacctccccttggaaatg
gaaatacctaacatgtaaggttgctttgacagttactttcactaggcatgtaaaggcacttgactctctgttatagaccact
gtattatgttaatgtccctctccttcctccctttaggtaaagtttttagggctaataaatcccaaatatcaatgttgatcag
tagtttgtgtttgtgtagtgttgtttatatcaaaaactacattgaagccgggcacagtggttcacgcctaaaatcgcaacac
tttgggaggccaaggtgggcctcccaccttgaactaaggagtttgagaccagcctgggcaacatggtgaatcccatctcta
caaaaaatataaaagctagctgggtgtggtggcatgcacctgtagtcctagctacttgggaggctgaggttgatcctgggag
tttgagcctgcagtgagctgtgaagatgccactgcactctagtctgggtgacagagcaagaccctgtctcaaaaacacacac
acacacacacacacacaaagaaatacattgatttttcacataggtagtaagagaaacattctttttgaactcagctgttt
gtgaattgaatttgtaattcaaatgctatattatgtaaactattgatgactttcaatctgcatttatttgtataattatt
tagttaatatttgccacttatattccttaaaaaataaaattgaggttgggcgtggtggctcacacttgtaatcccagcactt
tgggaggctgaggcaggcagattgcctgagctcaggagtttgagatcagcctgggcaacatcatgaaccccatttctactaa
aatacaaaaaattatctgggcatggtggtgtacacctgtagccctagctgtttgggaggctaaggcacgagaattgcttgaa
cccgggaggcagaggttgcagtgagccaagatcatgccactgcactccagcttggcaacagagcaagactcttgtctccaga
aataaaaataaataaattgtattaacatcctgatagtttatctgtttagtacctagcaagaaagaaaatgttgaacatctta
agaagagggtcatttaaaaggcctcttaaagatcatgtttgttacagtgcttaaaaattaatatgttcatctgcaaaatgga
ataaaaaatctgttaaaaatatatttcactaaatagtttaagatgagtcatatttgtgggtttttcatttaaatttttctttc
tctaggtgaagctgtacttcacaaaacagtagaggagccgtcaaatccagaggctagcagttcaacttctgtaacaccaga
tgttagtgacaatgaacctgatcattatagatattctgacaccactgactctgatccagagaatgaacctttgatgaagat
cagcatacacaaattacaaaagtctgaattttttttatcaagagggataaaacaccatgaaaataaacttgaataaactga
aaatggaccttttttttttaatggcaataggacattgtgtcagattaccagttataggaacaattctctttcctgaccaa
tcttgtcttaccctatacatccacagggttttgacacttgttgtccagttgaaaaaaggttgtgtagctgtgtcatgtatat
accttttgtgtcaaaaggacatttaaaattcaattaggattaataaagatggcactttcccgtttattccagttttataa
aaagtggagacagactgatgtgtatacgtaggaattttttcctttgtgttctgtcaccaactgaagtggctaaagagcttt
gtgatatactggttcacatcctaccccttgcacttgtggcaacagataagtttgcagttggctaagagaggttccgaagg
gttttgctacattctaatgcatgtattcgggttaggggaatggagggaatgcccagaaaggaaataatttatgctggactc
tggaccatataccatctccagctatttacacacacctttctttagcatgctacagttattaatctggacattcgaggaattg
gccgctgtcactgcttgttgtttgcgcattttttttaaagcatattggtgctagaaaaggcagctaaggaagtgaatctg
tattggggtacaggaatgaaccttctgcaacatcttaagatccacaaatgaagggatataaaaataatgtcataggtaagaa
acacagcaacaatgacttaaccatataaatgtggaggctatcaacaaagaatgggcttgaaacattataaaaattgacaatg
atttattaaatatgtttctcaattgtaacgacttctccatctcctgtgtaatcaaggccagtgctaaaattcagatgctgt
tagtacctacatcagtcaacaacttacacttatttttactagttttcaatcataatacctgctgtggatgcttcatgtgctgc
ctgcaagcttctttttctcattaaatataaaatatttgtaatgctgcacagaaatttcaatttgagattctacagtaag
cgtttttttcctttgaagatttatgatgcacttactcaatagctgtcagccgttccaccctttgaccttacacattctatt
acaatgaatttgcagttttgcacatttttaaatgtcattaactgttagggaatttacttgaatactgaatacatataat
gtttatattaaaaaggacatttgtgttaaaaaggaaattagagttgcagtaaactttcaatgctgcacacaaaaaaaagaca
tttgatttttcagtagaaattgtcctacatgtgctttattgatttgctattgaaagaatagggttttttttttttttttt
ttttttttttaaatgtgcagtgttgaatcatttctttcatagtgctcccccgagttgggactagggcttcaatttcacttctt
aaaaaaaatcatcatatatttgatatgcccagactgcatacgattttaagcggagtacaactactattgtaaagctaatgtg
aagatattattaaaaggtttttttttccagaaatttggtgtcttcaaattatacctttcaccttgacatttgaatatccagc
catttgtttcttaatggtataaaattccatttccaataacttattggtgctgaaattgttcactagctgtggtctgaccta
gttaatttacaaatacagattgaataggacctactagagcagcatttatagagtttgatggcaaatagattaggcagaactt

FIG. 4 (Continued)

catcctaaaatattcttagtaaataatgttgacacgttttccatacctgtcagtttcattcaacaatttttaaatttttaac
aaagctcttaggatttacacatttatatttaaacattgatatatagagtattgattgattgctcataagttaaattggtaaa
gttagagacaactattctaacacctcaccattgaaatttatatgccaccttgtctttcataaaagctgaaaattgttaccta
aaatgaaaatcaacttcatgttttgaagatagttataaatattgttctttgttacaatttcgggcaccgcatattaaaacgt
aactttattgttccaatatgtaacatggagggccaggtcataaataatgacattataatgggctttgcactgttattattt
ttcctttggaatgtgaaggtctgaatgagggttttgattttgaatgtttcaatgttttgagaagccttgcttacattttat
ggtgtagtcattggaaatggaaaaatggcattatatatattatatatataaatatatattatacatactctccttactttat
ttcagttaccatccccatagaatttgacaagaattgctatgactgaaaggttttcgagtcctaattaaaactttatttatgg
cagtattcataattagcctgaaatgcattctgtaggtaatctctgagtttctggaatatttttcttagactttttggatgtgc
agcagcttacatgtctgaagttacttgaaggcatcactttttaagaaagcttacagttgggccctgtaccatcccaagtcctt
tgtagctcctcttgaacatgtttgccatacttttaaaagggtagttgaataaatagcatcaccattctttgctgtggcacag
gttataaacttaagtggagtttacggcagcatcaaatgtttcagctttaaaaaataaaagtagggtacaagtttaatgttt
agttctagaaattttgtgcaatatgttcataacgatggctgtggttgccacaaagtgcctcgtttacctttaaatactgtta
atgtgtcatgcatgcagatggaaggggtggaactgtgcactaaagtgggggctttaactgtagtatttggcagagttgcctt
ctacctgccagttcaaaagttcaacctgttttcatatagaatatatatactaaaaaatttcagtctgttaaacagccttact
ctgattcagcctcttcagatactcttgtgctgtgcagcagtggctctgtgtgtaaatgctatgcactgaggatacacaaaaa
taccaatatgatgtgtacaggataatgcctcatcccaatcagatgtccatttgctattgtgtttgttaacaacccttttatct
cttagtgttataaactccacttaaaactgattaaagtctcattcttgtca

FIG. 5

Natural antisense sequence (p73as): SEQ ID NO: 8

>gi|16445433|ref|NM_017818.2| Homo sapiens WD repeat domain 8 (WDR8), mRNA

GTTGCAGCCTGCTGCCGCCCAGGGGTCCCGCGGGTTTTCGGGCGCAGGGTGGCGCCCGCGGCAGGCGGCGGCCATG
AACTTCTCCGAGGTATTCAAGCTCTCCAGCTTACTCTGCAAGTTCTCCCCGGACGGCAAGTACCTGGCTTCCTGTGT
CCAGTACCGGTTAGTGGTCCGGGATGTGAACACCCTTCAGATCCTTCAGCTGTACACGTGCCTAGACCAGATCCAGC
ACATCGAGTGGTCGGCAGACTCGCTCTTCATCCTGTGCGCCATGTACAAGCGAGGGCTGGTGCAGGTCTGGTCTTTA
GAGCAGCCCGAATGGCACTGCAAAATAGACGAGGGCTCAGCCGGGCTGGTGGCCTCGTGCTGGAGCCCGGACGGGCG
CCACATTCTCAACACCACGGAATTCCATCTGCGGATAACCGTCTGGTCCTTGTGCACAAAATCCGTGTCTTACATCA
AATACCCGAAAGCTTGTCTGCAGGGAATCACCTTCACCAGGGACGGCCGCTACATGGCGCTGGCAGAACGGCGCGAC
TGCAAAGATTACGTGAGCATCTTCGTCTGCAGTGATTGGCAGCTCCTGCGGCATTTTGATACGGACACCCAGGATCT
CACAGGGATTGAGTGGGCCCCAAACGGCTGTGTGCTGGCAGTGTGGGACACCTGCTTGGAGTACAAGATTCTGCTGT
ACTCATTGGATGGCCGGTTGTTGTCCACGTACAGCGCTTACGAGTGGTCCCTGGGCATCAAGTCTGTGGCCTGGAGC
CCCAGCAGTCAGTTCCTGGCAGTTGGGAGCTATGATGGAAAGGTGCGCATCCTTAATCACGTGACTTGGAAAATGAT
CACGGAGTTTGGGCATCCTGCAGCCATTAATGATCCCAAGATAGTGGTGTATAAGGAGGCCGAGAAGAGCCCACAGC
TGGGACTGGGCTGCCTCTCCTTCCCGCCGCCCCGGGCCGGGGCCGGCCCTCTCCCGAGCTCAGAGAGTAAATATGAG
ATCGCCTCTGTCCCAGTCTCCTTACAGACACTGAAACCTGTTACCGACAGAGCAAACCCGAAAATGGGCATAGGAAT
GCTGGCATTTAGTCCTGACAGCTACTTCCTGGCGACAAGGAACGACAACATTCCCAATGCCGTCTGGGTCTGGGACA
TTCAGAAGCTGAGGCTGTTCGCGGTGCTCGAGCAGCTGTCCCCAGTGCGCGCGTTTCAGTGGGACCCGCAGCAGCCG
CGGCTGGCCATCTGCACGGGAGGCAGCAGGCTCTACCTGTGGTCCCCAGCGGGCTGCATGTCGGTGCAGGTGCCTGG
GGAAGGCGACTTTGCAGTGCTCTCTCTGTGCTGGCATTTAAGCGGAGACTCGATGGCCCTCCTCAGCAAGGATCACT
TCTGCCTCTGCTTCCTGGAGACAGAGGCAGTGGTCGGCACAGCCTGCAGACAGCTGGGCGGCCACACGTAGCAGCGG
TGCACTAACGTGTGCAGAAACAGGGCTACTCTGTGTTTCCAGTGTGGGAAAAAACACAGCTTCACCAGGAGGTTCTC
CACTGTGGTGGTCTGGATTCAGTGATTGATTCTATTTTTCTATAGCAAAGCATTTTTGTAAATATGTATGGTATAAA
ACTGTAGTTTTATTATTTAAAATAAATACTTGCTGATTTAAAAAAAAAAAAAAAAAA

FIG. 5 (Continued)

p73Natural antisense sequence (Hs.668503): SEQ ID NO: 9 gcaagaggGCTGCCAACGCTACTAATCAGACATGCTGGGTCCACAGGGCTGTCCCCAAACTGGAAAGAAGTCCTAGAAAATA
GATGATTCTTCCTAAAACGTAAATTGGATCATGCCTCTCCCCCAACAGTCTCATGCCTATGGAAGGGAATCCTGTCCCCCAA
GGGGTTCTCCCTCCTGTCTCCTCCAAGAACCAGGCAGTGTGGGGTGGGCAGCAGGACCCAGGGTCTCgGAGCTGGGGCCTC
CCCAGCCTCACTTGGGGCCTCCAAGGCTAAGTTCTGTGACCTCCAGGCCCCAAGAGTGAGTTCCTCTGGCTGCTCCAGAAAG
TGAAGAGAGAAGAGCCAACCCCGGCTCGGGCCACGAGCCCCGAGGCaCTGACCACAGCCAGAGCAGGCCTGCTGGAAGCTCC
GTCCCTGCTGCAGATCCCTGCGCCACATGATATCAGCAATTGCTGCAATTTCGCCCTAAGTACTCTTGTTTCCCCTAATAAT
CCACGTTTCATCTCCACAATAAACAT p73Natural antisense sequence (Hs.674463): SEQ ID NO: 10

CACTACAGGGAACGGCCCAGGAACCCATCCACCCGTCCCCAGCTCTCATCACTCTGACCTCTGGCTTTTTGTTTCCTGGGGC
ATTTCACAGCAAATTCCACCTATGAGACCGTCTCATCCGTAATACACCAGTACATGCTTCCAGCAGCTTGGTGACATGAAAG
GACCTCCGTGGCTGGCCTTACTCCCTGTGGATGCCACAGCTGCAGGATCCTGGGGCCCCAACAGAAGCCGGTGAAGGAAGAG
TTCCTGCTCCAGCAGAACAAAACTGCCCTTTGCCCAGAAATCCTGCAAACTGAGGCTGGACGACTTGAAATACTCATCAGCG
AGATTACCACGAAGCCCAGGTGCCGAGGGACCCTCACGCCTGTTGCTGCGTGGGCCGCCCAGACATCGCCAGAGACCAAACCG
CAGAAGATGCTCGGAGCCCAACATCTACAAACCTGCCCCGCCACGGaCCCCAGGCTCAGAAACTGGTTTTTAGTCAGCTCCA
ATGATTAGCTTTTTTTTTTTTTctcTTTGgTTcCCATAGAAATGCCTCTTCAAAGCATTATGGGACAACACACCCACCCAGTT
TCTGTACCGgTGGAGCTTCTgGGGGAAGTTTCAGgACTAGGAAcacacagggcGGCTCAGGACACACtTCACCCCAAAGTATG
ACTGTGGAGACCAGAATACGCCACCCCTAAATATGACTATAGGAGACCAGAATACGTACCCCAAAATATGcCTGTGGAGACC
AGAATAGCCACCCAAATATcc Natural P73 antisense sequence (Mouse) (WD repeat domain 8): SEQ ID NO: 11

>mm9_knownGene_uc008wbj.1 range=chr4:153516481-153542372 5'pad=0 3'pad=0
strand=+ repeatMasking=none GTACTTCCGGCCGCTGCCTGGGCCGGTTGCGGGAGGTACTTCGGAGCCGGGCTGGCCCGGGCTGGCCGTGGCCATGAACTTC
TCGGAGTCATTCAAGCTCTCGGGCCTGCTCTGCAGGTTCTCCCCGGACGGCAAGTACCTGgtgagctgcggcgcgctgggcg
gaacctaagtgtgggcgcgcgacttgtgcacggggccggggcgggccgaaggggggcgggaagggggcccgagccgggcggc
cgcggggactcaggctggacttaggggggcggggtgggaggtgggagagggaggcaggcagaggggtttcagcccagatgagg
gagaaccagatgattagagagaacgaacctgaagccgaagagggatccaggccagccaggctggggatcctggcaggtgac
cagggtggagaaagaggacgtggagcagagtggggatggagttggggttgctattctggcaggtggtcagggttaggaagga
ggtcttggagcaggtggccagggctgggtgggtgccaggctcccggctccagtttcccttcatcaaagttggataagatgac
tctgctttcacacatttgagggcacaggggatggcagctcattgctatttgtatgtttctgtgagcgagctggttaaacg
gggccctcctttgtgaaactcgtcataagcaaatggtttaaataactagctttcattgccagggttggatgttagctgtcta
ttctttgggtggcagaatagtgttcagatgggtgtttcaaggtacgccaacatgaccattgtgcatttgtagaaggctgacg
ttaggaagccatcagggaaaactcaagtcttatttaaaaaactgtggttccgtgccagtcgggtagcttggctagtaacgg
tacctgccaccaaacctgatgacctgagtcccagctctaggacccacttaatggaaggagagaactgtctcctgcatgttgt
cctctggcctccacataagccgtaactagtgcctgacccttctcacatacaaatgcaatcctaatttttaacaagtttctt
tgattaatctatcattctctttttaactgactgataccattgattgattgattgactgattgacagggtttctctgtagctc
tgaccaggttggccttgaactcaaagatctgcccttgtctcctgagtgctgggattaacggagcatgccaccatgcctggc
tgtcttgattctcagttcacacccctgctgtgtttgtccaggcttttgagacatcctttaccctccttatacacatcatcct
aacaatgtaggaagtgtcagggtaggacctgcttagcagggaaaggtactgccatgcaagcccgaggacttgagctccggct
cgggaacccacgtaaaggtgggaggagaccatcagcctcgcacacattgatacatttaccttttttccaagtgcctccagag
actaaggttgctttacggttctgaaagtctcagtgaacagcaaagaagttgcatttgggttagctgatatttgtgcttgccg
ctcatcaaaatatcgtggagctcttaataattgtttctttcaagttttgtcctaaatcctgagcagagcgagtccatgtttc
cagtgttggtgtcttaagtgattcctaaggaatccattgtaacaggttactgctcaccaaactctaatgtgagaacacaagc
cctttgataggtcctccttctgatctgcacttgccctcttgctctctttccacagaagacaaatgtggcttcattaaaaaa

FIG. 5 (Continued)

aaagagtctgtgtgtgtgtgtgtgtgtgtgtgagtgagagagagagagagacagagacagagacagagagacagagatagaa
acagagagatgctacaacacacgtgtagagggcagaggacaaccccagtgttattccttaccttccaccttgtttgagaca
aggtctcttgctcttcactgcataaagcaggctagctggcccacatgtacctgcctcagcctcccctctgcctcccctctgc
ctcctcatagaaactaggattttaaacagtttttaggattaacacagttttatgtggcttctgtgcatccaaacctgtttct
gaggcaagtgcaagtttttggcttttagacaatggcataatatgcaaagctggcctcagactcagaaagtagttgagcacct
ccctagtacagtgattacaagtgtgcaccatcactcccaagtagtaaaaaaatacacacacacacacacacacacacacaca
cacaggctttttgagacagtttctctgtgtagccccagctgtcctggaactcactcagtagagggaggctggcctcaaactc
agggatctgcccacctctgacttctgagtgctgggattaaaggagtgcaccaccccccatctttaaatttacttgtacagatg
gctcagcgggtaagagcactgactgctcacccaaaggtcctgagttcaaatccccgcaaccacttggtggctcacaaccacc
cgtaatgagatctgatgccctcttctggtgcatctgaagacagctacagtgtacttactatataataataaataaatcttta
aaaaaatttacttgtacaaacttgtgggttagagtatgataatttggttaatatatactgtgtggaactttttaaacttttga
atgctccacctttttatcttttttcctaactcatttgcaatgagacccataagtcttggtccacatgaagctaagtgtgtcgaa
caggagggggaggagctggccattgaggcaaggctccctgctgtagaagagatgctatcccgtgctgtctgcctcactttta
gGCTTCCTGTGTCCAGTACCGATTAGTGATCCGGGATGTGACGACCCTTCAGATCCTTCAGTTGTACACATGCCTGGACCAG
ATCCAGCACATAGAGTGGTCTGCAGACTCCCTCTTCATCCTGTGTGCCATGTACAGGCGGGGGCTTGTGCAGgtttgtacca
ccatgtattagtagagtgtatagatgggtgctacatgtctgtgggccttgaacaggcatgtgccacttacatatatgatgtg
tgtaggcaggcacatgccacatatacataagactcacataagtgtgtctcatgtgtaactaactggtctggcgctgtttctg
tagcagagttagaattaggaaacgtttccaggagtgtgactaggaaggagtccaggtgtttgcacccttctttcaggtttag
gggaaatgcaatgagactcaaggttgccttcttttcttatgtgtaatttatttattttatgtgcattggtgttttatctgt
atgcatttctgtgtgatggtgtcaggtctcagagttaccgatagctgtgagctgcagtacggggggctgggaattgaacgggg
tcatcaggaagagcagtcagtgctctcggctgctgaggcatctctccagccccagatatgctttcttttaaaatgtaatgc
tctctaatagtttaatccaaacactttttgatgtggaaaaacaaacaaacaccaccaaaacagtaaattgttctcagtctttg
agcatgatttttctttttttctctttttaaagattctatttattggttatatgtaagtacactgtagctgtcttcagacact
ccagaagagggcgtcagatctcgttacagatggttgtgagccaccatgtggttgctgggatttgaactccggaccctcagaa
gaacagttgggtgctcttacccactgagccatctcaccagcccccgagcatgatttttctgagcgggaggtatttgcaatggc
agtggaacaacttggacagggttctaggaagttctagaaggttctagaaggccgtgttccagtattcactaagcctaactaa
tgaggtcacagggatgggcacatgagcagacccttcaaaggtgcactgcagtgaagtcaccaggaagtgtggcttgtagcca
ctgggccatctgaggtagcatggtgtatatccctctccctcagagaggcctcctgcgtggtacagctatttgcactcctctgt
gtttcttttatgaatcaagGTCTGGTCACTCGAGCAGCCAGAATGGCACTGCAAGATCGACGAGGCTCTGCGGGGCTGGTC
GCTTCCTGCTGGAGTCCAGATGGCCGCCACATCCTGAACACAACCGAATTTCATgtaagctggccaaacgtagcccactctg
ttcttcgcctaaaatagcctgggaatgtgaaagtctggttctggagcagtattcaggccagagttcataaacagtataattt
ttaaactctatttttaaagaaaaataggacattaaaaggagttggcaagatggctcagtgggtatggctcttgctaccaagcc
ttgccacatggtggagggtaagaacgacagatgccccaaagttagagtaacaagggaaaatgtatgtcttctgtaatgggct
gttacaggctgcagtgctcatgctgacatcttaaagggacaggtgctcatgttgacatcttaaagggacaggtgctcatgtt
gacatcttaaagggacaggtgctcatgttgacatcttaaagggacatttggcctgggctttttggctgcatatttgagtgttt
tctagaccactttggccagcaatcttcatgcttatggagttctgcagaccagagtccagcttccagatctcatagacttggg
ctcagtccctccgttaatggcccaaaggaaaggttacccactgcagaatttataaactgtttttttaatgtactttttttattc
agcagctgtgttacactcactgaaatggaaaggaacatttggacagagagtagactgtacagactgcctctgtacactgtta
acctactgctaggtcatagccactgtgcctgtgacattaaagtgaatggcaacatcctgtgtggaggaatatgtcacagcaa
ggggaccctgaaaaatataccctcccttttgttgtattgagatgggatctcactgtgtagccttgactggcctggaacgca
ctatgtagactaggcttgcctcaaactcagagagctgcctgcctctgcttcttgactactgggagtaaagtagccaccagtc
ctatcttattccaagcctttagattttagcttctaaaagtcccacagacttcatttaccaccagctatgctcagtagtcagg
aggtgaccctgtgcgcatgacagattcgtagagtggacacataactgagagtcatatgttcccgctcacaacagttagatcg
ctgtgtactcttctgggggcaggaagtccacgtgagggtgctgcaagatggagagaggcccagctcccatgagacaaggga
agacgattgaattgtgtggctggtgtctgtctggtccgtggaagacactcccctgcacacgcacacttcccagagcacctcc
aggccttgagaggctgccagcctccagagggcacctttgactgcattgcacaaaagccatttcacctttttttggagagtct
tggggtccccgatgcatatgacactgtgcggtttacagcagctcacaggttacattgcctgtacaagggccctcctagccgg
catagctgctgctcttgttccttgtgaggaaaggctctctggggcacactcacctgccgtctgctgctgggcatgagttgtg
aggcaccagtggctttggcctttcttatgcacctcttctagtgtctggatccttccaggctagtgcaggtgggtgtgtgcgc

FIG. 5 (Continued)

agcttccaggctagtgcaggtgggtgtgtgcgcagcttccaggctagtgcaggtgggtatgcgcagcttcccgagggtttgc
atcaggatttgaagtggcgagacgttgcagcatcgtggggcttttgaaaatctcagttactctccactttatattttgaggc
aatgtctcttacttgaacccagagctccccagttctgcagttcagctagcttcctgtccctggggtcatagacaggtcaccg
cacaccctggggtgtgcaggagtgctggggttccagactcacttgagcagtaaggcttccccggagatttccccagccccac
actgtgtgtgtgggctcagttgtcacctggcgaatggagacatttgctctcatggctgctctgtgtgggtgcactgaagtaa
actgcacatgagtgtgcggtgtgggtccatgtttatgtattccagctttaagactctttgtgaagatgggaagcatcctaac
ccttctctcccctttccctggcagCTGCGAATCACGGTCTGGTCCCTGTGCACCAAATCTGTATCTTACATCAAGTATCCCA
AGGCCTGCCAGCAGGgtgagtctgtctttacacagtccttgtaactgttctgagagtgtgcacttagagcagatagaggagc
tacagcagcacctctccccccagcctccatcactgtgcaccctccccagcctccatcactgtgcacccctcccccagcct
ccatcactgtgcacccctccccagcttccatcactgtgcacccctcccccagcctctatcactgtgcacctctcccca
gcctccatcactgtgcacccctccccagcctccatcactgtgtaccctcccccagcctccatcactgtgcacccctccc
ccagcctccatcactgtgcacacctcccccagcctccatcactgtgcacacctcccccagcctccatcactgtgcacccct
tcccccagcctctatcactgtgtacccccctctcccagcctccatcactgtgcacccccctcccccagcctccatcactgtgta
ccccccagcctccatcactgtgcacccccctcccccaagcctccatcactgtgcacccccctcccccaaagcctccatcact
gtgcacccccctcccccaaagcctccatcactgtgcacccccctcccccagtctccatcactgtgtaccccctcccccaaagcct
ccatcactgtgcacccccctcccccaagcctccatcactgtgtacccctccccaaagcctccatcactgtgccatcctctg
tgctccttcctgtgtgtctgtgagattccctccatgccatttctttgacaacaggatgctgtaaaagtagacaggcattgt
cctgggaggagaacctttaccttcattcacacagggcactcagcttgcctttggtgcctagctgtcagcttcacttcactaa
cttttttagtcaagatttattttaggatgtgtgtgtgtgtgtgtatgtgtgtgtgtgtgtataagagagagagagaggtg
tatctgtgtgtgtatgtgcatgcatatgtgtgtctgtgtgcatgtatgtgtgtgagagagagggagagggagaggaagagat
gtgtatctgtgtgtgtctatgtgtctgtatgcatgtgtgtgtgtgtataggtgtaggtataggtgtgtatgtctgtctgcgt
gcatgtgtgtgtgtatgtgtgtgtgtgtgtgtgcgtgtggtgtatgggtaatgtgaatgcaagttgaagttacaggtgatag
tgagctgcttgttctgggttctgggatcagttttcaggaaaagcagcacttttaaaaaagatttatttatattatacataa
gtacactgtagctgttttcagacatgccagaagagggcgtcagatctcattacaggtggttgggagccaccatctggttgct
gggatttgaactcaggacctcagtgcccctacctgctgagccctcgccagcccacagcacaagtctttatccagtgagccat
ctccagctcagctcactagctcttctgtcgggatggcatgctgtctgtcacctctgagcatctcagaacagggaaaggagga
aggctgggccgagtgcatggggtgacgggtggtcatgccacccacctgccccaaacccagaaactaacagtagagggcacac
agtaggggcacacagaggggcacgaagtaggggcacacataggcatgctcttgtttgtttgttgccacaaggacaatatgtc
taatgttgcagatcacattagactgatggcatcgtaagtctgttgtgggttttgtgtcttaagtgctactggatctaaagaa
cagtctggccctgggtgcaggtggtcctcaagtctgttatctgaagtgttcttgtcattcttgaggccttgaccgcaggcct
tttacagtaatgcagggctggaaaaaagttacttaatgtttttaagtaagattgtcccgaatattctttacaactttagtta
tttgaaatgacaagttcaaaaggtgactcagcatctttcagaggactctaggtcactgcccagcacccaggtcaggaggctc
acaactgccctgtagcttcagctccgacggaatgggactcttccgtcctcggcgcgcaccccctgcaggctgtgtgtataccta
tacacagatgtacacacatccatacactaattaaaaataaaagcgaaaacgaaatgcagtgacacagctgactcagtgtata
aagtgcttgtggagcatgagaacgggagttcaaatctccagacctacaataaaggccaggtacagaggcagaagtctgtgat
cccagcaccccacatcaagatgggaggtggaaactaagaattccagaagcttgcaggccagctagactggcatgtgcagtt
gcaaacaaaagatctgtctcaaacaaggtggatgagcaatatagacgcccaaggttgtcctcttagccctcatacatacata
tgcatggcacatgtgcctaaattcacacacatggaccaccaccaccacacacacacaactgcaagctgggttttgaccatca
ggtatgcctgtagttccctttgtgaaacatggccctctgctgtgtttcacaagtgacatttgtgactctttaagaatcagg
tccttgggtttgattctgtataatcacccgcctcacctgcaagagggataagggctctgcttgtcagagtcctacgtgacaa
tgtcttgctcatgggaagatgagaaggacacatttccggggcggggcggggagagctcgctcccccccttgtccctttaaaa
agtccctgatgtgctccagtcctttcccacacttggttccatctggttccagtttaccatctctctccacagGACTAACTTT
CACCAGGGATGGCCGCTACCTGGCCTTAGCAGAGAGGCGGGACTGCAGGGACTATGTCAGCATCTTTGTGTGCAGTGACTGG
CAGCTCCTCCGGgtaaggccatcctctgctgctggctgggaaaaggggtagaactagcgttcctggtgatcccagaggctgt
tgcagcccctggggtagacagaatgatggggttcccatggccagaggacaggggccctgtgtgtgactccaagcagtgcaca
ctacgtgtgatctagactccctggtgcatgcacacttggtgcacagtagaagttagcatgttgacatgaactttgaaccctc
tttctccataagggaattcctccctgggaggaatgcagttttgttggcctgggtaaaatgtctcaggagccgtgacactgag
caaatgctctctgtgcccacaagcttcagtgtcagagtgttagagagacatctgaaggggcgccctgggaagcagggtgcgg
gtgggcaggggtccatggggatgagggcatgcggccttgcccagcatggttggcacactgtgtgcactcaccagaacaacac

FIG. 5 (Continued)

acagatactttgtctgttgctgcatataaaatgatacatgaaccaaaagcattagttagaaaataaatgcactacttgtcta
aggacatgttttccaactgtcatgtttttttctcatctggaagCACTTTGACACAGACACCCAGGATCTCACAGGGATCGA
GTGGCCCCGAATGGCTGTGTACTGGCTGCGTGGACACCTGCTTGGAGgtatagcacatgaccagcagcacagtccctttc
aggaatgttcacctgcaggtacctgtgtgctcagtgcatcgagctgctgggtgctggcgtgccgcacgcagggcctgtgact
gtgtcaatgtctcatctgcagTACAAGGTTCTGCTGTACTCCTTGGACGGCTCGCCTGCTGTCAGCATACTGTGCCTATGAAT
GGTCCCTGGGCATCAAGTCTGTGGCTTGGAGCCCCAGCAGTCAGTTCCTGGCCATTGGGAGCTACGATGGAAAGgtaggaag
tggctcagggctcaggccaactcgacgagctgtaggacacctgcagccgtgagctacctgcatgtcattctcacggttcct
tccccagGTGCGCCTCCTAAATCACGTGACCTGGAAGATGATAACTGAGTTTGGGCATCCTGCAACCATTAACAACCCCAAG
ACAgtaagtcctgcatacgcttccacccgagcaccgtggtctcccgggtgcagggagccgcccttgaccctccttagttgctg
tgatgttgtcttccctgttctgcccctcatgccctccttggtgaagggcatttggagtccaggctcgtccgtggactgatcc
tgtcctagccggatgctcatcatgctctgccctcggcagatccctgggagagtgagctgaggaatcctgagcgtgggccatc
ctgccagagcagggcacaccgcaggcagagaggccgggagagctggtctgtatggactgcagctagggcggcccaggcccag
gcccaggggtgcagagttgaaggcaggttctgaagctcagaggtgctgagtccgctgtcttctgtcagtgctgaagctcagt
agtgctgagtcctctgtcttctgtcagtgctgaagctcagtagtgctgagtcctctgtcttctgtcagtgctgaagctcagt
agtgctgagtcctctgtcttctgtcagtgctgaagctcaggagtgctgagtcctctgtcttctgtcagtgctgaagctcagt
agtgctgagtcctctgtcttctgtcagtgctgaagctcagtagtgctgagtcctctgtcttctgtcagtgctgaagctcagg
agtgctgagtcctctgtcttctgtcagtgctgaagctcaggagtgctgagtcctctgtcttctgtcagtgctgaagctcagt
agtgctgagtcctctgtcttctgtcagtggtctggaccaaggacaggtttctgcttcccttggacaaggagggccagggcca
tggcccggggctcagttagctgccccaaagcctatgtctgcagaaccctgtaggaaggagaagctaggtggaggctgggctt
tagtcagggtgctcctcctgtaacagtggttgaaccttagagatgacagagtacaggctggccgtgcaggctgccaaggttt
gcctgtggttcaagcgcctgtctcccccacgtgtgcactggtggtttctctgcctgggactgcggagtaccccactaaccta
agcgtgtgagtgaactttgtgtcaccgggtcagaggacccggggacacgatcaacctagttaaagtagaacgggttcatttt
ggctcctaatttctgaggtttcagtccatggtcccttcaccatttactttgggtagcacattgtggtggggacaaatggcag
agcagagctgaccttcagctgctctggccaagaagcagagaggaaggacaggtgaggtcccaatgtggccttcaaagtcatg
ctcccagtggcccgggcctgtaaggtccatgctagcaccaagtctgtcaggcctggccgtttgctactccacaggctcgctg
ccaccactgtcctctcctggcctactttttctcctgtgcacacacaggccactgccgaatcgctgtgacatagctccaccatgt
aaacatagccatgtgctcagagccctctctaaaggacagcctggccagcagtactgcggtggcagctgcaaagggtcagact
tggccgccgcctcttcccagcgacctccgtgtggggcacatagataggttgggccaccttccactggctctcgtcacagact
gctagcagccacatcattgtttttcagGTTGTGTATAAGGAAGCTGAGAAGAGCCCACTGCTGGGGTTGGGCCACCTGTCCT
TCCCGCCGCCCCGAGCAATGGCTGGTGCCCTCTCTACCTCAGAGAGCAAATgtaagcagcagagggctgtgtcctccatggg
agaaagcttgtttttctctcttaaatgagaatcctctgtccacgtgaatctcagaggctgcttgttttgggtgtggaagat
gttaagatgggggtctcaatcctgcagtgtagagaccgcaggtgttctcctgtgaagcctgcctttcctccctgctctgcag
tccctgaaggagtgaggggacatcagctgtgcagcacccgcttggagggggggaggcagccaggctgtaggttgctcatgct
ggcttgtgcttacttatttctgttgggtgatagttctttgattcccagctggaaaggggtagccacctgtgccccgagacg
ctggaaatgggtggacagaactgccaggtgtccaagtagtggggactagctcagaaagcagggcttcagagcagggctgtat
cctgcactggaactgttgtccccagggaacctgtgaacgtgcctctcaccacagctgtcctcttaatccctcctgtgcttct
ctgcagtgtgtttccttccctctctttgccctctcccttaaccagtgccttagcccgtccccgtcgtgttgcagATGAG
ATCGCCTCGGGACCAGTTTCCTTGCAGACTCTGAAGCCAGTAGCTGACAGAGCGAACCCGAGGATGGGTGTAGGGATGCTGG
CTTTCAGCTCTGACAGCTACTTCCTGGCATCAAGAAATGgtcagtgccacactcatttcgtaggcagggtcagctgctcgcg
gccctttgaggcggagagtagagatgaaccgagaagcaaaggggcagctgtgtgctcctctccctggttcctgcagaaatgg
gcgttcagcacagcagctcctttctgcacagcagctccttgccatggcctggccgcctggctgctccctcctgcactcctc
actgtgcaagaacagggcttacctctagttttgtttgcatttttgggggggtgcctctgtgttttaatagtttatctcc
tttatatactttgtatcttgaccacagcctccctccttcctcgcctcccagttccacccatacaaatccttccccattgccc
tgtcccctcctcctcagaggaggcgccctcccccaccccacccctggggcaggactaagcacacttctccccactgaggccc
aactcggcagtccaggtaggggaaagggatccaggggcaggggctggacctaggcctccacactgtaggaaatgtacagttg
gtcttcttgtgggctccctaacaagtgaagtgggggggctgtcttgtttgcattttgtacatctacagatgtaaaaaccacag
gaagaagaggtgtggctttggcaggccatgtctttgttctgggtgctggtccctgagaacagccagagggctggcagtgcca
gcactgacatgtgtcccgtctctgcttccttgcagACAATGTCCCCAATGCTGTCTGGATCTGGGACATTCAAAAGCTGAAG
CTGTTTGTGGTACTAGAGCATATGTCTCCAGTGCGCTCATTTCAGTGGGACCCACAGCAGCCGAGGCTGGCCATCTGCACAG

FIG. 5 (Continued)

GAGGAAGCAAGGTGTACCTGTGGTCCCCAGCAGGCTGCGTGTCGGTGCAGGTGCCTGGGGAAGgtaagcgtaagccagcaca
tgctggcctcagacaggctgacctgcttaaacctattgccacgtgtcatgcatgggaaagatgcccttctgcatcctgtagg
accttgcccagattgtgtgcctcacaggaactggctgtccttaaggtttactggctttgtcttcagccctggggtgaccaga
ctcctcactcacccgcaggcccggtctctaaccctctggctgcctgtctctctaggtgactttccagtgctcggactgtgc
tggcacttaagtggggattcctggccctccttagtaaggaccacttctgtctctgcttcctggagaccaaggagagggttg
gcacagcctacgaacagcgggacggcatgcctaggacctgagtggaaaccaaggcagtagactgctgattccaacgtgagct
aacggctgcacaggttctccagatgggatggctattctgcccagttttctgtaaatatgtataaagttatgtaaagtaggt
atttgctaatccattgaacagtggtggttgtttcttcaaggccttagctcacagacccaaggtcttgggaggataaagaat
cctgaagtaaggactcaagcctgcctcatggccttgcagactctgaagccagtagcgaacccgaggatgggtgtagggatgc
tggctttcagctctaacagctacttcctggcatcaagaaatggtcagtgccacactcattcgtaggcagggtcagcattccc
tgaggggttttctgtcagtgggctttggaacaaggtggactaatgtcagactggccagccctcctgcagctggatgtactca
gaagtgccccgcacctgtgcctgtccccgtgtgagctgtaaatcccacaacagttgggcaggtctctggccttacaagtgaa
ttctgcagagaggcctgggtcactgcctggtagagtggaagagctcagcccacccaaacctctctatctctagtaagtgcct
tgaaagcagacagaccagtatgtctgtactggtgaccagggttcccaccaggactgcacacttgtgtatctgagtttctgta
aagaggaccatgctcacaagggtcctcagtcagccagacttcagtcctcaagacagtctttggcactcctgattctgtgaca
ataacttcaaaaggagcaactccatttggtttaaatgtctttactagaacaaaagcacaggctgaaaacaggtgcatctga
ggtcaccttcctcttggataggccatggcattccggtcacatccatgccggttaactaaagcgagaggtatagagtgacag
gccagcatctacagtgcactggcaaggctagaacgacagcagcaagctgtgtgtggctggcgtgtcaaagcttagcagtgct
cagtgagctctaggatgctcgtctgcttatagcatgcactttaaaacccaactattcagtccctttaaacagagacagga
tgatagaaacccaccaccatgacttccggaaggggctagcttatgttatgagagtaaccttttgggcctaggaaaactgctg
tattaacacaacctggattaatttataaagtgtgattctaagtcagacacattcacagaaaggcaggttcaccaggagctgc
caggcagactgtctttccttagtgactggctgctggctgctactgtatttagctttttaaaaaacgggctgaatttaaaat
acagcacttgagagttaatatatagggagagttaaatatgtgcagaagccgctcactgtactcagctgtatgcaacagtcta
cacagcacaagtgggtggacattgtgctcggcatgctggagggagaacgtggcgttacagaaggaacacagtggtatggggg
cagctgaatctgcctttgtaagattgtgttgccaagatgtccaatatccaactaaatatacataatccacttgactattcta
atcggatacatgccctccttccctccagccagtgggtggcatgaggtggcacagggagtccccaccaccttggtttccggga
cgcagctgtctagaagcctatcttgcccctggtcatggagtagcccagcttggcttcattgttgatgaaggacatgagcccc
acgtaggtctcgatgaggagggggcgctccagcaccagcacggtattcgcctgccctggcagtgggctctccttctgggcct
tcttgacagcttggatcaggagagccttgaagctttccaactttgaagagaataaacatggagccttaacctcatgccaaga
cagcagtactgggaaacgaggattctgagttcaaatcctcccaaataccacatagtgatgacatcaccaatgacaggttggg
ccctatgagctgtgtcatcaggtggttcatcatgtacaaacatcatgaagggacctgccttaagtccaacctagagagtacc
agtctatctctaaagatgcagtcaggagattcggcagcctgagacaaggtactgccagtgccaacaggtggaaaatcttttt
tacagacgcacatgctctggagtgcacctcactaagcaggtgatgctgtaattgcacacgctgcctgcactggtgtgctgtg
cactgactgacaggtagcatcacagatggaggaattcatgaggactatgatgtcaccaagtgacagggctttctcagcccta
ctctaactgtgcagaatgctcagcgctccctcagcacctctcctgggaacttccagagtacctgtgtcaccagcagcacctg
ccaagccccgccagtactgtgggctttcccatgctcgctcacccacccagtccagactgagcatcctgcaatgggatggtg
actctgttcttaaacagcaccacctagcttcctactgtggaactgcacctccagggttcacactgacagtggccttggcctg
cttacatggcacagagacgctgtcttctcgtccatgccagccattgggtgttctatgaaggtggcatagggcatgtttgtag
accaggggttccatctgttgatgaaggaagggcggctctgcttgtcccactgaatgcgaaccccaaagcctttctctcctgat
gggggagggggagaaagccttgcttaccacaggaatacaacattgcattcagtatcagggatggctggggaacctgtgacct
agtgtaacaatggcctccactaacagcttcacacacttccaaagcgtaacaagttaatgagcctcctttgcagcctatgaaa
ccggcacacagtccaacctggcctaattatggccgtgtttgttcttaatgttactgaatgatgcttaagttagtagccatta
gcttcctggagtccctagtcaaataattcttttatagcaagccaaccagtctctgaaggctgttaggtgttttgcgatgtat
cgaattttagtaatactgagcacatgccctgtgtctccctcctgctggagttaaaactcccagactccctacatagcttat
gacagtgggctctgattccatgtatcttaacggtatttaaatgaatggttttagtggggacagagtggccgactgtgccag
catccctttcaaggaggtactgagcaacccggaaatcaccagcctctacttaaaggtcctttccactggttcttcaagatga
gaccttacctcacaagagagtgggtcaataccacttacaggatccgctggggccctgccgtgtagtgcgctggtgcaccta
cttgttgagcgacttcggaggaaactggaattctccacaggagatggtgtctaccgcgctgagcgccaccctgaccacctgc
tggcactgaaggctgatgaagtcatatttgcagatgagcagcgactggtcggtgaccagcaccagccgctccttctcgttgt

FIG. 5 (Continued)

tccagtggtccaccctggagaggagaggggccgcccatcaccaagagccccgcctgcccccgcccgcccccgcccagtgtcc
ccgcagtcccctcgcgccggcttactcggtcagcagccacacccccctggatctcgccgtcctccacgggccgtaccacgggcg
cggatctcctcgaccgcctgctcgatggtgccgggccggaacacgaagtactccttgacgcgggcgcggcgtgtagggtcgt
ggacgttcagcggccacaacgtctggcgcagcggtgtgcccgccccaggccggccgcaccgcgtcctcgccggccgccag
caccgccgtggggctcgtgcccgccgagtccaccgtgtcccgcagctgcagcatcgcgccgccaccggcagcctccaccgac
ggccgccgcccccggcgtccgcccggccgcgcccccgcccctcccctcgttcgccttgtgattggttgagtcctgcagagcccgcc
ttccggacccgcctccagctccgtcgactgcgtctcgcgattggctttcccctaagctgtcttctgcaattgggtctaaagt
gctgccgttcatgattacggcggcccctcctgggccggaagctgccgccacgcgcggagccacttcctgtttacaggaaggg
cgagttaaaaaaaaaaaaaatgccggtcggggttcctggctgagaacggggaaaggacgccatggactcgcgcggaaggg
ggcacttgggggctcgtgcgtagggcgttgccccgacagtgtgtcctcgcttggctccgtgcccttcaccttcgggcttacg
gtgcacttcgggcggaggtgtgcggcgcacttaggaggtgtgcatgcctggggagtgtgaaagtgtgggcatgggtgtgtgc
gcgtctgaggattgtgaagcgtgggaatgggtgtgtgcgcgtctgaggattgtggacactgtgtcggggcacctcagatag
aggcttctcaggagtgtgctgcactccttgggcgtggtcaccttgggagtgtgggtttatagggtgtgtgcacactggagat
aggagtgtgtgcaggtcagaggtggctgtcagagggttctttatattgggcatgatacgcacaagtaagctaccatgtcacc
gaagagtgctgctggggcgggggtgggggagttggaaggaaacgccgtaggatgctcttgggccctgcagcttctccctg
ggacagaaggccatgcgagatgtccctgagttcctgctcccacgggggtgccagcagtgtgcctgggttgatggagctaatgg
accgctatgatagtgtggcccaaagtctttttctaacagtcaccaagacataggttagactcatcagtgaatgacagcccaa
gatacagctcaggcctgtagtctgtctcctgaccgttgtgagggctccttagcctgctggacctttttacagtgtggcttcgt
cagagaatccagtccaatgaggtctccgggacactggtgggagcagccacgatgacgtgaattcccacagaggttcctgaga
ccgctgtggatgtgaagagtgtgctgaaagctgacagagaaaggggagatgaatagataagtgcatataaggcaataagcca
gggatggagaggtggctcagcagttaagaacactggctgcgccgggcgtggtggcgcacgcctttaatcccagcactcggga
ggcagaggcaggcagatttctgagttccaggccagcctggtctacatagtgagttccaggacagccagggctacacagagaa
accctgtctcgaaaaaaaccaaaaaaaaaaaaaaaaaaaaatcaaggaggcttctacctttagggctggtaagatggctcagt
tggtaagagcacccgactgctcttccgaaggtccaaagttcaaatcccagcaaccacatggtggctcacaaccacccgtaat
gagatctgatgccctcttctggtgcatctgaagacagctacagtgtacttacatataataaataaataaataaatctttaaa
aaaaaaaacaaaaaacactggctgctcttccaaaggactggggttcaatcccagcacccacatggcagctcacgactctta
actccaggatccaataccctacacagacttatatgcagacaaaacaccaatgcacataagaataatgtttaataacacaaa
taagcaaatgtcaagtttgtggcatgcatgaatcctaggtgtgagagagaaacatcatctatttctggctcagcctttctta
tacaacacaggactaccttgccctaaggtggcaccacatgaaatgggcagagccccccccccccatattactcaccaattaag
aaaatgttacagccgggcgtggtggcacacgcctataatcccagcactcaggaggcagaggcaggtggatttctgatactgg
cacttagagcctctcattcaaaggatcacggctaagcaggtgctctgtatctgtccggagcagaggggacgagcagcaggtg
tccgctcctgaacctggcttctacagaagtgtaaatcctttactaccgtgaggagtctccagtatccacactgtgaataaac
accattatatcttacgtgaggctgccaggacagaccacagactggcttgctggaagtaaccgaagcatgtagtgaggttgct
gagaccagacggccagaaccacagtgtgtgtgcatgtgcgcttgcatgtgcatgtatgtgtgtccttctgatacctgagggc
acatgtcttcctttgcctttccagcctcccgtgttgtcagccatgctggatgtccctcagcctgtggctgcctctccccgtt
ggctgactttccatagtcatcgtcgcttctcatttgtaaggattcctgacgttggcacaggcctgccctaacggcccccctt
ttgacctgatcatgttcacagactatttccaaagatggtgagagtcatggagactggttgggacttgcgtgtatcattaac
aggtacataattcaactggtgtgtgtgtgggggggggggagggtgtttcgggcaggtgcaagcgatgaagcatttagatgacc
tccacgtgtgcacacaggtcacggcgggggcaaggagcaagacatgatgactgtgactagggagtaaggtattgggggccca
gagcttgggttggtcctgaggtccactagccgttgccagggatttcaagaggctgttcccaaagtggtcagcagatggcgc
aactacccacacatggcctccctgggagatcacagtttggcaggtatgggatgttttcaagtcctagatgaagctgttatct
ttctgtagaagactcagaagctcagctataacaagcagattcttgccttaatttcctgatgctgtgacttagcatttggga
actcagcgggccctccctttttgaagtgctgagaatggatcccaggcctcccacatgctctgccacttgagatgcttcctcta
agactgagcccccaccttgatacctgtgagaatcctgagcacgctggggtgggttctcagagctgcatgggctcctccaga
gctggtaccacacacacacacacacacacacacggaggattgttgtgtgtgtggtccttccagagccagctgcactttgggt
cgtgcacagggtgtgcaccgctggaagtttgcctcaggaggcaatcctcgcactgccccaagctctgcgattgttgtgcttc
ccatgttaacctcggtcactgagtcaaagaatccacaacagatgcagaggtaactttgaaagagaaccgggttcccagactg
gagaggtggctcagcaggcaaaggtctttgctgccaccctgatgaccagagttcaattcctgggtcccacacagtggaagga
gagaagaaactcatgtagattgtcctttgacctccacacactctgagacatacgtatatacacacatgagttaaatgcacac

FIG. 5 (Continued)

acagacgggactagagaaagagcacagctcctacccacccagccccatcttggcagttgtctccctgatgtcccctctcacat
ctccctctctgttctcctacagggacccattctgataatccagaatgatctgatctgagacccctctctcagtaacttcac
caaagacccgtttccaaatcaggccccacgggggatgtgggcatgaggacatgggctttcctagggaagctatgcaattc
agatgtgccatctccccagatgtgaacagataccatcctgcttgcagtgatgggtaaatatcccatacacttgccatccca
ggccttcctccctgaccccccctgtggtaaagggtagatatacagtgatgggtggaggcctgggatgggccaggccaggccta
tgctgggaaaccacatggtggctggacggcagtctgctgtgtagcgttatatcggcttgatactggctagagtcattgggga
aacctcagttgagaaaatagcccccaccagacaggcctgtgggcaaacttatgtaacatttcctttcttttcttttctttt
atttatttatttatttatttggtttttcgagacagtgtttctctgtatagccctggctgtcctggaactcactctgt
agaccaggctggcctcgaactcagaaatccgcctgcctctgcctcctgagtgctgggattataggcgtgtgccaccacgccc
ggctgtaacatttcttaattggtgagtaatatgggggggggggctctgcccatttcatgtggtgccaccttagggcaagg
tagtcctgtgttgtataagaaaggctgagccagccttgggaggtaatgcagtggtgagcagaatctctctacggcctctgct
tcagttcctgccttcaaattcctgcctcgagttcctggcctgacttccctcagtgatggactctgacctgagagttgtaaga
agaaataaatctttcctcttctaatcactttcgatcatggtgtttcatcacagcagtgaaaacagaaactaagacagtagct
agatacccattgaagctggacaggctggatgctcagttactgagcaggagccagcctccagggacatagttaggtttcatgt
catgctcaaggtcaggatagagtgagtggtataggccaggcagctggccgccaacagggccaagcctaagccctgggcaaaa
tcctatgccctgaccccgtagtgagccttagcccatgtgagtcagcgtacttaggggccctccatttggcttctctctcac
agcagggttggagctttagaaatggatgtgggaatgggcgaaccacaggcttgtaaatggatcgtttgtcgtttagatgggg
cattgcatgtgtgctttgctctcccagagactatcccatctgtctcttgagttttgccaaattctgctcaccctaatgatg
ccatctgcccaaacaggtgactgtggtcaccacactgcacctgaggacctgatgatactttaggtgtctgtttctctttgc
ttttgagagagagagtcttaacatgttgcacaggtcagcctccaaactccgatccttctgcctcagcctccttggtggagt
actgggatcaaagacaggcgtggctcttgggctgtgagccaacctttggtatcacttaggctagcctctcacctgttagaag
ctgacatgaaaactcagacaaaacactagattgtcctcttgggatggtggccttcggctcagcagctgatgtccctgtggct
gctggggtactttgggtttctgtctggagggctatctcttccagctctgagatgcgtcaggctggagagcaggcagccagca
tggttctgggaaaggagggagcggtttgctttggaaattagcgctgtggttcgagctctcctcttccccacattatttccc
tccagccaaagacgattctaattatttccagtagagaatgagacaggacagcgaaaagtatcgtctgctcggggaacaacg
gtgaaggccttaatccatgccactgggagagacaggcagagctctgtgaattcaggctaaactggtctctacagtgagctt
gagcacagccaaggctagtggaggtgtgggggagtgctttttaggaaaatgagagcagttgttctccaagtgtgaaaaaaa
tggaactgcagcctcgcctcttgtctccttgggatgaactgccaagcaaagtccaacccagagtgtcatcagggttgtgact
cagtgacattttagcacactgctggtggaagccacggcggcagggtggacggaggaagggaaaatcctaggagatcctagga
ggtgggtgctgtagccacgggttctggcctggtgtgaataccactcaattcgtgaaaactcaggactaaataaataaatata
tgtgtggccaggcatggtggcacatgcctttaatctttagcattcaggagtcagaggcaggtggatctttagttcaaggc
cagaatggtctacagaaagagttccaaggcagccagagctatatagagaaaccctgtctcaaaaaacaaaaacaaaaaaaca
acgaaatgtttgtgtgtggtgtattaatgttttgctttaatcaaatatatttgtgtttcacatgatgctcaatgtccacagag
gctcagaaggaggacattggatccctaggaattagagttacagagcattgagtgactggccatgtgggtgctgggaatcaaac
ccaggtccctctaggagagcagtcagtgctcttaaccactgatttatctttccagACTCAAGGGCAAATTCGATCTTTACCCT
GTGAATGGGATGATCAGACCCTAAAGTGGAATGTGACACGTGACCTATTTTCAATAAAGGATAGAACTGATGGCCCACCCTC
CTCCTGAAGCCAGCACTGTGGTTCGTCAATATGCCCAAGCCCACAAGAGGCGCCATGCCAACAGTCCAGTTCCTGCAGATA
TCCTGAGGTTCTTGACAGCACATTTAAGGCAGTTGCAGCTAAATTCCAAAGTAACTAAAAGGAACTGGATAGATTAACCTCT
AAATTAATTTGGAACAATGACCAAGAATTGCCATTATAAGACCAACAAGATTCCTCGGCAGGTAAAAGTGACTGTTGACAAG
CCTAATGACCTGGGTTTGACCCCCGTGGCACACATCATAGAGGAAAAGGACCAGTTCCATCAAGTTGTCCTCTGATCCCTAC
ACGTGCACAGCGGCACATGTGATACCCAATAAATGAATGAGTCTAATAAAAAAATTTAAAAGTATCTGCAGGGAAAACCAAG
TAACGGATTTCTCAGACCTATGGATACAGCTATGTAAAGCCAATACCCAGAGTTATATCAGGAAGGTCTCAGTGGCCAGCTC
TTGCTCTGTCTTGTTCCAGCAAGGAAGGACAACTGACACAACAATTCTAGATGCAGTCATTGGAAACACCCAGAAGCGGGTG
CTGCATGTGTTGAGCTAGGAGAGAATATGATATCAGTAGTATCCTGGTGACCAGCTAGCCATTCGTCCTCTCCCTGAATGGC
AGACAGGGATGGACTCCGAGTGAGAAAATACACACAACAGATTGAACAACAGAGCAAGCAGCCACCTTCCTGAGCCAAGTGC
CTTATGCATTTTCACAGGCATGTTTACATGAGGACATTATCATGCAAGTACTTGATGAACCCGGAGTGCGCTCTCCCCCTCG
ACTCGCCCCTGCACTTATTTCTGAGTGATGGGGAGACAAGCCGAGTGCACACCTCGTGGAATTGAGCCGCCCTGTTGACCAT
GTTGTGACTGTCACTCCAGCCCGTGAGACAATTTGAAATAATCATGTCCAACCAGCTGTCGTAATTTGTTAGCTGTAAAGTT
GCAATATGCTTGCTGTGAGTTACAGAACTGTATTAAATACATTGTCATTTGATTCCTAGTTT

FIG. 5 (Continued)

Natural Antisense sequence Human Hs.668503 aligned to mouse chr4:SEQ ID NO:12 atggagagagcagacatacatctccggtgcaggtaccctgctcagaccaagccggagccagcctactggcagcccattctct
ccggcaaagctagacacaATATgAGCAATTGCTGCgATTTCtCCaTAAGTgCTCTTGTTTCCCCTAATAATtCACGTTTCAT
CTCCACAATAAACATtgttagaactcttctctgggctttaaatatacataattgctccccgtgccagtaaaaggtattaatt
ccatttatgcattccataaacttttaggataac p53 Natural Antisense sequence (NM_018081.2):SEQ ID NO: 13

>gi|221136853|ref|NM_018081.2| Homo sapiens WD repeat containing, antisense
to TP53 (WRAP53), transcript variant 1, mRNA GTCCCGGCTCCGCGGGTTCCGTGGTCGCCCGCGAAATCTGATCCGGGATGCGGCGGCCCAATCGGAAGGTGGACCGAAATC
CCGCGACAGCAAGAGGCCCGTAGCGACCCGCGGTGCTAAGGAACACAGTGCTTTCAAAAGAATTGGCGTCCGCTGTTCGCCT
CTCCTCCCGGGAGTCTTCTGCCTACTCCCAGAAGAGGAGGGAAGCACAGGTGGGTTTCTTTAGCTCTGCGTCGGATCCCTGA
GAACTTCGAAGCCATCCTGGCTGAGGCTAATCTCCGCTGTGCTTCCTCTGCAGTATGAAGACTTTGGAGACTCAACCGTTAG
CTCCGGACTGCTGTCCTTCAGACCAGGACCCAGCTCCAGCCCATCCTTCTCCCCACGCTTCCCCGATGAATAAAAATGCGGA
CTCTGAACTGATGCCACCGCCTCCCGAAAGGGGGGATCCGCCCCGGTTGTCCCCAGATCCTGTGGCTGGCTCAGCTGTGTCC
CAGGAGCTACGGGAGGGGGACCCAGTTTCTCTCTCCACTCCCCTGGAAACAGAGTTTGGTTCCCCTAGTGAGTTGAGTCCTC
GAATCGAGGAGCAAGAACTTTCTGAAAATACAAGCCTTCCTGCAGAAGAAGCAAACGGGAGCCTTTCTGAAGAAGAAGCGAA
CGGGCCAGAGTTGGGGTCTGGAAAAGCCATGGAAGATACCTCTGGGGAACCCGCTGCAGAGGACGAGGGAGACACCGCTTGG
AACTACAGCTTCTCCCAGCTGCCTCGATTTCTCAGTGGTTCCTGGTCAGAGTTCAGCACCCAACCTGAGAACTTCTTGAAAG
GCTGTAAGTGGGCTCCTGACGGTTCCTGCATCTTGACCAATAGTGCTGATAACATCTTGCGAATTTATAACCTGCCCCCAGA
GCTGTACCATGAGGGGGAGCAGGTGGAATATGCAGAAATGGTCCCTGTCCTTCGAATGGTGGAAGGTGATACCATCTATGAT
TACTGCTGGTATTCTCTGATGTCCTCAGCCCAGCCAGACACCTCCTACGTGGCCAGCAGCAGCCGGGAGAACCCGATTCATA
TCTGGGACGCATTCACTGGAGAGCTCCGGGCTTCCTTTCGCGCCTACAACCACCTGGATGAGCTGACGGCAGCCCATTCGCT
CTGCTTCTCCCCGGATGGCTCCCAGCTCTTCTGTGGCTTCAACCGGACTGTGCGTGTTTTTTCCACGGCCCGGCCTGGCCGA
GACTGCGAGGTCCGAGCCACATTTGCAAAAAAGCAGGGCCAGAGCGGCATCATCTCCTGCATAGCCTTCAGCCCAGCCCAGC
CCCTCTATGCCTGTGGCTCCTACGGCCGCTCCCTGGGTCTGTATGCCTGGGATGATGGCTCCCCTCTCGCCTTGCTGGGAGG
GCACCAAGGGGGCATCACCCACCTCTGCTTTCATCCCGATGGCAACCGCTTCTTCTCAGGAGCCCGCAAGGATGCTGAGCTC
CTGTGCTGGGATCTCCGGCAGTCTGGTTACCCACTGTGGTCCCTGGGTCGAGAGGTGACCACCAATCAGCGCATCTACTTCG
ATCTGGACCCGACCGGGCAGTTCCTAGTGAGTGGCAGCACGAGCGGGGCTGTCTCTGTGTGGGACACGGACGGGCCTGGCAA
TGATGGGAAGCCGGAGCCCGTGTTGAGTTTTCTGCCCCAGAAGGACTGCACCAATGGCGTGAGCCTGCACCCTAGCCTGCCT
CTCCTGGCCACTGCCTCCGGTCAGCGTGTGTTTCCTGAGCCCACAGAGAGTGGGGACGAAGGAGAGGAGCTGGGCCTTCCCT
TGCTCTCCACGCGCCACGTCCACCTTGAATGTCGGCTTCAGCTCTGGTGGTGTGGGGGGCGCCAGACTCCAGCATCCCTGA
TGATCACCAGGCGAGAAAGGGCAGGGAGGAACGGAGGGAGGTGTGGGTGAGCTGATATAAAAAGGTTTTTATGATAAAAA
AAAAAAAAAAAAA PTEN Natural Antisense sequence (Hs.624903):SEQ ID NO:14 taaacgggnaaagatgccttnCTTTTTAAnCCTAATTGAATTTTAAATGTCCTTTTGACACAAAAGGTATATACATGACAC
AGCTACACAACCTTTTTTCAACTGGACAACAAGTGTCAAAACCCTGTGGATGTATAGGGTAAAACAGATTGGTCAGGAAAA
GAGAATTGTTCCTATAACTGGTAATCTGACACAATGTCCTATTGCCATTAAAAAAAAAGGTCCATTTTCAGTTTATTCAAG
TTTATTTTCATGGTGTTTTATCCCTCTTGATAAAAAAAAATTCAGACTTTTGTAATTTGTGTATGCTGATCTTCATCAAAG
GTTCATTCTCTGGATCAGAGTCAGTGGTGTCAGAATATCTATAATGATCAGGTTCATTGTCACTAACATCTGtTGTTACAGA
AGTTTtAACtTGCTAGCCTCcGGATTTGACGGCTCCTCTACTGccTTTGaGAAGTACAGtTTCACCTtaaattttggagaaa
cgttcacgttgactttgtctttattttcttacggcaagacaatttttgttataagtaagttcctatacttcccttgcattt
attttacaccctcctatatctgtcaatctttatctattttttgtttaacaataaacccactaatttccctactttttcttc
caacgttatccacctatcacctggatcataaataatgtttttcttccccataagttcaaaactttttcccctcttttttc
caccccctctttttgattcttcgcaataaacctttatttgttttctccccac

FIG. 5 (Continued)

PTEN Natural Antisense sequence (Hs. 607931): SEQ ID NO: 15

AAGAAATGGCATATTTGAAGAAATCATATGGCTAGACAAAACAAACTAGATAGATTGTGAAGCTAGATAGACTAAACCTCAG
TCTTGATTACTAATTACAAGCTGAATGTATAAATCTTTTCCTTCAGAGGCATAAAGGTAAGAGTTATGAATCAAATGGAAGG
ACCAAAATGCTTCCCAATGAAGTATTTTCTTGGTGAAGTTATTGCAATCTAAGGTCTGAAAATCAGCTGTACAGGAACTTTA
TCAGTAACCTAAAAGATGATCAATCAGCCTCAGTGACTAACGACACTGAGAAGAGACCAACGTAAAAACTAGCACACCAGAT
TAATTTACCACAAAGATATTCTCACCATAATCAGAAAACCTGCCCTCTATTCAGAGTATTCACTCTTTTTTGGTATGAGTAC
TAATCTGGCTGGGTcGAATTAGTGCTTAGTTGAATACAGAATTAAAATAATGTGAAG

FIG. 6

| Sequence ID | Sequence |
|---|---|
| SEQ ID NO:16 | G*C*C*T*C*C*T*T*A*T*A*C*A*C*C*A*C*T*A*T*C |
| SEQ ID NO:17 | G*T*G*C*T*G*G*A*T*C*T*G*G*T*C*T*A*G*G*C |
| SEQ ID NO:18 | A*C*C*A*C*T*G*C*C*T*C*T*G*T*C*T*C*C*A |
| SEQ ID NO:19 | rCrUrGrCrUrCrUrGrGrCrUrGrUrGrGrUrCrArGrUrGrCrCrUrCrGrG |
| SEQ ID NO:20 | rArUrUrCrCrCrUrUrCrCrArUrArGrGrCrArUrGrArGrArCrUrGrUrU |
| SEQ ID NO:21 | rCrCrArArGrCrUrGrCrUrGrGrArArGrCrArUrGrUrArCrUrGrGrUrG |
| SEQ ID NO:22 | rArGrArCrGrGrUrCrUrCrArUrArGrGrUrGrGrArArUrUrUrGrCrUrG |

FIG. 7

| Sequence ID | Sequence |
|---|---|
| SEQ ID NO:23 | G*A*T*G*T*A*T*G*T*C*T*G*C*T*C*T*C*T*C*C*A |
| SEQ ID NO:24 | G*G*C*T*T*G*G*T*C*T*G*A*G*C*A*G*G*G*T*A |
| SEQ ID NO:25 | C*C*T*G*C*A*C*C*G*G*A*G*A*T*G*T*A*T*G*T*C |
| SEQ ID NO:26 | C*C*G*G*A*G*A*T*G*T*A*T*G*T*C*T*G*C*T*C*T |
| SEQ ID NO:27 | G*C*C*C*A*C*C*A*C*C*T*C*A*T*T*A*T*T*C*C*C |
| SEQ ID NO:28 | C*C*A*G*T*C*C*C*A*A*G*T*C*C*A*G*C*A*G*A |
| SEQ ID NO:29 | G*C*C*T*C*C*G*T*G*A*A*C*T*C*C*T*C*C*T*T |
| SEQ ID NO:30 | G*T*T*C*C*G*C*C*C*A*C*C*A*C*C*T*C*A*T*T |

FIG. 8

| Sequence ID | Sequence |
|---|---|
| SEQ ID NO:31 | GGAGCAAGAACUUUCUGAAtt |
| SEQ ID NO:32 | CCAAUCAGCGCAUCUACUUtt |
| SEQ ID NO:33 | CCACCAAUCAGCGCAUCUAtt |

FIG. 9

| Sequence ID | Sequence |
|---|---|
| SEQ ID NO:34 | rUrUrCrArUrArArCrUrCrUrUrArCrCrUrUrUrArUrGrCrCrUrCrUrG |
| SEQ ID NO:35 | rArUrUrCrUrGrArCrArCrCrArCrUrGrArCrUrCrUrGrArUrCrCrArG |
| SEQ ID NO:36 | rArUrUrArCrCrArGrUrUrArUrArGrGrArArCrArArUrUrCrUrCrUrU |

FIG. 10

| Sequence ID | Sequence |
|---|---|
| SEQ ID NO:37 | rGrArGrGrCrArCrUrGrArCrCrArCrArGrCrCrArGrArGrCAG |
| SEQ ID NO:38 | rCrArGrUrCrUrCrArUrGrCrCrUrArUrGrGrArArGrGrGrAAT |
| SEQ ID NO:39 | rCrCrArGrUrArCrArUrGrCrUrUrCrCrArGrCrArGrCrUrUGG |
| SEQ ID NO:40 | rGrCrArArArUrUrCrCrArCrCrUrArUrGrArGrArCrCrGrUCT |

FIG. 11

| Sequence ID | Sequence |
|---|---|
| SEQ ID NO:41 | ACCTCTGGAGCTCTCTGGAAC |
| SEQ ID NO:42 | TATGATGGAAAGGTGCGCATCCTTA |

FIG. 12

| Sequence ID | Sequence |
|---|---|
| SEQ ID NO:43 | CTTCCCTGGATTGGCAGCCAGACTG |
| SEQ ID NO:44 | ATATGCAGAAATGGTCCCTGTCCTT |

FIG. 13

| Sequence ID | Sequence |
|---|---|
| SEQ ID NO:45 | rGrArGrGrCrArUrArArArGrGrUrArArGrArGrUrUrArUrGAA |
| SEQ ID NO:46 | rGrGrArUrCrArGrArGrUrCrArGrUrGrGrUrGrUrCrArGrAAT |
| SEQ ID NO:47 | rGrArGrArArUrUrGrUrUrCrCrUrArUrArArCrUrGrGrUrAAT |

SEQUENCE LISTING

```
<160> NUMBER OF SEQ ID NOS: 47

<210> SEQ ID NO 1
<211> LENGTH: 2845
<212> TYPE: DNA
<213> ORGANISM: homo sapiens

<400> SEQUENCE: 1

aggggacgca gcgaaaccgg ggcccgcgcc aggccagccg ggacggacgc cgatgcccgg      60

ggctgcgacg gctgcagagc gagctgccct cggaggccgg cgtggggaag atggcccagt     120
```

-continued

```
ccaccgccac ctcccctgat gggggcacca cgtttgagca cctctggagc tctctggaac    180
cagacagcac ctacttcgac cttccccagt caagccgggg gaataatgag gtggtgggcg    240
gaacggattc cagcatggac gtcttccacc tggagggcat gactacatct gtcatggccc    300
agttcaatct gctgagcagc accatggacc agatgagcag ccgcgcggcc tcggccagcc    360
cctacacccc agagcacgcc gccagcgtgc ccacccactc gccctacgca caacccagct    420
ccaccttcga caccatgtcg ccggcgcctg tcatcccctc caacaccgac taccccggac    480
cccaccactt tgaggtcact ttccagcagt ccagcacggc caagtcagcc acctggacgt    540
actccccgct cttgaagaaa ctctactgcc agatcgccaa gacatgcccc atccagatca    600
aggtgtccac ccgcccaccc ccaggcaccg ccatccgggc catgcctgtt tacaagaaag    660
cggagcacgt gaccgacgtc gtgaaacgct gccccaacca cgagctcggg agggacttca    720
acgaaggaca gtctgctcca gccagccacc tcatccgcgt ggaaggcaat aatctctcgc    780
agtatgtgga tgaccctgtc accggcaggc agagcgtcgt ggtgccctat gagccaccac    840
aggtggggac ggaattcacc accatcctgt acaacttcat gtgtaacagc agctgtgtag    900
ggggcatgaa ccggcggccc atcctcatca tcatcaccct ggagatgcgg gatgggcagg    960
tgctgggccg ccggtccttt gagggccgca tctgcgcctg tcctggccgc gaccgaaaag   1020
ctgatgagga ccactaccgg gagcagcagg ccctgaacga gagctccgcc aagaacgggg   1080
ccgccagcaa gcgtgccttc aagcagagcc cccctgccgt ccccgccctt ggtgccggtg   1140
tgaagaagcg gcggcatgga gacgaggaca cgtactacct tcaggtgcga ggccgggaga   1200
actttgagat cctgatgaag ctgaaagaga gcctggagct gatggagttg gtgccgcagc   1260
cactggtgga ctcctatcgg cagcagcagc agctcctaca gaggccgagt cacctacagc   1320
ccccgtccta cgggccggtc ctctcgccca tgaacaaggt gcacgggggc atgaacaagc   1380
tgccctccgt caaccagctg gtgggccagc ctcccccgca cagttcggca gctacaccca   1440
acctggggcc cgtgggcccc gggatgctca acaaccatgg ccacgcagtg ccagccaacg   1500
gcgagatgag cagcagccac agcgcccagt ccatggtctc ggggtcccac tgcactccgc   1560
caccccccta ccacgccgac cccagcctcg tcagtttttt aacaggattg ggtgtccaa   1620
actgcatcga gtatttcacc tcccaagggt tacagagcat ttaccacctg cagaacctga   1680
ccattgagga cctgggggcc ctgaagatcc ccgagcagta ccgcatgacc atctggcggg   1740
gcctgcagga cctgaagcag ggccacgact acagcaccgc gcagcagctg ctccgctcta   1800
gcaacgcggc caccatctcc atcggcggct caggggaact gcagcgccag cgggtcatgg   1860
aggccgtgca cttccgcgtg cgccacacca tcaccatccc caaccgcggc ggcccaggcg   1920
gcggccctga cgagtgggcg gacttcggct tcgacctgcc cgactgcaag gcccgcaagc   1980
agcccatcaa ggaggagttc acggaggccg agatccactg agggcctcgc ctggctgcag   2040
cctgcgccac cgcccagaga cccaagctgc ctcccctctc cttcctgtgt gtccaaaact   2100
gcctcaggag gcaggacctt cgggctgtgc ccggggaaag gcaaggtccg gcccatcccc   2160
aggcacctca caggccccag gaaaggccca gccaccgaag ccgcctgtgg acagcctgag   2220
tcacctgcag aaccttctgg agctgcccta gtgctgggct tgtggggcgg gggctggccc   2280
actctcagcc ctgccactgc cccggcgtgc tccatggcag gcgtgggtgg ggaccgcagc   2340
gtcggctccg acttccaggc ttcatcctag agactgtcat ctcccaacca ggcgaggtcc   2400
ttccaaagga aaggatcctc tttgctgatg gactgccaaa aagtattttg cgacatcttt   2460
tggttctgga tagtagtgag cagccaagtg actgtgtctg aaacaccagt gtattttcag   2520
```

```
ggaatgtccc taactgcgtc ttgcccgcgc cgggggctgg ggactctctc tgctggactt   2580

gggactggcc tctgccccca gcacgctgta ttctgcagga ccgcctcctt cctgccccta   2640

acaacaacca cagtgttgct gaaattggag aaaactgggg agggcgcaac ccccccccagg   2700

cgcggggaag catgtggtac cgcctcagcc agtgcccctc agcctggcca cagtcgcctc   2760

tcctcgggga cccctcagca gaaagggaca gcctgtcctt agaggactgg aaattgtcaa   2820

tatttgataa aatgataccc ttttc                                          2845


<210> SEQ ID NO 2
<211> LENGTH: 81339
<212> TYPE: DNA
<213> ORGANISM: homo sapiens

<400> SEQUENCE: 2

aggggacgca gcgaaaccgg ggcccgcgcc aggccagccg ggacggacgc cgatgcccgg     60

ggctgcgacg gctgcaggta ggaggcccag ggccgggggg cggttcggct ccgcgggcgg    120

gggctggagc gcagcgctgg gcaggcacct gggctcgcag ctccgaagct gggaggtgag    180

gggagagcga tcggggacga gctgggacaa ggcgacacag gggctccctc ggagttggat    240

cggcccctgg gacttggcgc tcgcgagagg ctggagcggc cagagtctag cctgcgagga    300

gacgcgggtc ctgccctcag cgccggccgc ctttggcgcc aaagacagcc ccgcaggggt    360

tccgggaggg ccctcctcct gctgtcccct ctccaccccg ggctccgagg gccgttggga    420

gggtaacccc gggaagaggc cggggtgcgg ggcgcgggtg caggtggaaa tcgccagcaa    480

gctcctcccc gcccgcgcgc tccctccgac ctgcagggct gtgccaatcc cgaggcctca    540

gcttccctga ggagccaggg ccaggccccc ctctggacag ggagaaggat ctgggcgggg    600

gccttgaccc atggagttgg ttactaagcg gtttcgatgg tttcccgagg gacagctccc    660

tgtggctctg agtttgtctg tcgagggctc ctggcctgtc tccggagcgg tcccaggtag    720

agaaagcccg tgaagaaatg gcccgggccg gcctggaggg agacacctca cgccccctta    780

gctcctgggc cgcctcctcc tgcagcccct gcctttcccg gggcttggac ttggggagcg    840

atgattacct ttgctcagct tgtattttgg cctggacgct aggagataag cccatgtagt    900

atgcacacgt ctgctacata aacaggggac agatagacga tcttcaacca gcaagggtgc    960

agggaaaagc aatgcacccc aaacttctga ccagaggtca tttgcttcca aagatgctgc   1020

catctgttta ttcactgtct ggacatttgg aaatggctca ggctcattaa cacaatgctt   1080

tggtttttgt tgttttgttt tttgttgctg tcattgctgt ttatttgttc agccttagct   1140

ctgggggagg agtaaacaaa gcgcgtggcc tctggcactt actgagcgct gagccacccc   1200

tctttggatt tattcgggga aagattaaaa agcatttcat taagaacagg acacggtgtt   1260

tgaaatgttg ccatatatga atgtatgcat tacgtatgta gtttttaaaa taagataaaa   1320

agttggctgg gcacggtagc tcacgcctgt catccctcac agcctttggg aggccaaggt   1380

gggtggatca cctgaggtca ggagttcgag accagcctgg ccatcatggt gaaacccagt   1440

ctctacttga aatacaaaaa ttagctgggc atggtggcag gcacctgtac tcccagctac   1500

tcgggaggct gaggcacaag aattgcttga acctgggatg gagaggttgc agcgagctga   1560

tatcatgcca ctgcactcca gcctgggcaa cagagcaaga ctctgtctca aaaaataaga   1620

tgaaataaga taaaagttgg tgtcagaggc tgcagtgtgg cagctgccta ttgtcaatca   1680

gaggtagcct ggggtgaacg gaaggcggac ctgagcgggg cttgtctatg cgcggcggcc   1740
```

-continued accagagaat ggctcgggat gtgagccctg ccttgcagtc cttctcgtga aagctacagc 1800
gaacagtagc tgtctccaaa tcccgaaggc cagtcgcatg gagaagctgg tctggcacag 1860
tggttaatgg ggtagtatgg aagtcagaat gctggggttc aaatctcctc ttccccattt 1920
actccagcaa gtcacttaac cacttggagc ctcaggttac ccatctgcag agtcgggtaa 1980
tagtagttcc tgcctcagag gcttggagaa cagtcagtga ggtgccgtcc gaagggcttg 2040
ggagagtgcc tggcacccac tcagtgtcct cacacatgat ggcttcgggt cccaggtgct 2100
gttccagagc tgggagagcc aggagccctg gggagagacc cggctcctta gtatctggta 2160
ggtatctcca gggcaggagg gatggcagtg aggcaggcat ctgcccaagg cgtgggtgga 2220
agctgatggc atctgtcaga agtatgcact ggggcaagga tgcctggttt agtatttatt 2280
tatagggcat gccccaccca ggtccaagaa tggattgata acactgagca cgtgtgaaag 2340
gcacggctaa agtggagaga agagaagagg ctgagggccg agagaggagc cgcacaccca 2400
ctccagaacc cggacgaggc cctgcccttg cccagcggcg gtattaaccc tgagattccg 2460
agcacaccaa agtgacatcg cgtacacggt gaaccctgtg tttgcaaaaa gtcagaaaaa 2520
gtcttcaaaa catcctttaa ggccaggcgc cgtggcccac gcctgtaatc tcagcccttt 2580
gggaggccga ggtgggtgga tcacttgaga tcaggagttc aagaccagcc tgggcaaaat 2640
ggtgaaatct tgtccccacc aaaaatacaa aaattagccg gggtggtgt ctggtgcctg 2700
tagtctcagc tactcaggag gctgaggcag gagaatcgct tgaacttggg aggcagaggt 2760
tgcagtgagc cgagatcacc ccactgcact ccagcccggg caacagagcg agactctgtc 2820
tcaaaaaaac acgcaaaaaa tacttttggt gtgtgtttca tgtaacgagc tgccattttg 2880
cggcttgcct ttgttttcca gtgtggggag ggctaaggca acctttaag atatctgtat 2940
gttatttcct cgtgattttg ctttaaaagc aaaaaagaaa aaagctgaga tgagttacta 3000
aatgacaata acgcctactt ttcttttgaa ttcccgtgtt atttgtatct gaatgtggtg 3060
aaagttttct aaatgtaatg ttttatcacc agtaagtagg ctgagtgatc acttactcct 3120
accagtattt aatacttcca tgttctgccc agattccttt aacaaataca caaaacacac 3180
ttgtagctgg caacatccac tcgtgtataa tgaaaacaca caatggcttt cttagaagtt 3240
tgccttctta agtgggttac acaggatgcc tcgaaaatcc ttctctgtgg gtcgtgcaga 3300
aggtatttta ttctaaaaat tccctctact cagccgggcg cagtggctca cgcctgtaat 3360
cccagcattt tgggaggctg aggcgggtgg atcacgaggt caggagatca agaccatcct 3420
ggctaacacg gtgaaacccc gtctctacta aaaatacaaa aaattagtcg ggcgtggtgc 3480
gggcacctgt agtcccagct acccaggagg ctgaggcagg agaatggcgt gaacccggaa 3540
ggcggagctt gcagtgagct gagatcacgc actacactcc agcctgggcg acagagcgag 3600
actacgtctc aaaaaaaaaa aaaaaaaatc cctctgctca ttggcatttg agtgtaagac 3660
agcttatacc aaagtgggct cagacagaca tatgcacatg tttacagact ttctgcctgc 3720
cccctggcag tccactctgt gctcagtatt tctttgcagg ctaaacactc gctcatccaa 3780
agtgctttct tttcctggac aagttgcaca tcacagaccc aaagaagaaa aagataatcc 3840
agcccaactc ttgtttttta atgtttcctg taataactca catttagccc atggtggctg 3900
tgagctggta cttggctaaa aagtttacat tttttccct gtaatcccca caatagcccg 3960
ttgaagtaga tactataatt atgcccattt acagatgagg aaactgaggc ttcaactggc 4020
tattctactt gcacagggtc acacagctgc aaagtacggg agtggggact ccagctatga 4080
ccacgaagct gggactgggg ctgccaaacc atcctttgcc tggtctgcc gttggctcag 4140 acacggcccc cagacaccta ggaccgtgga acattcaggc cggaagggcc cttccagaac 4200
atctaagcca ggggtagaga gtccagggtg ctgtgagcct ggatggggaa aaatggcacc 4260
ttgtattaac ctcaaagcaa atttcagcat ttcctctagt tttgaatgta ggcagcaaac 4320
tacagtcata gcagtacctg tgacctcacc agtgggaacc actgatattt tcatggtgtc 4380
cggtaatagc tgcagcatct taaaaagtgg tttgtgcttg tcgctccgtt gcaattatgg 4440
cggtgattag atctgctctc aggcttacga cttaatgtat gaacaaagaa gcgcacatat 4500
gatcacctcc cagttttgct ttttaaatat tagggtcact ttgtaagttt tctcaggctg 4560
ctgttacaaa tgaccacaaa ttaagtggct ggaaacaata gagagtgttg tctcacggtt 4620
gtggaggcag gaatctgaag ccaggtgtgg gcagggtcgg gttccctcgg aggctctgag 4680
agggggctcg cctcctgtct ccctcctagg atctgggggc tgccggccat cctgtggttc 4740
ccaggcatgc agatgcacca cccagtctct gccaccatct tgccatggcc ttctcctctg 4800
tgtccctgtg tgtctctcct tttttgtccc ttagatggac acctgtcctt ggatttcggg 4860
cccacctgga aaatccagaa tgatcttatc ttgagaccct tacctaagtg gcatctgcaa 4920
agaccctgat tccaaataac atcccattct gaggctcgtt cccagaggct gcatccaacc 4980
cactagagtg gctatgtttc agtaactcgt gatcctgtgt attttgcttc atgtatttaa 5040
aacattctcc cggacaaggc gtctgagatt ccccaggctg ccagaggggc catggcgcaa 5100
acggggaaga aacctggtct aagccacgcc cctcttttca ggacgaggat cttggaaccc 5160
ggacactgaa ggtcggggtt gggcacagcc ggggatgggc agccccccctc tcccccagca 5220
cctcccgcct ggcgcctcct ccacagcccc tgcatcctgg aaaacagact gttccacaca 5280
ctccagcagc tcctctacct ggggactgct tgggccgcat agcccccagt tagggacaga 5340
aaccagaggt attgaacaag aagccccacc gggagaggcg agacccgggc cccagccctg 5400
gacctggccg tgggtgctac agaaggtcgg gggacatcgg tctgcgcgga agggtctgga 5460
gaggcacctc tcagggagtt ggacagagag gagacgccgt cccagtggtg gcctccagtg 5520
aggcctggag agaccaggtg gcaggaaggg ccctgctggg gccagagcaa gggcacggaa 5580
ggcaggtctc atggagcagg gaccgtggag gggacatggg ggacacatta gggatggaca 5640
gtggccggaa gattccgtgg gccttggaga ttaaatcggg ttccccaaag agcaagctgt 5700
ggagagggga agggaaagtt gcctccctct tccctacggg gttcttgtca ataaacgatt 5760
gacaaaagac agactcacaa gagacaacag ttttaaggct gtgcccccgc ccggaagtgc 5820
cataaaaaca ggagactcag cagtaaccag atgggagcgg tgcagatgtc cgtcctctgt 5880
gacagaaagg aaagggggcc tgggcttctg gggagcggta gagacaaatg aggagagggt 5940
gagggaggaa acgtctgggc ataaaggctg cctcgtggtg cagctatcag tctcatggtg 6000
agaaaatgcg tcttggcgcg cggctctctt cctggcacac agaccattac taatgaaaat 6060
gtcctttata gatgtcaatt ttctttagaa aagagagttt tttactttat tttagggagc 6120
tgaagagctt tttttctgtt ggctggttct cagttgcttt tagctcaaag taatcaacat 6180
gtcaacatgg catattttgg ggtgacgtat tctggtctcc tacagtcata ttttggggtg 6240
acgtattctg gtctcctaca gtcatatttt ggggtgacgt attctagtct cctacagtca 6300
tatttagggg tggcgtattc tggtctccta cagtcatatt ttggggtggc gtattctggt 6360
ctcctacagt catattttgg ggtggcgtat tctggtctcc tacagtcata ttttggggtg 6420
acgtattctg gtctcctata gtcatattta ggggtggcgt attctggtct cctacagtca 6480

-continued

```
tactttgggg tgatgtgtcc tgagccccat tgtttcctag tctgaaactt ccccaagaag   6540
ctccacggta cagaaactgg gtgggtgtgt tgtcccataa tgctttgaag aggcatttct   6600
atggaaacaa aagaaaaaaa aaaaaagcta atcattggag ctgactaaaa accagtttct   6660
gagcctgggg gccgtggcgg ggcaggtttg tagatgttgg gctccgagca tcttctgcgg   6720
tttggtctct ggcgatgtct gggcggccca cgcagcaaca ggcgtgaggg tccctcgcac   6780
ctgggcttcg tggtaatctc gctgatgagt atttcaagtc gtccagcctc agtttgcagg   6840
atttctgggc aaagggcagt tttgttcttc gtgattccaa taagaacggt gggagaaaat   6900
tgaaagtgtt agtttgggag ttgcagccag atactggagg aaactagaaa catcaggaac   6960
ccgtccagtt tgtagacatc aatagataac aaaaccccaa agacgttaaa caggacaaga   7020
atctaatatg gggcgcacaa tatggctttc tactgaaata tatgttcttt ctacatcacc   7080
cctctttcta ctaaaaataa tctcagtaag attattatta ttattattat ttttgagaca   7140
gagttccact ccgtcgctca aggctagagt gtagtggcat catctcgact cactgcaaac   7200
tctgcctccc gggttcaagt gattctcctg cctcagcctc ctggagttac aggcatgcac   7260
caccactaat ttttgtatta ttattacttt tttttagtag agacagggtt ttgccatgtt   7320
ggccaggctg gtcttgaact cctgacctca caggatccac ccacttcggc ctcccaaagt   7380
gctaggatta cagacgtgag ccactgtgcc cagcctagtc agattaactt gtttgtaaag   7440
taagtctagc ctcattaaaa ttggcctgat tatttgcaca agtgcagcaa gaatagtaag   7500
tggccagcta ggctttcttt aggtcagctt tgctggaact tttaataaat ctcaggttag   7560
gctttcaaaa gcctcttgag gctaagaagt caagccaagg acttgatatc agacttcacc   7620
tgcaatacct atagatttgg gtggattcct ctttctcaag gttcccaacg tattcttgag   7680
aattactgcc aaaaaatcac agtctttcct caacccgtga ggctgcagaa gccctttaat   7740
ccaggtacaa gggcaatttt gttttcctcc aacgggtttc attggctcca taaagtcaac   7800
cttagttcct taaagctact cacatctgat tttatgcaca tcactctcaa atatgatatt   7860
ccggtcaaac acttggtgag ctaaccaaca tttccagttg tttcctatta caaggcagca   7920
gattcatctt gaacttaagc aaataactct atggccgtaa aaataaaaat gctaatagtt   7980
tctaaattct ggagagatca ggtagggaga aaagtcatca tttcaatttt gcttataaaa   8040
gtgtaatgta ccagaatgct gtaagttata aatagtttct tcatttacat tctggaaatt   8100
cttgccatcc agtggtgtga tcttaatgta tcagaaacct gtactggtca aagtcttccc   8160
catgaaatct tctcgaagac acaacatttt agaattatag ttgcttgcaa aagctttcgg   8220
gaaagcatca gagccaaaca gttaactgtg tatgacagaa aggcttaaaa tggccttggc   8280
taaagatgtg atgacatcat tacaatgtaa ctgatgagga agtttggtta ttcctgtggt   8340
gtatactttc acataataac tagaattaca actaatatag aatgtatcag atttctaaga   8400
atttcatata atttctggaa ctcttatatg aatatatatc catgcaaata taactcaccc   8460
agagaaggtt aatcatcact tcatatttta cagtgcttcc atgcaaattt agttgatcaa   8520
ataagcccaa tttatttaat atctttttat tttatctaaa acaattttcc ctttaacatt   8580
ggcaaaataa tctatgtttt tataaggaga gaaaataaat ccttttgaga tattccaggg   8640
gccaatctag gaaatcccaa acgttaattc agggtcaaaa agacttaatt tagagtgtgt   8700
gattttggaa agttgtcaaa atgtcaaaag gttgaaagca cttgattaaa tagaatccca   8760
gatcattatg aaataatact taattctcat ttaatcaaag taacaatgaa atattcaaag   8820
agaaatgcag aaagttagat agtttaaaat actcttagat ctggccaggc atggtgggtc   8880
```

-continued

```
atgcctgtaa ttccagcact ttgagaggct gacatgagcg gatcactaga gcccaggagt   8940
tcgagaccag cctgggcaac atggcaaaac cccgtctcta ccaaaaatac aaaaattagc   9000
caggcatggt ggcacatgcc tgtaatctca gctactcggg aagctgagat aggaggatcc   9060
cttgaaccca gggagattca tgccacagtg agctgagatc gcaccactgt actccagcct   9120
gagcaacaaa ctgtatatac acacacatgt attttgtgta tatatatata tatataatat   9180
gtattacata tatacataca ctatatataa tatgtattat atatatacat acactatata   9240
taatatatgt attatatata tacacgctat atatataata tatgtattat atatatacac   9300
acaatatata tttttattt tattttttat tttttatttt ttttaattag ctgggtgtgg   9360
tggtgcccac ctgtctccca gctactcggg aggctgaggt ggcaggatcc cttgaagccc   9420
aggagttgag gctgcgatga actatgatgg tgccactgca ctctagcctg ggtgacagag   9480
tgagaccctg tctcaaaaaa aaaaagaact agttcacacc catgtttcct cctgctgccc   9540
caaattgcca ctctcctgga gcagcccctg aaggtggaga ccaggcacct gctggagcag   9600
gaactcttcc ttcaccggct tctgttgggg ccccaggatc ctgcagctgt ggcatccaca   9660
gggagtaagg ccagccacgg aggtcctttc atgtcaccaa gctgcagggg aggaaaagtg   9720
acatcagaca gatcaacagg agaaaaccca ttttaatgat atgtccacga atgggagtcc   9780
cacacggaga tgaaactggg ggaaggggcc agatggcgga ggcgtctgcg tcatcctcag   9840
ctgcaggaag atacaggact gtggggctgc tgcaggctga accagctata gcaggggagt   9900
tgactggtga atgaaggtgg tttcgtcacg cggacatgcg tctctcaggc gatcagagtt   9960
acctggagcc gctctcctcc cggcatagag acctttacga atggaaatgt ctttcatttc  10020
tctcccagac aggcagctgg gcagagccac tcctgtgtct gcagttactc gaaataatgg  10080
atatacccaa ggcatgtttg gggtggcaca ttctgccccc tcaagccatg ttttggggtg  10140
gggtggcgtg tcctgagccc caacccaggt gtcagggcta tggaggggac attgcaaggg  10200
ggcctagagg ggcctctatg ggccttggag atggaatcag ctccccacca ggccccagga  10260
cagacctggc tggggagcgc agggaggggt ccccagtgtg aggacagcat ggggctgcct  10320
cttccagcag ctccgagcgc tctcagagaa aaacgaaatt ctcttttata agagaaactt  10380
gtctctggtc ccatgtgttg ccctttgggc actggcatga gtaatctgag ggcggcgctt  10440
tcctcactgc agtggcatca tacagatgag ggctttgctg atcattatct ggaaacagtg  10500
atcactgtcc cattcacaga tggggaggct gaagcctggg agatcaattc atgccaccaa  10560
gatcagctgc aggccgggcc acccatgcct gaggggagaa ggggcctctc ttcttcacga  10620
ggctggtggc tgcggcacct acaaagacag gttaacaaga ggaccctctg cctatcacga  10680
gcctggtggc tgccgtacca gtaatgaaag acaagttaac aagagggccg tgcaggctta  10740
tttacgagaa gttccatgtg acacaggagc cttgagaatg gaacacccat cgaaccgggg  10800
aactctgcat attttcctcc tgggtttgtg gggtgtggac agcacggagc gtgatgaaag  10860
gatacaggcg gctgggcgtg gtggctcacg cctgtaatcc cagcactttg ggaggctgag  10920
tcgggcggat cactaggtca ggagatcgag actatactgg ctcacacggt gaaaccccat  10980
ctctactaaa aaatacaaaa aattagccag gcgtggtggc gggcgcctgt agtcccagct  11040
actcgggagg ctgaggcagg agaatggcgt gaaccaggaa ggtggagctt gcagtgagcc  11100
aagatcgtgc aacaatgcga gactccatct caaaaaaaaa aaaaaagaaa gaaagaaagg  11160
atacagacat cctgaaccgg gggctggggc caggtctgaa ggctctgatc ttcctttctt  11220
```

-continued

```
ctgggtctag ggcacatgag ggtctgtgac ctaattcaga ggaaggccag agaactcttt  11280
tatggcctgc ctcagggtga cagggagcag gagagagcat acctgctttc cctggcttct  11340
cagatgccac cgtgccaggt tttggggtag tggtatgtct tgagcccaat cagtaccctg  11400
ggggtcgtgg ccggcccccc tccctccatg ccacaggctc tctggagagg ccactgctgt  11460
atccccactg tgagctcgat ctgagctgcc tatgggacca cacctgagaa cccccaaggg  11520
tggcactggc agacttgagg tgcccaagtg aggctggtgc agcccctctg ccctgccagt  11580
ctgggcacgg gcccctgggc atcgcgactc ctaccttcct accagcccag atgcagggcc  11640
tgagccggca gggcttccac ccagcccagg gtgtgtcccc ctaccagagg cgctgcattg  11700
gataggaagg acccacctgt ttccctgccc agtaccagct ggcaggcccc ccgtggctca  11760
gggtgcctgt gaggaggggt gggggctcta attgctcacc tgctgctctg aggtgtcagg  11820
cagggttggg ggtggcacct ggggaaggct gggctgaggg ggcaggctgc ccctcctgca  11880
ggagaggtgc agtatttcac tgggtccttt ggaaagggca gggaagctcc tgctcgcccg  11940
tactgcacca tttcctgtga tcttagcaat gacttcctgg ctccattttc tccaccagtc  12000
cgaatacatg agccagaccc gcagctttct cttccacagc ctcctggcct ccgggtccac  12060
ctgggtggtg cccacccgcc agactggggc ctggtggttg taggggacgg ggagcagcct  12120
tgcttcagtg tgggtcattc ctgactgtga gatggttggg gggcaggggt tgtagagtct  12180
gtgggaggcc tcggctgggc ctcagagagg ggtatctctt ctgcagaaaa cccagccacc  12240
cttaccagat gcggtcaggc tacaaaggga agatgtgctc cctctttaga ggcaggtgat  12300
tcctgtgaat ccgatgaccg agataaggtg cacgattcag tgggcaaggc aactcaccat  12360
cctctcttta tggtcctcgc aatttgcacc atgcacaatg cagggtgaag tcagcccccca  12420
aattacagag gaaagactct gcggtctttg tcagttaaac aggagatgca aactccaagc  12480
tagttaatga gctgtgatcg gccacgctca cgattcagtg caggtctctc cttcctgcta  12540
tcacagtctt tgccggctgc atcatgacta ccaaccagtc ccctcataat tacaagagtc  12600
tcctgtcatg ttttcttctg gagcgaggca tgctccaact tgcttctggg ttcttaattt  12660
ttgatcaggg acggctcctt gactaattat ttggcagtaa tgagggagga cagatcgagt  12720
tgtgaaagtc ccccccaagc ttttagaagg aagctgcaaa ttaaaaaatg aggtattggt  12780
aaacaggatg ctaattggat taatatgaaa atgatgaatt ctgataaaaa tagcaaaata  12840
caccgttgta agattgaggc cagtataact ccaagaattc attgtctaat gttcagctgg  12900
tcagtctggt ctttgaaagt attagaataa cagaaagagt ctactcttga cgatgaagta  12960
tacggttagt aatttatgca aaacagaact ttaaaaccgg aaggacttga tatgagtggg  13020
gtgcatggaa atcattcgta ttttgaagtt tcataactct gacccctagg tcctttggtt  13080
tgtctctctt ttcttttttt ttttttttta gacaatttct ctctctgtca cccaggctgg  13140
agtgcagtgg catgatcttg gctcactgaa acctccacct cccaggttca agcgattctc  13200
ctgcctcagc ctcctgagtg gctgggatta caggcatgaa ccaccgtgcc cggccttttt  13260
tttttttttt tttttaaga gacagaatca ccaggcaagg tggctcacac ctgtaatccc  13320
agcactttgg gaggccaagg caggtggatc accaggtcag gagtttgaga ccaacctggc  13380
caacatacag tgaaacccca tctctactaa aaatacaaaa attagctggg tatagtaatt  13440
ccagctactt gggaggctga ggcaggagaa tcgcttttga agccaggagg cggagtttgt  13500
ggtgagctga gatcgcacca ttgtactcca gcctgggcaa caagagcaaa actctgtctc  13560
aaaaaaaaaa aaaaaaaaaa aaaaaaagag agagagagag agagaatctc actctgcagc  13620
```

ctaggctggt gtgcagtggt gcagtcacag ctgaccacag cctccaactg ctgggctcag 13680
gccatcctct tgcctgtgtc ctgagtagct gtgaccatag acacacacca ccacatccag 13740
ttaatttagt tttgttgttt cttgctttta gagacagggt cttgctatgt atcccacact 13800
aatgaatgta aaatcttaaa atggtgcctg gtgcagagta agctgtgtgt tggtggggtg 13860
taattatggg tcatattgac agtttcactt ctgcggcatg ccctcaggaa ctcactgatg 13920
cacacagagg gacctgctgg caaatactga agagctgtgg ggagaaagga aggggtctga 13980
cagtgaaggt gggtgcgtgg gcggggggct tttaatggtc cctctgctgg ctccctcccc 14040
accacctcct gcccacctcc ctggccttgg ctgcaggcta gggtgccctt tgacctcaaa 14100
gaggcctgtc ctgtgtgtct cactgagcag gaacaaaccg tcccagaagc ccttcagctc 14160
ggaagtgagt aagcattggc ggtggggatg gtgctctgag cagacgcgac tcagtgccat 14220
gcgggcgtct ctcccagggc ggctttcaga ctgaccccca aacagagggc tcagaaaaga 14280
tgtttttcaa tgagggacat ttatggttgg caaaaaaaag tggctcccca aaggtcttca 14340
cgtcccaatc cccagaaccc gtgtctatgt tatttcccat ggcaaagggg accgtgattc 14400
agctattttg agatggggag gccatctggc aggatccagg tgggtccagt gtcatcaggg 14460
ggccccacaa gaggggtgag agagggagct gatgatggag gcagaggttg gagggatgca 14520
tttcagagat ggaggaaagt gtcacatgcc aaggaatatg cctgcggaag caggagagga 14580
cggggaggta gggattgtcc cagggcctcc agaaccaaga gaagacaggg gagtagggat 14640
tctcccaggg ccccccaaag acaggaagag ggggaaatgt attctcccgg ggtctccaga 14700
agcagccagc cctgcccgca gtttggcttt agctccctgg tacccatctc ggactctgac 14760
ctacagaact gtaagagagt aaatttatct cattctgtgc tgctcattgt gtggtcattg 14820
gttacggcag ccacagaaaa cagacagtgc gcacatccgc atggtcccct ctccagctct 14880
tgcctgatag gcataaacga gggcagctgg gcgcggtggc tcacgcttgc aatcccagca 14940
ctttgggagg ccgaggcggg tggatcatga ggtcagaaga ttgaaactat cctggcccac 15000
atggtgaaac cccgtttcta ctaaaaatac aaaaaattag ccaggcgtgg tggcacgtgc 15060
ctgtagtccc agctattcag gaggctgagg catgagaatc gcttgaacct gggaggcaaa 15120
ggttgcagtg agccaagatg gagccactgc actccagcct gggcgacaga gagagattct 15180
gtctcaaaaa aaaaaaaaaa gaaagaaaaa aagtaaaaaa gaaaaaaagg aaataaacaa 15240
gggcttgccc tgtagttcac atctggacca cccagcttaa aatagggcag gggagttcag 15300
gaatagcttt gcaacccttg tgttacggtg cacaggtgtg caaaaattct ccttgaactc 15360
ccccttcagt gtccccccag ggctcatggc cactgtcact ctgtgctagt tgctcttcag 15420
accagggaac agacttggcc atggctatgg ccagggtcca gctgctattg ctcctcctgt 15480
cacccaccca ccttttgtct ccaacaagga tgttgagagg agccaggcac cagcctccct 15540
gggttcaggt ctttcctctc ccctcacttt cctatgaact aggggtgggg gaggaggagt 15600
gcctgccagg aggtcactgc agccaaggaa cccaaattgg tgtgcttgag aatgacccat 15660
ggatacactt tccaaagagt cacccggctg cgatgagggg ccatctcccc tcctggagcc 15720
aacagccatg agtagctgtc acacacatcc gtgcagcacc tagacacaca tccgtgctgt 15780
ccactccgtg ctgctgcaat tgtgggggag gaaggtggca cagtggcagc gacacacact 15840
tccctctcca aaattggggc ggggctcctc aaaatcctct gaccagcatt aaagattcag 15900
aatttgatat tatggctgca tataatgttg aattatctga acttgctgca cgtgtgtgtg 15960

-continued

```
tgtgtgtgtg tgtgtgtgtg tgtattgttg gtaggaccaa aacggttaat tatcagcaat  16020
ttcatggttt gacctaatat tttaaaagag aggttcttac ctgctggaag catgtactgg  16080
tgtattacgg atgagacggt ctcataggtg gaatttgctg tgaaatgccc caggaaacaa  16140
aaagccagag gtcagagtga tgagagctgg ggacgggtgg atgggttcct gggccgttcc  16200
ctgtagtgct gagtgtgctt ggaagtgtcc acaatgagga gtagaaacga gtacaaagct  16260
gggtggagac agccctgtcc tggctgccct gagctcggcc ctgtcagtcg ccttgaggag  16320
ggttgggggg agcagggatg cagggtggcg cgtgcatgcc aggtggcagg cggcaggtgc  16380
tggctccagg cccgtctcca gccccagggc tccaggccat gctccgcccc cagctgccct  16440
gcagctccag gccggccacg ctgccgccta gtttcgcaac tccaatgtca tcacctaggt  16500
gacagggacg ctgctgccac cgcccgcctg cgggagccag gagccagccg agggccactt  16560
ccacctggcc ccaccgaccc tccggggccc aggcttagcc aaggtaggct tgggcttggc  16620
tcgccctcct ctcggcctga gtcgggggga gtctccttgc caccgtgggt gcagtggctc  16680
cgggggccca ccctggggtg cagagagccc ctctacggcc tcccaggagg cggcttggaa  16740
atgcagtact gttcaggcca gggtggggag gccttgccca cagttctcct gatgggacaa  16800
gccacagctc tggggagcca tctgccccaa gtggcacatc agggctcctc gtgtgaccct  16860
aggatcgggg gcagaagtgg ctctggtacc gccacctcca cccc ttggac ccaccaggag  16920
ctctttccac ttcctgccaa ggaggcgcag agtgactgcc ccagcctggc acgtccgggg  16980
gcttcccggc tgggggccgc catcctcagc ctcacacagc tgatccagaa cctcccagtt  17040
ctccccagcc ccctcactct tttgtggccc cggagcctct cccggcaaca gcaagccatg  17100
ccccggcctc cccggcactc acgcagctac tcccaagcct gaccatgacg tggacggcag  17160
gaaggggctg ggcatgtcct gttccttctg cctgggtcct gcttccaggg ctggactccc  17220
aggctgggga atcctcaggg acccatcaaa ctgggggaca ggggaggggc ttgtggggat  17280
ttgctgtgag gagggcagag tgtgtacgtg gcagtgcctg cggacacatg tgtgcgcata  17340
tgtgaatagg tgtgtccatg tgcatgtatg tgcaagtgtg ttgctagagg tgagagggtg  17400
ggtagggaaa ctgagtgacc agctcctccc tgaagccttg ggggaatgtc cgaggggcca  17460
gggcctctgg atcctgttcc cttggctctt tgcaaagtct ccagcctggc ctcctggatg  17520
ggcatgtggc tcgggggcg agaccatggg ctcttcctgg cttgctgtgt cgctctgggt  17580
gcgttttaca ccactctgag gatctctctg ctcatcccta aggcagggat gatgatgggg  17640
ccaggggacc acatgggcac aggtaaggca gggatgatga tggggccggg ggaccacatg  17700
ggcacaggct tctggaatgt gggtgtcgtc tccctggggt cccgcagtct gaactcaaga  17760
ctcaagagcc ccatgtccag gtggggatgt acaggagccc cttagaagtg gggaagaagg  17820
ccaggcgtgg tggctcacat ctgtaatccc agcactctgg gaggctgagg cgggtggatc  17880
aacagaggtc aggagttcga gagcaacctg gccaacatgg tgaaccctgt ctctactaaa  17940
aatacaaaaa ttagctgggc gtggtggcgc acacagctgt aatcccagct actggggagg  18000
ctgagtcaga agaatcattt gaacctggaa ggcggaggtt gcagtgagct gagatcgtac  18060
cactgcactc cagcctgggt gacagagcga gactctatct caaaaaaaat aaaataaaat  18120
aaaaaagata ggaaaagaaa aagaaaaagt gaggagaaat gaggaggaag tcgagcaatt  18180
taaccccaaa tggtgcttct ccagcagtca ctctgttcct gtcctgacct gacctgctgg  18240
gccccgcccg ctcaaaccaa atcatggatt ctgtcatcgc ttcttcacgg agcacctact  18300
gtgtgccagg cgggtgctgg ggctgcagcg cagagagcag tcagggcttg gtggtctggc  18360
```

-continued ccgcaaagag tcagcatgtg aatgtctctc catgcgatgg gtgctgggag ggaggagccc 18420
tggcaggtct ggggaagacc agcgtctctt aaatgggggt gcgcgggccc tgaggagtga 18480
ggcttcctga cagccgtccc tcgtgggtgc catgctggtc agagtggggt ctggctgcac 18540
agcctccctc agggctgggc tggaagcaca ggtcggctgg cacctgtcca ggtttcaggg 18600
ttccagggct ccagctggaa ctgcctcagg gatggcaggg gtgggcctgt ccctggagag 18660
gcgtggggtg tgggagctgg gagcgtgacg ggaagcagcc ccctcagacc tggagtagca 18720
tggagcctag gatccattgt gaccttggtg gtcctgtacc ctgtccagct ccagttgctg 18780
ttcctgcctc tccctgacct actggctgcc caggctgccc cttggccgag ctccaccatg 18840
gccagtgccc ctccattcgc ttgtgagtcc cacaagatca cagccctgcc cagggcctag 18900
gcagctcttg ggctgaccca gccatcgtcg ggagcccccct tcgtgacggg ggcaaaggct 18960
ggatcgttgt ctgccctgca ggagccgggg cctccagagg acgggctgcc tggcgggaag 19020
gtggagctca ccggagccca gcctaagcca gctgtggtgc ttctgagatg tgcggccctg 19080
ggcaggctgc tcgccctctc ggggcctctg ggaacacctg gggacttccc gctgggttcc 19140
tctgaggatt gaatgagctt gaaaatatgg aggatttggc acagggaatg ctgggcagca 19200
atatcagaaa ggcaaccctg agagccagcg gacagccact ctgaggaaca gcagtggctg 19260
cctctggaag gagtgagggg tgggtggacc cccgtgatcg ctgcacgggg gaggtcacgg 19320
ggctgagcgg ccaccactgt gcaggggagg tcacagggct gagcggctga ctccagaaca 19380
ggaagggaac acgccaggag ggaggattgc tcactgagtc agggcgggac tcagagggac 19440
gcatgacaag ttcagggagt tgacagctgt ctggaagggc acgtctgctc agaccgcagg 19500
gtagggagtg gtcagcaggg agacatgtcc actggtgcag cgggcgtgtc ccagacccct 19560
tagagaaaag cccagagcca ggggtgaggg gtatgtgtag ggtggggaca tctcagagtg 19620
gagcatcccc accaagggtg tccagaggag ggtggccagg tggggacagc agcttgagaa 19680
gggtcattct ctcttggttg gaggagtgga agtgcttctc tggggaaaga aagaagattc 19740
tggaggacag cacaggcact tccaacatgg gcgctggccg cacaaaggct agtgacaccc 19800
ggtgtgatcc cttggggtag aaagggggtg tgagaggagg atcggagggg gcagaggaca 19860
gggatgtgtc tgtgcagaac gaggctgtgg cagctccagc gaaggcggct gcggccccat 19920
cagtcacctg ccctgctgag ggcagcgctg tactcatcac ctgtgaacac aggtatcgac 19980
tcagacaccc actctggcca taagctccgc tctgtcccag ccctggaccc ctcacccccct 20040
atccttggca gtcggtcctc tgggtcttct tcctgtgccc actgtgctgg tctgaacctc 20100
ccttagtgac agatctgctc ctaccacccc cgccagggtc gcccttcctc taacaggtgg 20160
gctcctggca ggaaacatca ccaagctcag cgccccagtt ccctgacagg gccccacttc 20220
cctcctgccg ccaacctcgt ccccccaagg gccatgtccc tgcccacccc ttccacccct 20280
ttcttagagg aagctcagcc catcaggccg ctcatgcttc tgaccccacc tccaaaccct 20340
cctgacccgc ttacccccag gagcaccgcc cactccaagg cgcaagcaag ctggggctgg 20400
ggtgcagact tctcttccac cacccaccct cctcataccc agcctctgag ggcctcacag 20460
acatacatga tttgcctcca gtgggccagg gttatctgtt taccgcgttg catgcccccg 20520
ggcatggagc tggcaccggc tgccgctgca actgggcact acccgtttcg aggacgcctc 20580
attccctgag agactgagga taggctggtg ctctgcaaaa gggtgcggag accactgtaa 20640
aagtggggtg agacacgcgt gctgaccatg aaatggagag gcactcgaag gagccaggga 20700
cccggcagcc agcagacccc acctttccgc ccccgtgtgt gcagttctgt cgctcagcct 20760
ggtgcctttg ggacccgggc ctcattggtt cttcctccac tgccaccacc tgatactaaa 20820
taaccgtcgg tcaatggcaa ctcgatacgg tttatggggc atccacggtg tgcccagata 20880
gaggagtgct ttcgcttttg atatgcgtag agttacttca ttccacctag cgcttctagg 20940
aggcactaca attatctcca ttttacagac aaggaaacag aggctcagaa tgggcaagac 21000
atctatctga ggtcacacag ctagagcgcg gcagaggtgg gctgcgtggg cagagcagga 21060
gagggaactg gagtgtgtgc ccggcagtgc tgggcttcag ggcacgaagc ggtggggcag 21120
gaatcatgtg tcttggtatg acccaaacac atatatgaca gcaagaaggc ctgggcaggc 21180
agcagaggac aaggcgggcc tcttggatgt ctggatgtgg attgggcctc aatgtaccgg 21240
tgaagataga tggacaggca ggggatttcc agagaggggc ttcccaggca gggtgcgggg 21300
tgtggctgtg cggtgggaac acggactggg gaggggattg cagccgggcc cgtgcctccc 21360
ttgctcagct ccaggtcagg ccagggtaga gccaggctgc tgggttcgac ctccaccctg 21420
accagctgtg tgcccatgga gggctggtct tccctctctg tgcatgtctc ctggttggta 21480
acaggtgtgt ggcctcactg ggccgtcgtg gggtggctgg aatccccggg aattagccat 21540
gctttggtgt ttctacattt cacttggctg agtgtgaact gacccaggaa gctggttggg 21600 ggcacccccca cccacggggg gtcgggcatt ttggtttggt catggcctca aagcttctgg 21660
ggtgaggctc agggattccc ccagactgtc ctgggcatct gcctcccctc ccctcccgct 21720
tcccgtgggc cacggcccag gagagagagg gcagcttgct caggcacctc cagctgtccg 21780
catatttcac acggtgcacg ctaccccacc gtgggaggct gtgtttgtct ttcatcccca 21840
tgctgggctt ccccaaacta ggggagtggg gcagcaggcg tgccatctgt ggcggtgagg 21900
ggggctctca gccgcatcct cctcaccagg ccctgcggac aggccttcgt ccctgcccct 21960
gacctgctga cgaagccgtc ctggcaaccc tgtctgaagg acctggcccc atcgtaccca 22020
cagagggagg ccacatggtc cttagcctct gtcgggaggg gcaggcaatg ctggcagagg 22080
gccttgcccc tgagagggag gccctcctgg ccctcactcc gggggacccc tgtccttggc 22140
cccagcctgc caagcgagag cggcccctct tcttgcggtg gctggagggg agagtgaggc 22200
cccttggcac agagggcccc aggaggctgg gctctgatga cgccctgcag gaattccgct 22260
gggctgctgc ctgggagagc cgctgtctca cacagggcca gcctgcctgg cttcattctg 22320
gtgcgctgac cgcccgaccc ctctgcccag gcgggggctc ttctgggttc tgggtcctgg 22380
gacctgcctg agtccctggg aaaagggcac aaggggattg agacggtctc ctcccacaat 22440
ggcccaggtg tctcctccca caatggccca ggtgtctcct cccacaatgg cccaggtgtc 22500
tcctcccaca atggcccagg tgtctcctcc cacaatggcc caggtgtctc ctcccacaat 22560
ggcccaggtg tctcctccca caatggccca ggtgtctcct cccacaatgg cccaggtgtc 22620
tcctcccaca atggcccagg tgtctcctcc cacaatggcc caggtgtctc ctcccacaat 22680
ggcccaggtg tctcctccca caatggccca ggtgtctcct cccacaatgg cccaggtgtc 22740
tcctcccaca atggcccagg tgtctcctcc cacaatggcc ccaggtttct ttgccacttc 22800
agattggaat cgttgatctg ctgaaataac aggtaaaatc attggtggtt tgggaaccac 22860
cggaatcaga agtgcattga gatgtttgct ttaggggtgg cccggggcgg gtggagttcc 22920
tgggggcttt tccctcctcc ctgaatggag gaggacaccc tgcacccctc ctgtgatccc 22980
ccttaagagc cagtgtccgg gatggctggg ccagacgggg cagaggggcc tgtgtctcct 23040
gcccaggctg agtgcggacg gctcggtctc agagctccac cgaggggtgg gtaggtaaca 23100

-continued

```
gcagccctgc ggccagggcc cctgcaggtg ggagtgggtg tccccatggg gagtgcctct  23160
tccagagtgg gctcagtcgg ggtggagtgt cctggcttat caaaggtggt tgtggagccc  23220
tgtctgcccc aggcctgggc agaggtggaa ggggttgggg aactgacgag gccttacctg  23280
tgggcccatg gccaaggaaa tgtctggtct cccacctcct gtcaggtggt gaggggagag  23340
gatggggcgt cagccggaga cggggttcct agaggaggct gggtcctggc ctggcctgga  23400
gagataggga tgagatggga gggcaggaag ggggtggtag acaaaggctg aacacagaga  23460
gcacatagcc aggcatgtgg ggactgggga caggggacaa ggagggcacc catggggaca  23520
agagataggg agaggacaga gggacaggag acggggaggg acagaggatg ggggacaagg  23580
aggggacagg aggacgggga cagggagggg acacagaaac aggagctagg acggggacag  23640
aggatgggag aaggagaggt caaagggaca gggaacaggg aggggaccca tggggatagg  23700
gcagggatct atggggacaa gggacaggga ggggacagag aaacaggaga tggggagggg  23760
acagagggat gcagacaggg aggggataga agatgggggg ctaggggaca aagggaaagg  23820
ggacagggaa ggaacctatg ggggacaggg agacaggggg acagggagag gacagaggaa  23880
caggggacag ggaggggatg cttggggaca gggagggaat gcttgggaca gggcaggggg  23940
acagggggct gtggctttcg tgggaagcta tggaagacga ggccagaggg gttgggcagg  24000
gtgagatgag agaggctgag agcccctcac cggctgcgga ctcctcccca cagggcagag  24060
gggagcattc gggtgcggcc aggccatcag aggacctggg cttggctgga gtcccagctc  24120
ctcagccctc agtagctttg ggccagccac tgggcctcct ggcctccact tgctcatctc  24180
tgaactgggg cagggttggc gtgtgagcct gaggccctgc aaagtgcctg gccagcctca  24240
gctcggagcc atggcacagc accccctctc cgccacggcc ccgacagctg ggcgtgcgtt  24300
ctgctgtggg cagctgccct gagcaacgta gggtgctaag cagcatccct gtcttgcaca  24360
ctagattcca cagcaccctc tgaccccgtg gaaaatgtcc ccacatggga atatcctctg  24420
ggggtggaac tgcccctggt gagaacccct aggctgagac ctcagaaggc cctgagtcaa  24480
accgagaagt catcagagag ccttgttttc agctccaggg agcttgggca ggctggtttt  24540
ctgggccaca cagtcccctc cccagcccac ctgtgctccg tgggtcccgg ggaagctgtg  24600
ggggcctaat tgctggtgtg agttcctttc ctgttctgag tcacacgtgt gtgggggctc  24660
tccctgtggt gcagctggta cagcggcccc tggagttgag gatccaagca ggctgaggtc  24720
tgggtttgcc ggagggccct cggtggctgg tctttgtcct gctcccactg ctgtgggcac  24780
tgtaggactt ggaacgctgg tcacctttcc agcctggcaa agggagggga cttgtctgag  24840
gcctcatgga agttggggca gggtcgaggt gccctgcttc ctgggtgtgc cagcagccta  24900
cagcctggct acagcgtaac caggaacacc cagcacaact gtcctttgca actctgtgcc  24960
ctgacttgat ggtgccaggg ctggggggt gccggccagc agctccccaa tgaccacccc  25020
caaatgctgt ggccacacaa agccttccac tgcaagacct gtggtaatac acactggacg  25080
cccctgttac aactgagaac tcatttattt catttccttc cttccctttt tttttttttt  25140
ttttttagag ttgtggtcta gctctgttgc ccagactgga gtgcagtggt gcaatcatgg  25200
ctcactgcag cctcgagccc ctgggctcaa gtgattctcc cacctcagca ccctgcgtgg  25260
tttggactgc aggcacatgc catcacgccc tcatgcccag ctaatatttt tttaagtttt  25320
tggagagctg aggtctccct gtgttgccca ggctggtctc aagcccttgg gctcaagtaa  25380
tcctccctcc ttggcctcct aaagtgttgg gattacagtt atgaaccact gcacccagcc  25440
```

-continued

```
catccctcct agactaaatc ttcttagaaa aacctacact tccaataatg tatttgcatt  25500
ttatgatgtt gataaaactt cctaaagatg tcttatgaaa ttggtctcct ttccccattg  25560
atacacatga tttttaaaac tattggcaac gtttcaaaag caatttctgt tttgtcccag  25620
aaccgtgatc cccttgtgaa cgaattttca aattaaaagg caaatggttg ggaaaattgg  25680
atttaattga aaggccattt tattagaatt gacttatttt tctcgccact gggatccttg  25740
cctgaaaggc ggctgtgggc agagggcaca tactccccct gccccagcgc agcgtccctg  25800
cacccccaac agagcttcct gttcctcatg cccagtactc ccagatgcct gcggagccag  25860
tcatcagctc aggtgtgtga ggccggttgg gggagcccct gcctggcgcc tgtgcctgtg  25920
agcagtgttc ctgtggggcc ctgggaccaa tgctaccagc gttggcgttt tcccaggaag  25980
ttgggaatca ggcatctcgt ggcttccggt tcaagttcct ccgtgtgctt taagtctggg  26040
caggtttccg ggtcctggtt ttggctaatg aggaacccga ttcccatggg ggaggccggt  26100
ggctgcagca gggccccgag cagtggcaag gctggccctc atgacagtgt cctcctcagg  26160
gggcctgtcc caggctcttc atgactcccc tggaggcttg ttaaaggggc agattcctgg  26220
gccctgcccc agccccactg tggggagggg tgtcctggaa gatgcatctg cccagggctt  26280
ccggctggtc cacacgcctg cacctggagg cccactgccc acatctcagg caaacaggcc  26340
tggggatgtt tggggaccca actcctggcg tggaggaagc ccctttccca ccccacatgc  26400
tcctggtggt ggcctgtcct gtgagcctgg agggccggac gggtgggatc ggggacccac  26460
gaccacgctc gctggcctct gtcctgtgcc caggcaggga tgagaggcca agctggtgtc  26520
ctgcagtgca cagtgggtgc cggtcagggg atgtggaagc tgggtctccg gcaggcagag  26580
gcgcgctgac aagaagggtc gctgttcctc attcagggtt cagtgggaag agagggtgtc  26640
gcttcagggg gagttcacag gatgccgact tgaaaataca gccaacgccc atgtcccagg  26700
cataagatca caaatcatgt tttgccgacc agttcctgtg agccctgagc cctgcgcgga  26760
gggatgcccc gtgcacacct gttcacggaa cccctggacc tccagtaggg gtgcggcggg  26820
atgccgtcgg ctcccacgct gtctgtctcc ctgtccctct ctctttccct ctgtttctct  26880
gtctgtctct gtctgtctct gtctccctgt ctctctccat ctctctctgt ctctctccct  26940
gtctctctgt ctctgtctct ctccatctct ctgtctctct ttgtccttgt ctctccctgt  27000
ctctgtctct ctcactctct gtctctcttt gtccttgtct ctctgttttg tctctctttg  27060
tccctgtctc tctgtctctg tctctctctc tctttgtcct tgtatctctc tgtctctctt  27120
tgtccctgtc tctctctgcc tttgtctctc tccgtctctc tttgtccctg tctctctctg  27180
cctttgtctc tctccgtctc tctttgtcct tgtctctctg ttttgtctct ctttgtccct  27240
gtctctctgt ctctgtctct gtctctcttt gtccttgtat ctctctgtct ctctttgtcc  27300
ctgtctctct ctgcctttgt ctctctccgt ctctctgtct ctcttcctgt ctctctctat  27360
ctctttccct gtctctttct gtctctcttt gtctctctct ttgtccctgt ctctctgtct  27420
ctcttcctgt ctttctcttt ctttgtcctt gtctctctct ctctgtctct ctcttcctgt  27480
ctctatccct gtctctatgt ctctgtctct ctttgtcctt gtttctctct gtctctctgt  27540
ctctgtctct ctctgtcttt gtcccacctt agccttggga ggggacagct cacaggctga  27600
cagatgaggt catgtgtcct gagcatgagg ttttcaggtc tcacccacgc tgtagcatgt  27660
cagagcttcg ttccttttca tggccgcgta atgttccatt gcttgctggc accacatctc  27720
ctgtgcccgg ccctctgctg atgggcgtct gggctatgtg caccgttcag ctaccaggaa  27780
tggtgctgct gtgaagggag ctgggatttt gtcatccacc tgctgtggat ggcaagtcca  27840
```

tttccatctc tggactcagg tggcccatct acaaaatgaa ggggatgcga cccagaggcc 27900
tctggcggca aaaccttccc aggcttgtcc tcttggatct aagggaattt ctttcctccg 27960
agtccagccc ctccagtgct cctgcccttc aggaaacatg cctgggaccc ctcacttgtg 28020
cccacccagc cttggcccac atacctgcac caagaggcta ccctactcat actgctcagc 28080
ccaaagggac ccaccgtggg gtatgggcaa gggcgggttc tgctctcccc cggggccctg 28140
tgccagcctc agctggacct gcggttctgc ttcctgtcac actctcccat tttaaattaa 28200
cggaatggtg cggtccccat gcacaccctc agctccactg gggttttagc ccagcccagg 28260
atcggaggcc tgcaagggca cacccacctg gccacgtgat ggtgaagtgg ggtggggcag 28320
ggcaaccaaa ttaacttcta attctaagag cccctggagc attcatcacc agcacttaca 28380
gccgtgtgac ctcacacaag tcacttaacc cctctgagcc ttggggctcc tgaaaagtgg 28440
atggagcggt cacgcccacc tgggagaggt ggcttgggcc agcaccctct aagctgcttg 28500
tcccaggcca tcatggctca cggaccgccc ctcagcctgg cctgtgccac ttctccaggg 28560
cccggcacgt ggcagccaca ggcttctatc agctcccgcc tgcctgggga aggacaaaaa 28620
cgacaggttc caggccatgg cctgcacccc cgctggccgt gggcaggtcc aggcctgcct 28680
gcctgagcat tgcagggcgg tggccaagcc tgtcccatag cacctcaccg aggacctggg 28740
aggctggccc aggggagagg tcacctcagc cggggctggg ggctgtgggc agggtgggct 28800
cgggtttccc tgtcccctcc cccagctgtg ctctgcctgg acactgccac ctcctcatgg 28860
gtgtccaggg ccactgggag ctgggcccag gggttctcag gggagcaatg gtggagacaa 28920
agaccagcgg acgggcgctg gggtcagagc tctccaatcc ctgggtgtct ccttctcaag 28980
gcgtgaccac ccaggcagtg gccggctgca ggacagggca gcttcaagtt cccagccttg 29040
ccaggcttcc ctgtggccct ggggtgcagg aaggagcccc agctcagaag gcgagggggc 29100
gtctgtgtcc tgcagcagtg ggcacagcta ggctctagcc gggggcttgg ctgcagcctc 29160
cagcgcagcc ctcacacacg ctgttcccaa gatggggtga ccgggaccgg agccacctcc 29220
aggtcccggg catcagggag accccaaacc tggctgcatc cccaggcca aacccagaca 29280
caggggatcg taacagacca caggcctcac acacttgttc cggcccaagc atcccccagg 29340
ccaaacctag acacagtgga tcataacaga ccacaggcct cacacgcttg tcccggccca 29400
agcatctcaa agagtctgct ctcctgaagg ccctcaaggc agccccagga gcgggtgttg 29460
ctgtcacccc ctcttccaag gcgacggctc tgagaagctc ctgcctgccc agggcacccc 29520
cacggatggg tctgatccag gcccgccacc tccaaggcag agctgcccac ctggccttcg 29580
gtttccagcc gcggggaaca gggtggacga aatgacagtg gagagggcac agggagggca 29640
aggcgggggc acctgctcca gggatgcccc aggcaggccc acttgcctgc cgccccccacc 29700
gaggctgtca caggaggaca gagcacgagt tcccagggtg ctcaggtgtc attccttcct 29760
tcctgcagag cgagctgccc tcggaggccg gcgtggggaa gatggcccag tccaccgcca 29820
cctcccctga tgggggcacc acgtttgagc acctctggag ctctctgtga gtgcgcttgg 29880
ctggccagag ctgggggccc ccctgggagg cactctgggc tagcctcagc caccttcgct 29940
gggctaactg ggccagagca ggaggggtgg ccccgggagg actctgggct agccccagcc 30000
accctcactg agactttggg ctaaacttgg caaccctcac tgggattctg ggctagcctc 30060
gaccaccctt gctgcactaa ctggaccaga gcaggagagg tggctccaca ctagtcttgg 30120
gctagcctta gccaccctca tcagcttggg gacagggcgg gtcggagggg cagggaagag 30180

-continued

```
ggactgctgc cctaggcctt ccctggggat gcaggaccaa aattcagact cttttctctg  30240
gccagctctg gagagggccc atggccagca gaggcccaga ataacagagc ccatgactgg  30300
ctctgcctct ctggcactca cagcagccct ggaatggcag gtggaggaca gagatgggat  30360
gagagggaat gggaagggca ggagacgtag gcctcaccag gagtctcagg ctagccttga  30420
gctctgggcc tgggaggtat tggggtgaca cccaaactgg ggactgacgc ttctattttc  30480
ctctccctgc cccagggaac cagacagcac ctacttcgac cttccccagt caagccgggg  30540
gaataatgag gtggtgggcg gaacggattc cagcatggac gtcttccacc tggagggcat  30600
gactacatct gtcatggtga gtgggggggc tgccctctgc aagaggactg gagtggggac  30660
aacaaatgtg gcctgtcctg tcttgggagc ctggcagaac caggagatag cctcttggtt  30720
gtacagcttc ccctgtgggt ttctgaggac acttcaaatt gcaaaggaga aaatgtatca  30780
gctcatgtaa ctgtcaatcc agagatagga atggattcag gcatggctgg atccaggtgt  30840
aggaagggct tcaggcatgg ctagatccag gtgtaggaag ggcttcaggc acagctagat  30900
ccagatgtag gaagggcttt ggacatgggt gggtccaggt gtaggaaggg cttctactgg  30960
tggatccagg tatagaaagg gctttgggca tggctgtgtc caggtgcttc acagctgcct  31020
cgctcagtct cttggtctgc tttcccctgc agtgactttg tttttaggcc gcatctcctc  31080
tcatggtgaa gagtaccagg ctccaccagc atgccctatc cctgtggaga ggagatccct  31140
cttttcccat agtccagcag tcctgcctcc cgttgatctg aatgtggtca tgggcccatc  31200
tctgagccac atctgtgcct ctgattggcc tggcctccac catcagtgga acagggtgac  31260
aatggaatgg agtggggtgg gcctccccac acagggaccc ccaaaggaag atggaggtgc  31320
tgtttccagg agaagaggac tggatagggg gcaggcaggg ccagtgaggc ctccggcacc  31380
ccatcttggc aggctccccc attcctggga gtctcaagcc ctgccccatt ggctgctcct  31440
ctgggggaaa aggccaggct gtgggagctg gtgggggcca cgctcctgcc tacctctctg  31500
gctgcccata gccaggcctc gactgtgccg ggaggtggat ggcaggtggg caccacacgt  31560
gaggagagag caaagatccc gacctgggag gcccagcgag gccagccgtc cccgctggac  31620
tcgtcagctg ctcggccccg cccacaggct ggctgccccg ccccgcctcc gccgcccagg  31680
gattcgtagg tggggaattt gtttgcgctg cggaaaacca gcccgaactg tggggatacg  31740
cggaacagcg cgtctggggc agggtcgggc ctccctcact tatgctcagc ccgaaaggga  31800
gggaggcgat gctgggcctc tgggggcctg agagcacccg gcctggccct cctcctccct  31860
caagtcccca ttccaggagc tggagcccct tccttgcccc tgcgcacgac tgactgtctg  31920
aggcatgggg gtgggcggcc cagccaccct gagcactgga gggagtgggg gctgtggggc  31980
tccagtcaga acgaacagag tgaagcgggg tgggggagtg tagaggtgga ggggccgtgt  32040
tgcctgttcc gtctccattg cggatgctgg gctggcccag agccatgtgg ggccagagaa  32100
ggcacctcct tgggcagcca cagtcccggg gggtcaattc ctccgaggag cccctcagcc  32160
tgtatctgag ggttcgaccg cctgcccctg ccctcccacc cctgctcagg agaccgtccc  32220
agtggaaaca ctcgacagtg tctgcgcgtg ttctagtccc gtgttatggg tgaggaaacc  32280
gaggcagatg ctgggaaagg gtgggctggg gatggggccg ggtagtgcaa gaaagtgaga  32340
ctgcaacctc tcccctctct cgctttggaa cagttctgcc ggctgctctc tggggacaag  32400
ggtcctgacc ccaccccctc caggtcccct tctggacatc cgtgtcctcc aatctgggga  32460
ggggcaggaa ctggccgctg gaccccaggg agggagggag gaagacccat aagattgtcc  32520
cctgagatcc agaagccacc tcccaacccc aagttgctca gccactcccc ctgcagaggg  32580
```

cagaaggccc ctaagatggc acagacccac cctgtgtcgg gaggaggacc tggactcagg 32640
gaggcagaag gagcagttct acattcctga gtgggtggag cgtgcttgtc ctccccagcc 32700
ccggagggtt ccctgagctc catatcgggg tctggtccga gccccgcct gctggaacgt 32760
gccactcccc agccacaggg tgacagtggg agcctcgaac ctccgcaaac agcaaggtgg 32820
ctggatctgt ctggcagcga cacgcctcct cccaaagcca tgtatgaaat tcctaggtgc 32880
acagctcgac tcacggagat gggggattcc ctggaatgaa ggcaggccca ggcctgcgtg 32940
gggagagcca agcctcattc tgaccccagg gcccagcccc ctcacaacag tggctgctgg 33000
gccaagagca tgctgtcccc taccccctgac tcccatggga gcgccaggta caaagacaga 33060
gactccgaag ggcgccaacg ggtgggctcg ggcagcctgg cacagggccc agggcttagc 33120
tgccttgaga atggcccctg gcccgctaac tccaggggtc ccagagtggg gctggagctg 33180
aactgggggg cattgtttta aagttcagcc caggagctca gggaagctgc tgtgctgggg 33240
ctggggacct ggacccggtt cagtgcggat gcgggcatgg ggggctctga gtgcccctg 33300
gaaaactgcc acctgcagct caggggccca gttctagccc caccacgagg ctggtgacct 33360
tggacaagaa acaccacaca ggcccggcct cgggtcagac aggcggttct agtgccggat 33420
gtttccgggg ctaccgatag tcctgagttc gtggctcagg tggggggcct gcttgtggaa 33480
gtggctgcac acgcacctgc ccccacctgc ccctggcggc tccctctggc cacctgtccc 33540
tgggtgttgg tggcatctgg ctgctcccat actcaggggc gggtctggga ctcatccagc 33600
aaaggggcct cagctcgggc aggcacagtg cttgagcgca ggacactggt cctctgcagt 33660
ggggcgtgcc ttccgcatct gggggacgtg ggtctccccg aaccacgagc aggcagattg 33720
gttcccgttg gacacagggt gtctgaggga tgccttagcc acctgcttag cagccgtggg 33780
agacaggcgg agcaggtggt ttcaagctcc cacaattctc tgagcctcca tgtccttgct 33840
ggtgaagctg gggtgacagg gggtaggagc ccagagcaga gagccctttg ggaggtggca 33900
tagactctgg gatgccaggt gctgggtgct ggctctgccc aaccccgtgg gcctcggaca 33960
accctcctgc cacactggcc cctgcagagg aggctgagtt taggcagttc aggagagtgg 34020
ggtgtgggca agagcagttg aaccctcagt gggctctaga ggagtcccag gccacagact 34080
tattggggag actgtgagct ctgtgtggcc atagcaggaa acagaccccg tggtcactgt 34140
ggccatctga ctgaggtggc ccagaaagtc cagcaggccg aggtgggtgt ggctgggggc 34200
tccgaggcca ggtttgctga gctcaggacc taccccttcc cttctgagct gggcaacttt 34260
taaagaatta catagccctc tgggcctcag tttcctgtct ataaatggcg ctactgagag 34320
gctccaagtc acccacgatg tgaggatgtc cagtggtgcc gggcccatcg ggagtatgtg 34380
acaaacgcta ggtgtgaggg tgagggcagg gaggaggccc tgtgtttaag aaagctgctc 34440
ctcggacacc agaacagcag agccaggagg gcctaggata ggatctggga ccagggcctg 34500
ctgcctttgc ctggcacagt tcctgcctga gctgtcccgt gccttaggct ctggctgtcc 34560
ctgaagaccc tacatggctc acagggacct cactctaaaa tagggccccg ttctgcaaga 34620
ggagagcagg gggaagcctg tggcccgggc ctccccatgg gctggggagg gtgggccgag 34680
gagccacagc taaaactggc ccagcccctg ccctctcagg accctggctg gttccctgaa 34740
tgaggaaggc ttgacgggct tctggatgcc acctgggtgg ggtctgccct ggccaccccc 34800
acaccgtctg ggaagagctg cagaggataa agctccctcg taggctcgca ggctgcgagg 34860
aggcagtgtg ggtgtgatgg tggggcgggg gtcctatcct cacccggacc cacccgagga 34920

```
gtctctgcag tgctgggcct gggcttggaa gcgaatccct gcccctctga gcgctagcgt  34980
cccctcggac aaaaccagcg cagggcaatg agacctgcgg cccttgctgg ctctcaggat  35040
gctccacaag gagggaggac acaggagggg agaaaaggag agagaggcaa gtgtctcctc  35100
cctcccctcc cctccactct gctccgctcc cgtcctctcc cctcccctct ctgtccctag  35160
agcctcctcc agggctggcc cctcccctgt gccccttcct gcctctcctg gcgcctttct  35220
ctgacaacag gtgttgtggg caggtgggcc acagagcggg gtctacagct ggtggggcag  35280
aaggcaggct gatctaccct gggagccccg ggaacccagt ggcaggacag acacccgggg  35340
tcagaacctt cggacacttg gggggcttgag accctagagg tcaccccaga taggccttgg  35400
tgacttcagg gagaggtatt ctccccaggc ccaggagaag gaagggcgca ggtcccgtgc  35460
atgtgtggcc cccaggaaag ggcaggcgga cagagggaga aggacacccc tcccttccag  35520
ggaggatctg tagctggagg aagggtgggg tcatgcgtgg gagcagggag ggggctcagc  35580
tcaccacggt cagctctgag actccagccc acccgttacc ccctcccaga gagcccccac  35640
tcagcctttc ctttggtggg ctttcgtgac aaagcacttt ggggctgcac agaagtgaac  35700
cccacccagc acccaggtct cagagccttg cagcttctgc ggcctcttcc atgcggtggg  35760
atgaagccag ctgcccagca gggaccctgt gccatgagtt tggccttgaa ctgacacatc  35820
actggcacca ggaaacgaag tccccctgtc tgttctggca cataacccct cccactaact  35880
ggttcctgaa gagtgccgtg gcctgcggca gcgtcgttcc cccctgtcct gcggcccagg  35940
gtcctgcgga aagtcaggcg gaatccccgg tgagtcagaa gcagaatgaa agcagaatgg  36000
aggacccagc agggagggaa cctggaggag gcgctaaggg ccacgccaag gggtgtggc  36060
cccagatccc ctgtccctgt cctctgcaag gctgggcctt gggaacgttt gcagaaagct  36120
gggtgccgct ctggggcaga ggccagtggt tttgggtgct tttgagttgg aaacgtgtag  36180
ctcagccgca ctgggatccc cgcagcctgg cccagatgct aagggtggag agatgcgggg  36240
tctcaggcac ggtgccctgg gcatgggtgg ggctcgtgct gaaggcagcc tggctgtctt  36300
ccttcctcac gtccttccac ttggcgctct ccttttggct atttataaaa ccatcaggcc  36360
ggccctgtgc atgggactcg cctgagtctc cttttcaatg catcattccc tttggcagga  36420
gaggacaccg cctacagagg ctgaggatgt gccctgtggg ggtcgggagc ggaacccagg  36480
ccccgcctcg gccctgctct gagggtctgt ccatccctgg ggagcccgcc cccaacccaa  36540
gaggggtccc aggctcagaa gcagaaggca ccctcatccc cagggcatcc ccgatcccag  36600
caggagtctc ctagtgctcg ccctgggctc tcctgcaagg aggctgctgc tttccccaga  36660
acatccagtc tgggccccag ccgacccccct gcagggggct tcccagagac gcccttcctg  36720
aacctgatct accagacaaa actgtctttt tctcagtcgt ctcctcctga gtgctgctgc  36780
ccttcctgtt gggggctgag atcctctgcc acaggaagag acgggcgtcc aggactcacc  36840
tgctgcctcc cggccctagg gccctgagct gggctctcca ggccccagcc ccttggggca  36900
caacacctgg aatcgtcctt tcgtcctcag cccggcctgc tggtggggca gggcgggtcc  36960
ccagggctcc tcaggcagct gcagtccaaa cctcccctgc cctcacccag ctctgcccgc  37020
tctcccgggg gtgggggtgg ggagcgatga ggcccctgcc ggctctcggt ggggacgaca  37080
gggaggaagg aagctgggga gatggagaca agagaaagca ggcaggtggt ttgggatttg  37140
gcaggaaaag gttggaagga aaggggaaag ggtctccgca tggatttctc agctccccat  37200
ggatttctca gccctcgtga gagccacggc gccctgggga ctggaagtgt gggtccgcag  37260
gccccagtcc ccaggtttgt ctgagcatag atgccctgcc tgcttccagg gggactcggg  37320
```

-continued

```
ccccctctgcc agggtcaact ttgtacccaa gacggctgaa atacaatgga aattcagacg  37380
gcccaacagg gagtggcagt cacctcaaag gccccactag acgggtgcgg ggcaccactg  37440
cagagcccct ccctggctgt gccaaggccg tccacgcctg caggggggccc cactgccggg  37500
ctgttctttg gcaacagtgg cttgtccctg tttcctgggg gcttggccag tgccagggtg  37560
ggctccaaac gcacggctct gggctcttgg actcacccct gctttgggca ggcagtggaa  37620
ggcaggcccc acaagagctg ctcactcccg tcacctgtct ccctcggggg tctagggtcg  37680
aacctcctgt gagcccctcc tctccatgca gcccttggac tggtcctggc ggaccaccga  37740
gttccccgcg caggggggcag gtgcgcccca cctgggtgcc aagggaggcg acaccatctc  37800
tccccccttgg ggtggcccag ccttgcctac catgatctcc agggccgggg ctcagccctc  37860
atgcctggga acagaggctg ctttacgggg tgagggcctg gggcccccccg agccttcccc  37920
aggcaggcag catctcggaa ggagccctgg tgggtttaat tatggagccg gcgctgaccg  37980
gcgtccccgc cctccccacg cagcctcctt ggtgcggtcc aacacatcac cgggcaagct  38040
gaggcctgcc ccggacttgg atgaatactc atgaggaata aaggggtggg ccgcgggttt  38100
tgttgttgga ttcagccagt tgacagaact aagggagatg ggaaaagcga aaatgccaac  38160
aaacggcccg catgttcccc agcatcctcg gctcctgcct cactagctgc ggagcctctc  38220
ccgctcggtc cacgctgccg ggcggccacg accgtgaccc ttcccctcgg gccgcccaga  38280
tccatgcctc gtcccacggg acaccagttc cctggcgtgt gcagaccccc cggcgcctac  38340
catgctgtac gtcggtgacc ccgcacggca cctcgccacg gtaggtgtga cgcgccattc  38400
ataggatctc ttcggggact ttgcggggga ttttgctgca gtgtagggtt cagaggggca  38460
tccttctgcc tgccttcctg gcctggagtc tgctgccagt tggggtgagc agaggtagga  38520
agggaggcgt tgaggggcta gaggcaggtc ccaggcatgg aggcaagcag attcgggctc  38580
caacagcctg tgcccacctg ctgggcaggg acccgcagcc agggagagga ggccgggtcc  38640
atgccgatgg ggctgctggt gtttctgcct cgtgctcggg ggtctctgat gctccttggc  38700
tttggggctg gcggcttggt ccaggctcag agtttccgag ctgccctgcc ctgccccagc  38760
tgccaggagc tcagtgcacc ctagaagtca tctttgctcc tgggcttggg tgtgaagctg  38820
cccccgccct catcagggaa tttgctcatt tgacagcagt ggcagacggt gcttcttgtc  38880
agccccacgg gctcttctcg gtgtgggtct gagctccagg gccaggacct gtggcaaact  38940
gggcttgagg cctcttgcgc cacccgcccc ctgcagtggg ctgctggctt ggaagagggg  39000
agggaagggt ctgcagcttg tggttggccc ctgcagcctg agccctgggg acctggcctc  39060
acttccagac ttgccaggtc cctgggggcc aggcaggcac cagctgctaa ttgagaaggt  39120
ggaaggctcg gcacagctgc tccacgtggg gccgttcctc ctcccaggga agcagacagc  39180
tgggaccatg ggtacctgtg ccacacggga aactcagcca tgggcagggg gcagcgggca  39240
gataggcaga gtccaagtgc cccgaagctc tgctggcact gggatgtaga ggcccaaaga  39300
tctggggacg gaggcctttg gagccgtggg ctccccaggc agtgtgacca gggtgtgtgt  39360
gacagcgatg tgtgtgagcg tgcacatcaa tgtgcatgtg gcgggtgggt attggtgtgc  39420
gtgcatgtgt gtgtctaagc gtggatgtgc atgcaatacg caggcgagga tatgtgcaga  39480
tgtgtgtgtg tatgttatgg gtgtgtgtac aggctggtgt gtgtgtatgt acacgtgttt  39540
gcctgtgtgt tgtggtgtgt gtacgtgtga gcagattggt actgcaggtg tgattgtgtg  39600
atttgggtgg gtaggtgctc acgtgtgtcc gtatgtgtgt tgcgatggat acatggatgt  39660
```

-continued

```
ctgtgcctgt agctgtgtgt tcccaggcaa ggctttgaga agagaggcag tgtgtgtgtg  39720
tggcccagag ggtgggtgag ggtgtgggtg acccagcccc acagcctgcc cagatgctgg  39780
gtccatgcac tcgagtctgg cggcaccatg gcctctccac acgcctgcgt gatcttttta  39840
tctgaaaccc agtgctggga ctgtagccca gagcgtggaa cggctacatc aggcatgggg  39900
tgtccctctc tcccttgtct ggctgtcacc cacttgtgca ttgatacatg tatccaccaa  39960
cacgttgcta ttagaaacgc acagcaggcc tggggctcct ggggggctgc cttgtacccc  40020
cagactctcc caggaggtgt gtgagctggg aggggctatc tcccggctgc tggaccgcct  40080
ggaacccgag gtggatccag aagcctcggg tggagaggcc agtgtcgctg cctggccagc  40140
cgagaagcct ggggacctgg gggactctag tacaatcttt tcccttgaat ggagcagatg  40200
tcaccatgtg actcaccctc tcgggggact ccaccaaggt tgagtatgtg gttgcgcaga  40260
cgccattccc gggaggggtg gggaggtgga gccctgctgc cctggcctgc agaccctcac  40320
tgcctgcagg agctgctggt gtccactcgg ctgctgctgc ccggtgccct gggcgtcagc  40380
aatggccagc tgtgccatca ctgtttcttt ttacaccaag gattactgtg gttcgttcgt  40440
tcatttgtcc attcattcat cccatcagca agtgttaact gggcacgttt tgtgtgttag  40500
gctgagtgcc aggagcaggt ggaggcagtg cccagagcca gccatgtctc cagcacctct  40560
tccctctcgg ggggaggtgg gctaggctgg gccatcctaa tgggcggagt ggtgactcag  40620
tttccctgtt tctgtgccag agagagtatt catgacctca tcttactgca ggaacgtatt  40680
ttgagagaga aagtggtatt tggcccaaag ggttttaaac ccaaagtgag cgaatagagt  40740
tgtattggag ttggtggctt tgtgaggccc tggttattcc tatcaaagca cagtagctgc  40800
tccggagccc gctgggccag cctggccctg ggaagaggcc cctgggttgc aggacactgt  40860
ctgagccccc agctgggccc gccaattgcc cccagcctgg cacagggttc caggtgtggg  40920
cttggggtct gtctctctgg catctgccag ctgagtcttt ggtcagtgac gccgctctct  40980
gagcctcagt ctcctctatg atgaggacgg tgttcaccgt agctgctcgg ctgcggggcc  41040
caatgggagc cactggttac ttgctgcaga tggggacgca ggggggcctg gcctggagag  41100
ctgccgcctc agcccctcct cccacaatcc cacccatgca gccttagccc ctcctcctgc  41160
aatcccagcc ctgcagcctc agctcctcct cccacaatcc cacccatgca gcctcagccc  41220
ctcctcccgc aatcccagcc ctgcagcctc agcccctcct cccgcaatcc cagccatgca  41280
gcctcagctc ctcctcccac aatcccaccc atgcagcctc cgcccctcct cccgcaatcc  41340
cagccctgca gcctcagccc cctcctcccg caatcccagc catgcagcct cagcccctcc  41400
tcccgcaatc ccagccctgc agcctcagcc cctcctcccg caatcccagc catgcagcct  41460
cagcccctcc tcccgcaatc ccagccatgc agcctcagcc cctcctcccg caatcccagc  41520
cctgcattct cagcccctcc tcccgcaatc ccagccatgc agcctcagcc cctcctcccg  41580
caatcccagc cctgcagcct cagccccctc ctcccgcaat cccacccatg cagcctcagc  41640
ccctcctccc gcaatcccag ccctgcagcc tcagcccccct cctcccacaa tcccacccat  41700
gcagcctcag cccctcctcc cgcaatccca gccatgcagc ctcagccccc tcctcccgca  41760
atcccaccca tgcagcctcc gcccctcctc ccgcaatccc agccatgcag cctcagcccc  41820
tcctcccgca atcccagccc tgcagcctca gcccctcctc ccgcaatccc agccatgcag  41880
cctcagcccc tcctcccgca atcccagcca tgcagcctca gcccctcctc ccgcaatccc  41940
agccctgcag cctcagcccc tcctcccgca atcccagcca tgcagcctca gcccctcctc  42000
ccgcaatccc agccatgcag cctcagcccc tcctcccgca atcccagccc tgcagcctca  42060
```

-continued gcccctcctc ccgcaatccc acccatgcag cctcagcccc tcctcccgca atcccaccca 42120
tgcagcctca gcccctcctc ctgcaatccc agccatgcag cctcagcccc tcctcccgca 42180
atcccagcca tgcagcctca gcccctcctc ctgcaatccc agccatgcag cctcagaccc 42240
ttcctcccac aatcccaccc atgcagcctc agcccctcct cctgcaatcc cagccatgca 42300
gcctcagccc ctcctcctgc aatcccaccc atgcatcttc agcccctcct cccgcaatcc 42360
cagccctgca gcctcagccc ctcctcctgc aatcccagcc atgcagcctc agcccctcct 42420
cccgcaatcc cagccatgct cttcacttgc ttcccacact gtccttccac atgggggact 42480
ggataatcct gtggtggctc tggccaaaca aggccacgtt ctgagtctgc ggctcccacg 42540
gactggggtt gatcaatgcc caaccccgag gtggacacag agacattacc cacttctgcc 42600
tgtagcaagg aaggagccga tggctggatg agtggggccc ctctagaaga ggctgagcgc 42660
tggagacgtc ggagctgggt gctgtctacc aacacccagg agtctccctg acttcccaaa 42720
tgtccagttc atggcccctt gccccccact tcctcctggg gccgctgttc ttcagcttta 42780
gggtctcagg aggttagcca gggtgatggg agacacccct agctctcctg cgccctctct 42840
atggaggggc tggagcctgt ctcgccgcag ggcctgggct gtgcaccctt gggcctggcc 42900
tgttcccacc ctgcccctcc gcatggtggg catccatgcg ttgcgggaac gtggccaccc 42960
ctgtgctgag gagcagcacg gacggatctg gagctttgga cacccccact cccgtgcgcc 43020
ccatggagcc agtgtccact ctgttcctgc agaaagtgaa acctctgggc aggatgggcc 43080
tccaggacag ggccctgggg cggggggaag ccaatcagtg cagcaagctg cagttactag 43140
gcacctactc tgtacgtggg gctacggaac caagggacgc agctggcaga cgttctggga 43200
gggcccccgg ctgcagtgct ggggatagac cacagggggg cagggccaag gccaggagcc 43260
gcctgcaggc tgggacgatc cagggaatgg ggcagccccg ccggtcaggt ggtaccacac 43320
cgtgggattc tgggcaagat ttgctgatgg gctggatatg agggaagggg tgggggagac 43380
cccaagtttt ctgccctgag attggtagaa ctgcagcaga gcaggggtga aaacgccgcg 43440
gtcggccgtg gctgtgttgg agatgcccgg cagccattgc atagctgaga aggagccgca 43500
tgcagggagg aggacgacga gcgagcagtt cccaaagccc catgagggag gggtttccag 43560
tggtcctggg gcctgaaaag tgtgaccacc tggtggctca gtcctgtgtg catcagagga 43620
ggtggtgggt ggtggtcagg cttagggtgg agtttgaagg tgaccttaga ggaagagcag 43680
gggaggattc cagaaagatg ctgaggttcc atttgcaccc ttgcaggagg ctctgctgct 43740
ccccaaggca ggaaaggccg gcagggtctg gatgtgaggt gggtaaggag ttggggccac 43800
actggcagga gcggccatgt ggacactcag ttgctggtgt gggcaggcag gctgtggaga 43860
cgacctctag ggagtcctgc acatgggcac ttacagtcag ggctctgggg gatctgcacg 43920
gaggcaggga gagacagcgg ctggagctga gcactgggca ctacgacatc cgagacacca 43980
agcagagggg gagatgcaga ggggcagcct gggaggccag gaggcacgag aggctggctg 44040
ggagaacaga aaagggactg gggcttggca acccagaggc tgctgagttc ccacggtttg 44100
gagagggcag ggcccaactg ggaatggctc atgggattgc tgagcatggc caagggagcc 44160
ctcagcatcc tctccaggcc ttgtgtcatg aaagaccccg agcagcggtg gggctcaagc 44220
catgtggggc caggggaggg accagttgtc ctaactggag atccagggat cagaggagcc 44280
accccactca cccgcctgct gtgcctagtg cacgcccgcc tccggccccc ctgccaccct 44340
cggccagctg ctatttctgt ctcctttgtt ctgtccccca ttggacctcc ccccagtcac 44400

-continued

```
cagcctaata ggacctcaac ttgctaaacc caaactaaac ttatcttccc ctgagagggg  44460
atggtgccgt gtctcagcca gcaggaaatc cactctcgcc tttgctcagg ccagagccct  44520
ggaggcactc tccatgcctg aggtcctgtg aatcctgcct gcaaatgtgc ctggggcccc  44580
tgcggggccc acctcgcacc cgcggcccac gtcgcacccg cggcccacct cgcacccact  44640
gctcagatac atctcacaat tgctgccttt gctgacgccc gccctgtgtt ctcaacaccg  44700
gagccagagg gagcgctttg cagccccggg cgtctctgct cagctccgac cacctctccc  44760
gctatccccc tgggctccgt ctctccctgc acaggccctc ggcccttcct ctggctgcag  44820
gctctctgcc ctgctggtcc ccagcctgga aacaccccca ggcccaccca atacctgggg  44880
cagatctttc ccttcctgca ggcccgcctt cacctttttcc cgagcccgtc cttgcctgga  44940
cgccagccct ggcccctgtg cctggctctg tgtttctgag accacttttg atcccaagcc  45000
cctgcacgct tgctggctgg tttgtttact gtcgtcagca tggagggccg gggtcgtgtc  45060
tcgtgccggc tgccatcttc ctgcacctgg gagggtgcta ggatgtcaag cctaggaaat  45120
gggtgtgaag aggagacctg cctttgcagg agctgaccaa ggccagtgca ctgggcggga  45180
ccatccgtca ctcctgagcc cactaactgg ggaggggaca ggcagagcgg ggctgggtga  45240
ttcctgagca agcatgctgc tgtctctctg gctctggggc ctctgccctc tgcctcgatg  45300
gccccccaca gccgtcctgg accgccttct ccacctttgg gctcctgctc caatgtccgc  45360
ttatcaccga gggccatcgg aggtggcacg ccccgtgact gcctcccccct ccctgtaccc  45420
tgcactgcac gtgtcataat tcaagttctc ggctcagcca cccattctcg gctcagccac  45480
taatgtgtgc tggaaggtgt ccaggaagcc ctgctaagca tctgtcagtg tctccagcac  45540
agcaggaggc tgttacaggt ggcgcctgat tcacatctgc aggacaggtg gatggatggg  45600
cagacagatg ggcaggggca tgtgtgcaag gacacaggat gtcagggctg acacctgggt  45660
tgggctctgg ggtgctggca gcagggttcg gagaggggag agaagcgtgt gtgagctgtg  45720
ccttcccccct cgtcttcccg ggcactcggc attctgggtg ggagggcctg gaccagcccg  45780
tttccaggtg gttaaataaa gtctgtgcat cctgttggcc acctgcctct cataggcagc  45840
agcacagggc ctgatgggga tacagcctgg ataccccact ggggcctccc gcagacactc  45900
agggtccagg ctgcccctcg ccacaacctg gaagggaggg gctggtgggc cagccctctg  45960
gaggaggcct ctcaggggag gtgggctttg agcgggatcc gggaggcagg gggcagaagc  46020
tgagggacgt ggagaagggt ctgggggagg aggcggcggc accgtgagtg gactccgggg  46080
cggttagcag gtggaaggca gtgagggttg aggagagggt ggggcgaggc ccttgcacca  46140
ggccacagtg ggcggctcaa atgtgggtcc gtggaggccc gggggcacc aggctaccct  46200
ggagtcatct gaagtcacct gggcgtgtgg agggacatgc atctgcaagg cccccatgtg  46260
gcgctaagca cagagtgggt gctgcagacg ggctcagccg ctgcgggcag gtgcaggcag  46320
gatagcagcg gtggccctgg gcctcgcagt cctgcagaca cacgtctggg gactgctcct  46380
gggggcgcgt ttctccggtg tgaggtgtgg aaagttccac atggccctgg cacgggattg  46440
ggcaaggcct cgcctcagcc ccgggtgaga gcagagggtg ctgtgggtga gagcacaggg  46500
tgctgtgggt gagagcagag ggtgctgtgg atgagagcag agggtgctgt gtgcacattg  46560
tcgggagagg gaggcttccc cccagccgca tgtcgaatct tgttggcatt tccattcgtt  46620
taatcacggg ctccgggaga tgctgtggga agtaccggca ggacggaggt cttgccctgg  46680
tgggatgggc tctcttcctc cgaagcccag gctgcttgtc agtcactcac ccctgggtga  46740
ggttggggcc caagttcaga catgcccacg agagatcagg gagtttgagg agcggcatac  46800
```

tctcaaaaaa ccacaacagt ctggtctcaa tattctccag ggaacgagga cacggacctc 46860
cttgttctac aagagctggg gtcacagctc agagcccctg tccaggctgg agggagaagg 46920
ccaggaggcc agagggaggc cagctgagcc ctcaggagac tccaggcagg ccccgatgcc 46980
agactccagc cctcaaacat gctgccttct ggaaacgtct gtcacgggca caccatgcac 47040
catgccatgg ctgccagtgg tggatgaaga agagcatgtc tctgccccgt ctggagctcc 47100
cggttcctgt cctagttgaa cagaatgaat gagagtgcgg gataaatgcc gggcggggag 47160
cagggatgct cgggcggggg caggagctgg agaggtgaca ggagcgaggg aggcggaggt 47220
ggagctgggg aggggccagc ggggcgtcag gatttcagct gacatcccta ctacgctttt 47280
tcacgtgcct ccctctctga ctcggatcct aagtgattag gatcagagga atctctgttt 47340
ccaagagaag gggactgca tggccagacc gtgggctcgg gccccagtct cctgatctcc 47400
gccaagccca gggccccagg aagcggcccc atccttggga gctgtcctgg cctcagctcc 47460
caaggatggg gtccctcggg aagctgttat tgctgtctac ggggcaggag ctccgtcttt 47520
cgagcctctg cacttgtgga gacaaaggtt tccgaatgag catttgtgcc ccgccctccc 47580
caccacccct gccaggccca atgcagggac caggctgcat gtgccttccc cgcctcacat 47640
ctcctccgct ggaggagtca gccaaaaccg tggcctttgg agatgtggcc agagtcattg 47700
tgaattttgc tggcaggttt ctctgttgtc atttccacta aaaaatacgt tccgttctgg 47760
acagtaccac atctgtcccc tgtcatccga tggcacggtc gtgacctccc atgccttgct 47820
ttgcattgtg tcttaaatat cctaggctct gataaaaggc actgtggata ccgggaagcg 47880
agaggagtgg actagggggg aacagggaca caaacttgaa aaagatttat ttcccatcta 47940
cttgtaaaaa aaatcactca aatgccccac gcctgtaatc ccagcacttt gggaggctga 48000
ggtgggcaga tcacctgagg tcaggagttc gagaccagcc tggccaacat ggtgaaaccc 48060
ccgtctctac taaaaataca aaaattagcg tctgtaatcc cagctactgg ggaggctgag 48120
gcaagataat cgcttgaacc caggaggtgg aagttgcagt gagccgagat cccaccactg 48180
cactccagcc tgggcgacac agtgagactt cgtctcaaaa aaaaaaaaag tcacttgaga 48240
cggtttacac attttaaaca gtcaacaggt gcaatgggaa tcttttaaca aaaccacaaa 48300
atccaactta atctgaaata gaacagaacc catgcggcgg gagggtgatg atggggccca 48360
gctcccctcc agctcctggc cggtgaggac aaagagtctt tcaaggggct gtccccgccc 48420
tccacattct gaggaaggca gcctggaccc tgggcactgt ctgggcttgg ggctgtggcc 48480
gacatggcgg gcagtggcac accgtggcca cttcccccag ttggatggcc cgcgtggatt 48540
tcagggtctg tttcatccaa ccaagagttt ctgagcgtcc tgtcggtact ggctatctgg 48600
acacctcggg gaacaggaga gaccccgacc cctgtgagca cctgcccccg agagcacctg 48660
ctcttcccca tccgtccctg tgcccagggc ttagcgactg tcctctgcgt agtgaatctg 48720
gattcccgtc cctgttcctc ggcggagcct gcccagccgt cgttcctcct ggctgggttt 48780
ttgtgccaag gcgtggaggt catgcctcgt gcatgggagc ttcctggaca ttggttccag 48840
gagggctccc gggcgagagt cacttccgat gaagtctcag gttaccatac ttctggaccc 48900
tcttgatccc cacaaccatc ctacgaagtc cacgttgatt tcttttttgg tttttttcga 48960
gacagagtct tgctctgtca cccaggctgg agtgctgtgg cgtgatctca gctcactgca 49020
acctctgcct cccgggttca agcaattctc cttgctcatc ctcccaagta gctgggatta 49080
caggtgccca ccaccacgcc cagctaattt ttttttgtag ttttagtaga gacggggttt 49140

-continued caccatattg gctaggccag tcttgaactc cggacctcag gtgatccgcc tgcctcgtcc 49200
tcccaaattg ctgggatgac aggcatgagc caccacgcct ggccagtaca tgttgatttc 49260
atccccactc tgcagatgag aaaacgaaga cctagggagg tggagcgatg ggccaggtta 49320
cacaggtgga gctgagactt ggccccagga ctcctgacct cagagccctg cttggccccc 49380
caggtccctg ggaggtctct cctgcccctc tcctggatgg gcagagaggc ctggtttcca 49440
ggatggtggc gtaggggcat cagtagaccc agaagaacct gctgttctgg gatgggcagc 49500
cctggccacc acttcctgcc caccttgtgg gaacccccag acctcagcca tcaccgtccc 49560
cagcttggcc gacggtagat gctggtgctt ggattggggt gtccagccag tgggatgggg 49620
cttcagggct gggctgagct ctggcctccc ccacactgct cctctctgct ctcagacagg 49680
caggccaggg ggcaggcggg accctccaca gccctcctgg agggggccca gctactgggt 49740
ggcctctcag tctctgaccc ctcattttgg agcaaggtca ctggcctgct gccaccccag 49800
gggcatgggt ggatcaaacc agtgaggtct gggaactgtg ttgatacctg tgactggccc 49860
aggcgagaga gcagccccat ttaccactgc ctgctgccca caccccagcc cccagccccc 49920
agcccccagc ccagagctaa tctccagcac aggtgcaccc agggaggtcc ccaacccatc 49980
cgcagggagg agagatgagg cctcctgggt gggtgcgtgg gggctgcagt atttcccctg 50040
gcagagcact cctgccccgc aacaaggccc tggggcccca gcagggcctg gtgcgtccgc 50100
ggcctggagg ctggcgggaa ggccacccgc tggctctctg gctcccgcgc actccttggg 50160
tcaggcccag gagccctgca cacacatgta ggcacttgtg gccgccgcgg gccgggcgtg 50220
tcctaattag cccactatct tgggagctct tgttgaaagc aaaacaaacc aaaaaagtcc 50280
tggttgtgcc cgggttcctc cccgtggctt ccgggggccc tctggttgtg ggagaccccg 50340
ggctcctgtg caggcctgtg ttaggttcag ggttccctgt ttcagcagct tgaccccgag 50400
caggagccag gccccaggga aagctccttg ccgccaggca ggaagcgaaa gggaagacca 50460
gagtcccccg agccaggtgg aggggcttgt ggaggatgcc tggggaggcc taagggggag 50520
gtcagagacc cagaaagccc cctacacttc ccagatgctg cgttcccagc tgcattcata 50580
actgcagctg caaagcctct gccacccact gggggtgtga caggggcggt gaccacaggc 50640
agggccagcg tgcagggaga gaggtcccct ggaagcagga ggagaggaca gcgtcccctg 50700
ggcagaggac aggcccagta accctgggga ggagggggct tcagaggccc ccaccccgtg 50760
tcactgagcc tgaggatgag aggggaccag agggagaggc cgacatcggg gccctgcctg 50820
aggaaggccc tgctaaggga gcctgcctgg ggccctgggc cacagaggac ggcaccgaga 50880
gggcttcagg cctgctgtcc ggacacttgt ccactaatta ggattcccgc gtggggccgc 50940
ctgccgcaag ggcctggctc actcccgctg ggctgtgcta ggcgcagaga tcctatcagc 51000
tcttctcctc ttgcctcaat gactaattcc ttggcacctt cctcagatca tacaagaatg 51060
tggacaagtt aaaatatgaa acacgttgtc gtgggtctgc atcctgcttc tcccaaacaa 51120
gggaggcatg ggctttttgc cccactggct gtcctgttct cagggatgga gcagggatgg 51180
gagtcgggca gggggaccct ggagcctgcc cttgcctgtc atcctgacct gagaagcctc 51240
agctgggcag ccccttgagcc ccgggatgtt cttgcccggg ggactcaaat gagtcaggaa 51300
tggggaagtc gtgcatccct gaggccatcc ccgggcccaa aacagggaag acctttccag 51360
gaaggccacc gctggtcacc tggaagagag agggcaccac ggagagggga gggtgggcag 51420
gctggcaccc ggtacccggt gatgggaggg gccggctcat gtcccacact cactcctggg 51480
cagctggact gggggagccg tcctgcattc gcttgttcgt ttgttctgcc agctcgcttg 51540
ttcagcgagc ctttcaagca gccacgctgt aataggagca cggactgagg gtgtcggctc 51600
cgagccgtgt gtgtaattct gctttttcta gtagccgcat tcaaaaaggt ggaaaggagc 51660
tggcggaagt catttaatta tttcctgtat tcacccgtaa ctgtgatcgt ttcagcctgt 51720
aatcagtagg aaatggtgag cgaggtgttt tccgttcttt ccgtggtcct gagcccttgg 51780
aatcggggtg cgctcacaca ctgggctcag gtccatccac atttcacaca cccccaccct 51840
gtgtggccag tggccaccgt atccagggtc ctcgtgggtt cacagtcgag taggggagac 51900
agaagccatg gggacatgc gagcctgccc ttccggagaa tggctagaaa gatgctcaaa 51960
ccgggtgacg aaagagaaca cctgaggcct gggcgctgct cctgcccgtg tggccagggc 52020
tgacccctcg gaacagtgac ctctgagccc ggacagggct ggtgaagggt cgtgtgcaga 52080
ccacaagtgc aggcttccag gaagggcctg ggcccgtggt cgtaagcagg tctcagacac 52140
ctcagaggcc tcttgggcct cggtgaggag tctgggagcc ggggactctg gggcggggcc 52200
tgggctgtgc gaccagagcc tggcactgcc ccttgtcacc cccaccatca cccaacctcc 52260
catgtgtgta gctgaggcag gggtccatcc tctgtgccag aagcctactg gcagctcgcc 52320
ggtgcccagg gtgacaccca accagacacc aggaggagca ggagtagcct ttctacatct 52380
ttctctgagg ggggcagtgg ctgcttcccc agacccccctc acaatagccc aggagccagg 52440
agaggcgagg gtcacccttc cctgggatgt tatattttgt ttcgtttttt gagacaaagt 52500
cttgccctgt ctcccaggct ggagggcagt ggcgtgatct tggctctctg ccgtctcaga 52560
ttcctgggct caagagatcc tcccgcctct gccccccaga atgctgggat tacgggcgtc 52620
cccccgtgat gtttttaagc tggcaccatg gcttatccac gtggcagcgt gtgggagctt 52680
ccttctgtct tatggccgag gaagaggcca ctgtacagac acactgtttc tttatccatt 52740
tgccattcag tgaaccctgg gctcctggga aggacctgtg gtgcaggaag ttagggaggt 52800
tgtggggagc gcgacagacc aggaaggagg ctgcagtggt gccggagagg tgggcagggc 52860
ccgtgctgca gggggtcccc gttccactgg tgggtgggct ccccaggttg acagctcaca 52920
gccagcttaa tggtgccaga tgatggcagc ttcagccgag gcctcgtgcc aagacccttg 52980
cagtggagcc agggcacggg tcgcccctga cggctcaggc ctgctggggc tgttggctgt 53040
cctgggctgg agcacacagg gagagggcct gcctggcctt tggtggccct gggaacagtg 53100
gtgatggctc tggtgagcag cagtcccctg cctcctgccc ctccggcatc ccgggctgag 53160
ctgcctccac gttggactgc actcagtgga ggactcagta gaggactcag agaggacgca 53220
aactctggac ttgcctggcg tccttctcca ttggatgctg gaggggccgg gggatgcggc 53280
cctcgtcagg gacctcagtg gatgtgtgtc ctaggacctg cagagccgag ggcctctggg 53340
tcactaaacc caaccacctc tgatggagaa ggctgaggtg caggaagggg ctgagcctgg 53400
gagtcccggc gaggcccctg caccctcctg tgcgggcagt gcacgttttg ttttttggat 53460
tggagggggc aggctggtgg gagggaagag tgtgctcaca gcacaccaca gcttctctaa 53520
agagggacac agggcagaat gaccgccccc cgcccccggc ccgcctccgc ctggctctgc 53580
cccttcctgc cctgcaatcc cagttcacgg tctgggggtc tcagcctgca ccttgctgac 53640
tgctggtgac ctttgtgccg tctgctgggg ccgctagatc actggggtca atcgtttccc 53700
cagccccata gctcagtttc ctcatctgta aaatggggac aatcatggtg cccaccgcag 53760
gcctggggag aggggtaata gggacaatca cggtgcccgc cgcaggcccg gggagggggg 53820
taatagggac aatcacggtg cccgccgcag gcccggggag gggggtaata gggacaatca 53880

-continued

```
cggtgcccgc cgcaggcccg gggagagggg taatagggac aatcacggtg cccgccgcag  53940
gcccggggag agggggtaa aggcatttgt ttgcgttgag cctcgggggt cacagggaaa  54000
gcgctgttta tacatgtgca gtcttcctcc agcacccgcc tctggatttg gaaggagggt  54060
cttcctcagc agcccaccaa gtgaggtctg ccctgccctg gatctgagac atcgaggcca  54120
gaccagcacc ccctccctca gctggggcct cccttaagct cctggcagag gctgatccat  54180
gctggggtcc cggggcgcca cagacggtgg cgcaggggac acacccacag gggttcctgt  54240
tccttggtgt gtggtcctgg cgggggagct gcgggtaggg gcctaacgag agaaccccgg  54300
gccaggggc agcaggggtg aggctttgcc ggcccctgag cgtggagcgg cctttccagt  54360
cggggtgagg ccgttcaccg agagatgagg ccgcccaact gggaaaattg ggctcagcca  54420
ttgaacagca gttccacctt atcccaccac ctagagggcc agacctagtg agagcccgga  54480
tctggtctcc agcacctcag gggcacccac gcacccaagc ccaggtgtgc gcaccctgca  54540
ctcagggccc acttgtgccc agcccacctc ccccactgcc tggctccctg gggctggatc  54600
tccccacttt gagctgtgag gtccagaccc cgatgccgcc cggagggtac agtgaagccc  54660
gtgtgggcat cagggcctgg gagcctcccc cacccgacgc ctcccctcca ggtgtgcaga  54720
gagtctattc cgcctcatca acggctgggt ggatccccag aaaccctggc accgggaggc  54780
tgatggaggg gagggcgagg tgaatatgtc agtttatccc aatgcaagta gtggcctgtt  54840
gggatggggg agagacccgg ggaaatattt gggatgactg gagccgctgg ccctttaagg  54900
ctcctgtaac aggacacctc ctagacggga caggacgact gactgtgtgt gtttccccct  54960
ccctcctccc ctttcccgcg ccaggcccag ttcaatctgc tgagcagcac catggaccag  55020
atgagcagcc gcgcggcctc ggccagcccc tacaccccag agcacgccgc cagcgtgccc  55080
acccactcgc cctacgcaca acccagctcc accttcgaca ccatgtcgcc ggcgcctgtc  55140
atcccctcca acaccgacta ccccggaccc caccactttg aggtcacttt ccagcagtcc  55200
agcacggcca agtcagccac ctggacggtg agttccccta gtccctgagg gctgcgggct  55260
gcgggctgcg ggctggagag gaggtggctg cgttccccgc acctcaagag gtctgagctc  55320
gccccactgt ctgctcgggg ttcccacctg gcccgggcca ggaggagcat cgggcaggag  55380
gcgggtctca gggccgggca gtctgggtgt gcccacccct ctagacgtga gtggccagag  55440
ccagtcagcc tccaaagggc cacagagggg acggacttgg ccctgctggt gagatctctg  55500
ccaagactgg ccagcggctt ccccatgctc aggtgggatc tttggtttga aatcctgtcc  55560
tggacagagg cacgggctct gctgccaaga gttgtctgtc cgagacaggc ccacagccct  55620
agggtctgca gaacctgcct cctccaggca gcgagacgca tctgcgggtg ggtggatttg  55680
ggctttgctg gcactgtctc tggagtgtca tttccaggaa ttggcatgca ccaaggagat  55740
ggggtggaac caccgtgcca agggctcagg tcctcactgc ggtgcccctg gagacagact  55800
ggcccacggt ggggatcttg ctaattctga taacatcacc tgtgcacaag gccagtctcc  55860
tcgagccagg caccatgctc agggctttga gttgagctaa ctcttgcacc caccaacaac  55920
gcacagggct gactccatca ctgctcccct tttacagcca aggaggctga ggctcgggga  55980
gggaagtggt tcgcccagag ttctgctcat agtaagtggg ggcagccacc tctgcatctg  56040
tattcctaac cactgagctg ccctgcccag acagcttcag gggagggggt ctgtcaggag  56100
gggcaaggtg aaggctgcat gaccccagcc aggagtggag ggcacgcagg ggctgggcgg  56160
gaaaagcagc cccaagagcc ctccgggtct cccctcctgc accgaggagg gggcaagtga  56220
gccctgcctg ggcacccagg ccatggctgc aggaggggct ctatgggaca catgttggtc  56280
```

-continued

```
cggcccactg ggcagcgtcc cctcccccac gaggccccgc ctccccgggc acagctcagt  56340
gctggccccc tgaagtccat gcagggcggc cgcattccca cccectgtcg ggagtgctga  56400
gcaaggggcc cctcaggttt ttccgcttta agaatcgggt cccactgccc tgctggccat  56460
agctgcggtt ttcccacgct cctggagggc cgaggggcag ggcggagcct aaggtagact  56520
gtcaggctct gcaggtagcc ggacagtcct gccgggctgg tctggggtct gggttccagg  56580
ccccgcccgc ccccacctgc ggttgtttct gattctcact ccagccacgg gctcccccag  56640
ctgctggctc cgggctaaga gaaggctcag cccggactcg ctgggcttga tgggaggggg  56700
ctctgtgggc tgttgggctg aggggcagag gacctggcac ctcctccggg gcctcccacc  56760
tccatctggc aggcaatgcc gaccccagtg ctaacacccc gttttctcca tttggaaatt  56820
actcctccac gcaccttact gcacgatgga gataaggatg ggaagaccgt gccagggctg  56880
tggccagcac ggtgcttagc tcgcagcagg aggcccatgc gttgtcttaa ttgtggtggt  56940
ggtgtgctgg cctgggcctc ccaaatgagt ggttccgtgg cagctgcacc tgcctgtggg  57000
gcaaggggga ccaggcctat ccttccaccc cacttggagg tctgaagcca ggtcagaaag  57060
ccccaaggca tcctcacctg cacacctcca gcagcaggag cctcaccact gcttctctcc  57120
cacactcagg cttgttgcct aagtccactc tctcccctct aaggacactg acctcctgcc  57180
ctggggttta tgatgctggt ggtttctgga gagtgtctcc ctggagtcct ggcaggcagc  57240
ttgtgggagc tctgcctccc ttcctcccat ggtctgagga tgctgatggg gtcttcacca  57300
tgcttggaat gcactgcatg tggtctgagc tgatcctcat ggaaggacag gagcaacccc  57360
ctctctggct ggcttccccc atctagggta tctgccaccc ccaccccctg ccaggtgtgt  57420
ggcatcaggt tcaagggact tcatggtttt gtctcaactg ccttgtcctg caggacgggg  57480
tggccttgcc ctgtgggatg ggctggtctg ctcagaccag gcatcccggg ctggtcagct  57540
gcaccagcgg gaggggaaag ctgtgcctgg tgcccagcag aggagcagtg acacctcctc  57600
gctccctccc tgctgggctc tgtggatgct ggggcggggg gagggtgggg gggcgcgaac  57660
tggggaggaa aatgctgtcg cctgcaccca gggctcctcc tccgaagccc tgtggatcca  57720
gggggtggga caaacattga taatgagatt tttggcacct cagctctctg gggccagaac  57780
cccctccacc agggcttctt tccttgccca gggaggggca ggcaagtggt cggctcacag  57840
tgcagaacgg ggccgccggg cagcccgctt gctcccagct ctggggtccc accatgcggg  57900
tgctgcccag ccctgctgcc tgtgcttgcg tccggcctct gcaccgtgac tcctggggct  57960
cccggcacgc cagccggctg gtaactgata gataattcat atttttctca agtacaagtc  58020
cacattggct gccgccctcc tttctccccg atcaggaaaa acaccctcac cagcccccaa  58080
gtgaccacag atcagacctc agatctcctt gggcactgag aggtctggag gctgcggttc  58140
acaggtctgt gcatatgtgt gcatacacac gcatgtgcac acacacagac acagcaccct  58200
cccacatgca tgcacacacg tggatacaca agtaccttat gcacacgcag acacatgtaa  58260
acacacaggc atgcgtgtac atgcacaggc ctccccccat cactgcccag ggttctagta  58320
gctcccaccc catggaaacc caggaggagg aggaggcgag tcgtgggtaa ccgagcagcc  58380
agaggaagga tttgtgttta gccacgagag tgtaaccagt gaccagtgac agggcaaggc  58440
cggcatttgg tgagagggac cctgcatggt gagaggggtg gagctggcgt ctgctggggt  58500
cccaatccca gagctgcccg tgagcacctt ctgcttcgcc cctctgccct ggcatcctca  58560
cctgcaaaga gaggtatggc ctgccagcca tggtggggac aaaggagctg gctcttggga  58620
```

-continued

```
cttcttaggt cagggcaggg tacctgggga gcgctccaca cacgtgagct ctgagtgcag  58680
tgctgatggt gacaccagtg cccttctccc agttcaacac cctctgtggg acagtgtggg  58740
ctcagagtgt gggcagagct ctctgcaggg catgcatgac ctggcctctg agccctgctg  58800
gccactcctg tcctgggagc cctgcaggtt ggcagtggtg tggacagctg gttccaggag  58860
gccctcgggg cagagaatga acaggagttc ctctagctgt cagaacagcc cgacgcgatg  58920
ggcatcggat gctgtgacac cccggctcag ccgttctgcc cccagctcag cctcatcagg  58980
gaaggtggct gtccttggtg tttgggaagt ttggggacgg ggctctgagg tcaggcaaga  59040
aggcagtgtg gggttggaag ccctggccca gcacagcatc tgtgggcacc tcagggcatg  59100
ctgagtgaca ccacccacag cccacgaggc aggctgccat ggcaggatgg tgaggacaca  59160
cacaggtgcg atggccagct gccccagcat tcctccagac agaaagatgg cccggacaca  59220
gccccctgag tgccctccag ctgctctcag actcagcgtg tgtgtgtgcg cgagcgtgtg  59280
tatgtgtgtg tgtgtgtgtg tgtgcgcgag catgtgcaca catgtttgtc ttaggggaga  59340
gctggctcca cgggtaggaa agccccccgt ccaggaggga catatggaag gacggccagg  59400
gaagcacaaa ggctctgcac gggattcctg gggagaatga ggctgagtca acactaatgg  59460
gtctggagca accttcccag cgcctcggag gcttgcaagc aggagaataa tagcggaggt  59520
gtcccaacac gatcatggta tcaattgcat tatcctaaaa gtttatggaa tgcatgagtg  59580
gaattaatac cttttactgg caccagaagc aattatatgt gcgtaaagct gagggaagag  59640
ttctaacaat gtttattgtg gagatgaaac gtggattatt aggggaaaca agagtactta  59700
gggcgaaatt gcagcaattg ctgatatcat gtggcgcagg gatctgcagc agggacggag  59760
cttccagcag gcctgctctg gctgtggtca gcgcctcggg gctcgtggcc cgagccgggg  59820
ttggctcttc tctcttcact ttctggagca gccagaggaa ctcactcttg ggccctggag  59880
gtcacagaac ttagccttgg aggccccaag tgaggctggg gaggccccag ctctgagacc  59940
ctgggtcctg ctgccccacc ccacactgcc tggttcttgg aggagacagg agggagaacc  60000
ccttggggga caggattccc ttccataggc atgagactgt tgggggagag gcatgatcca  60060
atttacgttt taggaagaat catctatttt ctaggacttc tttccagttt ggggacagcc  60120
ctgtggaccc agcatgtctg attagtagcg ttggcagcag cattgcccct atgtgcaggg  60180
cctcccacac tccccatttt acagatgagg aaactgaggc tcccagaggg cacaccaggg  60240
tcacctgtca gcagagggca gagccggacc tggccccagc agccagaccc ctaaccttgc  60300
ccttgcagcc cgtgtggtgc cccaccccgg cccctacagg tccctggaca ggtccccacg  60360
agcagcccct gcccccctgcc ccaccctctg ctcccagctc tgtggggcag gtccctgtga  60420
ccctcagggc ccccagggga accagtgata aggaggtgct gacacctcag agggacctgc  60480
ctgtccctag gggagaaagc cttggaccga atggggtgtg gggggagccc aggctgtacc  60540
ttggccccca tgagccttcc actgctgtct gccagtgaat caaactggga ctgggggtgg  60600
agagctgtcc ctgtctgctt tcactgcttg gttttgttga caaaggaaaa tccctcaaga  60660
acgctttatc actggagtgc tccgaggctg gcgagcctca tgggcgagaa gccaggcagc  60720
tgggcttggg gaccggcctc tcctggtgcc tccctgcccc ctctgccttc acccctccca  60780
ggcctggcct cactgccact aactcccgtt gacaggggga aagagaggcc cacaggggag  60840
ggccgtccca ggcttctcct ggacccagtg ctgacgccaa gatgcggtcg taggtgacct  60900
ggaccttggg ccgtgtggga ctcggggcaa ggtggggggc tcagctgggc agtgagttag  60960
ttttgcttcc cggtctggtg ggtttctgcc accccaggcc agtggtcact tctgggattt  61020
```

tctgagattc caaaagttga agccacggac cctggagacc cggaccctgg aggcccagcc 61080
cctgcctctg ggtagagaag gccctgagcg acctccagac cttctgtccc ttttccgagg 61140
agcctcagga agagggggac agacaattcc agggtgtccc ggctggaaag aaaagcatct 61200
tctctgcact ccaggcggac agcgtgaggc tcagagatta cgtggcggcc gaggctggtg 61260
tccacagcca ggggttacga tggggctgca gaggccgtga gcggaacagg gcattttagg 61320
gcagaaagac ccttttggag aaggtaacag cactccaggc ttcagtgagg cagaagtcag 61380
agcccatggg gaaaccgcac agggggatta cctaaagccc agagccaccc caagggttgc 61440
aaacccaccc ctcccccagc catgccactg gagcgaggca cccagctcct tgcacctggc 61500
gttggggaga caccactctc tgcaggggtc agagattcgg aggccaaaat tctccttccc 61560
ccaggcattt caatgaagat ttacaaagtt tagcaaaaac ctagattcta gccaactatt 61620
accttaaaag ctgaagaggg accaccccac catgtccaca gcttactccc ctccctccgc 61680
tgtctccggc cacctccagc tgctgccaat tccagccccc aaggctgtcc caggaagctg 61740
tggccagaga ctccgggact gtcctgtgag cagagggcac ccactgaccc tggggcaccc 61800
ttccaatccc cacagctgac aaagccgggc ctcaaaaggc tgggttaatc ctggcttctc 61860
ctcaaagcca ccagtcaggg tgggggtgag gatggtgggg gcaaggatgg tgggggcttc 61920
ctccccagga gttaaggggc cctctctgca gtgagcagag caggcctgtt gccagcctgc 61980
tgggccccctc gtgggacagc tccagggcct ggcccacagt cccgctagct aggtccttgc 62040
cagaggccgg aggagaggcc aggctactgg caacgggccc tccagctggc gctgtcaaaa 62100
agcaagttgc gggcagagga ccctgcgctt ggtcccggcc cagggcagag gctgagtgtg 62160
gtgctttgaa cactctgtgt cttcagagcg gaggggcagc tgctggtggg cattccgggg 62220
ccctctgcaa gccccagctt ttgtctctgc ggacccaggg cactgccctg ccaccccctc 62280
tgtccccaag gccccagatg gggtacctgg gtcctggaat aagagcagat ggagttcctc 62340
gccctgcctg ggcagctcat tccttcccgg gcttgggcag agtgacagtg atagtagcag 62400
ccacagggca cccgcacgcg gtctcagtga atcaggacag cggcgaccgg gtggggactg 62460
ggccctgagc tcctcacaca gcatctcggc agcaaagtgg aggctggagc tgtccaggct 62520
gggccaccca atcccagcca gacacaaggc agtctgtgtg agtctcagtc tctattgtcc 62580
atggagaccc atccccagca ggaccagggc aggtgaggcc cctggctgtt gttcccctta 62640
cccctaaggg gcttaagtcc agccacgggg taagaagccc atgtcccacc tgacacctct 62700
gtagtaccgt ctttctggaa cccggggtga cgcctctgca gtgcccagtc ttcctggaac 62760
ccaggggtga cgcctctgca gtgccgtctt cctggaaccc aggggtgctt aaggcgggtc 62820
tctgcctaga ccccgacccc aggccccagg acccaagtca agcccagcag tgacaaaggg 62880
ctgggagatg gagcttgggg gtcagacagc tatggtctgg gtgctggtcc accccagctt 62940
agcaggcagg tttgggtcac taaacggagt gacagtgcct gacctcccag ggccaaggtc 63000
aggtgagggc cccgcgcagg gcaggcacca gtgggcagtg gatgtggcca tgagggtgga 63060
cccaggtgcc ccattccctg gcaggtggac agcactcact gtctccccag gtctccacac 63120
caacagaggc agacaccttg ggcaaacgct gcctcgcagc ctcccccaac actaggcccc 63180
tcttatctcc tctgcctgtg gccctcgtct cctactggac ccctgggcct tcactatgca 63240
ctggagacaa agccaccaag tctatcctgg gctcagcaca tacctgcttc cctcccctac 63300
cccgatcata gcccaggatg gagatcccta gaggcagccg tgcatgggac gaggatcgag 63360
caggctccag ctcctgtggt ctgggtgcac tcagtgtctc ccagggagcc gcgcttccag 63420
gccgttgaga gtcccccgtg tggctcctgc tcacctgttt aggacatggc tcaaggtcgt 63480
ggtggggcag actgcccagc tcctcagggt tcccacttgc ccctggcctg ccctccccag 63540
tgagcagttt cttgtccaca gcctctgggg ctctagcagg cctccgtcag ggctgaggat 63600
cgcttggcat ctgcagagga tgtttctgcc tctggttcat cctccataga gctcctggcc 63660
tgggagcccc ggctggccag catgggggtg ccagcagaca catctgtctc ctgcagcccc 63720
cccagccagg agctctttca cagcagcctc ttttcttggg cagcgctggg cctggcactg 63780
gctgtggcct cacaggcatt ctgaagctcg cttgggcctc tcatctgcct ggcccatggg 63840
ctgtggatgt cctggtgagt gagccgtcac tgcctcgacc atgggagccc cagcttaaca 63900
ccaaggtgtt ctgaaacagg ggcgattgcc acatgtgtcc tttccccctc cccaggctag 63960
tggcttccct ggggcaggga gggaccagcc ctgtgacatc ctgccaggcc tccctgacat 64020
ctgtcagagc ccagcctgtg ctcccagcag ctctctgagg gcgacagtga ctgtgcacca 64080
gtgaaggcca cagcctccca cgaagggggc tgtcaccaag gggggccctgt ggctgccacc 64140
tgaggatacc cttcctctct cagaaggaga aagggaccca ggaggaccct aatccacagg 64200
ctgttgaccc tggctcaggc atgtgtttta gggggtccat ctgtgaaccc acgaatttaa 64260
tggaaagggt tctgtggctc agccccagga gcttttctag ggagaggaag ggtccagggc 64320
cttggcagag ggtgggctca aagaggcccg taaccccaga gaggagagag atgcacccct 64380
aaacacacag acgcacacac aagcaaggga actggataaa agtgagcaat aaaaaaaatc 64440
gtttaaaaaa taaaagcccc cactgcaggc cccatcttcc agaatctgtt gcaacagatt 64500
cacccacgct ggttaacggt atttgcggtt tgcaagatgc tacacgtccc aggaaaatga 64560
cagacaagtt attatcacct ctccgctgtc ctcctgccca aacctgcccg tgccgggcac 64620
ccagctgccg gggagcgagg agcgggcaca aggaaattag cagccccccg ctgcaccctc 64680
ccctcaccca cccccgcacc agccctgcca ggcccagggc tcccagccag gccgggccca 64740
tgttgtactg gggcgggggga ggaggggaag gagaggaggg tcggagagga gccggcagcg 64800
tggggaggga tgggcacagt ggcgtttggg caaacccttt cctgcaagca ggacggtgca 64860
cgcaccctgg gcaggcaagt ccaggcggct ccgtgtcaac agccgaagat aaatacgatt 64920
ttatcagctc ggaatctgtt gaaacacatc catctagcgg ttctagggaa ggagaaggca 64980
ggaggggggc ggcggagggg aagtgtctcc acgtgacctt tcctatagaa taggctccac 65040
cggagtcctc ctcctcctgc ccgttttcca cagggccaag cccaggcctg aagcctagag 65100
gcctgctggg gagacaggag gaaggagctg ggggagcgct ggagccgtcc tgggctcagc 65160
caccctctag aaggacctgg atctctcagg gctcccttcc ctcctgtggc cacctgtgtc 65220
acccaccccc agatgctgcc agggcagggg acatcacaga catcctcccc gaggccaccc 65280
agctccggcc cggctgggca cctggggtcc agttagtgcc agggtgaggt ctgccaggca 65340
tgtatgcccc aaaggccatg tgagcactgc actggggaca cctgtgggga ggagagccag 65400
gcccaggacc ttggtggcct tactggccag aggggaggag aagtgctcac atcgcctgag 65460
gacaggggcc tccttgctct ccaccctgag gcctgggcct ccctccgcca ctggcccagg 65520
tcgaagacct gtccgttcta ggccgctcca cactccagtc cgagccccca cttcccgggg 65580
tgggtggtcc ggccgccgcc tgcaccgagt accagggaca gctcccggcg cgcccaagct 65640
cctccccggg gcggggcggg gcggggcatc cacagtgctc cccgcgcctg ggcccccagg 65700
acctcttgca gacgggagtc cctcagacag tgcagagacg ggagcacgca ctgggccctg 65760
cacccacttc gtagcgccct ggcctgggac gccccaccac gcagcttcca gagcaaggat 65820
cgccacttca ccctgcccgg agacccagag ggagtggggc gggctcagca gggcgctgct 65880
gagaggccgc tgcctaggtc tgcgaaatgg gagcactgct gaccctgagg cccaggcggg 65940
cgggagctca ggctccgcag aggactatgg ccgggggtgc tggggcaggg gcctagggga 66000
ggggctgcag gggccaggca ggagctgtga aacccctcac gctgttgaga ctccatgggg 66060
ctgtcaggga gcgacggctg ccggggcctc tgcccgcagg cttggttgca cccagagcct 66120
tactccatct gtgtccaact ggctgaggag cccaggcggc ctcccctccc cctgagtgtc 66180
tggggctcct tggtggatct aatgaccccc atctcaggcc atgggctgtg gcactagggt 66240
ggaagaagcc tcgggggact cagccccgga aagggaactg tagggaagcg gggcctgtgt 66300
ggctccagcc ccccgcaacc aacacctcct cacctggtgc tgagaataac gagggcgcag 66360
tagccactaa cacctgcagg ccactgtgtt cccaggggac acgcagtgag tcagagatgc 66420
aggtggagag gcttgtgcag tggctagagg catcccagct gacgagcaca aagccaaaac 66480
tgccacccac agggccggac ctcagaggcc cttctccttt tgccgcccct gagactctga 66540
cctgagccac cccggccggg gtctgtttca agggggggtct gccgcgccct ccctgctctg 66600
tggtttccct agggagcggc taggatggat ggcatttgtt gagtaccacc tgtgtacctc 66660
catctgctac acgttactga ggagagacga gggggacaga gccaggtgcc tgaattccag 66720
ggggcctgtg tgctctgcac acaagaggtg ctccataaat gctcagcaat gggcagctcg 66780
ccctgcaggc tgccctggcc tcggagaagc ctggcgacac ggctgccggc cctgtgttcc 66840
tctcccctgc tcggggcact ggcagacaag agcctgccac cacctggccc ctcctccttc 66900
tgtccccaac cagcacagat ggagaccagg cgtggtgtgt agcttcaggc agggcctttg 66960
tccaagagac cagtgcctgg acacaggcca ctgcaagttt gggccaagag ccctccctgt 67020
ctgagtctcc tgagggtccg agtcccagag ggtctgtgct gcgagctgtt cccatgtgcc 67080
ctgggggcag ggctacctgc ttatccttcc aagtgatgct gtggggagca aagggggcat 67140
ttgtaatggt ggggacactg tacatcagtg gtcacctcca gggaagccag actgacccca 67200
caacaaggag actgctgtac ttcccgctgt gcccaagcct gcagctccga cagtccaggg 67260
caggcgcccg cacaggggtg ggctgctagc tctgcaaggc tgtttctgct tttcttttt 67320 tctctttgtg tgtgtgtgtg tgtgtgtgtg tgtgtgtgtg tgtgtgtgtg tgacggattc 67380
tcactttgtc acccaggctg gagtgcaatg gtgcgatctc ggctcactgc aacctccacc 67440
tcccgagttc aagcgattct cctgcctcct gcctcagctt cctgagtagc tgggactaca 67500
ggcgcccgcc accttgcctg gctaatattt gtatttttgg tagagacagg gtttcaccat 67560
attggccagg ctggtcgaac tcctgacctc agctgcctgc cttggcctcc caaagtgctg 67620
ggattacagg cgtgagccac cgccctcagc ccgtttcctg cttttctaaa cagcgcccag 67680
cctcccctgc agggctgtgc atgatggttc cttcctgtgt tttaaacagg actggggatg 67740
ggcggcttcc tgcctaaggc cctgtgccca aggtgggggt cgcaggcagg ggcagtggag 67800
ccactctggc tccaggggct ccaggtggac ggaggaccta ggaggggcca gctctttggt 67860
atccaattcc catcctgagg aggccactga aggacccccct tccacttgtc cctccagccc 67920
cctcacaccc atggcaggga cagaccagcg ttcctggctg ggtctcattc ggggagccca 67980
agtagctcac cagagagggg accgctccca ctgcacagga acaagggcac tcagggtgcc 68040
ggggacccag gccccaccca ccatggctcg cagcctccgt cagctccatc tcccctgtct 68100

-continued

```
ctttcctttt tccttcctgg cttttcgtgt gcctgcacct gccaaggacc tatgtggctc  68160
ctgagagccc ctcatgtccc ttgatggcca gagaggcagt actggtggcc agtgggggtc  68220
agggggtcag ggccccctaa cttccttggc aaagggaaga ctccacctgc agcttccctg  68280
gttctgccag tagctccctg tctctgacct cagtttcccc aactgttcca cggtggagtg  68340
cgatgggaca ttctccaggg cacttgcggc tgcagtgact tgtgattctg agtcatcggg  68400
ggctggtgag gggcacagag ggcatggggt ggcagcagaa gtcattctct gagcctgaga  68460
ctggggatca ttcctgatgg ccctttgggg agagagcatg aggactccca gcaggtgacc  68520
aggagccaga cgcttgggaa atcagccagc ttggaagtga gtggacgccc ctgcagcggc  68580
ctcagcgggg tcacttttag aactcatgag agccggcctg ggtcctcaga tgggcagccg  68640
ggccctgtga ggcaaagaag ctggaggcct ctgcaggggc tggctcagga agggtgtcat  68700
ccagtcctcc tgcagcaggg cccacgccag ctccagacag acctattagc tcctcgagtc  68760
ccaagctggg gatactgggg ctgtgagccc agaggggccc ccagagtggc caagaccaag  68820
ccacacagct cggctgctca gacttggtgg ccccagcagg agagggtgtc agagtcacca  68880
gggctgctga ggccatgaga ggccttcaca ccaacccaga gagctctcta tggaagcttg  68940
aatgcatagt gggcaaccag cccatcacac attaaccact tgctctgtgc aaatgccaga  69000
gaagcctagc tctggtctta aaaacagatt caatgctgca aacccacctc ttcaaaatgc  69060
cgcagtcagg gacatggctt ccacaggcct ggctcccagc ccccgttccc gccctcactc  69120
tccagcagcc ccttcttgct ctcctggcct ttcttgtccc catccataaa cctaaagcct  69180
ctctgcctga ctgccaccgg cactcacacc cctgctgtca tggagcccaa atgacccgat  69240
ggctgtggag tgggtgccag ggcagctgtg cctggattca cgcctcaaag gacagacacc  69300
tggagggatt cagcagaggg gctgcttggg gcagtcttca tctgggggtt gtggaagggg  69360
cacccatggg gaggacgtgg ctcccaatgg ggggtggcct ggacaggggt gcagttggga  69420
ccactggtct cacccgctcc ctctccccca ctccagtact ccccgctctt gaagaaactc  69480
tactgccaga tcgccaagac atgccccatc cagatcaagg tgtccacccc gccaccccca  69540
ggcaccgcca tccgggccat gcctgtttac aagaaagcgg agcacgtgac cgacgtcgtg  69600
aaacgctgcc ccaaccacga gctcgggagg gacttcaacg aaggtgaggg cccccagctc  69660
ctctgcccac ggtggcactt tgcccagcat cccggacagc acagccgggg gctgcctaac  69720
tgggagagag tggggctgac agcatgggct tagccattcc cctgcggagg gctttcagtg  69780
cctccaccag cccccatttt cccagttctg agtgggacct ggggggggccc atgctcctgg  69840
gcaggggcaa gtggtctggg cagagtctga ggggcagcgg ccttctgggg ccccagagat  69900
cctatgagtc atagcccctc tctccagtgt gcctggcagg gcctacgggc taccccaagg  69960
attagcagga gaatcagggg gcagagccac tgggcaggca cccccagagc acaagggctg  70020
ccagctggcc tgagcctcac ctggaagccc acaggactgg gcctggtggt ctcagttctg  70080
ctgcgatgca cctggcacag ctgggcgcct ctctgcacct ggcacagggg tgggcacctc  70140
tctgcacctg gcacagggct gggcacctct cttcacctgg catggggctg ggcacctttc  70200
ttcacctggc atgggactgg gcacctctct gcatgtgaca cagaggtggg cacctggcat  70260
ggggccgggc acctctctgc acctggcatg gggctgggca cctctttgca cctggcacag  70320
ggtgggcacc tctgcaccta gcacaggagt gggcacctct ctgcacctgg catggggctg  70380
gacacctctc tgtgcctggc acagggctgg gcacctctgc atctggcatg gggctgggca  70440
tctctgcacc tgacaccggg gtgggcacct ctctgcacct ggcatgcagc tgggcacctc  70500
```

-continued

```
tctgcacctg gcactgggct gggcacctct gcacctaaca ggggtgggca cctttgcagg  70560
tggcacagag ctgggcacct ctctgtgcct ggcacggggc cagcacctct ctgcacctga  70620
catggggctg ggcacttctt tgaacctggc acggggctgg gtacctctct gcacctgaca  70680
tggggctggg caccctttga acccggcaca gggctgggca cctctctgca cctagcacag  70740
gggtgggcac ctctatgcac ctctctgaag tgtcgacccc tcccggcagg acagtctgct  70800
ccagccagcc acctcatccg cgtggaaggc aataatctct cgcagtatgt ggatgaccct  70860
gtcaccggca ggcagagcgt cgtggtgccc tatgagccac cacaggtagg ccaggagcca  70920
ggctgtgccc agggccctgc agtcagctgt acgggtcggg ggaggggtcc cctgaggcag  70980
cccctgtccc tcctcagttg gctgatctgc ctgcctgtcc tgtcggcatc tgtccagggc  71040
tccctgctct gtgataagtc tgtgtcggcg gctccttcct cacccacacc cgccccactg  71100
tgcacactgc tgctctgtcc ccacatccgc ctcgggcact ctcggggcct cagtgtgccc  71160
agctccatag tggggagtgg gtcttcagcc ttgccctctg ttggtgccca acactggttc  71220
cggcctgggg ctcccagaca cagggatttg ggagatgggg aggtccccgc ccatttagac  71280
cctggattgg ctggggcaga accaaaccag caacagcgcc tgaaggggtg gcaaattcta  71340
caaagggggt tgagggatgg tggaaagact cctaggccag gccaggggcc caggagaggt  71400
ggcctgcagg aggctgaggc tggtcagcag ggtggagagc cgggaggccc cgctgggcac  71460
cacgtgggtg gggggtgcag gggactgggg ggcatatagg ctggaggga ggggacacgg  71520
agaggctggg ggctttgact tttggcccaa aggcagcata agtttctggg acacaattct  71580
ggagctgatg tggggcccaa ctggtgtgaa aggctggggt agggggaaac agagggtttg  71640
aagttactgc gggatggtgg ggcaggggca gaacaggagg tgaggagtgg gtaccaggcc  71700
cccaggggaa ggcaggcaat ggcaggcctc tgccttccct gtacctggtt ctgagaccag  71760
gctccatgct gtacccagcc ccagcctccc ccaccaggtc cccatccctg taccagaccc  71820
ccaggacacc ccagactcct gtacccagtc tccaggtcct ccacaagcct ctaccctgta  71880
cccaggcccc cttcgacgtc cccatcccac catcctctaa gagcagcccc ttatgtcagc  71940
agaaccaggg cccgggaggg ctccctgaaa cccatgtccc accctcacct gcctaggcct  72000
gccaggaagg cagagctcta tcgcccccctg gtggctgccg tgtgacagca gttctgagaa  72060
aggccaagat tttcccaaac ccctaatagc ttttgtattt gtccccaggg tgacatgaaa  72120
actgcccaca ttgtggtctg gggacactca ttgatcaacg gttttggttc atggctgggc  72180
gcagtggctc acgcctgtaa tccaagcact ttgggaggcc aaggcgggtg gatcacttga  72240
ggttaggagt tcaagaccag cctggcccac agggcgaaac cctgtctgta ctaaaaacac  72300
aaaagttagc cgagcctcgt ggcgcatgcc tgtaattcca gctacttggg aggctgaggc  72360
aagagaatcg cttgaacccg ggaggcagaa gttgcagtga gccaagatcg cgccattgca  72420
ctccagcctg ggggacagag agagactccg tctcaaaaaa aaaaaaaaga gttttggttc  72480
atgtctcagc tgtactgcaa aatccctggg aaacaggagt gtgctggggg tgggttcgct  72540
ggggacagct ctggttcctc tttctgccca ggtgagcccg cagcatgcaa cacacacgta  72600
gggccacaaa atctgtgcag gcacactcac acccagcatc tgggcttgac ctccagcctg  72660
tgtcagggga gaaggttggg gcaaacagac cacaggactc tgtgcttctc tgagagcaga  72720
gaccaggtct gagccctccc agaacccaga accagcccag tgcttggggt tcagtgatct  72780
tcatgaatgg gtggctggat ggggtgagtg ggtggatggg tggatggatg ggggtgggtg  72840
```

-continued

```
gggtggatga atggatggat gggtaggtag gtgggtggat ggatggatgg ataaatgggg  72900
tgggtgggtg agtggatgaa tggatggagt ggtgaatggg tgaatggatg ggtgggtgga  72960
cggatggatg aatagggtgg gcggatggat ggggtgggtg ggtgaatgga tggatgggtg  73020
ggtgggtgaa tggatggttg ggtagaggga tgttgaatgg atgggtgggt agagggatgg  73080
gtagatgggg tgggtggatg gatggatgga tagactgata ttgttgaatg gatgagtggg  73140
tggatggatg tttagatgga tggatagata ataaatgggg gagtggatgg atggatgggg  73200
tggggggtg gatggatgga tggataggat gatggatgga tggatggggt gggtgtgggg  73260
ggtggatatg tgggtgggtg agtggatgga tggagtgggt gggtgggtgg atggatggat  73320
ggattgactg atattgaatg gatgggtggg tgaatggatg gttggatgga tggacagata  73380
atggggggag tggatggatg gatggggtgg atgggtggat ggatggatgg gatgggtgga  73440
tggatggggt gggtgtgggg gtggatgtgt gggtggatgg atggagtggg tgggtgggtg  73500
ggtggatgga tggatttatt gatattgaat gggtgggtgg gtggatggat ggatggattt  73560
attgatattg aatggatggg tgggtggatg gatggttgga tggatggata gataataaat  73620
ggggggagtg gatggatgga tgaatggggt gggtgggtgg atggatggat ggataggatg  73680
gatggatgag gtgggtgtgg ggggtggatg tgtgggtggg tgggtggatg gatggatgga  73740
tggagtgggt ggatgggtgg atggatgaat ggatgggttg atattgaatg gatgggtggg  73800
tggatagatg ggtagataat aaatggggga gtggatggat ggatggatgg atggggtggg  73860
tgttgggggt ggacgtgtgg gtgggtggat gggtggatgg atggattgat attgaatgga  73920
tgggtgggtg gatggatggg gttggtggat gaatggatgg atggatattg aatggatggg  73980
taggtggatg gatgggtaga taataagtgg gggagtggat ggatggatgg atggggtgga  74040
tggatgcatg gatagacggg tgggtggatg gatggggtgg atggatggat ggattgattg  74100
atattgaatg gatgggtggg tggatggatg gttggatggg gtgggtggat ggatggggtt  74160
cgtggatgga tggggttggt ggatggatgc atggatggat attgaatgga tgggtaggtg  74220
gatggatggg tagataataa atgggggagt ggatggatgg atggatagat gggtgggtgg  74280
atggatgggg ttggtggatg gatggatgga tggatggatg aatagataaa tgggttcgat  74340
ggatggatgg atggacggat ggatggatgg atggggtggg ttggtggatg gatgaatgag  74400
tggacagata tacaaatggc aacaactata gagcagggca tccccctgcc tacgtggagc  74460
caggaccaga catggagctg gggctgccca ccttagtgga ttggggctgc gtgctgatgc  74520
tagcccctct ccctgctccc ccatgtgcag gtggggacgg aattcaccac catcctgtac  74580
aacttcatgt gtaacagcag ctgtgtaggg ggcatgaacc ggcggcccat cctcatcatc  74640
atcaccctgg agatgcggga gtgagtcccg ggcacacggg gtggaggtgg gacagggctg  74700
ggcaggcacg gccgggggag aaggggagct gtcatggaga cctgcaggcc aaggctagct  74760
tggggaagag actttggggt gtgctgctgg aggaaggaac cgccccctgg cctgcagggc  74820
ctgcctgggc acaagctggg cctccggagg gaggtgggag tccccggcga ggtctcaggg  74880
cagcctcaca gctttgagcc tctgactccc tctagcggga acactcgctg ccggcactgg  74940
gtgctctgtg gtgaccgagg gctctcaagg ccggtcctgc agggtccgag gtgggtgggg  75000
aaggtgggca ggttgagggt gggcagggtt gagctcacaa ttctggctgt gcccacccga  75060
cagtgggcag gtgctgggcc gccggtcctt tgagggccgc atctgcgcct gtcctggccg  75120
cgaccgaaaa gctgatgagg accactaccg ggagcagcag gccctgaacg agagctccgc  75180
caagaacggg gccgccagca agcgtggtga gcggccggcc aggggaactg gacgcgtgtg  75240
```

```
ggaggagaag gggacacatt ggcaggacac aatgtgagcc cgcgtcccag ggacagggcc  75300
agtccctgaa cggcccccca cgcccagact cctccctgac ggagcctgag agcagccccc  75360
atataagtcg cttgtcctgg gccaagggca cctcagaggc ctgggtggca ccgcaggttt  75420
gcccgtccct gtgggttgct caccaccgga cccacctgga gaatcgattg gccccaaggg  75480
tggggcaggt ctccctcctc ccggaaggag gcctcaccct ctggtcctgc ctgctcaccc  75540
cgcctgccct gcctggcctt ccagccttca agcagagccc ccctgccgtc cccgcccttg  75600
gtgccggtgt gaagaagcgg cggcatggag acgaggacac gtactacctt caggtgagtg  75660
tgtgctcctg cacggcagcc gggagacctg cctcacctct gtcgtctgct gagcccaggc  75720
tgggccatgg ggagggactc tggagaccat ggtggagggg gcgggaggag cccagccctg  75780
tgtgagaggg tccagagggc agaacctgct tgcaagagcc agaccagcag gacccaactg  75840
cagggcattc ctgagagtcc cctcagtccc aaaaacccag cgtcatgcca tttacaatga  75900
agccatgtgt acatagcaca ggtagggtgg tgcggagtgc caccaggtta gaagttcagc  75960
aagaatccag gaccctaacg ttggccagga cccgtggcca cggccagccc ccatgagtgt  76020
gcctctcaca tgtggcctcc aacaggtgaa ttaaatcggc acaggcttgg ctgggagtca  76080
tcttccatga tgtgaacttt ctgtttttttg agctccagaa tgagccccag ttggggtcag  76140
tggctcatgc ctgtaatccc ggcattttgg gaggctgagg cgggtggatc acttgagccc  76200
aggagtttga gaccaaagtg ggcaacatgg tgagaaccca tctctacaaa aattagctgg  76260
gcgtggtggt ggcgtgcagc tgcagtccca gctactcaga agactgaggc aggaggatca  76320
cctgagggca ggaggatcgc ctgagcccag gagtccaagg ctgcagcgag ctatgatgat  76380
gccactgcac tctagcctag gcgacagagc aagacgctgt cgaaagaaag agagagagag  76440
agacagagag acagagagag acagacttgg tttctaaaaa cccagtatct gttggtaggg  76500
gaggaagagg gaggcttggg ggccacaagg agcaggcatg gttcttgggg acaggatacc  76560
tgcccactga gtcaggggct ctggttagac ctgcttcttg ggaagaggaa agaagatcag  76620
gggatcctga gcctctgggg tgctggggaa cccccagaaa ggacagatgc tttgccaagc  76680
ccaggtcctc ctgaggctgc ggccaccccc ctcccgtggg ggtctggggc acgtgggcag  76740
agatctgctc ctctgtgctc aggtgcgagg ccgggagaac tttgagatcc tgatgaagct  76800
gaaagagagc ctggagctga tggagttggt gccgcagcca ctggtggact cctatcggca  76860
gcagcagcag ctcctacaga ggccgtgagt cagccctagc ccaccatcag tgtggggaag  76920
gaggacatgg cttaaccccc caggagaagg ccaggaggac cagaaacccc tccagaaggc  76980
atcatctgcc agggacaggc agcagggtcc agagcagagc ccaccccaca tctcctcctc  77040
caggaagcct tctagcactt ggggctgccc tgggaccctg ggtcatggcc cttgctatgc  77100
ctctgccact gaggggcctt gtaaatgtct gctgagtgga aaggccagga ggggtggcca  77160
gagtgaccat gacccaccaa gaccagagtc cgattccagt ggcacaggtc atccccctgc  77220
ctcccggccc cgccatggcc agtgtccttc tcaggcgcag gcccagtggc cgtgcatggc  77280
catggttggg gacagggagg ctgggggagg atgaagccac tctctgacat cagaggctcc  77340
acccattcgc agcatggggg catcacgggc atgggtggtc ggtgggcacg aggctgcctt  77400
gcttcccacc catgcgagcc gttgcttctg agcaggagtc acctacagcc cccgtcctac  77460
gggccggtcc tctcgcccat gaacaaggtg cacgggggca tgaacaagct gccctccgtc  77520
aaccagctgg tgggccagcc tcccccgcac agttcggcag ctacacccaa cctggggccc  77580
```

gtgggtgagt cccttgggca gtgcgggccc acgggcaggg cggggaggcc cactgggggc 77640
gcctagctca ggacacacca cccagctcgg gacccagggc aggtgtctct gtggctggct 77700
ccttccagcg gttccaccct ctgggcagga ggcgcagcca cggatagccc tctctgccca 77760
ctcctggctg tgggaggtgg aggggggcgt ggttaagagc gtggaaccca catgcatgca 77820
ctgcctcttg gcaggcgagg gagcttgggg aaggctctta acattacaca gcctgtttcc 77880
ccatcagcaa atggccacag aagtaccagg ctcactcctt gtgaggaata aatggtgcaa 77940
gacctcatca ggggccccag cacaagccgg gggctccatt ggatagagtt tgggcccccct 78000
tcccctggaa ggtcctcatg tgggcaggac caagcatgtt cccagtgccg tgagcaagca 78060
cccccaggtg tttcctgagg ccctgggatg tggccagcac tccagtgcca gctgcgattg 78120
cccttacaac ccagtgcccc gtacgcacgg tcaccccccgt ccctactagg cggggcgagg 78180
agacagggcc ccaggtgttc agcccttgct caagcctcta gctggcaggg gtgatgccca 78240
gcgtcacatc gccaggcctt gggatggctc cctggtgtcc agaggtgtct ggagcctggg 78300
tggaggctgc acctggatgc ccagcctggc tgccctgatg gccccacctg cctctcaccc 78360
aggccccggg atgctcaaca accatggcca cgcagtgcca gccaacggcg agatgagcag 78420
cagccacagc gcccagtcca tggtctcggg gtcccactgc actccgccac ccccctacca 78480
cgccgacccc agcctcgtca ggtgcgtggg ctgccgaggg cctgagcatg tgctgtcacc 78540
ctgtctgttc acctctgtcc ttctggccat gtcagctgcc ctgccccacc ctgtgtgctc 78600
accactcgca accctggatc agacaggcgg gcgggggcag tcaggccagg agcatctgca 78660
gatgctgggg aaatggtcca cttagaggaa aagcacaaaa agccggggtc ctccactgac 78720
ctgtccccag ctgagcacgt cccctccctg agggatgccg tggccacctg tgggctggag 78780
ccacccttcg gagacagcgg cagtctccgc cccagccagg ccactctcag agatgggggc 78840
tcgcgcagcc ctgtgctcgg aagctaatgc tgcttccttt ctcaaattct ctctgcagtt 78900
ttttaacagg attggggtgt ccaaactgca tcgagtattt cacctcccaa gggttacaga 78960
gcatttacca cctgcagaac ctgaccattg aggtaacgcc cgggtggacc ccgctctgca 79020
gaggcagtag ctggaggggc ccctgtccgg agggcaaaga gccttctctt ccttgctctc 79080
gtggctggga aacttggaaa ccctttccca cgggcaagca gatgcgatga tttgactctt 79140
gagagcttag gcagatgcag ccaggcacgt ggctggtggc gcgggacaca ggcccaggcc 79200
tccggatgct gaactggtca tttgagcctt tttggactcc cagcagccag tgtgcctttg 79260
attttagggg atgggctgtt tccaaggcac aaagaacaga agaatgtaag gccccgaggg 79320
agtcagtcca gttcagtgcc atttacagag aggtcagcgc catttacaca gacaggaaag 79380
gggacctagg gaaggcaagc acctggcccg aggccacaca gctcttggca cccatggcag 79440
ctgactgcag gcaccatgat taaacagcca cggcttgtct ttgggttaga gactagtgga 79500
gtacaaagcc tgctggtagc ctaggacggt gtgaaccaca gggcaccgtc agtcaaggaa 79560
gagcaagccc tctggtggga acctgccccc cagccagtgc cgcggcccag gtccaaggcc 79620
cgtcccagac catccccagc ctggggctgc agacagagat gagggtcagt gcgagctagg 79680
gccagctgct cagcctaact gtccctcgtg cagagagtgg ccgcgtctgt gtccactaac 79740
cgccctcccc gcaacctgtc cccagtgacc cacgctgagc cagctccagg tcacgttaac 79800
ccttgcctcc cctgagtgat gtgtgtgctt ggtgtggtgc ccagagggtg ttgggagctc 79860
agggatgagc tgggggtcca ctccaggggg cagggacatg gagaccaagg agggccctgc 79920
cctgaggctg ggaggcagtt cctcccccag ggccaggtag atgctcaggg ggctccatgt 79980

```
ctaacactcc caggtcaggg cccaggcccc gcacaggcca ggagtgactc tggtgggctc  80040
tccccctccc ccgtctcctg cctactctgg ttgggggtgt aggggccagg gtgtggtgtg  80100
gccagacctc caggcccagg gcgacccccc ctgctctccc tgctccactg cccccTgccc  80160
ctaatgcgcc ggcctctcgc aggacctggg ggccctgaag atccccgagc agtaccgcat  80220
gaccatctgg cggggcctgc aggacctgaa gcagggccac gactacagca ccgcgcagca  80280
gctgctccgc tctagcaacg cggccaccat ctccatcggc ggctcagggg aactgcagcg  80340
ccagcgggtc atggaggccg tgcacttccg cgtgcgccac accatcacca tccccaaccg  80400
cggcggccca ggcggcggcc ctgacgagtg ggcggacttc ggcttcgacc tgcccgactg  80460
caaggcccgc aagcagccca tcaaggagga gttcacggag gccgagatcc actgagggcc  80520
tcgcctggct gcagcctgcg ccaccgccca gagacccaag ctgcctcccc tctccttcct  80580
gtgtgtccaa aactgcctca ggaggcagga ccttcgggct gtgcccgggg aaaggcaagg  80640
tccggcccat ccccaggcac ctcacaggcc ccaggaaagg cccagccacc gaagccgcct  80700
gtggacagcc tgagtcacct gcagaacctt ctggagctgc cctagtgctg ggcttgtggg  80760
gcgggggctg gcccactctc agccctgcca ctgccccggc gtgctccatg gcaggcgtgg  80820
gtggggaccg cagcgtcggc tccgacttcc aggcttcatc ctagagactg tcatctccca  80880
accaggcgag gtccttccaa aggaaaggat cctctttgct gatggactgc caaaaagtat  80940
tttgcgacat cttttggttc tggatagtag tgagcagcca agtgactgtg tctgaaacac  81000
cagtgtattt tcagggaatg tccctaactg cgtcttgccc gcgccggggg ctggggactc  81060
tctctgctgg acttgggact ggcctctgcc cccagcacgc tgtattctgc aggaccgcct  81120
ccttcctgcc cctaacaaca accacagtgt tgctgaaatt ggagaaaact ggggagggcg  81180
caaccccccc caggcgcggg gaagcatgtg gtaccgcctc agccagtgcc cctcagcctg  81240
gccacagtcg cctctcctcg gggacccctc agcagaaagg gacagcctgt ccttagagga  81300
ctggaaattg tcaatatttg ataaaatgat accctttttc                        81339
```

<210> SEQ ID NO 3
<211> LENGTH: 81365
<212> TYPE: DNA
<213> ORGANISM: Mus musculus

<400> SEQUENCE: 3

```
ggtcccgctt cgaccaagac tccggctacc agcttgcggg ccccgcggag gaggagaccc     60
cgctggggct agctgggcga cgcgcgccaa gcggcggcgg gaaggaggcg ggaggagcgg    120
ggcccagacc ccgactcggg cagagccagc tggggaggcg gggcgcgcgt gggagccagg    180
ggcccgggtg gccggccctc ctcccgccac ggctgagtgc ccgcgctgcc ttcccgccgg    240
tccgccaaga aaggcgctaa gcctgcggca gtcccctcgc cgccgcctcc ctgctccgca    300
cccttataac ccgccgtccc gcatccaggc gaggaggcaa cgctgcagcc cagccctcgc    360
cgacgccgac gcccggcccg gagcaggtag gcagctctgg gacccgagct agggccaggt    420
atttcgcacg aggctccgag gctggagttc gggtgtgcgg ctgcccgggt gctagccgag    480
tgaacggccc cagggactcc gcgtcagtgg caggaggggc cggccggagt gaggctagga    540
gtagaagcag ttggcacctc ggcaacccat ggacctgcct cctgcccaca ctgtccacta    600
caggtggcaa ggagtcgcca tacccggaga ttctggggct cgggtctggt aataggggaa    660
gttgggaggt gcgtgggtat cctacctcac aaggaatgca aatccccacc tctgtaaggc    720
```

-continued

```
agaaggcctt tcaggtcccg ctatggaagc agactaagag agaggaaagc caactagagc    780
ccaacctcta tgctggtccc aaggtgtggg gtcctggtgg gttactgctg ttctgtgatg    840
agtttactgt ggtgcctcac cagcctccct agtcttccag gtagagaacc cgggcagccc    900
acactctctc ctgctccact gggcagctgt caccttctca ctcttgagag atgagaacat    960
ctgtaggcac ctatccacat acacacccgt atgtgtgcgt gggcgggggc gggggggtgg   1020
tggtgtcagg aaaaaagctc tgacttctga gccccaagac acttggttcc ctgtatgtgc   1080
tgaggtctgt taattaatta agtgggcact tgggacctgg gtcgtaacaa tatttggggg   1140
aaggttgttg ttgtttttct tcatttaaaa gttaaattgt gtctgtgtga gtcgtgcacg   1200
ggtcagagga catctttagg agtcgattcc cattttccat tttatcagtc tcaaagattt   1260
actcaagtgg ccaggatagg cagcaagcac ctctacctgc tgagctccac tgcctcggat   1320
tggttttcgt ggtcgttgtt tgtgttgctg tttagctcta gaaaaaaaac tcaacagaga   1380
caaaatgtat cctgaatcct tggtgtgttg caaacgctgt cccggccccc cacccgcccc   1440
catcctttga tttattcaat aaaaatgtaa aacattactt tgtgaacaaa agataagtat   1500
ttaacatttt ctcatccatg actgtataga ttgtgtatgc agttttgaaa atcaggtaat   1560
cggtttcaaa ggtgttgcat acccactaac tagtcttgag ctactggcgg gcctatggga   1620
gcctgcctat caagcacagg taactaacga caggatgctg agcaatgttg tccttctagc   1680
gatggctctg tggaacaggc agggcttgcc cattctgatg gccaccctgt gtgacaacat   1740
tctggattag aagtcagatg ctgagttcaa atactctctg tgccctggga ccttgagcaa   1800
gttacttaaa tcctcagaac ctcagtttac ccatcttcga aatggagtca tagcactgct   1860
tttctcaaag agcttataga aacctggtca gtatgccttt gtaaacagaa tggaaactgc   1920
ctgaccctgg ctgaagaagg atatgagtga gatgcttgtg ttcatagagg tagagttatt   1980
tgtataagaa agaaactggc tcgggacctg tgagatggct ccttgtagaa gggtgcttgc   2040
tgccaagggt gatcatctga gttccatcca tggaatccac aagctggatt gtggatccac   2100
attgtcttct ggccatcaca tgtgcactgt ggcccacggg tgcacacata catacaaata   2160
gaaaagtaac caggatgcta tatccaaagt ccttggacaa gtgctgatac caagtgatct   2220
tttgagtcct agattttggc tctgggactg ggtggaccaa gaaagaactc agagaagaag   2280
gccagttcct aggttttgga gagatcatgg cagtaaggca ggaatttgcc tgcgacctgg   2340
gtggaggcta gcagcatctg tcaggagtat gtcctgtgat gaagatgctc ctgtttcatg   2400
tttatttata gagtatgccc aacccaggtc ctggaatggg cttctagtgc tgacacatgc   2460
gaaggagaat agctaaagtg gagatgaaga agggagacag ggatgagggc taaagggagc   2520
ttcatcaccc tgctgatatc cagggatgca ccaacccaag gctcctagca ctccaaagtt   2580
cttgtcattt ttgtcattgc atttttaaaa agtcccatgt acatctcagt gagaaactat   2640
ttctgtcacc aaattcaagg gtgatttacc tcccagaagc aagcacacac acacacacaa   2700
aaaaaattgc acttggtgaa tggtgttggg gcagggggcg gagagaaatc ctcaaaacac   2760
tcttctgtgt tccttctaag aaggaacttt gaggcagcct ttagttttcg cagaggatac   2820
ttttaaatgt tgctgacaac aactctactt atgagtaaca gtgtggcaga gactcctgga   2880
acccagatca ttcaatcttg tttcggtttg aatgtgcagc aaagagtgta acggatacat   2940
ttagtacagc tacagccacc ttacaaacag gcaaggtcct ctctatggga cccagcctgc   3000
agaacaaccc gtggtccatc tgcctttgta gactctgact ctctctgtct ctctctctgt   3060
ctctctctct gtctctctct ctctgtctct ctctctctgt ctctctctct gtctctctct   3120
```

-continued

```
ctgtctctgt ctctctctct ctctctctct ctctctctct ctctctctct ctccacttta   3180

tctttaaacc agtttgtttt ccctgaactt gttgctccac aggggaggat caaagagaag   3240

ggattgcttg gcaaaactat tgcttatgaa gtatctgcag gaattagcac ccagtgcaca   3300

tactggctgt gtgctggtat taggcttaat aatttaggat tttacctttg cttgtaattc   3360

tccaacatcc ccttgatgta ggttctgtaa ttatgcccat tttcagatga ggtcatggag   3420

gctttagcat gtgattcaag gggcctggag ttgtgccatc acagtgtggg atttgagatc   3480

tcagatctga caaacagtcc agggtatggg cttctgggtc gttctcgcca gtgtagctag   3540

tgctggatgt ataaatataa cctattaaac agagccacag gaccctagaa cccttgcaca   3600

gggcattctg ttgagaggac tgtttgaggc taggtgacta gaattaggcg tgatgtgaac   3660

tcatgtaggg agaaaagacg catcgtaatt tcatcagtac cgaagtgaaa tttctcatct   3720

tcagtcatga gtgtataaac aaacaagttt acagtccgtg gtactttata cagtccatgg   3780

tactttatac agtccgtggt gctcttctca ctcattgcag ttactgatct tttcactgga   3840

tgtcccagct tggcagaaag ctcaaatttt tgttctcatc gccaacctga aattctgagt   3900

tatgacagct gctgcttgac ttgaccttgt cctaacccag aggtatgatt gtcatagatt   3960

aatgtcactt gaacactgtg gccacttcat tagaaccatg ggtgggacca aacacctaca   4020

atggcagcac tggagaggct ggggtaaagg catcaagaat ccaagccccc acccccaggg   4080

tcagctctgt tgtgctgtcc ttattatgct gaaggtcaag agcacaaacc agtagtctaa   4140

tttgccacta tatattctga tggccagagg ctacatgtca gtgtgtgggc aagactagtt   4200

cccctcagat aggaatcccc tctatgttcc tccaagatct ggcaattctg gcagctcctt   4260

gccctgcagg tctgcctctg tcctatagtc tctgactctg tgcagcatgg ccttctcttt   4320

gctttctctg agtctaccct ctttgattgt agtcagatgt gtggctcgtc tgaggttctg   4380

gggagaattc cttgtattta attttatgta tttacaacac tcctccctgc ataaggttct   4440

acagtgtcag ggtcaggcag gttctgcttg ccccagctgt ctgtttaaac agaggctgct   4500

ggggtgcttc acaagacatc aacatggctt tcgggatagg agaggcatcc tgaagaagta   4560

gaaagagaag gggaggtgtt atcctaggac atctccactg aggctggagc gccggaccaa   4620

agaaacaacc ctgtctgtga aggaacaaga gctctgaaga caggtctagg caatggagga   4680

gacatgtgga catcagaggg ccagtggatg taacacttga tggcccttgc agatggagtc   4740

aggttcccca gagagtggcc tatgagggag gaaagcagtc ttcttccacc tgcccagact   4800

ctttgcttgg tgcgtgactt tgatggacat tgcccagatt gatgggagaa aaaaaaaatt   4860

ttttagaacc atgggtagga ccaaacacct acaatggcaa cactggagag gctggggtaa   4920

aggcatcaag aatccaagcc cccacccccca gggtcagctc tgttgtgctg tccaagcagg   4980

gtgcagggcc cactctccca aatgttgcag ccagtgaggg gcagggatag ctctcctgaa   5040

cttatgacct tgtggacagc tttccaacta ctggaagtgt ggagaggagg ggcatcatct   5100

ctacacccgt gccacctcat gacagacaag tggcagagtc agctattcca cactcatgct   5160

ctgagggtct gctcacccac actccacacc cacgagggtc atgtccactg tgctgcctgg   5220

gtgagggtgc agggcctgct ctccctagtg ctgctggtga gtgatggggc aagctctcca   5280

gagggcggca accagtgaag ggagggggcca gctctgccca gttcttggac atctgctctg   5340

acaagggata tcccatgttc tttaatggta atgtgagccg tggacatcaa cacccacctc   5400

tgcatagcca tgaacccagc tcaggctgcc acctcactat ggccccaggt ggctggccac   5460
```

-continued

```
tcacaacagg ctgctcctct ccatcctcca gtctccagat ccagctctct tcataatcct   5520
taagctgttc cacttctctc tctcccatct gaccaccaca tgctcgcaca ttgtggtggc   5580
tcccactgca ggctggccat gttgctgggg ggccctgggg tgacatcctt tggtccaagc   5640
tgcacggccg tgagcaggcc ctgcacctca cccaggcagc acagtggaca tgaccctggt   5700
gggtgtgggg tgtgggtgag ctgcatggca ttttggcaag tggttgtcca cagcctgcct   5760
gtgctgtgct ccagaggcag atctgtggat gctgtggcag gtttctgtct gcctttttcc   5820
ctcctcatgt gctgcactgc aggtggctat gtgtgtctat ggcctgctca tacagggtag   5880
agggcagatc tatggctatc tttccctgcc caaacattgt ggcatggtgg aacacagatc   5940
tctgtctatc ttcctcttcc cgtgccatgc tacctagatt tgatttgatt tgatttgatt   6000
tgatttgatt tgatttgatt tgatttgatt tgatttgatg agtcctagac ataaaacagc   6060
tttggtcacc aagccaggca tcgggccagg atgaacatag gactatcatc tgctctaccc   6120
ctgactgatg taagaatggc atcaccaata aggtgtctct ttgtccattg acaggggtta   6180
aagtttttta attggtaaat ttttactatg tagctctggc tagcctggaa ctctttatgt   6240
agaccaggct ggcctgaaac tttcagagct ctacctacta ttctctgcct cctgagtgct   6300
gggatcaaag gcgtgcattg cttggaatct cgaggggatg agggtgtggg gcttctgcag   6360
gagaaaggca ggtctcagga gcctgaggag gaatggaagg tcattagcag tctccttgct   6420
atgcagatat cttctgtcag ggaatgctct ctctctctct ctctctctct ctctctctct   6480
ctgacatttt ctatgtagta ctgatttcct gcacaagtag cggtttctca ttttgcttta   6540
ggcagttggg tggggttagg ctttgtatgt gttgctagtt ctccatcgat tttggcttct   6600
agtatcaggt aacgtcaaag tggcgggttc tggtttccta cagccccggt ctgaggtgac   6660
accatgaatc ccagcagttg tccacctaac actctccaaa gcaggctcac agtgcagacc   6720
ttggtgagtg tatttcttat cacagtccac taaagagggc tttatacaga ccaagggcaa   6780
aacagacatg aaccattgga agaggctgca aagcagtatg aactgcgagg gcagggcagg   6840
gcaggcacgg gtagggatgg agaggtctgc gggctgggcc ttccagttct tgcacagttg   6900
aggtcccagg aatgtgtgag tagccactgt cacccccttt gaaacctgcc cacagcagaa   6960
gcaccggagc ggggtttatg atgtgcagcc tcagcctgaa ggactttcgg gagaagggca   7020
ggatctacgc tccaaagcag aagcctgaga ggaaattaga accatggatt tgggcagtga   7080
cagccatgca cgggagctaa ctagctgatt caggatcctg cccattttgt agatgtttag   7140
tagtccagaa aggcagaaga tagtagatgc tagggacaaa cgtagttttc tatgaaaata   7200
tgatttttct ctatatcatt tcttcttaaa aaacatttag gtgggggctg gtgagatggc   7260
tcagtgggta agagcacccg actgctcttc tgaaggtcag gagttcaaat cccagcaacc   7320
acatggtggc tcacaaccat ccataacgag atctgactcc ctcttctgga gtgtctgagg   7380
gcacctacag tgtacttaca tataataaat aaataaatct aaaaaaaaaa aaaaaaaaaa   7440
aaaacattta ggtgtctatt tgttcatgtg tgtaggtgtg ccagggtgca tgtacaggtc   7500
agaggtcatg tccagtgtca tctttgcttc ctgcccacct tattgttttg agacagggtc   7560
tgtctcattg actctggact cagtgattgg gctggactaa ccagccaggg aactctggat   7620
ttcctctgac ttctgctccc cagagccacg cttgcaggca tttgttgcct acagtctgtt   7680
ttgttttaaa tttatattta ttcatttcat ttttatttgc attttgcctg catgtatgtc   7740
tgtgcaccac aagcttggca tgcctgtgga ggtcagaaga gggcatctga tcccttggaa   7800
ctggagttac agatatttgt gaaccagcat gtgggtgctg cggactaaac ccaggtcctc   7860
```

-continued

```
tgcaagagca gcaagtgctc ttaaccactg agacacccct ccagcccctt tgctgttgtt   7920
gtttaatgtg gattgtttat tggtattgct tttttttaaa tgtgggttct ggcatctgaa   7980
cacaggtctt cacactttcc tgactgagtt agttatcttg ctagtaaacc catttctacc   8040
aaaggtgatc acagtaaact gatttttatt ttcagaagca tgcctagtct tcctgaatgt   8100
gccctgcgta tttgcatagg tctggtgaaa ttactaagtg gctgtgctag tcaaataagg   8160
agcgtcagag cagatctcag aagcctgtgc tggcagcgga gccaggtcag ggtcccagca   8220
tcaaaatcca tctgcagagc ttctcccgct agagatgccc aaagaacttt aaggctggtg   8280
gtccctctgt cagttacagt ccttgtctgt gagaccatag agcccttgta agccagggac   8340
caaacaaagc attttatctg tctgtctgtc tgtctgtctg tctgtctgtg tgtatgtgca   8400
catgagcatg ccacagtgca tgtgtgatgg tcagaagaca atgttatctc cttccaccat   8460
atgaattcca tggatgacac tcaaataatc actattggta gtaagcatgc atatacacag   8520
agccatctta caggccctga ttcagtttct ttcttataca aataactcga cctctatgga   8580
aacaagcatc tcactcattt tccccttcag ccagggtcag gcagttccaa ttcagtttac   8640
aaaggttaat tgaccaggtt tctataacct atatatagct tctttaagtt tctagacatt   8700
tgtacccagt tcaaggggcc tgcctttgaa atgtgtgctg ggcagagtcc tttctcaaat   8760
ctccttgatc gaagctactg gcagaggccg tgagaacatg ggtagacagc ggctaactgc   8820
cagtggctgg agaaatggcc tgaatttgtg ggactcatca tccggtgggg ggtgtgtctt   8880
aaggcaactg gacgtgaaaa tctagatatt tctgtattag agaaaaaaac aatctgtttt   8940
aagaaaagtt tagaaggctc agtggttaag agcaccgact gctcttgcag aggacctgag   9000
ttcaattccc agtacctaca aggcagccca caaacactgt gactccaatt attctgacat   9060
ccatgggcac atggtactca cactacacgc tgacaacgca tttatacaca taaaataaaa   9120
tgaatctttt ttttaaaagt aactagaact actatagaga agtaggattt cttggggtat   9180
catataatta aataaatact cacacaagtg tgacaggatt gattttgtac tttattataa   9240
gggaaccatt ttttttttta atcgtccagg gttgcatctc agcctctgga gtaaggattc   9300
atggagagtt ttgtggggcc aatctgcaaa agttcagcag aaatcagaag ttaagaaagg   9360
tgatacagaa cttagcattg gaaagttctg gaactagagc tggaaagatg cctttgtgct   9420
gaagagcact cgctgttctt ccagagaacc agagttctgt tcccagtggc ccacaactgc   9480
ctgtatgtaa ctccagctcc aggagacctg acaccctctt ccagtctctg caggagcctg   9540
cacacacatg caatacacat acataaaaaa taataaaatt aagctttaaa acattttttt   9600
tatgaaagga agttatcagc caggcatccc cgcactcaca aaacagaggc agaggatctc   9660
ttgtgagttt gaagctgtag tggtagatac ataaaaagtt acaggtcagt cagggataca   9720
tagtgaaact ctgtctcaaa aaatatctac aatgaatcca attttagaca atttgtgctc   9780
agagatgtag ggcattcctg tgatcccagt acctaggatg ctaaagcaaa ggagaagctg   9840
agacggaaga gaaagatttg gagcttgagg ccagcctggg tcacacagtc caaatatata   9900
taaatatcca aatatataaa atagtttatg ccaacttgac acaggctaga gtcatttggg   9960
aagagggaac cttaattttt aaaaaaatga ctctactgaa tttacttgtg gtacattgtc  10020
ttgattgatg attgaatgtg aaagggtcta gctcactggg aggagggcca ctcatgggca  10080
ggtggttcca tggtgtaaga aagcagacca agaaaacaaa accacaggaa gcaagtcagt  10140
aagcagcttt cttcatggcc tctgacaatg gtcaacatga ccactgacac agtcctttgt  10200
```

-continued

```
ctctgttatg gttctttctc tccctccccc tccctctccc tcttaaagat ttatttattt  10260
tattaatatg agtacactgt cactgtcttc aggcacacca gaaaagggcg tcagatccca  10320
ttacagatgg ttgtaagcca ccgtgtggtt gctggaaatt gaacttagga ccctctggag  10380
ggtcagacag tgttctcaac tgctgagcca tctctccagc cccttatctc tttccaactt  10440
tctgtatcag ttgagttttt tttatccttc ctcttccccc acagtctgtc ttcctaccct  10500
tctttctccc ttccatccca gcctcccttc ctgtccttcc tcccctctcc cagtctacct  10560
tcttgtcctt tctctcccag ccccattcta agcccccctt ttttcctttc ctttcctttc  10620
ctttcctttc ctttcctttc ctttcctttc ctttcctttc ctttcctttc ctttcccttc  10680
ccttcccttc ccttccctcc cctcccctcc cctctcctct cctctctttt tctttcccct  10740
tcttccctcc ttctccctcc tcttttcttt tttctgaagc tgtttttttaa ttaaccttca  10800
aactaaacac attctttccc ttgaacctca gactttcttt accacaaaat gtccctgcat  10860
cttctcatgt agagtgggtt ctcttatagc ttccacacac agacaaaaga attttaactc  10920
tctgtaattc caactcccag aagaaaacga aaggtgagta cggacggacg gggcaagtgt  10980
gggaacgccc acccgagtgc cacagagcgg ttttgctagc tgctcttgcc aagggctggg  11040
gtctggtctt gctatgcaca cagtggctca ccatcaccag taacttctgt cccagggaat  11100
ctgacattct cttctgatcc tccttggaca ccaggaacac acatggtaca catacatata  11160
tgtaggaaaa cccaatcata cacataagat aacaaaaaag taaatctaaa agcattttca  11220
aagatgtggg cagctatttt taaagcaggc atattatgat tcctcattgt catagaaatc  11280
tttgcttctt atacttttat tttttgagat tcatttaatt ttatagtttc taacaactgt  11340
gccttaatta tgaaaacacc aggagaaatt ttatgaaagc atcctgtttt aaaatgttta  11400
ttttaaaagt ttaggtttta ttattattat ttacgggtat gtgtgtatgt gtgtgcttgt  11460
ggggtgtgca tgtgaatgca ggtacttcca agccagagag ggtgtcacag tcctttggag  11520
ctggaggtac ctctccatcc ccagagtttc ctgtttttaa acaaggctag ctattaccca  11580
acaaccgtac ctcctgctaa atatttttca gcacgtttgt atcaggaaga gtcagaaagg  11640
caaagcctga gagaggtata cttagttctg ctcatttatt gttgagatga cctgcagaca  11700
ctgctgtgtg cctgttagtt cctgggttac tgcaaggtta gctgtcccag ggttcgaaca  11760
gacatggcca ggaaacacag gaagagcagc agttgtatgt ctgccttgtg tttggatggc  11820
ttggaagata tgtgtatgtt agttaatcca gtaaacgtaa gctagcagcc caggcaggct  11880
aggtggtcat gattcttctg ccttgtcttc tggagtgagc catgccttga tttggaactt  11940
taagaaactt ttccactctt gcttcatctc acagcaaaca gctctgccaa attcagtctc  12000
tggaggtgag gccaacttct gataatagag ttgtgaaaaa aatcctttca agtattttat  12060
tatcaggttt tagccagcca aatacttaag tgtttctgaa agtactaggg tctctctctc  12120
tctctctctc tctctctctc tctctctctc tctctctctc tctctctctc tctccttccc  12180
tccctccctc cctccctccc tccctccctc cctccctttc tccttctctc ttacttgtat  12240
tggaaattca acacccaaac cagcaagact tttatgacaa ccatgaatat aaaatagtca  12300
tgttcaaaca ggggcgggca gcctgcagcc cctgtgaccc ccaagttcac ttttagacag  12360
gtgggtaaag actacatggg ctctccagtc tccacttgct attctatgat ggatgtaggg  12420
aagttcctgt gggaaggtac cctaccagca ctgaccaggc atgaaggatg aaggaggacg  12480
gagagcccct aatagacctg ggcctcttgt ttatatagga tcttttgaga gctggggcca  12540
tggtgagcca ttgaactctg cctgactcag gccagcattg tgctataccc acagctgaga  12600
```

-continued

```
gagggagaag aatgtctacc aatcatagag cagagtggtc aggactcagg acaaactaaa  12660
gggaggatat catctagttt gactcataac aaaactgctc tatgcagatg tcagcctacc  12720
agaacccaga gccgctaacc tgggaagcca gtgggcagca gccttccagg ctggggttct  12780
tgtcctgacc aagatgctat tcttcctgca aagacagagg ggaagaagcc agaaatgagc  12840
atgctcatac caatagagcc cagggctcag tagtaggaac gtgtctggtg tgcctggagg  12900
ctccgggctc catctcctgc tgcctagaaa gccagcaagg tctccgaatg agaactgtgt  12960
tccactgcat tccttctaaa tgagaactgc gttccactgg attccttcta ctgagcagag  13020
tctgaaaagg taaagacagt ttctgttctt attcccacca ggtccaggaa ggagtgtccc  13080
tcagtcaaac ctggtacctt tgctggcctc ctgctagggt tccaaatcct acagctgcta  13140
tgatcatccc agagaaggca ggcttcagcc actgaggtcc cttcccagtc actaaagtat  13200
aagggaaaaa agattacatc agatagggta cagtaagttg tgcctatcca tatgcacggg  13260
tgccgtacag gggaaggtgg ctcttctgag tcccagagag aaaagtagct ctgggtggca  13320
cagaggctaa tgtagggatg tgaggggaag tgggcaagga atatgcagat atagcattgt  13380
gtgtgtgcat gtgtgtacat atgtgtgtgc atgtgtgtgt gtgtgtgagc aaggaatatg  13440
cagatataac attgtgtgtg cacatgcatg tgtgcatgtg tgtacatatg tgtgtgcatg  13500
tgtgtgtatg tgagcaagga atatgcagat ataacatgtg tgtgtacacg tgcatgtgtg  13560
catgtgtgta catatgtgtg tgcatgtgtg tatgtgtgtg tgtgtgtatg tgagcaagga  13620
atatgcagat ataacattgt gtgtgtgcac gtgcatgtgt gcctgtgtct acatatgtgt  13680
gtgcgtgtgt gtgcatgtga gcaaggaata tgcagatata acattgtgtg tgtgcttgtg  13740
gatgtggatg tgcatatttg tgtgtgtgtg tacatgtggg caaggaatat gcagacataa  13800
ctgtgtgtgt gcatgtgtgt gcatatgagt gtatgcatgt atgcatgtgt gtttacatac  13860
atgtatgtac atgtgcgtgt gagtgcatgt gtgtgttgtt cctcaggagg catccacttt  13920
tttttttttt tttttttttt tgagcatgag cctctccctg aatctctcca tcaggtctcc  13980
atttcccatc tctaccttca aagcactgtg ataacaagaa catactatca cgcctgtttt  14040
tgtttttaaa ggcgccaata tctccttaaa ttttagtgca tttattattt ttcacatgtg  14100
cgggtactca catgccacag catgcccatg gtggtcaaag tacagttttt cagagttggg  14160
tctctcctgc catgtggggt ctgggtttca aactcaacat tccaggcttg gctaccaatg  14220
cctgctgagc caactcaatg actcctcaca ccccaccttt gaaacacacc ttctggggat  14280
cacactcagg tcctcatgcc tacaagtgtg tactgaccca gccccagacg tgactttggt  14340
ttgatggttg cccagctggg accccctttcc tgatgtatgt gtccttcaga gctgtaccat  14400
ctgctcctac acagggcagc ttctccatgt tcagtgcatc tgcagcctca gggtcacctg  14460
gactcactca gggtgcccaa caggttgttc tgcaatcatg tgtcccagtg tcctgcagac  14520
atgtgtcatg cagttatatg ttctgaatct caatatagac cttagaactg tggctgaaga  14580
aaggggatgt ggtgccagac tcagtttgcc caaagagcta gtgcaggatg gagctggctg  14640
gcactggcct agggcagact gaaaggtgca aggggccctt gggtggtgac acctggtgtt  14700
ttagaccgtt atgtgggttc ccaggaaaac cccctcttct gcaaaggaag cacttgtgtt  14760
ttcccagtat gctatgggta caaggatgac taacaatcat gacatttgca tggtgcttcc  14820
ttcaccgtag ctgcacacaa aggcccgtgc tttgctctct tggcagaggt aggctttgtt  14880
tcctcagttt acagataggg aggtggaggg ctgggaggtc attatagtca caagaggagt  14940
```

-continued

```
agagggctca gcacaaagta cgacaaagtc accgtaataa aattcaggcc tgggccatga  15000
tcctaactac tggggaggct gaagcaggag gatccaaagc ttaaagtgac cttcaagccg  15060
gtcctggttg acttagtgag accctgtttc aaaagggaaa gtcaaaagag tctggggtgc  15120
attttggcaa tacagtgtcc tgggtttgac ctcagagctg cggtgagagc aacgagaaag  15180
aacagattcg caacaggaaa gttcacaatg gatccagcac tagctttcaa tttttaagaa  15240
agattttaca ttttatgtct gttgtatggc catatgcttg tactctgtgg ggggggggag  15300
aaagagagag atagggaggg agagagagag ggagagggag agagagaaag agagagagaa  15360
agagagagag agggagggag agagggaggg acggagagag ggagggaggg agagagggag  15420
ggagggtggg agagagagga agaaggagag aggagagaga gagagagaga ggaagaatga  15480
gagagagaaa gagagagagc tctcttaact gctgagccat ctctccagcc cctcaacaat  15540
agttttattg gacactaagg acttcagcga tgaagatcca aagacctgac taactttctc  15600
ccaagtttgt gtgtgtgtgt gtgtgtgtgt gtgtgtgtgc gcaaacatgt gtgcatgcat  15660
gctagaggga gcctgcccaa ctgaaccatt gttagaggac aagggttaga acaggaatga  15720
gtcaatccca tagtagggag ggtctgcatc cctgtgggat cctgtcccca agaacaggac  15780
acacaaggtc tcatgctatt cagggtcagg ctgagaattt gctcttcaag gtttcgtggt  15840
atgtattcct tgtatgtcat actgtgttgc gtaaggacat cttcctgcag gcatctatta  15900
tacagcaagt gtacatgctt cttccccctt ggtccattta tccctttaga caagtcactt  15960
ctgctttcct gtcacgtata catatgtgat ttttagatac atatgcaaaa acccaggaac  16020
aaaatatgag agaaaacatg tgatgctcgc tttgctgaga ctggcttaat tcacatacta  16080
caatcatgtc cgattgcctc cattttcatg aaaaggatgt aactttgtcc ttctttatgg  16140
ctggataaat gtatgaccat gtatagttgt catacttttc ttgtctgctc ctctgctctt  16200
gggactagtg ctacactgag cgctccttga tatactatgt tctacaatgt gcgttgactt  16260
tggggtaggt gtccgtgggt ggtatggtca catggtagat ctatttctaa agaccctcca  16320
tactgacttc catagtggtg ggaatggttt gccttgcctc tgttggtctg ggagggcgtc  16380
cttctgtcca cgtccccacc agcattggcc acttctgttt tcagccggtg gctgagatgg  16440
attctcagta tggttttgat ttgcatttct cagattgcac cttttaaatg catgtattag  16500
ctccttgtac ttcctctttt gagaattgtc tgctcaattc cgttttaagc accaggttgc  16560
ttgtgtgtgt gtttagtttt ttaaatattt gctttaggtt tacgtgtgtg tgtgtgagcc  16620
tgagtgtcca tctgtgcaac atgtgtttgc aggaacccaa acataccaga aggtgtcgaa  16680
tcccctggaa ctggagatac gggcaggtgt aagtcagctg acacaggttc tgggaattga  16740
actccgtctt atgcaacagc actaagtctt ttgactgctg aaccacctct gtcaccctgt  16800
gtttagtttt ttgagttctt tgtatattct attattttat ggcaaggaat gtttttgcct  16860
gtatgtatgt cttatgtaca ccatgtgtgt gcctggtgcc catgaaggcc agaaccagaa  16920
aagagagtgt taggtcctgg aacagttaca gatggttgtg agccgccgtg tgggtgctac  16980
aggttgaatc tagctccgct ggaagagcag ccaatgttaa cagctgaact gctgctctcc  17040
agtcgctttt tgtaaactcc agatgtcaat cctctgccag actgacagcc agcaatgact  17100
cccctaccct ccctgagctg ttcttcaccc aaatagttgt tttcatctct gtacaaagcc  17160
ttttgaattt ctcaaagcct catttatcaa cggtcttctg ccggaggaag aggctaggga  17220
cagaaagcac ggcctgccta ctgctctctg gagtgccatg gtgccacgtg ctgagctaga  17280
gtgttctgag ccccatcctg ggagttgtga gtcacctacc tgcctccact gcaggctctc  17340
```

-continued

```
ctacatccct cctgtgatct ttcctgagac accacaaacc acacctgaga cccccggggg  17400
agaaccttac agggatacca ggtacccagg aacatcatca cagcctccct accaaccaac  17460
tccagcatag atgccttggg catcttcttg tcaaccaggg tcaggtcctg gagtaggcag  17520
ggcgtgggaa ggagacccat gagagcgggc tttgtcagcc tgctcagggc tactgtatct  17580
acgaagggct gttccagtgt ccctgcccag tggcagctgc cagatccctt ccatggggac  17640
agcagggact ctaattgctc acctgctgct cagagtctct gccagccctg gaggtgtgtc  17700
tggggaagct gtgctaatta ggcacacggt ccatccttgt aggggcaata ggcatagtgt  17760
caacctttcg gtgcgtcctt cacagcaagt aaaggagctc cagtctccca ttctgatcta  17820
catcccggac cttagggatg acgtcctagc tgttgcctca ttgatgtcca ccttccagat  17880
ggacactgcc ctgctcaagc acagacctgg tgactctcag ctcagctgac ctatgggaag  17940
ccttggtcct tgtggggact gaggagagca tcccaggttg ggaagagagc atgtaggatc  18000
tttagggtgt ttccaccagc agcagagggg ggcctcatag tagagagggg gtctaacttt  18060
tgcagagacc acacagcggc ccttgctaaa tgctgtagcg ccgcaaaggg gagtcgagct  18120
ccacagtggg tacgtcctgg tatctgtgcc gcccagatca tgaacagtaa gcggcatatc  18180
ttatcattca tttaccaagc ctccattctc tggggtccct gggactcctt accacacagt  18240
acagactaga ttcagctcct gctcgctata gaaggaggct ctgctggtga tagtcatgta  18300
agttagagac agcaggtccc tgatctgcaa gacttggatt agacaatgtg gccccccctcc 18360
ttctcgccac cactgtcctc tgtctccccg tggtcaaccg ccatcaacaa gcctaattac  18420
aaaggcctcc tggcactttt tcttttggag taaggcatgc tccggcttgc ttctgggccc  18480
ttaatttttg atcagggaca cctcttcgac taattatttg tcagtaatga gggaggagag  18540
atgaggttgc gaaagcgtcc ctgagcttat agagagaagc tgcaaattaa aatacgaggc  18600
atccgtaaac agggcgctaa ttggattaat tcaaaagtga tagattggga taagaacaga  18660
gaggaagacc acaggcagat tgaggtcaga ataattccag gagcgttgcc cgggcttcct  18720
gtgatagatg tgagcctcaa agtccgagag ctacagaaag taaaatatgc tgctgtgtgt  18780
gcaaaacaca tctgagtcac tcaggcacac caaccaccca ggatgcatgg ccgtttctta  18840
agccctggca ctatctgacc cttgagtcat ttttggagag accagaactt tcatatgaca  18900
accgcctttc tttcctctgt tgtaataaag ccctctctat ttgttttaag gtttttaaat  18960
tatatgtacg tgtgtatgta agggtatgtg cacatgagtg ggagtgccca tgaaagccag  19020
aatctccttg tagctgcagt cccaggcagc tgcctggtat gggtgctggg agctaagctc  19080
ccaagtacat gggcctatgt gcatgttctt gaccgctgag ccatctctcc aggccctcat  19140
tctgatttct cttggtgctg tttagtgttt ttgcattctt tgaatcttga gccacactta  19200
tgcgtgggct atctaatgta attgaattta aaaaaaaaac cattatgtca gaaggtgata  19260
aaaattatga tgggaacatc ccacttctga acaggcagag gtgagctgaa cttttcaaga  19320
taaggggaag catctccctg tgtcccagtg agcactgtct gtccgtggct gcttctcctg  19380
gtatctcagc gaggcatcag gtttctgtag ggcatttgaa tcgcctcata gaccaaatgt  19440
gccctgacca cttcccctgg ccacagtgat gctttatagt ctggattaac tctgggctac  19500
tggcctcact cccagtcttg gctgacacct aggctgtggg agagctaata gcttattcat  19560
attatttaga taagtagcat agtatttgag ccgtgtacgt ttttaaaagc atcaagtctt  19620
tattcttagg gtgagcctta tcatataatc acaactgtgc accatttcag ttctcatggt  19680
```

-continued

```
tcttccatgg atcacactga acagtaagtc ctggctgcag aagagaatta tttttgcacc  19740
tgtctccaag tctattggtt caacataaac acaggcaata ctcgaaccat atgttatcat  19800
tccaccgagg ggctcctaga cacaccccca gtcagcttcc tgaatttcta aattcagaaa  19860
gggaatgtgg agctgggaag aaatagtatt tcacttaaga ctttacttac ccatcctgtc  19920
catttatcca tcccatctat ctacccatcc aacacattct cccatccatc tatccatcca  19980
tccatctatc catctcttca tcccatatgt ccataaagcc catcatatct acccatccat  20040
tgtttgttta accatctatc catccatcca tctatccatc tcttcatccc atatgtccat  20100
aaagcccatc atatctaccc atccattgtt tgttcatcca tctatccatc cacccatcca  20160
tctatctatc catccataca tccatccatt catccaccca tctatccttc catccatatg  20220
tccatccacc cacccaccca tccatcatcc agtctatcca tctacccgcc tgtatatcca  20280
ctcacccgcc cacccaccca cccacccaca aaaccactat aaaaacatcc atctctcatt  20340
cattactgag tacctgctgc atactaggtc ctgatctggg accagacaat tcaaacttta  20400
tacactcact cagtcttcac cattctgtga catcaacttg aagctgaggg tttaattctg  20460
cagagcgcag gcctcttgga ggtccccggg gcacaccaca gtataagaca cttcgtgtgg  20520
agcacagaag ccagtgtgcc aaggacaccc tttgctcctg ttgttcaggt gtgggtgggg  20580
atgggtctgg cagtgagaca agagggggcca tgttggatat gcgcctcaag ggaccatcat  20640
ctagcaagca gggtagcttc cagtgatgcc ctaggcacct gctctccgag gtcactccct  20700
ttaacttctg gaagacagga gaggacacag ccaaatgtac tgaaggcaga tttgcttagg  20760
atccaggcca ggcgtccatg gatctctgca aagagtgaaa gtagacactg caggggagct  20820
cggatggatg ctctgtcaag gcagacgaag tgggcactgt tccagtcatg aactgtatgt  20880
tatataaatc gacccctctg tttcctcatc ggggaacaga ggtagaaact cttctcacgg  20940
taccagtgta atggttgtgc tatggatagg tgtagacgct gaaattcatg cttagtgagc  21000
agcatcagct agggcatgag gtgtttgtca cattctctgt gtgactccta tgtgctctca  21060
gaactcactg agttgaggat gagagcgccg acggcccgga tggaagagtc agatgagaca  21120
aagaacaggt gctctggcaa tgtcaagcag gttgggaggg cagggagtct taactgggcc  21180
tccatctgcc aacctccctg gccttggctg tcagccaggg cagcctctga cctctgaagg  21240
gcgtgtcctc tgtttttctg agcaggagtt gggcccacaa aggcagccct tcagtctcgg  21300
acgtgagtaa atattgacgc tggggctttg gggccctga ccgttgccac ttaagcatga  21360
tgtggatgtc tctattggaa gctcagagtg gctgaggact gagctagctg ggcaaacctg  21420
ctccctaagg caaccacgtt ctaaccagcc cccccactcc ctggagttct tcctcctgct  21480
tcagggctag gacgaccctg atcatcctgc acaattaatc aggcaggcaa cccagtgccg  21540
ccacaagcag tcattacgca ggtatttcta agatggaaga actggttgct tagaatagct  21600
aagaggaatg gaagccagtc cttccagcag cctctgtgga atgggggaga cccatggtct  21660
catatgttca gttgaaccaa tttagctgtc cccccccctg ccatcgccac ccccagtccc  21720
gtgtgagaag aggcacacgt ggtttgaagc caccaagcac cacctcagct ttgtattcat  21780
gagcactcgc gtgtgtgttc gttcacaagc tctctctgct gtccatggga atgcacagag  21840
gatatcttta aagtcagcac ctagacacca tcttgggccc ggtgtacagt gacagcagat  21900
cttcaacctt ggcctcattc gagagagatg tgcagaaaca cttgttgaat tccccacagg  21960
attccctgcc cggtgctgtc ctgtcacctt aacagttaag ctactgttgc ccaccgcaca  22020
gttgggcata tcttactttc caaacatttt tttttaattt gtattccctt tatccagtta  22080
```

-continued gtcctctcga tcctttccct ccctctttac ccaagccttt ccaccctcag cattccccct 22140
ttttacttat gttctttata ctgacggtct accatctccc tgcctctaaa agccagctgt 22200
atgaggccac tgtccctgaa atgactaggt gtgaacaggg aagattccct catgagcatc 22260
agggggaaat cctatgatat aaaaatgtct gcagtgggcg ttggagagac caactagcca 22320
ttaagagtgc atactgttct ctaaagggac ctgagtttgg tacccacatt gggcagctca 22380
aaaaccactc tcagctccag ttccgaggga cccgacactc cagcctccaa gaggatttgc 22440
acccacatgc acatacagtc acaaatgtta ctttttaacc ttaaaaatgg ctgcagtggg 22500
atgagaagct gggaagttta ggcctggaga ttcattcata gaaaggaagc tggctctgct 22560
tccccagcca atctctgctg gatgtttgta aaccccaaat ttgatgctgt taacctttgc 22620
tctaccagcc aggctactcc agatggctct accggatgtt gtaagcatct gatttgatga 22680
cctcatgaat ttgagcaata gaaatgtctg ctggaaatgg tttaccttct agagacaggg 22740
tcttactata caaccttggc cgtccctgaa ctcactccat acctcggaac gcaggctggc 22800
ctcaaactca cagagatctg ccgcctctac ctcccaagtg ctggggttaa cggtgtgcac 22860
caccacacta ccagcaaggg ctatattttt tatgctcttg ctgtggactg ttctccttgt 22920
tacagagact ggggccagcc tgtaccaaga catagggttt tgaggagaca agggaacctc 22980
cccaccccca gagtctgctt ctgcagagcc taactggcac atgagagttt accaatataa 23040
tgtgtattac aacaggaata tagtagggtg ccctcaaaac ccgtacacta gtggttaaga 23100
atatgggata gaaattctga attcagcatt ctggctgttc attatcctgg gtccacagca 23160
actggagtct ggtgtggtat gaacaggcaa agtagatttc tgacatttaa gagaggagtt 23220
cttatctgcc gccagcctat ggagacctgt gttgttgaga tgacggtata caggacgtat 23280
tgtgaattgc aggggagggc aaaaaacagg gagagagatg agcccaaggt gttaaggggt 23340
ccattgtacc atccttggat ttagcttatg tgcttgagac catcaacagg gggagcagac 23400
attgtagggt tgccctctga gatttcaccc ccccagttca ctttcccagg tagtgggagc 23460
ctgcccccat gttggtcgcc aggagtagga tcaaacacaa tacccgtaag cctggtagcc 23520
agtccccaga cccagggctc cctgccaggc tccacccact ggcttggagc tggccacaca 23580
ggcctcccag cttccgtaac ttcaatgtca tcacctaggc aactggacgc tgccgccact 23640
gccctgccac tgcaagccac cacggggcct ccagcacctc tacccaagtc tatggaccca 23700
cccagggccc aggctcagcc aaggtaggca ggggctctgc ttgactctca gctctcaagt 23760
cagggttcgc ttgctgtccc ccttccccac agggcaacag cctcaaggtt ccatcaggat 23820
aaggaaaccc ctccccatca actcacctgg tagcccagaa gtaaggctcc atgtaagcag 23880
gcctgccaca cgggcaggct ggtggccgag acagtctgaa gagacaccat ctgtggctct 23940
ggtggcacaa ggcaacatgg tatggcactt tggaaagtca catgtactga gtagtctcca 24000
gggtctctct gtgcccctgt actgtgacag gtcaggatgg agacaaggga ttctgagatc 24060
tcccaaaagt ggttctggta tctccacagc cttcattcct ttaagccacc tgaatttctc 24120
tttattccat gtccaagaga caccaaacag ctacctggat cttccaaggc catggttagt 24180
gctataagat gttgccccta cccagtgcct cttcctaact ctccctccgc tacttagtct 24240
cagagtctct ttcatcctta gcctgtgctg ggcttcccgc ccctcacatg gctggtgctc 24300
aacatgtcta catgcaggcc taagtgttga gagatggggc ctcggtaggc cctgttcctg 24360
atgttgtcca cttgtgctgc tgtcctgtga acagggctgg atgtcctagg actggcaaac 24420

```
tatacagcgt catatcagga tgagatagag aaaatcctgt atagaaatta ttgcaatgag  24480
gccagagtga gtgagtgagt gtgtgtgtgt gtgtgtgtgt gtgtgtgcgc atacacgtga  24540
acacctcggt tgtgtggtgc attgtgagcc agtgtgcaca cgtgggtgga gaagcagagt  24600
atcaggagtg tatgggccat acactctttg tggttttacc accgtgttct cagcaggacc  24660
tagcggtggc cctggagccc aaatggctgg agtattgcct gaaagagaga tatctgcccc  24720
cagttttaaa gtcaagatct cattttgtag cccaaactag aattcactgt gaaccccagg  24780
ctggtcttgg atcctgatcc tcctgcctca gtctccccat ggttgaaatt acagacatgt  24840
tttaccatgg ctagttgtct tgggttttct ctaatttgat tggttacttc cactgctggc  24900
cctgttagca tacactgtat gcacaagacc atcatagcct gagacccata gcctgagacc  24960
ctcatagcct gaaacaccca tagcctgaga tcctcatagc ctgagacccc catagcctga  25020
gacacccata acctgagata cccatagcct gagaccctat gcctcgaggg tcttgtgcct  25080
acagtggatg ctgacaagac cagcaagaag acacagggcc ctgctatgtg tcacacaaag  25140
ccagtgctat ttccttgggt cccaaaatct gaactcctaa gggcccaaag cccaaatgag  25200
gatatatttg ctttttctta ttgttttaat tttatatgta tttattcatt gtgtctatat  25260
gtatgaaggc atgtgagcat atcctgagac tgaactcacg tctttgagct tggcagctgt  25320
acatttagtt gctgagccat ctcacctagc ccctggggtg tgaatggtga gttttgacct  25380
ctaactgctc actcctgggt ctgcccaact ttccctgacc tgcaaggcct tgagatcatc  25440
atactaaccg gttaattctg cctccaatgt ctattcactg agcaccaaac ttgtgctgtg  25500
cacttgctga gctacatggc taagcctgtc catcctcggc attacatctg aacacacata  25560
gggttttacc cctgcagcag atgccatgat acttgggggg ctaggggctg tccagaaacc  25620
ccgaggggca aggctctgta gctgttccca ttctgagatg actagtaaga gtctatcagg  25680
cagcacagag cctttcctca tggccccagg gctgagcaca agggattctg atgtgtttga  25740
catcgaattc taccaggtta aaggccacct ggaaccttct ccaaggtagc cccttggagg  25800
ggtaagtggg actggtagtg cctgcgagaa gccactttcc aaattcaaaa ccaaatggaa  25860
gctgggccat gaggccccac aggtggctaa attacagaca tagaactgtt gggcccttgg  25920
taaccttgtc cagcaatctc ctgaaagcct tgtgtagacc attcatgcaa ggaaggtgtg  25980
atagcctact tgagggacaa gaggctacag actccacaca caggaagaga tggagggccc  26040
tgaattgtgg cttgttgagg gttctgatgt tggtcagtcc agaggtctga gggtcaggat  26100
ggacactcta gactccgttt ctgtctgtgt cctcacttgt tctacctgtc cctaccacgg  26160
cactccggtc aagtcagctt gccaggcagg gatgcctaaa agctgctcat gaggcaaaaa  26220
gagtttcaca gaaactcact cctggagtct ggcgtgctct ctaaattttc cattcccgcg  26280
ttagtctagt ggatggatcc acatgctctc tttattataa gtgcctttta agattgaatt  26340
ctgacatagc taaagccttt cgccagtgtt ccaacagtcc tagaacgtct ttgagctaga  26400
cagtgacatt cagaatagcc tctggtatta cactatcaat aaaagccaag tcgttcccat  26460
atacaggaat ttacaatggt ttaggaagta gatcgggctg tggttttaga gtattgcatt  26520
atttatgaga tggttaagta gaacagaact ccctagttag aaccatgact tgggtgtgaa  26580
agcccttgcc ctaggagagt aaagacctca cacctggctt ctaagactat agctgagtca  26640
cacccataca cacgtattta caatggctta aggggaaggt agactattca atagactaaa  26700
ataggagcta tggcaagggc acgaagccct tgaccctggc ttttaagatt aagcaaatct  26760
tagatagagc cctttttgat cccagttgtt aacaatgaat tttatcccag gtggttcctg  26820
```

ttagaccttc tgtgtttaca ttcctctgtt ttatgtaaga atccagtaac ctctttgtac 26880
cttgctagtg tgtcacccaa cttccttatt gtcttttgca taaaaagtct gatgctcaat 26940
ttgacattac attcagattc cacacgacct ctcctgtgtg tgtctgtctg tcaattcatc 27000
ctacgctttg tccacccgcg actagagacc cgttccacac aaacaaaggg gcccagaggg 27060
tctatggcag ttggcgcctt cgaacaggga caccagagcg ggttagtctt tatttctttt 27120
tctttcgtgt cctggatcgg gcttgtctct gtgacttgca gtctctgcac cccacagctc 27180
tgtcagggag ttgggctgag tgtggaagag ctagggctgc gacaactcct gtgaagagga 27240
tgcttgccct gctgagacct gttctggcta cctgtacaca cagtctagac agacacccac 27300
cctgactaca gtctcctgtc tctcctgact tcagcatgag ctccactctg ccctcgatgt 27360
cgatggacct ggtcctcttt cctctccatc cttgctggcc caaaccagtc ttgccactca 27420
ctccccccac cctgcctggt ctcccttgga agctctcgcc acattgccag gagggggctg 27480
ctcccttgaa ttgcccctct atcaggcctg gtgtacctct gaccccgcc ctccaaattc 27540
accggtcccc ttattttcag ccacgataac ttggaggcat agggtaggag tccagactcc 27600
ctgggcttcc tggtccttct ccctagtacc cagccttgga catcagcaca ggatgatcat 27660
ccattctgcc tcctagtaac caggttaccc aggatcccct cttctataca ataggaatca 27720
atttggtttt tgagacaccc agtgctaggg acagtgctca gcaggcttga gaacactttc 27780
aaagagtggt gagaccacag ttgccgtgat ggggcagaga ccagatcaac gtatgtatga 27840
cacacgtatg tctgtctctg tccacagacg tagtttctca ccaggccttc ccctgacaag 27900
aggaccggac ttgttctctt ccactctgag ccctatacta aaggggctgt gactttgctg 27960
tggtttgtcc cctgctctat gcaggattgt cacctgcccg atgcttcacg ctcatcctat 28020
tacatcattc cacaggggtg ggtgtgacaa tccgcagtta tcacagagga cactctgtga 28080
gtgtcctctt tacagaggag gacactgaca ctcatgtggg catgtcacct gccctggttc 28140
gcacagctgg agaatggcag agggccatgt ggccagcaca ggaagagccc cagcttaagt 28200
gcctagcagg gctgaatttc aggttaggga atggtggagc tagaggccat atgtcccaca 28260
tggccccacc atggggtgaa gaaatggaag cagaaggcag gcctgagcag gtcagcagag 28320
agtagggtcg tctttggttg tctgaacatg ggcagggctt tggaaatgag ggtgtgggct 28380
tccccaggaa ggtaagagtg tgtactcgaa gtactatcat ctccagggag gggagagtag 28440
agtgcagggg tcaatagcta ggcactgtgt gccctgagtg agcaaataag atgcaagaca 28500
cacttactct ctgtatatcg aggggttcct gctgtcttgg gtagatgcat ggaggtcagc 28560
atgctacaat gttcacttcc tttggtcttg tctgagtttc cacgtggtgc caggtgactt 28620
agcatggatg ggaagtttgg tcaactactg tctctttcaa gaagcacagg gaatgttggg 28680
tggcctgagg gatgcaggct agtcttcctc cagccctgtt cccattccct ggcggatggc 28740
ctgagcccag gcgagagaag gttaatgctt cacatagcac accctgcccc acatggggca 28800
gctaaatttg tcttccttca ccagtacttg gctcccccag cttggggaga aggccaccgc 28860
tgccatctgg acatctaggg ccacacctgg ctagggaaca gaatgtcctg ctgaaggatg 28920
aggttgtctt gtgagagaag gggagggatc cagccagttt ccagatgggg caggaccaag 28980
atggttgcca cactggccct gaagaaggag gtacttctgc ctgcatcggg tgggacctca 29040
gcctctgtgt agcctccttt tctggaggta gcttgaggga aacaggcttc cggcaccaag 29100
gccccgatgt ggccaggttc ttgatactct gagttctgtg tctttgccac tgcccagaga 29160

```
taccgtcatt tcaggagaga cactccctgg ccatgttcct gagcctggca cgccctctgc  29220
ccacacaagg atctcatggt gctagagcct tcatgtccgc tggagggaaa ttcacacagt  29280
ggctgacatg ggtccagagg gcccctcctg tcatcaccac taatatacta gttacttctg  29340
atttcaattc ccctgtccac tggaacaaat tattagaagg gatgacagtg gagacaaacc  29400
acagtattga tcacgtcatg tagacatacc ataacagaga tttcccaggc cgggtaagtt  29460
tctctgggga tttccttgct gacccgaaaa aggcccttgc catagccagg ggacccagtg  29520
tcatcatgct gaagatcctg cctctcctgt gtctgggcta tatgtggaca gacttgcttt  29580
agtttccact agggaaggtg ggtattcagg ctcctagaag gtggggggta catccccatg  29640
gatggggtac cccttccaga gcaggttcgg gataattatg ggcatctggt atatcacagg  29700
tggcagtgag gctggggctg agcaggggtg agaggagatg gggaataaca aggaaggagg  29760
tccccatcct gtgtgattga agtgttctat gtggccaagt gacatctgtg tctcctcctc  29820
cagtcaggtg gcagggatgg ggaaggaagg ctcagactca gagctggtca agacagaggt  29880
tttcttgagg agccagccac ctctggcttt taagggagag gggggcttgg agagccaaac  29940
atttgaagtc acatgtatcc aaagccgtgg tgacagggca tgatggggga atgcttggga  30000
gaaggactcg gctgagttgg gagtatgtgg gggccaggca ggaggttcga aggttggtag  30060
ctcttgctgg gaagttgaga ctcgcggcca cgtgcagggt gaggtaatgg gagagtcgga  30120
gacttcctta ggggccagag gatagaggac atccccggca aacctgctct ggtgcaagcc  30180
ctagctgaat tacttgggca agccccttgg gtctcaaaca cagtttactc atctctgaac  30240
tagttggggg agcccatcta ggctgctgcg tgggcccaga agtcctgcca ggagtctggt  30300
tagcatccct gggctctctc tctccgtgga ggcccacggg gccttccacc acccagtttt  30360
gaggatggaa ttgttcccag cagatgtaaa tatccatggg ctcaagtcca gtcagagctg  30420
ccggagctcc gtggaggagc cgcgcccgcc gttggctcag tgaggagctg tgtcctccag  30480
tgaggaggcc tgtcattggc tcggtgttgg ctcagtggag gagccgtgcc gttggctcag  30540
tgagcatgtg ctatccgtgt gtgtggcttt ccgtttacag ccttattctc ctccgcatat  30600
cctggcacca caggtctggc tgctgtaccc ctgactctca tgcttgttgg gactccttgg  30660
gggggggggg cgggtagcag gtgctgaggt ctgagtttgg cacagaccat ctttgtcagc  30720
ttgctgtggt cctgtttcat gatgcaggca ctgccaggcc tggaggagat ccagctcagc  30780
aaaggaggag gctcatctga ggctttgacg gagctggagg caaggctagg gcagggccag  30840
agacagccca gatccctgcc atgcccacag cctgtgacct ggctgctgac agagcttctg  30900
acacggcggg ccaggcgggg ccagccctcc ttggttggtg cttctcccta aagtctccct  30960
ctgccgattc tgggccttct atgcctctcc tcacaccacg ggatgcgtgt tctctctagg  31020
aaaactcaag tcttcagtaa aaactacaat ctcagagcca gtgagatggc tcagtgggtg  31080
aaggtgcttg ctaccagttc tgaaaactcg agtttgatcc ctgggactta cagagtagga  31140
ggagaaaact gactcccgga agctgtcctc tgacctctga gttgagcatc tgcactcaca  31200
ggcatgcaca cacgcacaac gtgattattt tctatatctg tgcttcccaa cactgatttt  31260
tttttgtact ttccagagga caagtagttt ctcaaaactg gcctctttgc catcatgact  31320
tgatgtttta aatcactttc cgtgcttatg taatctgttc ctgcggtgtc tggggatcgc  31380
tcctctggtg gacacatctc ttagctagag gagtgtgtgg gacctataga aagggctcag  31440
taaagagctt gccatgcatc tatcaatcta tcatctatct acctatctat ctacatctat  31500
atatctatct atcatctatg tttgtatgta tctatcatct atctatctat aatctatcaa  31560
```

-continued

```
tctatcgtct atcagtctat catctatgta tctatcatcc atgtatctat ctatgtatct  31620
atcatctatg tatatatgta tgtacctatc atctatctac catctagcaa taatctatca  31680
atctatcatc tatctatcta ccatctatca gtctatctat ccattcattt atcttgcctc  31740
tgcccctgcc tctgactgtc atatgtctgt ctctctataa tctatctatc tatctatcta  31800
tctatctatc tatctatcta tctatctatc tatctatcca tccatccatc caactatcct  31860
atccctgccc ctgactctgg ctctgactct tcaattatct ctctgtctct ctgtgcccct  31920
ccctcccttc ctccctccct ctttcccttt ctgtctctct gaagagagag actataagtt  31980
tataatatag taaggttggg ttaccagctg caggaatttt gtagaaaatg gggggagggt  32040
gacagggctg ggtgatagtg gtggcttccg tgaggctgtg gtgctccatg agttcagagc  32100
tagatgctag taaggaccat ttaaggacgt gggcaaggag gcatgtccca gctgaaggac  32160
tagaagtaca gagccaaaca ctagcaggtg gcccatgtgc ctcccattaa gactgttagg  32220
actctagcaa ccagtgaggg gcaagatagg agggtgagca ggggcctgtg tccctggcaa  32280
gcaggtcaga atttgatctt cagcatgaga ggtttggttg gatgctcctt ccttgtgtgg  32340
gtgcaggagg acctggtagg caggaggtgt ggaaagcaga ggacttggca aggggtcttg  32400
gggcagagct gcaaactctg ccaagctcct ggaagtctgc tgcctgcagg tagccccttt  32460
cccacctccc gctctatttc caggcactgg gcacctgcca tttttttctt ccctctgctt  32520
gagctggcca tgtggacaca aggggtgaag agggacccaa atcctccctt gctttctcag  32580
taggctgtcc accttcagat atgccgtttc tggaattggg aaggcaagcc agcatgggtg  32640
tcaacaggtg gggtaaggtg tggcaggtag agttaccagc agagtactcc tggtacaatc  32700
tgtactgtga tacccagatc ccatccaatc caaggctctt gctgacaact tccaaggcta  32760
catctatgat gggaatcttc caggaacata cacttggagt cctcagccta acagggggtc  32820
tcaaagtgct cattcctatc ctgagaacat cagtgggtgt ggcaaaggaa tttgggagac  32880
catctcagac agtgtggtca cagcaggact gacattcatt ccaggtgctg cctgccacaa  32940
atgtctttcc cttttttttt ttttaattaa aaaaaaatgt gggccagtga aatggctcag  33000
tgggtaaggg tgattgctgc caagcctgat gacctgagtt caatccctga accccatgta  33060
ctggaaagaa agaatccact cctcacaatc aatcaatcaa tcaatcaatc aatcgaccaa  33120
tgtaattaag taaaaattta aggaatgccc tgaaattctc ctaacatata actagcattt  33180
tattctaaaa gtattattgt tgttgttttt gactgacctt gatctgatga gcttgcctca  33240
gccttgtcac agcagggact gcacgtgtgc accactgctg tcttccaaac aacattttga  33300
agcttgaagc tcagcgactt ccagcgtctt aaatccccag gagaaaccct ggccccatga  33360
gcccttgctc gctgccgtag cacctcaggc tggcaccccc aacctgcctt tgcctccctg  33420
ttcggatttc ctgttcagta catgttgctc ggacactagg tggttcagca cggtcttcac  33480
agtccgtcta cactgtgctg ttttgaatca gcagttcgtt cctggtcaca gtcaaatgtc  33540
acctaacatg tccgggtcat attgtatctg gcagttcctc ttctgatgtg ttcccagtct  33600
ctcaccctgt ctggctaaag tgaataatgt cactgcgaag gggcctggag tccattcact  33660
gtgtgacatg agccatgtcc tttccctttc tgagcttggc gtagtccttg taaaagggag  33720
aagaggacca agtggtccct ggggtaggac ttctaagcat gtcctcttgg gtctcagggt  33780
gtccaccagc ctggcccagc tgaccagccc actctgactg cgaagagata cctccctgac  33840
caatggctcc tcaccagaaa gtaccattcc cccggagctg gtgaaggcag ctctgtccac  33900
```

-continued

```
cttccatgct ggttggccaa tggcttgtca aaaccttcat gactgtgata aatgggaggt  33960
gggaaaaatt aatccttatt actggagaag agcataaatt atgttaattc ctgtgcttat  34020
tatagttgtg tgaccttggg caaggcatgt aaggcctctg agcctgtctt ctgagtaggg  34080
caggactgcg atatgtacag ggtacttgtc ctgtgtcatc ctcccttgct gactgagccc  34140
ccaccccact ctctacctgt gctcagctgg tcccctttta ctggccctct cagcttgtgc  34200
cacttctctg aggacccatg gcctggcgcg tgccatctct agatgcgtgc cacaaaccac  34260
tatgagcagc ctcctgcctg gggtcagaca aaagcgacag atctgccctg ccagccctgg  34320
gcaagtctgg acctgtctgc ttggcagtgc agagctgggc caagctggtt tgcgggctta  34380
gaaggctgcc ccagggaggc tgctccttaa tgggcagcgg gcaggtgggc tggggtttcc  34440
ctgccccacc ctcccacaat ttactgtgcc tgagcgccct tacgctgccc cgcctccagg  34500
gtgactgtga gtgggcggag cctccgcgtg ggaggctgtg ctgaggaaat cgtggggaaa  34560
gcggttgtgg gtactagctg gggctagagt gaccctgctc ccctttatct cctttgagga  34620
gaccatccac aggtgacaac tccagggcag tcctaggact ttagccttag accttggagg  34680
gtgaggacca tagagggtct tgagtcccac ggtaacctgc ataactgtgc attacaggca  34740
tggttccagc agggggcgcc ctacacacgc tcttactaag aggaacggat gaagtttgag  34800
ctgtctcgaa gacctggcga caagtcacag ccttcccccct ccaacataca caaaccaaga  34860
cctggcttga cctaaccctg gccgtcattg taggtttagg acacggtgac ggcagtcatg  34920
gcccattctc tcaaaaaact gacccaagac cacaaagact aaattccctt ctccaacagc  34980
atctacccaa tgtgagggca catgcccttc ttacccgttt tctggcagca gaatccggga  35040
atggcgtctc taaaaccaag cttgcctcag tctcacctcc tggaccagag aatgagctgc  35100
ttgggagtgg tgatggtagg gaggaagaga aggggagcta gacagggaaa agggaggcaa  35160
gggggggggg agaaagcaac gtgagtggaa ggacttagca cagctctggg gtctccttgc  35220
accatcatag gcagccccgc cgtccacttg gctcgcctgg tactgaggaa ggcaggattc  35280
cccaattctc agtgtcctcc ctcttcttcc agaatgagcg gcagcgttgg ggagatggcc  35340
cagacctctt cttcctcctc ctccaccttc gagcacctgt ggagttctct gtgagtatgg  35400
agaactccgc ctcactgggt ttggttggct tagctggctt ggaataaata ggttgggaga  35460
ggggtctgct gaggtagcag ctgccttggg ccatgtcctg tgtgcatgtg acccacagtc  35520
atggtctgtc ctctggccag ttctctagag ggctgtgggc acagagatca tgtgtatgaa  35580
gcattttcta atagtcctga agggcaagcc gagggctggc agggattgtg ggagctggaa  35640
aactccggaa gtccaaggac atatggctta tctcctggga tggacacaca cacatggggt  35700
agcctgatat cctgaaccag gggagcacag cggattctgg agcagatgct aacatccagt  35760
gtccttcccc tccaccccca cagagagcca gacagcacct actttgacct cccccagccc  35820
agccaaggga ctagcgaggc atcaggcagc gaggagtcca acatggatgt cttccacctg  35880
caaggcatgg tgagcggggc tgcgctaaag actggatgtt ggtgataaat gcgggttggc  35940
ttttctccgg tggaacgagg aagcagggct ttgggtagcc caccttgggt cggaagaaaa  36000
atatgcaatg agctcatggt actgtcgatt cctaggtaag aatggattca agcatgattg  36060
gacccagcgg taggaagagc ttcgggcatg gctggaccca ggtggttccc tgggaccact  36120
tcctctttca cttgcatctc tctttctctg gtttttcctg gggtaccttt gttctttgga  36180
agcctcggcc ctcagagatt gtccaacatt ttgaggcccc gtggagaggc cacccctctt  36240
tttcctttgc ccagaaacac tgcttcttca tgttggtctg agcatacttg tttgctatgt  36300
```

gcctctgagc tgtccctatc tttctgattg gcccatgttt ctatagctat ctctggactg 36360
gtcaggatga agggtactaa ggcaggctcc ttatattagg agaggaagat gtggccagtg 36420
gagacagtgg ttttattcct catcttgtgc gctctttcct gggaccaaga ggggtaccaa 36480
gcagccagcc tttggaattt gcctcctatt gggagctcct cttggcaaga agacacagta 36540
gctgtgggat tctgttcctg cctcactctc tggctaccac tgccgtgccc tggtggtgcc 36600
aggaactgga ggaaggtgac tgaagcatgc aaagggcaag tgaaggcctc tgttcccgag 36660
gaagtccctc gaggccttct gtcctcagca tcctccccta ctggaccacc aaagtgctag 36720
gatcccaaag gcgagagggt tgggaaagcg tcaggcgggg acttgttgga ggaaccctgc 36780
aagcacatta aggaagagca aagcccaagc cgagttggca catgtcggct gcagaggcac 36840
cagacagctg agcatgtctc cagtgtagcc ttcctcccac tagcacctga tgagccatat 36900
gctagaggcc cagggactct agaagccaag caaagtgtga ggctaacccc tacttggagg 36960
gagaagcctg gccactttag gcattagtga acaagggttg aagagacagg aggcactatg 37020
cccttactct cccctctctc tgtagaggtg gaaggttggt cagagcccac tgatctccca 37080
tggaactggg tgagactctc tatagtggca gccccagggg gtaagggtat catcctggtg 37140
atgcccactt ctctgagctc tgcctgtcca gccctgatct ctgccagctc aggagcctgt 37200
ttcagaatag cagttcacct gtaagtgtcc attttacagg caagggaact gaggcagatg 37260
ctgtggaagg agagcctggg gcttggggaa gagaatggtc ctgcatcatg gtgaggatag 37320
tcccccatcc tgcctgttac tccgtagaga catgattctg acacccatca tctaggatat 37380
atgtgttctc cagtatagag ggataggagg tggctactag gctccaggga gggagggcct 37440
tacacaaaga ctctaaagat gcctgcttta ggagttctgg aagctgcctc ccacagtcta 37500
agctacccag cttatgcctg agagggcaga gtgctcagag accccactgt gactgaagga 37560
agaagcaggg aacagccctg gggccccgga ggctagggat gtggtaccca ccccggcccc 37620
aaagatgccc aacgtaaacg tgttggcggg tgctcctggg tgctcacctg ctggggcatg 37680
ctgctcccag caggggtaac acgggcgggg ctcaacacct ccacaaacaa ggggccgctt 37740
tctcaggtag caacacgcct tgcagtaaag ccatggacga aattcctggg cgcacagctc 37800
agctcctaga agtgggaatt ccctggaaac aggacttcct ggcctccctt ctgcagggct 37860
cagctgaccc tcatgcacag ttctttcaag agacagctac tggtccaaca gcttcctgta 37920
tgctcagaac ttccagcagt cctgacagca aaaatcaaga ctcagagatg agtgacagat 37980
agggccatgt ggcagcaatg ctccagagct catctggact gcagggaact gggggtgggg 38040
tgaggtcttg caggtgctgc aggaagttgg gggtgggtgg ggggatgcag agagcactag 38100
acattgcatg ccatgaaatg aggtagatga agtttgatct cataaattac atggtcgatt 38160
acagcttatt aggatggcag aggaaagggg catccaggca ccacagggag catctttgag 38220
tccagggatg gaggcagcta tggaaatgac agtttggggt acagatgtgt gagagtggtt 38280
tggggaccta cagaatccat catcgtttca gggtgcagcc cggaggaagc aatggtctgg 38340
gtatagacta cagagtacag actggtctgt gaatgctgca gacagggtag cctgcccagg 38400
cccacattca gctccacagg tgctctgcta tgtccagtgt ctgaagtcca ggagctgagc 38460
ctgctgactc accctggggg ggggggctcc aaagtctgat gggcatcaga gggaggggtt 38520
gtggagcact ctcagaggga ggagttggtg agcactctca tagggaggag ggtgtgcatg 38580
ccatggattc acgtgttgtt tgcagcggct tctaaagtgc tgggaggttt taagagagtg 38640

-continued

```
cctgagtgtg tgtggtttag agttccaggg gctatgggag gcacagagag gaaagggccc  38700
taagagggct gggataccag ggccagctca gcgctgtgat gaggtggaag ctcccaaatg  38760
ctatccccat ccctgagaac tctagcccca tccctagctg ggtccaggac aagaaacact  38820
acccaggcat gttctcaggt caataggcag ttctggcatt tgaggttcta aggacttcca  38880
gcaactccac ctcctgtgtt ctcaggtacc ccctccaccc ccacagagcc ctactcagtg  38940
atgactggtg tccagttgtt cctgtgtgct ggacaatccc acccaaatac caggatagtc  39000
cagcaaaggt gtcatggctt aagccagcat ggcccttgag tagatgggat atgtattctc  39060
ttcaatggtt ccttctgtgt ctaagggacc tcaaacggga gattgctttc tgtcacatgg  39120
aatgtcctga gcaggtctac cagctgtggt gaaccctcag aactccatga tgctcttctc  39180
ccccaactta atggctgtca gaaaccggtg cagtcagtga gttcaagttc tcacatgctc  39240
ccgagtctcc acatccttgc ttgtgaagtt gaggtgatgg aaagggctag aatggagagg  39300
accctgggag atcggtgcag cctcctgggt accagcttgt ctgcctggcc ttgtgcagag  39360
gggtgggcca ggcctcgaca tctaaccatt cccgagtctc attggagtag agtgtgttgt  39420
aagattaaag caaatgggat gggcaggagc ggatgaaccc ctagtgggtc tgaggagaac  39480
cctaggcatg gtgagggacg cccttgtggc cttagcttcc tgtggccatg tagatggcat  39540
agcagagcct agacagttgt gataggtaaa gagggaactg aaggtctctg gggctcgatg  39600
tcctgggttt gtagcccatc ctggtcttcc tagttgggag gttctcagga tcctttagtc  39660
tcctggatct gagtggcccc atctctaaga tggggaagtg gacagatcag aagcccataa  39720
gtgctgtttc tcccacaggg agtgacagtt agctcaaggg cgaaggccta tgttttccac  39780
actgttggag actctgcaca gtttgccatg caggggcacc ggactctaga gctggctttg  39840
ccccttggcc attttggctt ctgcatatgg agctccttgc tcctgcaaat ggccttcagt  39900
tctagctgtc cttttagatt ccgggtgctt cacagaaact ccactttaaa aatggcctgg  39960
agactaggtg cggtggcacg tgcttaaatc acagcccctg ggtggccagt ggaggtggat  40020
ctaaagtttg aagccagcct gacctacaca gagaaaccct atctcaaaag tgaaatgatc  40080
cccctgccca gctagaagag aactcagaga tgcctctccc gggtgctgtg tagggtgagc  40140
tgaggggccc atgccaaagg ctagggctag tcacagggtg ctcagcaagg ttgagaatca  40200
atgggtgttg tcacatgtcg ggggacaggt cccagatcaa taaggcccta ccacagggtc  40260
ttgggagatt gagtggaggg caaagttcac attgtgagca ccgtgtgcca agaggcagtg  40320
gagggcttga ccctgagggc agaaatccca gttctcaccc tccatgccca gtgtttgagc  40380
agacctttct ctctgcttcc ctggttctcc atggaccaca agaaggtgga caccaagagc  40440
cagaggccgg tccagctctt caaatacaga aaaaggacag agtgctgatg gtcagcagag  40500
gaaaggggag agaggcaggt gccctgggcg cggctgcagg atcactgccc tttcccgcct  40560
cttcatgtcc tcctccaggc ctgcacctcc cctcagatgc ccctttcccg ctgtttctgg  40620
cgcctttctc tagcaacagc tgttaggaac agatgggccg cagagggttg gggaggtgct  40680
gcagctggct gggcagaagg tgctctgctg atctccctgt ggcctgcagg ggactgagcc  40740
agggagtaga tgccctgaga ccccaaggga cacccaagga aaccttgctg gctttgagaa  40800
agggatcgtc tctctcctgc ccaagagaag catgtgtatg ggccctgtgt atgaatcctt  40860
ggggcaggta ggtcaggaag gatagacctt ggcagggaga atttatatca agggaagggc  40920
agggcaaacg gagatggaga ctgagtttta tgtgatcctc ttggggaccc ccagctcccc  40980
caccacttcc agtggtttct gaccactctt ccttggcagg ctttggtagc aagagggtcg  41040
```

-continued

```
aaggtgtata gtactgaact tagctgagcc ccctccccag ttccagagtc tcactgagag  41100
cccattcctc tccccaactc cagggtccag aggaagaggg acaaagccac cagcagggac  41160
agtatgtggt gtgtttgctc ctgaatcaac acaccatact tgggcactgt agtcttgagc  41220
atgtgttgtg gagagaacgc caggggagcc tgcagaactt cacttccacc tcagctgtga  41280
gagctacagg agcagtcagc aaggcagagc ctccagtgtg ttacccccag agaagcaggt  41340
gctgaggacc ctggcactac ctaggggcac cggcagtgga ggcagacagg caaaccacct  41400
aggaggaagc aggagccagg ctggggctgt ggcagagagg agagctcagt ggtgggcgtc  41460
cctttccctg gccagaccgt tcctcagggc tcacagactc tcaggccagg tgcttcctct  41520
gggagtcagg tgtgagttct cacggacagt cccattctcc tttccggcct taatccttcc  41580
ctttattttc tccttggggt gtttgtgaag ccaacacgac aattgattga tgaggaccca  41640
gagtggctga gggacacaat tccttaaacc ccaatctaga aacttgaagg ccatctcttc  41700
agggctctct ggagcagcct ggccacacct acggggtggg agtctgtaaa ctcagccctt  41760
agtccccatg gagggaggct gcagttgacc cctggtctat ctattataaa tagatccctg  41820
agcagtgttt ctccaaagat tgctccccaa aattagacta gaaactgact ttattgttca  41880
tagctgactt atgagcagtg cacacctgtg cagccccagc catgaacatg cctctcagac  41940
cagcgtaggg atcagtatga agtagtccat ctttactgct tctgtgaatt ccagagcttt  42000
gaacaggggc tacagccact gccacagccc tctgaccaag cccagatact gcaagctctc  42060
tggagggaga aggaagctgg tttggaactt ggcgagaaag ggttaaacag aggactctgt  42120
cttcacacca tctctgcgtc ttcttgaaca tccttagact ctaaatgtgt gtgtgtgtgt  42180
gtgtgtgtgt gtgtgtgtgt gtgtgtgtgg cggagggggc tcaagctgtc cttctaggag  42240
gcctagagat tcagggccga tgaccctttt cacaggacac gcatctgttg tggaccacta  42300
tggtgacttc atgcgtgaac cagacctgaa actcaaatgc ccccagacaa ggggcagtgg  42360
tatccactgt atggtcccca ctaggcagat gctgatatag agcccctggc tctacaaact  42420
ctaccatgcc tgtggtgcct tctcgggtgg tccttcaaaa attctctttg gtggagtggc  42480
cctgtctctg cttcctggac ttagctagag ccaggacaaa aatgctgtct gtaaaactct  42540
gttatgggtt ctttggctcc aaccgccact ttgggccttt gacggtagtt ggccgtgttc  42600
tcgactctcc cctagcccaa gcatactggt gtgtctttcc tctactcagt ccttggggtg  42660
gtccctgtag gtccacgatt ccctggaagg aggcaggttc tctcccctgg gtcgccaagg  42720
ctggcggcac catctcttcc ttcagggtga cccaacccag actgcaaagg tctccaggac  42780
cagggctgac tgctcatgct ttagagtgta ggctgtttgt aggtgactgc cacagccctc  42840
cggagccttc cctgagtggc agcttagaag ggtccgagtg ggagtgtatg atctccaagc  42900
cagccactga ccctgcatcc ccacctgctc cccctgctca gcctgcttgg tgcggtccaa  42960
cacatctccg ggcaagctga ggcctgccct gagttgatga atagtcataa ggaataaagg  43020
ggcgggcccc ggtttgttgt tggatgcagc cagttgacag aaatgaggga gatgggcagg  43080
gtgagaatgc caactctcag tccgcacgcc tctgagcatc ctccgctcct gccttcctag  43140
ccacagagcc tcaacccctc agtccacccc accgggcagc caccagtcta cccctacccc  43200
acctagccac ccagacccat gcctcgtccc gcggcacacc agctcctcag cgtgtgcaga  43260
cccccacgag cctaccatgc tttacgtcgg tgaccccatg agacacctcg ccacggtagg  43320
tgtaacgtgc ctggtatagg gtctgcttag aggcctgatg ccatccacct agggggcttg  43380
```

-continued

```
gcagagtctg ccatggttgg ggttcagaga gacgttctct tgactgcctg atggcagagg  43440
ggtaggctgg agagtggaca ggttctgctt ctgttcatcc ttggggcagc tctcgaggat  43500
cagcagctcc gggctgggca ggaagtggga tgtgggatgg gaggcttggc tggcgtctgg  43560
tcagggtggt agagctgctg cccaagcccc tgggttggat acttctgaga tgactgttga  43620
ggctggtggc tctggccatg ctcagggtcc ccaagatagt ctgccctagg agcgctgcaa  43680
agaggtcatc tttgtttggg ctttggcgtg aagctgcccc accctgccaa gagcatcctc  43740
acctgggagt ttgttcactt gacagcgcag atggggcgtt tctcatagcc atgggctctc  43800
ctccgtgtgg gtgtgaactc caaggcagag acaggcagcg ggctggaccc aaggctccct  43860
gttgctcctc tcaagcaggt acagccagcc tggcagagag cagaaggaca gaaggatgga  43920
aggagccaca gcctgtgctt ggcctgagcc caagggactt gggctcattt ccagacttgc  43980
caggtccctg gggtcaggca gacaccaggc tgctaattga gcagccttta ttgaccagtt  44040
aaaatggggg agatatcaca tgagatcacc tgagtaagtg acccactgca tgatcgtcat  44100
tgggggccag cccttcttga tgaagcagaa ttaacatcag aatacaaagg gcagcttaga  44160
agcagaatta acatcagaat acaaccagca gcaggacaac ccacaacacc tgggtacagc  44220
tgccccacaa ggctatttcc cttttaggag agcagagaga gtaaggaatt gtacaggaat  44280
cctgggatgg cagaggtgtg tgtgtgggtg taggggtgtg ctggtaaggg tgtgcatgtg  44340
gcgtgggggt gtgcatgtgg cgtgtatgca tcctcttatg atcagggaaa agactgagtg  44400
tgggttgaat cacggttttg cacaggtgcc cttcctgagg ccagtaggag gcagagtcac  44460
tatccaggac cacacagaga cctgccccca agacagccgc tgactctggt cctggtgccg  44520
ctgccctagg tctcagaacc agtggtggct accatgtcat gatatttctc attttgtgtg  44580
tgctgtggag cagtgtgctg tggtgtgtgt gtgtgtgtag tacaggtggt gtagtgtgtg  44640
tgcatgtggt atgtatgcat gtgatgtgta tatatgtgtg tgcatatggt gtgtgtgtgc  44700
gcgcgcgcat gtggtatgtg catggtgtgg tgtgtggtgt gtattcacat atgtgtgtgt  44760
ttgtacccac aaaccatgtg tggtgtgtgt gtgtttatgt gtatgcaaac gaaggctaga  44820
ggtgaacctt gggtatcact cctcaggtgc tgtccctgta ctctgagtct ctcacttgca  44880
cctggggtat gctgtgtgct gagtaggcta gactggtcta tctgtctgtc tctgcctccc  44940
aacactagaa ttacaagcac acactgccat gtctggtctg ttacatgggt cctttggatc  45000
aaatgcaggt ccttattttt tttgtggcat gcacactacc aacagagcca cctccctggg  45060
ccccgttgtt tcttcttaaa acgcaggctc tgtggctttc tctccccttc attgcttcat  45120
cacagcacca tgcgcttcct ctgcattctg accagcgtag cagtgtagct tgggatttgc  45180
tggggctcca aggctgggct gagccatcat tctacctgcg tgggtgactt agtttcctca  45240
tttctttgtg agaggatcgt gtaggagagc atagcctttt gcccagagaa tgttaaatcc  45300
aatgtggatg gagccttcgc ccgtgtgtca ctcccccacc atctgccttt gttgtcctta  45360
caacttgcag cagtcccttg ggagctcaca ggcaagacct gtccttggag accggactga  45420
ttttcaggat gccaccttat ccctggatgg gtttctcata agtgtatccc atcttggttt  45480
gggggctcag tatacaagtt caggctttat ctctggtgac cactagctat ggttttggga  45540
tgagacatgt gaggccatgg gctgagacag tttccttctc tgtaagcagg gtagtagcaa  45600
ctaactctca tgcctgctca ggccgcagat atgagctatg aggtaccatg gcctctggcc  45660
atgactgtgc cagcctttta taagtcagtg gaggtacaga gaagctggcc tagagaactg  45720
ggcacatgtt cttcctcctg tgagcctgcc tcccaccttc ccttctctct ctgaggacta  45780
```

gagactttga ccgagtgatg acctacagct gagtgcagcc ctgtatgtaa ggcgaggttg 45840
gctcggtcct cctgcacacg gtgagcccat ttacagagct ggaaagagct gaggccactg 45900
gagctgggcc tgatagatgg gatgagatga gcggggagag gctgcaactg ccactatctc 45960
ctgatgcccc aaactcttag cttcttcatc agcttccagt tctcctgcat gtacacgtct 46020
ctctctctct ctctctctct ctctctcaca cacacacaca cacacacaca cagagagaga 46080
gagagagaga gagagagagc agctcccagg atatagtaag gcaagtgtgc tctggttctt 46140
cagtgtcttc tgtgtgaagt ggggctcagc tttctttctg cagaaccagc atcatggttg 46200
caggactggt gaacctggtt atcctccaat cccttaaccc ccagaccaac acacacacac 46260
acacacacac acacacacac acacatgctc ttataggcac cacacataca tatgaacaca 46320
aacacaccat acatgcacac acaaacacac acatatgaac acacacatat gaacacaaac 46380
acaccacaca tgcacacaca aacacacaca tatgaacaca aacacaccac acatacacac 46440
acaaacacac acatatgaac acaaacacac cacacatgca cacaaacaca cacatatgaa 46500
cacaaacaca ccacacacgc acacacaaac acatagcaca gcacatatca atatacagtg 46560
gtgcatgaat acctcatact cttgtgtaag gcagcataga cgtgcatgca cagcccaggg 46620
ctggagttca ccctgtctgg agcaggcttc cctgtgctcc tgcagaaagc atggcttctg 46680
gaccggagga gcccgagggg gcagccccag gtgagagaag gtagccgagt aacaggaaag 46740
agctgtagga cagacgagtg gagctggtgc agtgctggta actgaccaca cgggggcagg 46800
gccgagactg ggagaaggga tttggtccag gtgggggcca ccagcaccta gggaagtcag 46860
agtagaggaa attctggaga ttctgcactg gacttgctga ctggctagat gtcggggaag 46920
gagtgtgtta gagtggcctc aaaggctttc gactgtgatg gggaattgct gcaggggctg 46980
agaagtgaga ttgggcattt ctgtgcagtg tttggggggg ggggggcttc agcagttgag 47040
cagatgaggt agagagggtg gccgggacag gacatctgtg gaggtggtca gatgtgagac 47100
caagaccagg ctagaggaca aggccacaat taccttagaa ggcctgtagt gatgattaga 47160
aacactgtag ggttcttctg tgtgggaggt agacaaagag cctgagcatg tgggtgggag 47220
tggccaggtg gacttgcagg tgtgggaggc aggtgggcag ggtggtgtga tggacagatg 47280
catgggtggg agtggccaag cagacatgca gttgtgggag gcaggtgggc agggtggtgt 47340
gatggacaga tgcatgggtg ggagtggcca agcagacatg caggtgtggg aggtaggtgg 47400
gcagggtggt gtgatggaca gatacatggg tgggagagga caggtggaca ttcaggtgtg 47460
ggaggcagga gggcagggtg gtgtaaagtg gacatgagtg ttatttaagt cggggaaggg 47520
ggctgtgtta agaggagtgg gagacaattt tgggaaagag agccacactg aggagcagcc 47580
tggaagccag aagagggctt catggtgacc cgggacaaag gaccccatta caaggttaga 47640
aaagggacca gaatcagctg cattgaggga gctggtgacc ccggggaggg tagaactaag 47700
taggatcagg tctgaggcca aggcataccc accagagtcg gatccaagta ggtcatcctg 47760
gacccatgtc ccttctcagt cccctcgctg tgttggaacg catctgcttt ccatgctccg 47820
tcccgctccc ctgaaagcca gctgatgggg tgtcagccca tggagccaat ctgagctcct 47880
aggaaacatc acctcagctg gtgggaagtc ttctccactg gcccaaaccc aaaccctgga 47940
actatcctcg atccccggca caacacctca tctatgccgt ctgtgtgtcc aagggcctca 48000
gagctggcca cccagtgctc agacgtgcac ggatccactg tcagatgtcc tccaccacca 48060
agcaagggga ctgtgcacgg ctagcctata accctctctg ctgaacccag aagttatgct 48120

-continued ctctcacctc ttctgctgtg ttcatcaccc atgcacttgc tctggccagg gtcctttccc 48180
tgccacccca cacagaacct tgccgaatcc cacaagacct acagattaaa aaccatggca 48240
gctcttgcct ttcccagagc cccacccttc caggacaccg gcttctgcct ctttggtggt 48300
cagtattttc tcccttacgt cccggaggcc ctaagcttga atgctggtta gctggatggc 48360
ttgttactgt actacgaggg gagagctcag aagcctctac caagagatgt caggagccta 48420
actgagccag tcgatgccct ggatatgtgg gcagcctttg tcctcacctt tcacagccca 48480
tcccccagct tatattggga tgccttctcc atgggggggg ggtcccaaga caacgtcaca 48540
gcctcgctat gggtcgctgc aggtgacagg gcgacacaca tgggcccaca tcacgcttag 48600
tgaacatctc atgtgtcact atctaatttc tcagcttagc tgctcattct ttgtttctcc 48660
ctgacctaag atttaggaag agcccgggag gtccccactg actgtcccat gaatggggac 48720
agtcccagtg gggactgtcc catgaatggg acagatgggc agaaaggcag tagggggcgg 48780
ggggaatgca cgaacaccaa tgctggattt gagactacaa gaatgtgcca gggagaggtg 48840
ctggcagagc tgtgtcccct cttctgttct ctcagacaga caactcgcct ttgctgttgg 48900
ggtacactcg gtgatttaaa aattcctgtg aatcactgca gcttgtaggc agtgccaaag 48960
agatggggga gctgcctaga gaacccctgg aaggctctgc tctgtgatac cctggttcag 49020
gctatgttgg tggaggggtg gcctgggtgg gtcttgcaga cacatgcctg gcagcccagt 49080
agagcttctg ggggcacgtt tcccgggttt gaggtgtgga aagttccaca tggccctggc 49140
atgggaccgg gcaaggccct gcctcggcgg gcaaaaggag ggtgcaatgc acatacctct 49200
agggaggcag ccgtcccccc atgcacaagt cctgtcttgt tgacatttcc attcgtttaa 49260
tcataggctc ggggagactg tgggaaacac catcaggatg gaggtctcca gctagcacag 49320
aggcgggaga gatggctgtc tccacagagc cagggggctg tcagtcacta accccaggca 49380
agcggaaccc aggctctgac ctgcctgcag gggaagaccc cggtttcaga cgctttcttc 49440
cctttagaag aatccacagt gttggctggt gttttggaag caggaggacc ctaactcccc 49500
atccctcagt gctgggctca gagcagaatg agtgacattt gtcaccaggg ggccctgggg 49560
tgagccattc ctgcagaaca ccaagattcc ctggaaacag atgtggtcac aaggtcatgt 49620
cactcatacc tgtgctggat gggtgaatgc ctcttgaccc ctacccagaa ttacttccta 49680
gtaagggagc ggtgaaggcc atggggcagc aaatcacgtg cccagaggct gggccttgaa 49740
tcgaggaagt gatgttggga taaaggaatg gaggctgcgc agtggaacct gagaagccac 49800
agcacactat gctctgtaag ctagctcctg tctccagttc ctaccccagt tgcttctgtg 49860
aggaagctag ggtgggccac aactaacctg aaatccatag gaagggggtg tgcagaggcc 49920
agggcaaatt ctagaaagaa gggaggaaag aaaatggagg aagggagaaa ggcaaagaag 49980
ggagaaaggg aggaagaaga gggaagggga gagagtgaga gaaggagagg gagggaagaa 50040
agagagggag gaagggaagg gagaggagag gtgagggagg gagagaggaa gggaaggaga 50100
gagggaagaa gaaaagggag aggggtagag ggagagaagg agggagggag agggaggagg 50160
gagggaaagg agaaagggaa gaagggagag aaggagagag ggaggaagga gagaagacag 50220
aaaggaagaa gaggaagtga tggagaaaat gcaggaaaag atggagaaag tgtgggggaa 50280
gggaggaagt agaagcctag gcaaaatcct ctcctactga ggtcactgga tttgggtagg 50340
gctgtgctcc atactctcca gttgtccggt ggtctatgag accatgttcc cagccgggca 50400
tggtggcgca cgcttgtaat cccagcactt gggaggcaga ggcaggtgga tttctgagtt 50460
cgaggtcaac ctggtctaca gagtgagttc caggacagcc agggctacac ctcgaaaccc 50520
tgtctcgaaa aacaaagcaa aaaaacaaca aacaaacaaa caagagccca tgttccctct 50580
gtacactttg gggaccacgg tgggaactct gaccttaagg ctgagttccc cctgctgtgt 50640
gctggggatc ctggtatcat tcctgagagc ctggctgagg attagaattg gtgggaccag 50700
gaagactgtc agagctgctg tgggctcagc atgaggccag cacacaggaa gttctccttc 50760
tgaaagggca tgctcaatac agggtatgga gatggtgggt gccccctgcc ggccaggcag 50820
atgagcctct ggctggtggc tgtgaatcag ggactggtgg gtcactgtgg cgagatctgg 50880
aggcctgtgt gtggcttctc agaagcacaa cagtgacaga gtcaagtgcc tgtgcctctc 50940
tgagagggca gcgccgggtc aggacccagc acacttgagg ccctgtgtgc taccgtgacc 51000
tgttctcatt tctttgtgtg tactgactcc gagtccctca tcagcatcac accgaatcac 51060
ctcgatgtaa actgaggcag aggagtcacg gaaagggttt ctgtgtgaag cagggttagg 51120
ggagaccgga gataacacag ataaactgga agggaagccc agagcgctgg ggcggcttca 51180
ggaggtagga tggctccgca ggctgatctc ctgccgagga gatgcaggtc agcctattct 51240
cctggaactc cgcatttaaa tgtgacaacc gacaggcagg cttttctgtc actgttttta 51300
tttgagaaat aaacttctcg ggggaattgg gtgtaatatg ccctttgttg ctaagcactg 51360
gatgcagcca gtccacctct gaggtccgtc ttggtgttct gtgctatagc aaaggctgcc 51420
gtgggtactg aagtcagaga ggagtcggtg tggaaggcac ctgctcccaa cctttaagag 51480
gtcgttcatt ttctgtctac atatataaga acagatcgat gagattgttt gtaggttaga 51540
aacagttaag atgtgagatg ggagtcttcg gggtaaaatc atagtatcca atgtgtgcat 51600
gtgagggcag gagcctgata gcaggacggt aagagcctcc ttgtctggtt aggacaagag 51660
agtggtggag aaaggagagg atagaggggg aggccctgcc ctcaatcagg catcaaagag 51720
cttgtctaac tatggttggg tatccacttc aatgccacgt gttggtacaa ccagtacacg 51780
tccaagagtg agaccccggc tgctgttccc catgtcccct gctttatgac gctgctcagc 51840
tgcctctgga gctcagcctt tggagacagc cttgctcctt gtgggcagac aggctctgtc 51900
ccttcctcac tgggccttgt gttagtgggc tggtgctgat gatggatcag ttgcaaagtg 51960
tcagagctcc tggattctgg cgtcctggtg gctgaagcag ggttgttcct tctgaaagaa 52020
cagccatagg ttttcttgct cccagacctc gcccccacaa ccatgcgaca agctatgtgt 52080
ggatttcatt ctcactatgc agaagataaa aatggaggcc cagggatgtg gaataatacc 52140
ccattcctct cctgctccta ctacctacct acctgccaag gtatagtgct caccctgggc 52200
tcatctgtca acctagctca gccaagagag agtgctagag gagtgaacca gcgtcatcta 52260
cgtctcccga tgctcaaggg agataagaaa ctcagctgcc ttgtagcagg agcttgggga 52320
cctaagggac ccgttgtgag tgttctatgc tgatgaccct ctgctagtag agcgaggtca 52380
ccagcctgct gtcaccccag gccctgaaga ggccaaggga gacaaggtgt gaatactgaa 52440
gtctgagcct aaggaaagag agtagaagca ccagtggctg tttccagcag aggtgccggg 52500
taagccccca gcagcactat ctgcaaggac caggaagaga ccccgggact aagggaataa 52560
gagatcctgg ccttctctgt agaggtgggg ctcactgaga cccccatctg tctgagccca 52620
aaataggtct taccctcaat tgccctgggg ttttctggat gatcccagac cctgtggtca 52680
cagtccagtg agcgacacag acctggcaat ggggccgtgt tctcaaaccc tcatccccat 52740
cggaactatt gtcccccaat tctgatgttg gcctttccca tgaaggctgg tccaccagtg 52800
gcctggacac tgtaggaagg gacacccttt ggctccatga cgccctcatt cctcagggcc 52860
tcttcaggtc acgcccagac actccacttg caagtatagg cacatgtgtg ccgccgcagg 52920
ccgggcatgc cctaattagc ccactatctt ggagttctca ttgaaagcaa aacaaaccaa 52980
aaaagtttgg gtttgcccag gttcttccct gaggccaagt gggtctcgtc tgggcttccg 53040
gggggcctct gggtctgggg gacccctggg cttctgtgta gacctgctta ggcctctctg 53100
acgaggcttc tcatttcaac agcatgacgg gaggcaaaag tggggggcca ggttgagcct 53160
cactgcctgg caatgaggaa atggtttcct tcccatgagc ctcaggagga gggaaccctg 53220
tgtagaagga acgtctctta cactctccag tcactggggt ctttaccatc tttgggagac 53280
acggtagaca ctaagaccag tgagggagtg gaagatgacc ttgggactgt aagaaacgag 53340
caggcacagg agatccagca ttcactagac aagggaacag actctactgg gcagcctagt 53400
gcccctatag aagtctgcag aggcctgcct ctctgagggc cccgggcttg ccacaccagc 53460
caggttttgc accccagtgc tgagggcctg ccttcccgaa gcgcctggtc cctcctgcat 53520
aagctcccac agatgctatc gctgttcctt ttggttcaat gactaagtcc ttggcaccca 53580
cctccaatca ttgaagaatg cagacaagtt aaaatatgaa cctcgctgcc gtgggcctgc 53640
accctgcttc tgagacaggg ctccctgccc atcaaggatg atggggatcg ggcacggagg 53700
ggctgctgct gccttctgca gatgtcatga cttcttccaa agccctttgc tgggaagaga 53760
gtgaacttgg ttgcaggaag gaggtggcgc tgcagcttca tcctggatct gaaacaatgt 53820
aaccaggttc tgggatccct ggaagcagga accaggaggt agagccatag tgcatctctg 53880
ctcattccta gacagccgca ccagagagag tgaccttcct gactatcaca tagatgtgtg 53940
aagctgtctt cagacttatc acattgttgt acattcactc attcattcac tcatttgtta 54000
actctttcat tcatccatcc atccattcat tcattcattc acttactcat tcattcactc 54060
attcattcct ctgccacttt gtcctgacag aaaacgcctt gagcaaccat tccaaatcgg 54120
gatcatgtgg tccagatcag caccactcag ggaacacagt gggtgggatc ctgtgtctat 54180
agagccatct gtctgtggga ttgcctgagt ctgttaaatc ctttgtatct tcaggatccc 54240
tgtgtctgtg gggacccgtc tctgtaggtt ctgcatcttc aaattctaat gagtaggaat 54300
ccagaaacat ttggaaaaaa tgcatttata ctgaacatgt acagacatga ttcccttcat 54360
cccttaagca gtgtgttcta atggctacac ggcatctgca gtgggttagg ttttgtgagc 54420
cagctcgggg atgtgtgcag gctctgtata aatactacgc cactgtctat aaagggcttt 54480
atttaagggt gtctgtgggg ttcctgggcc tgatctctca tgaacgctga gggtcacggg 54540
tagaatggga accacgtatg gaattctgaa ggtcagtagc tggtttcaca tggtgaaaag 54600
agggtcagag ctgtggctca gtagaggagt gtttgcctgg tgtgtgtgaa ttgtgggttc 54660
gatccccagt tctggaaagc aaaccaagaa agaaactggt gaatgtaatc aataacttac 54720
tcctgccact gtaggtcata gcggtgtgca gagagtccat tggggtactt ttcttcccac 54780
actcaaaccc tttgtagcca ttggtccaac cttcagttct gtgtggttcc tcacagactc 54840
acggctcaat tgaggcatag gagctgcctt ccagaggaga gcattatgac tggtcaaggc 54900
caacagcatg caggcgctct agctgctgta gccagggcta gcccctctga gctcagcaga 54960
gactgtggca agaccaaggt agaggcttcc actgggcggt tgggctgttg tcagaggccc 55020
gtgggagaat gggggtgctt gaatgggggg ctgtgctggg ccaaccggag ttctgacttg 55080
atgttgctca aattcctacc tcagcagaag tgggaccatg aattcctacc tggagtctgt 55140
tggcagacct tggagtgggg tggggtctcc tcagcctaga aaccccacag agtgggaggt 55200
ttacggcctg cctctttctg aagggggcag ctgtcgtatc ccttgttccc tttgaatggc 55260
cttggtgctg ggagaggtaa aggttgggtg ctttcctgtt ttagacaggg ttattaaggt 55320
ataattcaca gagcatacaa tcttctcact taaaatgtac agtttggtag ggttgtaac 55380 tcgcatggca gagtgcttct tgcctagagt gtatgaggcc atgggttcaa ttcccaacac 55440
tgcacacagt gggtaccctg gtgcctgcct gtaatcccag cactcgagag gcatcggcag 55500
gaggatcagg aaagagttca aggtcagctt cctatataat gagctccagg ctagcctggc 55560
tgacatgaga ccatgtctca gaaactaaaa ataataaagc aagaaagtaa ataatgaaat 55620
gtactgctca gaagcttttg tctgaacagt tgtatgtaag cattgcttct agaacattcc 55680
acccccacca gagagaaatc ccgagtccct ccactctcga tgtaaagcct agcagccttg 55740
tttgtgcctc ctctctgtct ggcttctgcc tctctgtctt tgccggttct gagtgtttac 55800
ctagttgaag tcacactgtg tgtctgctca aaacaaggtt ctgaatttca tccacactgt 55860
tgctatgtta tcacacccct gtggccagtg gcaattctaa cttgtttgtc cacttccctg 55920
gggtagaggt agggagacag ggcaggtgtc ctgtgacaca acaatttggg aaggcatagg 55980
aaggactatg ggggaggatt catgggttgg actatgtcct acaaacccag cccctctgta 56040
gagggatagt tttatcctat ggaaactttg gtccccttga caaggcttcc acccaagtaa 56100
agtagggcct tgcatattgg tgggaaggcg agtccgagat gccccagtgt cccagagctg 56160
gggccgccaa ggaaatctct gctggattct cagaggctca gggtacagag gtcacagtag 56220
tggcaagagc cagcactcgg ggttcgagag atggctcagt ggctaagagc atttacttcc 56280
tttacagagg acacaagttc ggttcctagc actcacacgg cagctcacaa ccacccataa 56340
ctccagttct ggggggtctg atgccctctc cgtaattgat ctggggatca cactctgtgt 56400
ccgcagccag gcttgaccac ccatacttag taagccaaat gccacactag gaagtgggac 56460
aaagagagcc actcaagttt ggcttcgggg tccaaagtga gagtgaaact taagctgagg 56520
accaagaagt tgctcatcta acactgggtc aaggtgtggg gcagcccact ggtgacccat 56580
cactgcagtt tagtttcagt gggggcaagg cattagaact ctgtgaagtc tctttctgag 56640
agacaatctt cccttttggg gcctttccct tctccaagta ggagattctt ggagggaaac 56700
tcccatttct ttggggtccg ttgttttaaa ctcccatact cagacacaag tttagattac 56760
cttcatttct accaatcctc ttacaccttt ctggcctgct tctgcacagg acacaagtgt 56820
gctgcacata cacgcatcca ggcaaatact catacatgta aatttaaaaa aatcttaaaa 56880
caaaacaaaa caaacaacca gggctggaga gatggcttag aggttaagag cactagatgc 56940
tctcttccag aggtcctgag ttcaattccc agcaaccaca tggtggctca caaccatcta 57000
taatgtgatc tggtgccctc ttctggcctg taggcataca tgcaggcaga acactgtata 57060
cataataaat taataaatct ttttagaaca aacaagcaaa taaaccaaca aactagactg 57120
ttacttgccc tttgcacgct cagctttttc tactgtctcc tgagctgctc tccctcctgc 57180
tgggcggtcc ttagtaggac ccttccttct gtatcagctt ccttgactct gacctaaccc 57240
caaaaactcc tgtcaagggt tcacagtgga ccactgaggc cttgtcttct ctggccacct 57300
cctgcaacca tcctccatcc tggactgagg cacaggaggg gctgagcaca aggtccccag 57360
cagagagaga cccgtggcat ggggcagtgt ccagtccagg ccttgggtct tagcctccct 57420
tgttgtctgc aaacacttct tgttctgagg cttagaggag gcaggctggt ggcaggagat 57480
atatgtgcag aggttccaag gcctctctga agagggcaat ggggtaaaag ggggcacttt 57540
gctctgagat cacacttccg cgtgatctag tctcccgtag attgctggtc aattggacct 57600

-continued

```
gctcattcct gcctcacacc tttgggcccc tcttctgtga tgtggggaca aggacagtgc  57660
ccacctcagg cctgcgggaa tccatctgag cttgagggaa ggttcgtcag cacagacagg  57720
atcgattaag catctacact tagggaccca ttctgcacag ccattgggta gtcttcccca  57780
aatcctgctt gccatctctg gacgtggact gggtagtcct cccattgata atttgttgaa  57840
acacccaagg aaggaaggtg agacttcctt aaagctccta gggaaggctg acttgtcctg  57900
gggtcccaag gacagagaaa gagggttccc agagctcagg ttccttgaat atgtgattta  57960
ggggaaggac tgggctgcct gggctagcct gagaaccagc agggatgctg ggaggagcta  58020
ccaaccctgg aggcctgggg aaggctttgt aatggagata aagtcagttt aaataaattc  58080
ctctggaggc tgtcacttag atctctggtg gctgagcagc cttggcggag tccatcactt  58140
agagggctgt atctaagaat cctgccttcc agggcaccca tgctctaaat cctgctgtac  58200
ccccacccca cccttgcagc cagcatccag gctctcaggt ctatgtgagc actccagcct  58260
ctgggctgac ctgggagcat ggtggtaccc acaggggtct ccggctggga actttcccaa  58320
ccaaacagct cccttccagg taggtgtgca aagccccaat ccaccttgct ggcagctggg  58380
tggatcccaa gaagccctgg cacccgggag gcggacggag aggggcaggc aggagaggtg  58440
aatgtgcgtt tatcccaaca caagtagtgg cctgttgggg tggggtgggg gccccaggaa  58500
atatttggga tgacttggag cccgctggcc ctttaaggct cctgtaacaa gacacctccc  58560
cgacgggaca gaagcggtag ctggggcttc caccttagcc cttgtttctc ccctcccacc  58620
tccccccttcc ttgccaggcc cagttcaatt tgctcagcag tgccatggac cagatgggca  58680
gccgtgcggc cccggcgagc ccctacaccc cggagcacgc cgccagcgcg cccacccact  58740
cgccctacgc gcagcccagc tccaccttcg acaccatgtc tccggcgcct gtcatccctt  58800
ccaataccga ctaccccggc ccccaccact tcgaggtcac cttccagcag tcgagcactg  58860
ccaagtcggc cacctggaca gtgagtagcc gtgttgccag tggatgcgtg aagggagggc  58920
agcggggttg agtgccacgg tcctggtact gaggactgaa tgagcacaca ggctgtccac  58980
atggggttcc cacctggcca gagccaggag gagcatcgag caggaggcgg gccctggggc  59040
tgggcagtgt gggtgtggcc accccttgga cttgtggcca gagtcagcca gcctcccact  59100
gagtccggaa aggtcagagt gttgttgcca gtgaggtcca tggggcagga agagtggccg  59160
ggttttctat actcagtgcc ttgaaattgg tctggtcctg aacttctgct gaaagtgttg  59220
ggagcccaca ggggcccacc cgtttgctag ttgtgggttt gtgttttgcc ctcatatctc  59280
tctgtgcatt ggcttgggac tggctctcca ggtgctgggg gctctggtcc tttccctggt  59340
gcctccagga acaacctggc atgtggctgg gattagcaga tgttgacaaa gtcccacctg  59400
tacacttgct gagagttggg cagacagcta agtactttga cttgcccaag gtggagtctg  59460
tgcccatttc acagtcaggg aagctgaggt atgaaaaggg aaagcagttt gctcaagtta  59520
tgcagaaagt gagtagatgc tggactgggg acacatggcc gtgagtgttc ttacccactg  59580
agcacccagg ctctctgtgg gagatggggc tgcaggaaga gcagactggg acttcagaac  59640
gctggtctgg gcacacagga cattgggtag gaagggcagc cctagagcca tccaggtctc  59700
catacccagc taagtctgag tagagggaac cctgagcctg ggacagtagg aggtgcactg  59760
agggatgtta agtcatccac ccactctctc cagggagcag ctggagatgc agccatccac  59820
gcagtgcaag ctctatctca ctctcctcca gcggctcttt aaaaactaac tcccacagtg  59880
tggctctcac attctctttg gagactgaag agctggacag agccagacct tgtaggtggc  59940
caccggtgat cagctgtgcc tgactggctc tggtttcagg ctttgacctc ctagagtttc  60000
```

```
ttttacctac tgttctggtg ggctccccag tcactagacc atcaccaatt gaatgctcag  60060
cccagctgct ggagctctga ggggcttcag tgggccgaga gggtctgggt acctgtggtg  60120
ctccatcccg agtcactgtg ggccagtgtg ctccactctc cgtgaccaca aattattgga  60180
aggcactgag gtcaggaggt ctgaatgaga caggaatggt agagtacaca gctgttactc  60240
ctgtcctggg acagtggagg aaaccatcta acatggcctc ctgaagttgg tctttgtgta  60300
gaactacctg ctaaaggcct cctcttctgc actgtctgta gttttggggg ttgaagggga  60360
cctaggctct tcctccaccc aagctgagtg acctagggtc aggtcaggaa gcccaggaga  60420
cacatgggta cctacctcag tcacagcggg ctctctacgc tgctcttcta cttccaatgc  60480
attccctagc tccatcttag agtgaggcgg ggtcctgtct gtcataaaga tctggtgatg  60540
ctgtatgtgg gattgcctcc cttcctcttc cttgccagag agtgttgatg aggtcgctct  60600
ttgccgtgcc tatgggctca ggtgcctctg atggtcaggg ctggtctttg acaggggtga  60660
cagtgcccac tctactgaat tcttcctccc atttgggtcc tgtgcagtcc cctctgaggc  60720
actggacatc aagcgtccca tgatggcctg tgttcctgct gctctgctct aactgtcccc  60780
aggggttagt ctgctcagac tggccagaca taccaaagat cagggaaggc ttggcctccc  60840
aacccaactt ccacccagga ccagggcagc agagctgagc tgtcaggcag gaggatgcta  60900
ctgccagccc cctcccggcc ctgtcacaca ggggcagagg tgggaccaac attgataatg  60960
agatttttgg cacctcggcg atctgggagc agacacccaa gggtttttct cgatgctgag  61020
agaagggact ggcagcagct gctctcagct ctgggggtcc aactgtgtgg gtgctgccca  61080
gacttgccac cgaggcccct gccacgccac cggctggtaa ctgatagata attcatattt  61140
ttctcaagta ctattccata ttgactgctg cccccattcc tctcagattg gcaaaaacat  61200
gctcactggc ctctaagtga ccacagctgt taatggggcc tttggtcttg ccattgctga  61260
agccactgtg ggactctctg accccaaagg atctacttac ttgtcctgac caacttccct  61320
tagcctgaaa atctgctggt gcaataagag gtctgggacc ttagagtgtg accctgcatg  61380
tatgaacaca tacgtgtata tatacatgca caaggtccca tatgcccgga cacctaggta  61440
cacaggtgtg tgttatgcat acatgtatat acctatgagc acacatgggt gtaaatatat  61500
atgtgctcag gggcctatat atatggatac acagatgcac tcacatatac ctgtaaacat  61560
gccggcatgt gtgtacatat gcacacacat acacatgcca acagatgagc atgtgaacat  61620
gcatgctaat ctccctggtt gctgcctggg ggacagctgg tctcaggagt ccctcagtgg  61680
aggaggaagt gggacaaggt cctttacata tccaaacagc aagatgggtt ccctgctgct  61740
gtctagcgcc agctcagccc cttcaccctg gctttgcctt gctgagagag acggctcttt  61800
tcagtattgg agacattgag agacagagtt ctgtggttag gcaagaggac ccgtgtggat  61860
ggatggtaac cctggcctgg tatgatgtct gtagaacacc aagggcaggc tgtgacaccg  61920
ccagcctact acagaggcag ctgcagagga gcccaagagt gagggcgcgc tcatgaatgg  61980
cttgactgcc tgagagcatt acagatagac agacagacag acagcctgga catagtctta  62040
agtgaccttc aggtgaagct gccttcaacc tgtgtgtgtg tgtgtgtgtg tgtgtgtgtg  62100
tgtgtatgtc tgtctgtctg tctttatgtc tgtctatgct tatctgtcct gagagagaga  62160
gcccctacct acccacccac ccacccaccc acccagccag gcagcagccc ctggagggaa  62220
gcacaaagcc tctgtgaggg attcttaggg aggacagggc tgagtcaaca ctaatggatt  62280
tggagcaaac tttccagccc ctcggaggtt tgcaaagcac aagaatagag gaggtgtccc  62340
```

-continued

```
gacatgattg tggtatcaat tgcgttatcc taaaagttta tggaatgcat aaatggaatt  62400
aataccttttt actggcacgg ggagcaatta tgtatattta aagcccagag aagagttcta  62460
acaatgttta ttgtggagat gaaacgtgaa ttattagggg aaacaagagc acttatggag  62520
aaatcgcagc aattgctcat attgtgtcta gctttgccgg agagaatggg ctgccagtag  62580
gctggctccg gcttggtctg agcagggtac ctgcaccgga gatgtatgtc tgctctctcc  62640
atccactagt ggtctaaagg actttggtcc ccaggaggca cagaatctag cctggagact  62700
ctgaactcct gaatccaact gcagctcgac actggcaggc tggtccctgt gtctaagggt  62760
gctccctccc cagctgagtg gtcacatcac atacctcagg gttctagcag gggacaggag  62820
acagggcacc ttggaggaca ggactctatc ctgtgatgct gagatgcagg gcagggctca  62880
gtccagcagg ggaaatgtac catgaatcaa caataggaaa tgaaggaggg gtgttccata  62940
ggtctgactg gcctcctcat cttggaggtt ggtcacttct agaacgttct aatcagaaac  63000
catttatgaa tctacccagg gaggatggtg ggcagatagt gtgtctctcg gccagcacag  63060
tgctaaggaa caagccaggc ccccctttttt gaggcaagca ggcgggcctc tgggcatcag  63120
agcctccttg ctcctgctca cagagctcct aggatcccag aaccactcct agggaacttg  63180
gagcagtggg cagggcagag agaaagagag ttcctcaaac tcttgggata tgctgttggg  63240
ttcaccattt tgtttctgcc ctttgctgat gggtgacctg cccttgaccg gccctccgag  63300
atcctcttct gtaaagtggg aaaggaggta tacatgccta ctgcaggccg agggatggca  63360
cctggggtcc cgagatgccc attcgggtcg ggtctctatc ccctctcctg taaagttctc  63420
cccagtgtgg catgagcaga tgtgagacag tctgaggaag ggtcagctct aggccttcca  63480
gagtcacacc agttctcctg aggggaggac cggggagtga accaggaaca cactcccagt  63540
acacacagcc agccctgaaa aatggacagt tctttgtaat gtgtgaatta gcactcaatc  63600
ctccattgac agcacccccc ccccaaacca caggggatag aggccagtgt gggagtgtcc  63660
atggtaggtt aaagctggtc aggagttggc taacactgcc aggtgagatc caggtgagtt  63720
gaatgttgct tacctgggcc ctccaggctg gtggtaggct ctagggaaac cacctgaaat  63780
gtattagact ccatcctgtg ccctgaaggc tcaggccctg tcacctcctc ttaggaaaag  63840
gtcacagcca catccaggac ctcttgctct tatatgagtt agaatattct aggctttgag  63900
agctgtaagt cagggtcctg caaccaccac ttatcagtgc aagaagccaa ggtgggctaa  63960
gactggcgct ctgagatcgg ataaccgggt tctaggtccg gctgtgcggt acacctgaag  64020
gtagagatgc tctttggaaa aattgttggt gtggtaggta aggcagaaac cattcagtga  64080
cccaaatccc acgcctgtgt ctgcctctca cctctgtctg tgataggtca gctctcatgg  64140
tgctgaacct ggggagggtg agatgggctg tgccgcgctc tgcacctggg cctggttcca  64200
gggaggctct cactagcttt gctcagtaca agatcagaga tttagacccc agagtgtccc  64260
tgtcctatag ttccaataaa gatgtttaaa gttcaatgac aacttatatt ttaaggagct  64320
attgcctaca gcactgaaga ctggctcttt caaacatgca cacgcatata tgcacataca  64380
cacactcagg tacatgcaca cacacattaa cacacacact catgcacaca catacacaca  64440
ctcatggcac acacacactc atgcacacac atacacacat acacacacac actcaggtac  64500
atgcacacac acattcacac acacacactc atgcacacac acacatacac acacacacac  64560
actcaggtat atacacacac attcacacac actcatgcac acacatacac acacacatgg  64620
cacacacaca ctcatgcaca cacatacaca cacacacaca cacacacaca cacacacaca  64680
cgcgcactca cgcacgcacg caccttgcct ccctggctcc tggctatcac tagcccctga  64740
```

-continued

```
gactgtatgg aaagtcacag gtccttagag aaggagctgg ctaagatgag tgtttagaag  64800
ggtcacagct ggagcggaat gtgtgactgc cctgagatac ccttgcaatc tcaagctgat  64860
gaggttgatc ccgactgtgg aagctacagc tggggatggg gtagggactt caccactgac  64920
agccaacagg ggatccatac tgtgcacaga gcaggctggc taccagcctc gctgtgggtt  64980
cctgtactgg acggtcctgt gacctgcacc ccagccctaa tcacaggtgg gagaggctga  65040
tggctggtgg ccagaggaga ggctactcag gactgcctga aggagtggcc aaggcacagc  65100
tctcctgctg gctgggtcag gaagaagggc agcaggggcc cctttgaact cacagggaag  65160
gtgagcctat ggttctttgg atctggtcac agactgttct cagactacac tcttttcttc  65220
ctgaagtccc cagatgggtc ctgggtcctg gaaaaagatt agatgtccaa gttagggctg  65280
gagtgacgga ggtgacaggg cctcctagga atatctctga aacccctgac agtggccttc  65340
tggagctgga gcatcataca gcaaaggagg tcagccgcac ccagccaacc agccacctgg  65400
agcctccatc ccccccatga cttgatgtca ggggagacac ttcccagtaa gaccagggca  65460
ggccaggttc ccccaccccc accccgcccc tgcctggcag cttcctcacc ccccaggaac  65520
acaaccccag cccagagctg cctgtctttc ctgcctttgg tgttctactt ggtcacctga  65580
ctgtcctctt aaccagccta tctggatcct gatctctggt ctctgacctg gtaagtctga  65640
tggaaatgaa agaccaaaga tggaggtgtc gggtcttgag aagacaaaac caaactggaa  65700
ctcacttcta agacttctat gaccccctca tccccaaagg tggttctcaa ccttccttta  65760
acacagttcc tcatgctgtg gtggccccca accataaaat tacctttatt gctattttgt  65820
aactataatt ttgcatgggg taaggtgagg tggggaagga agtaagagac aagatggaga  65880
aaggatgtga gtctcccagt cctctctggc tctgctctct ctgggcacca tctccaagta  65940
cctcctcact cctagctgtc caggagctga ccaagccctg tcctttggga tttgtacaga  66000
cacttcatta tgtagccatg attagtctcc tgacattcgg gacctgattg accttcatcc  66060
tctgtgctcc gtcccaaagg ctggggctga ggggtcacac atactaactg gatcttttca  66120
tcaggggtgc tcaggaaagc agcccccagc cctcagcccc cagcccccag cccccaggcc  66180
ccagccctca gcccccagcc cccatccccc agccctcagc cttcagcctc caggccccag  66240
tccccagccc tcagccccca gcccccagcc cccagccctc agccctcagc cccccagtccc  66300
cagcccccag cccttagccc ccagccctca tccagtcatt agcatgtaaa agagcaactg  66360
ttgcttggca gtcctctaga ttttatgagc attttaccag aaacccgagg tctacagcca  66420
atgcaatgca acctctgatt actgctctac ccccagctca gctggcaact tttagaaaca  66480
aaattctagt tcctaaaatg tccaggtgaa gggtcagagt aggcacctta cagagaaagc  66540
agcacagacc gggcccatgt tattcctttg gtctctatgt aaagccatca gctgcagagc  66600
tatgtagagc agcctcccaa attcccaacc actaccttct ccctctctga gatgagacta  66660
ccaggccctc acacatcagc tcctccgcct ggggcagaaa ctactggaag gttctctgct  66720
cctgccaagg ataaatgggc tccaaacccc atgacctggg accctctgac ttcccagtct  66780
tagtgcaaaa aaaaaaaaaa agaaagaaag aaagaaagaa agaaagaaag aaagaaagaa  66840
ggaggggggga ggggctggag agatggctca gcagttaaga gcattgactg ctcttccgca  66900
ggtcccgagt tcaaatccca gcaaccacat ggtggctcac aaccatctgt aatgagatct  66960
gagaccctct tctggggtgt ctgaagacag ctacagtgta cttacatata ataaataaat  67020
aactctttaa aaaagagaga gagaaagaaa gagagagaga gagagagaga gagagagaga  67080
```

-continued

```
aagaaagaaa gaaagaaaga aagaaagaaa gaaagaaaga aagaaagaaa agcactctgt  67140
ctcccaggcc accaaggtgc ccatatggct cttgcttgcc tgtttgagat cttgctcaag  67200
ggtcgggggt ggggagcagg ttactcagct cctgaggggt gccccagcta gctcctggcc  67260
aacctctctg taggggaaca gactatggcc ttccactcac agagcaatca gtcagacttc  67320
acatctgcct cccggagtgt cctttatctt ctttcagacc gctgttcttt aggaacaact  67380
acagcctctt tcctgcacac ttggcagggg caggcactgg ggcctccaat gatgtgttta  67440
tagaacatgg agcctccttg ccctcagcct gcatcctggc ttgatggtgc cagtccggtg  67500
acggttaccc gagcatcatt ccctccctaa ggttctatcg ggctccccta agctgtgcaa  67560
gagctcaccc ctgctctcag gtgctccctg aatgaccgaa taattgaaca atgtaaattg  67620
tgcgagtcaa ggccaagatg tacccacaaa ggggctgccc caggacctct tcttggatga  67680
taggatccat aggttgctcc tctcgcagtg gcatttctcc aagagaaacg aaaacatggt  67740
ggggagtcat attcaggggc tgtggacctg ggttcctcca gatttgagag atcagactga  67800
gtctaccaga cctgtgccct gctctgtgga tctgccctag gaagagtaaa agcctgtgat  67860
cccagagatg attctcaaag ggtctacgg cctcagagat cagaaactct cacacacacg  67920
tatacacaca cacacacaca cacacacaca cacacacaca cacacacaca caaagtgggc  67980
tacaaaaaaa agtattttta aaaagccccc accacagcct ttcgttctga atctgtccta  68040
acagattcac ccaagctggt taacggtatt tgcggtttgc aagatactac atgtcccggg  68100
aaaatgacag acaagttatt atcaccttcc cactgtcctc ctgcccaaac ctgcctgtgc  68160
cgggcaccca gctgccggga gcgggtgcga ggaaattaac agccctgtgc cgcgcccgcc  68220
cccgcccgcc ctctcaccca ccaccctgca ccggtcctgc caggctaggg gcttccagcc  68280
aggcccggcc catcttggac tgtggcgggg gggggggggt ggggggtggc gggggggtg  68340
gcgagggggg gcgcgggggg gggagggagg gagagaagga ggaggagggg tcaggatagc  68400
agccgtggca ggagggacgt ctgctccgct ccgatgttgg gcaaagtatt tcctgcaagc  68460
cccgcggaac acacgcatcc gcgcaggcaa gtctggacgg cgctgtgtca acagccgaag  68520
ataaataaga ttttatcagc tcggaatctg ttgaaacaca tccatctagc ggttctaggg  68580
aaggagaggc aggaggaggg cagcagggag gaagcatccc cacatgacat tctggaaaca  68640
gagtctgacc ctgtgtagga aggggagcgc tggcaacttc ctagtctccc ggagactcga  68700
tatcctggag tgttgttttt accacctgat cttcggaggt gtgggaaagc tttggtatct  68760
ctcgctgaaa ttccccacct ctggctaaaa tggactacca caaacttaac ctgtggccgg  68820
ggtggggctg gtaggtgtgt gcgcccaaag ccccacgatc attggattca agacggcatt  68880
caagggtgca gaagtgaagg agccatgtat cttcatgggc ttggattttc cttccaccct  68940
gaccgggtgg gagacgtgtc ccaccagaga tgactctctc aactctgatt ctttctctga  69000
gaggagacag cctttccgca gctgctgagt tggtaccagg gacagctcca ggcgctttaa  69060
gctcctcccc agggtggggc attcagtggc tcatccttac cagcccggct actctgcaac  69120
tatccttagc tttccctaga cctcctaggg tcccactcca ggccatggaa aacagtgcca  69180
ccttctgggg aggagggtca ggcctcagct acctctgacc acaccttggt agtgttagtg  69240
catggtttgg ggttgtaacc aattatccta ggtcctcaga ggacagggat ggaaaggaca  69300
attgccttca gggtcacagc agggctccag ggatgggcac tgtggtcagg cgaggtttga  69360
agcctcattg ctcaggagtg ggtgggtgag gggagctctg atgcccctcc ctgtggctga  69420
gctgtgccct gagcctggct ccatcctgat aagaacacgg aggtgaagct gatgcaccct  69480
```

-continued

```
ttctccctcc aggcatgttt gggcttccca ggaatgtggc cttaggcacc attacacctg  69540
acttgctccc agcccatctt ggctcctgcc ttggtgggtc tatgaccccc tcttaggtca  69600
ttgttcatga gctagagcac tggagggaaa ggttaactct gtaggagact ccaggtccat  69660
gagccccagc agctgtgcca acccacaaat taccttacct ggtaatgagc aaccatgcta  69720
gaataagggg cctctgacct tgctggctct ctaccacaca gctggcatct gggggttgag  69780
tggtaagtca gtggtagaca aacctggcag gtggtccaat ttaggggaat ccagcctgaa  69840
ttcctgagcc agaacaggga gccaagggcc agccttcaaa ggctaatctc ctttttccgc  69900
ccctggtgac tttggtctca gtgtctcccc aacccactgt gggcaaggcc tgtttcatgg  69960
gggtgttggc cacctccacc cctcagtcta ttttctttag gtagctaggc ctcacaaaca  70020
atgggcactc gggagatgtt tggtaatgct tgggactgtc acctttacca ggaagttgcc  70080
tgattggcct caggttgagt ctctctgagc tcaggatgag ctgggttccc ttcaccgtta  70140
ggcctttgca attgtctgag cctggggctt gctgggaaac cttcatttgt ggataagcaa  70200
gagcccaggg cacttcactg tcactgtata tgaatttact taatgtcggg aggggcacct  70260
cgcactgtga acttcatgcc accccgtgtc cttcctaggg agccacagta attacagagc  70320
tagtgtgctt tttaccaagt gcaggctgta gacccccaac acctgcaggc tgctgctgct  70380
gctgaaggac aggtgtgtgt gtgtagctgt ttattggcct ttccccaggg aaccagctac  70440
tcctgctact ctgtccccag cctgcacaga tggagaccag gctgcagtgt actaacttga  70500
ggagaggccg ttgcaaaaaa ccaaagccca gatttggatg tgcagaggtc aggtgtaccc  70560
tgtccaagtc tcagagtccc ccatgtatcc tggggatgag gctgtggctc cttcctccag  70620
aatgttagga tgaggatccc acacaccagc agacagtggt caccccccct cccgaaagtc  70680
acaccaacct gctggtgtgg ccattagctc tccctcagct gctccccctc ttaggctctc  70740
tcagcttttc aaaacagtcc ctgaagcctt ctgtggggtc cctatagtga gtatctcttg  70800
ctttttaaac aggagggaag ggactatgtc atggcgcctc tccctgccct cccttcattg  70860
catttgccta tggtatatgc tatttctgca tactccattg tggagaacca taagctatat  70920
agggttaggg tggtcagaat cccccactgt cccttgcaaa ggaaagattt ggtgtgtgag  70980
caccacctgc ccattcctgt tttgttaaca gcttaccatc tctggcctca gcttcattaa  71040
ctgtcacaag ggagcatggt gtatataatt catgtgtggt ggagacttta gagtgaagtg  71100
gagcttcata aaaatccctt gggagccagg cggtggtggc acacccccttt aataccagca  71160
cttgggaggc agaggcaggc agatttctga gtttgaggcc agcctggtct acaaagtgag  71220
ttccaggaca gccagggcta catagagaaa ccctgtctcg aaaaccaaaa accaaaccaa  71280
accaaaacaa aacaaaacaa acaaacaaaa aaaaaaaacc cttgggaaga gctagagaga  71340
tggctcagag gtcaagaggt cctgagttca attcccggca accacatggt gtctcataac  71400
catctataat gagatctggt gccctctctt ctggcctgca ggagtacatt cagacagaac  71460
actatataca taatagatag atagatagat agatagatag atagatagat agatagatct  71520
tttaaaacaa aatcacttgg gaaggaagac aagaggagtg agtcaccagg ggtttcagga  71580
gccatagtga gagtcagcta gcaggtgaat aaatgggtat cttgcttttc cagcctagat  71640
caggccgctg gctgcatagg taggatttgc agcattgagc ccgtttgaca agctcagaat  71700
tgcatcctct gccttgcata gaatagtctc actctgattc tgaaactgac ttggtcttgg  71760
cagggccagt acaatcctta gaagagtgac ctgggacacg gagggggcgg gggaggcatg  71820
```

-continued

```
atgacgtccc attgtccctg agagacatcc tggcatgacc tcaggtccag tcagtttcca  71880
ggatggggaa agcgggtctt gccccccaca acagcttggc tgcctggact tggtgacttt  71940
acttggtggc acagtgctgg tgactggtca acagcatgca aggtcttgct ggttcagaga  72000
gttctccatt ggaggataaa ggcaaaggca gaaggggcaa gccacccacc tactgagtga  72060
ttcttctatg caaggtagaa ggatgcaatt ctgagctcgt caaaccacct caatgctgca  72120
aatcctaccc ctgcagccag tggcctgatc caggctggga aagcaaaact aggactgatt  72180
cccactgacc tctgacccac acccccaaca ctgtcttacc ctttgtcatc cttatgcaac  72240
ggtccaccgc tcgcagcctt tgagatgcag gtgagacaca tagccaggca ggtgatgagc  72300
aggcaccagg cacgcccatc tctacaatct gaagcatgcc tgaagcatct ggaagcaggc  72360
ctcatcggag cgcttgggaa aggggtcttg tggaagcatc cggaactgag ctgccatctc  72420
aacctggccc ccttctctcc tccagtactc cccactcttg aagaagttgt actgtcagat  72480
tgctaagaca tgccccatcc agatcaaagt gtccacacca ccacccccgg gcacggccat  72540
ccgggccatg cctgtctaca agaaggcaga gcatgtgacc gacattgtta agcgctgccc  72600
caaccacgag cttggaaggg acttcaatga aggtgagccc cccctccccc tcccagctgt  72660
gggacactga ccagaggcat agctgagaga tgtaggccag tgagcacagc ggtaagctgc  72720
tctcaactct cccctcacag gaacccacac cctagccctc tttccatttc ctcagctctg  72780
actacagtcc aagaggctga tggtccagca agggtgtagt ctgagggacc agctgacctt  72840
ggagaatctt gtgaagcatc cctgcagtgt ccctggtgaa gcctgtgaca cccccagggt  72900
cagattatct ggggacagct tctgtcccgc tcaaggccac ctaaatgagg gttgcacagc  72960
tctgagcctt gcctgggact ctcacgggga caagccctgt ggcctcagtt ctgccacacg  73020
cctggtacag gggtatggga tggaagatgg gcccctctct aaagctgtgt cccctcctgg  73080
caggacagtc tgccccggct agccacctca tccgtgtaga aggcaacaac ctcgcccagt  73140
acgtggatga ccctgtcacc ggaaggcaga gtgtggttgt gccgtatgaa cccccacagg  73200
taggcggggt ccaggctggg atacaaagcc aaccttacag ggtggggttc cctgggcctc  73260
tgctctgacc tcagcctgcc tctcaggcct tttcctgaca gttcatttca ctgtgggcag  73320
cgagcttggg cctgtgctca agccaacttt agctctctgt ctctctgtct gtctctcgtc  73380
tgtctgtctc tgtctctgtc tgtctctcgt ctgtctgtct gtctgtctgt ctgtctgtct  73440
ctgtctctct ctgtctctgt ctctctctcg cctcagctat atagcgaggt atagttatat  73500
gacctccaac ctttcaaccc tgccctccct ggagggtcta atcttcaatc ttcttgcttg  73560
tttctctcaa gtacagtctt ctagacatgg aagaaagagt tcccagacat ctcaggctcc  73620
atttgcaggg acaaaagcaa gccagcaagc atggggtggt gggtagaggg tgggcaattc  73680
catgtgtggg ggggtagtga tcatgaaagg cctcctagac caggctgggg gaatcacaga  73740
ggacgcctac aggagattgg agccgtggaa cacaggctca ggagagtagg gaagacagag  73800
atgatcggtc agccttaaga gggcctgtgt gcagagcctc gggagagtgg tgccagctgg  73860
atggagggta cagtggaggt gaccagacat gctgcacact gaggtgcagg gtggatacgg  73920
aggttcaggc tggaggcgaa gggctcagac cacaggtgag ggctctaagg gagggaacca  73980
ggctggaggt ggtggttgcc aaaagtagac aagtgaagga agactggagg aggcagctgt  74040
ccactttgac accagaagag tgtgtggtca ccttctagat ctgatatgag ccccagttgg  74100
ggccaaaggc aaggtgaagg gacttcagta ctgatgtggg aggtatcagg gcggagactc  74160
aggaggactg gggttaggtc tcatctctga cccatcctct accaagccct ggggtcctgt  74220
```

```
gaggcagctt tgaatgtcag tgggacaggg ccccatatac acacagacac acacagacag  74280
acatacacat agacacagat tcacacacac agacatacac agagacacac agagacatac  74340
acacctacac acacacagac acacacacac agacaaacac acacacacac agacacaaac  74400
tgagaaacac atggacaaac acagagaccc cacccaccca caccacacac acagaaacag  74460
gcagagacac acagaacaca gaaacacaca cacacacata cacacagaca cacacacaca  74520
cacagacaca cagacacaca gacacacaca ccccacaagc atcctcccct ctcatcagaa  74580
aaagcctcac cagctcaggc atgagacaca acgtaggttt ctcttgccct ctagtggttg  74640
gcaggtgtaa gttctgtgaa ggactggggt ttatggcgtt tgtaccctaa cctttgaaac  74700
tcctttctgg ggatggagtc cctttcattc ctctgcccag atgagtccac agtactcatc  74760
acacacttga cacaaaggct cacacacacc cactcacata cagccctgac atttgacctc  74820
tgcctgtgtt aaggaagatg actgcagcaa gcacaccaca aactctgtac ctcccctaag  74880
agctgaaacc aagactgagc tctcagccca gagccagcac agggctgtga cggcacagat  74940
ggatcggtgg gagggcgggc aatctcacgt gagtgtagat ggctgaatgg atgggtgagt  75000
gagtggatgg gtgggtaggt aggtgggtga tagtcaggca ccactggggg tgggcaggag  75060
agcaggtgag caggagtgta agtgggtgta tgggtaggca agtgagcagg tgtgtggatg  75120
tatgtgtcaa tggatgagag gttgaccggc aagtgagtgg ggtaggtgga tacgtgggtg  75180
tgtagacagg cgtgtgagca gatggatgga tgtgtagaca ggcgtgtgag cggatggatg  75240
gtttggtgga tggtaggtgg ataagtggcg agatggatgg ataagtgcaa agatggggtg  75300
gttgggtaga tagatgggta gatgaccgtg aaccatactg cagcgtccct atgcctcctc  75360
agaaccaggg ccagaggtgg cagctacaag tccttttctt agaaggtggg ccctgcatgc  75420
tgactgatac taagcccttc ccctgtctcc cctgtggaca ggtgggaaca gaatttacca  75480
ccatcctgta caacttcatg tgtaacagca gctgtgtggg gggcatgaat cggaggccca  75540
tccttgtcat catcaccctg gagacccggg agtgagtctg ccgtggaagg atggtagagg  75600
tggggccgtg ggggggcatg tcatggacac agggagggct tgctctcctc ggtgggcatt  75660
cagcttcaag gccagtcacg aggggtctgc gggagttggg cagggtcaag agtggtctct  75720
tgagctcaca gccacgctgt gccgacccaa cagtggacag gtcctgggcc gccggtcttt  75780
cgagggtcgc atctgtgcct gtcctggccg tgaccgcaaa gctgatgaag accattaccg  75840
ggagcaacag gctctgaatg aaagtaccac caaaaatgga gctgccagca aacgtggtga  75900
gtggggctct gggtcagggt atgggcggag ggtggagttg gatgcacctg agtgtgggga  75960
gtacctgctc caaaggtgcc aagcatagct tcatccaaag atggatctgg gtctgaatgg  76020
ctgaggctgg gaagcctctc caggcgggac agggcgaatg tggcccaaga catctcactt  76080
gtctatgctc tgaggctagg agcatgtggg accctggtcc agctccttcc agcctaggtt  76140
tgccctgtgt gcacaccaca cccatggcag gtgttcacct gggcatctca gtctttgctc  76200
tctggctcat ttatctttcc cgacctgcct tctagcattc aagcagagcc cccctgccat  76260
ccctgccctg ggtaccaacg tgaagaagag acgccacggg gacgaggaca tgttctacat  76320
gcacgtgagt gggctgggag ggcaggtctg tgtgttccca tcacccaaga tcccaggctg  76380
gggaagtaca gatgtcacca gagatgggca agggtggcat gctgacacct gaggattgaa  76440
actgtggccc tgaaggaggt ggggttcaaa ggaggctctg tttagagtca gaccctgaac  76500
tcactgagtg tgaacatgcc agccaagtca gctgtgcatc aaggagacct aagggcaccc  76560
```

-continued

```
tttataatgg agacccccag ggtggagttt cagtaggaac ccatgatcct atagggttca  76620
gcctgtgttt aaatccatgg tcctataggg ttcagcctgt gtttaaatcc atggtcctat  76680
agggtatagc ctatgtttaa atccatggtc ctatagggta cagcctgtgt ttaaatccat  76740
ggtcctataa ggtatagcct atgtttaaat ccatggacct atggggtata gcctatgttt  76800
aaatccatgg tcctataggg tatagcttgt gtttaaatcc atggacctat agggtatagc  76860
ttgtgtttaa atccatggtc ctatagggta tagcttgtgt ttaaatccat ggtcctatag  76920
ggtatagcct gtgtttaaat ccatggtcct atagggtaca gcctgtgttt aaatccatgg  76980
tcctataagg tatagcctat gtttaaatcc atggacctat ggggtatagc ctatgtttaa  77040
atccatggtc ctatagggta tagcttgtgt ttaactccat ggacctatag ggtatagctt  77100
gtgtttaaat ccatggtcct atagggtata gcctgtgttt aaatccatgg ttgtataggg  77160
tatagcctgt gtttaaatca atagttctat agggtatcag cctacatggc tcgatgtgac  77220
tgtggtacca atcccagtgg taagatcatg gtgcactccg aaagagtgct atttccttgc  77280
ctgtgagtcc tcctttaaga cttagagctg ttataactta gagcctctta gcagggaaga  77340
ataaacatgg tctctgaacc ccgagggacc cacttctaaa cctgcccctg ggaagaggaa  77400
agccagagta tcctgagcgt tggggtacgg ggaaactcca agagcagatc aacactttgc  77460
catagcctgg agtcctcctg aggctacggc catccccgtc ccaccagggg tttggggcca  77520
gtggaatctc ccaggtacct gggccgagac tctgtttttc tgtgcccagg tgcgaggccg  77580
ggagaacttt gagatcttga tgaaagtcaa ggagagccta gaactgatgg agcttgtgcc  77640
ccagcctttg gttgactcct atcgacagca gcagcagcag cagctcctac agaggccgtg  77700
agtgaacccc accatctgta tggggaagta gggatattct gacccagcag ggagagggcc  77760
aggagcacag gaggtatggt accctggact ggactggact gtaagatcag cacagctcag  77820
ctggcacctt ctcctccagg aagccttctg ggacttagcc tgccctgaga tcctgggtcc  77880
ctgtgttcag cacacccctg cctcccacac aagggccttg gaaatgtgga tggggaaggg  77940
actggaaggg ctgtatttgc tgaagctggt gaggtgttag ctttcttcct aactctctga  78000
gaggcagggt ctacatctac ctgcatccca gggtgtccac agaggtacca cgtgggggag  78060
gagttgcttt tacctcttgc gaatgcgcac tgttgctttc caagcaggag tcacctgcag  78120
cctccatcct atgggcccgt gctctcccca atgaacaagg tacacggtgg tgtcaacaaa  78180
ctgccctccg tcaaccagct ggtgggccag cctccccgc acagctcagc agctgggccc  78240
aacctggggc ccatgggtga gtccctggag cattggaggc ctcatgtggg tcatagagac  78300
ccaagggagg gcctgggtgg atttaccgag atcacaaaca ggatggcggg ggacctttga  78360
tggccacctc ttcctgcagc tccagcctgc aggagggcaa tggctatgga ggcgttcatt  78420
ccaatcccag gagttctatg cctgggaggt tgcaaaggtg gtagagttaa gaactcatgc  78480
ctgccacagg atcttgaaga agatccctag cctcagtttc cccatcagta aaatggcaac  78540
accaaatccc ctcttctcag gggttacagg acatgagacc tcattgagag gcagctgtag  78600
ggaaccctta caatgctgta ccacactgcc aggctagacc acagcctggg acatacccca  78660
ctatgtgtgg ggcttgctct caggttccct gaccactctt ttgcccaggc tccgggatgc  78720
tcaacagcca cggccacagc atgccggcca atggtgagat gaatggaggc cacagctccc  78780
agaccatggt ttcgggatcc cactgcaccc cgccaccccc ctatcatgca gaccccagcc  78840
tcgtcaggtg tgtgggtcgc ggctggatct gggtttgtgg ttcaccctcc acccctcacc  78900
ccatgcctcc cactaactgt gcggttcctg ctggagggag cagccttgca tgtggctctg  78960
```

-continued

```
tctgaccctg ttttaattgc ttggctggcc tgagggaaga caggcctatc agggctcgtc  79020
agcagatgct gagaaaggca ctagatggtt aggcactgag ggtgggggtg gggtttggag  79080
gggtttgggg ggcatcctct tggagacagg gggatgagga atgagatgag cagctgtggg  79140
aggtcagacc aggagaggtg ggtaatgatt ggactgtaaa aatataaaag taacatacac  79200
acacacgtat atatgtgtat gtgtatgtgt atgtgtatgt gtatgtgtat gtgtatgtgt  79260
atatacacac atacacatat acacacatgt acatatatac atatatatgt gtacatatat  79320
atatacacac atatatgtac atatatatgt aacaaaaatt aaaataaaat aaataataaa  79380
ataaagaaat aaaaaagaaa acctgccctg agggagggac cagcagtttt gcccactgta  79440
acaggcagtt ccctccacgt cagggccact cctgtgagac ccgagtgcac agccagttga  79500
tgctactttc tcaaactctc tctgcagttt tttgacaggg ttggggtgtc caaactgcat  79560
cgagtgcttc acttcccaag ggttgcagag catctaccac ctgcagaacc ttaccatcga  79620
ggtaaatgtc ccaggtcttt ccaaagggac ggaggacctg tctggaggca cagtgcactg  79680
actagggtga ctagtgggga aactcccaga gactcccacc agcaatcaga ttctgttctg  79740
aagtcagcag gattcggtaa tgtgaaggag actgggtaga caatcacatg tcccggtccc  79800
cggcagttac ctggagagct ttctctcttg ttagagcctc ctggtggccc agccaggcta  79860
cctttgattt cttaggcagg gttgtttcca ggacccaatg tgtgagaagt gtagaagcta  79920
agggggggaac agacctagaa agaatgaatg ggtctccaca tccagcctac acgtgagaca  79980
cagaacattc tgggttgaaa gtgggataga aatcttctgg aaggccctgc atcctgttac  80040
agcctagcca cacagactgc cttgatgtat ccatgagaca tgggtccagt gtgcaacagc  80100
tcagcccctc ctgccccagg gcccagtgtg caacagctca gcccctcctg ccccagggcc  80160
cagtgtgcat cagctcagcc cctcctgccc cagggcccag ggtgcaacag ctcagcccct  80220
cctgccccag ggcccagggt gcaacagctc agcccctcct gccccagggc ccagagtgca  80280
acagctcagc ccctcctgcc atgcctccca aaactgtttt ctagactctc acccaggcta  80340
agaggccata tttgtcacct acccaggaac tcaggctgga cacaaatatt tataagaggt  80400
tgtggggcta gagtctaaca cctgcattta tgggaccact gaccactacc tttcccatcc  80460
ttgagtcata cattaaccct tgtctcacca gagcttgaag ctaaaggatg tgcctggagt  80520
tagctgccaa ttaatggctt ccaagggaca cctgtggcca agagatgcat gggtggtctc  80580
ctaggtctcc attgctgttc tcgctgtgtc caggcctcag gctgatgagc aggccctcgt  80640
cactgtcccc tctgtcacct acacatgtca tctagctgtc ctagacaatt atgtgactag  80700
acattctgtg caggtgaccc tgatgctgtc cctaccctgt cacccacaca gtcaaggtct  80760
gataagtcag ctgccccctc agacagaggc ttcctagcag gtaggacacc cttgcaggtg  80820
tgagggacac acaactctgt agcttccctc ttgtaaccca aaggtgccca tcgctcttgc  80880
aggaccttgg ggctctgaag gtccctgacc agtaccgtat gaccatctgg aggggcctac  80940
aggacctgaa gcagagccat gactgcggcc agcaactgct acgctccagc agcaacgcgg  81000
ccaccatctc catcggcggc tctggcgagc tgcagcggca gcgggtcatg gaagccgtgc  81060
atttccgtgt gcgccacacc atcacgatcc ccaaccgtgg aggcgcaggt gcggtgacag  81120
gtcccgacga gtgggcggac tttggctttg acctgcctga ctgcaagtcc cgtaagcagc  81180
ccatcaaaga ggagttcaca gagacagaga gccactgagg aacgtacctt cttctcctgt  81240
ccttcctctg tgagaaactg ctcttggaag tgggacctgt tggctgtgcc cacagaaacc  81300
```

-continued agcaaggacc ttctgccgga tgccattcct gaagggaagt cgctcatgaa ctaactccct 81360
cttgg 81365

<210> SEQ ID NO 4
<211> LENGTH: 2586
<212> TYPE: DNA
<213> ORGANISM: homo sapiens

<400> SEQUENCE: 4
gattggggtt ttcccctccc atgtgctcaa gactggcgct aaaagttttg agcttctcaa 60
aagtctagag ccaccgtcca gggagcaggt agctgctggg ctccggggac actttgcgtt 120
cgggctggga gcgtgctttc cacgacggtg acacgcttcc ctggattggc agccagactg 180
ccttccgggt cactgccatg gaggagccgc agtcagatcc tagcgtcgag ccccctctga 240
gtcaggaaac attttcagac ctatggaaac tacttcctga aaacaacgtt ctgtccccct 300
tgccgtccca agcaatggat gatttgatgc tgtccccgga cgatattgaa caatggttca 360
ctgaagaccc aggtccagat gaagctccca gaatgccaga ggctgctccc cccgtggccc 420
ctgcaccagc agctcctaca ccggcggccc ctgcaccagc cccctcctgg cccctgtcat 480
cttctgtccc ttcccagaaa acctaccagg gcagctacgg tttccgtctg ggcttcttgc 540
attctgggac agccaagtct gtgacttgca cgtactcccc tgccctcaac aagatgtttt 600
gccaactggc caagacctgc cctgtgcagc tgtgggttga ttccacaccc ccgcccggca 660
cccgcgtccg cgccatggcc atctacaagc agtcacagca catgacggag gttgtgaggc 720
gctgccccca ccatgagcgc tgctcagata gcgatggtct ggcccctcct cagcatctta 780
tccgagtgga aggaaatttg cgtgtggagt atttggatga cagaaacact tttcgacata 840
gtgtggtggt gccctatgag ccgcctgagg ttggctctga ctgtaccacc atccactaca 900
actacatgtg taacagttcc tgcatgggcg gcatgaaccg gaggcccatc ctcaccatca 960
tcacactgga agactccagt ggtaatctac tgggacggaa cagctttgag gtgcgtgttt 1020
gtgcctgtcc tgggagagac cggcgcacag aggaagagaa tctccgcaag aaaggggagc 1080
ctcaccacga gctgccccca gggagcacta agcgagcact gcccaacaac accagctcct 1140
ctccccagcc aaagaagaaa ccactggatg gagaatattt cacccttcag atccgtgggc 1200
gtgagcgctt cgagatgttc cgagagctga atgaggcctt ggaactcaag gatgcccagg 1260
ctgggaagga gccagggggg agcagggctc actccagcca cctgaagtcc aaaaagggtc 1320
agtctacctc ccgccataaa aaactcatgt tcaagacaga agggcctgac tcagactgac 1380
attctccact tcttgttccc cactgacagc ctcccacccc catctctccc tcccctgcca 1440
ttttgggttt tgggtctttg aacccttgct tgcaataggt gtgcgtcaga agcacccagg 1500
acttccattt gctttgtccc ggggctccac tgaacaagtt ggcctgcact ggtgttttgt 1560
tgtggggagg aggatgggga gtaggacata ccagcttaga ttttaaggtt tttactgtga 1620
gggatgtttg ggagatgtaa gaaatgttct tgcagttaag ggttagttta caatcagcca 1680
cattctaggt aggggcccac ttcaccgtac taaccaggga agctgtccct cactgttgaa 1740
ttttctctaa cttcaaggcc catatctgtg aaatgctggc atttgcacct acctcacaga 1800
gtgcattgtg agggttaatg aaataatgta catctggcct tgaaaccacc ttttattaca 1860
tggggtctag aacttgaccc ccttgagggt gcttgttccc tctccctgtt ggtcggtggg 1920
ttggtagttt ctacagttgg gcagctggtt aggtagaggg agttgtcaag tctctgctgg 1980
cccagccaaa ccctgtctga caacctcttg gtgaacctta gtacctaaaa ggaaatctca 2040

```
ccccatccca caccctggag gatttcatct cttgtatatg atgatctgga tccaccaaga   2100

cttgttttat gctcagggtc aatttctttt ttcttttttt tttttttttt tctttttctt   2160

tgagactggg tctcgctttg ttgcccaggc tggagtggag tggcgtgatc ttggcttact   2220

gcagcctttg cctccccggc tcgagcagtc ctgcctcagc ctccggagta gctgggacca   2280

caggttcatg ccaccatggc cagccaactt ttgcatgttt tgtagagatg gggtctcaca   2340

gtgttgccca ggctggtctc aaactcctgg gctcaggcga tccacctgtc tcagcctccc   2400

agagtgctgg gattacaatt gtgagccacc acgtccagct ggaagggtca acatctttta   2460

cattctgcaa gcacatctgc attttcaccc cacccttccc ctccttctcc ctttttatat   2520

cccattttta tatcgatctc ttattttaca ataaaacttt gctgccacct gtgtgtctga   2580

ggggtg                                                              2586
```

<210> SEQ ID NO 5
<211> LENGTH: 19144
<212> TYPE: DNA
<213> ORGANISM: homo sapiens

<400> SEQUENCE: 5

```
gattggggtt ttcccctccc atgtgctcaa gactggcgct aaaagttttg agcttctcaa     60

aagtctagag ccaccgtcca gggagcaggt agctgctggg ctccggggac actttgcgtt    120

cgggctggga gcgtgctttc cacgacggtg acacgcttcc ctggattggg taagctcctg    180

actgaacttg atgagtcctc tctgagtcac gggctctcgg ctccgtgtat tttcagctcg    240

ggaaaatcgc tggggctggg ggtggggcag tggggactta gcgagtttgg gggtgagtgg    300

gatggaagct tggctagagg gatcatcata ggagttgcat tgttgggaga cctgggtgta    360

gatgatgggg atgttaggac catccgaact caaagttgaa cgcctaggca gaggagtgga    420

gctttgggga accttgagcc ggcctaaagc gtacttcttt gcacatccac ccggtgctgg    480

gcgtagggaa tccctgaaat aaaagatgca caaagcattg aggtctgaga cttttggatc    540

tcgaaacatt gagaactcat agctgtatat tttagagccc atggcatcct agtgaaaact    600

ggggctccat tccgaaatga tcatttgggg gtgatccggg gagcccaagc tgctaaggtc    660

ccacaacttc cggacctttg tccttcctgg agcgatcttt ccaggcagcc cccggctccg    720

ctagatggag aaaatccaat tgaaggctgt cagtcgtgga agtgagaagt gctaaaccag    780

gggtttgccc gccaggccga ggaggaccgt cgcaatctga gaggcccggc agccctgtta    840

ttgtttggct ccacatttac atttctgcct cttgcagcag catttccggt ttctttttgc    900

cggagcagct cactattcac ccgatgagag gggaggagag agagagaaaa tgtcctttag    960

gccggttcct cttacttggc agagggaggc tgctattctc cgcctgcatt tctttttctg   1020

gattacttag ttatggcctt tgcaaaggca ggggtatttg ttttgatgca aacctcaatc   1080

cctccccttc tttgaatggt gtgccccacc ccgcgggtcg cctgcaacct aggcggacgc   1140

taccatggcg tgagacaggg agggaaagaa gtgtgcagaa ggcaagcccg gaggtatttt   1200

caagaatgag tatatctcat cttcccggag gaaaaaaaaa aagaatgggt acgtctgaga   1260

atcaaatttt gaaagagtgc aatgatgggt cgtttgataa tttgtcggaa aaacaatcta   1320

cctgttatct agctttgggc taggccattc cagttccaga cgcaggctga acgtcgtgaa   1380

gcggaagggg cgggcccgca ggcgtccgtg tggtcctccg tgcagccctc cggcccgagc   1440

cggttcttcc tggtaggagg cggaactcga attcatttct cccgctgccc catctcttag   1500
```

-continued ctcgcggttg tttcattccg cagtttcttc ccatgcacct gccgcgtacc ggccactttg 1560
tgccgtactt acgtcatctt tttcctaaat cgaggtggca tttacacaca gcgccagtgc 1620
acacagcaag tgcacaggaa gatgagtttt ggcccctaac cgctccgtga tgcctaccaa 1680
gtcacagacc cttttcatcg tcccagaaac gtttcatcac gtctcttccc agtcgattcc 1740
cgaccccacc tttattttga tctccataac cattttgcct gttggagaac ttcatataga 1800
atggaatcag gctgggcgct gtggctcacg cctgcacttt gggaggccga ggcgggcgga 1860
ttacttgagg ataggagttc cagaccagcg tggccaacgt ggtgaatccc cgtctctact 1920
aaaaaataca aaaattagct gggcgtggtg ggtgcctgta atcccagcta ttcgggaggg 1980
tgaggcagga gaatcgcttg aacccgggag gcagaggttg cagtgagcca agatcgtgcc 2040
actacactcc agcctgggcg acaagaacga aactccgtct caaaaaaaag gggggaatca 2100
tacattatgt gctcattttt gtcgggcttc tgtccttcaa tgtactgtct gacattcgtt 2160
catgttgtat atatcagtat tttgctcctt ttcatttagt atagtccatc gattgtatat 2220
ccgtcctttt gatggccttt tgagttgttt cccatttgcg gttatgaaat aaagctgcta 2280
taaacattct tgtacaattc tttttgtgat catatgtttt cgtgtttctt ggagaaatac 2340
ttaggagggg aattgcgagt ttggaagtaa aaagtagctg tattttgaac tttttcagaa 2400
gctctgagtt ttccagagcg gttgtaccat tttacactcc aactagcaag gtatgggagt 2460
tattatggtt gtgccacagc cttccggaca ttaggtattg tcagtctttc taatgtggta 2520
tatccttgtg gttgtaattt acagttctct attgactaag gatgttcagc atttttttcat 2580
gtgcctattg gccattcgta ttttgtttgt aaagtagctc ttcgagtctt ttacctgtta 2640
ttttggtttt ttgtttgttt ttattgttca gttgtgggac tgctttatac attctggata 2700
caagtccttt atcagatcca tgtgtcgtga atgttttctt ctgatctgtt gcttgcctat 2760
ttgtttgctt tacagagttt acagtatctt aagaggagtg gatttatctt ttttatgttc 2820
agtatttgcc ttgtcctgtt taggacatct tttttttttt ttttaacccc agggtcatga 2880
agatattatc ttacattttc ttttaggacc tttatggttg taagttttac agtaaggtcc 2940
ttgagccatt aattaattct taaaattaat tgtttatggt gtgaggtgta ggagtcagtc 3000
tctggtatct ttcctgtatg gaaatccagt tattctgtct ccacttgttg aaataggctt 3060
cctttctcta ctgaatgctt ttaattttaa ttattttaca gttggagtat agggctacca 3120
ttttagtgct attttctttt tttctttgtt aatttttgag acagggactc acactgttgc 3180
ccaggctaga gtacaatggc acaatcaagg cttactgcag cctcgaaccc ctgggctcaa 3240
gcagtcctct agcagcctca cgagtagctg ggattactcc accacaccca gctaactatt 3300
ttattttttt gtattgacag gatctcacta tgttgcccag gctggtctca aactgctggc 3360
ctcaagcttt catcccatct cggcctccca aagtgctggg attacaggtg tgagccacca 3420
tgcctgacct cttagtgcta ttttctattt atctcctctg ttctctgctc tctttaaacg 3480
ttggaggaag aaacagtacc catcttacac aaactcttca gaaaacagag gaacagactg 3540
ggcgcggtgg ctcatacctg taatctcagc actttggtac gctgaggcag gggatcattt 3600
gaggtcggga gttcgagacc agcctggcca acacggcgaa accccatctc tactaaaaat 3660
acaaaaagta gctaggcgtg gtgacacata cctgtaatgc cagttactca ggaggctgag 3720
gcacaagaat cccttgaacc tgggaagcgg aggttgcagt gagccgagat tgcgccactg 3780
cactccagcc tgggcaacag agtgagaccc tgtctcagaa aaaaaaagaa agaaagaaaa 3840
aatagaggaa tatttcccaa cttgttttcg aagccagcat aatcctggta ccaaaaccaa 3900
acaaggacat tataagaaaa gaaaatatag accaatattc ctgttagcat agacatgcaa 3960
cagctaacca attttagcaa accaaacctg gtaatataga aaaaaggata aataggccag 4020
tcgcggtggc tcacgcctgt aatcccagca ctttgggagg ctgaggcagg cagatcactt 4080
gaggtcagga gtttgagacc agcctgacca acatggtgaa accccgtttc taataaaaat 4140
acaaaaatca ggctgggcac ggtggctcac gcctgtaatc ccagcacttt gggaggccga 4200
ggtgggcaga tcacgaggtc aggagttcaa gaccagcctg accaatgtgg tgaaacgcca 4260
tctctactaa aaatacaaaa atcagccggt gtggtggcac ctgcctgtaa tcccagctac 4320
tcaggaggct gaggcagaat tgcttgaacc cgggaggcag aggttgcagt gagccaagat 4380
cgtgccactg cactccagcc tgggcgacag agcaagactt catctcaaaa aaaaaaaaaa 4440
attagctggg catggtggtg ggcacctgaa atcccagcta ctcgggagtc tgaggcagga 4500
gaatcgcttg aacccaggag gcagaagttg cactgagctg ggatcacacc attgcactcc 4560
agcctgggca acagagtgag actccatctc aaaaaaagaa aaagaaaaag gataaataca 4620
ttctaaccaa ataatgttta tctcatgatt gtagctgatt caacattcaa aaattggcct 4680
ggtgcagtag ctcaggcctg taatcccaac attttaggag gctgaggcag gaagatctct 4740
tgagcccagg atttcaagac cagcctgggc aacatagtca gactggtctt tactgggggg 4800
aaaaaaatca gtctgtgtaa ttcaccacat taacaaaggg aaacataaaa accctatgat 4860
catttcaaca gatgtagcaa aagcagttaa tgatattcaa cacatatgca tgattacaaa 4920
ccaaccaacc tcctagcaaa ctagggaaag gaaacttaac ctagtttgat aacagggcgt 4980
ccacagtcgg agttccacta gcagcataca taatggtaga aaactcagtg ctgccgggcg 5040
cggtggctca cgcctgtaat gccagcactt tgggaggcct aggcgggcgg atcacgaggt 5100
caggagatcg agactgtcct gactagcatg ctgaaacccc gtctctacta aaaatacaaa 5160
aacaaaaaat tagccgggca tggtggcggg cgcctatagt cccagctact cgggaggctg 5220
aggcgagaga atggcgtgaa cccgggaggc ggagcttgca gagcctagat cgtgccactg 5280
cactccagcc tgggtgacag agtgagactt cgtctcaaaa aaaaaaaaaa aaaaaaaaga 5340
aaagaaaact caacgctttt tcctctaaga tcaggaacta gaaaaggatt tgactctcac 5400
aacgttgata ccatactgga ggttttaacc aggcaagaaa aagaaataat gagggccggg 5460
tgcggtggct caggcctgta atcccagcac tttgggaagc cgagacgggt ggatcacgag 5520
gtcaggagat cgagaccatc ctggctaaca cggtgaaacc ctgtctctac taaatataca 5580
aaaaattagc cgggcgtagt ggcgggcgcc tgtagtccca gctactcggg aggctgaggc 5640
aggagaatgg cgtgaactca gggggcggag cttgcagtga gctgagatcg agccactgca 5700
ctccagcctg ggcgacagag caagactgtg tctcaaaaaa aaaaaaagaa aaagaaataa 5760
tgattagtgg cccgatgtct cacgcctata atcccagcac tttgggaggc cgaggtgggc 5820
agatcacctg aggtctggag ttggagacca gcctgacaaa gatggtgaaa cctcgtctct 5880
attaaaatat taaaaaaata gccaggcgtt ggccgggtac agtggctcat gcctgtaatc 5940
ccagcacttt gggaggccga ggtgggtgga tcacctgagg tcaggagttc aacaccagcc 6000
tggccaacat ggtgaaaccc catctctact aaaaatacaa aaattagccg ggcgtagtgg 6060
cgggcgcctg taatcccagc tacttgggag gcttaggcag gagaatcgct tgaacctggg 6120
aggcggaggt tgtagtgagc cgagattgca ccattgcact ccagcctggg tgacaaaagc 6180
aaaaactccg tctcaaaaaa aaaagaatta gccaggggta gtggtgaacg cctgtagtcc 6240

-continued

```
cagctactca ggaggcagag gcaggagaat cacttgaacc caggaggcag aggttgcagt   6300
gagccgagat tgtcccattg cactccagcc taggcgacaa gagcaaaatt ccatgtcaaa   6360
aaaaaaaaaa aaaaaggaaa gaaaaaaaat aacgattaga aaggaagaaa taaaacacat   6420
tcacagccag tatgattcta tacatacatg tcctaatggg gccaggcgtg gtggctcatg   6480
cctgtaatcc tagcactttt aggaggctga ggcaggtggc ttccctggga ccagcctggc   6540
caacatggtg aaaccccaac tctaataaaa atacaaaaaa tcagccaggc gtggtgacgg   6600
gcacctctaa tcccagctac tcaggaggct gaggcaggag aattgcttgg acctgggagg   6660
cagaggttgc agtgagccga gatcgcgcta ttgcactcca gcctgggcaa caagagtgaa   6720
actccggcag ggtgtggtgg cttacgcctg taatcccagc acttcgggag gctgaggcag   6780
gccgatcacc tgaggtcagg agtttgagac caacctaaca tggtgaaacc ccgtctctac   6840
taaaaataca agaattagct gggtgtagtg gtgggcgcct gtaatcccag ctacttggga   6900
ggctgagaca gaagaattgc ttgaacccag gaggtggagg ttgcagtgag ctgagatcat   6960
gccattgcac accacgccgg gcaacagagc gagattccgt ctcaaaaaaa aaaaaaaaga   7020
gtgaaactct atctcaaaaa aaaaaaaaag tcctaatgga aaatccataa aaagctacca   7080
aaactaataa ataaatatag cagggttgca ggttacaggg caatatagtt atccctctat   7140
ctgtaggggc ttggttctgg gactcctcac acaccaaacc cacagatgtc taagtcccat   7200
atataagacg gtatagtatt tggatttaac ctacacatat cctcccatat agtttaaatt   7260
atctctagat tacttacatt acccccatac aatgaaaatg ctaatgtaca tgcaagtatg   7320
tatgtaagta cttgtactat attgtttagg gaatcactgg acatataggc cttcaagact   7380
gataccagca gccactgtta agattctggt caggcctgcc cctgtttggg gtctcagttg   7440
atctcattgc cttcccaccc agccaagggc acctgcattt ctcttggctc cctggccatt   7500
tggaaggcct agttcagcct ggcacatttg tatcctggcc cactgatgct ggtacccctg   7560
ggaaggtcct gctctgaaaa acacggagat tttagttgct actgaagatt tgagagataa   7620
agacagggag acctgtctgt agacctgtgt ccctccaagt gggattgaga ctttgggccc   7680
cccatttcag gacagcacct cctggcctgt tgactgaata gatccctgaa ggaggtgtac   7740
ttgcattaat ggagtggggg tgggagcagt accacagatc cgcactaaca atcacacagt   7800
tctctctaga ataataatat agaacaagtg aaatagaaca attgcagaaa gagctaacct   7860
ttgttgagct cttactgtgt gcccagcact ttcctcaact ctacatttcc cataatacac   7920
agagtactag gtaggccagg cttggtggct cacgcctgta atcccagcac tttaggaggc   7980
caaggggggt ggatcacctg aggtcgggag ttcaagacca gcctgaccaa catggtgaaa   8040
ccccgtctct actagaagta caaaattagc caggtgtggt ggcacatgct tgtagtccta   8100
gctactcagc aggctgaggc aggagaatca tttgaatccg ggaggaggtt gcagtaagcg   8160
gagatagtgc cactgtactc cagcctgggc aataagagct gagactccgt ctcaaaataa   8220
aataaaataa aataaaataa aataaaataa aataaaaaaa gaaaagagcc tgccattaaa   8280
ggagctgttt ggtaggggat gttttgtcag tgcaaacaac agaaaagtgg gctgggcaca   8340
gtggttcatg cctgtaatcc cagcactttg ggaggccaag gcgggcggat cacctgaagt   8400
tgggagttca agaccagcct gaccaatatg gagaaacccc gtctctacta aaaatacaaa   8460
attagccggg cgcagtggcg catgcctgta atcccagcta ctcgggaggc tgaggcagga   8520
gaatcgcttg aacctgggag gcagaggttg cggtgagccg agatcgcacc attgcactcc   8580
agcctggacg agagcaaaac tctgtctcaa aaaaaaaaaa aaacagaaaa gtgtaacaaa   8640
```

-continued

```
cacttacagt aggcatgttt cttagcaaat ctgatgacaa atttggcata aagaaagaga   8700
gcatccctga aaaaaaaaaa aagaaaaaga aagagagcat cctgcctggg caacatagtg   8760
aaaccctgcc tctacaaaaa aactcaaaaa ttggccgggt gcagtggctc acacctgtaa   8820
tcccagcact ttgggagtcg gaggcgggag gatcacctga ggtcaggagt tcgaaaccag   8880
cctggccaac atggcaaaac cccatctcta ctaaaaatac aaaaaattaa tcaggcgcat   8940
tggtgggcgc ctgtaatccc agctactcag gaagttgagg caagaggatc gcttgaatct   9000
gggaggtgga ggttacagtg agtcgagatc acaccactgc actctagcct gggtgacagg   9060
gcgagactcc gtctccaaaa aaaaaaagaa aaagaaaaag actaaaaaat tagccaggca   9120
ggcctctgtg gtcccagcta cttgggaggc tgaggcagga gaatcactga gcccaggagt   9180
ccgaggctgt agtgagccat gattgcacca ctgtacccta gcttgggcaa caaagcaaga   9240
ccctgcctca aaagaaaaaa gaaagaaaga aagaacatgg cgggccaggc acagtggctc   9300
acacctgtaa tcccagcgct ttgagaggcc gaggcaggtg gatcacaagg tcaggagttc   9360
cacaccagcc tggccaacat ggtgaaaccc tgtctctact aaaaatacaa aaaatcagcc   9420
aggcatggtg gcaggggcct gtaatcccag ctactcggga ggctgaggca ggagaattgc   9480
ttgaaaccag aaggcagagg ttgcagtgag cctagactgc accactgcac tccagcctgg   9540
gcgaaaagag ccaaactcca tctcaaaaaa caaacaaaaa aacaaaacaa aagaaaacat   9600
ggcaaagcct ttgaaagctt gtctgggaga aggtgcgatg atagttgcat aacttcgtgc   9660
aagatgctgg tccacacagg ggctgcccct tgctctttct cgctctctta acctctcata   9720
taacaggctt gtgtgttatt cacatttatt gagcccaagc aggtgcaagg cattgtgatc   9780
taatactttg gtcagcaaga caacaagata gatcactgcc ctgcccttag gaagtgtata   9840
tgctattaga ggaaacagat aaaataaaca aggaaaagta tcagacaatg taagtgctat   9900
gagaatgcaa atgaggtgat gtgaattaaa ataggatgac ttaaagtctg cacgggaagg   9960
agcctacccc catgttcctg gctagccaag gaaccaccag ttgattagca gagaagggca  10020
gccagtctag ctagagcttt tggggaagag ggagtggttg ttaagagatg agattaaaga  10080
agccgagacg ggccattcgt gaggggtttg taatgcaggg ctgaggagtg tccgaagaga  10140
atgggcaggt gagcggtgag acagttgttc ttccagaagc tttgcagtga aaggaatcaa  10200
agaaatggag ccgtgtatca ggtggggaag ggtgggggcc aagggggtgt ccttccccat  10260
acagagattg caggctgaga atgactatat ccttgttaac aggaggtggg agcagggcac  10320
ggtagctcac acctgtaatc ttggcacttt aggaggctga ggcgggccga tcacctgaag  10380
taaggagttc gagaccagcc tggccaacat gcaaagccct gtctctacta aaaatacaaa  10440
aattagctgg gtgtggtggt actcgcctgt aatcccagct actcgggaga ctgaggcagg  10500
agaatggctt gaacccggaa ggtagaggtt gcagtgagct gagatcatgc cactgtgctc  10560
cagcctaggt gacagagaga gactccatct caaaaaaaaa aaaaaaatac aggaagggag  10620
ttgggaatag ggtgcacatt taggaagtct tggggattta gtggtgggaa ggttggaagt  10680
ccctctctga ttgtcttttc ctcaaagaag tgcatggctg gtgaggggtg gggcaggagt  10740
gcttgggttg tggtgaaaca ttggaagaga gaatgtgaag cagccattct tttcctgctc  10800
cacaggaagc cgagctgtct cagacactgg catggtgttg ggggaggggg ttccttctct  10860
gcaggcccag gtgacccagg gttggaagtg tctcatgctg gatccccact tttcctcttg  10920
cagcagccag actgccttcc gggtcactgc catggaggag ccgcagtcag atcctagcgt  10980
```

cgagccccct ctgagtcagg aaacattttc agacctatgg aaactgtgag tggatccatt 11040
ggaagggcag gcccaccacc cccaccccaa ccccagcccc ctagcagaga cctgtgggaa 11100
gcgaaaattc catgggactg actttctgct cttgtctttc agacttcctg aaaacaacgt 11160
tctggtaagg acaagggttg ggctggggac ctggagggct ggggacctgg agggctgggg 11220
ggctgggggg ctgaggacct ggtcctctga ctgctctttt cacccatcta cagtccccct 11280
tgccgtccca agcaatggat gatttgatgc tgtccccgga cgatattgaa caatggttca 11340
ctgaagaccc aggtccagat gaagctccca gaatgccaga ggctgctccc cccgtggccc 11400
ctgcaccagc agctcctaca ccggcggccc ctgcaccagc cccctcctgg cccctgtcat 11460
cttctgtccc ttcccagaaa acctaccagg gcagctacgg tttccgtctg ggcttcttgc 11520
attctgggac agccaagtct gtgacttgca cggtcagttg ccctgagggg ctggcttcca 11580
tgagacttca atgcctggcc gtatcccccct gcatttcttt tgtttggaac tttgggattc 11640
ctcttcaccc tttggcttcc tgtcagtgtt tttttatagt ttacccactt aatgtgtgat 11700
ctctgactcc tgtcccaaag ttgaatattc ccccttgaa tttgggcttt tatccatccc 11760
atcacaccct cagcatctct cctggggatg cagaactttt ctttttcttc atccacgtgt 11820
attccttggc ttttgaaaat aagctcctga ccaggcttgg tggctcacac ctgcaatccc 11880
agcactctca aagaggccaa ggcaggcaga tcacctgagc ccaggagttc aagaccagcc 11940
tgggtaacat gatgaaacct cgtctctaca aaaaaataca aaaaattagc caggcatggt 12000
ggtgcacacc tatagtccca gccacttagg aggctgaggt gggaagatca cttgaggcca 12060
ggagatggag gctgcagtga gctgtgatca caccactgtg ctccagcctg agtgacagag 12120
caagacccta tctcaaaaaa aaaaaaaaaa aagaaaagct cctgaggtgt agacgccaac 12180
tctctctagc tcgctagtgg gttgcaggag gtgcttacgc atgtttgttt ctttgctgcc 12240
gtcttccagt tgctttatct gttcacttgt gccctgactt tcaactctgt ctccttcctc 12300
ttcctacagt actcccctgc cctcaacaag atgttttgcc aactggccaa gacctgccct 12360
gtgcagctgt gggttgattc cacacccccg cccggcaccc gcgtccgcgc catggccatc 12420
tacaagcagt cacagcacat gacggaggtt gtgaggcgct gcccccacca tgagcgctgc 12480
tcagatagcg atggtgagca gctggggctg gagagacgac agggctggtt gcccagggtc 12540
cccaggcctc tgattcctca ctgattgctc ttaggtctgg cccctcctca gcatcttatc 12600
cgagtggaag gaaatttgcg tgtggagtat ttggatgaca gaaacacttt tcgacatagt 12660
gtggtggtgc cctatgagcc gcctgaggtc tggtttgcaa ctggggtctc tgggaggagg 12720
ggttaagggt ggttgtcagt ggccctccag gtgagcagta ggggggcttt ctcctgctgc 12780
ttatttgacc tccctataac cccatgagat gtgcaaagta aatgggttta actattgcac 12840
agttgaaaaa actgaagctt acagaggcta agggcctccc ctgcttggct gggcgcagtg 12900
gctcatgcct gtaatcccag cactttggga ggccaaggca ggcggatcac gaggttggga 12960
gatcgagacc atcctggcta acggtgaaac cccgtctcta ctgaaaaata caaaaaaaaa 13020
ttagccgggc gtggtgctgg gcacctgtag tcccagctac tcgggaggct gaggaaggag 13080
aatggcgtga acctgggcgg tggagcttgc agtgagctga gatcacgcca ctgcactcca 13140
gcctgggcga cagagcgaga ttccatctca aaaaaaaaaa aaaaaggcct cccctgcttg 13200
ccacaggtct ccccaaggcg cactggcctc atcttgggcc tgtgttatct cctaggttgg 13260
ctctgactgt accaccatcc actacaacta catgtgtaac agttcctgca tgggcggcat 13320
gaaccggagg cccatcctca ccatcatcac actggaagac tccaggtcag gagccacttg 13380

```
ccaccctgca cactggcctg ctgtgcccca gcctctgctt gcctctgacc cctgggccca  13440
cctcttaccg atttcttcca tactactacc catccacctc tcatcacatc cccggcgggg  13500
aatctcctta ctgctcccac tcagttttct tttctctggc tttgggacct cttaacctgt  13560
ggcttctcct ccacctacct ggagctggag cttaggctcc agaaaggaca agggtggttg  13620
ggagtagatg gagcctggtt ttttaaatgg gacaggtagg acctgatttc cttactgcct  13680
cttgcttctc ttttcctatc ctgagtagtg gtaatctact gggacggaac agctttgagg  13740
tgcgtgtttg tgcctgtcct gggagagacc ggcgcacaga ggaagagaat ctccgcaaga  13800
aaggggagcc tcaccacgag ctgcccccag ggagcactaa gcgaggtaag caagcaggac  13860
aagaagcggt ggaggagacc aagggtgcag ttatgcctca gattcacttt tatcaccttt  13920
ccttgcctct ttcctagcac tgcccaacaa caccagctcc tctccccagc caaagaagaa  13980
accactggat ggagaatatt tcacccttca ggtactaagt cttgggacct cttatcaagt  14040
ggaaagtttc cagtctaaca ctcaaaatgc cgttttcttc ttgactgttt tacctgcaat  14100
tggggcattt gccatcaggg ggcagtgatg cctcaaagac aatggctcct ggttgtagct  14160
aactaacttc agaacaccaa cttataccat aatatatatt ttaaaggacc agaccagctt  14220
tcaaaaagaa aattgttaaa gagagcatga aaatggttct atgactttgc ctgatacaga  14280
tgctacttga cttacgatgg tgttacttcc tgataaactc gtcgtaagtt gaaaatattg  14340
taagttgaaa atggatttaa tacacctaat ctaaggaaca tcatagctta gcctagcctg  14400
cttttttttt ttttttttt ggagacagag tctcactctg tcacccaggc tggagtgcag  14460
tggcgggatc tcggctcact gcaacctccg ccttctgggt tcaagcgatt ctcctgcctc  14520
agcccactga gtagctggga ttacaggcac ctgccccgac gcccagctaa ttttttgtta  14580
tttatttatt ttttttttta gtagagatga ggtttcacca tgttggccag gctagtctcg  14640
aactcctgac cttgtgatct gcctgccttg gcctcccaaa gtgctgggat tacaggcgtg  14700
agccaccgca cccggcctgc ctagcctact tttattttat ttttaatgga gacagcatct  14760
tgctctgttg cccaggctgg attacagtga tgtgatcata gctcattata ccctcctggg  14820
ctcaagcaat ccccctaact ctgcctcccc agtagctagg accacaggca tacaccacca  14880
tacccagcta atttttaaaa ttttttgtag atagatagag tctcactatg ttgcccaggc  14940
tggtctctag cctacttttt tgagacaagg tcttgctctg tcacccaggc tggatagagt  15000
gcagtagtgc agtcacagct cactgcagcc tccacctccc aggctccatc catcctccca  15060
gctcagcctc ccaagttgct tcaactacag gcctgcacca ccatgcctgg ctaattttta  15120
tttatttatt tttattttat tttattttat ttttttgaga ctcagtctca ctctgtcgcc  15180
caggctggag tgcagtggca tgatctcggc tcactgcaac ctctgcctcc tgggttcaag  15240
tgattctcct gcctcagcct cccgaatagc taggactaca agcgcctgct accacgccca  15300
gctaattttt gtatttttag tagagacagg gtttcaccat gttggccagg ctggtctcga  15360
acttctgacc atgtgatccg cccgcctcgg cctcccaaag tgctgggatt acaggtgtga  15420
gccaccacgc ccggctaatt tttatttatt tatttaaaga cagagtctca ctctgtcact  15480
caggctagag tgcagtggca ccatctcagc tcactgcagc cttgacctcc ctgggctccg  15540
gtgatttcac cctcccaagt agctaggact acaggcacat gccacgacac ccagctaatt  15600
ttttattttc tgtgaagtca aggtcttgct acgttgccca tgctggtatc aaacccctgg  15660
gctcaatcaa tccttccacc tcagcctccc caagtattgg ggttacaggc atgagctacc  15720
```

-continued

```
acactcagcc ctagcctact tgaaacgtgt tcagagcatt taagttaccc tacagttggg  15780
caaagtcatc taacacaaag cccttttat agtaataaaa tgttgtatat ctcatgtgat  15840
ttattgaata ttgttactga aagtgagaaa cagcatggtt gcatgaaagg aggcacagtc  15900
gagccaggca cagcctgggc gcagagcgag actcaaaaaa agaaaaggcc aggcgcactg  15960
gctcacgcct gtaatcccag catttcggga ggctgaggcg ggtggatcac ctgaggtcag  16020
gagttcaaga ccagcctagc caacatggtg aaaccccgtc tctactaaaa tacaaaaatt  16080
aaccgggcgt gatggcaggt gcctgtaatc ccagctactt gggaggctga ggcaggagaa  16140
tcgcttgaac caggaggcgg aggttgcagg gagccaagat ggcgccactg cactccagcc  16200
tgggcgatag agtgagactc cgtctcagaa aaaaaagaaa agaaacgagg cacagtcgca  16260
tgcacatgta gtcccagtta cttgagaggc taaggcagga ggatctcttg agcccaagag  16320
tttgagtcca gcctgaacaa catagcaaga catcatctct aaaatttaaa aaagggccgg  16380
gcacagtggc tcacacctgt aatcccagca ctttgggagg tggaggtggg tagatcacct  16440
gacgtcagga gttggaaacc agcctggcta acatggtgaa gccccatctc tactaaaaac  16500
acaaaaatta gccaggtgtg gtagcacacg cctgtagtcc cagctactcg ggaggctgag  16560
gcacaagaat cacttgaacc ccagaggcgg agattgcaat cagccaagat tgcaccattg  16620
cactcccgcc tgggcaacag agtgagaccc catctcaaaa taaataaata aatattttta  16680
aaagtcagct gtataggtac ttgaagtgca gtttctacta aatgcatgtt gcttttgtac  16740
cgtcataaag tcaaacaatt gtaacttgaa ccatctttta actcaggtac tgtgtatata  16800
cttacttctc cccctcctct gttgctgcag atccgtgggc gtgagcgctt cgagatgttc  16860
cgagagctga atgaggcctt ggaactcaag gatgcccagg ctgggaagga gccagggggg  16920
agcagggctc actccaggtg agtgacctca gccccttcct ggccctactc ccctgccttc  16980
ctaggttgga aagccatagg attccattct catcctgcct tcatggtcaa aggcagctga  17040
ccccatctca ttgggtccca gccctgcaca gacatttttt tagtcttcct ccggttgaat  17100
cctataacca cattcttgcc tcagtgtatc cacagaacat ccaaacccag ggacgagtgt  17160
ggatacttct ttgccattct ccgcaactcc cagcccagag ctggagggtc tcaaggaggg  17220
gcctaataat tgtgtaatac tgaatacagc cagagtttca ggtcatatac tcagccctgc  17280
catgcaccgg caggtcctag gtgacccccg tcaaactcag tttccttata tataaaatgg  17340
ggtaaggggg ccgggcgcag tggctcacga atcccacact ctgggaggcc aaggcgagtg  17400
gatcacctga ggtcgggagt ttgagcccag cctgaccaac atggagaaac cccatctcta  17460
ctaaaaatac aaaagtagcc gggcgtggtg atgcatgcct gtaatcccag ctacctactc  17520
gggaggctga ggcaggagaa tcgcttgaac ccgggaggca gaggttgcgg tgagctgaga  17580
tctcaccatt acactccagc ctgggcaaca agagtgaaac tccgtctcaa aaaagataaa  17640
taaagtaaaa tggggtaagg gaagattacg agactaatac acactaatac tctgaggtgc  17700
tcagtaaaca tatttgcatg gggtgtggcc accatcttga tttgaattcc cgttgtccca  17760
gccttaggcc cttcaaagca ttggtcaggg aaaaggggca cagaccctct cactcatgtg  17820
atgtcatctc tcctccctgc ttctgtctcc tacagccacc tgaagtccaa aaagggtcag  17880
tctacctccc gccataaaaa actcatgttc aagacagaag ggcctgactc agactgacat  17940
tctccacttc ttgttcccca ctgacagcct cccaccccca tctctccctc ccctgccatt  18000
ttgggttttg ggtctttgaa cccttgcttg caataggtgt gcgtcagaag cacccaggac  18060
ttccatttgc tttgtcccgg ggctccactg aacaagttgg cctgcactgg tgttttgttg  18120
```

tggggaggag gatggggagt aggacatacc agcttagatt ttaaggtttt tactgtgagg 18180
gatgtttggg agatgtaaga aatgttcttg cagttaaggg ttagtttaca atcagccaca 18240
ttctaggtag gggcccactt caccgtacta accagggaag ctgtccctca ctgttgaatt 18300
ttctctaact tcaaggccca tatctgtgaa atgctggcat ttgcacctac ctcacagagt 18360
gcattgtgag ggttaatgaa ataatgtaca tctggccttg aaaccacctt ttattacatg 18420
gggtctagaa cttgaccccc ttgagggtgc ttgttccctc tccctgttgg tcggtgggtt 18480
ggtagtttct acagttgggc agctggttag gtagagggag ttgtcaagtc tctgctggcc 18540
cagccaaacc ctgtctgaca acctcttggt gaaccttagt acctaaaagg aaatctcacc 18600
ccatcccaca ccctggagga tttcatctct tgtatatgat gatctggatc caccaagact 18660
tgttttatgc tcagggtcaa tttctttttt cttttttttt tttttttttc tttttctttg 18720
agactgggtc tcgctttgtt gcccaggctg gagtggagtg gcgtgatctt ggcttactgc 18780
agcctttgcc tccccggctc gagcagtcct gcctcagcct ccggagtagc tgggaccaca 18840
ggttcatgcc accatggcca gccaactttt gcatgttttg tagagatggg gtctcacagt 18900
gttgcccagg ctggtctcaa actcctgggc tcaggcgatc cacctgtctc agcctcccag 18960
agtgctggga ttacaattgt gagccaccac gtccagctgg aagggtcaac atcttttaca 19020
ttctgcaagc acatctgcat tttcacccca cccttcccct ccttctccct ttttatatcc 19080
catttttata tcgatctctt attttacaat aaaactttgc tgccacctgt gtgtctgagg 19140
ggtg 19144

<210> SEQ ID NO 6
<211> LENGTH: 5572
<212> TYPE: DNA
<213> ORGANISM: homo sapiens

<400> SEQUENCE: 6
cctcccctcg cccggcgcgg tcccgtccgc ctctcgctcg cctcccgcct cccctcggtc 60
ttccgaggcg cccgggctcc cggcgcggcg gcggaggggg cgggcaggcc ggcgggcggt 120
gatgtggcgg gactctttat gcgctgcggc aggatacgcg ctcggcgctg ggacgcgact 180
gcgctcagtt ctctcctctc ggaagctgca gccatgatgg aagtttgaga gttgagccgc 240
tgtgaggcga ggccgggctc aggcgaggga gatgagagac ggcggcggcc gcggcccgga 300
gcccctctca gcgcctgtga gcagccgcgg gggcagcgcc ctcggggagc cggccggcct 360
gcggcggcgg cagcggcggc gtttctcgcc tcctcttcgt cttttctaac cgtgcagcct 420
cttcctcggc ttctcctgaa agggaaggtg gaagccgtgg gctcgggcgg gagccggctg 480
aggcgcggcg gcggcggcgg cacctcccgc tcctggagcg ggggggagaa gcggcggcgg 540
cggcggccgc ggcggctgca gctccaggga gggggtctga gtcgcctgtc accatttcca 600
gggctgggaa cgccggagag ttggtctctc cccttctact gcctccaaca cggcggcggc 660
ggcggcggca catccaggga cccgggccgg ttttaaacct cccgtccgcc gccgccgcac 720
cccccgtggc ccgggctccg gaggccgccg gcggaggcag ccgttcggag gattattcgt 780
cttctcccca ttccgctgcc gccgctgcca ggcctctggc tgctgaggag aagcaggccc 840
agtcgctgca accatccagc agccgccgca gcagccatta cccggctgcg gtccagagcc 900
aagcggcggc agagcgaggg gcatcagcta ccgccaagtc cagagccatt tccatcctgc 960
agaagaagcc ccgccaccag cagcttctgc catctctctc ctcctttttc ttcagccaca 1020

-continued

```
ggctcccaga catgacagcc atcatcaaag agatcgttag cagaaacaaa aggagatatc   1080
aagaggatgg attcgactta gacttgacct atatttatcc aaacattatt gctatgggat   1140
ttcctgcaga aagacttgaa ggcgtataca ggaacaatat tgatgatgta gtaaggtttt   1200
tggattcaaa gcataaaaac cattacaaga tatacaatct ttgtgctgaa agacattatg   1260
acaccgccaa atttaattgc agagttgcac aatatccttt tgaagaccat aacccaccac   1320
agctagaact tatcaaaccc ttttgtgaag atcttgacca atggctaagt gaagatgaca   1380
atcatgttgc agcaattcac tgtaaagctg gaaagggacg aactggtgta atgatatgtg   1440
catatttatt acatcggggc aaatttttaa aggcacaaga ggccctagat ttctatgggg   1500
aagtaaggac cagagacaaa aagggagtaa ctattcccag tcagaggcgc tatgtgtatt   1560
attatagcta cctgttaaag aatcatctgg attatagacc agtggcactg ttgtttcaca   1620
agatgatgtt tgaaactatt ccaatgttca gtggcggaac ttgcaatcct cagtttgtgg   1680
tctgccagct aaaggtgaag atatattcct ccaattcagg acccacacga cgggaagaca   1740
agttcatgta ctttgagttc cctcagccgt tacctgtgtg tggtgatatc aaagtagagt   1800
tcttccacaa acagaacaag atgctaaaaa aggacaaaat gtttcacttt tgggtaaata   1860
cattcttcat accaggacca gaggaaacct cagaaaaagt agaaaatgga agtctatgtg   1920
atcaagaaat cgatagcatt tgcagtatag agcgtgcaga taatgacaag gaatatctag   1980
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt tttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
```

acccttttga ccttacacat tctattacaa tgaattttgc agttttgcac attttttaaa 3480
tgtcattaac tgttagggaa ttttacttga atactgaata catataatgt ttatattaaa 3540
aaggacattt gtgttaaaaa ggaaattaga gttgcagtaa actttcaatg ctgcacacaa 3600
aaaaaagaca tttgattttt cagtagaaat tgtcctacat gtgctttatt gatttgctat 3660
tgaaagaata gggttttttt tttttttttt tttttttttt ttaaatgtgc agtgttgaat 3720
catttcttca tagtgctccc ccgagttggg actagggctt caatttcact tcttaaaaaa 3780
aatcatcata tatttgatat gcccagactg catacgattt taagcggagt acaactacta 3840
ttgtaaagct aatgtgaaga tattattaaa aaggtttttt tttccagaaa tttggtgtct 3900
tcaaattata ccttcacctt gacatttgaa tatccagcca ttttgtttct taatggtata 3960
aaattccatt ttcaataact tattggtgct gaaattgttc actagctgtg gtctgaccta 4020
gttaatttac aaatacagat tgaataggac ctactagagc agcatttata gagtttgatg 4080
gcaaatagat taggcagaac ttcatctaaa atattcttag taaataatgt tgacacgttt 4140
tccatacctt gtcagtttca ttcaacaatt tttaaatttt taacaaagct cttaggattt 4200
acacatttat atttaaacat tgatatatag agtattgatt gattgctcat aagttaaatt 4260
ggtaaagtta gagacaacta ttctaacacc tcaccattga aatttatatg ccaccttgtc 4320
tttcataaaa gctgaaaatt gttacctaaa atgaaaatca acttcatgtt ttgaagatag 4380
ttataaatat tgttctttgt tacaatttcg ggcaccgcat attaaaacgt aactttattg 4440
ttccaatatg taacatggag ggccaggtca taaataatga cattataatg ggcttttgca 4500
ctgttattat ttttcctttg gaatgtgaag gtctgaatga gggttttgat tttgaatgtt 4560
tcaatgtttt tgagaagcct tgcttacatt ttatggtgta gtcattggaa atggaaaaat 4620
ggcattatat atattatata tataaatata tattatacat actctcctta ctttatttca 4680
gttaccatcc ccatagaatt tgacaagaat tgctatgact gaaaggtttt cgagtcctaa 4740
ttaaaacttt atttatggca gtattcataa ttagcctgaa atgcattctg taggtaatct 4800
ctgagtttct ggaatatttt cttagacttt ttggatgtgc agcagcttac atgtctgaag 4860
ttacttgaag gcatcacttt taagaaagct tacagttggg ccctgtacca tcccaagtcc 4920
tttgtagctc ctcttgaaca tgtttgccat acttttaaaa gggtagttga ataaatagca 4980
tcaccattct ttgctgtggc acaggttata aacttaagtg gagtttaccg gcagcatcaa 5040
atgtttcagc tttaaaaaat aaaagtaggg tacaagttta atgtttagtt ctagaaattt 5100
tgtgcaatat gttcataacg atggctgtgg ttgccacaaa gtgcctcgtt tacctttaaa 5160
tactgttaat gtgtcatgca tgcagatgga aggggtggaa ctgtgcacta aagtgggggc 5220
tttaactgta gtatttggca gagttgcctt ctacctgcca gttcaaaagt tcaacctgtt 5280
ttcatataga atatatatac taaaaaattt cagtctgtta aacagcctta ctctgattca 5340
gcctcttcag atactcttgt gctgtgcagc agtggctctg tgtgtaaatg ctatgcactg 5400
aggatacaca aaaataccaa tatgatgtgt acaggataat gcctcatccc aatcagatgt 5460
ccatttgtta ttgtgtttgt taacaaccct ttatctctta gtgttataaa ctccacttaa 5520
aactgattaa agtctcattc ttgtcaaaaa aaaaaaaaaa aaaaaaaaaa aa 5572

<210> SEQ ID NO 7
<211> LENGTH: 105338
<212> TYPE: DNA
<213> ORGANISM: homo sapiens

<400> SEQUENCE: 7

```
cctcccctcg cccggcgcgg tcccgtccgc ctctcgctcg cctcccgcct cccctcggtc     60
ttccgaggcg cccgggctcc cggcgcggcg gcggaggggg cgggcaggcc ggcgggcggt    120
gatgtggcgg gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cacctcccgc tcctggagcg ggggggagaa gcggcggcgg    540
cggcggccgc ggcggctgca gctccaggga gggggtctga gtcgcctgtc accatttcca    600
gggctgggaa cgccggagag ttggtctctc cccttctact gcctccaaca cggcggcggc    660
ggcggctggc acatccaggg acccgggccg gttttaaacc tcccgtgcgc cgccgccgca    720
ccccccgtgg cccgggctcc ggaggccgcc ggcggaggca gccgttcgga ggattattcg    780
tcttctcccc attccgctgc cgccgctgcc aggcctctgg ctgctgagga gaagcaggcc    840
cagtcgctgc aaccatccag cagccgccgc agcagccatt acccggctgc ggtccagagc    900
caagcggcgg cagagcgagg ggcatcagct accgccaagt ccagagccat ttccatcctg    960
cagaagaagc cccgccacca gcagcttctg ccatctctct cctccttttt cttcagccac   1020
aggctcccag acatgacagc catcatcaaa gagatcgtta gcagaaacaa aaggagatat   1080
caagaggatg gattcgactt agacttgacc tgtatccatt tctgcggctg ctcctcttta   1140
cctttctgtc actctcttag aacgtgggag tagacggatg cgaaaatgtc cgtagtttgg   1200
gtgactataa catttaaccc tggtcaggtt gctaggtcat atattttgtg tttcctttct   1260
gtgtattcaa cctagggtgt gtttggctag acggaactct tgcctggttg caagtgtcaa   1320
gccaccgatt gctttcttag gctatctata tggtctcttc ctgagggcta ttgtccgtta   1380
atacagaata cagtacactg ttagtggatt agcgagctcg gtaatccggt ctcctaaatg   1440
aacaaaaaag tagacgcttt ttgaggttga gcatatttcg attaaatctt ggcttaggcc   1500
ctagatcaag ggtttagatc agaataaaat gaaaattagt gttgcacgta cgcatattgc   1560
atcagaatct tgcagtgatt gttttagttt cctgagttgc attgatagat tcttttaaaa   1620
tatgactgat ttgcataact ttagaagcag aatcattttc agtatatatg gtgcacattg   1680
agggcaaaaa gtagttttgt taatgtttaa acttaagtta cctacaactt tgaactgtat   1740
gtagaagttt tgtagtttga agtcaatagt gccataatat accttataag gcgttcttac   1800
tagatctttg ttatatttac ctttttctct ccctatgggg tgatgtagga tagtgcttga   1860
aatttgcact tcagtagcat ttaatgttca gtgctcttgt cataaacata gaatggatat   1920
tgagtagttt ctgatcccag atggtaatgt gtaggttcaa gggtattgtg tgtagcaagt   1980
gaagattgca gaaataaaac ttcagttcat gcttgaaatt taagtattgt tgtgatgcca   2040
gaattgctgc tcaccgtttt taggtttcag gtcctctgac accttttggt atcgttaatt   2100
ttactgattt gtgtagaatg tcagttgtat tttaccagct aatatctaga aatgctggca   2160
agaggggttt actccagctt tagattgtag gtatgttagc ttttttcata cagtgtatta   2220
aatttactga gtcagcttgc tgaataagac agaagcccaa gaattttaac agtgtgtagc   2280
tttagttgtc taaaagttag gccttcgggc ttcaaaagtt agtggtcatc gaaaagcatt   2340
```

```
aatctttgca gtttcaggta caacacattg gttttgatta gggatgggga tggggccctc   2400
tttttgcaga atggggaaag tattgacagg aattgagagc tattggtagg ccagtgtata   2460
aggtatgtga aaacagaatt aagttattgg tctgaagtga ctgaagcatt taggctctat   2520
caaggcctaa aatttggtaa tatgagtttg gtaatgcgaa ttgtggcagt ggacaatatt   2580
tagttaaaat tatgtaattg cataagtact agcacagtat ttttaataaa agttatttct   2640
tagcaaatgt cagttgcatt ttgtctaaag gtagagtgac actacagtgt ctatatgtcc   2700
tgctaaaaat tgtggggaat attttttttt aagacagcgt ttatatcggg agaggtttta   2760
ttccgttgga ttatgttagc tgcatataaa tgtgcacagt taattttgcc caagtttttg   2820
ttttgaaatg aatgtaaaac ttactgaaga agtagcttcc caaaatttag ttttctgtta   2880
agccaaaaat attattttaa aagagtattt gcaaattttg aagttgacat taattgagaa   2940
tgttactaag gctaaactgg acccgcttgc ccagaagata attatggaaa aattcttttg   3000
tgacttccaa agcagtctac tattagcatg aattactgac agtcatccaa atatatagga   3060
acaaaaaatt aaatgtttat gtaactttga aaaaaaagcc tttgaagaaa ataattgaat   3120
gctgtctggg agacagattt ctttcagcac ttaaagtaca taacacacta cttttacttt   3180
tcccacttga ttttaaatta tcagggttat taagacctta aaattatttt accaggtttt   3240
tacatgtgag ctgtgacatg actggcattt tctttgattt cagcgtatgt tggtctctac   3300
acatgaaatt tgtgtgactt aaaactttct ctaaaactgt acttttagtt atgatatgca   3360
tagaaagcag tatcaaatat tgcgtcaaat gactaataac acttaatttc tagagttgtg   3420
gttttattga gccaaaagtt gatatgaaaa aaagtcagta aggaaagtca gtgaagtgct   3480
tgcttttttg ataattgcac tcccaataat tttgatattc caacgtactt ggtttgcttg   3540
ttttcacgtt aatgttttct gtttattgga gtgggaaggc attaaaattg tcattgaaga   3600
ctttgtcttt gacatgttgt agtatttatt tcagtaacta acctgtgaaa agttaaattc   3660
ctttatgaaa gtagtgattg gagtattttt atctgataaa gaaagattaa taatgaagcc   3720
atttctccga ggaaaattga ggacaataat tcagttttaa aatattatcg caaaattaaa   3780
ttattctaaa aatttgttag tagggttata tgcttaatat tagtctgaaa tatagtgctg   3840
aatttgagac tatagaaaaa ttaagtgtat ttagggtatg tggaaacgtt aggcttctgt   3900
tgtattttta ttgtttggta gatttgcctc ttttcaaata aatgttcaca gggaatactt   3960
ttaacttgta gagagtacag tgactattga agttacctaa attacctcaa ggtaagtgat   4020
tactgaaatt aatcatgagg gttttaaaaa gtattctatt cacaacattt attttacatt   4080
gttttgtatc tgctaagtta tatttcctga aaaacatgac tggaccacct aattgctgta   4140
tgataactta caaacttcat ttttcatagt gcttattcaa gtgtaaagca caactgaaag   4200
gagtaatgta cagtttatat gaggaaaaag gaattttatt gctgccagtg taaaagtttg   4260
cacagcagta tagtcatcaa tgcagattta cattgcttat aatatactaa gtaaatacta   4320
aatgattaaa gataataaaa tatggtgagg tataaccacc ttcattttaa acttagtttt   4380
agaagatagt aaagaaagat tcctttatta ccttttttaga attttatttt taataacatg   4440
ggaaaggcaa ctggtgatat tttaattttt gtatggaaca gtgcatctgc tttctcatag   4500
ccacataaaa tacataaact tcttagtgtt atgaaatggc ttactttttg gaagtgaaga   4560
agtcttcaat tcttattttc taatgttatt ttgaaatttg cctccatttg ctgtttgttc   4620
atttggtgat agcgcaacac ttaaaaaaat attttaagcc gcttctgaag taatcacttc   4680
```

-continued

```
agtgactttt aatggaggag tatttgttat gggaaattca cttcacaaag ttttaacatt   4740
aattcacttg aagtaaacgt gctattttta aattttcatc tcaatctttt aagtaagacg   4800
aaagcttagg aaatcacttt tattattgat attgtgtgtg acttcagagt ttgtaaagag   4860
aattgtagaa gtgttgcatg catatgacaa ttttctgctt aattgaaatg tgaggcctct   4920
gccatactac aaggatttag cttccagaaa atgtaatatt aacatagctt aagaaatgta   4980
ttttttttt tctgtagaaa ccgttgggtt aaacaaacag ttcagaagtt ttattacatg   5040
gaacccatta gttcttaatc ttgttacctt tttcttcatt ttttctgtta aacttgattt   5100
tcacagtcag cattgaagaa ttcatcttgt ggcctgaatt cattaagaaa agatgttagg   5160
atttgttctg aagatagtga cttaggaaat ttgtgagact ggggtcagtc agttctgttt   5220
tacaattgct ttctatttgg tagctttgaa attaatttag ttgcttatca gagagaataa   5280
tgttgaggtt agactaacct taaattggta aggctttgct gagcaaactg ataactgtaa   5340
gtcttttata gggtgcatta ctgccacata tacgttcttc cataggtggt taaaagtata   5400
ttggtctgtg tttggtgatt ctctttgtac atattgagta tatgcattca ctaatgtaaa   5460
ataatttgcc aagaaaggtg aaattagtat attgtacttg actattcacc tttcccttag   5520
tttttgaat tttttcatt ggttgcagag gaagtattag caatttaatt cttttaaaat   5580
aatttgcact ggaataaata agtatcggca aatataagaa gagtaacata atttaagggt   5640
gaattaattt tatttgggaa gttttagttc tgtatagtta aggcagattc ttcatttgca   5700
acagttgaca ttgggacatg tgtgaacatc ttcaaggtat taggacatct tcaaggcatt   5760
actttttggc agtgttgaga atttttttt tttttttt tttttgaga tggaatctcg   5820
ctctatcgcc cagtctgggg tgcagtggca ggatctcggc tcactggaac ctctgcctcc   5880
caggttcagg cgattctcct gcctgaacct cccaagcagc tgggattata ggtgcatgcc   5940
accacgccca gatagttttt gtacttttag tagagatggg gttttaccac cttggccagg   6000
ctggtctcaa actccagacc tcaagtgatc cgcctgcctc ggcctcccaa aatgctggga   6060
ttacaggcgt gagccactgc gcctggccag tgttgagaat attgagagat ggatattgta   6120
gctgtacctg ccatcaaaag aattttcttg acctccacat agtgtgaaaa agaagactgt   6180
ttacacatta tattttaagt aattatacac ataattatta tcagtactca ccacttcaaa   6240
tatgaacagt gaatctaacc agtgtttgat ttctctgtgt gtgtatgtgt atacaaagtt   6300
agcaaacctt ttatcttaat atttattaaa aaacgaattt ttgtttcttt aaagaaaaga   6360
ctaccttaga gaatattgtt ctatagtttt taaatatggt cagatctatt ttaaattatg   6420
ttaaaatttt gagtattacg tttatctata cttttaagca tatatacatt gtttcatttt   6480
agatttagg gaggcagtgt gggctctgga gccagactgc ttgttttgta atcctggatc   6540
ttccatttag tagctggatg actttgagta ggttatttag attttctcaa tctattttat   6600
ctgtaaaatg gggatgataa tggaacctac cgcatacgtt tatcttgaat agtaagtgag   6660
ataataataa gtaatttcat ttagcatagt acctgccaca ttgtaaatac ttaaatggta   6720
gctactgctc tgaaaaactg taatttcagg ttatgtatgt agggaaatta tttgtatttt   6780
catttatggt gtatgattgt aactgaattt cctcagtttg ggccatgtta ggattttgtt   6840
tcaagttata agtgttttta aaaataaggg tattccttta ggaagtctgg gtatgacatg   6900
tctgtgattt tgctggttca tcacaaatgg gaaataaatc tctgctaact caaactgttg   6960
accaaagtaa aattaattat gccaatcaaa aactatttgc tttaaaatat aaaaggcaaa   7020
aacttcctat tagcataatg aagtagaatt tttaaacttt gttataatct taaattttct   7080
```

ttagtgttga agataggtca acttaactat catacatttt tattcacata aagtaaactc 7140
tgcctcaaat gtaataaact taatatgagt tatgtaaact ttggtcaata gaggtatatt 7200
ttttagcatt tccttttgaa aatttcagcc ttttgaggga gtcttgcaac tgaatgtcaa 7260
gttacattta ttacaataaa atggacactt aatataatct gtaatgcatt aacataatat 7320
gggaactttt aaagtattca gtctctgtat tattgagtcc tatttccaca tttggccagg 7380
attctcaata tgatttaggc ccaagacgtg ggaagaaaga agtaaagaac taaaggattt 7440
ttttcttcat ttttttaatt gaatatgggg aaagatggaa taagcttatc tgtccagtaa 7500
aggccattat gtgtacatag ggattattat ttttcccccc cttgggctgt actgatttcc 7560
cagatgtacc acagcactct tagtagtgaa gcacttgact tctagtgagt ggattttttg 7620
tgtgtgtgtt ttatattgca gagtgaatac actctgtctg atactatgtg actttctgat 7680
tatgtgattt ttatgcattt tatgtgtttt gtaaactagc tgtatttttg gtccatgtct 7740
aggttgtaga attgaattgt gcattttggc atctgagcac agctgagttt tctaaatcaa 7800
tctctctcct tgcacctagt tttgctttta gatcactacc taagacttac tgttgattta 7860
atattagagc acttaagcat agctttgact tttatttcct ttgatttttg tagattttca 7920
ggctgaagta caataaggtt ctctgttctt tactagtaat tgcaaagatt gtattctgtg 7980
aattttattt gtttaatact tttgatcttt tgaagaggat gtaattattt aaggtattat 8040
gaaatgcatt gtgatttgaa ttagatactc tttggagatg gagttttgct gttgttgccc 8100
aggctggagt gcaatggtgt gatctcggct caccacagcc tccgcctcct gggttcaagc 8160
aattctcttg ccgcagcctc ccaagtagct ggaattacag gcatgcgcca ccacgcccgg 8220
ctaattttat attttttttt tcagtagaga tggggggttt ctccatgttg gtcaggctgg 8280
cctcgaactc ttgacctcag gtaatctgcc tgtctcagcc tgctaaagtg ctgagattac 8340
aggcatgagc cactgcgccc ggcctcagat actcttttaa ttagatgcgt ttaaaaattt 8400
aacccaccat tgctggcatg aatagatgta tttttagagt gattcataaa tatcgtatac 8460
atgtttaaag ttacaaactt tttgcttatt tcaaaatgca ggattctttt ccatttaaaa 8520
ttccctctct ttgtgagact tctttttgag tattctggtt actctaaact gattggagat 8580
gaaattagat agaattgaaa actgtacttt taaaatgaaa ttttggggat gtcattaagc 8640
ttgatttttt aggttttttt tttagtgtgt attataaatt attttacact gattgtcagc 8700
gataaaatgg aatgcctggg attttttaaa atttatttta ttcattttta taaggtaaaa 8760
acagtgtttt gctaggctta atttgaccat gttgtaaaat ttattgtata ccttgaaaga 8820
atcatttatg aaagatactg aattagctaa tatatactct gtcttatgta gtttttgatt 8880
aacaatacac tttttaaatc attagctcat ttgattttgc aaagaagaac aggtaaccta 8940
agaggcagac agaacaggca ttacttttat ttttctttct tttttatttt atttatttat 9000
ttatttattt attttttgca gcttaggaat tgtagctcca gtggaatcag tatcttgtta 9060
atggctagtg aaagactgag tctgaagaag gatgcaggac ttttttggca cttggtgcag 9120
tatttttccc attatgttac atgagtggtt cttaaacttc agtgtgttag aacaacctga 9180
agggcttatt aagctatgga ttgcttactc caccctcaga gtttctgatt cagtaggtct 9240
ggattgggac ctgagaattt ttatttctta gaagttttca agtgatgctg atgctggtgc 9300
tctggggatc acactttgag gaccaccaat gaacattatc tcccaccaag caaaccctta 9360
acatgttata ctcctttagg ttattagaat ttatacatgc attatttcat ttgacctgta 9420
aactctaagt aactttgcat ggaaaatgtt atcctgattt tatagacgag atagtgagtt 9480
tagaaaggca gtatggtgga atggagcata gatttggagt tggctagacc taaagtccag 9540
attaaatctc tgctcaaggc tgggcgtggt ggctcatgcc tgtaatccca gtgctttggg 9600
aggccagcgt tggcagattg cttgagtctg gaagttcgag accagtctgg gcaacatagg 9660
cagaccctgt ctctacaaaa aaaaatacaa aaattagtcg ggtgttatag tgcgcattgg 9720
tagtcccagc tactgaggag gctgaggtgg gatcacctga gactgggact ttgaggctgc 9780
attgagctgt gattgggaca ctgtactcct gcctgggtga cagagtgaga ccctctctca 9840
aaaataaata aataaataca tccccgctca gccacttatc agttacgtag atacactgcc 9900
taaccttagt gaaccctgtt tcgacaactc caaaatggga gtaaaaatcc taaacttgta 9960
cagtggtttt ttagttttgt taaaagtaca ggtgaggttt ttttcagagt attggttgcc 10020
atctgagagt gatccccttt cacctcctct aggactttta gcattttctg gagacatttt 10080
ggtggtcaca gctggggtgg tagagtgtgc tattggctag gggcttgaag ccagtgatgc 10140
tgcttaacat cctatatggc acaagacccc tccccatcaa caaagaatta tctagcccaa 10200
aatgctgtgt aaaatgtctg gtatataata agtataatat ttgatgaaaa tcagtacctt 10260
tgcccccagg tgtgatattt aagaaggtca acttactaaa tcagtgatgg agttagtcct 10320
aacatctggg tgttctgact gctgctaggc cagtattctt tatatgataa taagaacttt 10380
gtccacagaa gatatcccta ataacaaaaa aggtttattt gaagaggact catgtgttct 10440
ttggctgatt gtgaaagtgt tgctttgaac ttctgttaga aaaggttgaa gatgttttcc 10500
gtaagtgttt ttaatactgt acgtagtatt cagaaggatg tttaattttt tttttaattt 10560
tgctagtagt ttttaaagta atcctttttc ctttaattat gtagttgttg aactgttggg 10620
agttactttt ctcttactat tttgttattt aatgtattct ttgaccttat gctttttttat 10680
tctaaagctg cttttattat agtcagatat gatgaagtta aatgtacaat gtaaaattgc 10740
aaatttccaa cgagctatac aaacttaaat atttctaagt aaagaaaata gggctgactc 10800
taaggttctt tgatccatgt gttgcattct tttctaggcc ctaaatttgc tatgccagcc 10860
tgttgaatta aagtgcttta tttatctaaa ttagaaactt gtattaaagt gaagttttag 10920
aaaaaaagaa acaaaatcgg aatggagttt taggttagcc cagagatggg aagatgccaa 10980
gaaggtagct ttagtggatt ctgaattttt tggttttgtt ttgtttttag ggcaggcaaa 11040
tgtaattaca aaagggttct aggaatagat tgctgtgatt ttttttctgt ttgcatgatt 11100
ttacagtttg ctttgcctct cacttttgaa tgcagaataa aatgtcaagg ccttattttt 11160
ttttaaattc ttaagaaatt taagatttga ctgttaattc cttttgaaat atgggatatt 11220
ttgagatacc aattatttaa gacaaatagg actcattgtt acaattcagt tgaataaggc 11280
ttatgatgtt tatttcagta tatgaatgaa aactatgtgc ttattgtact taagaaaatt 11340
tcttttatta aaaacatgac taaagagaat tttaaaaatc acccactgtc ctacttctct 11400
aaaacttaat gttttcatat tagcttccag ttttgttcat atgcatatac tttaaaacct 11460
agttcatggt gaacttaaga gggtgttctt tttaaaaaac aatttccatt gcactttgtc 11520
gttgccttaa ttaaatggtg aaatcatcag aaatatttat tttcctatac ttatacattt 11580
attaagcttg tttccatttt tttattttgt gatttttttaa gtggatttaa gataacctaa 11640
acattagaga ggattttcat ggttttgatt catgaaatca taatgttata caaacctaac 11700
tgaagtgtta gagccttgaa gatttttccc ccgaattaca tatagtaact ctacttgtat 11760
ttaatactga aagcatattt tacttattta agtgagacaa agtaaaattt agctgaatac 11820

-continued

```
tttagatcta tcatttcctt ttcctgttgt aagaacatta cattgtgttg aaattaaagt  11880
ggatatagaa ggtaattaga ataaactgcc acatcatttt tatagtaaag tggtaataac  11940
actattgctt tctgtttttt taatcagaag gagtatgggc ttataatgat gttactgttc  12000
cctgaagcat attttgaatg atacggttta tatttgcaca gttgcccagg taatcattgt  12060
gatattaatt gatcaatttg ctatttattt gcgttttaaa tcagtactag tatttgtgct  12120
taaaaatttt gcatatgttt tatcagattt aatttttaag tgtcagatac taaaacaaat  12180
aaccttaact ttattaaatt ataatttttt atcatgaggt ggtattcatt tattcatata  12240
gttagaacaa aaaatattta aaatattgag gtagaaacaa attagtctct ttttaattaa  12300
aagccagatt acttgttaga gtaacatttt cccaaatgag gtaaaattgt tgcgactgtt  12360
aaacttaagg aaattttgat ctaggtgtgg tatatacctt cttgtggggt gctaatgaaa  12420
acagggatgg caaaaatatt ttgtttgtga gtgtatgcat ttatgctttt tgacaaccta  12480
agaaacactc ttacatctga gtatctttca tggactagct gtaggaaatc tatataaaat  12540
agcttagtat actgaaagta tgacatagtt ttacatatct agattgtggt tgtgattata  12600
tataatacta taaaatatgc taacgtgctg cttaataata ctatttggat ttttttaat  12660
actgaaaagg tcacacagat tgtgattatt gtgtagtgtc caagaactaa ggcctaccat  12720
ctgttactca aatgtatgaa aaagttaaga taatttagtg atataagtgg ttttgacacc  12780
actgtttttg gaataatcta attatgattt ttataaagac taatatcaaa ttttaaacgt  12840
ttgcaaaaat gaaacctaat agttatactg ttatttatat ttttctatta caatacagat  12900
actggctgag aactaaagat tgtgtaataa acgcctggcc ttcagtcatt tggttttttt  12960
tttccctcga ttgtttggat agttaactgg acatcatgtt ttaacttgag aaattaagtt  13020
atacaagatt ttgatatttt aaactagttt tcctaactgg ttgagatata taagaattta  13080
gtattacagg actcaatcag ggaactgatt taataagaat ttcttaaaaa tttgtttaaa  13140
tatttttcaa gttcttttct tcatcttcta caacttaatt cttgtctgta tgcaaatgag  13200
cttccccatt taaaatttg ctgttgcatt ttaggccact atagaagttg tttctttaat  13260
tttcactcac aagaatttgg tcttaccaaa ttgtgtaaat ctttaaaatt gtgtatttgg  13320
cttaatatta tagaatctga ttgatttaat ctaccttgtt tcatttagta tgttgacatt  13380
ttcttgagaa atttgttatg ccaaatgatt aacataataa tattttaagt ttagatatga  13440
ttttgaattt acattttcaa atgcaacttt gtgtctgtgg cctttttttt tttttttttt  13500
ttacgagaaa catcttgcca attttcagat taatctgtga ggaaagtaga ttggtttact  13560
agactcagtt tgtagacttt ggtgagaact gaattggagg ctatgaaaaa aataccttttt  13620
gggcctttct gaatagacat atatacataa attatatctc ttacattaag tgaggcacat  13680
atgtaggtga gatttttacc tgaatattaa aagtttaaaa gtcgttacct attctgttta  13740
cttaatagta tttaaagggt gtgagaggtg ttatgtgttt ctgtcccttg ttttattcc  13800
tatccctccc atctaactgt tggtactctt atcttcccag gtattaaact tgtatgtttt  13860
aaaagcttat ttacttgttg aaatggttaa cttaattagt tttttctttg aagtttcagc  13920
ctaaatattt tctgtttttt tatatgtcct ttaaatatga aaattctaca gctaatcata  13980
attagtaatt gtactttttc ccctattaca ataactggtt tcataataaa atggtatccc  14040
ttcaataaca agcatttata gtagtttatt aaaactaagg gtgttatcta ttcaaaccaa  14100
gcaatgcaga cttactgttg actctgttaa tatattttaa aattgcatat tactaaaatt  14160
```

-continued

```
taaaatatga ttttgactag tattttggtg tatgttattt tagatatttt gattatgcac  14220
tacttaagaa tgaattgtca agtatgatta taaagttgat ataatagtta accttcagtg  14280
ggaataggaa tcatttaata ttgttagata tttgtattat tagaacaatc tcctatgatt  14340
cttactaata tagtaatgaa tgacagacaa tatgttggct ttcatattta aaaattcaca  14400
tgcatttcta gtttatgttt ttcttcgact aaaattctgc agcacttagg caaagctatt  14460
tttaccagtt ggaaaaaaag taagtcattt ccaaccaatt ttcctggctt gtagtataga  14520
ataaagagac ttgattttat tacattaaag ccaaatataa aatgatgcaa tctagcacac  14580
acttgtttgg aacttttctc ttttaaatat tcagattaag aggacgttga aaggtaaatt  14640
ttttttttt tttgagacgg agtctagctc tgtcacccag gctggagtgc actggcacga  14700
tttcggctta ctgcaagctc tgcctcccag gttcatgcca ttctcctgcc tcagcctccc  14760
gagtagctgg gactacaggc gcctaccacg gtggcgcccg gctaattttt tgtattttta  14820
gtagagacgg ggtttcaccg tgttagccag gatggtctcg atctcctgac ctcgtgatct  14880
gcctgcctcg gcctcccaaa gtgctgggat tacaggtaaa ttttgattgt tattagcaac  14940
tataaaagtt ttgcagttgg cttattggaa aaagaaaacc tccttgccgg agacggagac  15000
gcatttgtat tagaactttg ttttctgagt accttaccta tagtaggttt caaatattgg  15060
tgaattagtt gatggttagg tctgcataat tactgcgtat ggaaattctg gaaccctatt  15120
ttttcaaaat gcagctaatg ttgagagaat atgcactaaa tattactaga tctttgtttt  15180
tcaagatgct gatatccctt aacatcttct gcactttacc tgtttgaata tctttttttgc  15240
tgtaaaaatt agtggcctta tgtctttctg cataattata gagtagccaa aacctgtttt  15300
aggttaatca cctctggcaa aataaatgat aaaagcatag cttttgtaag cagaatgata  15360
ttacagaagt taacttataa atctaagtgt attaaagaca cttaggaaat ttatgataat  15420
gctgggtcag cattacagtt ttaacttttt acagtttttc atatgctttt tttgtgattt  15480
tgctgtagaa aattaacagt tggcatttgg cttagttcaa gtataatgct gttgacaagt  15540
atatctgaca cgtcattgaa ctaataatat ttttgaaagc tgataggtaa gttatatcta  15600
ttttgtttca ttcgtcatta gtgatcggtc ttagatgttt ttagcgagag caaaactgta  15660
gaggaatgtg tgtctgtgtg tgtatatgtg tgtgtgtgtg tgtgtatttt aacagcagga  15720
gagttctgaa acaggaaacc agtcttatca tattcatcca gagacctagg aagaaggtaa  15780
ttgtttggta tactcgttaa aaccagttgg ttgggcaact taaattttta gaggatcaca  15840
gatgtaggct tgagcagttg tagatagatg atttcttttt ttttctttct tttttctttt  15900
ttttttgaga tagagtctct ctctgtcatc caggctggag tgcggtggcg cgatcttggc  15960
ttactgcaac ctctgcctcc caggttcagg cgtttctcct gtctcagcct cctgagtagc  16020
tgggattaca ggcgcatgct gccatgcccg gctaattttt tgtattttag tagagacggg  16080
gtttcaccgt gttccccagg ctggtctcga actcctgagc tcaggcaatc tacccacctc  16140
ggcctcccaa agtgctggga ttacaggcgt gagccaccgt gtctggcgat agattatttc  16200
ataattaaca cctgctatga agaaaaattg attaaaatag ttgagaagtc tagtacactc  16260
tcagctaata tactaaatta tactatggat tttagagtat tgttaacatt atcagtgact  16320
tgatatcttc ctgaggttct aatttgctta actttaaata attggggttc agatcacctt  16380
gattgttccc ttaaagatta aattttgtaa aactgtgtgt aattttcctg tatctggttt  16440
ggatagcttt aaaaatggtt cttaagttta atgagttcaa ctgggaaaaa agttagttct  16500
attttagatg ttgtgtcact ggaaattatg tttccctgtt tgttatatgc acattattac  16560
```

-continued

```
aaagttgtaa tcaatgtttt catactgttc tctggtctgt ttttttcaca aatacacttt  16620
ttatttgtcg ccaggtactt atttttaaag ctatagaggt aatatttcat caggtgaggg  16680
taactaccat ggtttgtttg ctatactgtg ttagggttat tttcgttttt tttttctttt  16740
ataaactata gttgtgaata tgtttatgta gtttactttt ggtttattag aatatattgc  16800
tagagtggga ttacaggatt aaagagtgta cagtatttta gttttttttt tttttttaca  16860
agttgcagat ttgttgccaa atgaacgagt ttgtagtatt gctaacaagg agaagaatta  16920
ctagcaagtc ttgatgttac ttttgaagag tgtgatgatt gcatttagga agatatctaa  16980
acttctgttt caaagcaaaa agtatgtgca aatttcttac tcatgacaaa ttcatataat  17040
ataaaaacat gaaagttgtg aggtcaggtt gtttggagaa gtagaaaact tcagtagagt  17100
ttatagatag gcagtcttcc tttctggttt ggcactgaca gcagattaac tagaaagtgt  17160
tagaaggaac ctaaaattta tactaaagtc aatttaagtt aattaatata ccagaattcc  17220
ttcttttaca atttatttat aaaaacacca tattgagttg ccttgtaatg agacatttaa  17280
actaaattta aataacagaa ttcatgcacc atctaataac aaccccttat ttacaattat  17340
agagtccttt gcaattttat agatattttc atgtatccca tttggtcctt gaaacaatta  17400
atgaagaagt tacagcaagt ggtattatca ttattttaca gaagaacaaa acaaaaatat  17460
atgtggccca gagattgagt gatttacctg aggttatagg ctttagattg catagctgga  17520
agtagaacct tgttcttcta tattaaatga caatattcat taagtactta gcacaggatt  17580
tggtacctag taaatattta aatgttcctg tgttattcct gactattcct tctttattct  17640
taaaacgcca tttttgagc  actcttaata tttatagttc aaactttgta cctatgtacc  17700
tttttctctt tagaaaataa gatttcaggc tgcattaatt tgatctgtac aggaatgatt  17760
atatgtttta catattggga caaattgctc ttttttttata taccttaagc tctagggtac  17820
atgtgcacaa catacagatt tgttacatat gtatacatgt gccatgttag tgtgctgcac  17880
ccattaactc atcacttaca ttaggtatat ctcctaatgc tatccctccc ccctccccat  17940
accccatgac aggccctggt gtgtgatgtt ccccaccctg tgtccaagtg ttctcattgt  18000
tcagttccca cctatgagtg agaacacgcg gtgtttggtt ttctgtcctt gcgatagttt  18060
gctcagaatg atggtttcta gcttcatcca tgtccctacc aaggacatga agctcatcct  18120
tttttatggc tgcatagtat tccatggtgt ctatgtgtca cattttctta atccagtcta  18180
tcattgatgg acatttgggt tggttccaag tctttgctat tgtgaatagt gctgcagtaa  18240
acatacatgt gcatgtgtct ttatagcagc atgatttata ctcctttggg tatataccca  18300
gtaatgggat tgctgggtca aatggtattt ctagttctag atcactgagg aattgccaca  18360
ctgacttgaa ctagtttaca gtcccaccaa cagtgtaaaa gtgttcctgt ttctccacat  18420
cctctccagc acctgttgtt tcctgacttt ttaatgatca ctattctaac tggtgtgaga  18480
tggtatctca ttgtggtttt gatttgcatt tctctgatgg ccagtgatga tgagcatttt  18540
ttcatgtgtc tgttcgctgc ataaatgtat tcttttgagt agtgtctgtt catatccttc  18600
gcccactttt tgatggggtt gtttgatttt ttcttggaag tttgtttaag ttctttgtag  18660
attctggata ttagcccttt gtcagatggg tagattgtaa aagttttctc ccattctcta  18720
ggttgcctgt tcactctcat ggtagtttct tttgctgtgc agaagctctt taggacaaat  18780
tgttcttaaa taatgaacag ttggcacttt ttcaactgga aaattcaagg aactgctctt  18840
tctgctttct gctcaatatg aatcttcaat ttagaaatga gagtccatca ttaacaattc  18900
```

```
aacatagctt attaatagga aaaaaaaacc tagtaacaaa tgtaaaatct ttgattaaat  18960
gagaaagtca tagaagttca tcagatttgt atttaaagca tgatttcatt agaaaagttg  19020
ataataagga tttaactgtg acataattgg aaaatacttg tttaaactta aaattttgaa  19080
aagaaatgta aatgtgatgt aacttatgaa tcagtggttg agtttctttt ttgctcacaa  19140
gaaccctaac tgtgtgttac ttgaaagcac tgatggaaat cagggaaaaa gctccagaag  19200
ttcctacgaa ataaaattaa atgataaagt cctggtatct gctaacttgc cttccattcc  19260
tgttatcttt tcttcttagt ctgacttcat taattctttc accctggcta ctggtttagc  19320
tcagtgtttt atgagccagg cagcttcaga ctttgctttt gatgctcttt gttcattacc  19380
tctaaagctg tattatcact ttcattttat cattaatgtt tcatgtatat gttatagttt  19440
catattgtta ctgcaacttt tacttagcta taatttaaaa aatatctgtg atctgtggaa  19500
ataattattc tatggcagaa aagtagttat tgcattttac tttataagtt gtttaaggat  19560
aagcatacct atatattaag cactacaaag aaacttttac aatggcttta tttttagcaa  19620
accatcatag ttaaaataag atttagtgta catgtcagga acacagtctt atgaaataag  19680
gtttagggag ctatttttag ttactatatc ctacttgaaa attgtagtta aatttctagc  19740
atatacccta ttaatttaga tgcaagtaca gatttgagat aaggtagata cattatttgg  19800
atgtcaactc ggaagttgtt caagaaaaga tattttgtta tttagatgta acttggaaca  19860
tatttctagt gtttcaagtc atgattgtat gcctagaaca ggcaataaaa atttacttag  19920
ctggtaaaac agccacatta tttcaaatat agtttagtta tattatggat taaattgatt  19980
tttgtggaca gactttagaa cttaattgct attaattaca ttttttcttt gggacggtat  20040
ttgttctttg gtgagaaagg attcttgtaa cacctaaatc aagactgtcc aaacatggca  20100
tatgcagttt accagtcaaa acaaactaat cacttaagat ctgtgtattt tgttttattt  20160
gaattatacc tcaattaaaa caaatttagc atgtttacac aaaggtgggg ggaaactgtc  20220
taatatatct gagatctgtt ggagctgggg tgaccatcca acttaggcaa gatagctagt  20280
accatgtatg catttctttt acctttctta ttgtatatac agtaatcact gatattatga  20340
gaaaaagaac tttttaataa ttcaggagat attttatcgc tagtatatat tgagtgctta  20400
ttatgtgcct tatatacttt ggactcattt aatcctcaac acaacaaccc tatgtagttc  20460
atactagaat tattcccatt taaagatggg gaaagtgatg tttagagagg ctaagtgact  20520
tgcccatggc caaagtatta gaactgggat ttgaacacag gtagcctgat tcctaaataa  20580
atgaccacta acattaaaaa gacataaaca tagaggtgtt tgttgcaatg ttagtcataa  20640
tacctaaaaa ttgtgaacta gttaaatgtc caatagtagt aaaatggttc attaaccatg  20700
gtacacccat caatataatg ttatattgtc atttaaaatt gtattcccaa gtttcgtatc  20760
aggaaaatat aataaatttt tgaaaaatgt aatgggatat attgtattta taatacagta  20820
atcactatgt aaccaacatt tttatttcca tcaaaaatta gttataaaga aatagaaatc  20880
taagaagttt aatagatatt accattgaac actagatttg tattagtatc ttttatattt  20940
atctctctca tttcctatat tggccatgtt tacttttaaa atagtaaaag tcataagctc  21000
tattttaaaa ataaatgtta gtttattaac ccaagaataa tagctaacta taaattcata  21060
tttgataaaa taaaaagatg acattcatca taagggatac atacctgtgc tagcatatgg  21120
catttttaaa atcacatgag taatttgtaa tcatcataga aatattagaa aatacaaata  21180
agcaaacaca tactgaaaat ttagtgttcc caaatctaaa acagagacac tgtttttttc  21240
ttttgggatt gtattttaga tatgttctta agttataata aagtaaatac ttaaaaggca  21300
```

-continued

```
aattgataca ttaaggattt caaagagtaa aactttttgt taagctttga tgttctttag  21360
aaagtttaga ttattccaca agtcactgtc gttgaaagaa aagtagttac agtggggtct  21420
tatgggataa ggcattacca tttgttcagt tgagagacag ctatcactat gttttaagca  21480
ttgttcatat attagctcat ttaatcctca tagcaacctt atatgatagg tacctttatt  21540
agccccattc tgcttaggaa gcaacagaaa gagtatgtat tttgcctaag gttgcacaat  21600
aagttaagct ggggttccaa ttctagcaag ttggttctag agtgtatgtt attaaccatt  21660
atgccgtagt gcctgcaagt agatctctag atgtcagaaa tactcatctt cctctggtta  21720
cctggttgtt ataaatcttt atgcttaata cttatgtcat tatatgtaaa tttcgtatta  21780
aacactcaac ttattcagaa gaatatcagg taagtgtagg ttaaggctgt tttctatcag  21840
aaatcattat atgtatatat attcctcagt tcttatgttg tttagttttt ctaaaatgtc  21900
aaattttata atatatggag aagtataaat gtatattaga aagattttgt ttatttgtgt  21960
aatttgtggc ataagaaata tttgcctcaa gatttggtgc ttgtttaggt agttgctggc  22020
attacttttg gaaatgtcag taaattttca tactgtcttg gaatttttttc aatttttaca  22080
ttttattagt aaatgtaatt acaggttagt aaatcactta tttgaacctg tttcctttga  22140
aagttttata tttttatttg gaaatagaaa aaccttaatt tcctctcgtt gggcagtatg  22200
gtgtcaaaag cttgggcttt ggagcttcgt atataatctg ggttcaaatt ataacttact  22260
agttactaac ttgggcaaat tacccagtct ttttgactct caatttcttt gtctatgaaa  22320
tgtaatacta tttaggattg ttaggattaa atgagaatat atttggcata ctgtctggta  22380
catgatactt aacaggtact agttgtctac atctttctaa cttaggatgg atgccgatgt  22440
cttgggtaac atctcaaact ttatcagtaa ggaaggtgag aatctgaaga aaatgaaacc  22500
ttaaaaagat tgaattcctg gactccattt aaaggagtaa atagctcacg aacaagactt  22560
gctgctctgc aaagtcttcc atgttgatcc tggtctttga ctccttatct gtctgattaa  22620
attgaattcg ctgccgtggc atccttaaag ctggacctta ctttgtcagt cctgccttct  22680
ccatgttgct ttgtgtgtaa gcttcactgg actgtttgct ttttgctgat tattttatgt  22740
atttccatat gtctacttta gcctttgctt ggaatgttct aactgctctt gtttcttcct  22800
ctgtttactg gtttctgact taactcttaa ggattatcta atatattacc tacttggtga  22860
aggtttatct gtgtccccac agaattaatc cttccctctt taactcttaa gctatcttat  22920
tttttatcta atcgggtctt tggcacaatt ataggtctgt gtgtctgtct tccctaatag  22980
aataggaaag ccttgaggac agtagtcttt gcttacttag ccttatattc tcagtgcccc  23040
ttgtgcaaaa cgttcaatat atgtttgaat gattatgtga atgaaggagg gggccagctg  23100
aatttacttt aatgattatg taacacccat ttatgtatag ttatagactt gtctgaaatg  23160
agttaaatcc tttgcaacgt ttgctgctat gctttgaatg tctcttacaa aactcatgtt  23220
gaaatttaat tgccattgta atggtattaa gagatggaac ctttaagagg tgattagata  23280
atggtatctc tatccttatg aatggattaa tgctgtttga atggtagtgg atgagttatc  23340
ttgggagttt ggcctcctcc gtctcacatg cttccttacc ttctgccatg tggtaactca  23400
acacaaagat ccttgccaga tgctgatgcc atgctcttgg acttcccagt ctccagaacc  23460
gtgagccaaa tacatttctg ttcattctaa actacctgtt ttgtggtatt ctagtaaagc  23520
aacataaaat ttactaagaa aactggtacc aagagtgtga ttgttgccat aacaaatacc  23580
tgaaaatgtt caaatggctt gggttctggc tagagaagga tggaagagtt tggatgaaca  23640
```

ggctagaaaa agcctgtatt gctgagaata gagcattaag gacaattctg atgaggattc 23700
agaagaagag agctgtaggg aaaatctgga acttcttaga gagttgtcat cagttggtag 23760
aactataagt ggtaaaggtc tttctgatga tatctcagaa atgaagaaca agatactgga 23820
cactggagta aaggccatcc ttgttaaata gttgcaaaga acttggcgaa attatgttca 23880
tatcctaaga ctttatggaa tgcagaattt aagagtgatg aactaggata tgctgcagaa 23940
gaaataactc agcagcagag catttaggtt actggatggc tacttttaac cacttaaact 24000
aagctggggg aagggaatga cttgaagaca gaatttataa ttaaaagaga ggcagaatgg 24060
aaatacttgg aaaatttgca gcctggccat agtaaagaat gcaaaaggta tgtttaggag 24120
agcaaaccaa gggtgtggtc caggaaccat ttgctgaaga gattaatatt cctagaggag 24180
acccaagggc tatttatcaa gacagtggaa aaagacccca gaggcatttt ggagatcttt 24240
gaggctgcct gccccatcac aggcccagag ctctaggagg gcagaatggt ttgtggctca 24300
ggtggtcctt cacaagcttg ctgcccaggg ctacctcagc tccccatatt tcaacccagt 24360
gggccttggc tgtcctaggt ctggttcaga ggggcccagg tgtggcttag gctactgctg 24420
agtactcaaa tggtaaacct tggcagcgtc tatatggtgc taattctgca ggctcacagg 24480
atgaaagagc tgtgggagac atggctacca ccaccaggat ttcaaaggat gatgggggata 24540 gtctgggaga gacttgccac aggcttggag cctctgaagg gtggaaatgt gggttggagt 24600
cactacagag agtccctact agggcattgc ataatggagc catggcagca ggcccaccac 24660
caaagcttca gaactgtaga gctacaagta tacagtgcca gcctgggaga acttcaggct 24720
tgagacccta acctgtgaaa gctgcatggg ctaagtacag caaagccatg gaggtggggc 24780
ttcccagggt ctattgggat gaaacgaatg tattttgtag gtgagaagga catgagtttt 24840
gaggcccagg ggcagaatgc tatggtttgg ttgtttcctt caaaactcat gttgaaactt 24900
cattgccatg tggcattatt atgaggtgga acctttcaga agtggttaca ttataagggc 24960
tttgccttca ttaatggatt aatgccatta ttgcaggtgt gggttagtta tctctggagt 25020
ttggccccct ttttctctat catgtgctca tgccctcttt tgccatgtga tgccttctac 25080
catgttatga tgcatccaga agactctcac cacatgcagc cccttgatct tagacttctc 25140
agcttctaga actgtgagtg aaataaactt cttttcttta taaattaccc cgtctgtggt 25200
attgtatagc agcagaaaat agacatcagc ctgaagttcc cccaggctgg cattaaatac 25260
taattattaa ttagtattta tagtgcaagg ataaattcaa gtttagccct ggttagaatg 25320
accacatttc aagggagggg ctttgtactt ctgtgcatat ctgtaaggat aaaaatctta 25380
atactattct cactgaaatt aatggtttag gttaggtaag gttgttagtg ctaataatta 25440
tttcttttaa taaaatattc ttagttgcgt tgttcaaaaa acatagatga tttgaattta 25500
tattttttgg ccaaaatata tttataattt tgagtaggaa ttccagagta ttggtagcta 25560
taaccacttt gggttccctg ccattgcttc tggtgcctca ttttttctga cgtcttccat 25620
tttcttacat ttgtcttcta aggtggagtt aagattactc agttaagatt atttcacttt 25680
aggcctctgc tgtcttctgc tttttttttt aaaatgaatg gatataatat cccaatacat 25740
tttgataatt gaacaacagc tacattttta agtgaggcta ctttcttcta attttttaaa 25800
tttatttttc tcagttttta aaaaaaatgt cagattggct aagagttggg gcagctttct 25860
tatgtgagag tagtagatga cagcaaatat ttgtgatgtt aaaatgataa tcctaatagt 25920
tttcttttag aatctttata ataaaaaccc tttgaggctg agggtgaatt tgtatgttcc 25980
taaagtgaca aaaaatgttc ttggggcata gtaatttaaa tcttagatgc ttttattagt 26040

-continued

```
ataatttttt ggtagaaatt tggcattaaa aaatgcatac agagcttttt ctacatacag  26100
ggcaagacag cattttgtca tggcaattag taaatagata attataaaac atctaatttt  26160
aagcaatttg ttacagaaac gatacaggta cattgtggca aaaatagaag atacaaaaca  26220
agcaaatatg agaaaaaata tacatgccac cacctatata tgacttttag tactttataa  26280
tcttttgtct atatatgtct atatggatat atacgtattc tttttatcca aatggtatta  26340
cattgtacat tctgttttga aacctgcctt ttttagtcat ttacatctac ttttccatct  26400
cagtaacttt tcatcttgtg taatgcccgg atcacattaa aatgtttcca attagctcaa  26460
aaatgtcctt tatggctggt ttggctaaaa cagtatccag gccagcattg cacctatgaa  26520
attggctgtt aggaatcttg tatctttaaa aatcaagggc agcaacccat cctcccgctt  26580
cccccacctc ccaccacccc cccacctttt ttttttctta aagatactgg cttgttgaag  26640
agagaatggg tcatgtccta caaactgtct gaatttgtcc agtttgctgt ctcatagtgt  26700
catttagctt gttttatcct atgtatttcc tgcaaattaa aatttgtatc tgaatccttg  26760
gtggatttga gttgaagatc cttaaccatc atagatgatg ctgtgtcctt tatattgcat  26820
gtcagaagtt acatgatctt tacttgattc atgatgagga gatggccact gaaattggac  26880
agtgacagtc ttttctgccc attgttcaat tatattcgtc tctttacatt agaaagtatt  26940
ttgggtagta gtattttggt gctgtaagaa agttcatttt ctcatcaacc actcacctat  27000
tggtttaaca ccatttgttg atctttgagt atatcagtaa tttcatcagg gtttgcaaaa  27060
taagacttta aattctattg ttttacatta ttaattgatg ttttttgata aggtagaact  27120
tgtgaaatgg gactatttgt ttgtctttaa atacagtctc tataggaaag acaaaataaa  27180
tacttaaatc tcactcttta ccatttttca aagtgaagaa ctattccgtt aaccacctca  27240
aaagatgata aataaaaagg gtatttttag ttgtttcaac tttttttttt tttttgagat  27300
ggggtcttac tctgttgccc aggctggtgt gctgtggtgc aatcatggta caccgaagcc  27360
tcagtctccc tgggctcaga tgattctccc acctcagcct gggactaaag gtgtacacca  27420
ccatggccag ccaatttttt tgtatttttt gtagagatgg ggttttgcca tattgcccag  27480
cctagcctca aactcctggg ctgaaggaat ccacccatct cagcctccca aagtgctagg  27540
attacagacg tgaccaacaa tatccggcct taactttttt cttttgagtg tctttataga  27600
ctcaaggact tttatttaat tcagggtgtt agtaccattt aaatgttttc tttgatgctc  27660
agattatcac agctagtcat ttggaccttt ataccacctc ctatgtccat ttgatatagg  27720
ccattaatct ctataagcct tcctccttct cttggaatga aaaggtatcc taggctcacc  27780
tgtaccttcc ctactccaga cctggcatta agtctttttc caaggagttt ggtacctttt  27840
agtttattat gatattagag atgaaaatct gtgttctagg aatgtttatt actgctagag  27900
tgatgttgct tttaggccat ttcagagaaa agacctagaa aacagatttt tacaaacatg  27960
aattcatact gatattttta gtttttttaca tgatttcttg attttacaat attatctgct  28020
ttcttaactt aaaattatga accttaaagt cattagcata acttctttgc ttatttctac  28080
aacataaaga aaatagtcct ggtgcggtgg ctcacactgt aatcccagca ctttgggaga  28140
ttgaggcagg tggattgctt gagctcagga gttcaagacc aacctgggca acatgatgaa  28200
accttgtctt tacaaaaaat tagctgggca tggtggcatg tgcttgtatt cccagctact  28260
caggaggctg aggtgggagg atcacctgag cccaggaggt caaggctcta gtgagccatg  28320
atcatgccac cacactccag cctgggtgac aaagtgagac cctgtttcag gggaaaaaaa  28380
```

-continued aagataaaat agtttgagga ggctggatgt agtggctcat gcatgtcatc ctggcacttt 28440
gggaggtcaa ggtgggagga tggcttgagc ccaggagttt gagaccagcc tgtgccacat 28500
catgagacct ggtctctatt taaaaaaaaa aaaaaaagaa aatagtttga ggatatcaat 28560
aatgatatta ctagaatcag taaaactacc aaaagaagtt taaagtttct tcctagtgtt 28620
tttttgttct tagaatactt cctaccaaga agtgcagtaa aagtgcagtg tccaaatagc 28680
ccttgtaaca aaacctttct ctttctcctg ggtgccaatt tgacatttaa tcagttttgt 28740
ttctagcagt gttcaattta ttagattata agtctttttt ttctttatat tattctaaga 28800
tcaaaaatat ataaagatat acacaggagt cctgctgcta cctgttcttg ctatgctttt 28860
ccccttttct tccctttctc tgtgaagcag ccatttttat tagtttcttg tttatcactc 28920
atgcatgcat atgtttattg aggatgttga cattcaagca aatatatggg ttaacattct 28980
ttttgtcatc cctatacgaa agatataccc agtatactct attgggtggg ttttttttcct 29040 taaaatattc agtagatctc tccagttagc acatagttat cttatagata gaacatatac 29100
atataacctt ttcttaaact atgctattaa aataatagct ttcagtaact tgataattat 29160
ttttggattg aaaatactac tgaaatcaac tcaatcatgt gaaagctgca gaaagaaaaa 29220
gacctagaaa aagggcattg gattaggtca actttgaatt ttatttggaa gataaatgag 29280
tccagaagtg agtgggcaga gattattgga gttggtcttg aaatgaggcg ttaggcagat 29340
tgactgggct ggtgtgaaag gtctgtcaga aaatcatgag attagattga ggtacctcaa 29400
aaaatgagag ctggtatgat gagtgggtaa gaatcataaa agcgtagagt gttgatgatt 29460
tttatagttt ataaatggtt cttgtgtgta gagttttgtt tttatgctag ctatagtctg 29520
taacataatt cactataatg ggcatgctaa atatccatga cagttgaccc ttgaacaaca 29580
cagagggtag gggcgcctac ccctgtgcag ttgaaaattc acatgtaact tttgactccc 29640
caaaacttaa tatttagcct atacttgact agaagtctta ctgatgacat aatgttcgtt 29700
aatacatatt ttatatatgt gtcagatagc atatttgtat aataaagtaa gctgcaggaa 29760
aaatattaaa atcataaaga agagaaaata tacttactat tcattaagtg gaagtggatc 29820
ctcataaagg tcttcatcct cactgccttc actttgagta ggccgaggag taggagagag 29880
aggaaaggtc agacttgctg tctcatgggt ggcagaggta gaagaaggtc cacatacaag 29940
tggtccgaca cagctcaaac cggttttgtt cattggccaa ctgtagtttg attgaaagta 30000
ataataaatg aagtttctgc ctcagttcag tattatcaag tcatagatag caagggctgg 30060
aagaaacctt agtagtaatc tctttgagtc taattatcat gtagaatagg aaattgcggt 30120
ctagaaaggt taagtgactt gtccaaatta cacaactagt tagagacata gccagctctt 30180
aaatctgact tccagatttt cactgtgtct tcttttttct gtaacgtgtt gccttttttta 30240 gccatgaaaa attagaagtt gaactcttgt cttttcaggc aggtgtcaat tttggggttt 30300
tgttttgatt tttggttttt gacataaagt actttagttc tgtgatgtat aaaccgtgag 30360
tttctgtttt tctcatatac ctgaatactg tccatgtgga agttaccttt tatctttacc 30420
agtattaaca cataaatggt tatacataaa tacattgacc acctttttatt actccagcta 30480 tagtggggaa aactttcttt tcataactag ctaatgtttt aaaaagtatt cttttagttt 30540
gattgctgca tatttcagat atttctttcc ttaactaaag tactcagata tttatccaaa 30600
cattattgct atgggatttc ctgcagaaag acttgaaggc gtatacagga acaatattga 30660
tgatgtagta aggtaagaat gctttgattt tctatttcaa atattgatgt ttatattcat 30720
gttgtgtttt catttagaaa agatttctaa gccacagaaa aagatacttt gtgatgtaaa 30780
ctattattgt agtgctctat aatcattttt tggcttaccg tacctaatgg acttcagggg 30840
gatacagttc atttgataag aactgacctt atacattaca taatcaggta cttatgtgat 30900
atcatttcct ggactccata aaatgctggt caccaggttt aatacctgga ttccattaca 30960
gtgtgatttt tgtcttattt catagttggg gattaggctt aaaatcctag agtggattta 31020
ttcagttaaa tttattcaca ctaagatgta gatgactaat actgtatatt tttatgtaga 31080
ccaaatttta aggtaccact gtgcatatgt ataccaacta cctgaagaag tatttggttg 31140
gtacaagaga tatagaaagg aatcgctggg tgtaccaagg ctaatcagtt ttataatttt 31200
gcataatttt ctaactgcga ttatcattta gtttagaaca atttatttct caaggcccat 31260
gtaaatatta tttttaaaat atacagtctt aagaattcat ggcatatttt atgaaaggag 31320
gaattcatgt ctgatgtgca aatagtctta acatattttc taatttcaga gcaaaaatat 31380
atatgtatga ataaattaac tgtaaattgt cagtaggaac cttaagaatt cgtggcgtat 31440
tttatgaaag gaattcatgt ctgatgtgca aatagtctta acatatttgc taatttcaga 31500
gcaaaaatat atgtgtatta ataaatcaac tgtaaattgt cagtaagaac cttaatggct 31560
ttaaaagtta aaatttcagg tcaagcattg tggtgtgctc ctgtagtccc agctacttgg 31620
gaggctgagg tgggaggatc acttggcttg aacccccagg tagagggtag aggccagtct 31680
gggtaacaca gcgagaaccc atctcttaaa aaaaaagttt aagttgtgga ttatttcctt 31740
tacactcttt cattagtatc tttcctggag actttcaatt taaatacttg gtgcttatga 31800
caattagatg ttaaaatgga tgggaaagta ctttgtaact tataaagcat tatgcagatg 31860
tagactcctt ttataatagt tgtgtaagta tataagacaa cctacattct tcatgagcta 31920
gccataagtt ttagcaactt gctttgaacc acggtagatt tacaattttc tgtagtattg 31980
agttgtgttc atttagaatt ttgtaatatt tatattgaaa atcaaatttt tgtacctaca 32040
aaaactacaa aaaatccccc tagtttttat agtttctatt aaaattatag ctggtacata 32100
gggatgccag aaggactgtt taagaagctg aaaatagaga aatgaattta tcttctcata 32160
gttaggcagg gcacagtaga aggatgctta acattgcaag ctgatgggaa cagcaggttg 32220
atatagcttg tgataacact tctaaagaaa aagcaatgag ccatagaaaa aagaaaaaga 32280
tacattttga attaaggaag atggtgaatc tgggaagtga gcagtacagt caccagacgt 32340
gtatcctctc ctatggtaca gaagtgttta ttgggtctct ttatggcctg catgatatat 32400
cccacaagat gacctacttc acattatttt aattctgtat tcaactaagc actaattcaa 32460
cccagccaga ttagtactca taccaaaaaa gagtgaatac tctgaataga gggcaggttt 32520
tctgattatg gtgagaatat ctttgtggta aattaatctg gtgtgctagt ttttacgttg 32580
gtctcttctc agtgtcgtta gtcactgagg ctgattgatc atcttttagg ttactgataa 32640
agttcctgta cagctgattt tcagacctta gattgcaata acttcaccaa gaaaatactt 32700
cattgggaag cattttggtc cttccatttg attcataact cttaccttta tgcctctgaa 32760
ggaaaagatt tatacattca gcttgtaatt agtaatcaag actgaggttt agtctatcta 32820
gcttcacaat ctatctagtt tgttttgtct agccatatga tttcttcaaa tatgccattt 32880
cttaaaaaaa aatgttttat gtatcccgat taatatttag ccagtggttc ttttagccga 32940
tggatcttgt cacctcttat gatactatta atagcatgtc aacatgaaga attatctgct 33000
gaatataata gctatgctgt ccttgtttcc ttttgtctca ttcttttttg attgggggat 33060
aattggccaa taaagctttg atagcctcta ttgcccaggc ccctcctctt cttttatgag 33120

-continued agaaaggatg aacagtgacc agaaataaag gtattgtttt tttctatcaa ctaaaatgga 33180
aataaataat tcctaagtaa tttgcctgtt aggattaaag tctccaagag aatggctgtg 33240
cctagtacct aagtgattaa tttccttgat tggttcacat tatattgagg atattagtaa 33300
tcagtagtga ttcctttttt ggttcaaaga tgatagtgtc acagtgaaaa atgtttttaa 33360
aatttttgta tacttaattt ttctgttaac gaaagtattt tcagttggat ttttgtttgc 33420
cctctctatt agaatgccca aagaatattt aaaatttttcc ttttctctta tactgcatat 33480
ttttcctgtg atttttcccc aaacggaaaa tactctgcag agattagact ttgttattgt 33540
tgtactacat cattgctttg actaaaataa actcagattg caaatacctt caagcttaca 33600
ttgctcagta tttttttttt tttttttttt tgagacggag tctcactctt gtcgcccagg 33660
ctggagtgca gtggtgccat ctcagctcac tgcaacctct gcctcctggg ttcaagcgat 33720
tctcctgcct cagcctgcgg agcagctggg attatagatg cccgccccca cgcccagctg 33780
atttttgtat ttgtagtaga gatggggttt taccttgttg gccagtctgg tctcaaactc 33840
ctgacctcgg gtgatccatc tgtctcggcc tctggaatta caggtgtgag ccgccacgcc 33900
tggctaaatt gatcagtatt atttaacttt gagggatatg atttgttatg gaatgcgaag 33960
ttttatactt gaggtactca gagtcctttt gagacaaata tttaacttct ccttttgagg 34020
ttaccgccta cgattgggaa ttaatgtaaa aaataagcca aaagaaagtg agggaaaagt 34080
gaaccaagct gtaatttttt tactcttttt tattgttgtt gttattgttg ctgtttttta 34140
ctatcttgat tgcaacagtt tggcttatat atatagcatt tggaattgac agtaagaaag 34200
ccacatctca tagaagctaa ctattcccaa attgtttttt tcttcttttc ctcttactac 34260
tgctgttttc ctcctttctt gctgctaagc tcttgtcctg acatgctggt aatatgaaac 34320
agtgttttat tcagataatt gattattctg taatatgtat gttaatcttt tttattacac 34380
tttaagtaat agggtacata tgcacaactt acagattcgt tacatatgta tacatgtgcc 34440
gtgttggttt gctgcaccca ttaactcgtc atttacatta ggtatttctc ctaatgttat 34500
ccctctccca accccccacc ccaggacagg ccccggtgtg tgatgttccc cgccctgtgt 34560
ccaagtgttc tcgttgttca gttgccacct gtgagtgaga acatgcggtg tttggttttc 34620
tgtccttgcg atagtttgct cagaatgatg gtttccagct tcatctatgt ccctacaaag 34680
gacgtgaagc tcatcctttt ttatggctgc atactactcc gtggtgtata tgtgccacat 34740
tttcttaatc cagtcagtca ttgatggaca tttgggttgg ttctaattct ttgctattgt 34800
gaatagtgct gcagtaaaca tacgtatgca tgtgtcttta tagtagcatg atttataatc 34860
ctttggatat atacccagta atggaattgc tgggtcaaat ggtatttcta gttctagatc 34920
cctgaggaat tgccacactg tcttccacaa tggttgaact agtttacagt cccaccaaca 34980
gtgtaaaaat gttcctgttc ctccacatcc tctccagcac ctgttgtttc ctgacttttt 35040
aatgatcgcc attctaactg gtgtgagatg gtatctcatt gtggttttga tttgcatttc 35100
tctgatggcc agtgatgatg agcatttttt catgtgtctg ttggctgcat aaatgtctat 35160
aaatgtcttc ttttggaaag tgtctgttca tatcctttgc ccactttttg atggggttgt 35220
ttgatttttt tcctgtaaat ttgtttaagt tctttgtaga ttctggatat tagccatttg 35280
tcagatgggt agattgcaga aattttcttc cattctatag gttgcctgtc cactctgatg 35340
gtagtttctt ttgctgtgca gaagctcttt agtttaatta gatcccattt gactattttg 35400
gcttttgttg ccattgcttt tggtgtttta gtcatgaagt ccttgcccat gcctatgtcc 35460
tgaatggtat tgcctaggtt tgcttctagg gtttttatgg ttttaggtct acatttaagt 35520

-continued

```
ctttaacatt taagtcttta atccatcttg aattaatttt tgtataaggt gtaaggaaat  35580
gatccaattt cagctttcta catatgacta gccagttttc ccagcaccat ttattaacta  35640
gggaaccctt tccccatttc ctgtttttgt caggtttgtc aaagatcaga tggttgtaga  35700
tgtgtcatgt tatttctgag ggctctgttc tgttccattg gtctatatct ctgttttggt  35760
accagtacca tgctgttttg gttactgtag ccttgtagta tagtttgaag tcaggtagtg  35820
tgatgcctcc agctttttc  tttctgctta ggattgtctt ggcagtgcgg gctcttttt   35880
ggctccatat gaactttaaa gtagtttttt ccaattctgt gaagaaattt attggtagct  35940
tgatggggat ggcattgttt ctataaatta ccttgggcag tgtggccatt ttcacgatat  36000
tgattcttcc tacccatgag catggaatgt tcttccattt gtttgtgtca tcttttattt  36060
cgttgagcag tggtttgtag ttcttgaaca ggtccttcac atcccttgta agttggattc  36120
ctaggtattt tattctcttt gtagcagttg tgagtgggag ttcactcatg atttggctct  36180
ctgtctgtct gttattggtg tataagaatg cttgtgattt ttgcacattg attttgtatc  36240
ctgagacttt gctgaagttg cttatcagct gaaggagatt ttgggctgag acagtggggc  36300
tttctaaata tacaatcatg tcatctgcaa acagggacaa tttgacttcc tcttttccta  36360
attgaatacc ctttatttct ttctcttgcc tgattgccct ggccagaact tccaacactg  36420
tgttgaatag gagtggtgag agagggcgtc cctgtcttgt gccagttttc aaagggaatg  36480
cttccagttt ttgcccattc agtatgatac tggctgtggg tttgtcataa atagctctta  36540
ttattttgag atacgttcca tcaataccta atttattgag agtttttagc atgaagggct  36600
gttgaatttt gtcaaaggcc ttttctgcat ctattgagat aatcatgtgg ttttttgtct  36660
ttggttctct ttatgtgatg gattatgttt attgatttgc gtatgttgaa ccagccttgc  36720
atcacaggga tgaagccaac ttgatcttgg tggataagct tttgatgtg  ctgctggatt  36780
cggtttgcca atattttatt gaggattttt gcattgatgt tcatcagggg tgttggtcta  36840
aaattctctt tttttgttgt gtctctgcca ggctttggta tcgggatggt gctggcctcc  36900
taaaatgagt tagggaggat tccctctttt tctatgaatt ggaatagttt cagaaggaat  36960
ggtaccagct cgtcttttta cctctggtag aattcggctg tgaatctgtc tggtcctgga  37020
ctttttcgg  ttggtaggct attaattatt gcctcaattt cagagcctgt tactggtcta  37080
ttcagggatt caacttcttc ctggtttagt cttgggaggg tgtatatgtc caggaattta  37140
tccatttctt ctagattttc tagtttattt gcatagaggt gtttatagta ttctctgatg  37200
gtagtttgta tttctgtggg atcagtggtg atatcccctt tatcattttt tattgcatct  37260
atttgattct tctctctttt cttccttatt agtcttgcta gcagtctatc aattttgttt  37320
tttaaaaaaa ccagctcctg gattcattga tttttttttt gaagggtttt ttgtgtccta  37380
tctccttcaa ttctgctctg atcttagtta tttcttgcct tctgctagct tttgaatttg  37440
tttgctcttg catctctagt tgttttaatt gtgatattag ggtgttgatt ttagatcttt  37500
cctgctttct cttgtgggca tttagtgcta taaatttccc tgtatacact gctttaaatg  37560
tgtcccagag attctggtac gttgtgtctt tgttctcatt ggtttcaaag aacatcttta  37620
tttctgcctt cattttgtta tttacccagt agtcattcag gagcaggttg atcagtttcc  37680
atgtagttgt gcagttttga gtgagtttct taatcctgag ttctaatttg attttactgt  37740
ggtctgagag acagtttgtt gtgattttta ttcttttaca tttgctgagg agtgagtgct  37800
ttacttccaa ctatgtggtc aattttggaa taagtgtgat gtggtgctga taagaatgta  37860
```

-continued tattctgttg atttgggatg gagagttctg tagatgtcta ttaggtctgc ttggtgcaga 37920
gctgagttca aatcctggat atccttgtta accttctgtc tcgttgatct gtctcatatt 37980
gacagtgggg tgttaaaatc tcccgatatt aactgtgtgg gagtctaagt ctctttgtag 38040
gtcactcagg acttgcttta tgaatctagg tgctcctgta ttgggtgtat atatatttag 38100
gatagttagc tcttcttgtt gaattgatcc ctttaccatt atgtaatgcc cttctttgtc 38160
tcttttgatc tttgttggtt tacagtttgt tttattagag actaggattg caacccctgc 38220
tttttcttgc tttccatttg cttggtagat cttcctccat ccctttattt tgagcctgtg 38280
tgtgtgtctg catgtgagat acatctcctg aatacagcac actgatgggt cttgactctt 38340
tatccaattt gccagtcttt gtcttttaat tggggcattt accccattta catttaaggt 38400
taatattgtt atgtgtgaat ttgatcctgt cattgtgatg ttagctggtt attttgccca 38460
ttagttgatg tagtttcttc ctagcatcaa tggtctttac aatttggcat gtttttgcag 38520
tggctgatac cagttgttcc tttccatgtt tagtgcttcc ttcaggagct cttgtaaggc 38580
aggcctggta gtgacaaaat ctctcagcat ttgcttgtct gtaaaggttt ttatttctcc 38640
ttcccttatg aagcttagtt tggctggata tgaaattctg ggttgaaaat tcttttcttt 38700
aagaatgtag actattggcc cccactctct tctggcttgt agagtttcag cggagagatc 38760
tgctgttagt ctgatgggct tccctttgtg ggtaacccga cctttctctc tggctgccct 38820
ttacattttt tcctgcattt ccaccttggt gaatctaaca attatgtgtc ttggggttgc 38880
tcttctctag gagtatcttt gtggtggtct ctgtattccc tgaatttgaa tgttggcgtg 38940
ccttgctatg ttggggaagt tctcctggat aatatcctga agagtgtttt ccagcttggt 39000
tccattctcc ccgtcactgt caagtacacc aatcaaacgt agatttggtc ttttcacata 39060
gtcccatatt tcttggaggc tttgttcatt tctttttact gtttttctc taaacttctc 39120 ttcttgcttc atttcattca tttgatctgc aattactgat accctttctt ccacttgatc 39180
gaatcggctg ctgaagcttg tgcatgcgtc atgtagttct cgagccatga ttttcagctc 39240
catcaggtca tttatggtct tctgtacact gtttattcta gttagccatt tgtctaatct 39300
tttttcaaga tttttagctt ccttgcgatg ggtttgaaca tcctccttta gctcggagaa 39360
gtttgttact actgaccttc tgaagcctac ttctgtcaac tcgtcaaagt cattcttcat 39420
ccagctttgt tccattgctg gtgaggagct gtgatccttt ggaggagaag aggcactctg 39480
ggttttagaa ttttcagctt ttctgctctg ttttctcccc atctttgtgg ttttatctac 39540
ctttggtctt tgattatggt gacctacaga tggggttttg gtgtggatgt ccttttgtt 39600 aatgttgatg ctattccttt ctgtttgtta gttttccttc taacagtcag gtccctcagc 39660
tgtaggtctg ttggagtttg ctggaggtcc actccagaca ctgtctggat atcaccagtg 39720
gaggctgcag aacagcaaat attgcagaac agcaaatatt gctgccggag ccttcctctg 39780
gaagcttcgt cttgggggca cccggctgta tgaggtgtca gtcggcccct actgggaggt 39840
gtctcccagt taggctacaa gggggtcagg gacccacttg aggaggcagt ctgtccgttc 39900
tcagagctca aacactgtgc tggtagaact actgctctct tcagagctgt cagagaggga 39960
tgtttaagtc tgaggaagtt tctgctgcct tttgttcagc tatgccctgc ctccagaggt 40020
ggagtctaca gaggcaggca ggcctccttg agctgtggtg ggctccaccc agttggagct 40080
tcccaaccac tttacctact caagcctcag caatgatgga cgcccctccc ccagccaggc 40140
tgctgccttg aagttcaatt tggaactgct acgctagcag tgagcaaggc tctgtgggcg 40200
taggacctgc tgagccaggc acgggatata atctcctgtt gtgccatttg ctaagaccgt 40260

-continued

```
tggaaaagcg cagtatttgg gtggcagtgt cccaattttc ccggtatagt gtgtcacagc  40320
ttcccttggc ttggaaaggg acatcccccg accccttgtg cttcctgggt gaggcaatgc  40380
cccgccctgc ttcagctcac cctccgtggg ctgcacccac tttccaacca gtcccagtga  40440
gaagaaccag gtacctcagt tggaaatgca gaaatcacct gtcttccgcg tggatcatgc  40500
tgggagctgc agacaggagc tgttcctatt tgaccatctt ggaatgccac cttttttttt  40560
tttttttttt ttttaaggca gtttcttgct ctgtcaccca ggctggggtg cagaggcatg  40620
atcacggctc actgcaacct ctgccttctg ggctcaagtg atcctcccac ctcagcctcc  40680
caagttgctg ggaccacagc cacgcatcac caggcctggc taatttttgt gtttttttgta  40740
gagatagggt ttcgctgtgt ttcccaggct ggtctcaaac tcctgcgctc aagcgatccg  40800
cctgcctcag cctcccaaag tgctgggatt acaggcatga gccactgcac ccggccaata  40860
tgtatgttaa tctcatccct caagctgata ctgaagtttt tcaatttatg ttatttggtg  40920
taaatctagg cagtctttaa caaaattggt gcttcatgtg tttaagaggc ataacttaag  40980
aattgtttgt ttcttataaa tcaggagaat ggaggtttaa tagaggtgaa ctgtctttct  41040
cactgcagaa cctttaatat gccactatgc attgtaaatc tcccaagagt gagattctag  41100
tatgatgctt ttcttttcct tttctgttct ttccctttcc ctctacctcc tttttctttt  41160
ctttgttggt ggcatgagtc ctatattata aggaaatgct tttagagtac agtcttctga  41220
tatatagtga tttttgaaaa agatttattt attgtcttgt tcactgtgag ctttttcccc  41280
catgtataag cagctgtgta atagattcaa gagcaccccc tcgccccttt tttttgaga  41340
cagagtctcg ctcggtcact caggctggag tacggtggtg ctgtgatcat ggttcacctc  41400
gacttctggg ctccagcgat cctcccacct catcctctca agtagctggg accacaggcg  41460
tgtgtcaccg tacatggcta atttttctat ttttagtaga ggcagagttt cgccatgttt  41520
tccaggctgg tctcgaactc ctgaactcaa gcagtccacc tgtctcagcc tcccaaagtg  41580
ctgggattac aggcgtgagc ctccactccc agtctcaaat attcttttga aatatttgaa  41640
atatgttgat ctctcagtct ttcaacctta gttgtatgtt gattttcaat aaaaaggaag  41700
tatttgttgc cctaacatca gtattggcta ttcagtttaa aaaaggagtt aaagagatgt  41760
tatttatagg caggcttcaa aagaggaaag aatgatcagt ttcattctct gtttctagca  41820
tattctgact ccttctctca tattacctcg tttttcccac attttttctt taataaagtg  41880
aaattcacat aacagctaac cattttaacc acggaaagtg tacattccgt ggcatttatt  41940
accttcacag tgttacctct acctttatca agtttcaaaa cattttatca ccccaaaaga  42000
aagccctgtt cttattgggt gcctcttgct tttttttttt tttttttttt taaatcttga  42060
gacggggtct tggtttgttt cccaggttgt agtgcaatgg ggcgatctca tctcattgca  42120
acctctgcct cccgagttca agcaattctc ctgcctcagc ctcccgtagc tgggactaca  42180
ggcacgcgcc acatgcctgg ctaattttttg tatttttagt agaaacgtgg tttcaccatg  42240
ttggccaggc tagccttgaa ctcctgacct taggtaatct gcctgccttg gcctcccaaa  42300
gtgctgggat tataggcgtg agccaccgtt ctggccacct cctacttctt tcattagtct  42360
taattcctta gtggatttga cagtgtttat attatctaca ccaatgcatt tttttgtatg  42420
ttaataatag gagatattta ttgggcattt atttacatac ttatttgcat gtgtaactgt  42480
tgtatagcca gtttatgtat ataatcttac taaatctcta cagtaaatct atccccattt  42540
catagatggt ttaaaagaag ttaacttccc caagcattac ttttagtaag tagtgagact  42600
```

-continued gaaggttgag ttctggtctg tcagattccg aagttgtttc cttaggaacc atattatctt 42660
gtgtacaact cttgggctaa tcttgttaat attctttatt tgacctcaca ctgttgattc 42720
ataccatgtt taaaattgaa atacattacc tatatttaaa aattgagacc tcacataaaa 42780
agctatattt ctagctgctt ttgaaatttc gaaggatctt ccaacacttg gctgacattc 42840
ctgcgtgaca aaaatcagct ggagctgtgt aatgtccgac ctgtctctgt caatgaacag 42900
attattcatt gtcatttctc atctgttttt gagattgtaa ctttgattct gtataactca 42960
tagaattagt agttagacct atatatgtta gttattacat tatttgtata tgtacagact 43020
gctttagaca atattgtagt gttatatgtt aattttatca attaaaatgt gctataggat 43080
cattgtagag atcttgtctc taattaacag gattcataaa gagaaaacaa aggagagaaa 43140
catccagatt gaaaagacct acatagtgcc aagcacaata aaagaaaccc tatactaggc 43200
aaattattat gaaatttgtt ttaggacacc agaaataaag ataatatcta aaaacttttt 43260
agaatcgcct aggagggatt aggaatatga atagcatcta acttgttggc agtagaattg 43320
aaggtagaag gtggtaaaac atcaccttga aagttctgca ttcagcctag aattctgtat 43380
ccagttaaac catcaatcaa gtgtgaaagt agggggaaaa actcaaggac taaaaaaatg 43440
tgctcatgaa gaacattttt tttggacatt acccagaaga tgtggttcaa caaaacaagg 43500
gaataaacca agaaaggaaa taaaagagct tcagtaaaca gagaatccca ctcagaagca 43560
acaaagaaga aagtcccagg atgacagctg tgacacaagc tgaaaagtta ccagttttgc 43620
ttggagcagg agattagaac ttccgggaaa ataatcaaat tgatagatgg atgttgaaat 43680
atttggagaa aaatgtaatg gattcttgca aaactgagca aattagaaaa aggaaacaat 43740
tattagcatt ggtggtttga gttaacccaa aattgtgatg ttgctatttt aggggaatta 43800
agataagtga aacacgtatg gaatactgct agttttgtaa gtctccttta ccatggcagg 43860
acatctgtag ttaataaatc tgtaagaagc agtattaaga ataatatttt aaaataccta 43920
attaaatagg aggaaaaaga atccgagtag ttgagggtga ttgcatctgg ggagaagcag 43980
gaataaaggt ttgaagataa atagggccag agatgagtaa ttttgttact gtgataaatat 44040 attttatata tatgtgtatg tgtgtgcgtg tgtatatata tatatgagat atatctcata 44100
tatatgagat atatatgata tatatatgat atatatgata tatatatata aaacatacag 44160
ttcagtagca ttaacatcta gcattcagta catttacatt gttgtgcaat tgtcaccact 44220
gtccatctct agaacttttt cattatccca cactgacata ccacacccat taaataataa 44280
ctcctcattg ctcctcctgt tagtaccaac cattgttcta ctttcatctc tatgtatttg 44340
actattctag gtacctcgta taagcggaat cacgtgatat ctttttgtaa ctggcttatt 44400
tcactaacta tcttcgaggt tcatccatgt tgtagcagtt gttagcattt ccttcctttt 44460
aaaaggccga ataatattcc attgttatgt atataccata ttttgtttat ccatttattc 44520
atcaatagac acttttggct gttgtgaata atgctgctat gaatatgggt atgtaatacc 44580
tgtttgagta tctgctttca tttcttttgg atatgtaccc aaaagtgaga ttgctggatt 44640
gaatggtaat tctatattta aatttttgag aaaccaccat actgtttgat atactggctg 44700
cccaatttta cattaccacc agcaatacac tagggttccg aatttgccac atcctcacca 44760
tcgtgttgtt ttgtttatgt ttttttttaa taatagccat cctaatgggt gtgaagtctc 44820
attgtggttt taatttgcat tttcctaatg atcagcgata ttgaacattt gcacatgctt 44880
atttggtcat ttgtatatca gctttggagc aatgatgtct cttgaagcct tttgcccatt 44940
tatgaattga gtagtttggg atttttaaat tgtgttttag aagttctttg tatactctgg 45000

-continued

```
ctgggcacgg tggctcgtgc ctttgggagg ccgaggcagg tggatcacga ggttaggagt  45060
tcaagaccag actggctggt atagtgaaac cccatctcta ctaaaaatac aaaaattagc  45120
tggtgtggtc gggcgtgatg gtgcacacct gtagtcccag ctgttgggga ggctgaggca  45180
ggagacttgc ttgaacccgg aaggtggggg ggttgcagtg agctgagatt gtgccactgc  45240
actcagcctg ggtgacagag cgagactctg tctcaaaaaa aaagaaaaag aagttctttg  45300
tattctctga atattaatcc cttattggat atgttatttg caaatatttt ctcccataaa  45360
gaatgggtta ctttttcact ctgttgattg tttcctttgc tgtgcaggag ctatttagct  45420
tgaaaaaatc caacttgtct gttttctttt gttgcctgta cctttggtgt cacattcaag  45480
aaataattgc caaattcata ccatgaaact ttcccccatg ttttctcctg aaggttttta  45540
tagttttagc tctcacattt aggtgtttga tccattttga gttaaatttt gtatataatg  45600
ttatgtaaga gtccagcttc acacttttgg atgtgaatat ctagttttcc cagcattatt  45660
tgttgaaaag agtgtctttt tccccattga atagtcttgg cactcttgtt gaaaattatt  45720
tgacaataga tgcaagggtt tatttttggg ctctctcgac tattctgtta gactatatgt  45780
ttgttttttt atgtcaggac caccctaatt ttagtactgt agctttatag taaaatttga  45840
aaccaggaag tatatgtctt gtgtatttat ttacttattt tttgaaatag catctggctc  45900
tgttgcccag gctggagtgc agtggcacaa tcttagctca ctgcaacctc cacatctgag  45960
gttcaagcaa tcctcccacc tcagcctcct gagtagctgg gattgtagac acataccacc  46020
atgctcagct agtttttgta tttcttgtag agacagggtt ttgccatatt gcccaggtgg  46080
gtctcgaact cctgagccca agcagtctgc cctcctcagt gtcccaaagt gttgcgatta  46140
caggtatgag ccaccgtgca tggccccaac ttcttatatt tcaagatggt tttggccctt  46200
cagggccctt tgtgagtttt aggatggatt tttttttaa cttttaagtt taggggtgca  46260
tgtgcaggtt tattacatag gtaaatttgt gtcaaggtgt tctgttgtat agattatttc  46320
atcacccagg tattaagcct agtacccatt agttattttt cctgagctcg cctcctccca  46380
cctggatttt tttttttatt tctaccagaa acattgttgg gattttggta gggattgtat  46440
tagtctgtag attgcattga atagtactga catcttaaca atattaagtc tttaaagcca  46500
tgaacaccag atgtctttcc atttatttac gtattctttc ttttctttca gcaatgtttt  46560
gtaattttca gtgtacaagt attttacctc cttggttaag ttaattccta agtattttat  46620
tcattctgat gatcttataa atctgttttc ttaatttcct ttcctaattg ttcattctta  46680
gggtatagaa acacaactga ttcttcgcac attaaatttg tgccctgctt cttcgcgggt  46740
ttgtttattc tttttttgtg tttgaaatcc ttgaggtttt ctgcatataa gattatatca  46800
tctgcaaatg agataatttt acttgttcct ttccaatttg agatgatttt tattcatttt  46860
cttaatgctc tctcatacat tcaatactat gttgaatgga agtggtgaaa gcaggcatcc  46920
tgtcttgttt ctgaccttat aggaaaagct ttcaattctt tgccattgac tatcatgtta  46980
gctatgggat tttttttttc cccccagata gagtctcgct gtgtcgccca ggctggagtg  47040
cagtggtgcg atctcggttc actgcaccct cctcctcccg ccaggttcaa gtgattctcc  47100
tgcttcagcc tcccaagtag ctgggattac aggtgtccac cactatgccc agctaatttt  47160
cgtattttta gtagaaacat ggtttcacca tgttggccaa gctggtctcg aactcttggc  47220
ctcaagtgat tcacctgcct cggcctccca tagtgctggg attatagtca gccaccatgc  47280
ctggccactg tgggattttt atatatggcc ttcattatgt tgtggtaatt tctttttatt  47340
```

-continued

```
cttagtttat tgagtgtttt tatcataaaa tcttgttgaa ttttttcaaa tatttttttct 47400
gtgctagttg agatgaccat gtgatttgtt ttcttctttc tattaacatg atatattgtt 47460
tttcatatat tgagccattt ttgcatccca ggaataaatt ttacttggtc ttcgtgtata 47520
atccatttaa taagctgtgg aattcagttt gttggttctg tgttgaggac tttatatcaa 47580
tgttcctaag ggctactggt ctatagtttt cttttgtagt ttctttgact ttgctatcag 47640
ggcaatgctg gcctcattga atgtgttagg aagtgtttcc tcatccattt ttggcaaaac 47700
tttgggaaaa aacgatgttc tttaaatgtt tgatagaatt cacagataaa aaaatcacat 47760
ctagggcttt tgtctggaat tttttattg ttattattga ttcagtcttg ttactagtta 47820
taggtctatt cagattttct ttttgtgtgt gtgattcagt attagtacat tttgtacttc 47880
tcgttatttc tccatttaat ctatattatc taatttgttg gcatacaatt gttcatagta 47940
ctgtcttctc ttttttttaa acttctgtgc agttgatact aatgtcccta cttttatttc 48000
agattttagt aatttgaatc ttctttatct taatacaggt aaagctgggt caattgttaa 48060
aatttttttca aagaaccagt ttttggtttc attgattttt ctctgttatt tttctattat 48120
ttatatcctc tctaagcttt gttatttcct tcatcctgct agctttgggt ttattagttt 48180
gttctttttc tagttcctta agatttgaag ttggattatt gatttgagat cgttttcaat 48240
taaatgtgta caactacaaa tttccctctt aggactgctt ttgctgttct gtaatttttg 48300
gcatgttgtg tttttttgtt ttaatttatt tctaagtatt ttctaagttc ccttgtgatt 48360
tcttctgcgt ttaaccgtgt atttttttaat ttccacagtt ggtgaatttt ctactttttc 48420
ttcagttatt gattttattg attttcagtg gcatcctgtt gtgatagaag atactttatt 48480
tggttccctg tttttttttt aaaacagagt gttgctctgt cacccaggct ggagtgcagt 48540
ggtgcgatct tggctcactg caacatccac ctcctgggtt cgagcaattc tcctggtctc 48600
agcctcccca gtaggtagga ttacaggcac atgccaccat gcccagctaa tttttgtatt 48660
tttagtagag acagggtttc gccatgttgg ccaggatgat ctcgaactcc tgacttcaag 48720
tgatccaccc gccttggcct cccgaagtgc taggattata ggcgttagcc accttgtctg 48780
gcccagatcc tctattttct tgcctatatt ctgactgggt gtttttgtcc attattgaga 48840
gtagggtatc gaagtgtcca gctgttattt cagaactgtc tgtttacctt caattctgtc 48900
aatttttgc ttcatataat tgggtggtct cttattaggc atgtaaatgt ttttgattat 48960
tatatcttct tgctatattg acacttattg atgtgtaata tctttttttgt ctcaaccttg 49020
ttttgattta gtttgtctaa tattaatgta gctacctgca ctctcatttg gttattactt 49080
gtatagaatg tctttttaca tcccttattt gtgtctttgg atctgaaatg agtctcttgt 49140
agacagcata tacaatctct tgtagattgt gtttttctta tacattctgt caaactctgc 49200
cttttgattg aagagtttta tcatttacaa ttaaagtaat tattgataag gatttaactg 49260
ctgccatttt gctgtttatt ttctatatgc cttacagctt ttttgtccct catttcctgc 49320
cttactggca cttgtgttta gttgatattt tgtggtgaag tgttttaatt tccttgttat 49380
ttcctttgt ttatattctg ctattttctg tgtgtgtgtg tgtgtggttg ccattggggg 49440
tcacatttaa tgccctaaag ttataacact gcaatttcaa tttataccaa tttactttca 49500
atagcataca aaaattcagc tcataagatt cagtccctgc tcccttccag ttattgatgt 49560
cataaaatta catttttatg tattgtgtgt ctaaaagcgt agactaataa ttgtttttta 49620
atgcagtagt gtcttaattt gtggaaaaca aaaagtggag ttgtaaacca atgttacaat 49680
aatgctagct ttggtaattg ctcatgtatt tatcatttct cagatcttta tttcttaata 49740
```

cagcttcaag ttactgtcta gtctcctttt atttcagcct gaaagactca cttcagcgtt 49800
tcttgcagga caggtctggt gataatgaac tctctcagat tttgttaatc tggaaatgtc 49860
ttaatgtctt catttttaag gacatttttg ctggatatag tattctcagt tgacaggtat 49920
ttgtgtttat ttgtttgttt cctttcagga ttttaaatat atcatcccac tgccttctgt 49980
ccttcaagag ttctgatgag aaatctgctg atattgagga tccctttgta tgttacaagt 50040
tgcttctctc attccatgtt caggattctc ttttttcata gtttgattat aatctatctc 50100
agtttttcct acttggatct ctgagttttt cctacttgga gttaattgag cttcttgaat 50160
atttatattc atgtctcatc aaatttggga agtttttgat taatatttct tcacataatc 50220
tttttgccc cttttctctc tttttattct gggattccca gagtgtgtat gtgttggtcc 50280
acttgatgat ggtgttccac aggtgtctta ggctcttgtc ttcaattttc cttcagtttt 50340
ttttttctgt tcctcagaca cgtggtattt tcagctgttc tgccttccaa gtttactgat 50400
tcttctgcct gcccaaattg gcttttgaat tcctctagta aatttttatt tcagtttttg 50460
tacttttcag ctccagcatt tattttttga tttttttatg ttttctcttt attgatattt 50520
caattttgtt ttttgacatt atccatatct tcctttagct ttttgagcac ctttcaacat 50580
ttgttttaaa gtctatgtct agtaagtgtc tgccatctga tcttctcagg cacagtttct 50640
gttaatttat ttttttcctt ttggcctata cttaatgttt tgcttggggt agtttttttt 50700
tttggtatgc tttgtgattt ttgttgttgt tgtcaaaaac tggaatttga atcttaaaga 50760
gtggtaactt tggaaattag atttttctct tttctctaag atgtgctatt ttgtttggtt 50820
tttttatttg ttgtagagta tttctatgct gggtgtaatc ttaagatctt ctcggcctgt 50880
gtttttccct gggcatgtgt agtgactttc taaattgccc tatgtatgca gttcttttgc 50940
agtagtatcc tccttaaatg tttggctcct aaaaggcaaa ataaataaat aaataaataa 51000
aaattaaaaa ttaaaaataa atcaaagggg tgaaatagct ctggatcttt aaatccctgg 51060
agcaattttt tcagccaatg gcagttaaat aatgatagtc tgcctctgtg tcacattttg 51120
atcagaagca gcaattagca atcagaacac agattcctga tatttggagg gcaaggtctt 51180
tgttgccaac cttgactctt acaaactgtg tgcagggtgc tctgggaaca tgtgcatggt 51240
tgcctgcttt gagagtgggt gatgggtagc cgcgacggca caaagagctg aaattgactc 51300
aaactaactg atttaccatt caagtctttc cttagaaact gaaaacctga atagactcca 51360
gagttccaga atcacagatt ctgcttacag tcgtctaggt ggggagatgg gttcctggta 51420
cttctgattc tgccatcttt ctttgactaa tttttttttt ttgttcttga gatggagtct 51480
tactctgttg cccgcccagg ctggagtaca gtagcatgac ctcggctcac tgcaacctct 51540
gcctcccggg ttcaggcaat tctcctgcct cagcttccca agtagctgga attacaggcg 51600
tgcaccacca tgcctggcta attttttgta tttttagtag agacagggtt tcaccatgtt 51660
ggccaggcta gtctcgaact cctgacctca ggtgatcaac ccgcctcagc ctcccaaagt 51720
gctaggatta caggtgtgag ccactgcacc cagctcttag acaaattttt tattccaaac 51780
ttttttatt ttatcatttg aaaggtatat gtttattatt ttgtcaaaaa taattttaaa 51840
acgtattctt gaagcttatt tagatctgtt tcataggaac tgtgaagaaa gtaaagaatt 51900
taaaaaatga agacagattt tctcaccctg cttatgggtg cttctcgtgc tagccttttg 51960
caagtgtcgg gaagtgtaac ctgcaggagg catcagggct ttgggcctgc atggtctgag 52020
tgctgccctg tgagtttcag aaggcgcagc aacctgtata cctgaaagcc atctctgctg 52080

-continued

```
gggcaggtac ctagtgtccc cacctacctg ggtcgtagtc aggccctggg caagcctgct  52140
atgcttttcc ttccctaatc cctcaggggt gggatagaga gcacagtggc ctcccaggga  52200
ggtagaagct gctccagact aacaatcaga gctgccagtt cttaatcccc aagaccgcca  52260
gacttcacaa agacataccg aggtctgtgc tgtcagtgcc ccactactac actcccttaa  52320
gtagccccac attcttgtgc ttgtttcttt tttctgctct ctttccttgc ccaggtaaga  52380
ggtctgccca taagggatat tttgcagcat gtgaagcttt ttaaaaagtt aggcttattg  52440
aagtataatt tacacacaaa gtacaaaaaa aaaaagactg tgttctcaaa tctgtgagtc  52500
attaatgggt ttagatgttt atatattgaa attattggaa gtaaggtatg tttatattag  52560
aaagatttgt agtctagatt atccaagttt tgggagtatt acctctctgc ttttgtttat  52620
ctactttttt agtctctact ttccaagtat ctataggcaa attttcccat ttccctttgg  52680
aaagtgctgt tttcttgctt tttttccgcc tttccattgt gtcagactta taaggcaatc  52740
agccaactgt gggcatgaaa tccttgggag gaaagagaag gaagtgggag gggcagccat  52800
ggtgaatgtt tccctaagtt atagtcaagt tctttgagag aacataacct catccccttt  52860
ttaaactgtt gtaatacttt cttttaaata gattgtttat tctcctgcaa gtctcacagt  52920
tgttcacagt ggtaggtaag aaatcataaa gttcaaatat taaagggagc tcacaaaaga  52980
gcatggtttc accagccctc actaaaaaca aaattatggg aaaatgctgt aaaagaaacc  53040
agaattcttg gttgcaaatg atagaaagtg actctgattt acctaatcag aaaggaattt  53100
ttaaaaaagt attaggtagg tcatagtttg acaacaagac ttggaagata ggtggaagct  53160
aagggaagca agacatggcc ccaaggtttc aacaggagca atctgcttag gactttgctg  53220
cttggacact tggtgtaata gctgctgcca ctatgcctcg aaactggtga ctctgctcat  53280
taactcacct cctctggtga tctctaggaa taatctctga ctctcctgta ccttgtcctc  53340
actaggattc ggtatccacg gcaaaaagat ctattaatag ttggtatcag gcctgtacat  53400
gtgttaagag aaagatgagg aaagaagtat ctgcttctaa tctcttgaaa ttatctccaa  53460
attgaaatgg tattttggtt gcctaacagc ctgaagatga caaatatccc ctacaaattt  53520
ctcctatttt accctcttcc taactatatc tgtaatttaa agtttcacat attcttttga  53580
aaattgtttt cattgtttac ccacttttta agaaaagcaa atgggaacat actaccactg  53640
tttggcccct ttcaaaaatt ttatatctga ggaatcttcc atattgttgt ggacatctac  53700
ctacctgatt cttttattaa ctacctttta tttcatttta tgatcatgct atcattaata  53760
ggcccctatg atgaatatat aagttgtttc cagttttttt tttgtcattg agaacagttc  53820
acatatgtat cttgttgtct tttccaagta tatctttaag gcaaattctt agcagtggag  53880
ttgctaggtc cattgcgtct atggtttaaa ctagtgcctt caaaaatggt attttatata  53940
ctcactgttt aagagtgctt cttccttcta tccccactaa ctttggcaaa ctgaatagtt  54000
tcaaacttta actttttata gcttgttggc aaaaaatggt atcttgttat ttgatcgtgt  54060
ttttttaatt gtgaggttta gcgacttttt gatgtattgg tcttatgtac tttctggtgt  54120
gtgtgtatgt atatactgac cctattttca acttattttt cttttagttt gtttgtattt  54180
tccttaatga ttttcaggaa accaatttta ttctttcttc agacagttgt ctaatgttct  54240
gcttctcttg ccatttgaat tttgtgacta caaaattcag atgaaacaat aatagcataa  54300
agaacttggt gggttatctt ttgttttgca ttattgattg tttattaaga aatattcttt  54360
aaaagtcacc ttgcttaaat tagcaagtag gaaatgcttt caataaagag aactgtcatg  54420
tacccactac tccttactta ctgaatcatc ttcttttgga tagagaagat aaaagtgaaa  54480
```

-continued

```
agggaattta agagttcctg ccttttcct tgtctttagc attatatagc tgtttaatgt  54540
gtgggagtct aatttctttt ttctttcttg agacaaagtc tcactctgtt gcccaggctg  54600
gagtgcagtg gcacagtctt ggctcactgc aacctctgcc tcccaggttc aagcaattct  54660
cctgccttag cctcctgagt agctgggact acaggcatgt gccaccatgc ccggctaatt  54720
tttgtatttt tagtagatat gggacttcac catgttggcc aggctggtct tgaactcctg  54780
acctctagtg atctgcctgc tttggcctcc caaagtgctg ggattacagg catgagccac  54840
tgcacctggc ctaattttt tattgttctt tttggtgtga acattctccc ctcctccaag  54900
ccttttgttt ttactatttt catgttcctt tatatgtgct gctgttttgt ttcatctgta  54960
attatctctc atccccttt ttggctatta taatatatat atgtacgttt tgaatctgag  55020
ctttgaaggt aaattcactg cagctgtgtt ggttgatttt agataatttg tgtatttcct  55080
cctttgtctt ttttaaactg gagtcatttg tagttgttta tacagaattt tagtttttaa  55140
aaccacaagt ctttcattat aggttgagtt atgaattcat agcctgttat ttaaatgaag  55200
cttttgaaat ctgttttact gatctgtatc atatctaact acgccagtat ttccttcctt  55260
gtctgacgtg aactctaaaa ttatgtgaac actttctccc tgtttcctgg catttccact  55320
caaacttgtt cctcattctt agttagaaat atatccagaa ttgtagtttc tttctaatct  55380
aatgacagaa gcaaattaat caagcatggc aagaatttat tggaaaactg catgtagttg  55440
aaaatatgtt tagtatatat tttgacagct gtgaagtctc taatttttac tgtacctttt  55500
ctctgttcca attttatgct ctattctaag gatgtaccca tttctactac ctgactaggg  55560
agcatgtgta ttgtatccca gcagattttt tttttcatag atagatatcc tttagatatc  55620
tgttatccag tgtaggtagc cactagccac atgtagctat cattatgttt aaatgtaaat  55680
aaaataaaat aaatttactg agttgttttt gctagctaca tttcttgtgc tcagtagcta  55740
catgtggctt gtgattactg tattaagaca gcacagatac agaacatttt cattattgca  55800
aaagttctgt tagacagtgc tgttctatac agtgtcattc tgcctctcat tctaaaaagt  55860
tctaattcct gaagttgatg tactctttct gttgctgtcc tctagcttaa tcaaaataaa  55920
tttgagtctt tttaaaggta ggttgcattt tacatactga tatttctaaa tcagaggcta  55980
tttatattac tttttttata ttacttttaa aaattagctt tattggagta taatttacat  56040
gcaataaaat ctacccattt taaatgtacg gttcattgac ttttgagaaa tacacacaca  56100
cacacacaca cacacacacc ttcttgtaaa cacacacctt cttgtaaaca caacaaccaa  56160
gatttagaac actcgcttta tgaaaagttt ccctcatgcc catttgtagt cagtccccaa  56220
acctggtttc aggcaatctc tgatctgctt tctatatgct ttgcctatac taggattaca  56280
tataaataca gtcatatagc atgtattcct ttttgtgtct ggcttctttc ttttagtata  56340
atatttttga aatttatccc tgttgttact agtatcaata atttgttctt ttttattgct  56400
gactaatatt acattgtatg gatatgacat ttctttatta gtgtggtggg catttgagtt  56460
gttttcagtt tgggtctgtt atgaacaaag ctgctgtaag cattcatgtg caagactttt  56520
gtggacatat atttttgttt ctgtttattc aatacctttg agtagaattg ttgggtcaca  56580
tgatgtagat cagttgaaca gagtagattc cagaaaagtt cacatacaca tttcttgaca  56640
aaggtgctga gattattcat gggaaaagga taatctttta aacaaataat actggaacaa  56700
tagagaaaac aaagtgaacc ttgactttta tgtcttatca tatacaaaaa ttaatttgaa  56760
gtggattgtt gacctaaatg taaaagtaaa atttaaaaat ataaaacttc tagatgaaaa  56820
```

-continued

```
cataggagaa aatctctgtg acttttggtt taaagatttc ttagacagta catataaaat  56880
taactatata aggaaaaaat ggacaaattt gactttatca acattaaaaa tttctgctca  56940
ttgaaagact caaaatgaaa aggcaagcag ttttggagaa aatatttgca atacatatat  57000
ctgaaaaagg acttgaatgt ataatatata cataaagatg ctcttacaac ttcataatga  57060
gaaaataacc ccataaagag aagggcaggc cgggtgcagt ggctcatgcc tataatgcca  57120
gcacttttgg aggctgaggt gggtgaattg cttgagccca ggagtttgag accagcctgg  57180
gcaacatggt gaaacccagt ctctacaaaa taaaaaaata caagaaatta gctgggcatg  57240
atggcatgca cctgtagtcc tagctgtttg ggaggctgag gtgggaggat agcttgagcc  57300
tgggaggcgg aggctgcagt gagctgtgat cgcaccgctg cacgcttgcc tgagcaacac  57360
agtgagatcc tgtctcaaaa caaacaaaca aaaaaaaaaa caaaaaatgg aaacagaaat  57420
tttacaaaag aagatatata gatggccagt aggcatatga aaagatgttt aaaatcagtc  57480
atcagggaaa tgaaaattta aacgtaatga gatagctcat atttactgga atggctcaaa  57540
aagggcttac aggaattggc aaagacatag attaactgga actcttatgc atgttggtta  57600
gagcacaaaa tgatatgatt tcttgggaga aatatttggc agtttttaag attatttttg  57660
atagccttct gaatttctta gtgagttata ggtcagttct gccactgttt ctttcttttc  57720
tttctttctt tctttccttc cttcccttcc ttcccttcct tgcctgtctt gcctgccttc  57780
cttgccttgc ctgccttgcc ttcctttctt cctttcttcc ctttcttttc tttcttttct  57840
ttttttttt aaaggagtct cgttttgttg cccaggctgg agtgcagtgg cacgatcttg  57900
gctcactgca acctccacct cccgggttca agcaattctc cctgcctcag cttccccaat  57960
agctgggatt acaggcgcgt tccaccatac ttggctaatt tttttaattt tggcagaggc  58020
agggtttcac tgtgttggcc aggctagtct cgaacacctg acctcaagtg atctgcccgc  58080
cttggcctcc cagagtactg ggattacagg tgtgagccac tgcgcctggc ctggcactgt  58140
ttatttcttt tccctccagt tttataccta tttagagaga ttagattttc ttgagtacta  58200
ggaatcacta tttttgagca gaattattca aaactgttat tattttttct ttaacttgag  58260
gcaatgtagg agaaagcagt actgtgcagg tgaaagttac aaacaagaac attttaaaca  58320
agatagttac tttccatgta ttggatacgt aacagaatta attctaataa ccatcctgaa  58380
gatggtcagg aggcattagt taagaattga aatgtttgga gcttgcctgt gttgatggga  58440
ttaaggcagg gatgatttat gtgtaaattt atgcgttagt aacagcagta accgctgtag  58500
ttacactagg gttctaagag caaatgttga ttaaacatga atgtagcagg agtgataagg  58560
tttggctctg tgtccccacc caaatctcat gtggagttgt gatcctcagt gttggaggag  58620
gggcttggta ggaggtgatt ggatcatggg agtggtttgt aatggtttta gcactatcac  58680
cctagagctg tctcgcgaaa gagttctcct gagatctgct tgtatataag tgtgtagcac  58740
ctcccctctt tgctctctct cttcctccta ctcctgccgc ggggacgtgc ttgctttccc  58800
ttggccttct gccatgattg taagtttcct gaggcctctg attaaacctt tcttcttcta  58860
aaagattacc cagtctcagg tagttcttta tagcagtgtg agaatggact aatacaaggg  58920
gaaatatata tggttaccaa atagcgaatt agccatggga aaaagtagca aataaataat  58980
tattttactt tttcagatgc taatttttct tttcgtttat tttaggattg gtgggagctg  59040
tccaatgtcc ttaggctgtt ttccaaatga gataccaaaa gctagttctc catcgggttt  59100
ctcaggctgc tagaagcatt cattattatg gttgtcatta cttcgagttc tgttgccgct  59160
atgcccacag tagtatttgt tacataacag gtgcttgata aatatttgct aaatgaattt  59220
```

ttggaaaata caatctgcca cacctttctt ctacagttta caatcttctg ttgagatcat 59280
ccgatagatt ttttttctta gatattgtac ttttgaggcc tcaaattgct gtcttttgta 59340
ttttctatgt ctgcagagac tttccatctt tcactcattg tattcattgt tttttaacat 59400
ctttgtacat atttatagta actgttttaa agtcactgtc tgttaattca aacatctggt 59460
tcatcttgga gtctgattct attgcctgct ctttttttctt tgtaataggt catgtttttc 59520
tgctttgcct gtctagtaaa ttttaatcgt atgttgaaat gtagggagtt tggattgtta 59580
cttcctttaa gggtgctgag tttcattttg tcaggcattt aaattgatag ttgatttagt 59640
attgtcaggt ttggttctct ttgttaaagc aggcattttt cagatttgtc ttttgtccta 59700
gggcatggtt tttaacttca aggttgccct ttccaatgtc tcagctaagt atctggggtg 59760
ttccatgagg tctcttccac tttgcctagg ccagaactcc agcttctccc agtattatat 59820
ttcgttacct ctggcgtcat ctccgttatg ctttcagatc ctgcgcatag acagcccagc 59880
ccccagccaa ggacctgaga tgaaatccat acaaaattct tagtcccttg ctccacaaac 59940
tccaacagcc ttagcagtct aatctcttcc tgtttacctc agtgaaatct gtgttccact 60000
tgagttccat ttccttctgt atcagagaag agccaccatg ctgaaagcaa ggggcactat 60060
gtttctttgt tcttaaggat ggtagcctat ctgcaacaac tgtagtgtga tataaaaata 60120
tataatttat gttgctgaca gttacaaata ctgcttgcag tactttgtaa cataattttt 60180
cagattcaag ttcatatact cttttttttcc acatcaccac acacatattt tcagacttcc 60240
tcctcatcct tcttcttgcc agtagttgta ttataattcc tgccagtagt tacattataa 60300
ttttggttat atcaatattg agtttttatg ggattataac tagataaatg ccattcatag 60360
ttaagtgata gagtatattg tgactttttt cctgcatgtt ttattttttc tggacttcac 60420
agttgtctct cttttttttta aaaaaattag ttttcaatgt tcttagcttt aattcataaa 60480
ctcacccccta attgtataaa tctctcaaca tgtttaagca catttggcat tatatcaatt 60540
ttatcttttc caggtgcctt ctaatctgtc ccagtctgga ctaattgttc ttcctggctt 60600
gctgtatggc tgtctactca agatgtccct tcaccatcat tctagggatt ccctttttcct 60660
ctcttgtggg ttagattctt cagttcttgg agactgtcat cttctttcat ggtttcccac 60720
tcttgttttg gcggagcaca tctttagtaa cttcctgaca aagtgtatgg tttgagattt 60780
cgctgatttt aaaatgccct tattatatag tcacacttga tttatagtct gtcttggtat 60840
agaattctag gctgagaaga gttttccctc aaaatcagaa ggttttgccc aattgttttt 60900
tagctgctag tattgctgtt aaaaaggata atgtcatttt gattctagat tcttttatga 60960
aacctgtttc ttctctggca gcttttagga tcttctgttt ctttggtatt cagaaatttc 61020
atgagatatg tgtgcttcta ttttggtctt attttcatct gttttgccag gtactcatgc 61080
aactttccag tttgaaaact cacatccttc acttttgagt atttttcttg agttatgtct 61140
tcggtttctt ctcagtgttc tctgtttctg gaactcctaa aatatattta acatcctgaa 61200
ctcttagttt ttgtttagtc ttctgatttt catttgtctt tttattctgt atattctgtt 61260
aattcctcgg cttcatggtc ttctagccct tcttttgcct atcttatggg gttgaggatt 61320
aaacagttta tatacctgag gtgcttagga tatgtctgtc atatagtaag tgcttgtgtt 61380
agctgtaatt gttgtttact ttcataactg tcttgaggga aaggtctttg gtcttgattc 61440
tttgacttct tggctgtaca tgaccttgga cgagttatgt aatctctttg agacctacct 61500
ccctcttctg tatagtgtta ataagctcta gctctcagat gtttgtgagg gtcgaatgga 61560

-continued

```
gtatatatgt gaaaatgttt aatacctttg tacagaatta atagttagta cgtggatctt  61620
tcaaatatca aaagttttca gtttgatggg aaaatgatgt ctgaattttc agggttattt  61680
ttaagagtac ttgattatga ctgtcttgta aatctctatg agctaggtat acttgcacta  61740
aatgctaatg ctttttaaag aagttatgtc ttaatattca gtctcattat gttaggttga  61800
agatagaaga ttatgaaaat attctctgaa aagctctggt tttacttcag attgtataaa  61860
tctgtgtaat gtaataatta tttaagaatg acatgattac tactctaaac ccatagaagg  61920
ggtatttgtt ggattattta ttttcactta aatggtattt gagattagga aaaagaaaat  61980
ctgtcttttg gtttttcttg atagtattaa tgtaatttca aatgttagct catttttgtt  62040
aatggtggct ttttgtttgt ttgttttgtt ttaaggtttt tggattcaaa gcataaaaac  62100
cattacaaga tatacaatct gtaagtatgt tttcttattt gtatgcttgc aaatatcttc  62160
taaaacaact attaagtgaa agttatctgc ttgttagagt gaggtagagt taaagataca  62220
ttttaacaga attgtattcc taaaccgatt aagtcaagaa gtccaagagc attgttagat  62280
catttagaaa gtgtagtgat gaggtaaaac attgttggca cagattcatg ttacttgatc  62340
tgctttaaat gacttggcat ctagcccata tttgagccca taaccgtgtg gtaatttgaa  62400
gtgtaattca cagtagagct tctgttaaag cactaatagc atcttccatg gaggtatact  62460
tcagagtgaa tataattttg tttatcctgt gtctctagag ctattgactg aaaaagctgt  62520
tagggcattc tctaactgta catcacctaa gttatttaaa attgctgaat taggtggctt  62580
gtcttgtcta ggacagagtt ttaaggactg cccacctgat tgatagagct agttgacctt  62640
atctttaact ttttgttttt cttttgactt tgggagtaga gatgtgaaaa ggtaaaaagg  62700
aaggaaggaa gagaaaactt aactcttttt gcccatgaag actgtttttc cttctcaaaa  62760
tattgactat tttctgattt gtaaaaatcg gcacataaaa cgtgttattt tttacttgac  62820
ttttatcttt cccatgtgat atctataaat tatagatagg aaaaatttat ctgtaattta  62880
gtgatctttc tagtgtgata aaacgtcaga agtactgaga gtggagtgga cattgatatt  62940
gttactctca gtaagttttc actgattttt ctcagagtca tgaaggaaca aacgtttgtt  63000
aagtccttat cacttattag ataacacaaa acatgttggg ggggtgtgta cagaggtgag  63060
taagatgtag ctcccattct caagtcgctt acattctaat gtaaaaggta gacaaagcat  63120
tacagaagaa gtaactctgc tatagaaggt tgcaatgaag agaacattgg aaacactaat  63180
tttaccttat aaagaaggtt tcataaagga aggcaagttt gagctggggt gaaaaggacc  63240
agtaagggtt gactttcaag ccaaggagag gaggggaagt gatgttacag gccaaaggaa  63300
tggcattgta agaagcttgt tggcataaaa gtgtttagaa tatggcagcg aattcattat  63360
catcagattg tggtgtctgt atgttggggg tgggagagaa ttgtggtggc aataggcaac  63420
aagataaaag aaagtaaaag gtgttatgga aacttaatgg gtccagctta caaatgatct  63480
atgcatttag gggtctttct cttttcctga taaacctctc ctacaaagag ccttgttgcg  63540
gataccatag tgtttctttg gaggaaaata aaaactacaa agctttgtat tttttgcaca  63600
actggattca gaatataagt aataaaaaag gacaagaact ttcaaaagct agaagccatt  63660
aaactgagtc acttcagggt tagactatca gaactgggga tttagaaagt ctcagaatgg  63720
aaatcgaagg acaccaaaga caaattcggc ctttttcaaa attttattct agtttaacat  63780
attcaaagaa agggaaggaa attcttttca ttcctgtgtg tagtgacttc ctgctttaag  63840
aacttaggac ttcagctgta ctatcagtat tgtaggccac ttaacattat tatggttaaa  63900
gttggcattg gagagagcct aggaacctaa ctgcctgttt gtttttatat ttccaaccat  63960
```

-continued tggattccca agttaatgaa gtctgtttat tagttgaggg tagctcttaa tgcatatatt 64020
ttaatgcccc ttccccacat ggaatcataa gctttcagaa ctggagagta cctgaaagag 64080
atcatttagt ccaaccttct cattttacag atggggaatc tgaggcctag agaagttaag 64140
tgagttgaac aaggtcacac aggtacatat ggtagccgac catccactgt ttatgccaat 64200
attcccttta cgttttgctt ttttgcttgt tcgttttaac ctctccaaat tttactgact 64260
tcagaagttt ctagaactaa gttatagcat gttttgagtt ctaatgtcac tttccgatct 64320
tctttacctt ttttctacct ctgtttgtat ttctggttct ggttaagtga gtctggtaag 64380
cagcaggtgt tctattttat ttcttttatt tttaggatag tattacatgt gatatatatg 64440
tctttgcaaa catacataat ttgaagatct taaaatattt gcactaggca tacccacatt 64500
taatagtatg ttaaatcttt tatagcaatt atgatataca tgggtgaaga agagttccta 64560
atatggcctt tctgattaac tgtatctgtt tatatctgtg ttttcttcag gcattcataa 64620
cattaagcaa attcaggtgt actgttactt aattgaatta atcagtttgt tttgtacaag 64680
tatattttat ttttgttcct tgttgtataa tctggtagga atggggaagg ggagatagtg 64740
aataaagaga tgtatacttc ttgcctttga ggaatttaag ttttcactgt ataccaattt 64800
tttaaaggta tttactatat ttcagtgcat attttatttg acatacttta tcattttgtg 64860
gtaaaccttt agctttacta attttcatct attaagtttt cttttgtaag atggtgatag 64920
cttcatcaaa gagagtaaag aagagacctg cctacctagc tgattctatg gcaaatctca 64980
cttctctgga agcttttcct gttaatctta ttccttcagt ttctgcctct tgtttcataa 65040
aaactcattc tttaaatgct tattcatttc tcttgtctca tataaaccaa tatgaggtac 65100
tggtatcttt tgagttttag ttataaggaa gcataaatgg ttaaatttaa atggctaaac 65160
cccatttgcc atttgtgtat ctttaatttt agtttgttga gagacttatc actaccaaac 65220
cacaaagaat ttaaaagaaa ctgtcagtag gtataggtgg aaggagggca tttatcagag 65280
attttaattt aagaagaaag tcttcatcct tatcctacca acccccattc cctgagcata 65340
tttatcatta ctagtcccag catatttgct cccatatttc ctatgcttac ctgtgaagat 65400
tttcataact ttttccttgc tttttactgt cactgttggt tctgtgattt atgacagata 65460
ctgctcttgt aggaatgctg gctttgactg aaatttgtta ctgcttttgt atttaaaact 65520
tttttttat tataagtaga attatggaac agtagtagaa aaagtttgac ttttgtaatc 65580
agagatactg agcttgagtt ctggctcttt catttgtata ctgttatttg gggcaagttt 65640
tttaatgctc ttaagtctta gctttctcat atataaaatg gagataataa cagttatcac 65700
gtgattgtga ggatgaaaca aaaaaaagtg gaaactcttt gtaaggtgtg ttcatctggt 65760
tgacacttag tagtcattac ttccactttc cgtccatata gtcctcttaa cagtaatatt 65820
tgagaggcat ttttattaaa gcagtcttaa ggagtgttcg tcaaaccaca tgttctggga 65880
tcctgagaaa gtaggggaag tttagagaac tgaagctgca caaaactaat gtttattttc 65940
tgttgtgttg tcctgagacc agcttcttag attgtgtttc ctagtcctac atctctgatt 66000
ccttataaaa tattccatta tgaattcttc actattgaca atttctcccc ttttatctta 66060
aaagtaccaa agaaaagtgta aaatgtgact gtcttgtcag tcctcttttt cctgtttttc 66120
atgtcagtgg gtatgaaatt actagcaagg atgcatatat gtgcatatgt cattactaaa 66180
tgcattttct ttctagaaaa actcaatata ctaaattgta ctaaaaagga aaagcttgtt 66240
ttgttttgag tggtagtatg aaagttgttt tattttaggt ctgaccagtt agaaaccaat 66300

-continued

```
ggattgtagt ttatttataa ttagttaaac cttcatgtga atttggtttt gaattacctt  66360
taaggtagag aagaaactat atagatgttt ttcagggttt ctaaatgtac aatacaggtt  66420
cacaatcact tatttgaaac tcttggggcc aagtatgttt ccattttcag aaattttagt  66480
tttcaaaagg tagcacagat aaatatactt ttacataaac accccagtgg ggtgtgggtc  66540
agtacctgaa atgaaatgtt ttactcttcg ctctaagtgt attaaatatt atgtacaatc  66600
ttattacttc agatcaggat ttgctgtagt tgagtttgcc ataaaactta agagaaaatt  66660
ttagatgttt tgaacttttg ggatattgaa attgcaggtt aaggagctat ggacctttat  66720
ttgttttaaa atgctaagag tttattttaa gtaattttta aaaaatttgt tttgcatagt  66780
agttggagtt accagggtac tgctaaccac actgatatgt aagatctctt tctgagcctt  66840
ttattgtttg taaacatggc ctgttaatca ttagaaagcc agtacatact aacatatcac  66900
tgctattaag acaaatatta gcatactcta gtaatgacaa gtcagcattt tactattctg  66960
tattgatttt acttattctt tcattactct catactgtaa ttaaaacttg caatctgaga  67020
gactgttgaa aaaggtgatc gttggctttt caacagggag taaggtctgg tttaaaaaaa  67080
aattagtaag catttggcca agtagattaa caacattcag tttttcttta ctgtccttat  67140
gcttttacta tttttaacat atatcttttt gaagaatagt ttgagaatta tgtatgctta  67200
actatgagat acagatacta ttgaaactag tcagttgttt ataggtactt gtaaaattaa  67260
aaatatattc caatagcatg cagatttttc atagaggaaa tttgaaagca tggaagcacc  67320
tgaatttaca gtactctgta ttagtggcat cacaagtttt taagcaaatg tattagctct  67380
aattgcatac acttaatctt ttaagctttg gttttattat tataatatgg gggtgataac  67440
agtatctact taatagaatt cttgttatta catgaaataa ttaatgttaa acacagcata  67500
atatgtgtca cattataaag attcaggcaa tgtttgttag tattagtact tttttttctt  67560
cctaagtgca aaagataact ttatatcact tttaaacttt tcttttagtt gtgctgaaag  67620
acattatgac accgccaaat ttaattgcag aggtaggtat gaatgtactg tactatgttg  67680
tataacttaa acccgataga ctgtatctta ctgtcataac aataatgagt catccagatt  67740
atcgagtgag atacatattt aagaattatc tttaaaaatt tcaaaaattt taattttact  67800
gttgtgtttt aggaaaaagt attgcataaa gctattaata ttgtcaggaa gactaaagtg  67860
cagcatagac taagaattag gaaaattcct agactaaaaa tagtataagg agagggttta  67920
cctactattt gaggcagttg gtctaatagt aagcaatcac agggagaaag cagaactact  67980
taactcttct gtgttgagga atgacataaa aggtaggaaa ggatataaca aatgttgata  68040
agaggagtct gatggatgag aggagggaac tgctttaaat gagtttctac ttcagacata  68100
agttaattct cagagcccac aaaaactttc acttttattt gtgaaataca actcagttct  68160
catggcttaa cactttaaac catgagaaaa ctgaagagtt gagaagcttg gcagatgctg  68220
ctgtgatagt caaaaagaaa gtgggtgcca tgagctacta ttgatgtatt tgccattgat  68280
ccctcctgaa aatctagaat ggactttcag acaaatggtt tgaaaattct aaatcactaa  68340
tgattgagat ttagtatagg tttactaaga acgggttttt tttgtttttg tttttggtgg  68400
atttaggctg ttgcttacta agcaaagcag gctttagttg aggtttatct tgctttaaac  68460
agatatttaa cagattttcc tggaggtttt tgtgtaccac tgggaaaatg aagttaggca  68520
gatgactaag tgaaagctgt cctgctgact ccttataatg atagtcattg tctaccagaa  68580
gatctctcct gtcacaccaa aggataattg attatatcct gtaccatatt atgagtcacc  68640
tgattggaga tataagacat acttctcaca tatttagatg acacaggtta gtacattgaa  68700
```

tatcagccag ggtttttaag gatcttaata gagtggaact aaggtagaaa ctattaagag 68760
caattaatag tgatatatct atagtcctgt ttctaaacaa gtttttttaa aaacctcaac 68820
tctgactata gtgaacagag aagtcttgga ctcttacaat tcatgtgaga agacctgaaa 68880
ctttgataac aattatatac attttgtgag taatttcttt ggtgtatgcc ttcacatatc 68940
tctggtatgt gacctatgct gcagtccatt gagcatagat tcccagaatg tattctcctg 69000
cagaaaatgg aggaaaataa tacttggctt ccctaatgat tacatgtgta tacaacacta 69060
acatttgcaa gaccaccttt aaataacaca cttagcattt ttattttatg aaatgtaata 69120
tgtagttctt tgcatagttt atcctattag taatctattc tgtctttgga atatgttttg 69180
tgatgatgaa ataaatacta taaatagtat tattcctttt gcattgagag tcctgacgaa 69240
atgtccatgt gacagttcat tttgggttta gctctacctc taatatgtga cctatgctac 69300
cagtccgtat agcgtaaatt cccagaatat atcctcctga ataaaatggg ggaaaataat 69360
acctggcttc cttaatgatt atatttaaga cttatcaaga gactattttc tatttaacaa 69420
ttagaaagtt aagcaataca ttatttttct ctggaatcca gtgtttcttt taaatacctg 69480
ttaagtttgt atgcaacatt tctaaagtta cctacttgtt aattaaaaat tcaagagttt 69540
ttttttctta ttctgaggtt atctttttac cacagttgca caatatcctt ttgaagacca 69600
taacccacca cagctagaac ttatcaaacc cttttgtgaa gatcttgacc aatggctaag 69660
tgaagatgac aatcatgttg cagcaattca ctgtaaagct ggaaagggac gaactggtgt 69720
aatgatatgt gcatatttat tacatcgggg caaattttta aaggcacaag aggccctaga 69780
tttctatggg gaagtaagga ccagagacaa aaaggtaagt tattttttga tgtttttcct 69840
ttcctcttcc tggatctgag aatttattgg aaaacagatt ttgggtttct ttttttcctt 69900
cagttttatt gaggtgtaat tgacaagtaa aaattatata taaatacaat gtataatatg 69960
atgttttgat gtatgtgtat atacattgtg aaatgattac tacagtcaaa ctacttaaca 70020
tattcatcac ctcacataat tattattctc cccccagggt gaaagcattt aagatctaca 70080
agctacaatt ttcaattata caatgttatt attaactata gtcactatgc tgtccagtag 70140
agcttcagat cttgttcatc ttgtgttcct ccctccccac cctcagtccc tggaaaacag 70200
gttttaaaga tagttgctaa tccttatttc ttctaaattt ttaaatcagt tgctgcctca 70260
atttctatat gagaaatgac tgattgattt catttttctg ttcacgctac cattttcata 70320
tcatactagc acatgttacc cattaactgt attgcagatt tggtctcaca aaattcttct 70380
aaaataacat ttttaaaaag catattaatc aaaaataagc tttatatttc tgaagcttgt 70440
ttgagcatag aatgcctttg gataaaatac cattacctag taaagtgtga acttttataa 70500
tccataaaaa ttattctttt ataagaatat tcataaatgt agttagatta atagaagatt 70560
ctcgattctt tgatcagaaa actaaggact atattgaaaa atcagtgaca aatttaattc 70620
ttatagtaca tctgaaagaa aaaagaaaac tcttgggaga acttttacag tgatttaatt 70680
ttgctgttga tatatttctt tgggtggtaa gtatggcaaa acatgttaaa atttaatgca 70740
aagagatttt gtacattttt ccatctctaa gaaggacaaa gcctaagccc ctccagatag 70800
atagaaaaac tcatttagag agttctcctt catgttaatc taatttcttc ttaattcagc 70860
tgtaaaacag aaatagaatg atcgtattaa tcatttaaag ctgtgtaatt gcatagattc 70920
cttgttcctt taccccctct tatatcttgt ttcctatcct ttgtgacttt ttttgcatta 70980
tatataagga tgccgaaata ctgtttattg ttgatagttt acaaaattga atcttacatt 71040

-continued

```
agtgcataat tttggtgaat gttgaagatt atggtagatt gccttacatt tctgcatatt  71100
gtttgcacct tggaatgata gcactggcat gaattataga gctgaggatc taaagatttt  71160
tactttgatt tatcccatta tcatctgcag ggaaacaatt gcttttactg attaaaaatg  71220
caggctgggc acagcggctc acgcctgtaa tcccagtact ttgggaggcc gaggcgggcg  71280
gatcacaagg tcaagagatc gagaccatcc tggccaacca acatggtgaa acctcatctc  71340
tactaaaaat acaaaaatta gctgggtgtg gtggcgcgtg cctgtaatcc cagctactca  71400
ggatgctgag gcaggagaat cgcttgaacc cgggaggtgg aggttgcagt gagccgagac  71460
tgtgccactg cactccagcc tggtgataga gggagactcc atctcaaaaa aaaaaaaaaa  71520
tgcagtagca aaagcgatgg tagaaattta aaacagagtt gatgagcagc atatattttg  71580
gtagtggaaa aaaaggtaaa aaattttttg taataaaata gaaaaatttt gtaatgtgga  71640
ggcgcagaac actagattta agccaggggg tcttaaattg tgttacattc cttttaaagt  71700
ctgatggaag gtataaatgt tctcccctca aaaaatgtgc atagtgtaca taaaattttg  71760
cagtttttat tacattgaaa tatattcttt tagacagaat gtaaaagaac cttcatgaaa  71820
actatgtcac tttttatgc aaaaaccagt ggctactaca tgagagcaat gaataaatct  71880
aagtggtaca aattaaccaa aattaagctt tagttctgtt caatactaaa ttttaatgaa  71940
aagactgcta tttaactttt aaaataacaa gttgaaacta tgctctttga ctttgacttt  72000
gcaactttta tatgatcttt gatatccaat cagtgttgac tttggtaaaa agtgctgaaa  72060
atgctatttt acaaaagaaa gaagagtaaa tggaatctgt agattctatt gcctgatgaa  72120
agtagacgtg tcaagaaata agaattctcc aaggctcttc agataaattc atgtttcatc  72180
atttctttg ccttcaagtt actgagatca tttttggcaa gatctgtatc attaatgctg  72240
tgttaggaaa gaaaagatta tgactccaca ttttactttc aaggttgaag agttaaactg  72300
tttaaaaaga gtgtatgtta tcctgtaaac agcagtatca ggctgtagaa tttgtcttct  72360
gaaagcaggg aacttatata tagcaaagaa cttcatagtg ctcccatttc ttgacaaaac  72420
ctctcgagaa gctcttgatt gaaagtcttg gctttcatga atctggcagc tttcacaata  72480
gtggattttt catgacaaat catcttacac agggaattat tcaagggttg gcacttgaaa  72540
cagtagaata ctttcacaac aagagataag atttctttca ggattgatga cagtcttgca  72600
ccctagcgca tactgatgaa gagagcagtg ggtgaccatg acatggagag cttctgtctt  72660
taccagtgcc ccaatatcag atgtgttgtc tggcagtaag gtgtactgtc tgcctacaga  72720
atactgaggt ttcttcagga gaagtttttt ggtaaagaaa ctttaccatt ttgaaagtgt  72780
taatgttttc tgaagcttcc aaaaagattc caaaatggga atgtttcctt gattgtgtca  72840
ccatgcttgc atttgatgaa aacttgtagc cggctatact gagaaatcat atctgaagaa  72900
aggtggtact tccaatcttt ttgtgaccta ctttattatt gttttttaa tgtcagggtt  72960
tttttggaa tggagaaaag tatttgatag aggtattgca acagtcttat tcttcttcat  73020
gctacaagta tatttgactc tttctaagat acttgccttc actgttcaac tgtgtgactt  73080
tttgtttgtt tagcattaca atcaatatcc tagtaggatg atttaatcaa tgatttttaa  73140
ttggaacaaa tagtttttgt aatggtctag gcttttccaa cttaactgtg ctctcacatg  73200
tggtctcttt ttctccctct ttcctccttc ttatacactc tcacccacac acatatgcat  73260
acatacctg tctgatgtat ctgcttcttc agaatagttg gctgtgctct gctgatgatg  73320
agaacttgcc atttaagaag gacttgggat agtccatgtc atcatgttca gggataaaag  73380
taaaacccaa gggcatttaa actttattgt attttatttt ctgtttccag tccaaattaa  73440
```

atccaagaga aggctccata atcaaaaagt aaggacatat tttaaatttg ccaatgggaa 73500
gatattctag tcattacagt ctggtaatac tatcaattct gtttctcttc agaggtgagg 73560
ggagactatt tgatgaaatc gtaagtcctg tagggtgttg tgaaataggg ccagaatgaa 73620
agatagcaag aatagtgtta tgaaaataaa atgcaaagtt tataatatca tgtggtaaaa 73680
tgtaatagta tttacttcat cagtagaact gctctagtag ctgtatattc tccatccttg 73740
cataggttgg aatatccccc aagtgaaaag agattgatgg gctaatagtt aatagaaaat 73800
ggagatctgt acatacagtg ttaagaatgt agatattaaa attgttatat ttagctgtta 73860
cataatatta agactcagag ttaagtaatt tcactgaaat tgattgcttt ttgtgtcttg 73920
gagtcaaaat aaataactga aatctactat acttggctca tgcttaatta atatacttag 73980
accatatttc ggatgaatta ttcacagaat ctaaaggagt atcctcgtgt tcttaccttc 74040
tttatccctg tgtttattta aaaaggcaaa aaaaatggag cagatgctgt tggttgacca 74100
tattttactg aacagtagca tttgtgttta ggttgaaaca gcattagaaa actagatacg 74160
gattaaagtc agtggtaggt tttttttttt ttttcttcca ggaatgtttc ttatagatga 74220
tcaaacaggc acaggaaggg gaagtgttgt gatcaatatt atccagttaa tattagcatt 74280
cagaggaaaa tttgagtcct ctgatacact gttaaatttc tttctatact atcaagtcca 74340
caaatcctgg aactgcaaaa gaattttgag actgttcaaa ataattaatc tctgtatagg 74400
ctcaggcttt cctgcaaggt tatgaaatgc tgataaaatt ggtcttattt tgaaaggctc 74460
ctcagcttat acctttcctt acaaatgctt ccttacaaat gctaaagcat ttaatgactc 74520
ctgacttaaa gggaatttgg acagattgag gttgttggtc ttggaaatat aatactgcag 74580
gcttctgtaa aatacttgaa atgtaattgt tttaaaactt tcaaagatac cacttgtttg 74640
cctgttggtt agaatactgg tgaaataatt tttaatcttt tatgaataac taatttcatc 74700
ataagaaaac ttagctaagc atggtaaagc tgttgttata caactgtgga attcttcctg 74760
aggagtaact atcttataat aaatgtagtt gattatctaa agtagtttta ttcttggaat 74820
atctcataat aggtttattc tcttcttgtc agtatttcct tgtagattga gcctgtggat 74880
ttgcattttt gtaattgtga atcaccatta taggagatac atgcatttta tctacttttc 74940
agtttgtatg gggttaactt tattagaatt atctttaatg ttattttgct tatatcctta 75000
attttaatta tagacaaaca ttaagaagct ggagaaaatt atgttctagt gacatttata 75060
tagaagaaga atctttttttc cccctttctt ttttgaaggg agatgaggca gtcatatttt 75120
ggtaaagaat ttgtagactt tgcagaggtc tcttcaaaat aatctggctc agagtcttga 75180
catatcctca gcagacatgg tgcaaattag atggcagagt ggtgggtaca agttgaccat 75240
aaaataacgc attaggttag taatgcccaa ataatacttt gggttttcag tgttgcagag 75300
aagtcagaca actgatagtt attataaaga aaaatgttct gagagtgagg taaccgctta 75360
agggaaggaa gcctccttct gtcttattca ctaatttaca agaagataat tgtgttacac 75420
ttccttagga gtcattcatt tgtatatttg acacttttgc tttatgaaca tgtgaagatt 75480
attcaaaagt aagctgttgg tgattttttt cttccaagaa agcatgccac agggcaactt 75540
ctagggttgg ttctcatcta gtcctgtgct ccacactatc tgcatctgca cttaagtttc 75600
aatattagat aactcacatg tttaaactat gaagaaagag ttaaaacatc ctgagaatgc 75660
tagtaagtat gtatttttga aaggacttcc aaaatttgag tttaaagagg taaactcctt 75720
ttacatgaca aagttactta gaaacactac tgctgtttcc ctctcccttg ccttctccct 75780

-continued gtcccatgca tacccccagc tgtgttccag aatgatggca cataaagtaa acattcatat 75840
ttatttccct tttttgttt ttttttttt ttttttttt tgcttgtttg ttttgttttt 75900
ttgtttgaga cagtctcact caatcaccca ggctggagtg cagtggcaac atctcagctc 75960
actgcaacct ctacctcctg agttcaagcg attctcctgc ctcagcctcc cgagcagctg 76020
ggattacagg cgcctgcccc cacgcctggc taatttttgt atttttagta gagatggggt 76080
ttcgccatgt tggccagact ggtcttgaac tcttgacctc aagtgatccg cccacctcgg 76140
cctcccaaag tgctgagatt acaggcatga gtcactgtgc ctggcctctt attttttctt 76200
tggttaaact tttagggaaa aagtttgagc tgcttttaat tttctttttg tttttaaata 76260
aattattaaa gtttctctat gttaggaact cttgtgtaca tgagttcatt gagcttattc 76320
ttaataaaga caaatcttct agaaataata gttgtatctt taaatgatct caaggaaaat 76380
gtttggtttc tctggggaat gaattttcat gacctaatct taaatcaggt tatttttttct 76440 agcctgttta ctaaatttct acatgttata acctaatgaa attttcttac ttcctcttta 76500
tttaaaacaa actataatta ctgtcttttt aaaaatcttc caatgtggcg ttcttatttt 76560
tcttaacatt tgaattttcc tgggccaaac catgttacta tgatacacat tatttaaggc 76620
tgttatataa tacagtaaaa ttgtagaact ttcatacctt gaaggatctt agcaattatt 76680
taattcaaac ccattctaac atagatgata aaacagattt gcagggttgg gcacggtggc 76740
tcatacctat attcccagca ctttgggaga ctcaagcggg aagattgctt gagcccagga 76800
gttcaagacc agcttgggca acatagtgag aggctgtctc tacaaaaaaa tatttaaaaa 76860
atagccgggc atggtgtcac gtgcctgtag ttccagctgc ttgggaggct gaggtgggag 76920
gattgccaga gcctgggagg ttgaggctgc agtgagccat gatcacacca cagcactcta 76980
gcctagagcc tccctgtgtg gcaggctcta cacttcagat aggcaacaga tcgagacctt 77040
gtttcacaaa acgaacagat ctgcaaagat caacctgtcc taagtcatat aatctctttg 77100
tgtaataata aaaaccccat cttctaacct taaacctggt atttttttct acgaaactat 77160
gttctgcagt ccaaattatt tttctttatt attttgaatc ctaaagtaga aatagaaact 77220
tagaaaaata aaaagcaact cctttatgac atatgaggac tttttcagtt ttaaataaga 77280
aaaacccaac tcaaagtagc ttaaataaaa ggagacattt tttgacttac ataacctaaa 77340
agctctggcc tggatctagg tgctcaacag atctcaagag tatctctctt attctctctc 77400
cctcccttac cctcctcctc ttttctctct tctgtatata tgttattttc aaacaggctc 77460
tcacaagtag tggcaagata tagttcctaa tagcttcagg tttgcattct acctacttta 77520
gcaactatga tgagaagaga gctacaattt gagcaaaaat ttgtagggtg agttctgatt 77580
tccctggatt gaggcacatg cctattattc ctgaaccaaa tattctgtcc agggaatgga 77640
attctctggg gcatgtatct aaagctgaag tgtagagcct gccacacagg gataataata 77700
gttttccaaa gaaaaatcaa ggaggggaaa gaatgttgga aagagaaaaa aatatcagtt 77760
gtctgcttca catttgttct caataattag tttcatagaa gtgaaatact gtgtaacacc 77820
ctaaacttta gagattcttc gtagacagga aaaataagaa ctcaatgaag ttgtgacttc 77880
attcaaatca cgtagtttat atacatgcta ttagtaaaac ccaggacagc tgagtacaag 77940
ttttaccctt atattcacat tgaggtccag atcctggttt tgaatgagat aattacgtgc 78000
agtcggactg ttttctgatc ctaaaaatag agacaataat atctatcttg taaagttatg 78060
gtagtgttaa agatatataa aatgttggca agtaccttaa tatacaataa ctactgctat 78120
atgttgtcat tgtaataata atcatatttc ttcctttgtt gaattgcttt cctgtagtaa 78180
tcttattgtg atcatcctga aacatagatt tccgagcttc aagcaaacac tattatgttg 78240
aaaaatctac attatttcta agtttagcag tgccagtgga aagtttattg aaatagaaaa 78300
ttactttttt aactgaggag tgtagattgt gaattcgtga ttcatcttct taggagatga 78360
tcggaatatt gataaatatt gatgcataga atatgaacaa aacattacat atcttgtgct 78420
gtgatattaa agtagtattc tgttctggta gtagtatggc agtattttag gtctgaaaga 78480
tgtacataat ctgtactttg aagtctgttt tttaagagat taatcacaag agatttacat 78540
aaaacaacta aggttaaaaa taaatggtgg attagagata catcaggcaa atttcaattt 78600
caaaagcaga tgacagaatc tcagtatcag ggtagcattt aaagcaaaaa gcattaaact 78660
ggatcaaaaa tgtcatttta catcaacaca gggtacactc caggtaaaga cttaacagtt 78720
atgaacgaat gtgctaaaca tcaaaatgta ttaagtaaaa gctgaaagaa atgaagaata 78780
attggtagaa aagcaatgat aggaatcctt aatgtacttc aaaaggcacg aagtaagaag 78840
gtacagtcat gtaccacata atgatgtttg agtcaacacc tgacctggta tacgacaatg 78900
gtcctataaa attataatgg agctaaaaag cttctatcac ctagtgatgt tgaagccgtt 78960
gcaatgcaat gtatcactca catgtttgtg gtaatgctgg tgtaagcaaa cttactgtac 79020
tgtcagttgt ataaaagcat agcacagtta tgttcagcac ataatacttt ataatgataa 79080
acgaatatgt tactagttta cgtgtttaca gtactattat tttagcatgt gcttctgctt 79140
attaaaaaat gttaactata aaataatctt taggcagatc ctacaggagg tattccagat 79200
aaaggcatta ttgtcatagg agatggcagc tccatggatg ttattgcccc ttaagacctt 79260
ccagtgggac aagatgtata ggtggaagac agtgatattg atgatcctga ccttgtagag 79320
gccaaggcta aagtatgtat ttattagttt ttaacaagag tttaaaaagt aaaaaaaaaa 79380
aataaattta aaaatagaaa aaatcttaat aaggatacaa agaaaaaatg tttttgtgta 79440
gctgtgtaat atgtttttgt tttaagttaa atgttacaaa agagtcagag ttaaattttt 79500
ttatatttat aaagtgaaaa agttataaaa tgctaaggtt aatttactga agaaagaaaa 79560
aatttttaaa cagatttaga gtagcatgtt tataaaatct acagtagttt acagtaatat 79620
cctaggcctt cacattaact caccactcac ccactgactc acccagagca gcttccaatc 79680
ctgtaagctc cattcgtggt aagtgcccta tacaggtgta caatttttat atcctttata 79740
ccatttttac tgaacctttt ctgtctttta gatacacaaa taacattgtg ttacagttgc 79800
ctatgatatt gaatacagta acttactgta caagtttgta gcataggagc tgtatcatat 79860
agcctgggtg tgtagtgaac tataccatct aggcttgtgt aagtatattt tatgacacag 79920
tgatgaaatc atccagatac agtttctctt aagcaacaca taactgtata tatatatata 79980
taggtggctt taataataaa ataatgaaat atatttcttt ttttctgtca ttgacaaaac 80040
aattaccagt cttactaatt agatcaactg caaaacaaaa tctcactcaa aaataaaaat 80100
atgtaagtcc cattccttga ttacaattca ttagaactgg agatttttaa aaatgtttaa 80160
atttatatgg aaatataaaa tcatgtttta aataattttt gattcaatga ggaaatgtaa 80220
atttagaact aaagattaat aactagagat ttataaaggc aaaaatgtta atgaattagg 80280
aaacagtaaa ccatttgaac taatctaaat actgattgca tgaaaatgcc aataaaatca 80340
atacatattt ttaaaagcca gtcaaggata aaagaaaaga gggaaactaa aagtgagaca 80400
ttaagtatga gaaaggagat aaaactaaag tgtggaggtg atgttaaaaa ttatattcag 80460
gtctgtgcta atcattttgg aaatttcagt gagaagtggg caattttcag tgaatatatc 80520

-continued attgtaaatg ctttgaggag agacaaaatc tgaatagacc ctgcaataat gaaaatgtct 80580
aggagccctc aagaaatacc tggtttaaat tgcatttcag gtggctggtt atcacacctt 80640
gaagtatcaa gtaattatgt tatctaaatt ggaccaggtg ttagaaaaat atgtgagact 80700
tcacaggtgg ctgcttatgt agcccttata ccttaatctg ataaaggtag catatattta 80760
aaaagagaga aaaccagaag gtacaattta gggaaaatta aatacttcta tttggccaaa 80820
gtaagagtac attcaaggga attgtgagag gtaagagtgg aaacagaggt tggagctgta 80880
tttttatgct gtgattgaat tacagtgtgt gataaatatt gctcttattt gggtagatta 80940
ccatttaaca ttttgaatta attggtaatt ggattaatct taacttttaa aaaactaatc 81000
tgagagtggt ataaaggata gattacagaa tggataaagg gtgataaatc agttggctat 81060
ggcaaaattg caggaagaaa ctgaaatagg ccacagaaaa ctgaaactga cattttgagt 81120
agtatttcag aatcaagatc tggattttgg caactgaata gatgcgtagg aatcaaagat 81180
gagtatacta aatgaactta atctatgatt tgtctgtcat tttattgtgt accattagtg 81240
tgtatgcatg tatgtatgtg ccaggtagtt aataggctga ctgtgtctct tagctccact 81300
ctgctgcctg ggcctttgcc atagtgctgg agttccctca cttctctttt ctgtaaccct 81360
attatattac tgctgtctct cagctgtgtt tcattcctca agcagaaaga agatgggagg 81420
atcatatagt agttgactag aagctgtgga gtttgagtgc tgggattata tctagttcca 81480
ttacttatga agattatatc tagttccatt acttcacctc atctataaaa tggtttacca 81540
atagtaccta ccttacatgg ttttatgagt attaaattat gtatttctaa agacatttag 81600
aacaatacaa agaatatagt gtgggctcaa taagtgacga tggtgttagt tattagaagg 81660
ccatcgagtg ctggagaaaa taattgaata tcattgatgg aaataaagga agttttccac 81720
gttaaaaagc ttcggttttt ggaaatgtgt gttttcagta tttctgagat taccaggtag 81780
aaattccagc cagatgttgg aattctgcac tggcagttgg gaataaagtc atgttaaagg 81840
agataagttt tggagttatt gtgtaaaatt ggtaaagcac tggaatagat tggtttgaca 81900
gaggggaaac tctttttgag ataggcctat atttagggac aagagaagag acaaccaata 81960
agggttgaaa gaaaccttga gagagtaagt cctatgacag aagcagggaa gtttcagaat 82020
gattgcagaa agatcagcca ggctcttcct gttctccatc gtggtgcagg atcaaggtga 82080
aaaggataac cccatgcagg aattttgcat ctgcaggctc cgcttcaaca tctgtttagg 82140
agaaagtgga gacagactga cctgagtaac taaggtcttg gaacagctta caggtcagaa 82200
ccaggtgttt tccaaagcta gatatactgt tagcgccttt ggcaacagaa gaaatgaaaa 82260
gactgttgtc tgctgcacag ttcgaggggc caaggcagac gaaatcctgg agaatgatct 82320
aaaggtgcag gagtgtgagt taagaaaaaa taacttctca gatactggaa actttggttt 82380
tgggacccag gaacacattg atctgggtat cagatatgac ccaagcattg atgtctacag 82440
cctggacttc tatgtggtgc tggaaaagcc aggtttcatc attgcaggta agaagtgcgg 82500
gacaggcttc attggtgcca aatagaatca gcaaagagga ggccatgcgc tggttccagc 82560
agaagtatga tgggatcatc cttcctggca aataaattct catttctacc caaaagggta 82620
ataaaaagtt ttcagtgaaa tgtttaaaaa aaaaataaaa aaaagatcag ccagcagcca 82680
ggatgggatt gtgaaaacag caggaaatta gttgttgaca aagcattaat gaccattaag 82740
aaatcagcct cggctgggca tggtggctca tccctgtaat cgtaacactt tgggaggcca 82800
aggcagattt cttgagtcca ggagttgaga ccagcctagg caacatggca aaaccctcgt 82860
tcctccttaa taaataaata aatgaataaa taaacaagca agcaagcagg gcttggtgtt 82920

```
aggcgcctgt actcctagct actcgggagg ctgagggggt tgaacctggg aggcaaaggt  82980
tgcagtgagc caagattgca ctactgcact ccagcctggg tgacagagtg agaccatggc  83040
acccccctcc ccttcaaaaa gaaatcagcc tcataatcaa tttctctgga ttaaggagta  83100
agagcgtctc aagatttgct gtttatagag agggaggcta atagtttgag agagatacag  83160
aatctaggga gagtgtgggt ttttggtctt tcagttgttt gccagccttg gataaagaat  83220
gaagattact tgagcatatt atttagagac aagtggagag aataaaggca catgccagat  83280
aggagataat taataaagca cttgtccaaa atagaaactt gttgaacagg aagagacgtc  83340
aagtataagg agattttaag atgggagaag ggaattttga gtgtttgtat tggatgacct  83400
cagggttccc agtaaagcag gagctgaatt catcgaaggt gatgtgttgg tcaggatcaa  83460
gagagaggtt gggagaacaa agtgctaaaa tcgttgtggt caagagttta aaaagtgtat  83520
accagaagag ttattgagtg atagggg ttt gaaataggca aagctgtagg aaagggggct  83580
ggaaggaata ttaggaggaa cactaaatat acttctgagg tctacctcct ggtctgtgaa  83640
cataaaggag ctgaaagagt aatggctgaa gttctttagt ttagctaaag ttttttagct  83700
aaagctagaa ttgttgaaag ttgtatttga ggaaaaaaag ttaaggatac agttgaccgt  83760
tcgataatgt agcccactgt tgaccagaag ccctacccac aacataaaca ggcaataaca  83820
catattttgt atgtgtatta tatagtatat tcttaacaat aaagtaaact agagaaaaga  83880
acatgtatca agaaaatcat aaggaagaga aaacacattt acagtactgt actgtattta  83940
ttggtaccat acatttatgt tgctgtttac aagatgaagc atctgtctga aatggccagc  84000
agctacagct gtacctatct actgtacata tcaagcaagt cactttattc ttataatgtc  84060
tatgacttct ttctttgaaa gcgcttccat catcactgtt ggcacttcat atgggtctca  84120
tggtgttaag gtttacggca ttgcactaga cacaatgaaa actacacaag agggccgggc  84180
acggtggctc acgcctgtaa tcccagcact ttgggaggcc gaggcgggcg gatcatgagg  84240
tcaggagatt gagaccatcc tggctaacac agtgaaaccc tgtctctatt aaaaataaaa  84300
aaattagcca ggcatggtgg cacgtgcctg taatcccagc taatcgggag gctgaggcag  84360
gagaatcgct tttcccagaa aggcgtaggt tgcagtgagc cgagatcgtg ccactgcact  84420
ccagcctgga tgatagaggg agactctgtc gcaaaaaaaa agaaaagaaa aagaaaagaa  84480
aagaaaaaca cacaagagcc gtgagagaga tagcttttga ttgcaataca caatttactg  84540
gagagatgag ctgatcatac agagatgatt agtgtcacac agtgttttaa acagattctt  84600
gcaaccctgg agttcactgc agtagcaaca gaagttagct atgagatttt aacagtagta  84660
tagtatgtac tacagttaat attaggtagc tatgatttaa tgctgcatct ttgcatttgt  84720
ttacatttat cttgactaca agtggtatta tgtctggtct taaggtttgt gtgcatatgt  84780
tttgatgaat tttaactttt tataataggt ttgtgtatat tttatggcag taaatgataa  84840
aacagactaa tctacatata ttttatgtag tcatgacata aacctaactt tttcttaact  84900
ttttgatatt tctagtctat gtgtttcatc tgcaggtttt ttcaaattgt tgaaatctct  84960
gaaaaatttt attgaaaaaa aatccatata tgtaagtgga cccacacatt tcaaacctgt  85020
gttcaagggt cagctgtgta aataattttc ctcaaaatta aagtggaaaa ggagagttac  85080
tactagtaga aagtagaact gtacccttgg gcaggggtgt gtgtgtgtag ttaaagatca  85140
atttaactta aaaggtcttg gttagagaat aaaaactggc ccttattagc tttaatttac  85200
atgaaaaatg aaaaatttta ggccaggcac agtggctcag gcctgtaatc ccttaacttt  85260
```

gggagaccaa ggggagtgga tcacttgagg tcaggagttc aagacagcct ggccaacatg 85320
ctgactcacc cttccctact gaaaatacaa aagttagcca ggcgcagtgg ccatccctac 85380
agtgctagct actcgggagg ctgaggcagg agaattgctt gaacccggga ggcaaggttg 85440
cggtgagctg agatcgcacc actgcactcc agactgggtg acagagcgag actccatctc 85500
aaaaaaaaaa aaaaaaaaaa aagatttgaa aacagagtat tttttaatct gcaagagctt 85560
tacagccttt tattcatatg tataagcttt taaagatgac taaaatttta gtgtggactt 85620
tccactcatt ggaaatccta tattgcaggt gttaattcaa ttttagtgag tgtgcatcat 85680
ggctcagaga gataggacta gaatgaggag gtcacattgg agactctgaa acagatacat 85740
gtgagcctcc caacttttta atatttgtta atctagaagt gttgaatttt gggtgctgac 85800
aaggcagcag gtagataaga attgcaaagt taagaaaata gactgtaata ttgatggtaa 85860
actaattgat taaattttaa aatgtacttt tccatgtttt tctttgaatt gtcagtaatt 85920
ttgtttcaac tggtattcat acatagatta ttcacccaat gttgacaact agtagattta 85980
tatatttttt atgttgccta tccttttttg ggtaaggatt aacagaatgt ataatcacct 86040
acattatagg tacactacta atcacttgct acttgaaaaa acctaaagct ttgaaatctt 86100
tttattattg cacacaaact tatgccaaaa atggagataa agagaaaaat gtcatccact 86160
aaaccccaac aaataatgtt gacaatgtgg tctactcgta gactcgcatt gacttaattt 86220
ttttaaatct tattgcatat tttgactaga taataaatgc atatggttaa aaaattcaca 86280
tggttcaaaa aagtacacct cccactcatc ttccatgtga tatttccttt ctgcttagca 86340
attctgtatt tatcttgcta aacatgaatg acagttgttt gctgaaatta cattaaatgt 86400
gacgtaataa aatcattgta agtttacatt ttttaacttt aataattttt aatgttttaa 86460
tgaagagtat gaagagtagt agtactgctc ttcaaagtac tactacttta ccttaccttt 86520
tactgttttg ttaagaaaat taggccgggc gcagtggctc acgcctgtaa tcccagcact 86580
ttgggaggcc gagacgggcg gatcacgagg tcaggagatc gagaccatcc tggctaacac 86640
ggtgaaaccc cgtctctact aaaaatacaa aaattagccg ggcatggtgg tgcgcgcctg 86700
tagtcccagc tacacgggag gctgaggcag gagaatggcg tgaacccggg aggcagagct 86760
tgcagtgagc cgagatcgca ccactgcact ccagcctggg cgacagagcg aaactccgtc 86820
tcaaaaaaaa aaaaaaaaaa aagaaaaaag aaaattatat agaaataaaa ttccagctat 86880
tccaaaactg caccttgaat acaggtacag aattgctaaa accgtgtacc attttgtagt 86940
tttagcatgc ttttgtgtaa ctgcatctgg tgtttgatcc tcatgagagc cctgttaagg 87000
aagggtacat attattgtcc tcattttcct tcgaaaacac atcagagttt gtattttgac 87060
tgtcagcatt caaatacaag tcttttattt ataaaatttt ggtctttata ctgtggctaa 87120
aaatcttaaa tcacttgtca tgatttgaaa tggtttatac cgattttttt tgacatttat 87180
acacacatac acatattttt aaattgtcta taataaaatc atgctcatct ttgaaaaaat 87240
attaggagta ctacagtgga tacctacata cttgctattc agcatacctg gtttttttgtt 87300
tgttttttga gacagtcttc tctgtggtcc aggttggagt gcagtggcac gatctcagct 87360
cattgcaacc tccgtctccc aggctcaagt gattgtcctg cctcagcctc ccaagtagct 87420
gggactgcag gtacacatca ccacgcccag ctaatttttt gtatttttgg tagagacggg 87480
gtttcaccat gttggccagg ctggtctcca actcctgacc tcaagtgatc agcccacctc 87540
ggcctcccag agtgctggga ttacaggttg tgagccactg cacctggcct gtttttaaat 87600
tcacataaat atgttttata tttttcatta gggagaagaa ggttgtgtct acaattttta 87660
agacattggg gagatttaga tgccagtagt aacttaaaag agaaataatt gcaaattctt 87720
tttcctcttg agtatacttt catttaaggt acagtgttct gtaagttact tttaccgtta 87780
aacttcttaa tgttgcttat tgtttgtctt acatttttag gttggatttt tcttaagtca 87840
catgtctaat aaaaaaaacc cttaaatacc tcatttattc gtcttcgtta gtgaatgcat 87900
tgttgtacat attagatttt tctctttaga taactcagct tcccctatta agtgccacat 87960
gtattacaaa attttattta tgttttattg tttaataaac tcttgagaac tagatacatt 88020
ttaatcattt gtaatactta cattttctaa aacacttcat ttttccctgg tttcttcaac 88080
aaagagatgc atgtagtaca aggatagctt tacctgtgtt agaagattgt ttcacacatt 88140
tacatcaact gcatagtcct gtttttgttg ggccctaatg ccagcatcac tttttgctac 88200
tgctgtttct gccttaaagg caatatgcct ctgtctagtt tgctgattct gatactcttt 88260
cccctggaaa gtaggtaatc aagtttgtga ggagctgtgt gtttaaggag tccataaatc 88320
cttgtgggga gccctaggtg tatagagcat agctgtaggg cagaggcctt tgacacttat 88380
tctggatatg cagtggcctt tgcctatggg gttcatgggt cagagcgctg ttgtgacctt 88440
tgaataaatg ggttgttatg ataattgttt taagggagga gagttattct gatatccttt 88500
gtattgatat tgctcttatt tattattgag ctggatttaa gtattaatca tttaaggtca 88560
aatttctaat gtatatatgt tcttaaatgg ctacgaccca gttaccatag caatttagtg 88620
aaataactat aatggaacat ttttttcaa tttggcttct cttttttttc tgtccaccag 88680
ggagtaacta ttcccagtca gaggcgctat gtgtattatt atagctacct gttaaagaat 88740
catctggatt atagaccagt ggcactgttg tttcacaaga tgatgtttga aactattcca 88800
atgttcagtg gcggaacttg cagtaagtgc ttgaaattct catccttcca tgtattggaa 88860
cagttttctt aaccatatct agaagtttac ataaaaattt agaaagaaat ttaccacatt 88920
tgaaatttat gcaggagact atatttctga agcatttgaa caaattaatt agctttgttg 88980
ttcaactcat tgggctaaag aagccaaaag caatgggttt taatgtagtc gaagccaaat 89040
tatatttatg aaagaaatat tctgtgttat aaccaccaaa tacagcccaa ttctgactag 89100
atgatggaag aacctgtccc atcagaggtc cagcatgagg tccagcagag gtccaccaga 89160
ggagttcagc aatttgctgc tcttagggca gggatcaatt ccttaatatc ttaggaagac 89220
taggtattga cagtaatggt gacaaagcaa tgaaaaggaa aggaagaagt gataagacgt 89280
ggcagcaagc tgaagtatga tgagtaaaga ataggaatca aagtatgtgg agtgttagag 89340
aaaacctgga tttagatcca gattctagtc ctatctctgt cattaatcta ttgcgtaacc 89400
ctgagcatat catctacctc tctttgagtt tgcttgtcaa taaaatgaag agactttgaa 89460
atctgagact tcctggataa gtactaaata cagattatgt cactgatgtc tgcctctatt 89520
tatttctccc ttttacccta atctctataa gtctacctca gtcatcctga tcctattcta 89580
cttctctgat gttgttgtca gataggtgtg atcatcctca tcagatcttt tctgtattct 89640
tagagacaga taactttatc aaagaccaca gatttattag tatagcatgt taaagtcttc 89700
taaagagtct cattgatgct cttttcatct cagtacaatt tttaaaactg ctgaatgcaa 89760
ggtactgagc tgttggaagt gactgacaga tgaatgtaac agattcatag agaaggaaaa 89820
aggaagaaaa actcatgctc ttcctatagt attgatatca gtgtaagagc caagagaaag 89880
gtataaagta tcatgcagat attaagggaa agaaaacatt cactttagta atctttcctc 89940
attttctagt ttcctcttat gtactatgat ttaatactgt agtaaagttt taataaaata 90000

-continued

```
tgagctatat gtaattaagt gggaggttgt ggggctaggc acgaggctca cacgtgtaac  90060
cccagcactt tgggaggctg aggcaggcgg atcgcttgat ctcaggagtt cgagaccagc  90120
ctggacaaca aggtgaaacc ccatctctac taaaaacaca aaaattagct gggcatagtg  90180
gcacacacct gtagtcccag cttcttggga ggctgaggca ggagaatcgc ttgaatccag  90240
gaggcagagg ttgcagttag ccgagatcat gccactgcac tgcagcctgg acatcggagc  90300
aagactttgt cttagaaata aataaataaa tataaaataa aataaatggg aagttgtgta  90360
tataaattat aaatgctaca ttcagaaaag cttttgaagg ttgtcagaca gtttcttaaa  90420
ggaagttcac cagttcttta ttgaacattg aagaaaacat acagtttaga ctggcattaa  90480
aactgaaaga agtggccaga cgcagtggta gacgcagtgg ttcacgcctg taatcccagc  90540
actttgggag gtcaaggtgg atggatcacc tgaggtcagg agtttgagat caggctggcc  90600
gacatggtga aaccctgtct ctactaaaaa tacaaaaatt agccaggcat ggtgatgcgt  90660
gcctgtagtc ccagctactt gggaggctga ggcaggagaa ttgcttgaag ccgaaggtgg  90720
aggttgcagt gagccgagat tgcgtcattg cactccagcc agggcggtaa gagtgaggct  90780
ccgtcttaaa aaaaaaataa gtaaataaat taaaaactac tgaaagaagt attacaggca  90840
atgggaaata gcttgagtgg aagtgcagca gaaggaaaaa gctggacaag aatgtagtgt  90900
cagagaatag gtatggaacg tgtgagtgac tgttagagga tcttgaatgg ggataacaga  90960
cttgatttca taaatactga gatgtcatga taatacttga ggactaaacc atgttttaag  91020
gacagttgta tgcaaagttg taatcgcaag aggaaaaaat agtggaaaag aaaccagtaa  91080
taaaacttgc cttaatgcag gtatgctaag acaatcaaat gggatttcat taattttta  91140
tttgccattt atagccaaag attttgtaaa agttttgagc ccagtcaggt gaaatagtct  91200
cagaaagaaa gaaaagtgaa tctgagactt ggagacatta atgttgatat tttggtttta  91260
aacgtgtttt aaatccggta aaagtgagct tctcacatga caatattcag tgggtacttg  91320
ggagtatggg ttcgaatcta ggtaggagat atatcgatat tttgggcatc atcaggaaag  91380
ggagagtagt taagcctttc atataaataa tggtgtggcg tttgggcatg ggaagtcttg  91440
gaggaaagga agaaaaggag agggtgagga ctgagataag aatggcaact tgggtttagg  91500
aagaagaaga ggaatcaatg tagagaacag atagtgctga aaaatacagc atcttctgta  91560
gggattggca gctttttctt gatttttgtc ttaatatttc taagagatgg aaaaagctac  91620
tatattctag acatttaaca gggttaaaaa tgttactaaa agatgatcaa tgtggttttc  91680
attcaagact ataacaatat gtatatatcc aaggaaattt aattctgact taaaaaaatt  91740
gttttgcttg tatagattta gggacacaag tgtaattttg ttacatgcat agagtgtata  91800
gtttcaagtc agggctttta ggttgtccat catctgaata atatacattg tacccattaa  91860
gtaatttctc atcttctact caccgtttca agtctccact atttatcatt ccattcttta  91920
cattctgatt ttcatttact aggtgtatta gtctgttttt gcattgcttt aaagaaatac  91980
ctgagactga gtattaaaca ggtttaacct gttttcttta tgaattcttc tttaattggc  92040
tcatggttct gcacgctgta cagaaagcat agcagcatct gcttctgggg aggcctcagg  92100
aagcctccaa tcatggctga aggcaaaagg ggagcatggt gagaatggga gcaagaaaga  92160
gaaggagtgg tggggagaag gtgccaccca cttttaaatg ccagctcact taccaccaag  92220
aggatggccc aagccattca tgtgggatct gcccccatga ttcaagcttc ttccaccagg  92280
ccccacctct agcactgggg attacaattc aacctgagat ttgggaggga aagatatcca  92340
aactatatca ctaggtctgg atcttgttat ttattttttg gaacatagtc atatatatcc  92400
```

```
aaggatatat attgtagaag tccacagaac catactaata ttggacttct gcttagttag  92460
gtcttatcta tctgaaacat gatattcata ttgcagagaa gattattttc tttagtgatt  92520
gaggaaatct ttactactta tacattttta atataatact ataatatttg aagatgcaca  92580
ttttagatgt agtttaattg aaacctggaa atactattaa tttgcttttt aaagtcctaa  92640
aatcaggatt atcagattct gaattaatgg agtttaaatc aaaaagatta caaggcagtt  92700
tttcagtttt attctggtta attttatcac agctttggaa tcctactttg tttatttgct  92760
tcttgaagtt agatttccca gtgaaatttc agtatcacat aaagtcttat gaaatggctc  92820
attgcacttt gaactttgag tcaaggaagt gaaatttatt gatagattgt tggtgtaata  92880
tttatcctgt ttgtggtagc ttttttgaat aataagtgtc ttagaagacc atgttggagt  92940
agcctgcatg cttttatcaa acatattaat tatgtgatgg ctgatactgc tttagatatt  93000
acatagaaat agtagtaggt gtttactaaa ctggaaattt catttaactt ggtttagctt  93060
tgccttgttc tcagtcacat tgataaaaat gtaagacttt tgtttatctt ttagaataat  93120
gacacctttt ggtgctgaga attttttgtt ttatatatat atatatatat acgtaatata  93180
aatacaaaat atatttaaat atgtataata tttctcatac actttatgta actttgtgtt  93240
cctgtttctc tattatcttg gcatgttttc ttcaaatggc acttcttaac ctcctaaggt  93300
taataaattt ctttgtaatg gacttttgtt ttctaattcc tcagcgtatg acaaatgaat  93360
tatactttgt caaattattt aggtaacttt cagtttttga agtcctggga tcataacatt  93420
catcagtctt taatttctgt cattaaggtc attagctata aatgaattta tgagtagatt  93480
taaaaaataa aacatacaat ccttccctta acacactttc ccaccatttg gttcaactgc  93540
tagtgtaaaa gcatgatgaa ttttgagaag ttatatttta ccagttactt tattttttac  93600
cagttattta aaacagacat gagccaaagc cagaatactt gttaatgaaa atgaggtgtt  93660
ttggaggaaa ggaaggttgt gctgcagttt ttacttgaaa tctgttacat ttctttacag  93720
aaatttcaaa tctcttgttt cctgttatga tggtggcatt atataccttt aaaatgtgag  93780
ctataggaaa atgaatgatg gttaattttt taataaatat ttagacttgt gtttttgaaa  93840
ttttttataa cattgttata ggttttatcc tctttctctt gtgaacatgt agtgatttgt  93900
attttgtgat ctttgccgca tgctagagac ttaagaatac tatagcaaat atctgtcttc  93960
tttacattta aaaatttttc gtgactactc cctgttgata tctgtcttaa aagttacttt  94020
tgatgtagtt cacaaatgta ccagataatt atttcatcgt ttttaatgct taaagttttt  94080
atttgtatta ggatttttag tatgatttta atgttaaagt tttgaagtta ctctgccact  94140
agaagtctaa ttttgggact tactattcat gaaataggaa ttgactttta tataagtaat  94200
aggaccttat tttgaaggtt caaactggag aaaatcttac attgtttata tttttatttc  94260
atttatttca gttgatttgc ttgagatcaa gattgcagat acagaatcca tatttcgtgt  94320
atattgctga tattaatcat taaaatcgtt tttgacagtt tgacagttaa aggcatttcc  94380
tgtgaaataa tactggtatg tatttaacca tgcagatcct cagtttgtgg tctgccagct  94440
aaaggtgaag atatattcct ccaattcagg acccacacga cgggaagaca agttcatgta  94500
ctttgagttc cctcagccgt tacctgtgtg tggtgatatc aaagtagagt tcttccacaa  94560
acagaacaag atgctaaaaa aggtttgtac tttactttca ttgggagaaa tatccaaaat  94620
aaggacagat taaaagctat attttatttt atgacatgta aggaactata atttgttttc  94680
tattagatct gcaggtgttt tgcttactct ggcattggtg agacattata agggtaaata  94740
```

-continued

```
atcctgtttg aaggaaaagg ccttatggca ttgtaacatg agaggaattt ttcttaacaa  94800
ggatggttaa ctgagaagaa attagcatgg gaccaatatt ttaaaaattt tggtctatag  94860
gtagaaatga gatctgttct gtggtcttat gtagtgacac aaaccacttt ttctccattt  94920
tggcttatgt ttctttttct ttcctttttt ttttttttcc tttttgttag agacagggtc  94980
ttgttctatt gcccaggctg agtagctaag actacaagca tgtgccacca cacccagcta  95040
attttttta ttttatttt tgtagggaca gggtctcact atgttgccca ggctggtctc  95100
aaactcctgg gcacaagcag tcctcacgct ttggcatccc aaagagttgg aattacaggt  95160
gtgcgccatc atgcctggcc ttaacgtttc ttaagacttg attattttct atttagcttc  95220
tgtggattta ctgattaatt ttttaactag gagagaaatc agtatgaaga ggaagtaata  95280
aagaatgaaa acatggtatt taaatgtgca ggtttagaaa gttaatgaag tttgaatttg  95340
attgatctgt atttagagaa ggcaacgtct tattatttta aaaccaacta tccgccctgt  95400
gcggtggctc acgcctgtaa ttccagcact ttgggaggct gaggtgggca gatcagctga  95460
ggtcaggagt tcgagaccag cctggccaac atggttaaac cccatctcta ctaaaaatac  95520
aaaaaaatta gccgggtgtg gtggcaggcg cctgttttcc cagctactca ggaggcttga  95580
ggcaggataa ttgctgaacc cgagaggcgg aggttgcagt aagccaagaa tgcaccattg  95640
tactccagcc tgggcaacaa gagtgaaact ccatctcaaa aaaaaagaaa aaaaaaacaa  95700
caactatctt catttaaaat attaaatgtg aatatttaaa gtgagactaa ggtgcaacat  95760
ttttagatag taatgaagaa aaggactaac tttgtagtgt tgctgccttg ttaaacatac  95820
tagatagcat attgccaatc tttaaacatt ctcaatgata ggatttattt actttttctg  95880
atttttagct tttcttttga aagaaaataa gaggaagttt catttactgc aaaattttaa  95940
atgctgcttt gatgtatcag tagagatata attttccttt atccagaatc caagtagctg  96000
gaaaaaaaaa tcaaaatatg ctgaactttt tttttttag ccagaaaccc atttcctatc  96060
gtctgtacaa ataaaagtta aatatatctc aataacttag aaaaattatt ttttgataat  96120
ccaggaagta ttagcaactg ttttaaaatt aagataacta gtaagtttta tttagcttc  96180
aaaaataggc atctacatca tcatctctgc ataccttag gaatttccta attcttattt  96240
cccttcatct gtactttaac acatgcaaaa ttgaaggtta gattaaatat ttatgattta  96300
tttgtttatc cttgactaca taaatttcca ttttattgat tttccctgcc ttatttaaga  96360
atatgctatg attaaaacac aaaaaatttt agtataaccc atatatatat agaattcacc  96420
tttttgttat ttaaatatta ttggcttatt ttcttctaag taaaatacaa ttactggcta  96480
aaataattga aataagcaaa aaaaaaattt taaagacctt gtatacaaga ttactttgcc  96540
aggtactgtt aaaagatgca atgacattta agacgtaaca tccttaagga tcttattttc  96600
tgggggataa aaaactttaa gataaattag aataaaagat ttaaatggca ttttaaggta  96660
ccaggtacca gataagatgt cacaaggctg tatatcatta attgccaaat gatttataca  96720
ggccagattt ctttgttggt caatagaggt ttaaagtgat gaacttctgt tgtgtttttt  96780
tattaagaag gtattatctt attagtaaga agtgattttt tttaagaaca agcattttat  96840
aacatcaaaa gaaatcagta gtactctttc ctaccccctc atatttattc tgaaagtatt  96900
caagcattat attgtcatgt aagaaactgg agcttctcat gtttgtattg ctgtagaagt  96960
aaacatgtat ttgccatgcg tcatcaggga agttgcactc accgtccaag aacttttgtt  97020
aaagtaaatc ttggaatagg tagctcattt gaaatgtaga aaaaattaaa tccatatctg  97080
aattttgttt atatgtatgt acacgtaaac taaaaacgta tttaaagcta gtattagatg  97140
```

agaaaagagg tttttttact taaaatttta aggcaaaagt agtttatctt agatcttgtg 97200
agattgtatt tttggtttaa aatttgagaa tttgagtgaa gaaaaatcat gtgaatgaaa 97260
atgcaacaga taactcagat tgccttataa tagtctttgt gtttaccttt attcagaata 97320
tcaaatgata gtttattttg ttgacttttt gcaaatgttt aacataggtg acagattttc 97380
tttttaaaa aaataaaaca tcattaatta aatatgtcat ttcatttctt tttcttttct 97440
ttttttttt ttttaggaca aaatgtttca cttttgggta aatacattct tcataccagg 97500
accagaggaa acctcagaaa aagtagaaaa tggaagtcta tgtgatcaag aaatcgatag 97560
catttgcagt atagagcgtg cagataatga caaggaatat ctagtactta ctttaacaaa 97620
aaatgatctt gacaaagcaa ataaagacaa agccaaccga tacttttctc caaattttaa 97680
ggtcagttaa attaaacatt ttgtgggggt tgttgacttg tatgtatgtg atgtgtgttt 97740
aattctagga gtacagctga tgaagaactt gcttgacaag tttttaactt atgtattatt 97800
tcgaagcagt gtttacgtag cagtaacatg aaagtttcta ataaaatacc caatgtacac 97860
agcgtcaaaa aagctgcatt tttcctttc ctaattcttc gttgtttgct gaaatctggg 97920
gcaaaggtgc gggaggggc taaatgactg ggatatgaag taggaatggg agaggaaaga 97980
aatagatggg aactcagtca tttgggaatg attcatatgg aatgttttta ctgcttccac 98040
tcctgtctgc cttccaattt attctcaatc cctcagagtg atcttaaaaa tagacttgat 98100
tgtgtcactt ctgtttacac tttataagga ccttgtgttt ttttttttac catgacctac 98160
aaggcccagc ataatttagc acagggctac ctcctacatc agcactagtc accttctctc 98220
cttgtttctt gagattcagt catactggtc tttcttcagt tcttcaaaat gctaagcttc 98280
tgcctcttct agtctttcca gttattttcc ttctccctgt accttttcat ctcagccttt 98340
tcccctgacc ttccatagct atcttcatat ttccagcctt agcttcaatc tcatattctc 98400
tgaagtcctt tgattgtcct cccgttattc tttttttaaa aatcctattt ccttatattg 98460
tatcttagaa ttatttggtt tgtttcattt ttgcctatgt gtgatatatg tatttctaca 98520
taggtatata tatctactta tagacaagaa ttcttcagat taaaaaaatc tgatttgtaa 98580
acattcccaa gtggttgttt accatttttt tcttcccct tcctatttct tattctacct 98640
gattttcccc tgttcattca ccacactcgt ttctttctct tttttactct ctcttaattt 98700
ttcattcaat ttttataaca tgtaataaat ctaactgtag cgtctgagta ttaagaatat 98760
tgctagtaat acttcacctg taatcccagc actttgggag gctaaggcag gcggatcact 98820
tgaggcccag gagtttaaga ccagccggcc aatatggcga aaccctatct gcactacaaa 98880
tacaaaaatt agctgggcat ggtgtcgcac acctgtaatc ccagctactt gggaggctga 98940
ggcacaagaa ttgcttgagc ctgtgagatg gaggttgcag tgagccgaga tcacaccagt 99000
gcacgtgcac ttcagcctgg gcaacagagc aagactctgt cttaaaaaaa aaaaaaaaaa 99060
aaaaatatat acacacacac acacacacac acacacacac acacactatt actaccaata 99120
tacatacata tatgtatgta tgtatgtatg tatattggta gtaatagtaa tacttgggcc 99180
cctgcacgtt ttaagtgaaa atagatctaa tattaaatgt ctttagccct taaatttttt 99240
ttaagtgttc agaagtttcc ctttaaaaaa atttttaata tataataatt gtacatattt 99300
atgggataca gagtgatatt ttcatgtatg cagtgtgtga tgatcaaatc aggataatta 99360
gcatatggat cacctcaaac atttgtcatt tctttgtgtt aggaacattc aaaattctgt 99420
cttctagcta tttgaaaata tacagtaaat tattgttgac tagttacagt tctatagaac 99480

-continued

```
actataattt attcctcctg tgtgtaattt tttatctttt aaccaacatc tccctatcct  99540
cccctcccac tccctttccc ggcctctaat aaccacactc ttatgagctc aacttttttta  99600
gcttccatat atgagtgaga acatacggta tttatctttc tgtacctgac ttattttact  99660
taacatcatg tcctccgggc tagacattct ctttagaatc cacaggtttc ctttcttttc  99720
tctaaatctg catttttgctc agccattaac ttttaaaatg tctttttccc tttagtttta  99780
ttgttttcta ttttaatatt gcaagatgtt ttatatttgt gattacaaat aaaaactcca  99840
ttattagtaa acaaatacaa tgtcatatag tagtaagtgc tataaaaaat agacaggata  99900
gaaagtaatc ttggtttgta tgttttttgt tttttagcaa agatgattag agaaggccca  99960
accaagcaga taacatttaa gcagaggcct aaatcatata agtgagttat acaaatatct 100020
gggaaaagag ttaagagtac agatgcaaaa gcccttagac aagagaatga gcttggtata 100080
tctgaagagt ggataagtca ttttgactga aacagagtgg acaagaaaac cagtccaagt 100140
gtaaagacac tagtgtgtgt tcagcatagg aaggatgtaa tctgaatttt gtgtttaata 100200
ttccctgtgt tcatgctttc aaaatacaga tgagtgagga aagtagggag aaggggtaat 100260
aaaggaagct gagagatcag ttaagaggta cttgaatagt ttagtaaaga tgagagaaga 100320
tgtttgcttc ttgttgcccc tcactgctta gaatagtggc agtgaagggt aacaagaagc 100380
tgtcagatta acttaaagag tttactgatg cagtggatgt tggttgtaag agaagaattg 100440
ataatgactc ttggataata ggggagggag gggctgtcaa tataatataa tgaagaaggg 100500
atttgaagtc atttctgatt taaatctcac atccactacc tacttttaat agatatgtag 100560
cctttaacaa gttccctaac ctttctgggc cttagctacc tccccttgga aatggaaata 100620
cctaacatgt aaggttgttt tgacagttat tttcactagg catgtaaagg cacttgactc 100680
tctgttatag accactgtat tatgttaatg tccctctcct tcctcccttt aggtaaagtt 100740
tttagggcta ataaatccca aatatcaatg ttgatcagta gtttgtgttt gtgtagtgtt 100800
gtttatatca aaaactacat tgaagccggg cacagtggtt cacgcctaaa atcgcaacac 100860
tttgggaggc caaggtgggc ctcccacctt gaactaagga gtttgagacc agcctgggca 100920
acatggtgaa atcccatctc tacaaaaaat ataaaagcta gctgggtgtg gtggcatgca 100980
cctgtagtcc tagctacttg ggaggctgag gttgatcctg ggagtttgag cctgcagtga 101040
gctgtgaaga tgccactgca ctctagtctg ggtgacagag caagaccctg tctcaaaaac 101100
acacacacac acacacacac acacaaagaa atacattgat ttttcacata ggtagtaaga 101160
gaaacattct ttttgaactc agctgtttgt gaattgaatt ttgtaattca aatgctatat 101220
tatgtaaact attgatgact ttcaatctgc atttattttg tataattatt tagttaatat 101280
ttgccactta tattccttaa aaaataaaat tgaggttggg cgtggtggct cacacttgta 101340
atcccagcac tttgggaggc tgaggcaggc agattgcctg agctcaggag tttgagatca 101400
gcctgggcaa catcatgaac cccatttcta ctaaaataca aaaaattatc tgggcatggt 101460
ggtgtacacc tgtagcccta gctgtttggg aggctaaggc acgagaattg cttgaacccg 101520
ggaggcagag gttgcagtga gccaagatca tgccactgca ctccagcttg gcaacagagc 101580
aagactcttg tctccagaaa taaaaataaa taaattgtat taacatcctg atagtttatc 101640
tgtttagtac ctagcaagaa agaaaatgtt gaacatctta agaagagggt catttaaaag 101700
gcctcttaaa gatcatgttt gttacagtgc ttaaaaatta atatgttcat ctgcaaaatg 101760
gaataaaaaa tctgttaaaa atatatttca ctaaatagtt taagatgagt catatttgtg 101820
ggttttcatt ttaaattttc tttctctagg tgaagctgta cttcacaaaa acagtagagg 101880
```

agccgtcaaa tccagaggct agcagttcaa cttctgtaac accagatgtt agtgacaatg 101940
aacctgatca ttatagatat tctgacacca ctgactctga tccagagaat gaaccttttg 102000
atgaagatca gcatacacaa attacaaaag tctgaatttt tttttatcaa gagggataaa 102060
acaccatgaa aataaacttg aataaactga aaatggacct tttttttttt aatggcaata 102120
ggacattgtg tcagattacc agttatagga acaattctct tttcctgacc aatcttgttt 102180
taccctatac atccacaggg ttttgacact tgttgtccag ttgaaaaaag gttgtgtagc 102240
tgtgtcatgt atataccttt ttgtgtcaaa aggacattta aaattcaatt aggattaata 102300
aagatggcac tttcccgttt tattccagtt ttataaaaag tggagacaga ctgatgtgta 102360
tacgtaggaa tttttttcctt ttgtgttctg tcaccaactg aagtggctaa agagctttgt 102420
gatatactgg ttcacatcct accccctttgc acttgtggca acagataagt ttgcagttgg 102480
ctaagagagg tttccgaagg gttttgctac attctaatgc atgtattcgg gttaggggaa 102540
tggagggaat gctcagaaag gaaataattt tatgctggac tctggaccat ataccatctc 102600
cagctattta cacacacctt tctttagcat gctacagtta ttaatctgga cattcgagga 102660
attggccgct gtcactgctt gttgtttgcg catttttttt taaagcatat tggtgctaga 102720
aaaggcagct aaaggaagtg aatctgtatt ggggtacagg aatgaacctt ctgcaacatc 102780
ttaagatcca caaatgaagg gatataaaaa taatgtcata ggtaagaaac acagcaacaa 102840
tgacttaacc atataaatgt ggaggctatc aacaaagaat gggcttgaaa cattataaaa 102900
attgacaatg atttattaaa tatgttttct caattgtaac gacttctcca tctcctgtgt 102960
aatcaaggcc agtgctaaaa ttcagatgct gttagtacct acatcagtca acaacttaca 103020
cttattttac tagttttcaa tcataatacc tgctgtggat gcttcatgtg ctgcctgcaa 103080
gcttcttttt tctcattaaa tataaaatat tttgtaatgc tgcacagaaa ttttcaattt 103140
gagattctac agtaagcgtt ttttttcttt gaagatttat gatgcactta ttcaatagct 103200
gtcagccgtt ccaccctttt gaccttacac attctattac aatgaatttt gcagttttgc 103260 acattttttta aatgtcatta actgttaggg aattttactt gaatactgaa tacatataat 103320
gtttatatta aaaaggacat ttgtgttaaa aaggaaatta gagttgcagt aaactttcaa 103380
tgctgcacac aaaaaaaaga catttgattt ttcagtagaa attgtcctac atgtgcttta 103440
ttgatttgct attgaaagaa tagggttttt tttttttttt tttttttttt ttttaaatgt 103500
gcagtgttga atcatttctt catagtgctc ccccgagttg ggactagggc ttcaatttca 103560
cttcttaaaa aaaatcatca tatatttgat atgcccagac tgcatacgat tttaagcgga 103620
gtacaactac tattgtaaag ctaatgtgaa gatattatta aaaaggtttt tttttccaga 103680
aatttggtgt cttcaaatta taccttcacc ttgacatttg aatatccagc cattttgttt 103740
cttaatggta taaaattcca ttttcaataa cttattggtg ctgaaattgt tcactagctg 103800
tggtctgacc tagttaattt acaaatacag attgaatagg acctactaga gcagcattta 103860
tagagtttga tggcaaatag attaggcaga acttcatcta aaatattctt agtaaataat 103920
gttgacacgt tttccatacc ttgtcagttt cattcaacaa tttttaaatt tttaacaaag 103980
ctcttaggat ttacacattt atatttaaac attgatatat agagtattga ttgattgctc 104040
ataagttaaa ttggtaaagt tagagacaac tattctaaca cctcaccatt gaaatttata 104100
tgccaccttg tctttcataa aagctgaaaa ttgttaccta aaatgaaaat caacttcatg 104160
ttttgaagat agttataaat attgttcttt gttacaattt cgggcaccgc atattaaaac 104220
gtaactttat tgttccaata tgtaacatgg agggccaggt cataaataat gacattataa 104280
tgggcttttg cactgttatt atttttcctt tggaatgtga aggtctgaat gagggttttg 104340
attttgaatg tttcaatgtt tttgagaagc cttgcttaca ttttatggtg tagtcattgg 104400
aaatggaaaa atggcattat atatattata tatataaata tatattatac atactctcct 104460
tactttattt cagttaccat ccccatagaa tttgacaaga attgctatga ctgaaaggtt 104520
ttcgagtcct aattaaaact ttatttatgg cagtattcat aattagcctg aaatgcattc 104580
tgtaggtaat ctctgagttt ctggaatatt ttcttagact ttttggatgt gcagcagctt 104640
acatgtctga agttacttga aggcatcact tttaagaaag cttacagttg ggccctgtac 104700
catcccaagt cctttgtagc tcctcttgaa catgtttgcc atacttttaa aagggtagtt 104760
gaataaatag catcaccatt ctttgctgtg gcacaggtta taaacttaag tggagtttac 104820
cggcagcatc aaatgtttca gctttaaaaa ataaaagtag ggtacaagtt taatgtttag 104880
ttctagaaat tttgtgcaat atgttcataa cgatggctgt ggttgccaca aagtgcctcg 104940
tttaccttta aatactgtta atgtgtcatg catgcagatg gaaggggtgg aactgtgcac 105000
taaagtgggg gctttaactg tagtatttgg cagagttgcc ttctacctgc cagttcaaaa 105060
gttcaacctg ttttcatata gaatatatat actaaaaaat ttcagtctgt taaacagcct 105120
tactctgatt cagcctcttc agatactctt gtgctgtgca gcagtggctc tgtgtgtaaa 105180
tgctatgcac tgaggataca caaaaatacc aatatgatgt gtacaggata atgcctcatc 105240
ccaatcagat gtccatttgt tattgtgttt gttaacaacc ctttatctct tagtgttata 105300
aactccactt aaaactgatt aaagtctcat tcttgtca 105338

<210> SEQ ID NO 8
<211> LENGTH: 1675
<212> TYPE: DNA
<213> ORGANISM: homo sapiens

<400> SEQUENCE: 8
gttgcagcct gctgcgcgcc caggggtccc gcgggttttc gggcgcaggg tggcgcccgc 60
ggcaggcggc ggccatgaac ttctccgagg tattcaagct ctccagctta ctctgcaagt 120
tctccccgga cggcaagtac ctggcttcct gtgtccagta ccggttagtg gtccgggatg 180
tgaacaccct tcagatcctt cagctgtaca cgtgcctaga ccagatccag cacatcgagt 240
ggtcggcaga ctcgctcttc atcctgtgcg ccatgtacaa gcgagggctg gtgcaggtct 300
ggtctttaga gcagcccgaa tggcactgca aaatagacga gggctcagcc gggctggtgg 360
cctcgtgctg gagcccggac gggcgccaca ttctcaacac cacggaattc catctgcgga 420
taaccgtctg gtccttgtgc acaaaatccg tgtcttacat caaatacccg aaagcttgtc 480
tgcagggaat caccttcacc agggacggcc gctacatggc gctggcagaa cggcgcgact 540
gcaaagatta cgtgagcatc ttcgtctgca gtgattggca gctcctgcgg cattttgata 600
cggacaccca ggatctcaca gggattgagt gggccccaaa cggctgtgtg ctggcagtgt 660
gggacacctg cttggagtac aagattctgc tgtactcatt ggatggccgg ttgttgtcca 720
cgtacagcgc ttacgagtgg tccctgggca tcaagtctgt ggcctggagc cccagcagtc 780
agttcctggc agttgggagc tatgatggaa aggtgcgcat ccttaatcac gtgacttgga 840
aaatgatcac ggagtttggg catcctgcag ccattaatga tcccaagata gtggtgtata 900
aggaggccga gaagagccca cagctgggac tgggctgcct ctccttcccg ccgccccggg 960
ccggggccgg ccctctcccg agctcagaga gtaaatatga gatcgcctct gtcccagtct 1020

```
ccttacagac actgaaacct gttaccgaca gagcaaaccc gaaaatgggc ataggaatgc   1080

tggcatttag tcctgacagc tacttcctgg cgacaaggaa cgacaacatt cccaatgccg   1140

tctgggtctg ggacattcag aagctgaggc tgttcgcggt gctcgagcag ctgtccccag   1200

tgcgcgcgtt tcagtgggac ccgcagcagc cgcggctggc catctgcacg ggaggcagca   1260

ggctctacct gtggtcccca gcgggctgca tgtcggtgca ggtgcctggg gaaggcgact   1320

ttgcagtgct ctctctgtgc tggcatttaa gcggagactc gatggccctc ctcagcaagg   1380

atcacttctg cctctgcttc ctggagacag aggcagtggt cggcacagcc tgcagacagc   1440

tgggcggcca cacgtagcag cggtgcacta acgtgtgcag aaacagggct actctgtgtt   1500

tccagtgtgg gaaaaaacac agcttcacca ggaggttctc cactgtggtg gtctggattc   1560

agtgattgat tctatttttc tatagcaaag catttttgta aatatgtatg gtataaaact   1620

gtagttttat tatttaaaat aaatacttgc tgatttaaaa aaaaaaaaaa aaaaa        1675


<210> SEQ ID NO 9
<211> LENGTH: 518
<212> TYPE: DNA
<213> ORGANISM: homo sapiens

<400> SEQUENCE: 9

gcaagagggc tgccaacgct actaatcaga catgctgggt ccacagggct gtccccaaac     60

tggaaagaag tcctagaaaa tagatgattc ttcctaaaac gtaaattgga tcatgcctct    120

cccccaacag tctcatgcct atggaaggga atcctgtccc ccaaggggtt ctccctcctg    180

tctcctccaa gaaccaggca gtgtggggtg gggcagcagg acccaggtc tcggagctgg     240

ggcctcccca gcctcacttg gggcctccaa ggctaagttc tgtgacctcc agggcccaag    300

agtgagttcc tctggctgct ccagaaagtg aagagagaag agccaacccc ggctcgggcc    360

acgagccccg aggcactgac cacagccaga gcaggcctgc tggaagctcc gtccctgctg    420

cagatccctg cgccacatga tatcagcaat tgctgcaatt tcgccctaag tactcttgtt    480

tcccctaata atccacgttt catctccaca ataaacat                            518


<210> SEQ ID NO 10
<211> LENGTH: 759
<212> TYPE: DNA
<213> ORGANISM: homo sapiens
<220> FEATURE:
<221> NAME/KEY: misc_feature
<222> LOCATION: (457)..(457)
<223> OTHER INFORMATION: n is a, c, g, t or u

<400> SEQUENCE: 10

cactacaggg aacggcccag gaacccatcc acccgtcccc agctctcatc actctgacct     60

ctggcttttt gtttcctggg gcatttcaca gcaaattcca cctatgagac cgtctcatcc    120

gtaatacacc agtacatgct tccagcagct tggtgacatg aaaggacctc cgtggctggc    180

cttactccct gtggatgcca cagctgcagg atcctggggc cccaacagaa gccggtgaag    240

gaagagttcc tgctccagca gaacaaaact gccctttgcc cagaaatcct gcaaactgag    300

gctggacgac ttgaaatact catcagcgag attaccacga agcccaggtg cgagggaccc    360

tcacgcctgt tgctgcgtgg gccgcccaga catcgccaga gaccaaaccg cagaagatgc    420

tcggagccca acatctacaa acctgccccg ccacggnccc caggctcaga aactggtttt    480

tagtcagctc caatgattag cttttttttt tttctctttg gttcccatag aaatgcctct    540
```

```
tcaaagcatt atgggacaac acacccaccc agtttctgta ccggtggagc ttctggggga    600

agtttcagga ctaggaacac acagggcggc tcaggacaca ttcaccccaa agtatgactg    660

tggagaccag aatacgccac ccctaaatat gactatagga gaccagaata cgtaccccaa    720

aatatgcctg tggagaccag aatagccacc caaatatcc                           759
```

<210> SEQ ID NO 11
<211> LENGTH: 25892
<212> TYPE: DNA
<213> ORGANISM: Mus musculus

<400> SEQUENCE: 11

```
gtacttccgg ccgctgcctg gggcggttgc gggaggtact tcggagccgg gctggcccgg     60

gctggccgtg gccatgaact tctcggagtc attcaagctc tcgggcctgc tctgcaggtt    120

ctccccggac ggcaagtacc tggtgagctg cggcgcgctg ggcggaacct aagtgtgggc    180

gcgcgacttg tgcacggggc cggggcgggc cgaagggggg cgggaagggg gcccgagccg    240

ggcggccgcg gggactcagg ctggacttag ggggcggggt gggaggtggg agagggaggc    300

aggcagaggg gtttcagccc agatgaggga gaaccagatg attagagaga acgaacctga    360

agccgaagag ggatccaggc cagccaggct gggggatcct ggcaggtgac cagggtggag    420

aaagaggacg tggagcagag tggggatgga gttggggttg ctattctggc aggtggtcag    480

ggttaggaag gaggtcttgg agcaggtggc cagggctggg tgggtgccag gctcccggct    540

ccagtttccc ttcatcaaag ttggataaga tgactctgct ttcacacatt tgagggcaca    600

ggggatggca gctcattgct attttgtatg ttttctgtga gcgagctggt taaacggggc    660

cctcctttgt gaaactcgtc ataagcaaat ggtttaaata actagctttc attgccaggg    720

ttggatgtta gctgtctatt ctttgggtgg cagaatagtg ttcagatggg tgtttcaagg    780

tacgccaaca tgaccattgt gcatttgtag aaggctgacg ttaggaagcc atcagggaaa    840

actcaagtct tattttaaaa aactgtggtt ccgtgccagt cgggtagctt ggctagtaac    900

ggtacctgcc accaaacctg atgacctgag tcccagctct aggacccact taatggaagg    960

agagaactgt ctcctgcatg ttgtcctctg gcctccacat aagccgtaac tagtgcctga   1020

cccttctcac atacaaatgc aatcctaatt tttaacaagt tttctttgat taatctatca   1080

ttctcttttt aactgactga taccattgat tgattgattg actgattgac agggtttctc   1140

tgtagctctg accaggttgg ccttgaactc aaagatctgc cccttgtctc ctgagtgctg   1200

ggattaacgg agcatgccac catgcctggc tgtcttgatt ctcagttcac acccctgctg   1260

tgtttgtcca ggcttttgag acatccttta ccctccttat acacatcatc ctaacaatgt   1320

aggaagtgtc agggtaggac ctgcttagca gggaaaggta ctgccatgca agcccgagga   1380

cttgagctcc ggctcgggaa cccacgtaaa ggtgggagga gaccatcagc ctcgcacaca   1440

ttgatacatt ttaccttttt ccaagtgcct ccagagacta aggttgcttt acggttctga   1500

aagtctcagt gaacagcaaa gaagttgcat ttgggttagc tgatatttgt gcttgccgct   1560

catcaaaata tcgtggagct cttaataatt gtttctttca agttttgtcc taaatcctga   1620

gcagagcgag tccatgtttc cagtgttggt gtcttaagtg attcctaagg aatccattgt   1680

aacaggttac tgctcaccaa actctaatgt gagaacacaa gccctttgat aggtcctcct   1740

tctgatctgc acttgccctc ttgctctctt tccacagaag acaaatgtgg cttcattaaa   1800

aaaaaaagag tctgtgtgtg tgtgtgtgtg tgtgtgagtg agagagagag agagacagag   1860

acagagacag agagacagag atagaaacag agagatgcta caacacacgt gtagagggca   1920
```

```
gaggacaacc cccagtgtta ttccttacct tccaccttgt ttgagacaag gtctcttgct   1980
cttcactgca taaagcaggc tagctggccc acatgtacct gcctcagcct cccctctgcc   2040
tcccctctgc ctcctcatag aaactaggat tttaaacagt ttttaggatt aacacagttt   2100
tatgtggctt ctgtgcatcc aaacctgttt ctgaggcaag tgcaagtttt tggcttttag   2160
acaatggcat aatatgcaaa gctggcctca gactcagaaa gtagttgagc acctccctag   2220
tacagtgatt acaagtgtgc accatcactc ccaagtagta aaaaaataca cacacacaca   2280
cacacacaca cacacacaca ggctttttga gacagtttct ctgtgtagcc ccagctgtcc   2340
tggaactcac tcagtagagg gaggctggcc tcaaactcag ggatctgccc acctctgact   2400
tctgagtgct gggattaaag gagtgcacca cccccatctt taaatttact tgtacagatg   2460
gctcagcggg taagagcact gactgctcac ccaaaggtcc tgagttcaaa tccccgcaac   2520
cacttggtgg ctcacaacca cccgtaatga gatctgatgc cctcttctgg tgcatctgaa   2580
gacagctaca gtgtacttac tatataataa taaataaatc tttaaaaaaa tttacttgta   2640
caaatttgtg ggttagagta tgataatttg gttaatatat actgtgtgga acttttaaac   2700
ttttgaatgc tccacctttt atctttttct aactcatttt gcaatgagac ccataagttt   2760
tggtccacat gaagctaagt gtgtcgaaca ggaggggagg agctggccat tgaggcaagg   2820
ctccctgctg tagaagagat gctatcccgt gctgtctgcc tcacttttta ggcttcctgt   2880
gtccagtacc gattagtgat ccgggatgtg acgacccttc agatccttca gttgtacaca   2940
tgcctggacc agatccagca catagagtgg tctgcagact ccctcttcat cctgtgtgcc   3000
atgtacaggc gggggcttgt gcaggtttgt accaccatgt attagtagag tgtatagatg   3060
ggtgctacat gtctgtgggc cttgaacagg catgtgccac ttacatatat gatgtgtgta   3120
ggcaggcaca tgccacatat acataagact cacataagtg tgtctcatgt gtaactaact   3180
ggtctggcgc tgtttctgta gcagagttag aattaggaaa cgtttccagg agtgtgacta   3240
ggaaggagtc caggtgtttg caccccttctt tcaggtttag ggggaaatgc aatgagactc   3300
aaggttgcct tcttttctta tgtgtaattt atttatttta tgtgcattgg tgttttatct   3360
gtatgcattt ctgtgtgatg gtgtcaggtc tcagagttac cgatagctgt gagctgcagt   3420
acgggggctg ggaattgaac ggggtcatca ggaagagcag tcagtgctct cggctgctga   3480
ggcatctctc cagcccccag atatgctttc ttttaaaatg taatgctctc taatagttta   3540
atccaaacac ttttgatgtg gaaaaacaaa caaacaccac caaaacagta aattgttctc   3600
agtctttgag catgattttt cttttttttt tttttttaaa gatttattta ttggttatat   3660
gtaagtacac tgtagctgtc ttcagacact ccagaagagg gcgtcagatc tcgttacaga   3720
tggttgtgag ccaccatgtg gttgctggga tttgaactcc ggaccttcag aagaacagtt   3780
gggtgctctt acccactgag ccatctcacc agccccgagc atgatttttc tgagcgggag   3840
gtatttgcaa tggcagtgga acaacttgga cagggttcta ggaagttcta gaaggttcta   3900
gaaggccgtg ttccagtatt cactaagcct aactaatgag gtcacaggga tgggcacatg   3960
agcagaccct tcaaaggtgc actgcagtga agtcaccagg aagtgtggct tgtagccact   4020
gggccatctg aggtagcatg gtgtatatcc tctccctcag agaggcctcc tgcgtggtac   4080
agctatttgc actcctctgt gtttctttta tgaatcaagg tctggtcact cgagcagcca   4140
gaatggcact gcaagatcga cgagggctct gcggggctgg tcgcttcctg ctggagtcca   4200
gatggccgcc acatcctgaa cacaaccgaa tttcatgtaa gctggccaaa cgtagcccac   4260
```

```
tctgttcttc gcctaaaata gcctgggaat gtgaaagtct ggttctggag cagtattcag   4320
gccagagttc ataaacagta taatttttaa actctatttt aaagaaaaat aggacattaa   4380
aaggagttgg caagatggct cagtgggtat ggctcttgct accaagcctt gccacatggt   4440
ggagggtaag aacgacagat gccccaaagt tagagtaaca agggaaaatg tatgtcttct   4500
gtaatgggct gttacaggct gcagtgctca tgctgacatc ttaaagggac aggtgctcat   4560
gttgacatct taaagggaca ggtgctcatg ttgacatctt aaagggacag gtgctcatgt   4620
tgacatctta aagggacatt tggcctgggc ttttggctgc atatttgagt gttttctaga   4680
ccactttggc cagcaatctt catgcttatg gagttctgca gaccagagtc cagcttccag   4740
atctcataga cttgggctca gtccctccgt taatggccca aaggaaaggt tacccactgc   4800
agaatttata aactgttttt taatgtactt ttttattcag cagctgtgtt acactcactg   4860
aaatggaaag gaacatttgg acagagagta gactgtacag actgcctctg tacactgtta   4920
acctactgct aggtcatagc cactgtgcct gtgacattaa agtgaatggc aacatcctgt   4980
gtggaggaat atgtcacagc aaggggaccc tgaaaaatat accctccctt tttgttgtat   5040
tgagatggga tctcactgtg tagccttgac tggcctggaa cgcactatgt agactaggct   5100
tgcctcaaac tcagagagct gcctgcctct gcttcttgac tactgggagt aaagtagcca   5160
ccagtcctat cttattccaa gcctttagat tttagcttct aaaagtccca cagacttcat   5220
ttaccaccag ctatgctcag tagtcaggag gtgaccctgt gcgcatgaca gattcgtaga   5280
gtggacacat aactgagagt catatgttcc cgctcacaac agttagatcg ctgtgtactc   5340
ttctgggggc aggaagtcca cgtgagggtg ctgcaagatg gagagaggcc cagctcccat   5400
gagacaaggg gaagacgatt gaattgtgtg gctggtgtct gtctggtccg tggaagacac   5460
tcccctgcac acgcacactt cccagagcac ctccaggcct tgagaggctg ccagcctcca   5520
gagggcacct ttgactgcat tgcacaaaag ccattttcac cttttttgga gagtcttggg   5580
gtccccgatg catatgacac tgtgcggttt acagcagctc acaggttaca ttgcctgtac   5640
aagggccctc ctagccggca tagctgctgc tcttgttcct tgtgaggaaa ggctctctgg   5700
ggcacactca cctgccgtct gctgctgggc atgagttgtg aggcaccagt ggctttggcc   5760
tttcttatgc acctcttcta gtgtctggat ccttccaggc tagtgcaggt gggtgtgtgc   5820
gcagcttcca ggctagtgca ggtgggtgtg tgcgcagctt ccaggctagt gcaggtgggt   5880
atgcgcagct tcccgagggt ttgcatcagg atttgaagtg gcgagacgtt gcagcatcgt   5940
ggggcttttg aaaatctcag ttactctcca ctttatattt tgaggcaatg tctcttactt   6000
gaacccagag ctccccagtt ctgcagttca gctagcttcc tgtccctggg gtcatagaca   6060
ggtcaccgca caccctgggg tgtgcaggag tgctggggtt ccagactcac ttgagcagta   6120
aggcttcccc ggagatttcc ccagccccac actgtgtgtg tgggctcagt tgtcacctgg   6180
cgaatggaga catttgctct catggctgct ctgtgtgggt gcactgaagt aaactgcaca   6240
tgagtgtgcg gtgtgggtcc atgtttatgt attccagctt taagactctt tgtgaagatg   6300
ggaagcatcc taacccttct ctcccctttc cctggcagct gcgaatcacg gtctggtccc   6360
tgtgcaccaa atctgtatct tacatcaagt atcccaaggc ctgccagcag ggtgagtctg   6420
tctttacaca gtccttgtaa ctgttctgag agtgtgcact tagagcagat agaggagcta   6480
cagcagcacc tctcccccca gcctccatca ctgtgcaccc ctcccccagc ctccatcact   6540
gtgcacccct cccccagcct ccatcactgt gcacccctcc cccagcttcc atcactgtgc   6600
accccctccc cccagcctct atcactgtgc acctctcccc cagcctccat cactgtgcac   6660
```

-continued

```
ccctccccca gcctccatca ctgtgtaccc ctccccccag cctccatcac tgtgcacccc   6720
tcccccagcc tccatcactg tgcacacctc ccccagcctc catcactgtg cacacctccc   6780
ccagcctcca tcactgtgca cccccttccc ccagcctcta tcactgtgta ccccctctcc   6840
cagcctccat cactgtgcac cccctccccc agcctccatc actgtgtacc cccccagcct   6900
ccatcactgt gcaccccctc cccccaagcc tccatcactg tgcaccccct cccccaaagc   6960
ctccatcact gtgcaccccc tcccccaaag cctccatcac tgtgcacccc ctcccccagt   7020
ctccatcact gtgtacccct cccccaaagc ctccatcact gtgcaccccc tccccccaag   7080
cctccatcac tgtgtacccc tcccccaaag cctccatcac tgtgccatcc tctgtgctcc   7140
ttcctgtgtg tctgtgagat tccctccatg ccatttcttt gacaacagga tgctgtaaaa   7200
agtagacagg cattgtcctg ggaggagaac ctttaccttc attcacacag ggcactcagc   7260
ttgcctttgg tgcctagctg tcagcttcac ttcactaact ttttttagtc aagatttatt   7320
tttaggatgt gtgtgtgtgt gtgtatgtgt gtgtgtgtgt ataagagaga gagagaggtg   7380
tatctgtgtg tgtatgtgca tgcatatgtg tgtctgtgtg catgtatgtg tgtgagagag   7440
agggagaggg agaggaagag atgtgtatct gtgtgtgtct atgtgtctgt atgcatgtgt   7500
gtgtgtgtat aggtgtaggt ataggtgtgt atgtctgtct gcgtgcatgt gtgtgtgtat   7560
gtgtgtgtgt gtgtgtgcgt gtggtgtatg ggtaatgtga atgcaagttg aagttacagg   7620
tgatagtgag ctgcttgttc tgggttctgg gatcagtttt caggaaaagc agcacttttt   7680
aaaaaagatt tatttatatt atacataagt acactgtagc tgttttcaga catgccagaa   7740
gagggcgtca gatctcatta caggtggttg ggagccacca tctggttgct gggatttgaa   7800
ctcaggacct cagtgcccct acctgctgag ccctcgccag cccacagcac aagtctttat   7860
ccagtgagcc atctccagct cagctcacta gctcttctgt cgggatggca tgctgtctgt   7920
cacctctgag catctcagaa cagggaaagg aggaaggctg ggccgagtgc atggggtgac   7980
gggtggtcat gccacccacc tgccccaaac ccagaaacta acagtagagg gcacacagta   8040
ggggcacaca gaggggcacg aagtaggggc acacataggc atgctcttgt ttgtttgttg   8100
ccacaaggac aatatgtcta atgttgcaga tcacattaga ctgatggcat cgtaagtctg   8160
ttgtgggttt tgtgtcttaa gtgctactgg atctaaagaa cagtctggcc ctgggtgcag   8220
gtggtcctca agtctgttat ctgaagtgtt cttgtcattc ttgaggcctt gaccgcaggc   8280
cttttacagt aatgcagggc tggaaaaaag ttacttaatg tttttaagta agattgtccc   8340
gaatattctt tacaacttta gttatttgaa atgacaagtt caaaaggtga ctcagcatct   8400
ttcagaggac tctaggtcac tgcccagcac ccaggtcagg aggctcacaa ctgcctgtag   8460
cttcagctcc gacggaatgg gactcttccg tcctcggcgc gcacccctgc aggctgtgtg   8520
tatacctata cacagatgta cacacatcca tacactaatt aaaaataaaa gcgaaaacga   8580
aatgcagtga cacagctgac tcagtgtata aagtgcttgt ggagcatgag aacgggagtt   8640
caaatctcca gacctacaat aaaggccagg tacagaggca gaagtctgtg atcccagcac   8700
ccccacatca agatgggagg tggaaactaa gaattccaga agcttgcagg ccagctagac   8760
tggcatgtgc agttgcaaac aaaagatctg tctcaaacaa ggtggatgag caatatagac   8820
gcccaaggtt gtcctcttag ccctcataca tacatatgca tggcacatgt gcctaaattc   8880
acacacatgg accaccacca ccacacacac acaactgcaa gctgggtttt gaccatcagg   8940
tatgcctgta gttccctttg tgaaacatgg ccctctgctg tgtttcacaa agtgacattt   9000
```

-continued gtgactcttt aagaatcagg tccttgggtt tgattctgta taatcacccg cctcacctgc 9060
aagagggata agggctctgc ttgtcagagt cctacgtgac aatgtcttgc tcatgggaag 9120
atgagaagga cacatttccg gggcggggcg gggagagctc gctccccccct tgtccctttt 9180
aaaaagtccc tgatgtgctc cagtcctttc ccacacttgg ttccatctgg ttccagttta 9240
ccatctctct ccacaggact aactttcacc agggatggcc gctacctggc cttagcagag 9300
aggcgggact gcagggacta tgtcagcatc tttgtgtgca gtgactggca gctcctccgg 9360
gtaaggccat cctctgctgc tggctgggaa aaggggtaga actagcgttc ctggtgatcc 9420
cagaggctgt tgcagcccct ggggtagaca gaatgatggg gttcccatgg ccagaggaca 9480
ggggccctgt gtgtgactcc aagcagtgca cactacgtgt gatctagact ccctggtgca 9540
tgcacacttg gtgcacagta gaagttagca tgttgacatg aactttgaac cctctttctc 9600
cataagggaa ttcctccctg ggaggaatgc agttttgttg gcctgggtaa aatgtctcag 9660
gagccgtgac actgagcaaa tgctctctgt gcccacaagc ttcagtgtca gagtgttaga 9720
gagacatctg aaggggcgcc ctgggaagca gggtgcgggt gggcaggggt ccatggggat 9780
gagggcatgc ggccttgccc agcatggttg gcacactgtg tgcactcacc agaacaacac 9840
acagatactt tgtctgttgc tgcatataaa atgatacatg aaccaaaagc attagttaga 9900
aaataaatgc actacttgtc taaggacatg ttttccaact gtcatgtttt ttttctcatc 9960
tggaagcact ttgacacaga cacccaggat ctcacaggga tcgagtgggc cccgaatggc 10020
tgtgtactgg ccgcgtggga cacctgcttg gaggtatagc acatgaccag cagcacagtc 10080
cctttcagga atgttcacct gcaggtacct gtgtgctcag tgcatcgagc tgctgggtgc 10140
tggcgtgccg cacgcagggc ctgtgactgt gtcaatgtct catctgcagt acaaggttct 10200
gctgtactcc ttggacggcc gcctgctgtc agcatactgt gcctatgaat ggtccctggg 10260
catcaagtct gtggcttgga gccccagcag tcagttcctg gccattggga gctacgatgg 10320
aaaggtagga agtggctcag ggctcaggcc aactcgacga gctgtaggac acctgcagcc 10380
cgtgagctac ctgcatgtca ttctcacggt tccttcccca ggtgcgcctc ctaaatcacg 10440
tgacctggaa gatgataact gagtttgggc atcctgcaac cattaacaac cccaagacag 10500
taagtctgca tacgcttcca cccgagcacc gtggtctccc gggtgcaggg agccgccctt 10560
gaccctcctt agttgctgtg atgttgtctt ccctgttctg cccctcatgc cctccttggt 10620
gaagggcatt tggagtccag gctcgtccgt ggactgatcc tgtcctagcc ggatgctcat 10680
catgctctgc cctcggcaga tccctgggag agtgagctga ggaatcctga gcgtgggcca 10740
tcctgccaga gcagggcaca ccgcaggcag agaggccggg agagctggtc tgtatggact 10800
gcagctaggg cggcccaggc ccaggcccag gggtgcagag ttgaaggcag gttctgaagc 10860
tcagaggtgc tgagtccgct gtcttctgtc agtgctgaag ctcagtagtg ctgagtcctc 10920
tgtcttctgt cagtgctgaa gctcagtagt gctgagtcct ctgtcttctg tcagtgctga 10980
agctcagtag tgctgagtcc tctgtcttct gtcagtgctg aagctcagga gtgctgagtc 11040
ctctgtcttc tgtcagtgct gaagctcagt agtgctgagt cctctgtctt ctgtcagtgc 11100
tgaagctcag tagtgctgag tcctctgtct tctgtcagtg ctgaagctca ggagtgctga 11160
gtcctctgtc ttctgtcagt gctgaagctc aggagtgctg agtcctctgt cttctgtcag 11220
tgctgaagct cagtagtgct gagtcctctg tcttctgtca gtggtctgga ccaaggacag 11280
gtttctgctt cccttggaca aggagggcca gggccatggc ccggggctca gttagctgcc 11340
ccaaagccta tgtctgcaga accctgtagg aaggagaagc taggtggagg ctgggcttta 11400

-continued

```
gtcagggtgc tcctcctgta acagtggttg aaccttagag atgacagagt acaggctggc  11460
cgtgcaggct gccaaggttt gcctgtggtt caagcgcctg tctcccccac gtgtgcactg  11520
gtggtttctc tgcctgggac tgcggagtac cccactaacc taagcgtgtg agtgaacttt  11580
gtgtcaccgg gtcagaggac ccggggacac gatcaaccta gttaaagtag aacgggttca  11640
ttttggctcc taatttctga ggtttcagtc catggtccct tcaccattta ctttgggtag  11700
cacattgtgg tggggacaaa tggcagagca gagctgacct tcagctgctc tggccaagaa  11760
gcagagagga aggacaggtg aggtcccaat gtggccttca aagtcatgct cccagtggcc  11820
cgggcctgta aggtccatgc tagcaccaag tctgtcaggc ctggccgttt gctactccac  11880
aggctcgctg ccaccactgt cctctcctgg cctacttttc tcctgtgcac acacaggcca  11940
ctgccgaatc gctgtgacat agctcaccat gtaaacatag ccatgtgctc agagccctct  12000
ctaaaggaca gcctggccag cagtactgcg gtggcagctg caaagggtca gacttggccg  12060
ccgcctcttc ccagcgacct ccgtgtgggg cacatagata ggttgggcca ccttccactg  12120
gctctcgtca cagactgcta gcagccacat cattgttttt caggttgtgt ataaggaagc  12180
tgagaagagc ccactgctgg ggttgggcca cctgtccttc ccgccgcccc gagcaatggc  12240
tggtgccctc tctacctcag agagcaaatg taagcagcag agggctgtgt cctccatggg  12300
agaaagcttg ttttttctct cttaaatgag aatcctctgt ccacgtgaat ctcagaggct  12360
gcttgttttg ggtgtggaag atgttaagat gggggtctca atcctgcagt gtagagaccg  12420
caggtgttct cctgtgaagc ctgcctttcc tccctgctct gcagtccctg aaggagtgag  12480
gggacatcag ctgtgcagca cccgcttgga ggggggggagg cagccaggct gtaggttgct  12540
catgctggct tgtgcttact tattttctgt tgggtgatag ttctttgatt cccagctgga  12600
aaggggtagc cacctgtgcc ccgagacgct ggaaatgggt ggacagaact gccaggtgtc  12660
caagtagtgg ggactagctc agaaagcagg gcttcagagc agggctgtat cctgcactgg  12720
aactgttgtc cccagggaac ctgtgaacgt gcctctcacc acagctgtcc tcttaatccc  12780
tcctgtgctt ctctgcagtg tgtttccttc cctctctttg ccctctcccc ttaaccagtg  12840
cccttagccc gtcccccgtc gtgttgcaga tgagatcgcc tcgggaccag tttccttgca  12900
gactctgaag ccagtagctg acagagcgaa cccgaggatg ggtgtaggga tgctggcttt  12960
cagctctgac agctacttcc tggcatcaag aaatggtcag tgccacactc atttcgtagg  13020
cagggtcagc tgctcgcggc cctttgaggc ggagagtaga gatgaaccga gaagcaaagg  13080
ggcagctgtg tgctcctctc cctggttcct gcagaaatgg gcgttcagca cagcagctcc  13140
tttctgcaca gcagctcctt gcccatggcc tggccgcctg gctgctccct cctgcactcc  13200
tcactgtgca agaacagggc ttacctctag ttttgtttgc attttttggg gggggtgcct  13260
ctgtgttttt aatagtttat ctcctttata tactttgtat cttgaccaca gcctccctcc  13320
ttcctcgcct cccagtccca cccatacaaa tccttcccca ttgccctgtc ccctcctcct  13380
cagaggaggc gccctccccc cacccccacc ctggggcagg actaagcaca cttctcccac  13440
tgaggcccaa ctcggcagtc caggtagggg aaagggatcc aggggcaggg gctggaccta  13500
ggcctccaca ctgtaggaaa tgtacagttg gtcttcttgt gggctcccta acaagtgaag  13560
tggggggctg tcttgtttgc attttgtaca tctacagatg taaaaaccac aggaagaaga  13620
ggtgtggctt tggcaggcca tgtctttgtt ctgggtgctg gtccctgaga acagccagag  13680
ggctggcagt gccagcactg acatgtgtcc cgtctctgct tccttgcaga caatgtcccc  13740
```

-continued

```
aatgctgtct ggatctggga cattcaaaag ctgaagctgt ttgtggtact agagcatatg  13800
tctccagtgc gctcatttca gtgggaccca cagcagccga ggctggccat ctgcacagga  13860
ggaagcaagg tgtacctgtg gtccccagca ggctgcgtgt cggtgcaggt gcctggggaa  13920
ggtaagcgta agccagcaca tgctggcctc agacaggctg acctgcttaa acctattgcc  13980
acgtgtcatg catgggaaag atgcccttct gcatcctgta ggaccttgcc cagattgtgt  14040
gcctcacagg aactggctgt ccttaaggtt tactggcttt gtcttcagcc ctggggtgac  14100
cagactcctc actcacccgc aggccccggt ctctaaccct ctggctgcct gtctctctag  14160
gtgactttcc agtgctcgga ctgtgctggc acttaagtgg ggattccttg gccctcctta  14220
gtaaggacca cttctgtctc tgcttcctgg agaccaagga gagggttggc acagcctacg  14280
aacagcggga cggcatgcct aggacctgag tggaaaccaa ggcagtagac tgctgattcc  14340
aacgtgagct aacggctgca caggttctcc agatgggatg ggctattctg cccagttttc  14400
tgtaaatatg tataaagtta tgtaaagtag gtatttgcta atccattgaa cagtggtggt  14460
tgttttcttc aaggccttag ctcacagacc caaggtcttg ggaggataaa gaatcctgaa  14520
gtaaggactc aagcctgcct catggccttg cagactctga agccagtagc gaacccgagg  14580
atgggtgtag ggatgctggc tttcagctct aacagctact tcctggcatc aagaaatggt  14640
cagtgccaca ctcattcgta ggcagggtca gcattccctg aggggttttc tgtcagtggg  14700
ctttggaaca aggtggacta atgtcagact ggccagccct cctgcagctg gatgtactca  14760
gaagtgcccc gcacctgtgc ctgtccccgt gtgagctgta aatcccacaa cagttgggca  14820
ggtctctggc cttacaagtg aattctgcag agaggcctgg gtcactgcct ggtagagtgg  14880
aagagctcag cccacccaaa cctctctatc tctagtaagt gccttgaaag cagacagacc  14940
agtatgtctg tactggtgac cagggttccc accaggactg cacacttgtg tatctgagtt  15000
tctgtaaaga ggaccatgct cacaagggtc ctcagtcagc cagacttcag tcctcaagac  15060
agtctttggc actcctgatt ctgtgacaat aacttcaaaa aggagcaact ccatttggtt  15120
taaatgtctt tactagaaca aaagcacagg ctgaaaacag gtgcatctga ggtcaccttt  15180
cctcttggat aggccatggc attccggtca catccatgcc ggttaactaa agcgagaggt  15240
atagagtgac aggccagcat ctacagtgca ctggcaaggc tagaacgaca gcagcaagct  15300
gtgtgtggct ggcgtgtcaa agctcagcag tgctcagtga gctctaggat gctcgtctgt  15360
ttatagcatg cacttttaaa acccaactat tcagtccctt ttaaacagag acaggatgat  15420
agaaacccac caccatgact tccggaaggg gctagcttat gttatgagag taaccttttg  15480
ggcctaggaa aactgctgta ttaacacaac ctggattaat ttataaagtg tgattctaag  15540
tcagacacat tcacagaaag gcaggttcac caggagctgc caggcagact gtctttctta  15600
gtgactggct gctggctgct actgtattta gcttttttaa aaaacgggct gaattttaaa  15660
atacagcact tgagagttaa tatataggga gagttaaata tgtgcagaag ccgctcactg  15720
tactcagctg tatgcaacag tctacacagc acaagtgggt ggacattgtg ctcggcatgc  15780
tggagggaga acgtggcgtt acagaaggaa cacagtggta tgggggcagc tgaatctgcc  15840
tttgtaagat tgtgttgcca agatgtccaa tatccaacta aatatacata atccacttga  15900
ctattctaat cggatacatg ccctccttcc ctccagccag tgggtggcat gaggtggcac  15960
agggagtccc caccaccttg gtttccggga cgcagctgtc tagaagccta tcttgcccct  16020
ggtcatggag tagcccagct tggcttcatt gttgatgaag gacatgagcc ccacgtaggt  16080
ctcgatgagg agggggcgct ccagcaccag cacggtattc gcctgccctg gcagtgggct  16140
```

```
ctccttctgg gccttcttga cagcttggat caggagagcc ttgaagcttt ccaactttga  16200
agagaataaa catggagcct taacctcatg ccaagacagc agtactggga aacgaggatt  16260
ctgagttcaa atcctcccaa ataccacata gtgatgacat caccaatgac aggttgggcc  16320
ctatgagctg tgtcatcagg tggttcatca tgtacaaaca tcatgaaggg acctgcctta  16380
agtccaacct agagagtacc agtctatctc taaagatgca gtcaggagat tcggcagcct  16440
gagacaaggt actgccagtg ccaacaggtg gaaaatcttt tttacagacg cacatgctct  16500
ggagtgcacc tcactaagca ggtgatgctg taattgcaca cgctgcctgc actggtgtgc  16560
tgtgcactga ctgacaggta gcatcacaga tggaggaatt catgaggact atgatgtcac  16620
caagtgacag ggctttctca gccctactct aactgtgcag aatgctcagc gctccctcag  16680
cacctctcct gggaacttcc agagtacctg tgtcaccagc agcacctgcc aagccccgcc  16740
agtactgtgg gcttttccca tgctcgctca cccacccagt ccagactgag catcctgcaa  16800
tgggatggtg actctgttct taaacagcac cacctagctt cctactgtgg aactgcacct  16860
ccagggttca cactgacagt ggccttggcc tgcttacatg gcacagagac gctgtcttct  16920
cgtccatgcc agccattggg tgttctatga aggtggcata gggcatgttt gtagaccagg  16980
ggttccatct gttgatgaag gaagggcggc tctgcttgtc ccactgaatg cgaaccccaa  17040
agccttctct cctgatgggg gagggggaga aagccttgct taccacagga atacaacatt  17100
gcattcagta tcagggatgg ctggggaacc tgtgacctag tgtaacaatg gcctccacta  17160
acagcttcac acacttccaa agcgtaacaa gttaatgagc ctcctttgca gcctatgaaa  17220
ccggcacaca gtccaacctg gcctaattat ggccgtgttt gttcttaatg ttactgaatg  17280
atgcttaagt tagtagccat tagcttcctg gagtccctag tcaaataatt cttttatagc  17340
aagccaacca gtctctgaag gctgttaggt gttttgcgat gtatcgaatt tttagtaata  17400
ctgagcacat gccctgtgtc tccctcctgc tggagttaaa actcccagac tccctacata  17460
gcttatgaca gtgggctctg attccatgta tcttaacggt atttaaatga atggttttta  17520
gtggggacag agtggccgac tgtgccagca tccctttcaa ggaggtactg agcaacccgg  17580
aaatcaccag cctctactta aaggtccttt ccactggttc ttcaagatga gacctttacc  17640
tcacaagaga gtgggtcaat accacttaca ggatccgctg gggccctgcc gtgtagtgcg  17700
ctggtgcacc tacttgttga gcgacttcgg aggaaactgg aattctccac aggagatggt  17760
gtctaccgcg ctgagcgcca ccctgaccac ctgctggcac tgaaggctga tgaagtcata  17820
tttgcagatg agcagcgact ggtcggtgac cagcaccagc cgctccttct cgttgttcca  17880
gtggtccacc ctggagagga gaggggccgc ccatcaccaa gagccccgcc tgcccccgcc  17940
cgcccccgcc cagtgtcccc gcagtcccct cgcgccggct tactcggtca gcagccacac  18000
cccctggatc tcgccgtcct ccacgggccg taccacggcg cggatctcct cgaccgcctg  18060
ctcgatggtg ccgggccgga acacgaagta ctccttgacg cgggcgcggc gtgtagggtc  18120
gtggacgttc agcggccaca acgtctggcg cagcggtgtg cccgccccag gccggcccgc  18180
acccgcgtcc tcgccggccg ccagcaccgc cgtggggctc gtgcccgccg agtccaccgt  18240
gtcccgcagc tgcagcatcg cgccgccacc ggcagcctcc accgacggcc gccgccccgg  18300
cgtccgcccg gccgcgcccc gccctccctc gttcgccttg tgattggttg agtcctgcag  18360
agcccgcctt ccggacccgc ctccagctcc gtcgactgcg tctcgcgatt ggctttcccc  18420
taagctgtct tctgcaattg ggtctaaagt gctgccgttc atgattacgg cggcccctcc  18480
```

-continued

```
tgggccggaa gctgccgcca cgcgcggagc cacttcctgt ttacaggaag ggcgagttaa  18540
aaaaaaaaaa aatgccggtc gggggttcct ggctgagaac ggggaaaggg acgccatgga  18600
ctcgcgcgga agggggcact tgggggctcg tgcgtagggc gttgccccga cagtgtgtcc  18660
tcgcttggct ccgtgccctt caccttcggg cttacggtgc acttcgggcg gaggtgtgcg  18720
gcgcacttag gaggtgtgca tgcctgggga gtgtgaaagt gtgggcatgg gtgtgtgcgc  18780
gtctgaggat tgtgaaagcg tgggaatggg tgtgtgcgcg tctgaggatt gtggacactg  18840
tgtcggggca cctcagatag aggcttctca ggagtgtgct gcactccttg ggcgtggtca  18900
ccttgggagt gtgggtttat agggtgtgtg cacactggag ataggagtgt gtgcaggtca  18960
gaggtggctg tcagagggtt ctttatattg ggcatgatac gcacaagtaa gctaccatgt  19020
caccgaagag tgctgctggg gcggggggtg gggggagttg gaaggaaacg ccgtaggatg  19080
ctcttgggcc ctgcagcttc tccctgggac agaagccatg cgagatgtcc ctgagttcct  19140
gctcccacgg gggtgccagc agtgtgcctg ggttgatgga gctaatggac cgctatgata  19200
gtgtggccca aaagtctttt ctaacagtca ccaagacata ggttagactc atcagtgaat  19260
gacagcccaa gatacagctc aggcctgtag tctgtctcct gaccgttgtg agggctcctt  19320
agcctgctgg accttttaca gtgtggcttc gtcagagaat ccagtccaat gaggtctccg  19380
ggacactggt gggagcagcc acgatgacgt gaattcccac agaggttcct gagaccgctg  19440
tggatgtgaa gagtgtgctg aaagctgaca gagaaagggg agatgaatag ataagtgcat  19500
ataaggcaat aagccaggga tggagaggtg gctcagcagt taagaacact ggctgcgccg  19560
ggcgtggtgg cgcacgcctt taatcccagc actcgggagg cagaggcagg cagatttctg  19620
agttccaggc cagcctggtc tacatagtga gttccaggac agccagggct acacagagaa  19680
accctgtctc gaaaaaaacc aaaaaaaaaa aaaaaaaaaa tcaaggaggc ttctaccttt  19740
agggctggta agatggctca gttggtaaga gcacccgact gctcttccga aggtccaaag  19800
ttcaaatccc agcaaccaca tggtggctca caaccacccg taatgagatc tgatgccctc  19860
ttctggtgca tctgaagaca gctacagtgt acttacatat aataaataaa taaataaatc  19920
tttaaaaaaa aaaacaaaaa acactggctg ctcttccaaa ggactggggt tcaatcccca  19980
gcacccacat ggcagctcac gactcttaac tccaggatcc aataccctta cacagactta  20040
tatgcagaca aaacaccaat gcacataaga ataatgttta ataacacaaa taagcaaatg  20100
tcaagtttgt ggcatgcatg aatcctaggt gtgagagaga aacatcatct atttctggct  20160
cagcctttct tatacaacac aggactacct tgccctaagg tggcaccaca tgaaatgggc  20220
agagcccccc cccccatatt actcaccaat taagaaaatg ttacagccgg gcgtggtggc  20280
acacgcctat aatcccagca ctcaggaggc agaggcaggt ggatttctga tactggcact  20340
tagagcctct cattcaaagg atcacggcta agcaggtgct ctgtatctgt ccggagcaga  20400
ggggacgagc agcaggtgtc cgctctgaaa cctggcttct acagaagtgt aaatccttta  20460
ctaccgtgag gagtctccag tatccacact gtgaataaac accattatat cttacgtgag  20520
gctgccagga cagaccacag actggcttgc tggaagtaac cgaagcatgt agtgaggttg  20580
ctgagaccag acggccagaa ccacagtgtg tgtgcatgtg cgcttgcatg tgcatgtatg  20640
tgtgtccttc tgatacctga gggcacatgt cttcctttgc ctttccagcc tcccgtgttg  20700
tcagccatgc tggatgtccc tcagcctgtg gctgcctctc cccgttggct gactttccat  20760
agtcatcgtc gctttctcat ttgtaaggat tcctgacgtt ggcacaggcc tgccctaacg  20820
gccccctttt gacctgatca tgttcacaga ctattttcca aagatggtga gagtcatgga  20880
```

gactggttgg gacttgcgtg tatcattaac aggtacataa ttcaactggt gtgtgtgtgg 20940
gggggggggag ggtgtttcgg gcaggtgcaa gcgatgaagc atttagatga cctccacgtg 21000
tgcacacagg tcacggcggg ggcaaggagc aagacatgat gactgtgact agggagtaag 21060
gtattggggg cccagagctt gggttggtcc tgaggtccac tagccgttgc cagggatttt 21120
caagaggctg ttcccaaagt ggtcagcaga tggcgcaact acccacacat ggcctccctg 21180
ggagatcaca gtttggcagg tatgggatgt tttcaagtcc tagatgaagc tgttatcttt 21240
ctgtagaaga ctcagaagct cagctataac aagcagattc ttgccttaat ttcctgatgc 21300
tgtgacttag cattttggga actcagcggg ccctcctttt tgaagtgctg agaatggatc 21360
ccaggcctcc cacatgctct gccacttgag atgcttcctc taagactgag ccccaccttt 21420
gatacctgtg agaatcctga gcacgctggg gtgggttctc agagctgcat ggggctcctc 21480
cagagctggt accacacaca cacacacaca cacacacgga ggattgttgt gtgtgtggtc 21540
cttccagagc cagctgcact ttgggtcgtg cacagggtgt gcaccgctgg aagtttgcct 21600
caggaggcaa tcctcgcact gccccaagct ctgcgattgt tgtgcttccc atgttaacct 21660
cggtcactga gtcaaagaat ccacaacaga tgcagaggta actttgaaag agaaccgggt 21720
tcccagactg gagaggtggc tcagcaggca aaggtctttg ctgccaccct gatgaccaga 21780
gttcaattcc tgggtcccac acagtggaag gagagaagaa actcatgtag attgtccttt 21840
gacctccaca cactctgaga catacgtata tacacacatg agttaaatgc acacacagac 21900
gggactagag aaagagcaca gctcctacca cccagcccca tcttggcagt tgtctccctg 21960
atgtcccctc tcacatctcc ctctctgttc tcctacaggg acccattctg ataatccaga 22020
atgatctgat ctgagacccc ctctctcagt aacttcacca aagaccccgt ttccaaatca 22080
ggccccacgg ggggatgtgg gcatgaggac atgggctttc ctagggaagc tatgcaattc 22140
agatgtgcca tctccccaga tgtgaacaga taccatccct gcttgcagtg atgggtaaat 22200
atcccataca cttgccatcc caggccttcc tccctgaccc ccctgtggta aagggtagat 22260
atacagtgat gggtggaggc ctgggatggg ccaggccagg cctatgctgg gaaaccacat 22320
ggtggctgga cggcagtctg ctgtgtagcg ttatatcggc ttgatactgg ctagagtcat 22380
tggggaaacc tcagttgaga aaatagcccc caccagacag gcctgtgggc aaacttatgt 22440
aacattttct tttcttttct tttcttttat ttatttattt atttatttat tttggttttt 22500
cgagacagtg tttctctgta tagccctggc tgtcctggaa ctcactctgt agaccaggct 22560
ggcctcgaac tcagaaatcc gcctgcctct gcctcctgag tgctgggatt ataggcgtgt 22620
gccaccacgc ccggctgtaa cattttctta attggtgagt aatatggggg gggggggctc 22680
tgcccatttc atgtggtgcc accttagggc aaggtagtcc tgtgttgtat aagaaaggct 22740
gagccagcct tgggaggtaa tgcagtggtg agcagaatct ctctacggcc tctgcttcag 22800
ttcctgcctt caaattcctg cctcgagttc ctggcctgac ttccctcagt gatggactct 22860
gacctgagag ttgtaagaag aaataaatct ttcctcttct aatcactttc gatcatggtg 22920
tttcatcaca gcagtgaaaa cagaaactaa gacagtagct agatacccat tgaagctgga 22980
caggctggat gctcagttac tgagcaggag ccagcctcca gggacatagt taggtttcat 23040
gtcatgctca aggtcaggat agagtgagtg gtataggcca ggcagctggc cgccaacagg 23100
gccaagccta agccctgggc aaaatcctat gccctgaccc cgtagtgagc cttagcccat 23160
gtgagtcagc gtacttaggg gccttccatt ttggcttctc tctcacagca gggttggagc 23220

-continued tttagaaatg gatgtgggaa tgggcgaacc acaggcttgt aaatggatcg tttgtcgttt 23280
agatggggca ttgcatgtgt gctttgctct ccagagacta tccccatctg tctcttgagt 23340
tttgccaaat tctgctcacc cctaatgatg ccatctgccc aaacaggtga ctgtggtcac 23400
cacactgcac ctgaggacct gatgatactt taggtgtctg tttctctttt gctttttgag 23460
agagagagtc ttaacatgtt gcacaggtca gcctccaaac tccgatcctt ctgcctcagc 23520
ctccttggtg gagtactggg atcaaagaca ggcgtggctc ttgggctgtg agccaacctt 23580
tggtatcact taggctagcc tctcacctgt tagaagctga catgaaaact cagacaaaac 23640
actagattgt cctcttggga tggtggcctt cggctcagca gctgatgtcc ctgtggctgc 23700
tggggtactt tgggtttctg tctggagggc tatctcttcc agctctgaga tgcgtcaggc 23760
tggagagcag gcagccagca tggttctggg aaaggaggga gcggtttgct ttggaaatta 23820
gcgctgtggt tcgagctctc ctcttcccca cattattttc cctccagcca aagacgattc 23880
taattatttc cagtagagaa tgagacaagg acagcgaaaa gtatcgtctg ctcggggaac 23940
aacggtgaag gccttaatcc atgccactgg gagagacagg cagagctctg tgaattcaag 24000
gctaaactgg tctctacagt gagcttgagc acagccaagg ctagtggagg tgtgggggga 24060
gtgcttttta ggaaaatgag agcagttgtt ctccaagtgt gaaaaaaatg gaactgcagc 24120
ctcgcctctt gtctccttgg gatgaactgc caagcaaagt ccaacccaga gtgtcatcag 24180
ggttgtgact cagtgacatt ttagcacact gctggtggaa gccacggcgg cagggtggac 24240
ggaggaaggg aaaatcctag gagatcctag gaggtgggtg ctgtagccac gggttctggc 24300
ctggtgtgaa taccactcaa ttcgtgaaaa ctcaggacta aataaataaa tatatgtgtg 24360
ggccaggcat ggtggcacat gcctttaatc tttagcattc aggagtcaga ggcaggtgga 24420
tcttttagtt caaggccaga atggtctaca gaaagagttc caaggcagcc agagctatat 24480
agagaaaccc tgtctcaaaa aacaaaaaca aaaaaacaac gaaatgtttg tgtgtggtgt 24540
attaatgttt tgctttaata aatatatttg tgtttcacat gatgctcaat gtccacagag 24600
gctcagaaga ggacattgga tccctaggaa ttagagttac agagcattga gtgactggcc 24660
atgtgggtgc tgggaatcaa acccaggtcc tctaggagag cagtcagtgc tcttaaccac 24720
tgatttatct ttccagactc aagggcaaat tcgatcttta ccctgtgaat gggatgatca 24780
gaccctaaag tggaatgtga cacgtgacct attttcaata aaggatagaa ctgatggccc 24840
accctcctcc tgaagccagc actgtggttc gtcaatatgc ccaagcccac aagagggcgc 24900
catgccaaca gtccagttcc tgcagatatc ctgaggttct tgacagcaca tttaaggcag 24960
ttgcagctaa attccaaagt aactaaaagg aactggatag attaacctct aaattaattt 25020
ggaacaatga ccaagaattg ccattataag accaacaaga ttcctcggca ggtaaaagtg 25080
actgttgaca agcctaatga cctgggtttg acccccgtgg cacacatcat agaggaaaag 25140
gaccagttcc atcaagttgt cctctgatcc ctacacgtgc acagcggcac atgtgatacc 25200
caataaatga atgagtctaa taaaaaaatt taaaagtatc tgcagggaaa accaagtaac 25260
ggatttctca gacctatgga tacagctatg taaagccaat acccagagtt atatcaggaa 25320
ggtctcagtg gccagctctt gctctgtctt gttccagcaa ggaaggacaa ctgacacaac 25380
aattctagat gcagtcattg gaaacaccca gaagcgggtg ctgcatgtgt tgagctagga 25440
gagaatatga tatcagtagt atcctggtga ccagctagcc attcgtcctc tccctgaatg 25500
gcagacaggg atggactccg agtgagaaaa tacacacaac agattgaaca acagagcaag 25560
cagccacctt cctgagccaa gtgccttatg cattttcaca ggcatgttta catgaggaca 25620
ttatcatgca agtacttgat gaacccggag tgcgctctcc ccctcgactc gcccctgcac 25680
ttatttctga gtgatgggga gacaagccga gtgcacacct cgtggaattg agccgccctg 25740
ttgaccatgt tgtgactgtc actccagccc gtgagacaat ttgaaataat catgtccaac 25800
cagctgtcgt aatttgttag ctgtaaagtt gcaatatgct tgctgtgagt tacagaactg 25860
tattaaatac attgtcattt gattcctagt tt 25892

<210> SEQ ID NO 12
<211> LENGTH: 279
<212> TYPE: DNA
<213> ORGANISM: Mus musculus

<400> SEQUENCE: 12
atggagagag cagacataca tctccggtgc aggtaccctg ctcagaccaa gccggagcca 60
gcctactggc agcccattct ctccggcaaa gctagacaca atatgagcaa ttgctgcgat 120
ttctccataa gtgctcttgt ttcccctaat aattcacgtt tcatctccac aataaacatt 180
gttagaactc ttctctgggc tttaaatata cataattgct ccccgtgcca gtaaaaggta 240
ttaattccat ttatgcattc cataaacttt taggataac 279

<210> SEQ ID NO 13
<211> LENGTH: 1982
<212> TYPE: DNA
<213> ORGANISM: homo sapien

<400> SEQUENCE: 13
gtcccggctc cgcgggttcc gtgggtcgcc cgcgaaatct gatccgggat gcggcggccc 60
aatcggaagg tggaccgaaa tcccgcgaca gcaagaggcc cgtagcgacc cgcggtgcta 120
aggaacacag tgctttcaaa agaattggcg tccgctgttc gcctctcctc ccgggagtct 180
tctgcctact cccagaagag gagggaagca caggtgggtt tctttagctc tgcgtcggat 240
ccctgagaac ttcgaagcca tcctggctga ggctaatctc cgctgtgctt cctctgcagt 300
atgaagactt tggagactca accgttagct ccggactgct gtccttcaga ccaggaccca 360
gctccagccc atccttctcc ccacgcttcc ccgatgaata aaaatgcgga ctctgaactg 420
atgccaccgc ctcccgaaag gggggatccg ccccggttgt ccccagatcc tgtggctggc 480
tcagctgtgt cccaggagct acgggagggg gacccagttt ctctctccac tcccctggaa 540
acagagtttg gttcccctag tgagttgagt cctcgaatcg aggagcaaga actttctgaa 600
aatacaagcc ttcctgcaga agaagcaaac gggagccttt ctgaagaaga agcgaacggg 660
ccagagttgg ggtctggaaa agccatggaa gatacctctg gggaacccgc tgcagaggac 720
gagggagaca ccgcttggaa ctacagcttc tcccagctgc ctcgatttct cagtggttcc 780
tggtcagagt tcagcaccca acctgagaac ttcttgaaag gctgtaagtg ggctcctgac 840
ggttcctgca tcttgaccaa tagtgctgat aacatcttgc gaatttataa cctgccccca 900
gagctgtacc atgaggggga gcaggtggaa tatgcagaaa tggtccctgt ccttcgaatg 960
gtggaaggtg ataccatcta tgattactgc tggtattctc tgatgtcctc agcccagcca 1020
gacacctcct acgtggccag cagcagccgg gagaacccga ttcatatctg ggacgcattc 1080
actggagagc tccgggcttc ctttcgcgcc tacaaccacc tggatgagct gacggcagcc 1140
cattcgctct gcttctcccc ggatggctcc cagctcttct gtggcttcaa ccggactgtg 1200
cgtgtttttt ccacggcccg gcctggccga gactgcgagg tccgagccac atttgcaaaa 1260

-continued

```
aagcagggcc agagcggcat catctcctgc atagccttca gcccagccca gcccctctat   1320

gcctgtggct cctacggccg ctccctgggt ctgtatgcct gggatgatgg ctcccctctc   1380

gccttgctgg gagggcacca agggggcatc acccacctct gctttcatcc cgatggcaac   1440

cgcttcttct caggagcccg caaggatgct gagctcctgt gctgggatct ccggcagtct   1500

ggttacccac tgtggtccct gggtcgagag gtgaccacca atcagcgcat ctacttcgat   1560

ctggacccga ccgggcagtt cctagtgagt ggcagcacga gcggggctgt ctctgtgtgg   1620

gacacggacg ggcctggcaa tgatgggaag ccggagcccg tgttgagttt tctgccccag   1680

aaggactgca ccaatggcgt gagcctgcac cctagcctgc ctctcctggc cactgcctcc   1740

ggtcagcgtg tgtttcctga gcccacagag agtggggacg aaggagagga gctgggcctt   1800

cccttgctct ccacgcgcca cgtccacctt gaatgtcggc ttcagctctg gtggtgtggg   1860

ggggcgccag actccagcat ccctgatgat caccagggcg agaaagggca gggaggaacg   1920

gagggaggtg tgggtgagct gatataaaaa ggtttttatg ataaaaaaaa aaaaaaaaaa   1980

aa                                                                  1982
```

```
<210> SEQ ID NO 14
<211> LENGTH: 789
<212> TYPE: DNA
<213> ORGANISM: homo sapiens
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u

<400> SEQUENCE: 14

taaacgggna aagatgcctt ncttttttaan cctaattgaa ttttaaatgt ccttttgaca     60

caaaaaggta tatacatgac acagctacac aacctttttt caactggaca acaagtgtca    120

aaaccctgtg gatgtatagg gtaaaacaag attggtcagg aaaagagaat tgttcctata    180

actggtaatc tgacacaatg tcctattgcc attaaaaaaa aaaggtccat tttcagttta    240

ttcaagttta ttttcatggt gttttatccc tcttgataaa aaaaaattca gacttttgta    300

atttgtgtat gctgatcttc atcaaaaggt tcattctctg gatcagagtc agtggtgtca    360

gaatatctat aatgatcagg ttcattgtca ctaacatctg ttgttacaga agtttaactt    420

gctagcctcc ggatttgacg gctcctctac tgcctttgag aagtacagtt tcaccttaaa    480

ttttggagaa aacgttcacg ttgactttgt ctttattttc ttacggcaag acaatttttt    540

gttataagta agttcctata cttcccttgc atttatttta caccctccta tatctgtcaa    600

tctttatcta tttttttgtt taacaataaa cccactaatt tccctacttt ttcttccaac    660

gttatccacc tatcacctgg atcataaata atgtttttct tccccataag ttcaaaactt    720

tttccccctc ttttttttcca cccctctttt tgattcttcg caataaacct ttatttgttt    780

tctccccac                                                            789
```

```
<210> SEQ ID NO 15
<211> LENGTH: 467
<212> TYPE: DNA
<213> ORGANISM: homo sapiens
```

<400> SEQUENCE: 15

| | | | | | |
|---|---|---|---|---|---|
| aagaaatggc | atatttgaag | aaatcatatg | gctagacaaa | acaaactaga | tagattgtga | 60 |
| agctagatag | actaaacctc | agtcttgatt | actaattaca | agctgaatgt | ataaatcttt | 120 |
| tccttcagag | gcataaaggt | aagagttatg | aatcaaatgg | aaggaccaaa | atgcttccca | 180 |
| atgaagtatt | ttcttggtga | agttattgca | atctaaggtc | tgaaaatcag | ctgtacagga | 240 |
| actttatcag | taacctaaaa | gatgatcaat | cagcctcagt | gactaacgac | actgagaaga | 300 |
| gaccaacgta | aaaactagca | caccagatta | atttaccaca | aagatattct | caccataatc | 360 |
| agaaaacctg | ccctctattc | agagtattca | ctcttttttg | gtatgagtac | taatctggct | 420 |
| gggtcgaatt | agtgcttagt | tgaatacaga | attaaaataa | tgtgaag | | 467 |

<210> SEQ ID NO 16
<211> LENGTH: 21
<212> TYPE: DNA
<213> ORGANISM: artificial
<220> FEATURE:
<223> OTHER INFORMATION: targets natural antisense

<400> SEQUENCE: 16
gcctccttat acaccactat c    21

<210> SEQ ID NO 17
<211> LENGTH: 20
<212> TYPE: DNA
<213> ORGANISM: artificial
<220> FEATURE:
<223> OTHER INFORMATION: targets natural antisense

<400> SEQUENCE: 17
gtgctggatc tggtctaggc    20

<210> SEQ ID NO 18
<211> LENGTH: 19
<212> TYPE: DNA
<213> ORGANISM: artificial
<220> FEATURE:
<223> OTHER INFORMATION: targets natural antisense

<400> SEQUENCE: 18
accactgcct ctgtctcca    19

<210> SEQ ID NO 19
<211> LENGTH: 27
<212> TYPE: DNA
<213> ORGANISM: artificial
<220> FEATURE:
<223> OTHER INFORMATION: targets natural antisense

<400> SEQUENCE: 19
cugcucuggc uguggucagu gccucgg    27

<210> SEQ ID NO 20
<211> LENGTH: 27
<212> TYPE: DNA
<213> ORGANISM: artificial
<220> FEATURE:
<223> OTHER INFORMATION: targerts natural antisense

<400> SEQUENCE: 20
auucccuucc auaggcauga gacuguu    27

<210> SEQ ID NO 21
<211> LENGTH: 27
<212> TYPE: DNA
<213> ORGANISM: artificial
<220> FEATURE:
<223> OTHER INFORMATION: targets natural antisense

<400> SEQUENCE: 21
ccaagcugcu ggaagcaugu acuggug 27

<210> SEQ ID NO 22
<211> LENGTH: 27
<212> TYPE: DNA
<213> ORGANISM: artificial
<220> FEATURE:
<223> OTHER INFORMATION: targets natural antisense

<400> SEQUENCE: 22
agacggucuc auagguggaa uuugcug 27

<210> SEQ ID NO 23
<211> LENGTH: 21
<212> TYPE: DNA
<213> ORGANISM: artificial
<220> FEATURE:
<223> OTHER INFORMATION: targets natural antisense

<400> SEQUENCE: 23
gatgtatgtc tgctctctcc a 21

<210> SEQ ID NO 24
<211> LENGTH: 20
<212> TYPE: DNA
<213> ORGANISM: artificial
<220> FEATURE:
<223> OTHER INFORMATION: targets natural antisense

<400> SEQUENCE: 24
ggcttggtct gagcagggta 20

<210> SEQ ID NO 25
<211> LENGTH: 21
<212> TYPE: DNA
<213> ORGANISM: artificial
<220> FEATURE:
<223> OTHER INFORMATION: targets natural antisense

<400> SEQUENCE: 25
cctgcaccgg agatgtatgt c 21

<210> SEQ ID NO 26
<211> LENGTH: 21
<212> TYPE: DNA
<213> ORGANISM: artificial
<220> FEATURE:
<223> OTHER INFORMATION: targets natural antisense

<400> SEQUENCE: 26
ccggagatgt atgtctgctc t 21

<210> SEQ ID NO 27
<211> LENGTH: 21
<212> TYPE: DNA
<213> ORGANISM: artificial
<220> FEATURE:
<223> OTHER INFORMATION: targets natural antisense

<400> SEQUENCE: 27
gcccaccacc tcattattcc c 21

<210> SEQ ID NO 28
<211> LENGTH: 20
<212> TYPE: DNA
<213> ORGANISM: artificial
<220> FEATURE:
<223> OTHER INFORMATION: targets natural antisense

<400> SEQUENCE: 28
ccagtcccaa gtccagcaga 20

<210> SEQ ID NO 29
<211> LENGTH: 20
<212> TYPE: DNA
<213> ORGANISM: artificial
<220> FEATURE:
<223> OTHER INFORMATION: targets natural antisense

<400> SEQUENCE: 29
gcctccgtga actcctcctt 20

<210> SEQ ID NO 30
<211> LENGTH: 20
<212> TYPE: DNA
<213> ORGANISM: artificial
<220> FEATURE:
<223> OTHER INFORMATION: targets natural antisense

<400> SEQUENCE: 30
gttccgccca ccacctcatt 20

<210> SEQ ID NO 31
<211> LENGTH: 21
<212> TYPE: DNA
<213> ORGANISM: artificial
<220> FEATURE:
<223> OTHER INFORMATION: targets natural antisense

<400> SEQUENCE: 31
ggagcaagaa cuuucugaat t 21

<210> SEQ ID NO 32
<211> LENGTH: 21
<212> TYPE: DNA
<213> ORGANISM: artificial
<220> FEATURE:
<223> OTHER INFORMATION: targets natural antisense

<400> SEQUENCE: 32
ccaaucagcg caucuacuut t 21

<210> SEQ ID NO 33
<211> LENGTH: 21
<212> TYPE: DNA
<213> ORGANISM: artificial
<220> FEATURE:
<223> OTHER INFORMATION: targets natural antisense

<400> SEQUENCE: 33
ccaccaauca gcgcaucuat t 21

-continued

<210> SEQ ID NO 34
<211> LENGTH: 27
<212> TYPE: DNA
<213> ORGANISM: artificial
<220> FEATURE:
<223> OTHER INFORMATION: targets natural antisense

<400> SEQUENCE: 34
uucauaacuc uuaccuuuau gccucug 27

<210> SEQ ID NO 35
<211> LENGTH: 27
<212> TYPE: DNA
<213> ORGANISM: artificial
<220> FEATURE:
<223> OTHER INFORMATION: targets natural antisense

<400> SEQUENCE: 35
auucugacac cacugacucu gauccag 27

<210> SEQ ID NO 36
<211> LENGTH: 27
<212> TYPE: DNA
<213> ORGANISM: artificial
<220> FEATURE:
<223> OTHER INFORMATION: targets natural antisense

<400> SEQUENCE: 36
auuaccaguu auaggaacaa uucucuu 27

<210> SEQ ID NO 37
<211> LENGTH: 25
<212> TYPE: DNA
<213> ORGANISM: artificial
<220> FEATURE:
<223> OTHER INFORMATION: targets natural antisense

<400> SEQUENCE: 37
gaggcacuga ccacagccag agcag 25

<210> SEQ ID NO 38
<211> LENGTH: 25
<212> TYPE: DNA
<213> ORGANISM: artificial
<220> FEATURE:
<223> OTHER INFORMATION: targets natural antisense

<400> SEQUENCE: 38
cagucucaug ccuauggaag ggaat 25

<210> SEQ ID NO 39
<211> LENGTH: 25
<212> TYPE: DNA
<213> ORGANISM: artificial
<220> FEATURE:
<223> OTHER INFORMATION: targets natural antisense

<400> SEQUENCE: 39
ccaguacaug cuuccagcag cuugg 25

<210> SEQ ID NO 40
<211> LENGTH: 25
<212> TYPE: DNA
<213> ORGANISM: artificial
<220> FEATURE:
<223> OTHER INFORMATION: targets natural antisense

<400> SEQUENCE: 40
gcaaauucca ccuaugagac cguct 25

<210> SEQ ID NO 41
<211> LENGTH: 21
<212> TYPE: DNA
<213> ORGANISM: artificial
<220> FEATURE:
<223> OTHER INFORMATION: targets natural antisense

<400> SEQUENCE: 41
acctctggag ctctctggaa c 21

<210> SEQ ID NO 42
<211> LENGTH: 25
<212> TYPE: DNA
<213> ORGANISM: artificial
<220> FEATURE:
<223> OTHER INFORMATION: targets natural antisense

<400> SEQUENCE: 42
tatgatggaa aggtgcgcat cctta 25

<210> SEQ ID NO 43
<211> LENGTH: 25
<212> TYPE: DNA
<213> ORGANISM: artificial
<220> FEATURE:
<223> OTHER INFORMATION: targets natural antisense

<400> SEQUENCE: 43
cttccctgga ttggcagcca gactg 25

<210> SEQ ID NO 44
<211> LENGTH: 25
<212> TYPE: DNA
<213> ORGANISM: artificial
<220> FEATURE:
<223> OTHER INFORMATION: targets natural antisense

<400> SEQUENCE: 44
atatgcagaa atggtccctg tcctt 25

<210> SEQ ID NO 45
<211> LENGTH: 25
<212> TYPE: DNA
<213> ORGANISM: artificial
<220> FEATURE:
<223> OTHER INFORMATION: targets natural antisense

<400> SEQUENCE: 45
gaggcauaaa gguaagaguu augaa 25

<210> SEQ ID NO 46
<211> LENGTH: 25
<212> TYPE: DNA
<213> ORGANISM: artificial
<220> FEATURE:
<223> OTHER INFORMATION: targets natural antisense

<400> SEQUENCE: 46
ggaucagagu caguggaguc agaat 25

-continued

```
<210> SEQ ID NO 47
<211> LENGTH: 25
<212> TYPE: DNA
<213> ORGANISM: artificial
<220> FEATURE:
<223> OTHER INFORMATION: targets natural antisense

<400> SEQUENCE: 47

gagaauuguu ccuauaacug guaat                                   25
```

TREATMENT OF TUMOR SUPPRESSOR GENE RELATED DISEASES BY INHIBITION OF NATURAL ANTISENSE TRANSCRIPT TO THE GENE

CROSS REFERENCE

This application is a continuation of U.S. Ser. No. 13/133,039 filed on Jun. 15, 2011, which is a national stage application of PCT/US2009/066654 filed Dec. 3, 2009, which claims priority to U.S. Provisional Application No. 61/119,973, filed on Dec. 4, 2008, U.S. Provisional Application No. 61/154,594 filed on Feb. 23, 2009; U.S. Provisional Application No. 61/157,249, filed Mar. 4, 2009, and U.S. Provisional Application No. 61/166,381, filed Apr. 3, 2009, which are all incorporated herein by reference in their entirety.

FIELD OF THE INVENTION

Embodiments of the invention comprise oligonucleotides modulating expression and/or function of Tumor Suppressor genes and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRA VENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an Tumor Suppressor gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 1675 of SEQ ID NO:8 or nucleotides 1 to 518 of SEQ ID NO: 9 or nucleotides 1 to 759 of SEQ ID NO: 10 or nucleotides 1 to 25892 of SEQ ID NO: 11 or nucleotides 1 to 279 of SEQ ID NO: 12, or nucleotides 1 to 1982 of SEQ ID NO: 13, or nucleotides 1 to 789 of SEQ ID NO: 14, or nucleotides 1 to 467 of SEQ ID NO: 15 (FIG. 5) thereby modulating function and/or expression of the Tumor Suppressor gene polynucleotide in patient cells or tissues in vivo or in vitro.

In another preferred embodiment, an oligonucleotide targets a natural antisense sequence of Tumor Suppressor gene polynucleotides, for example, nucleotides set forth in SEQ ID NOS: 8, 9, 10, 11, 12, 13, 14 or 15, and any variants, alleles, homo logs, mutants, derivatives, fragments and complementary sequences thereto. Examples of antisense oligonucleotides are set forth as SEQ ID NOS: 16 to 36 (FIG. 6 to 9).

Another embodiment provides a method of modulating function and/or expression of an Tumor Suppressor gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the Tumor Suppressor gene polynucleotide; thereby modulating function and/or expression of the Tumor Suppressor gene polynucleotide in patient cells or tissues in vivo or in vitro.

Another embodiment provides a method of modulating function and/or expression of an Tumor Suppressor gene polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an Tumor Suppressor gene antisense polynucleotide; thereby modulating function and/or expression of the Tumor Suppressor gene polynucleotide in patient cells or tissues in vivo or in vitro.

In a preferred embodiment, a composition comprises one or more antisense oligonucleotides which bind to sense and/or antisense Tumor Suppressor gene polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

One embodiment provides a method of modulating a function of and/or the expression of a Tumor Suppressor gene polynucleotide in patient cells or tissues in vivo or in vitro comprising contacting said cells or tissues with at least one antisense oligonucleotide 5 to 30 nucleotides in length wherein said at least one oligonucleotide has at least 50% sequence identity to a reverse complement of a natural antisense of a Tumor Suppressor gene polynucleotide, thereby modulating a function of and/or the expression of the Tumor Suppressor gene polynucleotide in patient cells or tissues in vivo or in vitro.

One embodiment provides a method of modulating a function of and/or expression of a Tumor Suppressor gene polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to the Tumor Suppressor gene polynucleotide; thereby modulating a function of and/or the expression of the Tumor Suppressor gene polynucleotide in patient cells or tissues in vivo or in vitro.

Another embodiment provides a method of modulating a function of and/or the expression of a Tumor Suppressor gene polynucleotide in patient cells or tissues in vivo or in vitro comprising contacting said cells or tissues with at least one antisense oligonucleotide that targets a region of the natural antisense of a Tumor Suppressor gene polynucleotide; thereby modulating a function of and/or the expression of the Tumor Suppressor gene polynucleotide in patient cells or tissues in vivo or in vitro.

In an embodiment, a function of and/or the expression of the Tumor Suppressor gene polynucleotide is increased in vivo or in vitro with respect to a control.

In another embodiment, the at least one antisense oligonucleotide targets a natural antisense sequence of a Tumor Suppressor gene polynucleotide.

In an embodiment, the at least one antisense oligonucleotide targets a nucleic acid sequence comprising coding and/or non-coding nucleic acid sequences of a Tumor Suppressor gene polynucleotide.

In an embodiment, the at least one antisense oligonucleotide targets overlapping and/or non-overlapping sequences of a Tumor Suppressor gene polynucleotide.

In a particular embodiment, the at least one antisense oligonucleotide comprises one or more modifications selected from: at least one modified sugar moiety, at least one modified internucleoside linkage, at least one modified nucleotide, and combinations thereof.

In a related embodiment, the one or more modifications comprise at least one modified sugar moiety selected from: a 2'-O-methoxyethyl modified sugar moiety, a T-methoxy modified sugar moiety, a 2'-O-alkyl modified sugar moiety, a bicyclic sugar moiety, and combinations thereof.

In another embodiment, the one or more modifications comprise at least one modified internucleoside linkage selected from: a phosphorothioate, T-O-methoxyethyl (MOE), T-fluoro, alkylphosphonate, phosphorodithioate, alkylphosphonothioate, phosphoramidate, carbamate, carbonate, phosphate triester, acetamidate, a carboxymethyl ester, and combinations thereof.

In an embodiment, the one or more modifications comprise at least one modified nucleotide selected from: a peptide nucleic acid (PNA), a locked nucleic acid (LNA), an arabino-nucleic acid (FANA), an analogue, a derivative, and combinations thereof.

In another embodiment, the at least one oligonucleotide comprises at least one of the oligonucleotide sequences set forth as SEQ ID NOS: 16 to 36.

The invention also provides a method of modulating a function of and/or the expression of a Tumor Suppressor gene in mammalian cells or tissues in vivo or in vitro comprising contacting said cells or tissues with at least one short interfering RNA (siRNA) oligonucleotide 5 to 30 nucleotides in length, said at least one siRNA specific for an antisense polynucleotide of a Tumor Suppressor gene polynucleotide wherein said oligonucleotide has at least 50% sequence identity to a complementary sequence of at least about five consecutive nucleic acids of the antisense and/or sense nucleic acid molecule of a Tumor Suppressor gene polynucleotide; and, modulating a function of and/or the expression of the Tumor Suppressor gene in mammalian cells or tissues in vivo or in vitro.

In an embodiment, the oligonucleotide has at least 80% sequence identity to a complementary sequence of at least about five consecutive nucleic acids of the antisense and/or sense nucleic acid molecule of the Tumor Suppressor gene polynucleotide.

Another embodiment provides a method of modulating a function of and/or the expression of a Tumor Suppressor gene in mammalian cells or tissues in vivo or in vitro comprising contacting said cells or tissues with at least one antisense oligonucleotide of about 5 to 30 nucleotides in length specific for noncoding and/or coding sequences of a sense and/or natural antisense strand of a Tumor Suppressor gene polynucleotide wherein said at least one antisense oligonucleotide has at least 50% sequence identity to at least one nucleic acid sequence set forth as SEQ ID NOS: 1, 2, 3, 4, 5, 6, 7, 7, 9, 10, 11, 12, 13, 14 and 15; and, modulating the function and/or expression of the Tumor Suppressor gene in mammalian cells or tissues in vivo or in vitro.

One embodiment provides a synthetic, modified oligonucleotide comprising at least one modification, wherein the at least one modification is selected from: at least one modified sugar moiety; at least one modified internucleotide linkage; at least one modified nucleotide; and combinations thereof; and further wherein said oligonucleotide is an antisense compound which hybridizes to and modulates expression and/or function of a Tumor Suppressor gene polynucleotide in vivo or in vitro as compared to a normal control.

In an embodiment, the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof.

In another embodiment, the oligonucleotide comprises at least one phosphorothioate internucleotide linkage.

In a related embodiment, oligonucleotide comprises a backbone of phosphorothioate internucleotide linkages.

In an embodiment, the oligonucleotide comprises at least one modified nucleotide, said modified nucleotide selected from: a peptide nucleic acid, a locked nucleic acid (LNA), analogue, derivative, and a combination thereof.

In another embodiment, the oligonucleotide comprises a plurality of modifications, wherein said modifications comprise internucleotide linkages selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

In an embodiment, the oligonucleotide comprises a plurality of modifications, wherein said modifications comprise modified nucleotides selected from: peptide nucleic acids, locked nucleic acids (LNA), analogues, derivatives, and a combination thereof.

In another embodiment, the oligonucleotide comprises at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and a combination thereof.

In another embodiment, the oligonucleotide comprises a plurality of modifications, wherein said modifications comprise modified sugar moieties selected from: a 2'-O-methoxyethyl modified sugar moiety, a 2'-methoxy modified sugar moiety, a 2'-O-alkyl modified sugar moiety, a bicyclic sugar moiety, and a combination thereof.

In another embodiment, the oligonucleotide is of at least about 5 to 30 nucleotides in length and hybridizes to an antisense and/or sense strand of a Tumor Suppressor gene polynucleotide wherein said oligonucleotide has at least about 20% sequence identity to a complementary sequence of at least about five consecutive nucleic acids of the antisense and/or sense coding and/or noncoding nucleic acid sequences of the Tumor Suppressor gene polynucleotide.

In another embodiment, the oligonucleotide has at least about 80% sequence identity to a complementary sequence of at least about five consecutive nucleic acids of the antisense and/or sense coding and/or noncoding nucleic acid sequence of the Tumor Suppressor gene polynucleotide.

In another embodiment, said oligonucleotide hybridizes to and modulates expression and/or function of at least one Tumor Suppressor gene polynucleotide in vivo or in vitro, as compared to a normal control.

In an embodiment, the oligonucleotide comprises one of the sequences set forth as SEQ ID NOS: 16 to 36.

The invention further provides a composition comprising one or more oligonucleotides specific for one or more Tumor Suppressor gene polynucleotides, said polynucleotides comprising antisense sequences, complementary sequences, alleles, homologs, isoforms, variants, derivatives, mutants, fragments, or combinations thereof.

In a certain embodiment, wherein the oligonucleotides have at least about 40% sequence identity as compared to any one of the nucleotide sequences set forth as SEQ ID NOS: 16 to 36.

In an embodiment, the one or more oligonucleotides comprise any of the nucleotide sequences set forth as SEQ ID NOS: 16 to 36.

In another embodiment, the oligonucleotides set forth as SEQ ID NOS: 16 to 36 comprise one or more modifications or nucleotide substitutions.

In another embodiment, the one or more modifications are selected from: phosphorothioate, methylphosphonate, peptide nucleic acid, locked nucleic acid (LNA) molecules, and combinations thereof.

An embodiment of the invention provides a method of preventing or treating a disease associated with at least one Tumor Suppressor gene polynucleotide and/or at least one encoded product thereof, comprising administering to a patient a therapeutically effective dose of at least one antisense oligonucleotide that binds to a natural antisense sequence of said at least one Tumor Suppressor gene polynucleotide and modulates expression of said at least one Tumor Suppressor gene polynucleotide; thereby preventing or treating the disease associated with the at least one Tumor Suppressor gene polynucleotide and/or at least one encoded product thereof.

In a certain embodiment, a disease associated with the at least one Tumor Suppressor gene polynucleotide is selected from: a disease associated with decreased or increased apoptosis, tissue/cell aging, a cancer (including those mentioned in Table 1), an autoimmune disease, an immunodeficiency disease including AIDS, senescence, a neurodegenerative disease or disorder (e.g. Alzheimer's disease, ataxia telangiectasia, Parkinson's disease, amyotrophic lateral sclerosis, Huntington's disease etc.), a hyperplastic disease (e.g., cheloid), rheumatoid arthritis, coronary heart disease ischemic cell death, a lymphoproliferative disorder, atherosclerosis, osteoporosis, a myelodysplastic syndrome, a toxin-induced disease, a viral infection, wound-healing, Cowden disease (CD), Lhermitte-Duclos disease (LDD), Bannayan-Zonana syndrome (BZS, also known as Bannayan-Riley-Ruvalcaba syndrome, Ruvalcaba-Myhre-Smith syndrome and Riley-Smith syndrome), transplantation, an apotosis-related disease or disorder, a metabolic disease or condition (e.g., diabetes), a kidney diseases or disorder, myocardial infarction/heart failure, ischemia, sepsis, an inflammatory disease where particular haematopoeitic inflammatory cells are in excess, a proliferative disease, or a disease or disorder wherein there is a therapeutic paradigm for treatment of inflammatory disease through increasing apoptosis.

An embodiment provides a method of identifying and selecting at least one oligonucleotide for in vivo administration comprising: selecting a target polynucleotide associated with a disease state; identifying at least one oligonucleotide comprising at least five consecutive nucleotides which are complementary to, or in an antisense orientation to the selected target polynucleotide; measuring the thermal melting point of an hybrid of an antisense oligonucleotide and the target polynucleotide under stringent hybridization conditions; and selecting at least one oligonucleotide for in vivo administration based on the information obtained.

Other aspects are described infra.

BRIEF DESCRIPTION OF THE DRAWINGS

FIG. 4 shows:

Figure 1A:
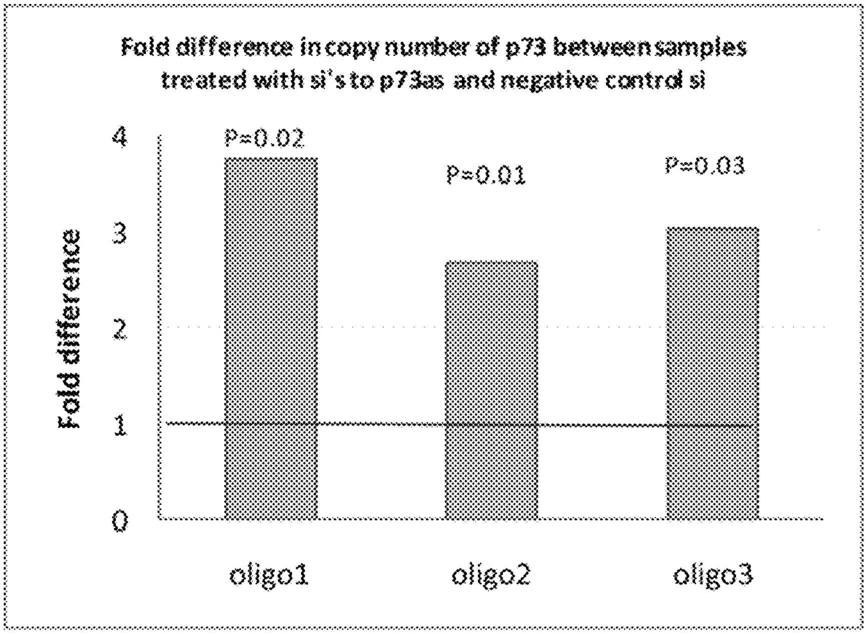
FIG. 1A and FIG. 1B: is a graph of real time PCR results showing the fold change in TP73 mRNA after treatment of HepG2 cells with phosphorothioate oligonucleotides introduced using Lipofectamine 2000, as compared to control. Real time PCR results show that the levels of the p73 mRNA in HepG2 cells are significantly increased 48 h after treatment with the oligos designed to p73as (FIG. 1A). In the same samples the levels of p73as RNA were significantly reduced after treatment with oligos to p73as (FIG. 1B). Bars denoted as oligo 1, oligo 2 and oligo 3 correspond to samples treated with SEQ ID NOS 16, 17 and 18 respectively.

SEQ ID NO: 1: *Homo sapiens* Tumor Suppressor gene (TP73) transcript variant 1, mRNA. (NCBI Accession No.: NM_005427.2)

SEQ ID NO: 2 shows the genomic sequence of p73 (exons are shown in capital letters, introns in small).

SEQ ID NO: 3 shows the mouse genomic sequence of p73 (exons are shown in capital letters, introns in small). SEQ ID NO: 2: *Homo sapiens* tumor protein p53 (TP53), transcript variant 1, mRNA. (NCBI Accession No.: NM_000546.4)

SEQ ID NO: 4: shows the *Homo sapiens* transcript variant 1 mRNA sequence of p53.

SEQ ID NO: 5 shows the genomic sequence of p53 (exons are shown in capital letters, introns in small).

SEQ ID NO: 6: *Homo sapiens* phosphatase and tensin homolog (PTEN), mRNA. (NCBI Accession No.: NM_000314).

SEQ ID NO: 7: shows the genomic sequence of PTEN (exons are shown in capital letters, introns in small).

FIG. 5 shows:

SEQ ID NO: 8: Natural antisense sequence p73as (NCBI Accession No.: NM_017818.2)

SEQ ID NO: 9: p73 Natural antisense sequence Hs.668503

SEQ ID NO: 10: p73 Natural antisense sequence Hs.674463

SEQ ID NO: 11: p73 Mouse Natural antisense sequence

SEQ ID NO: 12: p73 Mouse natural antisense sequence: Hs.668503 (Matching bases in cDNA and genomic sequences are indicated by capital letters)

SEQ ID NO: 13: p53 Natural Antisense sequence (NCBI Accession No.: NM_018081.2)

SEQ ID NO: 14: PTEN Natural Antisense sequence (Hs.624903)

SEQ ID NO: 15: PTEN Natural Antisense sequence (Hs.607931)

FIG. 6 shows the antisense oligonucleotides, SEQ ID NOs: 16 to 22. 'r' indicates RNA and * indicates phosphorothioate bond.

FIG. 7 shows the antisense oligonucleotides, SEQ ID NOs: 23 to 30. * indicates phosphorothioate bond.

FIG. 8 shows the p53 antisense oligonucleotides to natural antisense sequence NM O 18081, SEQ ID NOs: 31 to 33.

FIG. 9 shows the PTEN antisense oligonucleotides to natural antisense sequence Hs.624903 and Hs.607931, SEQ ID NOs: 34 to 36. 'r' indicates RNA.

FIG. 10 shows the sense oligonucleotides, SEQ ID NOs: 37 to 40. 'r' indicates RNA.

The sense oligonucleotide SEQ ID NO: 37 is the reverse complement of the antisense oligonucleotide SEQ ID NO: 19, the sense oligonucleotide SEQ ID NO: 38 is the reverse complement of the antisense oligonucleotide SEQ ID NO: 20, the sense oligonucleotide SEQ ID NO: 39 is the reverse complement of the antisense oligonucleotide SEQ ID NO: 21; and the sense oligonucleotide SEQ ID NO: 40 is the reverse complement of the antisense oligonucleotide SEQ ID NO: 22.

FIG. 11 shows SEQ ID NOs: 41 and 42 of the assays designed by Applied Biosystems Taqman gene Expression Assay SEQ ID No.: 41 is the p73 target sequence, exon 2 (Hs00232088_ml)

SEQ ID No.: 42 is the p73as target sequence, exon 7 (Hs00215135_ml and Hs00892470_gl)

FIG. 12 shows SEQ ID NOs: 43 and 44 of the assays designed by Applied Biosystems Taqman gene Expression Assay.

SEQ ID No.: 43 is the p53 target sequence (HsOO 153340 ml)

SEQ ID No.: 44 is the p53 as (WDR79) target sequence (Hs00216360_ml)

FIG. 13 shows the sense oligonucleotides, SEQ ID NOs: 45 to 47. 'r' indicates RNA.

The sense oligonucleotide SEQ ID NO: 45 is the reverse complement of the antisense oligonucleotide SEQ ID NO: 34, the sense oligonucleotide SEQ ID NO: 46 is the reverse complement of the antisense oligonucleotide SEQ ID NO: 35; and the sense oligonucleotide SEQ ID NO: 47 is the reverse complement of the antisense oligonucleotide SEQ ID NO: 36.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates.

Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms “a”, “an” and “the” are intended to include the plural forms as well, unless the context clearly indicates otherwise. Furthermore, to the extent that the terms “including”, “includes”, “having”, “has”, “with”, or variants thereof are used in either the detailed description and/or the claims, such terms are intended to be inclusive in a manner similar to the term “comprising.”

The term “about” or “approximately” means within an acceptable error range for the particular value as determined by one of ordinary skill in the art, which will depend in part on how the value is measured or determined, i.e., the limitations of the measurement system. For example, “about” can mean within 1 or more than 1 standard deviation, per the practice in the art. Alternatively, “about” can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term “about” meaning within an acceptable error range for the particular value should be assumed.

As used herein, the term “mRNA” means the presently known mRNA transcript(s) of a targeted gene, and any further transcripts which may be elucidated.

By “antisense oligonucleotides” or “antisense compound” is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al, (1991) Ann. Rev. Biochem. 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term “oligonucleotide” refers to an oligomer or polymer of ribonucleic acid (RNA) or deoxyribonucleic acid (DNA) or mimetics thereof. The term “oligonucleotide”, also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoógsteen or reverse Hoógsteen types of base pairing, or the like.

The oligonucleotide may be “chimeric”, that is, composed of different regions. In the context of this invention “chimeric” compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in “register”, that is, when the monomers are linked consecutively, as in native DNA, or linked via spacers. The spacers are intended to constitute a covalent “bridge” between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein “Tumor Suppressor gene” and “Tumor Suppressor gene” are inclusive of all family members, mutants, alleles, fragments, species, coding and noncoding sequences, sense and antisense polynucleotide strands, etc.

As used herein, the words Tumor Protein 73, p73, TP73 are used interchangeably in the present application.

As used herein, the words TRP53, Tumor suppressor p53, p53, P53 Antigen NY-CO-13, Cellular tumor antigen p53, FLJ92943, LFS1, and Phosphoprotein p53 are used interchangeably in the present application.

As used herein, the words PTEN, 10q23del, BZS, MGCI 1227, MHAM, MMACI, Mutated in multiple advanced cancers 1, Phosphatase and tensin homo log, Phosphatidylinositol-3,4,5-trisphosphate 3-phosphatase and dual-specificity protein phosphatase PTEN, PTENI, TEPI are used interchangeably in the present application.

As used herein, the term “oligonucleotide specific for” or “oligonucleotide which targets” refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term “target nucleic acid” encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N. J., et al. (2001) Proc. Natl. Acad. Sci. USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) Nature 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) Nature 409:363-366; Boutla, A., et al. (2001) Curr. Biol. 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) J. American. Med. Assoc. 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al. (1990) Cell, 63, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and T-hydroxyl sugars, e.g., as described in Komberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) Nucl. Acid. Res., 25(22), 4429-4443, Toulme, J. J., (2001) Nature Biotechnology 19:17-18; Manoharan M., (1999) Biochemica et Biophysica Acta 1489:117-139; Freier S. M., (1997) Nucleic Acid Research, 25:4429-4443, Uhlman, E., (2000) Drug Discovery & Development, 3: 203-213, Herdewin P., (2000) Antisense & Nucleic Acid Drug Dev., 10:297-310); T-O, 3^-C-linked [3.2.0]bicycloarabinonucleosides (see e.g. N. K Christiensen., et al, (1998) J. Am. Chem. Soc, 120: 5458-5463;

Prakash T P, Bhat B. (2007) Curr Top Med Chem. 7(7):641-9; Cho E J, et al. (2009) Annual Review of Analytical Chemistry, 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoógsteen or reversed Hoógsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1.1X sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al, (1990) J. Mol. Biol, 215, 403-410; Zhang and Madden, (1997) Genome Res., 7, 649-656). Percent homology, sequence identity or complementarity, can be determined by, for example, the Gap program (Wisconsin Sequence Analysis Package, Version 8 for Unix, genetics Computer Group, University Research Park, Madison Wis.), using default settings, which uses the algorithm of Smith and Waterman {Adv. Appl. Math., (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, the term "cancer" refers to any malignant tumor, particularly arising in the lung, kidney, or thyroid. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. As noted above, the invention specifically permits differential diagnosis of lung, kidney, and thyroid tumors.

Polynucleotide and Oligonucleotide Composition and Molecules

Targets: In one embodiment, the targets comprise nucleic acid sequences of Tumor Suppressor gene, including without limitation sense and/or antisense noncoding and/or coding sequences associated with Tumor Suppressor gene.

Tumor Suppressors are genes whose products act to control cell division. They differ from oncogenes in that tumor suppressors produce products that inhibit the division of cells if conditions for growth are not met. The conditions that would trigger the 'brakes' of the cell include DNA damage, a lack of growth factors or defects in the division apparatus. When the tumor suppressor gene is mutated to cause a loss or reduction in its function, the cell can progress to cancer, usually in combination with other genetic changes. This is in contrast to the oncogenes which have gained functions (or lost the ability to be controlled) in their mutant form. Examples of tumor suppressor genes include p53 (TP53): a transcription factor that regulates cell division; Rb: alters the activity of transcription factors and therefore controls cell division; APC: controls the availability of the transcription factor, BRCA: involved in DNA repair.

p53 tumor suppressor exerts anti-proliferative effects, including growth arrest, apoptosis, and cell senescence, in response to various types of stress (Levine A. J., (1997) Cell 88:323-31; Oren M., (1999) J. Biol. Chem. 274: 36031-034). p53 can be thought of as the central node of a regulatory circuit that monitors signaling pathways from diverse sources, including DNA damage responses (e.g., ATM/ATR activation), abnormal oncogenic events (e.g., Myc or Ras activation) and everyday cellular processes (e.g., growth factor stimulation). While p53 mutations have been in more than half of all the human tumors (Hollstein et ah, (1999) Mutat Res. 431:199-209), defects in other components of p53 pathway, such as ARF tumor suppressor, are observed in tumor cells that retain wildtype p53 (Sherr, C. J., (2001) Nat Rev Mol Cell Biol 2:731-737; Sharpless N. E., et al, (2004) J Clin Invest 113:160-8). Activation of the p53 pathway appears to be a common, if not universal, feature of human cancer.

Regulation of these polynucleotides would be of great benefit in the treatment of cancer and other disorders in which abnormal cell proliferation plays a role. For example, p53 is a short-lived protein whose activity is maintained in low levels in normal cells. The molecular function of p53 that is required for tumor suppression involves ability of p53 to act as a transcriptional factor in regulating endogenous gene expression. Thus the regulation of p53 itself is important for its effect on tumorigenesis and the maintenance of normal cell growth. An antisense compound is specifically hybridizable when binding of the compound to the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which assays are performed.

Table 1 shows a list of some tumor suppressor genes

| Tumor Suppressor | Function | Cancer |
|---|---|---|
| APC | Controls the function of specific transcription factors | Familial adenomatous and non-inherited colorectal carcinomas |
| BRCA1, 2 | DNA damage and repair | Inherited Breast cancers; ovarian cancers |
| CDKN2A | Gene locus that encodes p16 and p14 ARF | Brain tumors |
| DCC | Function is still unknown | Colorectal carcinomas |
| DPC4 (SMAD4) | Mediates signaling from growth factor receptors | Colorectal tumors, pancreatic neoplasia |
| MADR2/JV18 (SMAD2) | Mediates signaling from growth factor receptors | Colorectal cancer |
| MEN1 | Codes for the menin protein that interacts with transcription factors and prevents transcription of certain genes. | Multiple endocrine neoplasia type 1 |
| MTS1 | Inhibitor of cyclin-dependent kinases | Melanomas |
| NF1 | RAS GTPase activating protein | Neurofibromatosis type 1 |
| NF2 | RAS GTPase activating protein | Neurofibromatosis type 2 |
| p53 | Encodes a transcription factor for p21 that arrests the cell cycle in G1 phase | Bladder, breast, colorectal, esophageal, liver, lung, prostate and ovarian carcinomas; brain tumors, sarcomas. Lymphomas and leukemias |
| PTEN | Lipid phosphatase that regulates cell survival | Cowden syndrome; increases risk of breast and thyroid cancer; Lhermitte-Duclos disease (LDD), Bannayan-Zonana syndrome (BZS); Source: |
| Rb | Alters activity of certain transcription factors that play a role in the control of cell division | Retinoblastoma, sarcomas; bladder, breast, esophageal, prostate and lung carcinomas |
| VHL | May target proteins for degradation | Renal cell carcinomas |
| WRN | Involved in DNA repair | Werner syndrome |
| WT1 | Transcriptional repressor | Wilm's tumors (pediatric kidney cancer) |
| TSC1 | Forms complex with TSC2 protein, inhibits signaling to downstream effectors of mTOR | Seizures, mental retardation, facial angiofibromas |
| TSC2 | Sec TSC1 above | Benign growths (hamartomas) In many-tissues, astrocytomas, |
| LKB1, a nuclear localized kinase, also called STK11 (Serine threonine kinase 11 ) | Phosphorylates and activates AMP-activated kinase (AMPK), AMPK involved in stress responses, lipid and glucose metabolism | Hyperpigmentation, multiple hamartomatous polyps, colorectal breast and ovarian cancers |
| MSH1.2 | DNA mismatch repair | Colon Cancer |
| CDH1 | Cell-Cell adhesion protein | Gastric cancer, lobular breast cancer |

-continued

| Tumor Suppressor | Function | Cancer |
|---|---|---|
| PTCH | Transmembrane receptor for sonic hedgehog (shh) | Basal cell skin carcinoma |

It is understood that this list is non-limiting, and that the invention encompasses the use of other tumor suppressors not specifically listed herein. One of skill in the art working in the field of tumor suppressors can identify additional tumor suppressors described in, e.g., the published literature.

It should be appreciated that in the above Table 1, an indicated gene means the gene and all currently known variants thereof, including the different mRNA transcripts that the gene and its variants can give rise to, any further gene variants which may be elucidated, and antisense sequences. The list also includes the non-coding RNA molecules or the portions of polynucleotides. In general, however, such variants will have significant sequence identity to a sequence of any polynucleotide in Table 1 above, e.g., a variant will have at least about 70 percent sequence identity to a sequence of the Table 1 above, typically at least about 75, 80, 85, 90, 95, 97, 98 or 99 percent sequence identity to a sequence of the above Table 1. Sequence identity of variant can be determined by any number of standard techniques such as BLAST program (ncbi.nclm-.nih.gov/blast/).

In another embodiment, the oligonucleotides are specific for one or more molecules that inhibit abnormal cell growth or tumors. This includes factors which inhibit molecular activities such as for example: transform cells, factors involved in pre-tumor stages, malignancy, pre-metastasis, metastasis and the like. Other examples include without limitation: developmental gene products (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene products (e.g., ABL1, BCL1, BCL2, BCL6, CBFA2, CBL, CSFIR, ERBA, ERBB, ERB2, ETS1, ETV6, FGR, FOS, FYN, HCR, HRAS, JUN, KRAS, LCK, LYN, MDM2, MLL, MYB, MYC, MYCL1, MYCN, NRAS, PIMI, PML, RET, SRC, TAL1, TCL3, AND YES); tumor suppressor gene products (e.g., APC, BRCA1, BRCA2, MADH4, MCC, NF1, NF2, RBI, TP53, and WT1) and enzymes (e.g., ACC synthases and oxidases, ACP desaturases and hydroxylases, ADP-glucose pyrophosphorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthesis, octopine synthases, pectinestrases, peroxidases, phosphatases, phospholipases, phosphorylases, phytases, plant growth regulator synthesases, polygalacturonases, proteinases and peptidases, pullanases, recombinases, reverse transcriptases, RUBISCOs, topoisomerases and xylanases.

Exemplary Tumor Suppressor gene-mediated diseases and disorders which can be treated with cell/tissues regenerated from stem cells obtained using the antisense compounds comprise diseases associated with decreased or increased apoptosis, tissue/cell aging, cancer (including those mentioned in Table 1), autoimmune diseases, immunodeficiency diseases including AIDS, senescence, neurodegenerative disease or disorders (e.g. Alzheimer's disease, ataxia telangiectasia, Parkinson's disease, amyotrophic lateral sclerosis (ALS), Huntington's disease etc.), hyperplastic diseases (e.g., cheloid) rheumatoid arthritis, coronary heart disease ischemic cell death, lymphoproliferative disorders, atherosclerosis, osteoporosis, myelodysplastic syndromes, toxin-induced diseases, and viral infections, wound-healing, Cowden disease (CD), Lhermitte-Duclos disease (LDD), Bannayan-Zonana syndrome (BZS, also known as Bannayan-Riley-Ruvalcaba syndrome, Ruvalcaba-Myhre-Smith syndrome and Riley-Smith syndrome), transplantation, apoptotic related diseases and disorders, metabolic disease or condition (e.g., diabetes) modulating apoptosis in acute diseases, kidney diseases and disorders, myocardial infarction/heart failure ischemia, sepsis, inflammatory diseases where particular haematopoeitic inflammatory cells are in excess, and proliferative diseases, or where there is a therapeutic paradigm for treatment of inflammatory disease through increasing apoptosis.

In a preferred embodiment, the oligonucleotides are specific for polynucleotides of Tumor Suppressor gene, which includes, without limitation noncoding regions. The Tumor Suppressor gene targets comprise variants of Tumor Suppressor gene; mutants of Tumor Suppressor gene, including SNPs; noncoding sequences of Tumor Suppressor gene; alleles, fragments and the like. Preferably the oligonucleotide is an antisense RNA molecule.

In accordance with embodiments of the invention, the target nucleic acid molecule is not limited to Tumor Suppressor gene polynucleotides alone but extends to any of the isoforms, receptors, homologs, non-coding regions and the like of Tumor Suppressor gene.

In another preferred embodiment, an oligonucleotide targets a natural antisense sequence (natural antisense to the coding and non-coding regions) of Tumor Suppressor gene targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of Tumor Suppressor gene including without limitation, antisense sequences which are identified and expanded, using for example, PCR, hybridization etc., one or more of the sequences set forth as SEQ ID NO.: 8, 9, 10, 1, 12, 13, 14 and 15, and the like, modulate the expression or function of Tumor Suppressor gene. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 16 to 36 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Tumor Suppressor gene.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of Tumor Suppressor gene and modulate the expression and/or function of Tumor Suppressor gene (SEQ ID NO: 1, 4 and 6). Examples of antisense sequences include SEQ ID NOS: 8 to 36.

In another preferred embodiment, the antisense oligonucleotides bind to one or more segments of Tumor Suppressor gene polynucleotides and modulate the expression and/or function of Tumor Suppressor gene. The segments comprise at least five consecutive nucleotides of the Tumor Suppressor gene sense or antisense polynucleotides.

In another preferred embodiment, the antisense oligonucleotides are specific for natural antisense sequences of Tumor Suppressor gene wherein binding of the oligonucleotides to the natural antisense sequences of Tumor Suppressor gene modulate expression and/or function of Tumor Suppressor gene.

In another preferred embodiment, oligonucleotide compounds comprise sequences set forth as SEQ ID NOS: 16 to 36, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Tumor Suppressor gene, regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) Science 308 (5725), 1149-1154; Kapranov, P. et al. (2005). Genome Res 15 (7), 987-997). The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as “DNA-like” (i.e., generally having one or more 2'-deoxy sugars and, generally, T rather than U bases) or “RNA-like” (i.e., generally having one or more T-hydroxyl or 2'-modified sugars and, generally U rather than T bases). Nucleic acid helices can adopt more than one type of structure, most commonly the A- and B-forms. It is believed that, in general, oligonucleotides which have B-form-like structure are “DNA-like” and those which have A-formlike structure are “RNA-like.” In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA): or a short, hairpin RNA (shRNA); small RNA-induced gene activation (RNAa); small activating RNAs (saRNAs), or combinations thereof.

dsRNA can also activate gene expression, a mechanism that has been termed “small RNA-induced gene activation” or RNAa. dsRNAs targeting gene promoters induce potent transcriptional activation of associated genes. RNAa was demonstrated in human cells using synthetic dsRNAs, termed “small activating RNAs” (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Tumor Suppressor gene polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the “preferred target segments” identified herein may be employed in a screen for additional compounds that modulate the expression of Tumor Suppressor gene polynucleotides. “Modulators” are those compounds that decrease or increase the expression of a nucleic acid molecule encoding Tumor Suppressor gene and which comprise at least a 5-nucleotide portion that is complementary to a preferred target segment. The screening method comprises the steps of contacting a preferred target segment of a nucleic acid molecule encoding sense or natural antisense polynucleotides of Tumor Suppressor gene with one or more candidate modulators, and selecting for one or more candidate modulators which decrease or increase the expression of a nucleic acid molecule encoding Tumor Suppressor gene polynucleotides, e.g. SEQ ID NOS: 16 to 36. Once it is shown that the candidate modulator or modulators are capable of modulating (e.g. either decreasing or increasing) the expression of a nucleic acid molecule encoding Tumor Suppressor gene polynucleotides, the modulator may then be employed in further investigative studies of the function of Tumor Suppressor gene polynucleotides, or for use as a research, diagnostic, or therapeutic agent in accordance with the present invention.

Targeting the natural antisense sequence preferably modulates the function of the target gene, for example, for example, the p73 gene (NCBI accession number NM_005427.2), p53 gene (NCBI Accession No.: NM_000546.4) and PTEN gene (NCBI Accession No.: NM 000314). In a preferred embodiment, the target is an antisense polynucleotide of the Tumor Suppressor gene. In a preferred embodiment, an antisense oligonucleotide targets sense and/or natural antisense sequences of Tumor Suppressor gene polynucleotides (p73: NCBI accession number NM_005427.2; p53: NCBI Accession No.: NM_000546.4; PTEN: NCBI Accession No.: NM_000314), variants, alleles, isoforms, homologs, mutants, derivatives, fragments and complementary sequences thereto. Preferably the oligonucleotide is an antisense molecule and the targets include coding and noncoding regions of antisense and/or sense Tumor Suppressor gene polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al, (1998) Nature, 391, 806-811; Timmons and Fire, (1998) Nature, 395, 854; Timmons et al, (2001) gene, 263, 103-112; Tabara et al, (1998) Science, 282, 430-431; Montgomery et al, (1998) Proc. Natl. Acad. Sci. USA, 95, 15502-15507; Tuschl et al, (1999) genes Dev., 13, 3191-3197; Elbashir et al, (2001) Nature, 411, 494-498; Elbashir et al, (2001) genes Dev. 15, 188-200). For example, such double-stranded moieties have been shown to inhibit the target by the classical hybridization of antisense strand of the duplex to the target, thereby triggering enzymatic degradation of the target (Tijsterman, et al, (2002) Science, 295, 694-697).

In a preferred embodiment, an antisense oligonucleotide targets Tumor Suppressor gene polynucleotides (p73: NCBI accession number NM_005427.2; p53: NCBI Accession No.: NM_000546.4; PTEN: NCBI Accession No.: NM_000314), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Tumor Suppressor gene alone but extends to any of the isoforms, receptors, homologs and the like of Tumor Suppressor gene molecules.

In another preferred embodiment, an oligonucleotide targets a natural antisense sequence of Tumor Suppressor gene polynucleotides, for example, polynucleotides set forth as SEQ ID NOS: 8, 9, 10, 11, 12, 13, 14 and 15, and any variants, alleles, homologs, mutants, derivatives, fragments and complementary sequences thereto. Examples of antisense oligonucleotides are set forth as SEQ ID NOS: 16 to 36.

In one embodiment, the oligonucleotides are complementary to or bind to nucleic acid sequences of Tumor Suppressor gene antisense, including without limitation noncoding sense and/or antisense sequences associated with Tumor Suppressor gene polynucleotides and modulate expression and/or function of Tumor Suppressor gene molecules.

In another preferred embodiment, the oligonucleotides are complementary to or bind to nucleic acid sequences of Tumor Suppressor gene natural antisense, set forth as SEQ ID NOS: 8, 9, 10, 11, 12, 13, 14 and 15 and modulate expression and/or function of Tumor Suppressor gene molecules.

In a preferred embodiment, oligonucleotides comprise sequences of at least 5 consecutive nucleotides of SEQ ID NOS: 16 to 36 and modulate expression and/or function of Tumor Suppressor gene molecules.

The polynucleotide targets comprise Tumor Suppressor gene, including family members thereof, variants of Tumor Suppressor gene; mutants of Tumor Suppressor gene, including SNPs; noncoding sequences of Tumor Suppressor gene; alleles of Tumor Suppressor gene; species variants, fragments and the like. Preferably the oligonucleotide is an antisense molecule.

In another preferred embodiment, the oligonucleotide targeting Tumor Suppressor gene polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of Tumor Suppressor gene polynucleotides, e.g. SEQ ID NOS: 8, 9, 10, 11, 12, 13, 14 and 15, modulates the expression or function of these targets. In one embodiment, expression or function is up-regulated as compared to a control. In another preferred embodiment, expression or function is down-regulated as compared to a control.

In another preferred embodiment, antisense compounds comprise sequences set forth as SEQ ID NOS: 16 to 36. These oligonucleotides can comprise one or more modified nucleotides, shorter or longer fragments, modified bonds and the like.

In another preferred embodiment, SEQ ID NOS: 16 to 36 comprise one or more LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, Nature 429 1986; Cech, 260 JAMA 3030, 1988; and Jefferies et al., 17 Nucleic Acids Research 1371, 1989).

Because of their sequence-specificity, trans-cleaving enzymatic nucleic acid molecules show promise as therapeutic agents for human disease (Usman & McSwiggen, (1995) Ann. Rep. Med. Chem. 30, 285-294; Christoffersen and Marr, (1995) J. Med. Chem. 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) Proc. R. Soc. London, B 205, 435) have been used to evolve new nucleic acid catalysts capable of catalyzing a variety of reactions, such as cleavage and ligation of phosphodiester linkages and amide linkages, (Joyce, (1989) gene, 82, 83-87; Beaudry et al, (1992) Science 257, 635-641; Joyce, (1992) Scientific American 267, 90-97; Breaker et al, (1994) TIBTECH 12, 268; Bartel et al, (1993) Science 261:1411-1418; Szostak, (1993) TIBS 17, 89-93; Kumar et al, (1995) FASEB J., 9, 1183; Breaker, (1996) Curr. Op. Biotech., 1, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) Nature, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) Nature, 334, 585; Walbot and Bruening, (1988) Nature, 334, 196; Uhlenbeck, O. C. (1987) Nature, 328: 596-600; Koizumi, M., et al. (1988) FEBS Lett., 228: 228-230). This has allowed use of the catalytic RNA to cleave specific target sequences and indicates that catalytic RNAs designed according to the "hammerhead" model may possibly cleave specific substrate RNAs in vivo, (see Haseloff and Gerlach, (1988) Nature, 334, 585; Walbot and Bruening, (1988) Nature, 334, 196; Uhlenbeck, O. C. (1987) Nature, 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al, (1991) Nat. Rev. genet., 2, 110-119; Matzke et al, (2001) Curt. Opin. genet. Dev., 11, 221-227; Sharp, (2001) genes Dev., 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more T-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 16 to 30 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with Tumor Suppressor gene and the sequences set forth as SEQ ID NOS: 1, 2, 3, 4, 5, 6, 7, 8, 9, 10, 11, 12, 13, 14 and 15. The oligonucleotides are also targeted to overlapping regions of SEQ ID NOS: 1, 2, 3, 4, 5, 6, 7, 8, 9, 10, 11, 12, 13, 14 and 15.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) Ace. Chem. Res., 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 [known as a methylene (methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH). The amide backbones disclosed by De Mesmaeker et al. (1995) Ace. Chem. Res. 28:366-374 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone (Nielsen et al. (1991) Science 254, 1497). Oligonucleotides may also comprise one or more substituted sugar moieties. Preferred oligonucleotides comprise one of the following at the 2' position: OH, SH, SCH3, F, OCN, OCH3 OCH3, OCH3 O(CH2)n CH3, O(CH2)n NH2 or O(CH2)n CH3 where n is from 1 to about 10; Cl to ClO lower alkyl, alkoxyalkoxy, substituted lower alkyl, alkaryl or aralkyl; Cl Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a rTumor Suppressor generter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2 CH2 OCH3, also known as 2'-O-(2-methoxyethyl)] (Martin et al, (1995) Helv. Chim. Acta, 78, 486). Other preferred modifications include 2'-methoxy (2'-O—CH3), T-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxy cytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl) adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W. H. Freeman & Co., San Francisco, 1980, pp 75-77; Gebeyehu, G., (1987) et al. Nucl. Acids Res. 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al, (1989) Proc. Natl. Acad. Sci. USA 86, 6553), cholic acid (Manoharan et al (1994) Bioorg. Med. Chem. Let. 4, 1053), a thioether, e.g., hexyl-S-tritylthiol (Manoharan et al. (1992) Ann. NY. Acad. Sci. 660, 306; Manoharan et al. (1993) Bioorg. Med. Chem. Let. 3, 2765), a thiocholesterol (Oberhauser et al., (1992) Nucl. Acids Res. 20, 533), an aliphatic chain, e.g., dodecandiol or undecyl residues (Saison-Behmoaras et al. EMBO J. 1991, 10, 111; Kabanov et al. (1990) FEBS Lett.

259, 327; Svinarchuk et al. (1993) Biochimie 75, 49), a phospholipid, e.g., di-hexadecyl-rac-glycerol or triethylammonium 1,2-di-O-hexadecyl-rac-glycero-3-H-phosphonate (Manoharan et al. (1995) Tetrahedron Lett. 36, 3651; Shea et al. (1990) Nucl. Acids Res. 18, 3777), a polyamine or a polyethylene glycol chain (Manoharan et al. (1995) Nucleosides & Nucleotides, 14, 969), or adamantane acetic acid (Manoharan et al. (1995) Tetrahedron Lett. 36, 3651). Oligonucleotides comprising lipophilic moieties, and methods for preparing such oligonucleotides are known in the art, for example, U.S. Pat. Nos. 5,138,045, 5,218,105 and 5,459, 255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) Current Opinions in Drug Discovery & Development Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkyiphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596, 086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In another preferred embodiment of the invention the oligonucleotides with phosphorothioate backbones and oligonucleosides with heteroatom backbones, and in particular —CH2-NH—O—CH2-, —CH2-N(CH3)-O—CH2- known as a methylene (methylimino) or MMI backbone, —CH2-O—N(CH3)-CH2-, —CH2N(CH3)—N(CH3) CH2- and —O—N(CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240.

Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are O(CH2)n OmCFB, O(CH2)n, OCH3, O(CH2)nNH2, O(CH2)nCH3, O(CH2)nONH2, and O(CH2nON(CH2)nCH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a rTumor Suppressor generter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) (Martin et al, (1995) Helv. Chim. Acta, 78, 486-504) i.e., an alkoxyalkoxy group. A further preferred modification comprises T-dimethylaminooxyethoxy, i.e., a O(CH2)2ON(CH3)2 group, also known as 2'-DMAOE, as described in examples herein below, and T-dimethylaminoethoxyethoxy (also known in the art as 2'-O-dimethylaminoethoxyethyl or T-DMAEOE), i.e., 2'-O—CH2-O—CH2-N(CH2)2.

Other preferred modifications comprise 2'-methoxy (2'-0 CH3), 2'-aminopropoxy (T-O CH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514, 785; 5,519,134; 5,567,811; 5,576,427; 5,591,722; 5,597,909; 5,610,300; 5,627,053; 5,639,873; 5,646, 265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine. 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617, 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., (1989) Proc. Natl. Acad. ScL USA, 86, 6553-6556), cholic acid (Manoharan et al., (1994) Bioorg. Med. Chem. Let., 4, 1053-1060), a thioether, e.g., hexyl-S-tritylthiol (Manoharan et al., (1992) Ann. N. Y. Acad. ScL, 660, 306-309; Manoharan et al., (1993) Bioorg. Med. Chem. Let., 3, 2765-2770), a thiocholesterol (Oberhauser et al., (1992) Nucl. Acids Res., 20, 533-538), an aliphatic chain, e.g., dodecandiol or undecyl residues (Kabanov et al., (1990) FEBS Lett., 259, 327-330; Svinarchuk et al., (1993) Biochimie 75, 49-54), a phospholipid, e.g., di-hexadecyl-rac-glycerol or triethylammonium 1,2-di-O-hexadecyl-rac-glycero-3-H-phosphonate (Manoharan et at, (1995) Tetrahedron Lett., 36, 3651-3654; Shea et al, (1990) Nucl. Acids Res., 18, 3777-3783), a polyamine or a polyethylene glycol chain (Mancharan et al, (1995) Nucleosides & Nucleotides, 14, 969-973), or adamantane acetic acid (Manoharan et al, (1995) Tetrahedron Lett., 36, 3651-3654), a palmityl moiety (Mishra et al, (1995) Biochim. Biophys. Acta, 1264, 229-237), or an octadecylamine or hexylamino-carbonyl-t oxycholesterol moiety (Crooke et al, (1996) J. Pharmacol. Exp. Ther., 277, 923-937).

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

Drug discovery: The compounds of the present invention can also be applied in the areas of drug discovery and target validation. The present invention comprehends the use of the compounds and preferred target segments identified herein in drug discovery efforts to elucidate relationships that exist between Tumor Suppressor gene polynucleotides and a disease state, phenotype, or condition. These methods include detecting or modulating Tumor Suppressor gene polynucleotides comprising contacting a sample, tissue, cell, or organism with the compounds of the present invention, measuring the nucleic acid or protein level of Tumor Suppressor gene polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a rTumor Suppressor generter gene in the upstream portion of the gene and a potential RNAi target in the 3' non-coding region. The effectiveness of individual antisense oligonucleotides would be assayed by modulation of the rTumor Suppressor generter gene. RTumor Suppressor generter genes useful in the methods of the present invention include acetohydroxyacid synthase (AHAS), alkaline phosphatase (AP), beta galactosidase (LacZ), beta glucuronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a rTumor Suppressor generter gene are well known in the art, and include, but are not limited to, fluorometric methods (e.g. fluorescence spectroscopy, Fluorescence Activated Cell Sorting (FACS), fluorescence microscopy), antibiotic resistance determination.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Tumor Suppressor gene genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) FEBS Lett, 480, 17-24; Celis, et al, (2000) FEBS Lett, 480, 2-16), SAGE (serial analysis of gene expression) (Madden, et al, (2000) Drug Discov. Today, 5, 415-425), READS (restriction enzyme amplification of digested cDNAs) (Prashar and Weissman, (1999) Methods Enzymol, 303, 258-72), TOGA (total gene expression analysis) (Sutcliffe, et al, (2000) Proc. Natl. Acad. Sci. U.S.A., 97, 1976-81), protein arrays and proteomics (Celis, et al, (2000) FEBS Lett., 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. BiotechnoL, 2000, 80, 143-57), subtractive RNA fingerprinting (SuRF) (Fuchs, et al, (2000) Anal. Biochem. 286, 91-98; Larson, et al, (2000) Cytometry 41, 203-208), subtractive cloning, differential display (DD) (Jurecic and Belmont, (2000) Curr. Opin. Microbiol 3, 316-21), comparative genomic hybridization (Carulli, et al, (1998) J. Cell Biochem. Suppl, 31, 286-96), FISH (fluorescent in situ hybridization) techniques (Going and Gusterson, (1999)

Eur. J. Cancer, 35, 1895-904) and mass spectrometry methods (To, Comb. (2000) Chem. High Throughput Screen, 3, 235-41).

The compounds of the invention are useful for research and diagnostics, because these compounds hybridize to nucleic acids encoding Tumor Suppressor gene. For example, oligonucleotides that hybridize with such efficiency and under such conditions as disclosed herein as to be effective Tumor Suppressor gene modulators are effective primers or probes under conditions favoring gene amplification or detection, respectively. These primers and probes are useful in methods requiring the specific detection of nucleic acid molecules encoding Tumor Suppressor gene and in the amplification of said nucleic acid molecules for detection or for use in further studies of Tumor Suppressor gene. Hybridization of the antisense oligonucleotides, particularly the primers and probes, of the invention with a nucleic acid encoding Tumor Suppressor gene can be detected by means known in the art. Such means may include conjugation of an enzyme to the oligonucleotide, radiolabeling of the oligonucleotide, or any other suitable detection means. Kits using such detection means for detecting the level of Tumor Suppressor gene in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of Tumor Suppressor gene polynucleotides is treated by administering antisense compounds in accordance with this invention. For example, in one non-limiting embodiment, the methods comprise the step of administering to the animal in need of treatment, a therapeutically effective amount of Tumor Suppressor gene modulator. The Tumor Suppressor gene modulators of the present invention effectively modulate the activity of the Tumor Suppressor gene or modulate the expression of the Tumor Suppressor gene protein. In one embodiment, the activity or expression of Tumor Suppressor gene in an animal is inhibited by about 10% as compared to a control. Preferably, the activity or expression of Tumor Suppressor gene in an animal is inhibited by about 30%. More preferably, the activity or expression of Tumor Suppressor gene in an animal is inhibited by 50% or more. Thus, the oligomeric compounds modulate expression of Tumor Suppressor gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Tumor Suppressor gene and/or in an animal is increased by about 10% as compared to a control. Preferably, the activity or expression of Tumor Suppressor gene in an animal is increased by about 30%. More preferably, the activity or expression of Tumor Suppressor gene in an animal is increased by 50% or more. Thus, the oligomeric compounds modulate expression of Tumor Suppressor gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Tumor Suppressor gene may be measured in serum, blood, adipose tissue, liver or any other body fluid, tissue or organ of the animal. Preferably, the cells contained within said fluids, tissues or organs being analyzed contain a nucleic acid molecule encoding Tumor Suppressor gene peptides and/or the Tumor Suppressor gene protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, rTumor Suppressor generter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 16 to 36) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al, (1995) J. Neurochem, 64: 487; Lim, F., et al, in DNA Cloning: Mammalian Systems, D. Glover, Ed. (Oxford Univ. Press, Oxford England) (1995); Geller, A. I. et al, (1993) Proc Natl. Acad. ScL: U.S.A.: 90 7603; Geller, A. I., et al., (1990) Proc Natl. Acad. Sci USA: 87:1149], Adenovirus Vectors (LeGal LaSalle et al., Science, 259:988 (1993); Davidson, et al., (1993) Nat. genet. 3: 219; Yang, et al, (1995) J. Virol. 69: 2004) and Adeno-associated Virus Vectors (Kaplitt, M. G., et al, (1994) Nat. genet. 8:148).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclobexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MIX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Tumor Suppressor gene, and the second target may be a region from another nucleotide sequence. Alternatively, compositions of the invention may contain two or more antisense compounds targeted to different regions of the same Tumor Suppressor gene nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 μg to 100 g per kg of body weight, and may be given once or more daily, weekly, monthly or yearly, or even once every 4 to 30 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Design of Antisense Oligonucleotides Specific for a Nucleic Acid Molecule Antisense to and/or Sense Strand of Tumor Suppressor Gene Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's STumor Suppressor genene Plus Real Time PCR System or LightTyper instrument, Roche Diagnostics, Lewes, UK).

Melting peaks are constructed by plotting the negative derivative of fluorescence with respect to temperature (−d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2

Modulation of Tumor Suppressor Gene Oligonucleotide Gene Expression

Treatment of HEPG2 Cells with Antisense Oligonucleotides

HepG2 cells from ATCC (cat# HB-8065) were grown in growth media (MEM/EBSS (Hyclone cat #SH30024, or Mediatech cat # MT-IO-OlO-CV)+10% FBS (Mediatech cat# MT35-OH-CV)+penicillin/streptomycin (Mediatech cat# MT30-002-CI)) at 37° C. and 5% $CO_2$. One day before the experiment the cells were replated at the density of $1.5\times10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat#31985-070) and 4 μl of Lipofectamine 2000 (Invitrogen cat#11668019) at room temperature for 20 min and applied to each well of the 6 well plates with HepG2 cells. Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat#74181) following the manufacturers' instructions. 600 ng of RNA was added to the reverse transcription reaction performed using Verso cDNA kit from Thermo Scientific (cat#AB1453B) or High Capacity cDNA Reverse Transcription Kit (cat#4368813) as described in the manufacturer's protocol. The cDNA from this reverse transcription reaction was used to monitor gene expression by real time PCR using ABI Taqman gene Expression Mix (cat#4369510) and primers/probes designed by ABL. The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems Inc. or Mx4000 thermal cycler (Stratagene).

Fold change in gene expression after treatment with antisense oligonucleotides was calculated based on the difference in 18S-normalized dCt values between treated and mock-transfected samples.

p73 Expression Assays used (ABI cat#s), all probes with MGB

```
p73: Hs00232088_ml
(target sequence ACCTCTGGAGCTCTCTGGAAC,
exon 2 SEQ ID No.: 41)

p73as: Hs00215135_ml
(target sequence TATGATGGAAAGGTGCGCATCCTTA,
exon 7 SEQ ID No.: 42)
and

Hs00892470_gl
```

Figure 1B:
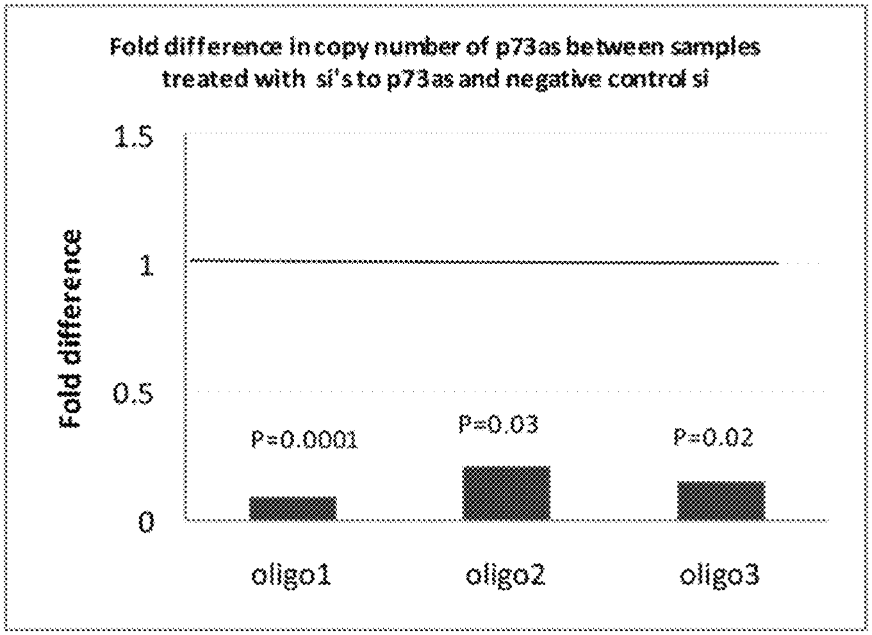

Results:

Real time PCR results show that the levels of the Tumor Suppressor gene mRNA in HepG2 cells are significantly increased 48 h after treatment with two of the siRNAs designed to Tumor Suppressor gene (Tumor Suppressor gene 1, P=O.0.02, and Tumor Suppressor gene 2, P=O.0.04, FIG. 1A). In the same samples the levels of Tumor Suppressor gene RNA were possibly decreased after treatment with siRNAs to Tumor Suppressor gene (FIG. 1B).

Figure 1C:
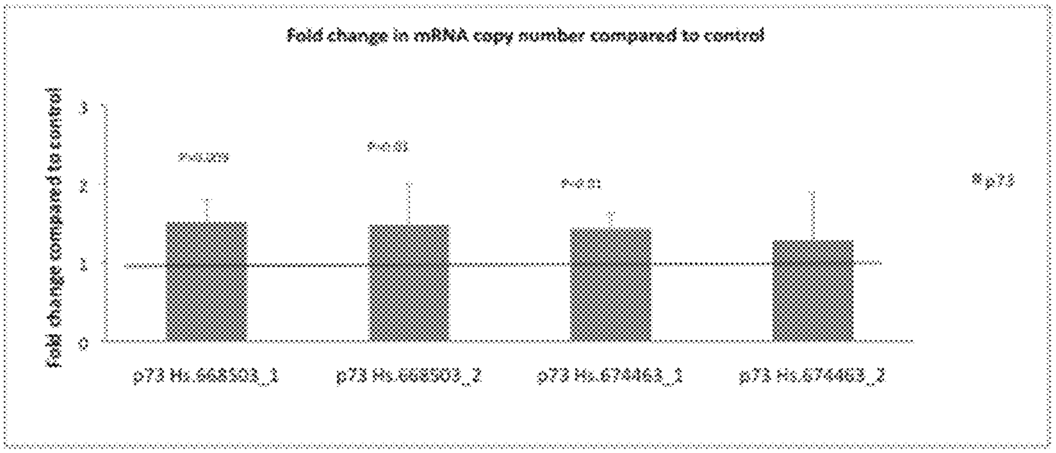
FIG. 1C: is a graph of real time PCR results showing the fold change+standard deviation in TP73 mRNA after treatment of HepG2 cells with siRNA oligonucleotides introduced using Lipofectamine 2000, as compared to control. Real time PCR results show that the levels of the p73 mRNA in HepG2 cells are significantly increased 48 h after treatment with two of the oligos designed to p73 antisense Hs.668503 and one of the oligos designed to p73 antisense Hs.674463. Bars denoted as p73 Hs.668503_1, p73 Hs.668503_2, p73 Hs.674463 1 and p73 Hs.674463_2 correspond to samples treated with SEQ ID NOS 19, 20, 21 and 22 respectively.

In FIG. 1C, the Real time PCR results show that the levels of the Tumor Suppressor gene mRNA in HepG2 cells are significantly increased 48 h after treatment with two of the oligos designed to Tumor Suppressor gene antisense Hs.668503 and one of the oligos designed to Tumor Suppressor gene antisense Hs.674463.

Figure 3:
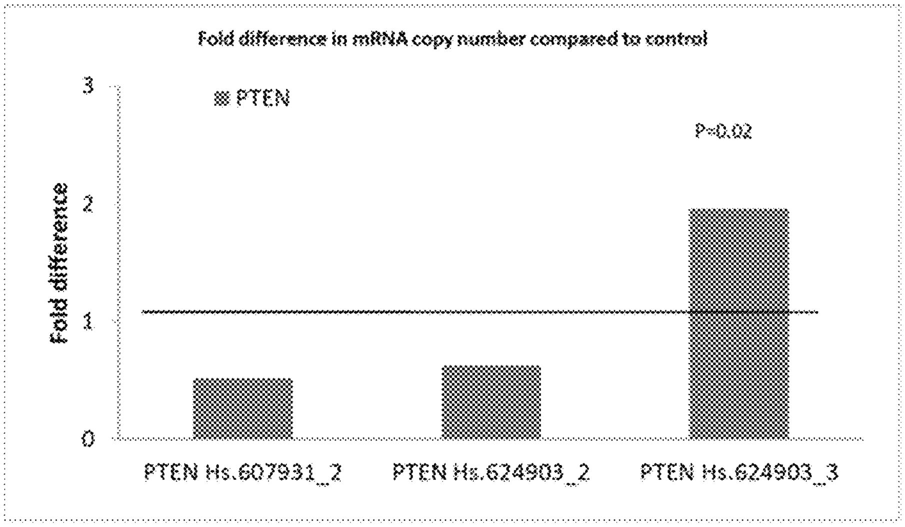
FIG. 3 is a graph of real time PCR results showing the fold change in PTEN mRNA after treatment of HepG2 cells with phosphorothioate oligonucleotides introduced using Lipofectamine 2000, as compared to control. Real time PCR results show that the levels of PTEN mRNA in HepG2 cells are significantly increased 48 h after treatment with one of the oligos designed to PTEN antisense Hs.624903. Bars denoted as PTEN Hs.607931_2, PTEN Hs.624903 2, PTEN Hs.624903_3 correspond to samples treated with SEQ ID NOS 34, 35 and 36 respectively.

Real time PCR results show that the levels of PTEN mRNA in HepG2 cells are significantly increased 48 h after treatment with one of the oligonucleotides designed to PTEN antisense hs.624903 (FIG. 3). (Detection probes: Applied Biosystems Taqman Gene Expression Assay: Hs02621230_sl)

Treatment of TM4 Cells with Antisense Oligonucleolides

TM4 cells from ATCC (cat# CRL-1715) were grown in growth media (MEM/EBSS (Hyclone cat #SH30024, or Mediatech cat # MT-IO-OlO-CV)+10% FBS (Mediatech cat# MT35-OH-CV)+penicillin/streptomycin (Mediatech cat# MT30-002-CI)) at 37° C. and 5% $CO_2$. One day before the experiment the cells were replated at the density of $1.5\times10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat#31985-070) and 4 μl of Lipofectamine 2000 (Invitrogen cat#11668019) at room temperature for 20 min and applied to each well of the 6 well plates with TM4 cells. Similar mixture including 2 μl of water instead of the oligonucleotide solution was used for the mock-transfected controls. After 3-18 h of incubation at 37° C. and 5% CO: the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat#74181) following the manufacturers' instructions. 600 ng of RNA was added to the reverse transcription reaction performed using Verso cDNA kit from Thermo Scientific (cat#AB1453B) or High Capacity cDNA Reverse Transcription Kit (cat#4368813) as described in the manufacturer's protocol. The cDNA from this reverse transcription reaction was used to monitor gene expression by real time PCR using ABI Taqman gene Expression Mix (cat#4369510) and primers/probes designed by ABI (Applied Biosystems Taqman gene Expression Assay: Mm00660220_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 1D:
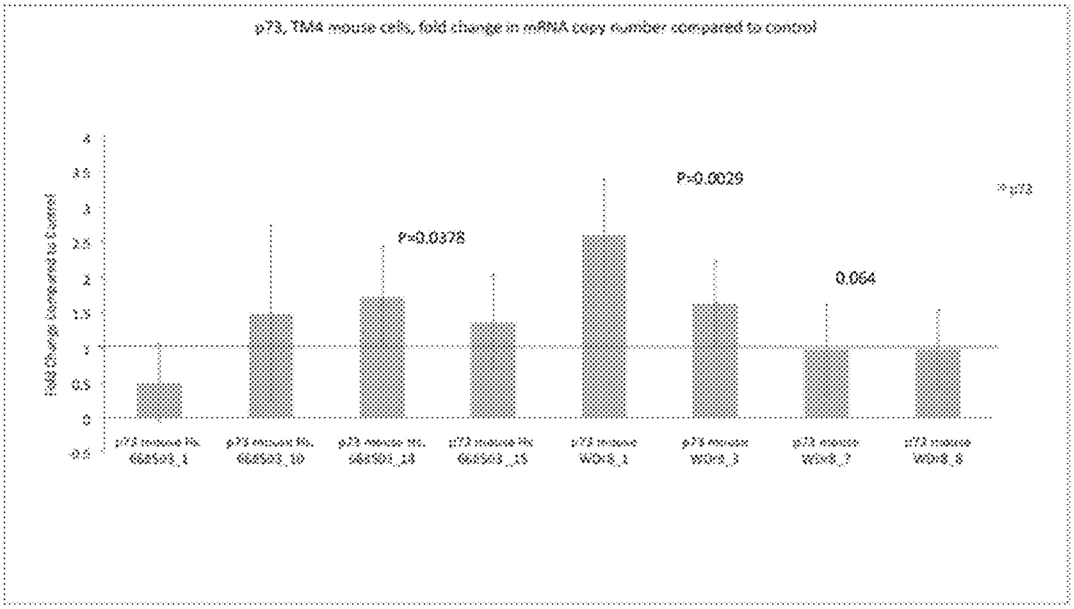
FIG. 1D: is a graph of real time PCR results showing the fold change+standard deviation in TP73 mRNA after treatment of TM4 cells with phosphothioate oligonucleotides introduced using Lipofectamine 2000, as compared to control. Real time PCR results show that the levels of the p73 mRNA in mouse TM4 cells are significantly increased 48 h after treatment with one of the oligos designed to mouse p73 antisense Hs.668503 and one of the oligos designed to mouse p73 antisense WDR8. Bars denoted as p73 mouse Hs.668503_1, p73 mouse Hs.668503 10, p73 mouse Hs.668503 14, p73 mouse Hs.668503 15, p73 mouse WDr8_1, p73 mouse WDr8_7, p73 mouse WDr8_8 and p73 mouse WDr8_3 correspond to samples treated with SEQ ID NOS 20 to 30 respectively.

Results:

Real time PCR results show that the levels of the Tumor Suppressor gene mRNA in mouse TM4 cells are significantly increased 48 h after treatment with one of the oligos designed to Tumor Suppressor gene antisense Hs.668503 and one of the oligos designed to Tumor Suppressor gene antisense WDR8 (FIG. 1D).

Treatment of HUVEC Cells with Antisense Oligonucleotides

HUVEC cells from ATCC (Promo Cell cat# C-12253) were grown in Epithelial Growth Media (Promo Cell cat #C-22010) at 37° C. and 5% $CO_2$. One day before the experiment the cells were replated using Promo Cell Detach Kit (cat#C-41200) at the density of 1.5×10^5/ml into 6 well plates and incubated at 37° C. and 5% $CO_2$. On the day of the experiment the media in the 6 well plates was changed to fresh Epithelial Growth Media. All antisense oligonucleotides were diluted to the concentration of 20 μM. Two μl of this solution was incubated with 400 μl of Opti-MEM media (Gibco cat#31985-070) and 4 μl of Lipofictamine 2000 (Invitrogen cat#11668019) at room temperature for 20 min and applied to each well of the 6 well plates with HUVEC cells. Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat#74181) following the manufacturers' instructions. 600 ng of RNA was added to the reverse transcription reaction performed using Verso cDNA kit from Thermo Scientific (cat#AB1453B) as described in the manufacturer's protocol. The cDNA from this reverse transcription reaction was used to monitor gene expression by real time PCR using ABI Taqman gene Expression Mix (cat#4369510) and primers/probes designed by ABI (Applied Biosystems Taqman Gene Expression Assays: Hs00153340_ml and Hs00216360_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems Inc.) or Mx4000 thermal cycler (Stratagene).

Fold change in gene expression after treatment with antisense oligonucleotides was calculated based on the difference in 18S-normalized dCt values between treated and mock-transfected samples.

P53 Expression Assays used (ABI cat#s), all probes with FAM/MGB: 18S: 4319413E

```
P53: Hs00153340_ml
(target sequence CTTCCCTGGATTGGCAGCCAGACTG,
SEQ ID No.: 43)

P53as: Hs00216360_ml
(target sequence ATATGCAGAAATGGTCCCTGTCCTT,
SEQ ID No.: 44)
```

Figure 2:
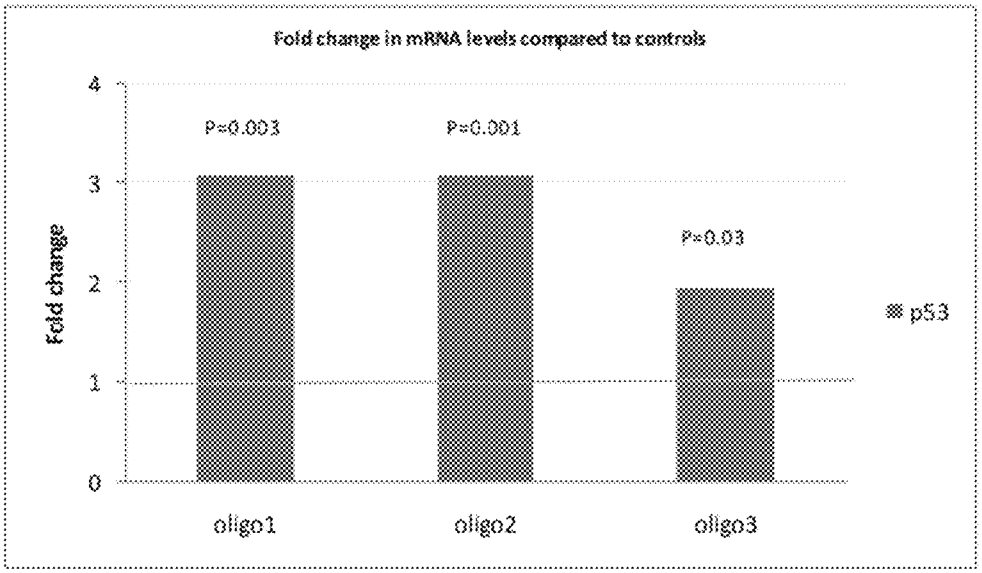
FIG. 2 is a graph of real time PCR results showing the fold change in p53 mRNA after treatment of HUVEC cells with phosphothioate oligonucleotides introduced using Lipofectamine 2000, as compared to control. Real time PCR results show that the levels of p53 mRNA in HUVEC cells are significantly increased 48 h after treatment with all of the siRNAs designed to p53as (oligol, P=0.003, oligo2 P=0.001, and oligo2 P=0.03). Bars denoted as oligol, oligo2 and oligo3 correspond to samples treated with SEQ ID NOs: 31, 32 and 33 respectively.

Results:

Real time PCR results show that the levels of p53 mRNA in HUVEC cells are significantly increased 48 h after treatment with all of the siRNAs designed to p53as (FIG. 2).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

---

What is claimed is:

1. A method of upregulating a function of and/or the expression of a PTEN Tumor Suppressor gene polynucleotide in patient cells or tissues in vivo or in vitro comprising:

contacting said cells or tissues with at least one single-stranded antisense oligonucleotide of 15 to 30 nucleotides in length that targets, is 100% complementary to and specifically hybridizes to a complementary region of a natural antisense polynucleotide of a Tumor Suppressor gene polynucleotide selected from the group consisting of nucleotides 1-189 of SEQ ID NO: 14 and nucleotides 1-467 of SEQ ID NO: 15; thereby upregulating a function of and/or the expression of the Tumor Suppressor gene polynucleotide in patient cells or tissues in vivo or in vitro.

2. The method of claim 1, wherein the at least one antisense oligonucleotide targets a natural antisense polynucleotide antisense to coding and/or non-coding nucleic acid sequences of a Tumor Suppressor gene polynucleotide.

3. The method of claim 1, wherein the at least one antisense oligonucleotide targets a natural antisense polynucleotide having overlapping and/or non-overlapping sequences with a Tumor Suppressor gene polynucleotide.

4. The method of claim 1, wherein the at least one antisense oligonucleotide comprises one or more modifications selected from: at least one modified sugar moiety, at least one modified internucleoside linkage, at least one modified nucleotide, and combinations thereof.

5. The method of claim 4, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

6. The method of claim 4, wherein the one or more modifications comprise at least one modified internucleoside linkage selected from: a phosphorothioate, alkylphosphonate, phosphorodithioate, alkylphosphonothioate, phosphoramidate, carbamate, carbonate, phosphate triester, acetamidate, a carboxymethyl ester, and combinations thereof.

7. The method of claim 4, wherein the one or more modifications comprise at least one modified nucleotide selected from: a peptide nucleic acid (PNA), a locked nucleic acid (LNA), an arabino-nucleic acid (FANA), and combinations thereof.

8. The method of claim 1, wherein the at least one oligonucleotide comprises at least one of the oligonucleotide sequences set forth as SEQ ID NO: 36.

9. A method of upregulating a function of and/or the expression of a Tumor Suppressor gene in mammalian cells or tissues in vivo or in vitro comprising:

contacting said cells or tissues with at least one antisense oligonucleotide of about 20 to 30 nucleotides in length specifically hybridizing to a natural antisense strand of a PTEN Tumor Suppressor gene polynucleotide wherein said at least one single-stranded antisense oligonucleotide has at least 100% sequence complementarity to 20 to 30 nucleotides within at least one nucleic acid sequence set forth as SEQ ID NO: 14 and, upregulating the function and/or expression of the PTEN Tumor Suppressor gene in mammalian cells or tissues in vivo or in vitro and further wherein the target region includes nucleotides 1-189, 431-789 of SEQ ID NO: 14 and nucleotides 1-467 of SEQ ID NO: 15.

10. A method of preventing or treating a disease associated with at least one Tumor Suppressor gene polynucleotide and/or at least one encoded product thereof, comprising:

administering to a patient a therapeutically effective dose of at least one antisense oligonucleotide of 15 to 30 nucleotides in length that is 100% complementary to and specifically hybridizes to a complementary region of a natural antisense sequence of said at least one Tumor Suppressor gene polynucleotide having nucleotides 1-189 of SEQ ID NO: 14 or nucleotides 1-467 of SEQ ID NO: 15 and upregulates expression of said at least one Tumor Suppressor gene polynucleotide; thereby preventing or treating the disease associated with the at least one Tumor Suppressor gene polynucleotide and/or at least one encoded product thereof and further wherein the disease is selected from cancer.

* * * * *